(12) United States Patent
Paoletti et al.

(10) Patent No.: US 6,267,965 B1
(45) Date of Patent: *Jul. 31, 2001

(54) RECOMBINANT POXVIRUS—CYTOMEGALOVIRUS COMPOSITIONS AND USES

(75) Inventors: Enzo Paoletti, Delmar; Steven E. Pincus, East Greenbush; William I. Cox, Troy; Elizabeth K. Kauffman, Averill Park, all of NY (US)

(73) Assignee: Virogenetics Corporation, Troy, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/085,273

(22) Filed: May 26, 1998

Related U.S. Application Data

(63) Continuation of application No. 08/471,014, filed on Jun. 6, 1995, now abandoned, which is a continuation-in-part of application No. 08/105,483, filed on Aug. 12, 1993, now Pat. No. 5,494,807, which is a continuation of application No. 07/847,951, filed on Mar. 6, 1992, now abandoned, which is a continuation-in-part of application No. 07/713,967, filed on Jun. 11, 1991, now abandoned, which is a continuation-in-part of application No. 07/666,056, filed on Mar. 7, 1991, now abandoned, application No. 08/036,217, filed on Mar. 24, 1993, which is a continuation of application No. 07/666,056, application No. 09/085,273, which is a continuation-in-part of application No. 08/124,668, filed on Sep. 21, 1993, now Pat. No. 5,482,713, which is a division of application No. 07/502,834, filed on Apr. 4, 1990, now Pat. No. 5,338,683, said application No. 07/502,834, is a continuation-in-part of application No. 07/394,488, filed on Aug. 16, 1989, now abandoned, which is a continuation-in-part of application No. 07/339,004, filed on Apr. 17, 1989, now abandoned, and a continuation-in-part of application No. 07/090,209, filed on Aug. 27, 1987, now abandoned, which is a division of application No. 06/622,135, filed on Jun. 19, 1984, now Pat. No. 4,722,848, which is a continuation-in-part of application No. 06/446,824, filed on Dec. 8, 1982, now Pat. No. 4,603,112, which is a continuation-in-part of application No. 06/334,456, filed on Dec. 24, 1981, now Pat. No. 4,769,330.

(51) Int. Cl.[7] ......................... A61K 39/12; A61K 39/245; A61K 38/00; C12N 15/00; C07H 21/04
(52) U.S. Cl. ................................... 424/199.1; 424/204.1; 424/230.1; 424/232.1; 435/320.1; 435/235.1; 536/23.72; 530/300; 530/388.1
(58) Field of Search ............................. 424/199.1, 204.1, 424/230.1, 232.1; 435/320.1, 235.1; 536/23.72; 530/388.1, 300

(56) References Cited

PUBLICATIONS

Wathen, M. W. and Wathen, L. M. K., Virol. 51, 57–62 (1984).
Watson et al., DNA Cloning, vol. 1., ed. Glover, D.M., (IRL Press, Washington, D.C.), pp. 79–88 (1985).
Watson, R., Gene 26, 307–312 (1983).
Waxham et al., Virology 159, 381–388 (1987).
Waxham et al., Virology 164, 318–325 (1988).
Weibel, R. E., In: Vaccines, eds. Plotkin, S. A., and Mortimer, E. A., (W. B. Saunders, pp. 223–234 (1988).
Weir et al., J. Gen. Virol. 70, 2587–2594 (1989).
Weir, J.P. and B. Moss, J. Virol. 46, 530–537 (1983).
Weiss et al., Nature 316, 69–72 (1985).
Wengler et al., J. Gen. Virol. 70, 987–992 (1989b).
Wengler, G., and Wengler, G., J. Virol. 63, 2521–2526 (1989a).
Weston, K., and B.G. Barrell, J. Mol. Biol. 192, 177–208 (1986).
Whalley, J.M. et al. 1989, J. Gen. Virol. vol. 70 pp. 383–394.
WHO Meeting, Geneva, Jun. 19–22, Vaccine 8, 425–437 (1990).
Wiktor et al., Proc. Natl. Acad. Sci. USA, 81, 7194–7198 (1984).
Wiktor, T. J., Dev. Biol. Stand 40, 255–264 (1977).
Wiktor et al., J. Immunol. 110, 269–276 (1973).
Wiktor et al., Proc. Natl. Acad. Sci. USA 81, 7194–7198 (1984).
Wiktor et al., In Vaccines, eds. Plotkin, S.A. and E.A. Mortimer (W.B. Saunders, Philadelphia), 474–491 (1988).
Wild F., Giraudon P., Spenner D., et al., Vaccine 8, 441–442 (1990).
Wild et al., Vaccine 8, 441–442 (1991a).
Wild et al., J. Gen. Virol. 72, 439–447 (1991b).
Winkler et al., Virol 162, 187–196 (1988).
Wittmann et al., Herpesvirus Diseases of Cattle, Horses and Pigs, ed Wittmann, G., (Kluwer Academic Publishers), 230–325 (1989).
Wolff et al., J. Immunol. Meth. 26, 151–156 (1979).
Wolinsky et al., Virology, eds. Fields, B. N., and Knipe, D. M., (Raven Press), pp. 989–1011 (1990).

(List continued on next page.)

Primary Examiner—Ali Salimi
(74) Attorney, Agent, or Firm—McDonnell Boehnen Hulbert & Berghoff

(57) ABSTRACT

Attenuated recombinant viruses containing DNA encoding an HCMV antigen, as well as methods and compositions employing the viruses, expression products therefrom, and antibodies generated from the viruses or expression products, are disclosed and claimed. The recombinant viruses can be NYVAC or ALVAC recombinant viruses. The recombinant viruses and gene products therefrom and antibodies generated by the viruses and gene products have several preventive, therapeutic and diagnostic uses. The DNA of the recombinant viruses can be used as probes or for generating PCR primers.

21 Claims, 82 Drawing Sheets

PUBLICATIONS

Wunner et al., *J. Gen. Virol.* 64, 1649–1650 (1983).
Wunsch et al., *EMBO J.* 2, 2239–2246 (1983).
Yamagishi A., *J. Vet. Med.* 820, 14–18 (1989).
Yamanishi et al., *Virology* 52, 231–237 (1984).
Yasuda et al., *Science* 219, 614–620 (1983).
Yoshida et al., *Biken J.* 24, 47–67 (1981).
Yoshinaka et al., *J. Virol.* 55, 870–873 (1985).
Yuen et al., *Proc. Natl. Acad. Sci.* USA 84, 6417–6421 (1987).
Zagury et al., *Nature* 332, 728–731 (1988).
Zanetti et al., *J. Med. Virol.* 32, 219–224 (1990).
Zarling et al., *Nature* 323, 344–346 (1986).
Zhang et al., *Arch. Virol.* 105, 235–246 (1989).
Zhou et al., *J. Gen Virol.* 71, 2185–2190 (1990).
Zingernagel et al., *Eur. J. Immunol.* 14, 14–23 (1984).
Zweig et al., *J. Virol.* 47, 185–192 (1983).

FIG. I

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTACGACAA TAAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGCTGTTGA GAGACGACTA CAAAATAGTG
1021 AAAGATCTGT TGAAGAATAA CTATGTAAAC AATGTTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAAGCTG TTAATCGATC ATGGAGCTGA TGTAAACTCT TTAACTATTG
2581 CTAAAGATAA TCTTATTAAA AAAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAATAGGA TGTAAGAACT TACTAGAATG TTTTATCAAT AATGATATGA ATACAGTATC
2821 TAGGGCTATA AACAATGAAA CGATTAAAAA TTATAAAAAT CATTTCCCTA TATATAATAC
2881 GCTCATAGAA AAATTCATTT CTGAAAGTAT ACTAAGCACG GAATTATTGG ATGGAGTTAT
2941 AAATTCTTTT CAAGGATTCA ATAATAAATT GCCTTACGAG ATTCAGTACA TTATACTGGA
3001 GAATCTTAAT AACCATGAAC TAAAAAAAAT TTTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

FIG.8

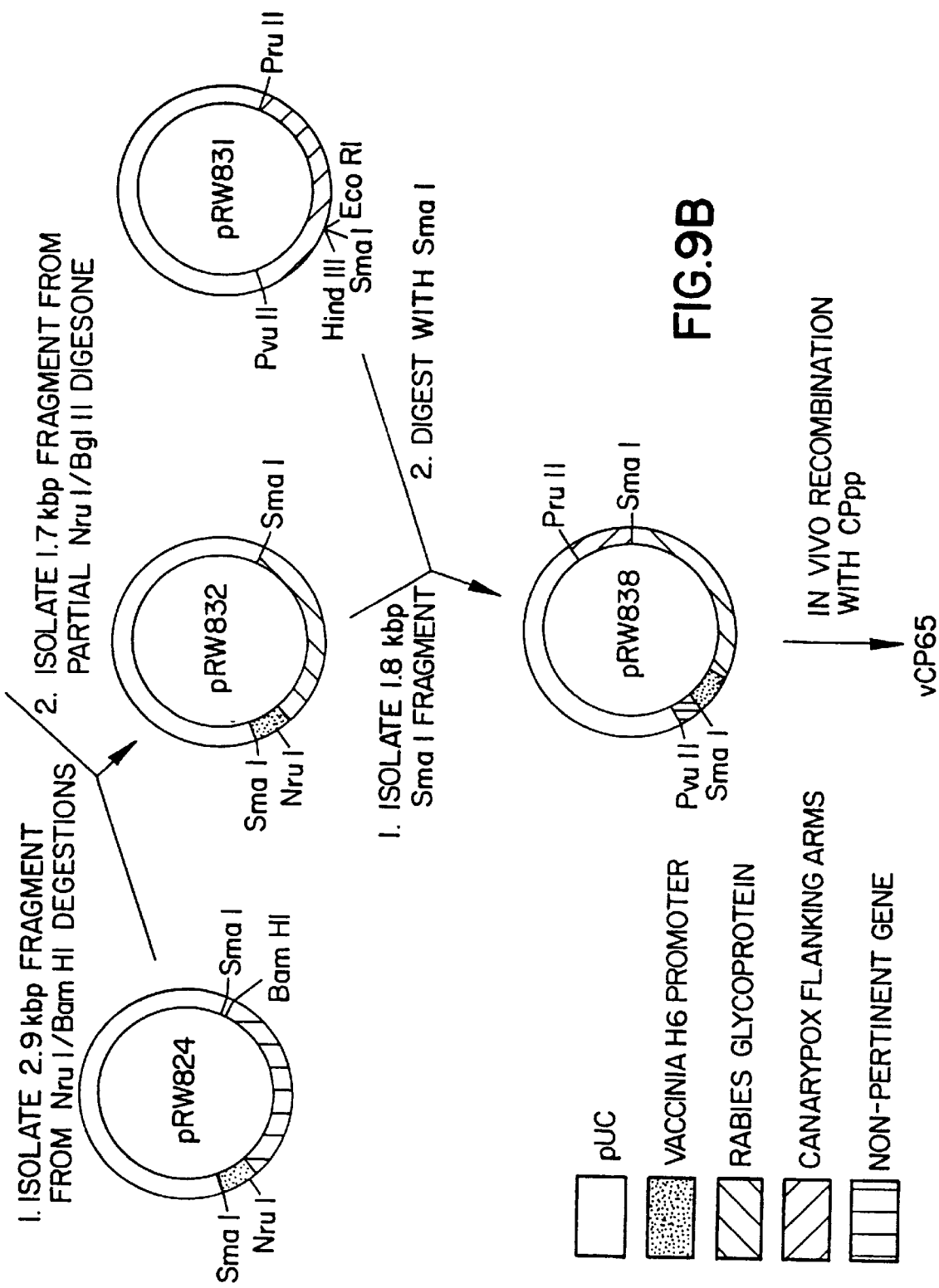

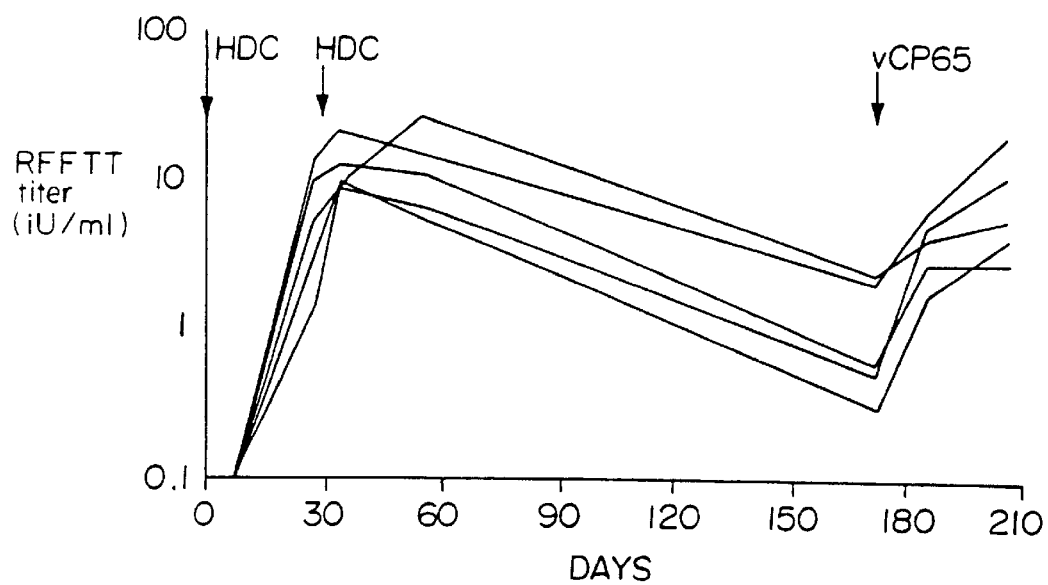
FIG.IIB
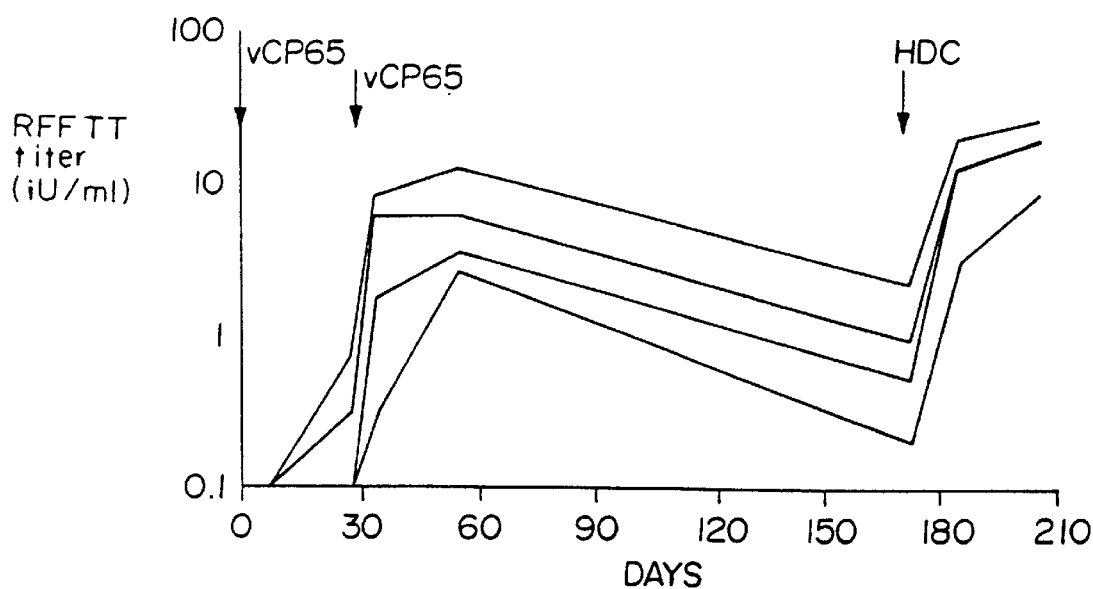
FIG.IID

FIG.12

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC ACAGGGTACG
 301 GATCTTATTC GCTTTGAACG TAATATCGTC TGCACCTCGA TGAAGCCCAT CAATGAAGAC
 361 CTGGACGAGG CATCATGGT GGTCTACAAA CGCAACATCG TCGCCACAC CTTTAAGGTA
 421 CGAGTCTACC AGAAGGTTTT GACGTTTCGT CGTAGCTACG CTTACATCCA CACCACTTAT
 481 CTGCTGGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTGAACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA AATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCAAAAGA
1381 AGTACAGATG GCAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTG TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TTCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG GCAACCACCG CACTGAGGAA TGTCAGCTTC CAGCCTCAA GATCTTCATC
1861 GCCGGCAACT CGGCCTACGA GTACGTGGAC TACCTCTTCA ACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTCCGCCC CTACCTCAAG GGTCTGGACG ACCTCATGAG CGGCCTGGGC
2161 GCCGCGGGAA AGGCCGTTGG CGTAGCCATT GGGGCCGTGG GTGGCGCGGT GGCCTCCGTG
2221 GTCGAAGGCG TTGCCACCTT CCTCAAAAAC CCCTTCGGAG CCTTCACCAT CATCCTCGTG
2281 GCCATAGCCG TCGTCATTAT CATTTATTTG ATCTATATCC GACAGCGGCG TCTCTGCATG
2341 CAGCCGCTGC AGAACCTCTT TCCCTATCTG GTGTCCGCCG ACGGGACCAC CGTGACGTCG
2401 GGCAACACCA AAGACACGTC GTTACAGGCT CCGCCTTCCT ACGAGGAAAG TGTTTATAAT
2461 TCTGGTCGCA AAGGACCGGG ACCACCGTCG TCTGATGCAT CCACGGCGGC TCCGCCTTAC
2521 ACCAACGAGC AGGCTTACCA GATGCTTCTG GCCCTGGTCC GTCTGGACGC AGAGCAGCGA
2581 GCGCACGAGA ACGGTACAGA TTCTTTGGAC GGACAGACTG GCACGCAGGA CAAGGGACAG
2641 AAGCCCAACC TGCTAGACCG ACTGCGACAC CGCAAAAACG GCTACCGACA CTTGAAAGAC
2701 TCCGACGAAG AAGAGAACGT CTGA
```

FIG.13A

```
   1 AAGCTTTTGC GATCAATAAA TGGATCACAA CCAGTATCTC TTAACGATGT TCTTCGCAGA
  61 TGATGATTCA TTTTTTAAGT ATTTGGCTAG TCAAGATGAT GAATCTTCAT TATCTGATAT
 121 ATTGCAAATC ACTCAATATC TAGACTTTCT GTTATTATTA TTGATCCAAT CAAAAAATAA
 181 ATTAGAAGCC GTGGGTCATT GTTATGAATC TCTTTCAGAG GAATACAGAC AATTGACAAA
 241 ATTCACAGAC TCTCAAGATT TTAAAAAACT GTTTAACAAG GTCCCTATTG TTACAGATGG
 301 AAGGGTCAAA CTTAATAAAG GATATTTGTT CGACTTTGTG ATTAGTTTGA TGCGATTCAA
 361 AAAAGAATCC TCTCTAGCTA CCACCGCAAT AGATCCTATT AGATACATAG ATCCTCGTCG
 421 CGATATCGCA TTTTCTAACG TGATGGATAT ATTAAAGTCG AATAAAGTGA ACAATAATTA
 481 ATTCTTTATT GTCATCATGT AATTAACTAG CTACCCGGGA GATCTCTCGA GCTGCAGAAG
 541 CTTATAAAAA TCACAAGTCT CTGTCACTTT TTTTGTCTAG TTTTTTTTTC TCCTCTTGGT
 601 TCAGACGTTC TCTTCTTCGT CGGAGTCTTT CAAGTGTCGG TAGCCGTTTT TGCGGTGTCG
 661 CAGTCGGTCT AGCAGGTTGG GCTTCTGTCC CTTGTCCTGC GTGCCAGTCT GTCCGTCCAA
 721 AGAATCTGTA CCGTTCTCGT GCGCTCGCTG CTCTGCGTCC AGACGGACCA GGGCCAGAAG
 781 CATCTGGTAA GCCTGCTCGT TGGTGTAAGG CGGAGCCGCC GTGGATGCAT CAGACGACGG
 841 TGGTCCCGGT CCTTTGCGAC CAGAATTATA AACACTTTCC TCGTAGGAAG GCGGAGCCTG
 901 TAACGACGTG TCTTTGGTGT TGCCCGACGT CACGGTGGTC CCGTCGGCGG ACACCAGATA
 961 GGGAAAGAGG TTCTGCAGCG GCTGCATGCA GAGACGCCGC TGTCGAGTAT AGATCAAATA
1021 AATGATAATG ACGACGGCTA TGGCCACGAG GATGATGGTG AAGGCTCCGA AGGGGTTTTT
1081 GAGGAAGGTG GCAACGCCTT CGACCACGGA GGCCACCGCG CCACCCACGG CCCCAATGGC
1141 TACGCCAACG GCCTTTCCCG CGGCGCCCAG GCCGCTCATG AGGTCGTCCA GACCCTTGAG
1201 GTAGGGCGGC AGCGGGTCGA CTACCTTGTC CTCCACGTAC TTTACCCGCT GCTTATACGA
1261 ATTGAACTCG CGCATGATCT CCTCGAGATC AAAAACGTTG CTGGAACGCA ATTCTTTCTG
1321 CGAGTAAAGT TCCAGTACCC TGAAGTCGGT GTTTTCCAGC GGGTCGATGT CTAGGGCGAT
1381 CATGCTGTCG ACGGTGGAGA TGCTGCTGAG GTCAATCATG CGTTTGAAGA GGTAGTCCAC
1441 GTACTCGTAG GCCGAGTTGC CGGCGATGAA GATCTTGAGG CTGGGAAGCT GACATTCCTC
1501 AGTGCGGTGG TTGCCCAACA GGATTTCGTT ATCCTCGCCC AGTTGACCGT ACTGCACGTA
1561 CGAGCTGTTG GCGAAATTAA AGATGACCAC TGGTCGTGAG TAGCAGCGTC CTGGCGATTC
1621 CTTCACATTC ATATCACGCA GCACCTTGAC GCTGGTTTGG TTAATGGTCA CGCAGCTGGC
1681 CAGACCCAGG ACATCACCCA TGAAACGCGC GGCAATCGGT TTGTTGTAGA TGGCCGAGAG
1741 AATAGCTGAC GGGTTGATCT TGCTAAGTTC CTTGAAGACC TCTAGGGTGC GCCGTTGATC
1801 CACACACCAG GCTTCTGCGA TTTCGGCCAG CGCCCGGTTG ATGTAACCGC GCAACGTGTC
1861 ATAGGTGAAC TGCACTGGG CGTAGACCAG ATTGTGCACC GACTCCATGT TGGATAAATG
1921 AGTTGCATTG TTGCCATCTG TACTTCTTTT GGTTCTATTA TGAGTAAGAT TCAGACTGGA
1981 GCGGTTGGCC AAACGTTCGA GTTCCACCAG AGATTTTGC TTGATACCTT GCCAGAACAC
2041 CACCAAACCA CCAGTGGTTT CAAAGACGGA CACGTTTCCA TATTTTCAT ATGTTTGATT
2101 GTATGAAGTA TTGAAAATCT GCTGTAACTT ATTTATGCC TCATCACGTA CACAGTCCAG
2161 CGCAGAGTCG GACATGTTCA CCTCTTGCTT CTTAGATAAG AAAGTGGCGG TCATTTTGGC
2221 AGAAGAAAAG TGATACGAGT CCTCGGCTTC GGAACGAATG GTGCGTTCCG AGGCTTCCCA
2281 GAAAGTGAGT TGACAAGTAA CATTCTTCTC GTCCTGTATA TCCCAGGAGA TCACTGAGTC
2341 CGCACGTTCA AGAAAGCCA CCAACCTGTG GGTCTCTAAC GCAGAATTCG GTCTTTCAAA
2401 GTCGGAGACG ATAGTGTAGT TCGGAAAAAT GAAAAACTTG TCGGCGTTTT CTCCAAAATA
2461 GCTGGCATTG CGATTAGTTC CGTTGTAGAA AGGAGAAATG TCAACCACAT CACCCGTGGA
2521 AGTTGCGAAA AAATGATAGG GATACTTGGA GCGCGCAGTA GTGATGGTCA CCATACAATT
2581 CAGATTACAG GTCTACGAT AGAGCCAGGT GCTGCCGCGG CTGTGCCATT GATCCTTGAC
2641 CGTCACGTAA CGGGTACTGT GGGTGTTGGA ATAATCGTCG GCATTAATT GCATGGTTTT
2701 GTTTTCATAG CTGTCCCTAT GATAAGCCAC GAAAACCGTG CCTGCTATAA CGCGGCTGTA
2761 GGAACTGTAG CACTGACTGT GACTGTTGAT ATGATGAATC TCCCACATAG GAGGCGCCAC
2821 GTATTCCGTG TTGCTGCCCA GCAGATAAGT GGTGTGGATG TAAGCGTAGC TACGACGAAA
2881 CGTCAAAACC TTCTGGTAGA CTCGTACCTT AAAGGTGTGC GCGACGATGT TGCGTTTGTA
2941 GACCACCATG ATGCCCTCGT CCAGGTCTTC ATTGATGGGC TTCATCGAGG TGCAGACGAT
3001 ATTACGTTCA AAGCGAATAA GATCCGTACC CTGAGCCATA AACACACGC GATAGGGGTA
3061 CTTGGTGGTG TTGACCCCCA CCACATCTCC GTACTTGAGG GTAGTGTTGT AGATGGTCTC
```

```
3121 GTTAACACCA TGGCTGACCG TTTGGGAAGA AGTTACGCGT TGAGAGACTG AACCGGATCG
3181 AGAATGAGCA GCAGACGTCG TATGAGAGGA ATGGTGACTG TGAGTAGCAG AAGTTCCACG
3241 AGTAGAAGAT GAGGAAACCG CAGCACCCAG ACAGACGATA CACAAGTTAA CGCAGACTAC
3301 CAGGCACCAG ATCCTGGATT CCATTACGAT ACAAACTTAA CGGATATCGC GATAATGAAA
3361 TAATTTATGA TTATTTCTCG CTTTCAATTT AACACAACCC TCAAGAACCT TTGTATTTAT
3421 TTTCACTTTT AAGTATAGAA TAAAGAAGCT TGCATGCCAC GCGTCTCGAG GGCCCCTGCA
3481 GGTCGACTCT AGAGGATCCT GATCCTTTTT CTGGGTAAGT AATACGTCAA GGAGAAAACG
3541 AAACGATCTG TAGTTAGCGG CCGCCTAATT AACTAATATT ATATTTTTA TCTAAAAAAC
3601 TAAAAATAAA CATTGATTAA ATTTTAATAT AATACTTAAA AATGGATGTT GTGTCGTTAG
3661 ATAAACCGTT TATGTATTTT GAGGAAATTG ATAATGAGTT AGATTACGAA CCAGAAAGTG
3721 CAAATGAGGT CGCAAAAAAA CTGCCGTATC AAGGACAGTT AAAACTATTA CTAGGAGAAT
3781 TATTTTTTCT TAGTAAGTTA CAGCGACACG GTATATTAGA TGGTGCCACC GTAGTGTATA
3841 TAGGATCGGC TCCTGGTACA CATATACGTT ATTTGAGAGA TCATTTCTAT AATTTAGGAA
3901 TGATTATCAA ATGGATGCTA ATTGACGGAC GCCATCATGA TCCTATTTTA AATGGATTGC
3961 GTGATGTGAC TCTAGTGACT CGGTTCGTTG ATGAGGAATA TCTACGATCC ATCAAAAAAC
4021 AACTGCATCC TTCTAAGATT ATTTTAATTT CTGATGTGAG ATCCAAACGA GGAGGAAATG
4081 AACCTAGTAC GGCGGATTTA CTAAGTAATT ACGCTCTACA AAATGTCATG ATTAGTATTT
4141 TAAACCCCGT GGCGTCTAGT CTTAAATGGA GATGCCCGTT TCCAGATCAA TGGATCAAGG
4201 ACTTTTATAT CCCACACGGT AATAAAATGT TACAACCTTT TGCTCCTTCA TATTCAGCTG
```

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTATG AATACTACTA ATCACGAAGA ATGCAGTAAA ACATATGATA
1501 CAAACATGTT AACAGTTTTA AAAGCCATTA GTAATAAACA GTACAATATA ATTAAGTCTT
1561 TACTTAAAAA AGATATTAAT GTTAATAGAT TATTAACTAG TTATTCTAAC GAAATATATA
1621 AACATTTAGA CATTACATTA TGTAATATAC TTATAGAACG TGCAGCAGAC ATAAACATTA
1681 TAGATAAGAA CAATCGTACA CCGTTGTTTT ATGCGGTAAA GAATAATGAT TATGATATGG
1741 TTAAACTCCT ATTAAAAAAT GGCGCGAATG TAAATTTACA AGATAGTATA GGATATTCAT
1801 GTCTTCACAT CGCAGGTATA CATAATAGTA ACATAGAAAT AGTAGATGCA TTGATATCAT
1861 ACAAACCAGA TTTAAACTCC CGCGATTGGG TAGGTAGAAC ACCGCTACAT ATCTTCGTGA
1921 TAGAATCTAA CTTTGAAGCT GTGAAATTAT TATTAAAGTC AGGTGCATAT GTAGGTTTGA
1981 AAGACAAATG TAAGCATTTT CCTATACACC ATTCTGTAAT GAAATTAGAT CACTTAATAT
2041 CAGGATTGTT ATTAAAATAT GGAGCAAATC CAAATACAAT TAACGGCAAT GGAAAAACAT
2101 TATTAAGCAT TGCTGTAACA TCTAATAATA CACTACTGGT AGAACAGCTG CTGTTATATG
2161 GAGCAGAAGT TAATAATGAT GGTTATGATG TTCCAGCTCC TATTATATCC GCTGTCAGTG
2221 TTAACAATTA TGATATTGTT AAGATACTGA TACATAATGG TGCGAATATA AATGTATCCA
2281 CGGAAGATGG TAGAACGTCT TTACATACAG CTATGTTTTG GAATAACGCT AAAATAATAG
2341 ATGAGTTGCT TAACTATGGA AGTGACATAA ACAGCGTAGA TACTTATGGT AGAACTCCGT
2401 TATCTTGTTA TCGTAGCTTA AGTTATGATA TCGCTACTAA ACTAATATCA CGTATCATTA
2461 TAACAGATGT CTATCGTGAA GCACCAGTAA ATATCAGCGG ATTTATAATT AATTTAAAAA
2521 CTATAGAAAA TAATGATATA TTCAAATTAA TTAAAGATGA TTGTATTAAA GAGATAAACA
2581 TACTTAAAAG TATAACCCTT AATAAATTTC ATTCATCTGA CATATTTATA CGATATAATA
2641 CTGATATATG TTTATTAACG AGATTTATTC AACATCCAAA GATAATAGAA CTAGACAAAA
2701 AACTCTACGC TTATAAATCT ATAGTCAACG AGAGAAAAAT CAAAGCTACT TACAGGTATT
2761 ATCAAATAAA AAAAGTATTA ACTGTACTAC CTTTTTCAGG ATATTTCTCT ATATTGCCGT
2821 TTGATGTGTT AGTATATATA CTTGAATTCA TCTATGATAA TAATATGTTG GTACTTATGA
2881 GAGCGTTATC ATTAAATGA AATAAAAAGC ATACAAGCTA TTGCTTCGCT ATCGTTACAA
2941 AATGGCAGGA ATTTGTGTA AACTAAGCCA CATACTTGCC AATGAAAAAA ATAGTAGAAA
3001 GGATACTATT TTAATGGGAT TAGATGTTAA GGTTCCTTGG GATTATAGTA ACTGGGCATC
```

FIG. 14B

```
3061 TGTTAACTTT TACGACGTTA GGTTAGATAC TGATGTTACA GATTATAATA ATGTTACAAT
3121 AAAATACATG ACAGGATGTG ATATTTTCC TCATATAACT CTTGGAATAG CAAATATGGA
3181 TCAATGTGAT AGATTTGAAA ATTTCAAAAA GCAAATAACT GATCAAGATT TACAGACTAT
3241 TTCTATAGTC TGTAAAGAAG AGATGTGTTT TCCTCAGAGT AACGCCTCTA AACAGTTGGG
3301 AGCGAAAGGA TGCGCTGTAG TTATGAAACT GGAGGTATCT GATGAACTTA GAGCCCTAAG
3361 AAATGTTCTG CTGAATGCGG TACCCTGTTC GAAGGACGTG TTTGGTGATA TCACAGTAGA
3421 TAATCCGTGG AATCCTCACA TAACAGTAGG ATATGTTAAG GAGGACGATG TCGAAAACAA
3481 GAAACGCCTA ATGGAGTGCA TGTCCAAGTT TAGGGGGCAA GAAATACAAG TTCTAGGATG
3541 GTATTAATAA GTATCTAAGT ATTTGGTATA ATTTATTAAA TAGTATAATT ATAACAAATA
3601 ATAAATAACA TGATAACGGT TTTTATTAGA ATAAAATAGA GATAATATCA TAATGATATA
3661 TAATACTTCA TTACCAGAAA TGAGTAATGG AAGACTTATA AATGAACTGC ATAAAGCTAT
3721 AAGGTATAGA GATATAAATT TAGTAAGGTA TATACTTAAA AAATGCAAAT ACAATAACGT
3781 AAATATACTA TCAACGTCTT TGTATTTAGC CGTAAGTATT TCTGATATAG AAATGGTAAA
3841 ATTATTACTA GAACACGGTG CCGATATTTT AAAATGTAAA AATCCTCCTC TTCATAAAGC
3901 TGCTAGTTTA GATAATACAG AAATTGCTAA ACTACTAATA GATTCTGGCG CTGACATAGA
3961 ACAGATACAT TCTGGAAATA GTCCGTTATA TATTTCTGTA TATAGAAACA ATAAGTCATT
4021 AACTAGATAT TTATTAAAAA AAGGTGTTAA TTGTAATAGA TTCTTTCTAA ATTATTACGA
4081 TGTACTGTAT GATAAGATAT CTGATGATAT GTATAAAATA TTTATAGATT TTAATATTGA
4141 TCTTAATATA CAAACTAGAA ATTTTGAAAC TCCGTTACAT TACGCTATAA AGTATAAGAA
4201 TATAGATTTA ATTAGGATAT TGTTAGATAA TAGTATTAAA ATAGATAAAA GTTTATTTTT
4261 GCATAAACAG TATCTCATAA AGGCACTTAA AAATAATTGT AGTTACGATA TAATAGCGTT
4321 ACTTATAAAT CACGGAGTGC CTATAAACGA ACAAGATGAT TTAGGTAAAA CCCCATTACA
4381 TCATTCGGTA ATTAATAGAA GAAAAGATGT AACAGCACTT CTGTTAAATC TAGGAGCTGA
4441 TATAAACGTA ATAGATGACT GTATGGGCAG TCCCTTACAT TACGCTGTTT CACGTAACGA
4501 TATCGAAACA ACAAAGACAC TTTTAGAAAG AGGATCTAAT GTTAATGTGG TTAATAATCA
4561 TATAGATACC GTTCTAAATA TAGCTGTTGC ATCTAAAAAC AAAACTATAG TAAACTTATT
4621 ACTGAAGTAC GGTACTGATA CAAAGTTGGT AGGATTAGAT AAACATGTTA TTCACATAGC
4681 TATAGAAATG AAAGATATTA ATATACTGAA TGCGATCTTA TTATATGGTT GCTATGTAAA
4741 CGTCTATAAT CATAAAGGTT TCACTCCTCT ATACATGGCA GTTAGTTCTA TGAAAACAGA
4801 ATTTGTTAAA CTCTTACTTG ACCACGGTGC TTACGTAAAT GCTAAAGCTA AGTTATCTGG
4861 AAATACTCCT TTACATAAAG CTATGTTATC TAATAGTTTT AATAATATAA AATTACTTTT
4921 ATCTTATAAC GCCGACTATA ATTCTCTAAA TAATCACGGT AATACGCCTC TAACTTGTGT
4981 TAGCTTTTTA GATGACAAGA TAGCTATTAT GATAATATCT AAAATGATGT TAGAAATATC
5041 TAAAAATCCT GAAATAGCTA ATTCAGAAGG TTTTATAGTA AACATGGAAC ATATAAACAG
5101 TAATAAAAGA CTACTATCTA TAAAGAATC ATGCGAAAAA GAACTAGATG TTATAACACA
5161 TATAAAGTTA AATTCTATAT ATTCTTTTAA TATCTTTCTT GACAATAACA TAGATCTTAT
5221 GGTAAAGTTC GTAACTAATC CTAGAGTTAA TAAGATACCT GCATGTATAC GTATATATAG
5281 GGAATTAATA CGGAAAAATA AATCATTAGC TTTTCATAGA CATCAGCTAA TAGTTAAAGC
5341 TGTAAAAGAG AGTAAGAATC TAGGAATAAT AGGTAGGTTA CCTATAGATA TCAAACATAT
5401 AATAATGGAA CTATTAAGTA ATAATGATTT ACATTCTGTT ATCACCAGCT GTTGTAACCC
5461 AGTAGTATAA AGTGATTTA TTCAATTACG AAGATAAACA TTAAATTTGT TAACAGATAT
5521 GAGTTATGAG TATTTAACTA AAGTTACTTT AGGTACAAAT AAAATATTAT GTAATATAAT
5581 AGAAAATTAT CTTGAGTCTT CATTTCCATC ACCGTCTAAA TTTATTATTA AAACCTTATT
5641 ATATAAGGCT GTTGAGTTTA GAAATGTAAA TGCTGTAAAA AAAATATTAC AGAATGATAT
5701 TGAATATGTT AAAGTAGATA GTCATGGTGT CTCGCCTTTA CATATTATAG CTATGCCTTC
5761 AAATTTTCT CTCATAGACG CTGACATGTA TTCAGAATTT AATGAAATTA GTAATAGACT
5821 TCAAAAATCT AAAGATAGTA ACGAATTTCA ACGAGTTAGT CTACTAAGGA CAATTATAGA
5881 ATATGGTAAT GATAGTGATA TTAATAAGTG TCTAACATTA GTAAAACGG ATATACAGAG
5941 TAACGAAGAG ATAGATATTA TAGATCTTTT GATAAATAAA GGAATAGATA TAAATATTAA
6001 AGACGATTTA GGAAACACAG CTTTGCATTA CTCGTGTGAT TATGCTAAGG GATCAAAGAT
6061 AGCTAAAAAG TTACTAGATT GTGGAGCAGA TCCTAACATA GTTAATGATT TAGGTGTTAC
```

FIG.14C

```
6121 ACCACTAGCG TGTGCCGTTA ATACTTGCAA CGAGATACTA GTAGATATTC TGTTAAATAA
6181 TGATGCGAAT CCTGATTCAT CTTCCTCATA TTTTTTAGGT ACTAATGTGT TACATACAGC
6241 CGTAGGTACC GGTAATATAG ATATTGTAAG ATCTTTACTT ACGGCTGGTG CCAATCCTAA
6301 TGTAGGAGAT AAATCTGGAG TTACTCCTTT GCACGTTGCT GCAGCTGATA AAGACAGTTA
6361 TCTGTTAATG GAGATGCTAC TAGATAGCGG GGCAGATCCA AATATAAAAT GCGCAAACGG
6421 TTTTACTCCT TTGTTTAATG CAGTATATGA TCATAACCGT ATAAAGTTAT TATTTCTTTA
6481 CGGGGCTGAT ATCAATATTA CTGACTCTTA CGGAAATACT CCTCTTACTT ATATGACTAA
6541 TTTTGATAAT AAATATGTAA ATTCAATAAT TATCTTACAA ATATATCTAC TTAAAAAAGA
6601 ATATAACGAT GAAAGATTGT TTCCACCTGG TATGATAAAA AATTTAAACT TTATAGAATC
6661 AAACGATAGT CTTAAAGTTA TAGCTAAAAA GTGTAATTCG TTAATACGCT ATAAGAAAAA
6721 TAAAGACATA GATGCAGATA ACGTATTATT GGAGCTTTTA GAGGAAGAGG AAGAAGATGA
6781 AATAGACAGA TGGCATACTA CATGTAAAAT ATCTTAAATA GTAATTAAAT CATTGAAATA
6841 TTAACTTACA AGATGATCGA GGTCACTTAT TATACTCTTT AATAATGGGT ACAAAGAGTA
6901 TTCATACGTT AGTTAAATCT AACGATGTAA TACGTGTTCG TGAATTAATA AAGGATGATA
6961 GATGTTTGAT AAATAAAAGA AATAGAAGAA ATCAGTCACC TGTATATATA GCTATATACA
7021 AAGGACTTTA TGAAATGACT GAAATGTTAT TGCTAAATAA TGCAAGTCTA GATACTAAAA
7081 TACCTTCTTT AATTATAGCA GCTAAAAATA ATGACTTACC TATGATAAAA TTATTGATAC
7141 AATACGGGGC AAAATTAAAT GATATTTATT TAAGGGACAC AGCATTAATG ATAGCTCTCA
7201 GAAATGGTTA CCTAGATATA GCTGAATATT TACTTTCATT AGGAGCAGAA TTTGTTAAAT
7261 ACAGACATAA GGTAATATAT AAATATCTAT CAAAAGATGC GTATGAATTA CTTTTTAGAT
7321 TTAATTATGA CGTTAATATA ATAGATTGAG A
```

FIG. 15A

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTTAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTTGA CTAATTAGCT ATAAAAACCC GGGCTGCAGG AATTCCTCGA
1501 GACGCGTGGC ATGCAAGCTT ATAAAAATCA CAAGTCTCTG TCACTTTTTT TGTCTAGTTT
1561 TTTTTTCTCC TCTTGGTTCA GACGTTCTCT TCTTCGTCGG AGTCTTTCAA GTGTCGGTAG
1621 CCGTTTTTGC GGTGTCGCAG TCGGTCTAGC AGGTTGGGCT TCTGTCCCTT GTCCTGCGTG
1681 CCAGTCTGTC CGTCCAAAGA ATCTGTACCG TTCTCGTGCG CTCGCTGCTC TGCGTCCAGA
1741 CGGACCAGGG CCAGAAGCAT CTGGTAAGCC TGCTCGTTGG TGTAAGGCGG AGCCGCCGTG
1801 GATGCATCAG ACGACGGTGG TCCCGGTCCT TTGCGACCAG AATTATAAAC ACTTTCCTCG
1861 TAGGAAGGCG GAGCCTGTAA CGACGTGTCT TTGGTGTTGC CCGACGTCAC GGTGGTCCCG
1921 TCGGCGGACA CCAGATAGGG AAAGAGGTTC TGCAGCGGCT GCATGCAGAG ACGCCGCTGT
1981 CGAGTATAGA TCAAATAAAT GATAATGACG ACGGCTATGG CCACGAGGAT GATGGTGAAG
2041 GCTCCGAAGG GGTTTTGAG GAAGGTGGCA ACGCCTTCGA CCACGGAGGC CACCGCGCCA
2101 CCCACGGCCC CAATGGCTAC GCCAACGGCC TTTCCGCGG CGCCCAGGCC GCTCATGAGG
2161 TCGTCCAGAC CCTTGAGGTA GGGCGGCAGC GGGTCGACTA CCTTGTCCTC CACGTACTTT
2221 ACCCGCTGCT TATACGAATT GAACTCGCGC ATGATCTCCT CGAGATCAAA AACGTTGCTG
2281 GAACGCAATT CTTTCTGCGA GTAAAGTTCC AGTACCCTGA AGTCGGTGTT TTCCAGCGGG
2341 TCGATGTCTA GGGCGATCAT GCTGTCGACG GTGGAGATGC TGCTGAGGTC AATCATGCGT
2401 TTGAAGAGGT AGTCCACGTA CTCGTAGGCC GAGTTGCCGG CGATGAAGAT CTTGAGGCTG
2461 GGAAGCTGAC ATTCCTCAGT GCGGTGGTTG CCCAACAGGA TTTCGTTATC CTCGCCCAGT
2521 TGACCGTACT GCACGTACGA GCTGTTGGCG AAATTAAAGA TGACCACTGG TCGTGAGTAG
2581 CAGCGTCCTG GCGATTCCTT CACATTCATA TCACGCAGCA CCTTGACGCT GGTTTGGTTA
2641 ATGGTCACGC AGCTGGCCAG ACCAGGACA TCACCCATGA AACGCGCGGC AATCGGTTTG
2701 TTGTAGATGG CCGAGAGAAT AGCTGACGGG TTGATCTTGC TAAGTTCCTT GAAGACCTCT
2761 AGGGTGCGCC GTTGATCCAC ACACCAGGCT TCTGCGATTT CGGCCAGCGC CCGGTTGATG
2821 TAACCGCGCA ACGTGTCATA GGTGAACTGC AGCTGGGCGT AGACCAGATT GTGCACCGAC
2881 TCCATGTTGG ATAAATGAGT TGCATTGTTG CCATCTGTAC TTCTTTTGGT TCTATTATGA
2941 GTAAGATTCA GACTGGAGCG GTTGGCCAAA CGTTCGAGTT CCACCAGAGA TTTTTGCTTG
3001 ATACCTTGCC AGAACACCAC CAAACCACCA GTGGTTTCAA AGACGGACAC GTTTCCATAT
3061 TTTTCATATG TTTGATTGTA TGAAGTATTG AAAATCTGCT GTAACTTATT TATGGCCTCA
```

FIG. 15B

```
3121 TCACGTACAC AGTCCAGCGC AGAGTCGGAC ATGTTCACCT CTTGCTTCTT AGATAAGAAA
3181 GTGGCGGTCA TTTTGGCAGA AGAAAAGTGA TACGAGTCCT CGGCTTCGGA ACGAATGGTG
3241 CGTTCCGAGG CTTCCCAGAA AGTGAGTTGA CAAGTAACAT TCTTCTCGTC CTGTATATCC
3301 CAGGAGATCA CTGAGTCCGC ACGTTCAAGA AAAGCCACCA ACCTGTGGGT CTCTAACGCA
3361 GAATTCGGTC TTTCAAAGTC GGAGACGATA GTGTAGTTCG GAAAAATGAA AAACTTGTCG
3421 GCGTTTTCTC CAAAATAGCT GGCATTGCGA TTAGTTCCGT TGTAGAAAGG AGAAATGTCA
3481 ACCACATCAC CCGTGGAAGT TGCGAAAAAA TGATAGGGAT ACTTGGAGCG CGCAGTAGTG
3541 ATGGTCACCA TACAATTCAG ATTACAGGTC TCACGATAGA GCCAGGTGCT GCCGCGGCTG
3601 TGCCATTGAT CCTTGACCGT CACGTAACGG GTACTGTGGG TGTTGGAATA ATCGTCGGGC
3661 ATTAATTGCA TGGTTTTGTT TTCATAGCTG TCCCTATGAT AAGCCACGAA AACCGTGCCT
3721 GCTATAACGC GGCTGTAGGA ACTGTAGCAC TGACTGTGAC TGTTGATATG ATGAATCTCC
3781 CACATAGGAG GCGCCACGTA TTCCGTGTTG CTGCCCAGCA GATAAGTGGT GTGGATGTAA
3841 GCGTAGCTAC GACGAAACGT CAAAACCTTC TGGTAGACTC GTACCTTAAA GGTGTGCGCG
3901 ACGATGTTGC GTTTGTAGAC CACCATGATG CCCTCGTCCA GGTCTTCATT GATGGGCTTC
3961 ATCGAGGTGC AGACGATATT ACGTTCAAAG CGAATAAGAT CCGTACCCTG AGCCATAGAA
4021 CACACGCGAT AGGGGTACTT GGTGGTGTTG ACCCCACCA CATCTCCGTA CTTGAGGGTA
4081 GTGTTGTAGA TGGTCTCGTT AACACCATGG CTGACCGTTT GGGAAGAAGT TACGCGTTGA
4141 GAGACTGAAC CGGATCGAGA ATGAGCAGCA GACGTCGTAT GAGAGGAATG GTGACTGTGA
4201 GTAGCAGAAG TTCCAGAGT AGAAGATGAG GAAACCGCAG CACCCAGACA GACGATACAC
4261 AAGTTAACGC AGACTACCAG GCACCAGATC CTGGATTCCA TTACGATACA AACTTAACGG
4321 ATATCGCGAT AATGAAATAA TTTATGATTA TTTCTCGCTT TCAATTTAAC ACAACCCTCA
4381 AGAACCTTTG TATTTATTTT CACTTTTTAA GTATAGAATA AAGAAGCTCT AATTAATTAA
4441 GCTACAAATA GTTTCGTTTT CACCTTGTCT AATAACTAAT TAATTAACCC GGATCCCGAT
4501 TTTTATGACT AGTTAATCAA ATAAAAGCA TACAAGCTAT TGCTTCGCTA TCGTTACAAA
4561 ATGGCAGGAA TTTTGTGTAA ACTAAGCCAC ATACTTGCCA ATGAAAAAAA TAGTAGAAAG
4621 GATACTATTT TAATGGGATT AGATGTTAAG GTTCCTTGGG ATTATAGTAA CTGGGCATCT
4681 GTTAACTTTT ACGACGTTAG GTTAGATACT GATGTTACAG ATTATAATAA TGTTACAATA
4741 AAATACATGA CAGGATGTGA TATTTTTCCT CATATAACTC TTGGAATAGC AAATATGGAT
4801 CAATGTGATA GATTTGAAAA TTTCAAAAAG CAAATAACTG ATCAAGATTT ACAGACTATT
4861 TCTATAGTCT GTAAAGAAGA GATGTGTTTT CCTCAGAGTA ACGCCTCTAA ACAGTTGGGA
4921 GCGAAAGGAT GCGCTGTAGT TATGAAACTG GAGGTATCTG ATGAACTTAG AGCCCTAAGA
4981 AATGTTCTGC TGAATGCGGT ACCCTGTTCG AAGGACGTGT TTGGTGATAT CACAGTAGAT
5041 AATCCGTGGA ATCCTCACAT AACAGTAGGA TATGTTAAGG AGGACGATGT CGAAAACAAG
5101 AAACGCCTAA TGGAGTGCAT GTCCAAGTTT AGGGGCAAG AAATACAAGT TCTAGGATGG
5161 TATTAATAAG TATCTAAGTA TTTGGTATAA TTTATTAAAT AGTATAATTA TAACAAATAA
5221 TAAATAACAT GATAACGGTT TTTATTGAAA TAAAATAGAG ATAATATCAT AATGATATAT
5281 AATACTTCAT TACCAGAAAT GAGTAATGGA AGACTTATAA ATGAACTGCA TAAAGCTATA
5341 AGGTATAGAG ATATAAATTT AGTAAGGTAT ATACTTAAAA AATGCAAATA CAATAACGTA
5401 AATATACTAT CAACGTCTTT GTATTTAGCC GTAAGTATTT CTGATATAGA AATGGTAAAA
5461 TTATTACTAG AACACGGTGC CGATATTTTA AAATGTAAAA ATCCTCCTCT TCATAAAGCT
5521 GCTAGTTTAG ATAATACAGA AATTGCTAAA CTACTAATAG ATTCTGGCGC TGACATAGAA
5581 CAGATACATT CTGGAAATAG TCCGTTATAT ATTTCTGTAT ATAGAAACAA TAAGTCATTA
5641 ACTAGATATT TATTAAAAA AGGTGTTAAT TGTAATGAT TCTTTCTAAA TTATTACGAT
5701 GTACTGTATG ATAAGATATC TGATGATATG TATAAAATAT TTATAGATTT TAATATTGAT
5761 CTTAATATAC AAACTAGAAA TTTTGAAACT CCGTTACATT ACGCTATAAA GTATAAGAAT
5821 ATAGATTTAA TTAGGATATT GTTAGATAAT AGTATTAAAA TAGATAAAAG TTTATTTTG
5881 CATAAACAGT ATCTCATAAA GGCACTTAAA AATAATTGTA GTTACGATAT AATAGCGTTA
5941 CTTATAAATC ACGGAGTGCC TATAAACGAA CAAGATGATT TAGGTAAAAC CCCATTACAT
6001 CATTCGGTAA TTAATAGAAG AAAAGATGTA ACAGCACTTC TGTTAAATCT AGGAGCTGAT
6061 ATAAACGTAA TAGATGACTG TATGGGCAGT CCCTTACATT ACGCTGTTTC ACGTAACGAT
6121 ATCGAAACAA CAAAGACACT TTTAGAAAGA GGATCTAATG TTAATGTGGT TAATAATCAT
```

```
6181 ATAGATACCG TTCTAAATAT AGCTGTTGCA TCTAAAAACA AAACTATAGT AAACTTATTA
6241 CTGAAGTACG GTACTGATAC AAAGTTGGTA GGATTAGATA AACATGTTAT TCACATAGCT
6301 ATAGAAATGA AAGATATTAA TATACTGAAT GCGATCTTAT TATATGGTTG CTATGTAAAC
6361 GTCTATAATC ATAAAGGTTT CACTCCTCTA TACATGGCAG TTAGTTCTAT GAAAACAGAA
6421 TTTGTTAAAC TCTTACTTGA CCACGGTGCT TACGTAAATG CTAAAGCTAA GTTATCTGGA
6481 AATACTCCTT TACATAAAGC TATGTTATCT AATAGTTTTA ATAATATAAA ATTACTTTTA
6541 TCTTATAACG CCGACTATAA TTCTCTAAAT AATCACGGTA ATACGCCTCT AACTTGTGTT
6601 AGCTTTTTAG ATGACAAGAT AGCTATTATG ATAATATCTA AAATGATGTT AGAAATATCT
6661 AAAAATCCTG AAATAGCTAA TTCAGAAGGT TTTATAGTAA ACATGGAACA TATAAACAGT
6721 AATAAAAGAC TACTATCTAT AAAAGAATCA TGCGAAAAAG AACTAGATGT TATAACACAT
6781 ATAAAGTTAA ATTCTATATA TTCTTTTAAT ATCTTTCTTG ACAATAACAT AGATCTTATG
6841 GTAAAGTTCG TAACTAATCC TAGAGTTAAT AAGATACCTG CATGTATACG TATATATAGG
6901 GAATTAATAC GGAAAAATAA ATCATTAGCT TTTCATAGAC ATCAGCTAAT AGTTAAAGCT
6961 GTAAAAGAGA GTAAGAATCT AGGAATAATA GGTAGGTTAC CTATAGATAT CAAACATATA
7021 ATAATGGAAC TATTAAGTAA TAATGATTTA CATTCTGTTA TCACCAGCTG TTGTAACCCA
7081 GTAGTATAAA G
```

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGTCT CTGACACTTT TTTTGTCTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAAGAGG TTCTGCAGCG GCTGCATGCA GAGACGCCGC
 901 TGTCGAGTAT AGATCAAATA AATGATAATG ACGACGGCTA TGGCCACGAG GATGATGGTG
 961 AAGGCTCCGA AGGGGTTTTT GAGGAAGGTG GCAACGCCTT CGACCACGGA GGCCACGGCG
1021 CCACCCACGG CCCCAATGGC TACGCCAACG GCCTTTCCCG CGGCGCCCAG GCCGCTCATG
1081 AGGTCGTCCA GACCCTTGAG GTAGGCGGC AGCGGGTCGA CTACCTTGTC CTCCACGTAC
1141 TTTACCCGCT GCTTATACGA ATTGAACTCG CGCATGATCT CCTCGAGATC AAAAACGTTG
1201 CTGGAACGCA ATTCTTTCTG CGAGTAAAGT TCCAGTACCC TGAAGTCGGT GTTTTCCAGC
1261 GGGTCGATGT CTAGGGCGAT CATGCTGTCG ACGGTGGAGA TGCTGCTGAG GTCAATCATG
1321 CGTTTGAAGA GGTAGTCCAC GTACTCGTAG GCCGAGTTGC CGGCGATGAA GATCTTGAGG
1381 CTGGGAAGCT GACATTCCTC AGTGCGGTGG TTGCCCAACA GGATTTCGTT ATCCTCGCCC
1441 AGTTGACCGT ACTGCACGTA CGAGCTGTTG GCGAAATTAA AGATGACCAC TGGTCGTGAG
1501 TAGCAGCGTC CTGGCGATTC CTTCACATTC ATATCACGCA GCACCTTGAC GCTGGTTTGG
1561 TTAATGGTCA TCGCAGCTGG CAGACCCAGG ACATCACCCA TGAAACGCGC GGCAATCGGT
1621 TTGTTGTAGA TGGCCGAGAG AATAGCTGAC GGGTTGATCT TGCTAAGTTC CTTGAAGACC
1681 TCTAGGGTGC GCCGTTGATC CACACACCAG GCTTCTGCGA TTTCGGCCAG CGCCCGGTTG
1741 ATGTAACCGC GCAACGTGTC ATAGGTGAAC TGCAGCTGGG CGTAGACCAG ATTGTGCACC
1801 GACTCCATGT TGGATAAATG AGTTGCATTG TTGCCATCTG TACTTCTTTT GGTTCTATTA
1861 TGAGTAAGAT TCAGACTGGA GCGGTTGGCC AAACGTTCGA GTTCCACCAG AGATTTTTGC
1921 TTGATACCTT GCCAGAACAC CACCAAACCA CCAGTGGTTT CAAAGACGGA CACGTTTCCA
1981 TATTTTCAT ATGTTTGATT GTATGAAGTA TTGAAAATCT GCTGTAACTT ATTTATGGCC
2041 TCATCACGTA CACAGTCCAG CGCAGAGTCG GACATGTTCA CCTCTTGCTT CTTAGATAAG
2101 AAAGTGGCGG TCATTTTGGC AGAAGAAAG TGATACGAGT CCTCGGCTTC GGAACGAATG
2161 GTGCGTTCCG AGGCTTCCCA GAAAGTGAGT TGACAAGTAA CATTCTTCTC GTCCTGTATA
2221 TCCCAGGAGA TCACTGAGTC CGCACGTTCA AGAAAGCCA CCAACCTGTG GGTCTCTAAC
2281 GCAGAATTCG GTCTTTCAAA GTCGGAGACG ATAGTGTAGT TCGAAAAAT GAAAACTTG
2341 TCGGCGTTTT CTCCAAAATA GCTGGCATTG CGATTAGTTC CGTTGTAGAA AGGAGAAATG
2401 TCAACCACAT CACCCGTGGA AGTTGCGAAA AATGATAGG GATACTTGGA GCGCGCAGTA
2461 GTGATGGTCA CCATACAATT CAGATTACAG GTCTCACGAT AGAGCCAGGT GCTGCCGCGG
2521 CTGTGCCATT GATCCTTGAC CGTCACGTAA CGGGTACTGT GGGTGTTGGA ATAATCGTCG
2581 GGCATTAATT GCATGGTTTT GTTTTCATAG CTGTCCCTAT GATAAGCCAC GAAAACCGTG
2641 CCTGCTATAA CGCGGCTGTA GGAACTGTAG CACTGACTGT GACTGTTGAT ATGATGAATC
2701 TCCCACATAG GAGGCGCCAC GTATTCCGTG TTGCTGCCCA GCAGATAAGT GGTGTGGATG
2761 TAAGCGTAGC TACGACGAAA CGTCAAAACC TTCTGGTAGA CTCGTACCTT AAAGGTGTGC
2821 GCGACGATGT TGCGTTTGTA GACCACCATG ATGCCCTCGT CCAGGTCTTC ATTGATGGGC
2881 TTCATCGAGG TGCAGACGAT ATTACGTTCA AAGCGAATAA GATCCGTACC CTGAGCCATA
2941 GAACACACGC GATAGGGTA CTTGGTGGTG TTGACCCCCA CCACATCTCC GTACTTGAGG
3001 GTAGTGTTGT AGATGGTCTC GTTAACACCA TGGCTGACCG TTTGGGAAGA AGTTACGCGT
3061 TGAGAGACTG AACCGGATCG AGAATGAGCA GCAGACGTCG TATGAGAGGA ATGGTGACTG
```

```
3121 TGAGTAGCAG AAGTTCCACG AGTAGAAGAT GAGGAAACCG CAGCACCCAG ACAGACGATA
3181 CACAAGTTAA CGCAGACTAC CAGGCACCAG ATCCTGGATT CCATTACGAT ACAAACTTAA
3241 CGGATATCGC GATAATGAAA TAATTTATGA TTATTTCTCG CTTTCAATTT AACACAACCC
3301 TCAAGAACCT TTGTATTTAT TTTCACTTTT TAAGTATAGA ATAAAGAAGC TGGGAATCGA
3361 TTCGCGATAG CTGATTAGTT TTTGTTAACA AAAATGTGGG AGAATCTAAT TAGTTTTTCT
3421 TTACACAATT GACGTACATG AGTCTGAGTT CCTTGTTTTT GCTAATTATT TCATCCAATT
3481 TATTATTCTT GACGATATCG AGATCTTTTG TATAGGAGTC AGACTTGTAT TCAACATGCT
3541 TTTCTATAAT CATCTTAGTT ATTTCGGCAT CATCCAATAG TACATTTTCC AGATTAACAG
3601 AGTAGATATT AATGTCGTAT TGAACAGAG CCTGTAACAT CTCAATGTCT TTATTATCTA
3661 TAGCCAATTT AATGTCCGGA ATGAAGAGAA GGGAATTATT GGTGTTTGTC GACGTCATAT
3721 AGTCGAGCAA GAGAATCATC ATATCCACGT GTCCATTTTT TATAGTGGTG TGAATACAAC
3781 TAAGGAGAAT AGCCAGATCA AAAGTAGATG GTATTTCTGA AAGAAAGTAT GATACAATAC
3841 TTACATCATT AAGCATGACG GCATGATAAA ATGAAGTTTT CCATCCAGTT TTCCCATAGA
3901 ACATCAGTCT CCAATTTTTC TTAAACAGTT TCACCGTTTG CATGTTACCA CTATCAACCG
3961 CATAATACAA TGCGGTGTTT CCTTTGTCAT CAAATTGTGA ATCATCCATT CCACTGAATA
4021 GCAAAATCTT TACTATTTTG GTATCTTCTA ATGTGGCTGC CTGATGTAAT GGAAATTCAT
4081 TCTCTAGAAG ATTTTTCAAT GCTCCAGCGT TCAACAACGT ACATACTAGA CGCACGTTAT
4141 TATCAGCTAT TGCATAATAC AAGGCACTAT GTCCATGGAC ATCCGCCTTA AATGTATCTT
4201 TACTAGAGAG AAAGCTTTTC AGCTGCTTAG ACTTCCAAGT ATTAATTCGT GACAGATCCA
4261 TGTCTGAAAC GAGACGCTAA TTAGTGTATA TTTTTTCATT TTTTATAATT TTGTCATATT
4321 GCACCAGAAT TAATAATATC TCTAATAGAT CTAATTTAAT TTAATTTATA TAACTTATTT
4381 TTTGAATATA CTTTTAATTA ACAAAGAGT TAAGTTACTC ATATGGACGC CGTCCAGTCT
4441 GAACATCAAT CTTTTAGCC AGAGATATCA TAGCCGCTCT TAGAGTTTCA GCGTGATTTT
4501 CCAACCTAAA TAGAACTTCA TCGTTGCGTT TACAACACTT TTCTATTTGT TCAAACTTTG
4561 TTGTTACATT AGTAATCTTT TTTTCCAAAT TAGTTAGCCG TTGTTTGAGA GTTTCCTCAT
4621 TGTCGTCTTC ATCGGCTTTA ACAATTGCTT CGCGTTTAGC CTCCTGGCTG TTCTTATCAG
4681 CCTTTGTAGA AAAAAATTCA GTTGCTGGAA TTGCAAGATC GTCATCTCCG GGGAAAAGAG
4741 TTCCGTCCAT TTAAAGCCGC GGGAATTC
```

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC TCAGGGTACG
 301 GATCTTATTC GCTTTGAACG TAATATCGTC TGCACCTCGA TGAAGCCCAT CAATGAAGAC
 361 CTGGACGAGG GCATCATGGT GGTCTACAAA CGCAACATCG TCGCGCACAC CTTTAAGGTA
 421 CGAGTCTACC AGAAGGTTTT GACGTTTCGT CGTAGCTACG CTTACATCCA CACCACTTAT
 481 CTGCTGGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTGAACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA ATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCAAAAGA
1381 AGTACAGATG CAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTC TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TTCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG CAACCACCG CACTGAGGAA TGTCAGCTTC CCAGCCTCAA GATCTTCATC
1861 GCCGGCAACT CGGCCTACGA GTACGTGGAC TACCTCTTCA AACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTGCCGCC CTACCTCAAG GGTCTGGACG ACACTCGACA GCGGCGTCTC
2161 TGCATGCAGC CGCTGCAGAA CCTCTTTCCC TATCTGGTGT CCGCCGACGG GACCACCGTG
2221 ACGTCGGGCA ACACCAAAGA CACGTCGTTA CAGGCTCCGC CTTCCTACGA GGAAAGTGTT
2281 TATAATTCTG GTCGCAAAGG ACCGGGACCA CCGTCGTCTG ATGCATCCAC GGCGGCTCCG
2341 CCTTACACCA ACGAGCAGGC TTACCAGATG CTTCTGGCCC TGGTCCGTCT GGACGCAGAG
2401 CAGCGAGCGC ACGAGAACGG TACAGATTCT TTGGACGGAC AGACTGGCAC GCAGGACAAG
2461 GGACAGAAGC CCAACCTGCT AGACCGACTG CGACACCGCA AAAACGGCTA CCGACACTTG
2521 AAAGACTCCG ACGAAGAAGA GAACGTCTGA
```

FIG.18A

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGACT CTGTCACTTT TTTTGACTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAGAGG TTCTGCAGCG GCTGCATGCA GAGACGCCGC
 901 TGTCGAGTGT CGTCCAGACC CTTGAGGTAG GGCGGCAGCG GTCGACTAC CTTGTCCTCC
 961 ACGTACTTTA CCCGCTGCTT ATACGAATTG AACTCGCGCA TGATCTCCTC GAGATCAAAA
1021 ACGTTGCTGG AACGCAATTC TTTCTGCGAG TAAAGTTCCA GTACCCTGAA GTCGGTGTTT
1081 TCCAGCGGGT CGATGTCTAG GGCGATCATG CTGTCGACGG TGGAGATGCT GCTGAGGTCA
1141 ATCATGCGTT TGAAGAGGTA GTCCACGTAC TCGTAGGCCG AGTTGCCGGC GATGAAGATC
1201 TTGAGGCTGG GAAGCTGACA TTCCTCAGTG CGGTGGTTGC CAACAGGAT TTCGTTATCC
1261 TCGCCCAGTT GACCGTACTG CACGTACGAG CTGTTGGCGA AATTAAAGAT GACCACTGGT
1321 CGTGAGTAGC AGCGTCCTGG CGATTCCTTC ACATTCATAT CACGCAGCAC CTTGACGCTG
1381 GTTTGGTTAA TGGTCACGCA GCTGGCCAGA CCCAGGACAT CACCCATGAA ACGCGCGGCA
1441 ATCGGTTTGT TGTAGATGGC CGAGAGAATA GCTGACGGGT TGATCTTGCT AAGTTCCTTG
1501 AAGACCTCTA GGGTGCGCCG TTGATCCACA CACCAGGCTT CTGCGATTTC GGCCAGCGCC
1561 CGGTTGATGT AACCGCGCAA CGTGTCCATA GTGAACTGCA GCTGGGCGTA GACCAGATTG
1621 TGCACCGACT CCATGTTGGA TAAATGAGTT GCATTGTTGC CATCTGTACT TCTTTTGGTT
1681 CTATTATGAG TAAGATTCAG ACTGGAGCGG TTGGCCAAAC GTTCAGTTC CACCAGAGAT
1741 TTTTGCTTGA TACCTTGCCA GAACACCACC AAACCACCAG TGGTTTCAAA GACGGACACG
1801 TTTCCATATT TTTCATATGT TTGATTGTAT GAAGTATTGA AAATCTGCTG TAACTTATTT
1861 ATGGCCTCAT CACGTACACA GTCCAGCGCA GAGTCGGACA TGTTCACCTC TTGCTTCTTA
1921 GATAAGAAAG TGGCGGTCAT TTTGGCAGAA GAAAAGTGAT ACGAGTCCTC GGCTTCGGAA
1981 CGAATGGTGC GTTCCGAGGC TTCCCAGAAA GTGAGTTGAC AAGTAACATT CTTCTCGTCC
2041 TGTATATCCC AGGAGATCAC TGAGTCCGCA CGTTCAAGAA AAGCCACCAA CCTGTGGGTC
2101 TCTAACGCAG AATTCGGTCT TTCAAAGTCG GAGACGATAG TGTAGTTCGG AAAAATGAAA
2161 AACTTGTCGG CGTTTTCTCC AAAATAGCTG GCATTCGAT TAGTTCCGTT GTAGAAAGGA
2221 GAAATGTCAA CCACATCACC CGTGGAAGTT GCGAAAAAAT GATAGGGATA CTTGGAGCGC
2281 GCAGTAGTGA TGGTCACCAT ACAATTCAGA TTACAGGTCT CACGATAGAG CCAGGTGCTG
2341 CCGCGGCTGT GCCATTGATC CTTGACCGTC ACGTAACGGG TACTGTGGGT GTTGGAATAA
2401 TCGTCGGGCA TTAATTGCAT GGTTTTGTTT TCATAGCTGT CCCTATGATA AGCCACGAAA
2461 ACCGTGCCTG CTATAACGCG GCTGTAGGAA CTGTAGCACT GACTGTGACT GTTGATATGA
2521 TGAATCTCCC ACATAGGAGG CGCCACGTAT TCCGTGTTGC TGCCCAGCAG ATAAGTGGTG
2581 TGGATGTAAG CGTAGCTACG ACGAAACGTC AAAACCTTCT GGTAGACTCG TACCTTAAAG
2641 GTGTGCGCGA CGATGTTGCG TTTGTAGACC ACCATGATGC CCTCGTCCAG GTCTTCATTG
2701 ATGGGCTTCA TCGAGGTGCA GACGATATTA CGTTCAAAGC GAATAAGATC CGTACCCTGA
2761 GCCATAGAAC ACACGCGATA GGGGTACTTG GTGGTGTTGA CCCCCACCAC ATCTCCGTAC
2821 TTGAGGGTAG TGTTGTAGAT GGTCTCGTTA ACACCATGGC TGACCGTTTG GGAAGAAGTT
2881 ACGCGTTGAG AGACTGAACC GGATCGAGAA TGAGCAGCAG ACGTCGTATG AGAGGAATGG
2941 TGACTGTGAG TAGCAGAAGT TCCACGAGTA GAAGATGAGG AAACCGCAGC ACCCAGACAG
3001 ACGATACACA AGTTAACGCA GACTACCAGG CACCAGATCC TGGATTCCAT TACGATACAA
3061 ACTTAACGGA TATCGCGATA ATGAAATAAT TTATGATTAT TTCTCGCTTT CAATTTAACA
```

```
3121 CAACCCTCAA GAACCTTTGT ATTTATTTTC ACTTTTTAAG TATAGAATAA AGAAGCTGGG
3181 AATCGATTCG CGATAGCTGA TTAGTTTTTG TTAACAAAAA TGTGGGAGAA TCTAATTAGT
3241 TTTTCTTTAC ACAATTGACG TACATGAGTC TGAGTTCCTT GTTTTTGCTA ATTATTTCAT
3301 CCAATTTATT ATTCTTGACG ATATCGAGAT CTTTTGTATA GGAGTCAGAC TTGTATTCAA
3361 CATGCTTTTC TATAATCATC TTAGTTATTT CGGCATCATC CAATAGTACA TTTTCCAGAT
3421 TAACAGAGTA .GATATTAATG TCGTATTTGA ACAGAGCCTG TAACATCTCA ATGTCTTTAT
3481 TATCTATAGC CAATTTAATG TCCGGAATGA AGAGAAGGGA ATTATTGGTG TTTGTCGACG
3541 TCATATAGTC GAGCAAGAGA ATCATCATAT CCACGTGTCC ATTTTTTATA GTGGTGTGAA
3601 TACAACTAAG GAGAATAGCC AGATCAAAAG TAGATGGTAT TTCTGAAAGA AAGTATGATA
3661 CAATACTTAC ATCATTAAGC ATGACGGCAT GATAAAATGA AGTTTTCCAT CCAGTTTTCC
3721 CATAGAACAT CAGTCTCCAA TTTTTCTTAA ACAGTTTCAC CGTTTGCATG TTACCACTAT
3781 CAACCGCATA ATACAATGCG GTGTTTCCTT TGTCATCAAA TTGTGAATCA TCCATTCCAC
3841 TGAATAGCAA AATCTTTACT ATTTGGTAT CTTCTAATGT GGCTGCCTGA TGTAATGGAA
3901 ATTCATTCTC TAGAAGATTT TTCAATGCTC CAGCGTTCAA CAACGTACAT ACTAGACGCA
3961 CGTTATTATC AGCTATTGCA TAATACAAGG CACTATGTCC ATGGACATCC GCCTTAAATG
4021 TATCTTTACT AGAGAGAAAG CTTTTCAGCT GCTTAGACTT CCAAGTATTA ATTCGTGACA
4081 GATCCATGTC TGAAACGAGA CGCTAATTAG TGTATATTTT TTCATTTTTT ATAATTTGT
4141 CATATTGCAC CAGAATTAAT AATATCTCTA ATAGATCTAA TTTAATTTAA TTTATATAAC
4201 TTATTTTTTG AATATACTTT TAATTAACAA AAGAGTTAAG TTACTCATAT GGACGCCGTC
4261 CAGTCTGAAC ATCAATCTTT TTAGCCAGAG ATATCATAGC CGCTCTTAGA GTTTCAGCGT
4321 GATTTTCCAA CCTAAATAGA ACTTCATCGT TGCGTTTACA ACACTTTTCT ATTTGTTCAA
4381 ACTTTGTTGT TACATTAGTA ATCTTTTTTT CCAAATTAGT TAGCCGTTGT TTGAGAGTTT
4441 CCTCATTGTC GTCTTCATCG GCTTTAACAA TTGCTTCGCG TTTAGCCTCC TGGCTGTTCT
4501 TATCAGCCTT TGTAGAAAAA AATTCAGTTG CTGGAATTGC AAGATCGTCA TCTCCGGGGA
4561 AAAGAGTTCC GTCCATTTAA AGCCGCGGGA ATTC
```

```
   1 ATGGAATCCA GGATCTGGTG CCTGGTAGTC TGCGTTAACT TGTGTATCGT CTGTCTGGGT
  61 GCTGCGGTTT CCTCATCTTC TACTCGTGGA ACTTCTGCTA CTCACAGTCA CCATTCCTCT
 121 CATACGACGT CTGCTGCTCA TTCTCGATCC GGTTCAGTCT CTCAACGCGT AACTTCTTCC
 181 CAAACGGTCA GCCATGGTGT TAACGAGACC ATCTACAACA CTACCCTCAA GTACGGAGAT
 241 GTGGTGGGGG TCAACACCAC CAAGTACCCC TATCGCGTGT GTTCTATGGC TCAGGGTACG
 301 GATCTTATTC GCTTTGAACG TAATATCGTC TGCACCTCGA TGAAGCCCAT CAATGAAGAC
 361 CTGGACGAGG CATCATGGT GGTCTACAAA CGCAACATCG TCGCGCACAC CTTTAAGGTA
 421 CGAGTCTACC AGAAGGTTTT GACGTTTCGT CGTAGCTACG CTTACATCCA CACCACTTAT
 481 CTGCTGGCA GCAACACGGA ATACGTGGCG CCTCCTATGT GGGAGATTCA TCATATCAAC
 541 AGTCACAGTC AGTGCTACAG TTCCTACAGC CGCGTTATAG CAGGCACGGT TTTCGTGGCT
 601 TATCATAGGG ACAGCTATGA AAACAAAACC ATGCAATTAA TGCCCGACGA TTATTCCAAC
 661 ACCCACAGTA CCCGTTACGT GACGGTCAAG GATCAATGGC ACAGCCGCGG CAGCACCTGG
 721 CTCTATCGTG AGACCTGTAA TCTGAATTGT ATGGTGACCA TCACTACTGC GCGCTCCAAG
 781 TATCCCTATC ATTTTTTCGC AACTTCCACG GGTGATGTGG TTGACATTTC TCCTTTCTAC
 841 AACGGAACTA ATCGCAATGC CAGCTATTTT GGAGAAAACG CCGACAAGTT TTTCATTTTT
 901 CCGAACTACA CTATCGTCTC CGACTTTGAA AGACCGAATT CTGCGTTAGA GACCCACAGG
 961 TTGGTGGCTT TTCTTACACG TGCGGACTCA GTGATCTCCT GGGATATACA GGACGAGAAG
1021 AATGTTACTT GTCAACTCAC TTTCTGGGAA GCCTCGGAAC GCACCATTCG TTCCGAAGCC
1081 GAGGACTCGT ATCACTTTTC TTCTGCCAAA ATGACCGCCA CTTTCTTATC TAAGAAGCAA
1141 GAGGTGAACA TGTCCGACTC TGCGCTGGAC TGTGTACGTG ATGAGGCCAT AAATAAGTTA
1201 CAGCAGATTT TCAATACTTC ATACAATCAA ACATATGAAA AATATGGAAA CGTGTCCGTC
1261 TTTGAAACCA CTGGTGGTTT GGTGGTGTTC TGGCAAGGTA TCAAGCAAAA ATCTCTGGTG
1321 GAACTCGAAC GTTTGGCCAA CCGCTCCAGT CTGAATCTTA CTCATAATAG AACCATAAGA
1381 TCTACAGATG GCAACAATGC AACTCATTTA TCCAACATGG AGTCGGTGCA CAATCTGGTC
1441 TACGCCCAGC TGCAGTTCAC CTATGACACG TTGCGCGGTT ACATCAACCG GGCGCTGGCC
1501 GAAATCGCAG AAGCCTGGTG TGTGGATCAA CGGCGCACCC TAGAGGTCTT CAAGGAACTT
1561 AGCAAGATCA ACCCGTCAGC TATTCTCTCG GCCATCTACA ACAAACCGAT TGCCGCGCGT
1621 TCATGGGTG ATGTCCTGGG TCTGGCCAGC TGCGTGACCA TTAACCAAAC CAGCGTCAAG
1681 GTGCTGCGTG ATATGAATGT GAAGGAATCG CCAGGACGCT GCTACTCACG ACCAGTGGTC
1741 ATCTTTAATT TCGCCAACAG CTCGTACGTG CAGTACGGTC AACTGGGCGA GGATAACGAA
1801 ATCCTGTTGG GCAACCACCG CACTGAGGAA TGTCAGCTTC CCAGCCTCAA GATCTTCATC
1861 GCCGGCAACT CGGCCTACGA GTACGTGGAC TACCTCTTCA AACGCATGAT TGACCTCAGC
1921 AGCATCTCCA CCGTCGACAG CATGATCGCC CTAGACATCG ACCCGCTGGA AAACACCGAC
1981 TTCAGGGTAC TGGAACTTTA CTCGCAGAAA GAATTGCGTT CCAGCAACGT TTTTGATCTC
2041 GAGGAGATCA TGCGCGAGTT CAATTCGTAT AAGCAGCGGG TAAAGTACGT GGAGGACAAG
2101 GTAGTCGACC CGCTGCCGCC CTACCTCAAG GGTCTGGACG ACACTCGACA GCGGCGTCTC
2161 TGCATGCAGC CGCTGCAGAA CCTCTTTCCC TATCTGGTGT CCGCCGACGG GACCACCGTG
2221 ACGTCGGGCA CACCAAAGA CACGTCGTTA CAGGCTCCGC CTTCCTACGA GGAAAGTGTT
2281 TATAATTCTG GTCGCAAAGG ACCGGGACCA CCGTCGTCTG ATGCATCCAC GGCGGCTCCG
2341 CCTTACACCA ACGAGCAGGC TTACCAGATG CTTCTGGCCC TGGTCCGTCT GGACGCAGAG
2401 CAGCGAGCGC ACGAGAACGG TACAGATTCT TTGGACGGAC AGACTGGCAC GCAGGACAAG
2461 GGACAGAAGC CCAACCTGCT AGACCGACTG CGACACCGCA AAAACGGCTA CCGACACTTG
2521 AAAGACTCCG ACGAAGAAGA GAACGTCTGA
```

FIG. 20A

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGGGTACCG GATCCCCCAG CTTATAAAAA TCACAAGTCT CTGACACTTT TTTTGTCTAG
 481 TTTTTTTTTC TCCTCTTGGT TCAGACGTTC TCTTCTTCGT CGGAGTCTTT CAAGTGTCGG
 541 TAGCCGTTTT TGCGGTGTCG CAGTCGGTCT AGCAGGTTGG GCTTCTGTCC CTTGTCCTGC
 601 GTGCCAGTCT GTCCGTCCAA AGAATCTGTA CCGTTCTCGT GCGCTCGCTG CTCTGCGTCC
 661 AGACGGACCA GGGCCAGAAG CATCTGGTAA GCCTGCTCGT TGGTGTAAGG CGGAGCCGCC
 721 GTGGATGCAT CAGACGACGG TGGTCCCGGT CCTTTGCGAC CAGAATTATA AACACTTTCC
 781 TCGTAGGAAG GCGGAGCCTG TAACGACGTG TCTTTGGTGT TGCCCGACGT CACGGTGGTC
 841 CCGTCGGCGG ACACCAGATA GGGAAAGAGG TTCTGCAGCG GCTGCATGCA GAGACGCCGC
 901 TGTCGAGTGT CGTCCAGACC CTTGAGGTAG GGCGGCAGCG GGTCGACTAC CTTGTCCTCC
 961 ACGTACTTTA CCCGCTGCTT ATACGAATTG AACTCGCGCA TGATCTCCTC GAGATCAAAA
1021 ACGTTGCTGG AACGCAATTC TTTCTGCGAG TAAAGTTCCA GTACCCTGAA GTCGGTGTTT
1081 TCCAGCGGGT CGATGTCTAG GGCGATCATG CTGTCGACGG TGGAGATGCT GCTGAGGTCA
1141 ATCATGCGTT TGAAGAGGTA GTCCACGTAC TCGTAGGCCG AGTTGCCGGC GATGAAGATC
1201 TTGAGGCTGG GAAGCTGACA TTCCTCAGTG CGGTGGTTGC CCAACAGGAT TTCGTTATCC
1261 TCGCCCAGTT GACCGTACTG CACGTACGAG CTGTTGGCGA AATTAAAGAT GACCACTGGT
1321 CGTGAGTAGC AGCGTCCTGG CGATTCCTTC ACATTCATAT CACGCAGCAC CTTGACGCTG
1381 GTTTGGTTAA TGGTCACGCA GCTGGCCAGA CCCAGGACAT CACCCATGAA ACGCGCGGCA
1441 ATCGGTTTGT TGTAGATGGC CGAGAGAATA GCTGACGGGT TGATCTTGCT AAGTTCCTTG
1501 AAGACCTCTA GGGTGCGCCG TTGATCCACA CACCAGGCTT CTGCGATTTC GGCCAGCGCC
1561 CGGTTGATGT AACCGCGCAA CGTGTCATAG GTGAACTGCA GCTGGGCGTA GACCAGATTG
1621 TGCACCGACT CCATGTTGGA TAAATGAGTT GCATTGTTGC CATCTGTAGA TCTTATGGTT
1681 CTATTATGAG TAAGATTCAG ACTGGAGCGG TTGGCCAAAC GTTCGAGTTC CACCAGAGAT
1741 TTTTGCTTGA TACCTTGCCA GAACACCACC AAACCACCAG TGGTTTCAAA GACGGACACG
1801 TTTCCATATT TTTCATATGT TTGATTGTAT GAAGTATTGA AAATCTGCTG TAACTTATTT
1861 ATGGCCTCAT CACGTACACA GTCCAGCGCA GAGTCGGACA TGTTCACCTC TTGCTTCTTA
1921 GATAAGAAAG TGGCGGTCAT TTTGGCAGAA GAAAAGTGAT ACGAGTCCTC GGCTTCGGAA
1981 CGAATGGTGC GTTCCAGGGC TTCCCAGAAA GTGAGTTGAC AAGTAACATT CTTCTCGTCC
2041 TGTATATCCC AGGAGATCAC TGAGTCCGCA CGTTCAAGAA AAGCCACCAA CCTGTGGGTC
2101 TCTAACGCAG AATTCGGTCT TTCAAAGTCG GAGACGATAG TGTAGTTCGG AAAAATGAAA
2161 AACTTGTCGG CGTTTTCTCC AAAATAGCTG GCATTGCGAT TAGTTCCGTT GTAGAAAGGA
2221 GAAATGTCAA CCACATCACC CGTGGAAGTT GCGAAAAAAT GATAGGGATA CTTGGAGCGC
2281 GCAGTAGTGA TGGTCACCAT ACAATTCAGA TTACAGGTCT CACGATAGAG CCAGGTGCTG
2341 CCGCGGCTGT GCCATTGATC CTTGACCGTC ACGTAACGGG TACTGTGGGT GTTGGAATAA
2401 TCGTCGGGCA TTAATTGCAT GGTTTTGTTT TCATAGCTGT CCCTATGATA AGCCACGAAA
2461 ACCGTGCCTG CTATAACGCG GCTGTAGGAA CTGTAGCACT GACTGTGACT GTTGATATGA
2521 TGAATCTCCC ACATAGGAGG CGCCACGTAT TCCGTGTTGC TGCCCAGCAG ATAAGTGGTG
2581 TGGATGTAAG CGTAGCTACG ACGAAACGTC AAAACCTTCT GGTAGACTCG TACCTTAAAG
2641 GTGTGCGCGA CGATGTTGCG TTTGTAGACC ACCATGATGC CCTCGTCCAG GTCTTCATTG
2701 ATGGGCTTCA TCGAGGTGCA GACGATATTA CGTTCAAAGC GAATAAGATC CGTACCCTGA
2761 GCCATAGAAC ACACGCGATA GGGGTACTTG GTGGTGTTGA CCCCCACCAC ATCTCCGTAC
2821 TTGAGGGTAG TGTTGTAGAT GGTCTCGTTA ACACCATGGC TGACCGTTTG GGAAGAAGTT
2881 ACGCGTTGAG AGACTGAACC GGATCGAGAA TGAGCAGCAG ACGTCGTATG AGAGGAATGG
2941 TGACTGTGAG TAGCAGAAGT TCCACGAGTA GAAGATGAGG AAACCGCAGC ACCCAGACAG
3001 ACGATACACA AGTAACGCA GACTACCAGG CACCAGATCC TGGATTCCAT TACGATACAA
3061 ACTTAACGGA TATCGCGATA ATGAAATAAT TTATGATTAT TTCTCGCTTT CAATTTAACA
```

```
3121 CAACCCTCAA GAACCTTTGT ATTTATTTTC ACTTTTTAAG TATAGAATAA AGAAGCTGGG
3181 AATCGATTCG CGATAGCTGA TTAGTTTTTG TTAACAAAAA TGTGGGAGAA TCTAATTAGT
3241 TTTTCTTTAC ACAATTGACG TACATGAGTC TGAGTTCCTT GTTTTTGCTA ATTATTTCAT
3301 CCAATTTATT ATTCTTGACG ATATCGAGAT CTTTTGTATA GGAGTCAGAC TTGTATTCAA
3361 CATGCTTTTC TATAATCATC TTAGTTATTT CGGCATCATC CAATAGTACA TTTTCCAGAT
3421 TAACAGAGTA GATATTAATG TCGTATTTGA ACAGAGCCTG TAACATCTCA ATGTCTTTAT
3481 TATCTATAGC CAATTTAATG TCCGGAATGA AGAGAAGGGA ATTATTGGTG TTTGTCGACG
3541 TCATATAGTC GAGCAAGAGA ATCATCATAT CCACGTGTCC ATTTTTTATA GTGGTGTGAA
3601 TACAACTAAG GAGAATAGCC AGATCAAAAG TAGATGGTAT TTCTGAAAGA AAGTATGATA
3661 CAATACTTAC ATCATTAAGC ATGACGGCAT GATAAAATGA AGTTTTCCAT CCAGTTTTCC
3721 CATAGAACAT CAGTCTCCAA TTTTTCTTAA ACAGTTTCAC CGTTGCATG TTACCACTAT
3781 CAACCGCATA ATACAATGCG GTGTTTCCTT TGTCATCAAA TTGTGAATCA TCCATTCCAC
3841 TGAATAGCAA AATCTTTACT ATTTTGGTAT CTTCTAATGT GGCTGCCTGA TGTAATGGAA
3901 ATTCATTCTC TAGAAGATTT TTCAATGCTC CAGCGTTCAA CAACGTACAT ACTAGACGCA
3961 CGTTATTATC AGCTATTGCA TAATACAAGG CACTATGTCC ATGGACATCC GCCTTAAATG
4021 TATCTTTACT AGAGAGAAAG CTTTTCAGCT GCTTAGACTT CCAAGTATTA ATTCGTGACA
4081 GATCCATGTC TGAAACGAGA CGCTAATTAG TGTATATTTT TTCATTTTTT ATAATTTTGT
4141 CATATTGCAC CAGAATTAAT AATATCTCTA ATAGATCTAA TTTAATTTAA TTTATATAAC
4201 TTATTTTTTG AATATACTTT TAATTAACAA AAGAGTTAAG TTACTCATAT GGACGCCGTC
4261 CAGTCTGAAC ATCAATCTTT TTAGCCAGAG ATATCATAGC CGCTCTTAGA GTTTCAGCGT
4321 GATTTTCCAA CCTAAATAGA ACTTCATCGT TGCGTTTACA ACACTTTTCT ATTTGTTCAA
4381 ACTTTGTTGT TACATTAGTA ATCTTTTTTT CCAAATTAGT TAGCCGTTGT TTGAGAGTTT
4441 CCTCATTGTC GTCTTCATCG GCTTTAACAA TTGCTTCGCG TTTAGCCTCC TGGCTGTTCT
4501 TATCAGCCTT TGTAGAAAAA AATTCAGTTG CTGGAATTGC AAGATCGTCA TCTCCGGGA
4561 AAAGAGTTCC GTCCATTTAA AGCCGCGGGA ATTC
```

```
   1 ATGCGGCCAG GCCTCCCCTC CTACCTCATC GTCCTCGCCG TCTGTCTCCT CAGCCACCTA
  61 CTTTCGTCAC GATATGGCGC AGAAGCCATA TCCGAACCGC TGGACAAAGC GTTTCACCTA
 121 CTGCTCAACA CCTACGGGAG ACCCATCCGC TTCCTGCGTG AAAACACCAC CCAGTGTACC
 181 TACAATAGCA GCCTCCGTAA CAGCACGGTC GTCAGGGAAA ACGCCATCAG TTTCAACTTT
 241 TTCCAAAGCT ATAATCAATA CTATGTATTC CATATGCCTC GATGTCTTTT TGCGGGTCCT
 301 CTGGCGGAGC AGTTTCTGAA CCAGGTAGAT CTGACCGAAA CCCTGGAAAG ATACCAACAG
 361 AGACTTAACA CTTACGCGCT GGTATCCAAA GACCTGGCCA GCTACCGATC TTTTTCGCAG
 421 CAGCTAAAGG CACAGGACAG CCTAGGTGAA CAGCCCACCA CTGTGCCACC ACCCATTGAC
 481 CTGTCAATAC CTCACGTTTG GATGCCACCG CAAACCACTC CACACGGCTG GACAGAATCA
 541 CATACCACCT CAGGACTACA CCGACCACAC TTTAACCAGA CCTGTATCCT CTTTGATGGA
 601 CACGATCTAC TATTCAGCAC CGTCACACCT TGTTTGCACC AAGGCTTTTA CCTCATCGAC
 661 GAACTACGTT ACGTTAAAAT AACACTGACC GAGGACTTCT TCGTAGTTAC GGTGTCCATA
 721 GACGACGACA CACCCATGCT GCTTATCTTC GGCCATCTTC CACGCGTACT CTTTAAAGCG
 781 CCCTATCAAC GCGACAACTT TATACTACGA CAAACTGAAA AACACGAGCT CCTGGTGCTA
 841 GTTAAGAAAG ATCAACTGAA CCGTCACTCT TATCTCAAAG ACCCGGACTT TCTTGACGCC
 901 GCACTTGACT TCAACTACCT GGACCTCAGC GCACTACTAC GTAACAGCTT TCACCGTTAC
 961 GCCGTGGATG TACTCAAAAG CGGTCGATGT CAGATGCTGG ACCGCCGCAC GGTAGAAATG
1021 GCCTTCGCCT ACGCATTAGC ACTGTTCGCA GCAGCCCGAC AAGAAGAGGC CGGCGCCCAA
1081 GTCTCCGTCC ACGGGCCCT AGACCGCCAG GCCGCACTCT ACAAATACA AGAATTTATG
1141 ATCACCTGCC TCTCACAAAC ACCACCACGC ACCACGTTGC TGCTGTATCC CACGGCCGTG
1201 GACCTGGCCA AACGAGCCCT TTGGACACCG AATCAGATCA CCGACATCAC CAGCCTCGTA
1261 CGCCTGGTCT ACATACTCTC TAAACAGAAT CAGCAACATC TCATCCCCCA GTGGGCACTA
1321 CGACAGATCG CCGACTTTGC CCTAAAACTA CACAAAACGC ACCTGGCCTC TTTTCTTTCA
1381 GCCTTCGCGC GTCAAGAACT CTACCTCATG GGCAGCCTCG TCCACTCCAT GCTAGTACAT
1441 ACGACGGAGA GACGCGAAAT CTTCATCGTA GAAACGGGCC TCTGTTCATT AGCCGAGCTA
1501 TCACACTTTA CGCAGTTGCT AGCTCATCCG CACCACGAAT ACCTCAGCGA CCTGTACACA
1561 CCCTGTTCCA GTAGCGGGCG ACGCGATCGA TCGCTCGAAC GCCTCACACG TCTCTTCCCC
1621 GATGCCACCG TCCCACTAC CGTTCCGCC GCCCTCTCCA TCCTATCTAC CATGCAACCA
1681 AGCACGCTAG AAACCTTCCC CGACCTGTTT TGTCTGCCGC TCGGCGAATC CTTCTCCGCG
1741 CTGACCGTCT CCGAACACGT CAGTTATGTC GTAACAAACC AGTACCTGAT CAAAGGTATC
1801 TCCTACCCTG TCTCCACCAC CGTCGTAGGC CAGAGCCTCA TCATCACCCA GACGGACAGT
1861 CAAACTAAAT GCGAACTGAC GCGCAACATG CATACCACAC ACAGCATCAC AGCGGCGCTC
1921 AACATTTCCC TAGAAAACTG CGCCTTTTGC CAAAGCGCCC TACTAGAATA CGACGACACG
1981 CAAGGCGTCA TCAACATCAT GTACATGCAC GACTCGGACG ACGTCCTTTT CGCCCTGGAT
2041 CCCTACAACG AAGTGGTGGT CTCATCTCCG CGAACTCACT ACCTCATGCT TTTGAAAAAC
2101 GGTACGGTCC TAGAAGTAAC TGACGTCGTC GTGGACGCTA CCGACAGTCG TCTCCTCATG
2161 ATGTCCGTCT ACGCGCTATC GGCCATCATC GGCATCTATC TGCTCTACCG CATGCTCAAG
2221 ACATGCTGA
```

FIG. 22A

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCCG GTACCCTCGA GTTTATTGGG AAGAATATGA
 661 TAATATTTTG GGATTTCAAA ATTGAAAATA TATAATTACA ATATAAAATG CGGCCCGGGC
 721 TCCCCTCCTA CCTCATCGTC CTCGCCGTCT GTCTCCTCAG CCACCTACTT TCGTCACGAT
 781 ATGGCGCAGA AGCCATATCC GAACCGCTGG ACAAAGCGTT TCACCTACTG CTCAACACCT
 841 ACGGGAGACC CATCCGCTTC CTGCGTGAAA ACACCACCCA GTGTACCTAC AATAGCAGCC
 901 TCCGTAACAG CACGGTCGTC AGGGAAAACG CCATCAGTTT CAACTTTTTC CAAAGCTATA
 961 ATCAATACTA TGTATTCCAT ATGCCTCGAT GTCTTTTTGC GGGTCCTCTG GCGGAGCAGT
1021 TTCTGAACCA GGTAGATCTG ACCGAAACCC TGGAAAGATA CCAACAGAGA CTTAACACTT
1081 ACGCGCTGGT ATCCAAAGAC CTGGCCAGCT ACCGATCTTT TTCGCAGCAG CTAAAGGCAC
1141 AGGACAGCCT AGGTGAACAG CCCACCACTG TGCCACCACC CATTGACCTG TCAATACCTC
1201 ACGTTTGGAT GCCACCGCAA ACCACTCCAC ACGGCTGGAC AGAATCACAT ACCACCTCAG
1261 GACTACACCG ACCACACTTT AACCAGACCT GTATCCTCTT TGATGGACAC GATCTACTAT
1321 TCAGCACCGT CACACCTTGT TTGCACCAAG GCTTTTACCT CATCGACGAA CTACGTTACG
1381 TTAAAATAAC ACTGACCGAG GACTTCTTCG TAGTTACGGT GTCCATAGAC GACGACACAC
1441 CCATGCTGCT TATCTTCGGC CATCTTCCAC GCGTACTCTT TAAAGCGCCC TATCAACGCG
1501 ACAACTTTAT ACTACGACAA ACTGAAAAAC ACGAGCTCCT GGTGCTAGTT AAGAAAGATC
1561 AACTGAACCG TCACTCTTAT CTCAAAGACC CGGACTTTCT TGACGCCGCA CTTGACTTCA
1621 ACTACCTGGA CCTCAGCGCA CTACTACGTA ACAGCTTTCA CCGTTACGCC GTGGATGTAC
1681 TCAAAAGCGG TCGATGTCAG ATGCTGGACC GCCGCACGGT AGAAATGGCC TTCGCCTACG
1741 CATTAGCACT GTTCGCAGCA GCCCGACAAG AAGAGGCCGG CGCCAAGTC TCCGTCCCAC
1801 GGGCCCTAGA CCGCCAGGCC GCACTCTTAC AAATACAAGA ATTTATGATC ACCTGCCTCT
1861 CACAAACACC ACCACGCACC ACGTTGCTGC TGTATCCCAC GGCCGTGGAC CTGGCCAAAC
1921 GAGCCCTTTG GACACCGAAT CAGATCACCG ACATCACCAG CCTCGTACGC CTGGTCTACA
1981 TACTCTCTAA ACAGAATCAG CAACATCTCA TCCCCCAGTG GGCACTACGA CAGATCGCCG
2041 ACTTTGCCCT AAAACTACAC AAAACGCACC TGGCCTCTTT TCTTTCAGCC TTCGCGCGTC
2101 AAGAACTCTA CCTCATGGGC AGCCTCGTCC ACTCCATGCT AGTACATACG ACGGAGAGAC
2161 GCGAAATCTT CATCGTAGAA ACGGGCCTCT GTTCATTAGC CGAGCTATCA CACTTTACGC
2221 AGTTGCTAGC TCATCCGCAC CACGAATACC TCAGCGACCT GTACACACCC TGTTCCAGTA
2281 GCGGGCGACG CGATCACTCG CTCGAACGCC TCACACGTCT CTTCCCCGAT GCCACCGTCC
2341 CCACTACCGT TCCCGCCGCC CTCTCCATCC TATCTACCAT GCAACCAAGC ACGCTAGAAA
2401 CCTTCCCCGA CCTGTTTTGT CTGCCGCTCG GCGAATCCTT CTCCGCGCTG ACCGTCTCCG
2461 AACACGTCAG TTATGTCGTA ACAAACCAGT ACCTGATCAA AGGTATCTCC TACCCTGTCT
2521 CCACCACCGT CGTAGGCCAG AGCCTCATCA TCACCCAGAC GGACAGTCAA ACTAAATGCG
2581 AACTGACGCG CAACATGCAT ACCACACACA GCATCACAGC GGCGCTCAAC ATTTCCCTAG
2641 AAAACTGCGC CTTTTGCCAA AGCGCCTAC TAGAATACGA CGACACGCAA GGCGTCATCA
2701 ACATCATGTA CATGCACGAC TCGGACGACG TCCTTTTCGC CCTGGATCCC TACAACGAAG
2761 TGGTGGTCTC ATCTCCGCGA ACTCACTACC TCATGCTTTT GAAAAACGGT ACGGTCCTAG
2821 AAGTAACTGA CGTCGTCGTG GACGCTACCG ACAGTCGTCT CCTCATGATG TCCGTCTACG
2881 CGCTATCGGC CATCATCGGC ATCTATCTGC TCTACCGACT GCTCAAGACA TGCTGATTTT
2941 TATCTCGAGC CCGGGAGATC TTAGCTAACT GATTTTTCTG GGAAAAAAAT TATTTAACTT
3001 TTCATTAATA GGGATTTGAC GTATGTAGCG TACAAAATTA TCGTTCCTGG TATATAGATA
3061 AAGAGTCCTA TATATTTGAA AATCGTTACG GCTCGATTAA ACTTTAATGA TTGCATAGTG
```

```
3121 AATATATCAT TAGGATTTAA CTCCTTGACT ATCATGGCGG CGCCAGAAAT TACCATCAAA
3181 AGCATTAATA CAGTTATGCC GATCGCAGTT AGAACGGTTA TAGCATCCAC CATTTATATC
3241 TAAAAATTAG ATCAAAGAAT ATGTGACAAA GTCCTAGTTG TATACTGAGA ATTGACGAAA
3301 CAATGTTTCT TACATATTTT TTTCTTATTA GTAACTGACT TAATAGTAGG AACTGGAAAG
3361 CTAGACTTGA TTATTCTATA AGTATAGATA CCCTTCCAGA TAATGTTCTC TTTGATAAAA
3421 GTTCCAGAAA ATGTAGAATT TTTTAAAAAG TTATCTTTTG CTATTACCAA GATTGTGTTT
3481 AGACGCTTAT TATTAATATG AGTAATGAAA TCCACACCGC CTCTAGATAT GGGGAATTC
```

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGCA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC TTAATTAATT AGTCATCAGA CAGGGCGAGA ACGAGACTAT
1621 CTGCTCGTTA ATTAATTAGG TCGACGGATC CGGTACCCTC GAGTTTATTG GAAGAATAT
1681 GATAATATTT TGGGATTTCA AAATTGAAAA TATATAATTA CAATATAAAA TGCGGCCCGG
1741 GCTCCCCTCC TACCTCATCG TCCTCGCCGT CTGTCTCCTC AGCCACCTAC TTTCGTCACG
1801 ATATGGCGCA GAAGCCATAT CCGAACCGCT GGACAAAGCG TTTCACCTAC TGCTCAACAC
1861 CTACGGGAGA CCCATCCGCT TCCTGCGTGA AAACACCACC CAGTGTACCT ACAATAGCAG
1921 CCTCCGTAAC AGCACGGTCG TCAGGGAAAA CGCCATCAGT TTCAACTTTT TCCAAAGCTA
1981 TAATCAATAC TATGTATTCC ATATGCCTCG ATGTCTTTTT GCGGGTCCTC TGGCGGAGCA
2041 GTTTCTGAAC CAGGTAGATC TGACCGAAAC CCTGGAAAGA TACCAACAGA GACTTAACAC
2101 TTACGCGCTG GTATCCAAAG ACCTGGCCAG CTACCGATCT TTTTCGCAGC AGCTAAAGGC
2161 ACAGGACAGC CTAGGTGAAC AGCCCACCAC TGTGCCACCA CCCATTGACC TGTCAATACC
2221 TCACGTTTGG ATGCCACCGC AAACCACTCC ACACGGCTGG ACAGAATCAC ATACCACCTC
2281 AGGACTACAC CGACCACACT TTAACCAGAC CTGTATCCTC TTTGATGGAC ACGATCTACT
2341 ATTCAGCACC GTCACACCTT GTTTGCACCA AGGCTTTTAC CTCATCGACG AACTACGTTA
2401 CGTTAAAATA ACACTGACCG AGGACTTCTT CGTAGTTACG GTGTCCATAG ACGACGACAC
2461 ACCCATGCTG CTTATCTTCG GCCATCTTCC ACGCGTACTC TTTAAAGCGC CCTATCAACG
2521 CGACAACTTT ATACTACGAC AAACTGAAAA ACACGAGCTC CTGGTGCTAG TTAAGAAAGA
2581 TCAACTACCG CGTCACTCTT ATCTCAAAGA CCCGGACTTT CTTGACGCCG CACTTGACTT
2641 CAACTACCTG GACCTCAGCG CACTACTACG TAACAGCTTT CACCGTTACG CCGTGGATGT
2701 ACTCAAAAGC GGTCGATGTC AGATGCTGGA CCGCCGCACG GTAGAAATGG CCTTCGCCTA
2761 CGCATTAGCA CTGTTCGCAG CAGCCCGACA AGAAGAGGCC GGCGCCCAAG TCTCCGTCCC
2821 ACGGGCCCTA GACCGCCAGG CCGCACTCTT ACAAATACAA GAATTTATGA TCACCTGCCT
2881 CTCACAAACA CCACCACGCA CCACGTTGCT GCTGTATCCC ACGGCCGTGG ACCTGGCCAA
2941 ACGAGCCCTT TGGACACCGA ATCAGATCAC CGACATCACC AGCCTCGTAC GCCTGGTCTA
3001 CATACTCTCT AAACAGAATC AGCAACATCT CATCCCCCAG TGGGCACTAC GACAGATCGC
3061 CGACTTTGCC CTAAAACTAC ACAAAACGCA CCTGGCCTCT TTTCTTTCAG CCTTCGCGCG
```

```
3121 TCAAGAACTC TACCTCATGG GCAGCCTCGT CCACTCCATG CTAGTACATA CGACGGAGAG
3181 ACGCGAAATC TTCATCGTAG AAACGGGCCT CTGTTCATTA GCCGAGCTAT CACACTTTAC
3241 GCAGTTGCTA GCTCATCCGC ACCACGAATA CCTCAGCGAC CTGTACACAC CCTGTTCCAG
3301 TAGCGGGCGA CGCGATCACT CGCTCGAACG CCTCACACGT CTCTTCCCCG ATGCCACCGT
3361 CCCCACTACC GTTCCGCCG CCCTCTCCAT CCTATCTACC ATGCAACCAA GCACGCTAGA
3421 AACCTTCCCC GACCTGTTTT GTCTGCCGCT CGGCGAATCC TTCTCCGCGC TGACCGTCTC
3481 CGAACACGTC AGTTATGTCG TAACAAACCA GTACCTGATC AAAGGTATCT CCTACCCTGT
3541 CTCCACCACC GTCGTAGGCC AGAGCCTCAT CATCACCCAG ACGGACAGTC AAACTAAATG
3601 CGAACTGACG CGCAACATGC ATACCACACA CAGCATCACA GCGGCGCTCA ACATTTCCCT
3661 AGAAAACTGC GCCTTTTGCC AAAGCGCCCT ACTAGAATAC GACGACACGC AAGGCGTCAT
3721 CAACATCATG TACATGCACG ACTCGGACGA CGTCCTTTTC GCCCTGGATC CCTACAACGA
3781 AGTGGTGGTC TCATCTCCGC GAACTCACTA CCTCATGCTT TTGAAAAACG GTACGGTCCT
3841 AGAAGTAACT GACGTCGTCG TGGACGCTAC CGACAGTCGT CTCCTCATGA TGTCCGTCTA
3901 CGCGCTATCG GCCATCATCG GCATCTATCT GCTCTACCGC ATGCTCAAGA CATGCTGATT
3961 TTTATCTCGA GTCTAGAATC GATCCCGGGT TTTTATGACT AGTTAATCAC GGCCGCTTAT
4021 AAAGATCTAA AATGCATAAT TTCTAAATAA TGAAAAAAAA GTACATCATG AGCAACGCGT
4081 TAGTATATTT TACAATGGAG ATTAACGCTC TATACCGTTC TATGTTTATT GATTCAGATG
4141 ATGTTTTAGA AAAGAAAGTT ATTGAATATG AAAACTTTAA TGAAGATGAA GATGACGACG
4201 ATGATTATTG TTGTAAATCT GTTTTAGATG AAGAAGATGA CGCGCTAAAG TATACTATGG
4261 TTACAAAGTA TAAGTCTATA CTACTAATGG CGACTTGTGC AAGAAGGTAT AGTATAGTGA
4321 AAATGTTGTT AGATTATGAT TATGAAAAAC CAAATAAATC AGATCCATAT CTAAAGGTAT
4381 CTCCTTTGCA CATAATTTCA TCTATTCCTA GTTTAGAATA CCTGCAG
```

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGATAAA AATCAGCATG TCTTGAGCAT
 181 GCGGTAGAGC AGATAGATGC CGATGATGGC CGATAGCGCG TAGACGGACA TCATGAGGAG
 241 ACGACTGTCG GTAGCGTCCA CGACGACGTC AGTTACTTCT AGGACCGTAC CGTTTTTCAA
 301 AAGCATGAGG TAGTGAGTTC GCGGAGATGA GACCACCACT TCGTTGTAGG GATCCAGGGC
 361 GAAAAGGACG TCGTCCGAGT CGTGCATGTA CATGATGTTG ATGACGCCTT GCGTGTCGTC
 421 GTATTCTAGT AGGGCGCTTT GGCAAAAGGC GCAGTTTTCT AGGGAAATGT TGAGCGCCGC
 481 TGTGATGCTG TGTGTGGTAT GCATGTTGCG CGTCAGTTCG CATTTAGTTT GACTGTCCGT
 541 CTGGGTGATG ATGAGGCTCT GGCCTACGAC GGTGGTGGAG ACAGGGTAGG AGATACCTTT
 601 GATCAGGTAC TGGTTTGTTA CGACATAACT GACGTGTTCG GAGACGGTCA GCGCGGAGAA
 661 GGATTCGCCG AGCGGCAGAC AAAACAGGTC GGGGAAGGTT TCTAGCGTGC TTGGTTGCAT
 721 GGTAGATAGG ATGGAGAGGG CGGCGGGAAC GGTAGTGGGG ACGGTGGCAT CGGGGAAGAG
 781 ACGTGTGAGG CGTTCGAGCG AGTGATCGCG TCGCCCGCTA CTGGAACAGG GTGTGTACAG
 841 GTCGCTGAGG TATTCGTGGT GCGGATGAGC TAGCAACTGC GTAAAGTGTG ATAGCTCGGC
 901 TAATGAACAG AGGCCCGTTT CTACGATGAA GATTTCGCGT CTCTCCGTCG TATGTACTAG
 961 CATGGAGTGG ACGAGGCTGC CCATGAGGTA GAGTTCTTGA CGCGCGAAGG CTGAAAGAAA
1021 AGAGGCCAGG TGCGTTTTGT GTAGTTTTAG GGCAAAGTCG GCGATCTGTC GTAGTGCCCA
1081 CTGGGGGATG AGATGTTGCT GATTCTGTTT AGAGAGTATG TAGACCAGGC GTACGAGGCT
1141 GGTGATGTCG GTGATCTGAT TCGGTGTCCA AAGGGCTCGT TTGGCCAGGT CCACGGCCGT
1201 GGGATACAGC AGCAACGTGG TGCGTGGTGG TGTTTGTGAG AGGCAGGTGA TCATAAATTC
1261 TTGTATTTGT AAGAGTGCGG CCTGGCGGTC TAGGGCCCGT GGGACGGAGA CTTGGGCGCC
1321 GGCCTCTTCT TGTCGGGCTG CTGCGAACAG TGCTAATGCG TAGGCGAAGG CCATTTCTAC
1381 CGTGCGGCGG TCCAGCATCT GACATCGACC GCTTTTGAGT ACATCCACGG CGTAACGGTG
1441 AAAGCTGTTA CGTAGTAGTG CGCTGAGGTC CAGGTAGTTG AAGTCAAGTG CGGCGTCAAG
1501 AAAGTCCGGG TCTTTGAGAT AAGAGTGACG GTTCAGTTGA TCTTTCTTAA CTAGCACCAG
1561 GAGCTCGTGT TTTTCAGTTT GTCGTAGTAT AAAGTTGTCG CGTTGATAGG GCGCTTTAAA
1621 GAGTACGCGT GGAAGATGGC CGAAGATAAG CAGCATGGGT GTGTCGTCGT CTATGGACAC
1681 CGTAACTACG AAGAAGTCCT CGGTCAGTGT TATTTTAACG TAACGTAGTT CGTCGATGAG
1741 GTAAAAGCCT TGGTGCAAAC AAGGTGTGAC GGTGCTGAAT AGTAGATCGT GTCCATCAAA
1801 GAGGATACAG GTCTGGTTAA AGTGTGGTCG GTGTAGTCCT GAGGTGGTAT GTGATTCTGT
1861 CCAGCCGTGT GGAGTGGTTT GCGGTGGCAT CCAAACGTGA GGTATTGACA GGTCAATGGG
1921 TGGTGGCACA GTGGTGGGCT GTTCACCTAG GCTGTCCTGT GCCTTTAGCT GCTGCGAAAA
1981 AGATCGGTAG CTGGCCAGGT CTTTGGATAC CAGCGCGTAA GTGTTAAGTC TCTGTTGGTA
2041 TCTTTCCAGG GTTTCGGTCA GATCTACCTG GTTCAGAAAC TGCTCCGCCA GAGGACCCGC
2101 AAAAAGACAT CGAGGCATAT GGAATACATA GTATTGATTA TAGCTTTGGA AAAAGTTGAA
2161 ACTGATGGCG TTTTCCCTGA CGACCGTGCT GTTACGGAGG CTGCTATTGT AGGTACACTG
2221 GGTGGTGTTT TCACGCAGGA AGCGGATGGG TCTCCCGTAG GTGTTGAGCA GTAGGTGAAA
2281 CGCTTTGTCC AGCGGTTCGG ATATGGCTTC TGCGCCATAT CGTGACGAAA GTAGGTGGCT
2341 GAGGAGACAG ACGGCGAGGA CGATGAGGTA GGAGGGGAGC CCGGGCCGCA TTTTATATTG
2401 TAATTATATA TTTTCAATTT TGAAATCCCA AAATATTATC ATATTCTTCC CAATAAACTC
2461 GAGCCCGGGG AATTCGGATC CTCGCGACTG CAGGGTACCT GAGTAGCTAA TTTTTAAACA
2521 AAAATGTGGG AGAATCTAAT TAGTTTTTCT TTACACAATT GACGTACATG AGTCTGAGTT
2581 CCTTGTTTTT GCTAATTATT TCATCCAATT TATTATTCTT GACGATATCG AGATCTTTTG
2641 TATAGGAGTC A
```

```
   1 ATGGAGTCCT CTGCCAAGAG AAAGATGGAC CCTGATAATC CTGACGAGGG CCCTTCCTCC
  61 AAGGTGCCAC GGCCCGAGAC ACCCGTGACC AAGGCCACGA CGTTCCTGCA GACTATGTTG
 121 AGGAAGGAGG TTAACAGTCA GCTGAGTCTG GGAGACCCGC TGTTTCCAGA GTTGGCCGAA
 181 GAATCCCTCA AAACTTTTGA ACAAGTGACC GAGGATTGCA ACGAGAACCC CGAGAAAGAT
 241 GTCCTGGCAG AACTCGTCAA ACAGATTAAG GTTCGAGTGG ACATGGTGCG GCATAGAATC
 301 AAGGAGCACA TGCTGAAAAA ATATACCCAG ACGGAAGAGA AATTCACTGG CGCCTTTAAT
 361 ATGATGGGAG GATGTTTGCA GAATGCCTTA GATATCTTAG ATAAGGTTCA TGAGCCTTTC
 421 GAGGAGATGA AGTGTATTGG GCTAACTATG CAGAGCATGT ATGAGAACTA CATTGTACCT
 481 GAGGATAAGC GGGAGATGTG GATGGCTTGT ATTAAGGAGC TGCATGATGT GAGCAAGGGC
 541 GCCGCTAACA AGTTGGGGGG TGCACTGCAG GCTAAGGCCC GTGCTAAAAA GGATGAACTT
 601 AGGAGAAAGA TGATGTATAT GTGCTACAGG AATATAGAGT TCTTTACCAA GAACTCAGCC
 661 TTCCCTAAGA CCACCAATGG CTGCAGTCAG GCCATGGCGG CACTGCAGAA CTTGCCTCAG
 721 TGCTCCCCTG ATGAGATTAT GGCTTATGCC CAGAAAATAT TTAAGATTTT GGATGAGGAG
 781 AGAGACAAGG TGCTCACGCA CATTGATCAC ATATTTATGG ATATCCTCAC TACATGTGTG
 841 GAAACAATGT GTAATGAGTA CAAGGTCACT AGTGACGCTT GTATGATGAC CATGTACGGG
 901 GGCATCTCTC TCTTAAGTGA GTTCTGTCGG GTGCTGTGCT GCTATGTCTT AGAGGAGACT
 961 AGTGTGATGC TGGCCAAGCG GCCTCTGATA ACCAAGCCTG AGGTTATCAG TGTAATGAAG
1021 CGCCGCATTG AGGAGATCTG CATGAAGGTC TTTGCCCAGT ACATTCTGGG GGCCGATCCT
1081 CTGAGAGTCT GCTCTCCTAG TGTGGATGAC CTACGGGCCA TCGCCGAGGA GTCAGATGAG
1141 GAAGAGGCTA TTGTAGCCTA CACTTTGGCC ACCGCTGGTG TCAGCTCCTC TGATTCTCTG
1201 GTGTCACCCC CAGAGTCCCC TGTACCCGCG ACTATCCCTC TGTCCTCAGT AATTGTGGCT
1261 GAGAACAGTG ATCAGGAAGA AAGTGAGCAG AGTGATGAGG AAGAGGAGGA GGGTGCTCAG
1321 GAGGAGCGGG AGGACACTGT GTCTGTCAAG TCTGAGCCAG TGTCTGAGAT AGAGGAAGTT
1381 GCCCCAGAGG AAGAGGAGGA TGGTGCTGAG GAACCCACCG CCTCTGGAGG TAAGAGTACC
1441 CACCCTATGG TGACTAGAAG CAAGGCTGAC CAGTAA
```

FIG. 25

```
   1 ATATAATCCT CCACCAAAAT AGAGAATATA TATATCATCA TTTCATGATG TATACTACTG
  61 ACATAGTTTC AATGTGAACT TTTCACTTTC TTGCCGGTTA TGAAGAATAT TTTTTATTTT
 121 AATGGTCATT ACTAATCGTA TATTATAATT GAAAATGAAT TAGTTTAATA TGACGCTCGT
 181 CATGGGATCC ATAAAAATTA CTGGTCAGCC TTGCTTCTAG TCACCATAGG GTGGGTACTC
 241 TTACCTCCAG AGGCGGTGGG TTCCTCAGCA CCATCCTCCT CTTCCTCTGG GGCAACTTCC
 301 TCTATCTCAG ACACTGGCTC AGACTTGACA GACACAGTGT CCTCCCGCTC CTCCTGAGCA
 361 CCCTCCTCCT CTTCCTCATC ACTCTGCTCA CTTTCTTCCT GATCACTGTT CTCAGCCACA
 421 ATTACTGAGG ACAGAGGGAT AGTCGCGGGT ACAGGGGACT CTGGGGGTGA CACCAGAGAA
 481 TCAGAGGAGC TGACACCAGC GGTGGCCAAA GTGTAGGCTA CAATAGCCTC TTCCTCATCT
 541 GACTCCTCGG CGATGGCCCG TAGGTCATCC ACACTAGGAG AGCAGACTCT CAGAGGATCG
 601 GCCCCAGAA TGTACTGGGC AAAGACCTTC ATGCAGATCT CCTCAATGCG GCGCTTCATT
 661 ACACTGATAA CCTCAGGCTT GGTTATCAGA GGCCGCTTGG CCAGCATCAC ACTAGTCTCC
 721 TCTAAGACAT AGCAGCACAG CACCCGACAG AACTCACTTA AGAGAGAGAT GCCCCGTAC
 781 ATGGTCATCA TACAAGCGTC ACTAGTGACC TTGTACTCAT TACACATTGT TTCCACACAT
 841 GTAGTGAGGA TATCCATAAA TATGTGATCA ATGTGCGTGA GCACCTTGTC TCTCTCCTCA
 901 TCCAAAATCT TAAATATTTT CTGGGCATAA GCCATAATCT CATCAGGGGA GCACTGAGGC
 961 AAGTTCTGCA GTGCCGCCAT GGCCTGACTG CAGCCATTGG TGGTCTTAGG GAAGGCTGAG
1021 TTCTTGGTAA AGAACTCTAT ATTCCTGTAG CACATATACA TCATCTTTCT CCTAAGTTCA
1081 TCCTTTTTAG CACGGGCCTT AGCCTGCAGT GCACCCCCA ACTTGTTAGC GGCGCCCTTG
1141 CTCACATCAT GCAGCTCCTT AATACAAGCC ATCCACATCT CCCGCTTATC CTCAGGTACA
1201 ATGTAGTTCT CATACATGCT CTGCATAGTT AGCCCAATAC ACTTCATCTC CTCGAAAGGC
1261 TCATGAACCT TATCTAAGAT ATCTAAGGCA TTCTGCAAAC ATCCTCCCAT CATATTAAAG
1321 GCGCCAGTGA ATTTCTCTTC CGTCTGGGTA TATTTTTCA GCATGTGCTC CTTGATTCTA
1381 TGCCGCACCA TGTCCACTCG AACCTTAATC TGTTTGACGA GTTCTGCCAG GACATCTTTC
1441 TCGGGGTTCT CGTTGCAATC CTCGGTCACT TGTTCAAAAG TTTTGAGGGA TTCTTCGGCC
1501 AACTCTGGAA ACAGCGGGTC TCCCAGACTC AGCTGACTGT TAACCTCCTT CCTCAACATA
1561 GTCTGCAGGA ACGTCGTGGC CTTGGTCACG GGTGTCTCGG CCGTGGCAC CTTGGAGGAA
1621 GGGCCCTCGT CAGGATTATC AGGGTCCATC TTTCTCTTGG CAGAGGACTC CATTACGATA
1681 CAAACTTAAC GGATATCGCG ATAATGAAAT AATTTATGAT TATTTCTCGC TTTCAATTTA
1741 ACACAACCCT CAAGAACCTT TGTATTTATT TTCACTTTTT AAGTATAGAA TAAAGAGATC
1801 CTGCTGTGGT AGATTCTGTG ACGCTAAGAA TAAGAATAAG AAGGAAGATG TAGAAGAGGG
1861 AAGAGAAGGA TGTTACAATT ATAAGAACCT TAATGATCTG GATGAATCCG AAGCACGTGT
1921 AGAATTTGGA CCATTATATA TGATAAATGA AGAAAAATCA GACATAAATA CATTG
```

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGATAAAAA TTACTGGTCA GCCTTGCTTC TAGTCACCAT AGGGTGGGTA CTCTTACCTC
 481 CAGAGGCGGT GGGTTCCTCA GCACCATCCT CCTCTTCCTC TGGGGCAACT TCCTCTATCT
 541 CAGACACTGG CTCAGACTTG ACAGACACAG TGTCCTCCCG CTCCTCCTGA GCACCCTCCT
 601 CCTCTTCCTC ATCACTCTGC TCACTTTCTT CCTGATCACT GTTCTCAGCC ACAATTACTG
 661 AGGACAGAGG GATAGTCGCG GGTACAGGGG ACTCTGGGGG TGACACCAGA GAATCAGAGG
 721 AGCTGACACC AGCGGTGGCC AAAGTGTAGG CTACAATAGC CTCTTCCTCA TCTGACTCCT
 781 CGGCGATGGC CCGTAGGTCA TCCACACTAG GAGAGCAGAC TCTCAGAGGA TCGGCCCCCA
 841 GAATGTACTG GGCAAAGACC TTCATGCAGA TCTCCTCAAT GCGGCGCTTC ATTACACTGA
 901 TAACCTCAGG CTTGGTTATC AGAGGCCGCT TGGCCAGCAT CACACTAGTC TCCTCTAAGA
 961 CATAGCAGCA CAGCACCCGA CAGAACTCAC TTAAGAGAGA GATGCCCCCG TACATGGTCA
1021 TCATACAAGC GTCACTAGTG ACCTTGTACT CATTACACAT TGTTTCCACA CATGTAGTGA
1081 GGATATCCAT AAATATGTGA TCAATGTGCG TGAGCACCTT GTCTCTCTCC TCATCCAAAA
1141 TCTTAAATAT TTTCTGGGCA TAAGCCATAA TCTCATCAGG GGAGCACTGA GGCAAGTTCT
1201 GCAGTGCCGC CATGGCCTGA CTGCAGCCAT TGGTGGTCTT AGGGAAGGCT GAGTTCTTGG
1261 TAAAGAACTC TATATTCCTG TAGCACATAT ACATCATCTT TCTCCTAAGT TCATCCTTTT
1321 TAGCACGGGC CTTAGCCTGC AGTGCACCCC CCAACTTGTT AGCGGCGCCC TTGCTCACAT
1381 CATGCAGCTC CTTAATACAA GCCATCCACA TCTCCGCTT ATCCTCAGGT ACAATGTAGT
1441 TCTCATACAT GCTCTGCATA GTTAGCCCAA TACACTTCAT CTCCTCGAAA GGCTCATGAA
1501 CCTTATCTAA GATATCTAAG GCATTCTGCA AACATCCTCC CATCATATTA AAGGCGCCAG
1561 TGAATTTCTC TTCCGTCTGG GTATATTTTT TCAGCATGTG CTCCTTGATT CTATGCCGCA
1621 CCATGTCCAC TCGAACCTTA ATCTGTTTGA CGAGTTCTGC CAGGACATCT TTCTCGGGGT
1681 TCTCGTTGCA ATCCTCGGTC ACTTGTTCAA AAGTTTTGAG GGATTCTTCG GCCAACTCTG
1741 GAAACAGCGG GTCTCCCAGA CTCAGCTGAC TGTTAACCTC CTTCCTCAAC ATAGTCTGCA
1801 GGAACGTCGT GGCCTTGGTC ACGGGTGTCT CGGGCCGTGG CACCTTGGAG GAAGGGCCCT
1861 CGTCAGGATT ATCAGGGTCC ATCTTTCTCT TGGCAGAGGA CTCCATTACG ATACAAACTT
1921 AACGGATATC GCGATAATGA ATAATTTTAT GATTATTCT CGCTTTCAAT TTAACACAAC
1981 CCTCAAGAAC CTTTGTATTT ATTTTCACTT TTTAAGTATA GAATAAAGAA GCTCTAATTA
2041 ATTAAGCTAC AAATAGTTTC GTTTTCACCT TGTCTAATAA CTAATTAATT AACCCCGATA
2101 GCTGATTAGT TTTTGTTAAC AAAAATGTGG GAGAATCTAA TTAGTTTTTC TTTACACAAT
2161 TGACGTACAT GAGTCTGAGT TCCTTGTTTT TGCTAATTAT TTCATCCAAT TTATTATTCT
2221 TGACGATATC GAGATCTTTT GTATAGGAGT CAGACTTGTA TTCAACATGC TTTTCTATAA
2281 TCATCTTAGT TATTTCGGCA TCATCCAATA GTACATTTTC CAGATTAACA GAGTAGATAT
2341 TAATGTCGTA TTTGAACAGA GCCTGTAACA TCTCAATGTC TTTATTATCT ATAGCCAATT
2401 TAATGTCCGG AATGAAGAGA AGGGAATTAT TGGTGTTTGT CGACGTCATA TAGTCGAGCA
2461 AGAGAATCAT CATATCCACG TGTCCATTTT TTATAGTGGT GTGAATACAA CTAAGGAGAA
2521 TAGCCAGATC AAAAGTAGAT GGTATTTCTG AAAGAAAGTA TGATACAATA CTTACATCAT
2581 TAAGCATGAC GGCATGATAA AATGAAGTTT TCCATCCAGT TTTCCCATAG AACATCAGTC
2641 TCCAATTTTT CTTAAACAGT TTCACCGTTT GCATGTTACC ACTATCAACC GCATAATACA
2701 ATGCGGTGTT TCCTTTGTCA TCAAATTGTG AATCATCCAT TCCACTGAAT AGCAAAATCT
2761 TTACTATTTT GGTATCTTCT AATGTGGCTG CCTGATGTAA TGGAAATTCA TTCTCTAGAA
2821 GATTTTCAA TGCTCCAGCG TTCAACAACG TACATACTAG ACGCACGTTA TTATCAGCTA
2881 TTGCATAATA CAAGGCACTA TGTCCATGGA CATCCGCCTT AAATGTATCT TTACTAGAGA
2941 GAAAGCTTTT CAGCTGCTTA GACTTCCAAG TATTAATTCG TGACAGATCC ATGTCTGAAA
3001 CGAGACGCTA ATTAGTGTAT ATTTTTCAT TTTTTATAAT TTGTCTATAT TGCACCAGAA
3061 TTAATAATAT CTCTAATAGA TCTAATTTAA TTAATTTAT ATAACTTATT TTTTGAATAT
```

```
3121 ACTTTTAATT AACAAAAGAG TTAAGTTACT CATATGGACG CCGTCCAGTC TGAACATCAA
3181 TCTTTTTAGC CAGAGATATC ATAGCCGCTC TTAGAGTTTC AGCGTGATTT TCCAACCTAA
3241 ATAGAACTTC ATCGTTGCGT TTACAACACT TTTCTATTTG TTCAAACTTT GTTGTTACAT
3301 TAGTAATCTT TTTTTCCAAA TTAGTTAGCC GTTGTTTGAG AGTTTCCTCA TTGTCGTCTT
3361 CATCGGCTTT AACAATTGCT TCGCGTTTAG CCTCCTGGCT GTTCTTATCA GCCTTTGTAG
3421 AAAAAAATTC AGTTGCTGGA ATTGCAAGAT CGTCATCTCC GGGGAAAAGA GTTCCGTCCA
3481 TTTAAAGCCG CGGGAATTC
```

FIG.27B

```
   1 ATGGAGTCCT CTGCCAAGAG AAAGATGGAC CCTGATAATC CTGACGAGGG CCCTTCCTCC
  61 AAGGTGCCAC GGCCCGAGAC ACCCGTGACC AAGGCCACGA CGTTCCTGCA GACTATGTTG
 121 AGGAAGGAGG TTAACAGTCA GCTGAGTCTG GGAGACCCGC TGTTTCCAGA GTTGGCCGAA
 181 GAATCCCTCA AAACTTTTGA ACAAGTGACC GAGGATTGCA ACGAGAACCC CGAGAAAGAT
 241 GTCCTGGCAG AACTCGTCAA ACAGATTAAG GTTCGAGTGG ACATGGTGCG GCATAGAATC
 301 AAGGAGCACA TGCTGAAAAA ATATACCCAG ACGGAAGAGA AATTCACTGG CGCCTTTAAT
 361 ATGATGGGAG GATGTTTGCA GAATGCCTTA GATATCTTAG ATAAGGTTCA TGAGCCTTTC
 421 GAGGAGATGA AGTGTATTGG GCTAACTATG CAGAGCATGT ATGAGAACTA CATTGTACCT
 481 GAGGATAAGC GGGAGATGTG GATGGCTTGT ATTAAGGAGC TGCATGATGT GAGCAAGGGC
 541 GCCGCTAACA AGTTGGGGGG TGCACTGCAG GCTAAGGCCC GTGCTAAAAA GGATGAACTT
 601 AGGAGAAAGA TGATGTATAT GTGCTACAGG AATATAGAGT TCTTTACCAA GAACTCAGCC
 661 TTCCCTAAGA CCACCAATGG CTGCAGTCAG GCCATGGCGG CACTGCAGAA CTTGCCTCAG
 721 TGCTCCCCTG ATGAGATTAT GGCTTATGCC CAGAAAATAT TTAAGATTTT GGATGAGGAG
 781 AGAGACAAGG TGCTCACGCA CATTGATCAC ATATTTATGG ATATCCTCAC TACATGTGTG
 841 GAAACAATGT GTAATGAGTA CAAGGTCACT AGTGTGATGC TGGCCAAGCG GCCTCTGATA
 901 ACCAAGCCTG AGGTTATCAG TGTAATGAAG CGCCGCATTG AGGAGATCTG CATGAAGGTC
 961 TTTGCCCAGT ACATTCTGGG GGCCGATCCT CTGAGAGTCT GCTCTCCTAG TGTGGATGAC
1021 CTACGGGCCA TCGCCGAGGA GTCAGATGAG GAAGAGGCTA TTGTAGCCTA CACTTTGGCC
1081 ACCGCTGGTG TCAGCTCCTC TGATTCTCTG GTGTCACCCC CAGAGTCCCC TGTACCCGCG
1141 ACTATCCCTC TGTCCTCAGT AATTGTGGCT GAGAACAGTG ATCAGGAAGA AAGTGAGCAG
1201 AGTGATGAGG AAGAGGAGGA GGGTGCTCAG GAGGAGCGGG AGGACACTGT GTCTGTCAAG
1261 TCTGAGCCAG TGTCTGAGAT AGAGGAAGTT GCCCCAGAGG AAGAGGAGGA TGGTGCTGAG
1321 GAACCCACCG CCTCTGGAGG TAAGAGTACC CACCCTATGG TGACTAGAAG CAAGGCTGAC
1381 CAGTAA
```

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGATAAAAA TTACTGGTCA GCCTTGCTTC TAGTCACCAT AGGGTGGGTA CTCTTACCTC
 481 CAGAGGCGGT GGGTTCCTCA GCACCATCCT CCTCTTCCTC TGGGGCAACT TCCTCTATCT
 541 CAGACACTGG CTCAGACTTG ACAGACACAG TGTCCTCCCG CTCCTCCTGA GCACCCTCCT
 601 CCTCTTCCTC ATCACTCTGC TCACTTTCTT CCTGATCACT GTTCTCAGCC ACAATTACTG
 661 AGGACAGAGG GATAGTCGCG GGTACAGGGG ACTCTGGGGG TGACACCAGA GAATCAGAGG
 721 AGCTGACACC AGCGGTGGCC AAAGTGTAGG CTACAATAGC CTCTTCCTCA TCTGACTCCT
 781 CGGCGATGGC CCGTAGGTCA TCCACACTAG GAGAGCAGAC TCTCAGAGGA TCGGCCCCCA
 841 GAATGTACTG GGCAAAGACC TTCATGCAGA TCTCCTCAAT GCGGCGCTTC ATTACACTGA
 901 TAACCTCAGG CTTGGTTATC AGAGGCCGCT TGGCCAGCAT CACACTAGTG ACCTTGTACT
 961 CATTACACAT TGTTTCCACA CATGTAGTGA GGATATCCAT AAATATGTGA TCAATGTGCG
1021 TGAGCACCTT GTCTCTCTCC TCATCCAAAA TCTTAAATAT TTTCTGGGCA TAAGCCATAA
1081 TCTCATCAGG GGAGCACTGA GGCAAGTTCT GCAGTGCCGC CATGGCCTGA CTGCAGCCAT
1141 TGGTGGTCTT AGGGAAGGCT GAGTTCTTGG TAAAGAACTC TATATTCCTG TAGCACATAT
1201 ACATCATCTT TCTCCTAAGT TCATCCTTTT TAGCACGGGC CTTAGCCTGC AGTGCACCCC
1261 CCAACTTGTT AGCGGCGCCC TTGCTCACAT CATGCAGCTC CTTAATACAA GCCATCCACA
1321 TCTCCCGCTT ATCCTCAGGT ACAATGTAGT TCTCATACAT GCTCTGCATA GTTAGCCCAA
1381 TACACTTCAT CTCCTCGAAA GGCTCATGAA CCTTATCTAA GATATCTAAG GCATTCTGCA
1441 AACATCCTCC CATCATATTA AAGGCGCCAG TGAATTTCTC TTCCGTCTGG GTATATTTTT
1501 TCAGCATGTG CTCCTTGATT CTATGCCGCA CCATGTCCAC TCGAACCTTA ATCTGTTTGA
1561 CGAGTTCTGC CAGGACATCT TTCTCGGGGT TCTCGTTGCA ATCCTCGGTC ACTTGTTCAA
1621 AAGTTTTGAG GGATTCTTCG GCCAACTCTG GAAACAGCGG GTCTCCCAGA CTCAGCTGAC
1681 TGTTAACCTC CTTCCTCAAC ATAGTCTGCA GGAACGTCGT GGCCTTGGTC ACGGGTGTCT
1741 CGGGCCGTGG CACCTTGGAG GAAGGGCCCT CGTCAGGATT ATCAGGGTCC ATCTTTCTCT
1801 TGGCAGAGGA CTCCATTACG ATACAAACTT AACGGATATC GCGATAATGA AATAATTTAT
1861 GATTATTTCT CGCTTTCAAT TTAACACAAC CCTCAAGAAC CTTTGTATTT ATTTTCACTT
1921 TTAAGTATA GAATAAAGAA GCTCTAATTA ATTAAGCTAC AAATAGTTTC GTTTTCACCT
1981 TGTCTAATAA CTAATTAATT AACCCCGATA GCTGATTAGT TTTTGTTAAC AAAAATGTGG
2041 GAGAATCTAA TTAGTTTTTC TTTACACAAT TGACGTACAT GAGTCTGAGT TCCTTGTTTT
2101 TGCTAATTAT TTCATCCAAT TTATTATTCT TGACGATATC GAGATCTTTT GTATAGGAGT
2161 CAGACTTGTA TTCAACATGC TTTTCTATAA TCATCTTAGT TATTTCGGCA TCATCCAATA
2221 GTACATTTTC CAGATTAACA GAGTAGATAT TAATGTCGTA TTTGAACAGA GCCTGTAACA
2281 TCTCAATGTC TTTATTATCT ATAGCCAATT TAATGTCCGG AATGAAGAGA AGGGAATTAT
2341 TGGTGTTTGT CGACGTCATA TAGTCGAGCA AGAGAATCAT CATATCCACG TGTCCATTTT
2401 TTATAGTGGT GTGAATACAA CTAAGGAGAA TAGCCAGATC AAAAGTAGAT GGTATTTCTG
2461 AAAGAAAGTA TGATACAATA CTTACATCAT TAAGCATGAC GGCATGATAA AATGAAGTTT
2521 TCCATCCAGT TTTCCCATAG AACATCAGTC TCCAATTTTT CTTAAACAGT TTCACCGTTT
2581 GCATGTTACC ACTATCAACC GCATAATACA ATGCGGTGTT TCCTTTGTCA TCAAATTGTG
2641 AATCATCCAT TCCACTGAAT AGCAAAATCT TTACTATTTT GGTATCTTCT AATGTGGCTG
2701 CCTGATGTAA TGGAAATTCA TTCTCTAGAA GATTTTCAA TGCTCCAGCG TTCAACAACG
2761 TACATACTAG ACGCACGTTA TTATCAGCTA TTGCATAATA CAAGGCACTA TGTCCATGGA
2821 CATCCGCCTT AAATGTATCT TTACTAGAGA GAAAGCTTTT CAGCTGCTTA GACTTCCAAG
2881 TATTAATTCG TGACAGATCC ATGTCTGAAA CGAGACGCTA ATTAGTGTAT ATTTTTTCAT
2941 TTTTTATAAT TTTGTCATAT TGCACCAGAA TTAATAATAT CTCTAATAGA TCTAATTTAA
3001 TTTAATTTAT ATAACTTATT TTTGAATAT ACTTTTAATT AACAAAAGAG TTAAGTTACT
3061 CATATGGACG CCGTCCAGTC TGAACATCAA TCTTTTTAGC CAGAGATATC ATAGCCGCTC
```

```
3121 TTAGAGTTTC AGCGTGATTT TCCAACCTAA ATAGAACTTC ATCGTTGCGT TTACAACACT
3181 TTTCTATTTG TTCAAACTTT GTTGTTACAT TAGTAATCTT TTTTTCCAAA TTAGTTAGCC
3241 GTTGTTTGAG AGTTTCCTCA TTGTCGTCTT CATCGGCTTT AACAATTGCT TCGCGTTTAG
3301 CCTCCTGGCT GTTCTTATCA GCCTTTGTAG AAAAAAATTC AGTTGCTGGA ATTGCAAGAT
3361 CGTCATCTCC GGGGAAAAGA GTTCCGTCCA TTTAAAGCCG CGGGAATTC
```

FIG. 29B

```
   1 ATGAAACAGA TTAAGGTTCG AGTGGACATG GTGCGGCATA GAATCAAGGA GCACATGCTG
  61 AAAAAATATA CCCAGACGGA AGAGAAATTC ACTGGCGCCT TTAATATGAT GGGAGGATGT
 121 TTGCAGAATG CCTTAGATAT CTTAGATAAG GTTCATGAGC CTTTCGAGGA GATGAAGTGT
 181 ATTGGGCTAA CTATGCAGAG CATGTATGAG AACTACATTG TACCTGAGGA TAAGCGGGAG
 241 ATGTGGATGG CTTGTATTAA GGAGCTGCAT GATGTGAGCA AGGGCGCCGC TAACAAGTTG
 301 GGGGGTGCAC TGCAGGCTAA GGCCCGTGCT AAAAAGGATG AACTTAGGAG AAAGATGATG
 361 TATATGTGCT ACAGGAATAT AGAGTTCTTT ACCAAGAACT CAGCCTTCCC TAAGACCACC
 421 AATGGCTGCA GTCAGGCCAT GGCGGCACTG CAGAACTTGC CTCAGTGCTC CCCTGATGAG
 481 ATTATGGCTT ATGCCCAGAA AATATTTAAG ATTTTGGATG AGGAGAGAGA CAAGGTGCTC
 541 ACGCACATTG ATCACATATT TATGGATATC CTCACTACAT GTGTGGAAAC AATGTGTAAT
 601 GAGTACAAGG TCACTAGTGA CGCTTGTATG ATGACCATGT ACGGGGCAT CTCTCTCTTA
 661 AGTGAGTTCT GTCGGGTGCT GTGCTGCTAT GTCTTAGAGG AGACTAGTGT GATGCTGGCC
 721 AAGCGGCCTC TGATAACCAA GCCTGAGGTT ATCAGTGTAA TGAAGCGCCG CATTGAGGAG
 781 ATCTGCATGA AGGTCTTTGC CCAGTACATT CTGGGGGCCG ATCCTCTGAG AGTCTGCTCT
 841 CCTAGTGTGG ATGACCTACG GGCCATCGCC GAGGAGTCAG ATGAGGAAGA GGCTATTGTA
 901 GCCTACACTT TGGCCACCGC TGGTGTCAGC TCCTCTGATT CTCTGGTGTC ACCCCAGAG
 961 TCCCCTGTAC CCGCGACTAT CCCTCTGTCC TCAGTAATTG TGGCTGAGAA CAGTGATCAG
1021 GAAGAAAGTG AGCAGAGTGA TGAGGAAGAG GAGGAGGGTG CTCAGGAGGA GCGGGAGGAC
1081 ACTGTGTCTG TCAAGTCTGA GCCAGTGTCT GAGATAGAGG AAGTTGCCCC AGAGGAAGAG
1141 GAGGATGGTG CTGAGGAACC CACCGCCTCT GGAGGTAAGA GTACCCACCC TATGGTGACT
1201 AGAAGCAAGG CTGACCAGTA A
```

FIG. 30

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCCT TCTTTATTCT ATACTTAAAA AGTGAAAATA
 661 AATACAAAGG TTCTTGAGGG TTGTGTTAAA TTGAAAGCGA GAAATAATCA TAAATTATTT
 721 CATTATCGCG ATATCCGTTA AGTTTGTATC GTAATGAAAC AGATTAAGGT TCGAGTGGAC
 781 ATGGTGCGGC ATAGAATCAA GGAGCACATG CTGAAAAAAT ATACCCAGAC GGAAGAGAAA
 841 TTCACTGGCG CCTTTAATAT GATGGGAGGA TGTTTGCAGA ATGCCTTAGA TATCTTAGAT
 901 AAGGTTCATG AGCCTTTCGA GGAGATGAAG TGTATTGGGC TAACTATGCA GAGCATGTAT
 961 GAGAACTACA TTGTACCTGA GGATAAGCGG GAGATGTGGA TGGCTTGTAT TAAGGAGCTG
1021 CATGATGTGA GCAAGGGCGC CGCTAACAAG TTGGGGGGTG CACTGCAGGC TAAGGCCCGT
1081 GCTAAAAAGG ATGAACTTAG GAGAAAGATG ATGTATATGT GCTACAGGAA TATAGAGTTC
1141 TTTACCAAGA ACTCAGCCTT CCCTAAGACC ACCAATGGCT GCAGTCAGGC CATGGCGGCA
1201 CTGCAGAACT TGCCTCAGTG CTCCCCTGAT GAGATTATGG CTTATGCCCA GAAAATATTT
1261 AAGATTTTGG ATGAGGAGAG AGACAAGGTG CTCACGCACA TTGATCACAT ATTTATGGAT
1321 ATCCTCACTA CATGTGTGGA AACAATGTGT AATGAGTACA AGGTCACTAG TGACGCTTGT
1381 ATGATGACCA TGTACGGGGG CATCTCTCTC TTAAGTGAGT TCTGTCGGGT GCTGTGCTGC
1441 TATGTCTTAG AGGAGACTAG TGTGATGCTG GCCAAGCGGC CTCTGATAAC CAAGCCTGAG
1501 GTTATCAGTG TAATGAAGCG CCGCATTGAG GAGATCTGCA TGAAGGTCTT TGCCCAGTAC
1561 ATTCTGGGGG CCGATCCTCT GAGAGTCTGC TCTCCTAGTG TGGATGACCT ACGGGCCATC
1621 GCCGAGGAGT CAGATGAGGA AGAGGCTATT GTAGCCTACA CTTTGGCCAC CGCTGGTGTC
1681 AGCTCCTCTG ATTCTCTGGT GTCACCCCA GAGTCCCCTG TACCCGCGAC TATCCCTCTG
1741 TCCTCAGTAA TTGTGGCTGA AACAGTGAT CAGGAAGAAA GTGAGCAGAG TGATGAGGAA
1801 GAGGAGGAGG GTGCTCAGGA GGAGCGGGAG GACACTGTGT CTGTCAAGTC TGAGCCAGTG
1861 TCTGAGATAG AGGAAGTTGC CCCAGAGGAA GAGGAGGATG GTGCTGAGGA ACCCACCGCC
1921 TCTGGAGGTA AGAGTACCCA CCCTATGGTG ACTAGAAGCA AGGCTGACCA GTAATTTTTA
1981 TCTCGAGCCC GGGAGATCTT AGCTAACTGA TTTTTCTGGG AAAAAAATTA TTTAACTTTT
2041 CATTAATAGG GATTTGACGT ATGTAGCGTA CAAAATTATC GTTCCTGGTA TATAGATAAA
2101 GAGTCCTATA TATTTGAAAA TCGTTACGGC TCGATTAAAC TTTAATGATT GCATAGTGAA
2161 TATATCATTA GGATTTAACT CCTTGACTAT CATGGCGGCG CCAGAAATTA CCATCAAAAG
2221 CATTAATACA GTTATGCCGA TCGCAGTTAG AACGGTTATA GCATCCACCA TTTATATCTA
2281 AAAATTAGAT CAAAGAATAT GTGACAAAGT CCTAGTTGTA TACTGAGAAT TGACGAAACA
2341 ATGTTTCTTA CATATTTTT TCTTATTAGT AACTGACTTA ATAGTAGGAA CTGGAAAGCT
2401 AGACTTGATT ATTCTATAAG TATAGATACC CTTCCAGATA ATGTTCTCTT TGATAAAAGT
2461 TCCAGAAAAT GTAGAATTTT TTAAAAAGTT ATCTTTTGCT ATTACCAAGA TTGTGTTTAG
2521 ACGCTTATTA TTAATATGAG TAATGAAATC CACACCGCCT CTAGATATGG GGAATTC
```

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGAA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC CGGGTTAATT AATTAGTCAT CAGGCAGGGC GAGAACGAGA
1621 CTATCTGCTC GTTAATTAAT TAGAGCTTCT TTATTCTATA CTTAAAAAGT GAAAATAAAT
1681 ACAAAGGTTC TTGAGGGTTG TGTTAAATTG AAAGCGAGAA ATAATCATAA ATTATTTCAT
1741 TATCGCGATA TCCGTTAAGT TTGTATCGTA ATGAAACAGA TTAAGGTTCG AGTGGACATG
1801 GTGCGGCATA GAATCAAGGA GCACATGCTG AAAAAATATA CCCAGACGGA AGAGAAATTC
1861 ACTGGCGCCT TTAATATGAT GGGAGGATGT TTGCAGAATG CCTTAGATAT CTTAGATAAG
1921 GTTCATGAGC CTTTCGAGGA GATGAAGTGT ATTGGGCTAA CTATGCAGAG CATGTATGAG
1981 AACTACATTG TACCTGAGGA TAAGCGGGAG ATGTGGATGG CTTGTATTAA GGAGCTGCAT
2041 GATGTGAGCA AGGGCGCCGC TAACAAGTTG GGGGGTGCAC TGCAGGCTAA GGCCCGTGCT
2101 AAAAAGGATG AACTTAGGAG AAAGATGATG TATATGTGCT ACAGGAATAT AGAGTTCTTT
2161 ACCAAGAACT CAGCCTTCCC TAAGACCACC AATGGCTGCA GTCAGGCCAT GGCGGCACTG
2221 CAGAACTTGC CTCAGTGCTC CCCTGATGAG ATTATGGCTT ATGCCCAGAA AATATTTAAG
2281 ATTTTGGATG AGGAGAGAGA CAAGGTGCTC ACGCACATTG ATCACATATT TATGGATATC
2341 CTCACTACAT GTGTGGAAAC AATGTGTAAT GAGTACAAGG TCACTAGTGA CGCTTGTATG
2401 ATGACCATGT ACGGGGGCAT CTCTCTCTTA AGTGAGTTCT GTCGGGTGCT GTGCTGCTAT
2461 GTCTTAGAGG AGACTAGTGT GATGCTGGCC AAGCGGCCTC TGATAACCAA GCCTGAGGTT
2521 ATCAGTGTAA TGAAGCGCCG CATTGAGGAG ATCTGCATGA AGGTCTTTGC CCAGTACATT
2581 CTGGGGGCCG ATCCTCTGAG AGTCTGCTCT CCTAGTGTGG ATGACCTACG GGCCATCGCC
2641 GAGGAGTCAG ATGAGGAAGA GGCTATTGTA GCCTACACTT TGGCCACCGC TGGTGTCAGC
2701 TCCTCTGATT CTCTGGTGTC ACCCCAGAG TCCCCTGTAC CCGCGACTAT CCCTCTGTCC
2761 TCAGTAATTG TGGCTGAGAA CAGTGATCAG GAAGAAAGTG AGCAGAGTGA TGAGGAAGAG
2821 GAGGAGGGTG CTCAGGAGGA GCGGGAGGAC ACTGTGTCTG TCAAGTCTGA GCCAGTGTCT
2881 GAGATAGAGG AAGTTGCCCC AGAGGAAGAG GAGGATGGTG CTGAGGAACC CACCGCCTCT
2941 GGAGGTAAGA GTACCCACCC TATGGTGACT AGAAGCAAGG CTGACCAGTA ATTTTTATCT
3001 CGAGTCTAGA ATCGATCCCG GGTTTTATG ACTAGTTAAT CACGGCCGCT TATAAAGATC
3061 TAAAATGCAT AATTTCTAAA TAATGAAAAA AAGTACATC ATGAGCAACG CGTTAGTATA
```

```
3121 TTTTACAATG GAGATTAACG CTCTATACCG TTCTATGTTT ATTGATTCAG ATGATGTTTT
3181 AGAAAAGAAA GTTATTGAAT ATGAAAACTT TAATGAAGAT GAAGATGACG ACGATGATTA
3241 TTGTTGTAAA TCTGTTTTAG ATGAAGAAGA TGACGCGCTA AAGTATACTA TGGTTACAAA
3301 GTATAAGTCT ATACTACTAA TGGCGACTTG TGCAAGAAGG TATAGTATAG TGAAAATGTT
3361 GTTAGATTAT GATTATGAAA AACCAAATAA ATCAGATCCA TATCTAAAGG TATCTCCTTT
3421 GCACATAATT TCATCTATTC CTAGTTTAGA ATACCTGCAG
```

FIG.32B

```
   1 ATGACGACGT TCCTGCAGAC TATGTTGAGG AAGGAGGTTA ACAGTCAGCT GAGTCTGGGA
  61 GACCCGCTGT TTCCAGAGTT GGCCGAAGAA TCCCTCAAAA CTTTTGAACA AGTGACCGAG
 121 GATTGCAACG AGAACCCCGA GAAAGATGTC CTGGCAGAAC TCGTCAAACA GATTAAGGTT
 181 CGAGTGGACA TGGTGCGGCA TAGAATCAAG GAGCACATGC TGAAAAAATA TACCCAGACG
 241 GAAGAGAAAT TCACTGGCGC CTTTAATATG ATGGGAGGAT GTTTGCAGAA TGCCTTAGAT
 301 ATCTTAGATA AGGTTCATGA GCCTTTCGAG GAGATGAAGT GTATTGGGCT AACTATGCAG
 361 AGCATGTATG AGAACTACAT TGTACCTGAG GATAAGCGGG AGATGTGGAT GGCTTGTATT
 421 AAGGAGCTGC ATGATGTGAG CAAGGGCGCC GCTAACAAGT GGGGGGTGC ACTGCAGGCT
 481 AAGGCCCGTG CTAAAAAGGA TGAACTTAGG AGAAAGATGA TGTATATGTG CTACAGGAAT
 541 ATAGAGTTCT TTACCAAGAA CTCAGCCTTC CCTAAGACCA CCAATGGCTG CAGTCAGGCC
 601 ATGGCGGCAC TGCAGAACTT GCCTCAGTGC TCCCCTGATG AGATTATGGC TTATGCCCAG
 661 AAAATATTTA AGATTTTGGA TGAGGAGAGA GACAAGGTGC TCACGCACAT TGATCACATA
 721 TTTATGGATA TCCTCACTAC ATGTGTGGAA ACAATGTGTA ATGAGTACAA GGTCACTAGT
 781 GACGCTTGTA TGATGACCAT GTACGGGGGC ATCTCTCTCT TAAGTGAGTT CTGTCGGGTG
 841 CTGTGCTGCT ATGTCTTAGA GGAGACTAGT GTGATGCTGG CCAAGCGGCC TCTGATAACC
 901 AAGCCTGAGG TTATCAGTGT AATGAAGCGC CGCATTGAGG AGATCTGCAT GAAGGTCTTT
 961 GCCCAGTACA TTCTGGGGGC CGATCCTCTG AGTCTGCT CTCCTAGTGT GGATGACCTA
1021 CGGGCCATCG CCGAGGAGTC AGATGAGGAA GAGGCTATTG TAGCCTACAC TTTGGCCACC
1081 GCTGGTGTCA GCTCCTCTGA TTCTCTGGTG TCACCCCCAG AGTCCCTGT ACCCGCGACT
1141 ATCCCTCTGT CCTCAGTAAT TGTGGCTGAG AACAGTGATC AGGAAGAAAG TGAGCAGAGT
1201 GATGAGGAAG AGGAGGAGGG TGCTCAGGAG GAGCGGGAGG ACACTGTGTC TGTCAAGTCT
1261 GAGCCAGTGT CTGAGATAGA GGAAGTTGCC CCAGAGGAAG AGGAGGATGG TGCTGAGGAA
1321 CCCACCGCCT CTGGAGGTAA GAGTACCCAC CCTATGGTGA CTAGAAGCAA GGCTGACCAG
1381 TAA
```

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCCT TCTTTATTCT ATACTTAAAA AGTGAAAATA
 661 AATACAAAGG TTCTTGAGGG TTGTGTTAAA TTGAAAGCGA GAAATAATCA TAAATTATTT
 721 CATTATCGCG ATATCCGTTA AGTTTGTATC GTAATGACGA CGTTCCTGCA GACTATGTTG
 781 AGGAAGGAGG TTAACAGTCA GCTGAGTCTG GGAGACCCGC TGTTTCCAGA GTTGGCCGAA
 841 GAATCCCTCA AAACTTTTGA ACAAGTGACC GAGGATTGCA ACGAGAACCC CGAGAAAGAT
 901 GTCCTGGCAG AACTCGTCAA ACAGATTAAG GTTCGAGTGG ACATGGTGCG GCATAGAATC
 961 AAGGAGCACA TGCTGAAAAA ATATACCCAG ACGGAAGAGA AATTCACTGG CGCCTTTAAT
1021 ATGATGGGAG GATGTTTGCA GAATGCCTTA GATATCTTAG ATAAGGTTCA TGAGCCTTTC
1081 GAGGAGATGA AGTGTATTGG GCTAACTATG CAGAGCATGT ATGAGAACTA CATTGTACCT
1141 GAGGATAAGC GGGAGATGTG GATGGCTTGT ATTAAGGAGC TGCATGATGT GAGCAAGGGC
1201 GCCGCTAACA AGTTGGGGGG TGCACTGCAG GCTAAGGCCC GTGCTAAAAA GGATGAACTT
1261 AGGAGAAAGA TGATGTATAT GTGCTACAGG AATATAGAGT TCTTTACCAA GAACTCAGCC
1321 TTCCCTAAGA CCACCAATGG CTGCAGTCAG GCCATGGCGG CACTGCAGAA CTTGCCTCAG
1381 TGCTCCCCTG ATGAGATTAT GGCTTATGCC CAGAAAATAT TTAAGATTTT GGATGAGGAG
1441 AGAGACAAGG TGCTCACGCA CATTGATCAC ATATTTATGG ATATCCTCAC TACATGTGTG
1501 GAAACAATGT GTAATGAGTA CAAGGTCACT AGTGACGCTT GTATGATGAC CATGTACGGG
1561 GGCATCTCTC TCTTAAGTGA GTTCTGTCGG GTGCTGTGCT GCTATGTCTT AGAGGAGACT
1621 AGTGTGATGC TGGCCAAGCG GCCTCTGATA ACCAAGCCTG AGGTTATCAG TGTAATGAAG
1681 CGCCGCATTG AGGAGATCTG CATGAAGGTC TTTGCCCAGT ACATTCTGGG GGCCGATCCT
1741 CTGAGAGTCT GCTCTCCTAG TGTGGATGAC CTACGGGCCA TCGCCGAGGA GTCAGATGAG
1801 GAAGAGGCTA TTGTAGCCTA CACTTTGGCC ACCGCTGGTG TCAGCTCCTC TGATTCTCTG
1861 GTGTCACCCC CAGAGTCCCC TGTACCCGCG ACTATCCCTC TGTCCTCAGT AATTGTGGCT
1921 GAGAACAGTG ATCAGGAAGA AAGTGAGCAG AGTGATGAGG AAGAGGAGGA GGGTGCTCAG
1981 GAGGAGCGGG AGGACACTGT GTCTGTCAAG TCTGAGCCAG TGTCTGAGAT AGAGGAAGTT
2041 GCCCCAGAGG AAGAGGAGGA TGGTGCTGAG GAACCCACCG CCTCTGGAGG TAAGAGTACC
2101 CACCCTATGG TGACTAGAAG CAAGGCTGAC CAGTAATTTT TATCTCGAGC CCGGGAGATC
2161 TTAGCTAACT GATTTTCTG GGAAAAAAAT TATTTAACTT TTCATTAATA GGGATTTGAC
2221 GTATGTAGCG TACAAAATTA TCGTTCCTGG TATATAGATA AAGAGTCCTA TATATTTGAA
2281 AATCGTTACG GCTCGATTAA ACTTTAATGA TTGCATAGTG AATATATCAT TAGGATTTAA
2341 CTCCTTGACT ATCATGGCGG CGCCAGAAAT TACCATCAAA AGCATTAATA CAGTTATGCC
2401 GATCGCAGTT AGAACGGTTA TAGCATCCAC CATTTATATC TAAAAATTAG ATCAAAGAAT
2461 ATGTGACAAA GTCCAGTTG TATACTGAGA ATTGACGAAA CAATGTTTCT TACATATTTT
2521 TTTCTTATTA GTAACTGACT TAATAGTAGG AACTGGAAAG CTAGACTTGA TTATTCTATA
2581 AGTATAGATA CCCTTCCAGA TAATGTTCTC TTTGATAAAA GTTCCAGAAA ATGTAGAATT
2641 TTTTAAAAAG TTATCTTTTG CTATTACCAA GATTGTGTTT AGACGCTTAT TATTAATATG
2701 AGTAATGAAA TCCACACCGC CTCTAGATAT GGGGAATTC
```

FIG.35A

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AAGAAATGAA AATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC CGGGTTAATT AATTAGTCAT CAGGCAGGGC GAGAACGAGA
1621 CTATCTGCTC GTTAATTAAT TAGAGCTTCT TTATTCTATA CTTAAAAAGT GAAAATAAAT
1681 ACAAAGGTTC TTGAGGGTTG TGTTAAATTG AAAGCGAGAA ATAATCATAA ATTATTTCAT
1741 TATCGCGATA TCCGTTAAGT TTGTATCGTA ATGACGACGT TCCTGCAGAC TATGTTGAGG
1801 AAGGAGGTTA ACAGTCAGCT GAGTCTGGGA GACCCGCTGT TTCCAGAGTT GGCCGAAGAA
1861 TCCCTCAAAA CTTTTGAACA AGTGACCGAG GATTGCAACG AGAACCCCGA GAAAGATGTC
1921 CTGGCAGAAC TCGTCAAACA GATTAAGGTT CGAGTGGACA TGGTGCGGCA TAGAATCAAG
1981 GAGCACATGC TGAAAAAATA TACCCAGACG GAAGAGAAAT TCACTGGCGC CTTTAATATG
2041 ATGGGAGGAT GTTTGCAGAA TGCCTTAGAT ATCTTAGATA AGGTTCATGA GCCTTTCGAG
2101 GAGATGAAGT GTATTGGGCT AACTATGCAG AGCATGTATG AGAACTACAT TGTACCTGAG
2161 GATAAGCGGG AGATGTGGAT GGCTTGTATT AAGGAGCTGC ATGATGTGAG CAAGGGCGCC
2221 GCTAACAAGT TGGGGGGTGC ACTGCAGGCT AAGGCCCGTG CTAAAAAGGA TGAACTTAGG
2281 AGAAAGATGA TGTATATGTG CTACAGGAAT ATAGATTTCT TTACCAAGAA CTCAGCCTTC
2341 CCTAAGACCA CCAATGGCTG CAGTCAGGCC ATGGCGGCAC TGCAGAACTT GCCTCAGTGC
2401 TCCCCTGATG AGATTATGGC TTATGCCCAG AAAATATTTA AGATTTTGGA TGAGGAGAGA
2461 GACAAGGTGC TCACGCACAT TGATCACATA TTTATGGATA TCCTCACTAC ATGTGTGGAA
2521 ACAATGTGTA ATGAGTACAA GGTCACTAGT GACGCTTGTA TGATGACCAT GTACGGGGGC
2581 ATCTCTCTCT TAAGTGAGTT CTGTCGGGTG CTGTGCTGCT ATGTCTTAGA GGAGACTAGT
2641 GTGATGCTGG CCAAGCGGCC TCTGATAACC AAGCCTGAGG TTATCAGTGT AATGAAGCGC
2701 CGCATTGAGG AGATCTGCAT GAAGGTCTTT GCCCAGTACA TTCTGGGGGC CGATCCTCTG
2761 AGAGTCTGCT CTCCTAGTGT GGATGACCTA CGGGCCATCG CCGAGGAGTC AGATGAGGAA
2821 GAGGCTATTG TAGCCTACAC TTTGGCCACC GCTGGTGTCA GCTCCTCTGA TTCTCTGGTG
2881 TCACCCCCAG AGTCCCTGGT ACCCGCGACT ATCCCTCTGT CCTCAGTAAT GTGGCTGAG
2941 AACAGTGATC AGGAAGAAAG TGAGCAGAGT GATGAGGAAG AGGAGGAGGG TGCTCAGGAG
3001 GAGCGGGAGG ACACTGTGTC TGTCAAGTCT GAGCCAGTGT CTGAGATAGA GGAAGTTGCC
3061 CCAGAGGAAG AGGAGGATGG TGCTGAGGAA CCCACCGCCT CTGGAGGTAA GAGTACCCAC
```

```
3121 CCTATGGTGA CTAGAAGCAA GGCTGACCAG TAATTTTTAT CTCGAGTCTA GAATCGATCC
3181 CGGGTTTTTA TGACTAGTTA ATCACGGCCG CTTATAAAGA TCTAAAATGC ATAATTTCTA
3241 AATAATGAAA AAAAAGTACA TCATGAGCAA CGCGTTAGTA TATTTTACAA TGGAGATTAA
3301 CGCTCTATAC CGTTCTATGT TTATTGATTC AGATGATGTT TTAGAAAAGA AAGTTATTGA
3361 ATATGAAAAC TTTAATGAAG ATGAAGATGA CGACGATGAT TATTGTTGTA AATCTGTTTT
3421 AGATGAAGAA GATGACGCGC TAAAGTATAC TATGGTTACA AAGTATAAGT CTATACTACT
3481 AATGGCGACT TGTGCAAGAA GGTATAGTAT AGTGAAAATG TTGTTAGATT ATGATTATGA
3541 AAAACCAAAT AAATCAGATC CATATCTAAA GGTATCTCCT TTGCACATAA TTTCATCTAT
3601 TCCTAGTTTA GAATACCTGC AG
```

FIG.35B

```
   1 ATGGAGTCGC GCGGTCGCCG TTGTCCCGAA ATGATATCCG TACTGGGTCC CATTTCGGGG
  61 CACGTGCTGA AAGCCGTGTT TAGTCGCGGC GACACGCCGG TGCTGCCGCA CGAGACGCGA
 121 CTCCTGCAGA CGGGTATCCA CGTGCGCGTG AGCCAGCCCT CGCTGATCCT GGTGTCGCAG
 181 TACACGCCCG ACTCGACGCC ATGCCACCGC GGCGACAATC AGCTGCAGGT GCAGCACACG
 241 TACTTTACGG GCAGCGAGGT GGAGAACGTG TCGGTCAACG TGCACAACCC CACGGGCCGG
 301 AGCATCTGCC CCAGCCAAGA GCCCATGTCG ATCTATGTGT ACGCGCTGCC GCTCAAGATG
 361 CTGAACATCC CCAGCATCAA CGTGCACCAC TACCCGTCGG CGGCCGAGCG CAAACACCGA
 421 CACCTGCCCG TAGCTGACGC TGTGATTCAC GCGTCGGGCA AGCAGATGTG GCAGGCGCGT
 481 CTCACGGTCT CGGGACTGGC CTGGACGCGT CAGCAGAACC AGTGGAAAGA GCCCGACGTC
 541 TACTACACGT CAGCGTTCGT GTTTCCCACC AAGGACGTGG CACTGCGGCA CGTGGTGTGC
 601 GCGCACGAGC TGGTTTGCTC CATGGAGAAC ACGCGCGCAA CCAAGATGCA GGTGATAGGT
 661 GACCAGTACG TCAAGGTGTA CCTGGAGTCC TTCTGCGAGG ACGTGCCCTC CGGCAAGCTC
 721 TTTATGCACG TCACGCTGGG CTCTGACGTG GAAGAGGACC TGACGATGAC CCGCAACCCG
 781 CAACCCTTCA TGCGCCCCCA CGAGCGCAAC GGCTTTACGG TGTTGTGTCC CAAAAATATG
 841 ATAATCAAAC CGGGCAAGAT CTCGCACATC ATGCTGGATG TGGCTTTTAC CTCACACGAG
 901 CATTTTGGGC TGCTGTGTCC CAAGAGCATC CCGGGCCTGA GCATCTCAGG TAACCTATTG
 961 ATGAACGGGC AGCAGATCTT CCTGGAGGTG CAAGCGATAC GCGAGACCGT GGAACTATTG
1021 CAGTACGATC CCGTGGCTGC GCTCTTCTTT TTCGATATCG ACTTGCTGCT GCAGCGCGGG
1081 CCTCAGTACA GCGAACACCC CACCTTCACC AGCCAGTATC GCATCCAGGG CAAGCTTGAG
1141 TACCGACACA CCTGGGACCG GCACGACGAG GGTGCCGCCC AGGGCGACGA CGACGTCTGG
1201 ACCAGCGGAT CGGACTCCGA CGAGGAACTC GTAACCACCG AGCGCAAGAC GCCCCGCGTT
1261 ACCGGCGGCG CGCCATGGCG GGCGCCTCC ACTTCCGCGG CCGCAAACG CAAATCAGCA
1321 TCCTCGGCGA CGGCGTGCAC GGCGGGCGTT ATGACACGCG GCCGCCTTAA GGCCGAGTCC
1381 ACCGTCGCGC CCGAAGAGGA CACCGACGAG GATTCCGACA ACGAAATCCA CAATCCGGCC
1441 GTGTTCACCT GGCCGCCCTG GCAGGCCGGC ATCCTGGCCC GCAACCTGGT GCCCATGGTG
1501 GCTACGGTTC AGGGTCAGAA TCTGAAGTAC CAGGAGTTCT CTGGGACGC CAACGACATC
1561 TACCGCATCT TCGCCGAATT GGAAGGCGTA TGGCAGCCCG CTGCGCAACC CAAACGTCGC
1621 CGCCACCGGC AAGACGCCTT GCCCGGGCCA TGCATCGCCT CGACGCCCAA AAAGCACCGA
1681 GGTTGA
```

```
   1 GTCGACGATT GTTCATGATG GCAAGATTTA TATATCTGGA GGTTACAACA ATAGTAGTGT
  61 AGTTAATGTA ATATCGAATC TAGTCCTTAG CTATAATCCG ATATATGATG AATGGACCAA
 121 ATTATCATCA TTAAACATTC CTAGAATTAA TCCCGCTCTA TGGTCAGCGC ATAATAAATT
 181 ATATGTAGGA GGAGGAATAT CTGATGATGT TCGAACTAAT ACATCTGAAA CATACGATAA
 241 AGAAAAAGAT TGTTGGACAT TGGATAATGG TCACGTGTTA CCACGCAATT ATATAATGTA
 301 TAAATGCGAA CCGATTAAAC ATAAATATCC ATTGGAAAAA ACACAGTACA CGAATGATTT
 361 TCTAAAGTAT TTGGAAAGTT TTATAGGTAG TTGATAGAAC AAAATACATA ATTTTGTAAA
 421 AATAAATCAC TTTTTATACT AATATTTAAT TAATTAAGCT TGGTACCCTC GAAGCTTCTT
 481 TATTCTATAC TTAAAAAGTG AAAATAAATA CAAAGGTTCT TGAGGGTTGT GTTAAATTGA
 541 AAGCGAGAAA TAATCATAAA TTATTTCATT ATCGCGATAT CCGTTAAGTT TGTATCGTAA
 601 TGGAGTCGCG CGGTCGCCGT TGTCCCGAAA TGATATCCGT ACTGGGTCCC ATTTCGGGGC
 661 ACGTGCTGAA AGCCGTGTTT AGTCGCGGCG ACACGCCGGT GCTGCCGCAC GAGACGCGAC
 721 TCCTGCAGAC GGGTATCCAC GTGCGCGTGA GCCAGCCCTC GCTGATCCTG GTGTCGCAGT
 781 ACACGCCCGA CTCGACGCCA TGCCACCGCG GCGACAATCA GCTGCAGGTG CAGCACACGT
 841 ACTTTACGGG CAGCGAGGTG GAGAACGTGT CGGTCAACGT GCACAACCCC ACGGGCCGGA
 901 GCATCTGCCC CAGCCAAGAG CCCATGTCGA TCTATGTGTA CGCGCTGCCG CTCAAGATGC
 961 TGAACATCCC CAGCATCAAC GTGCACCACT ACCCGTCGGC GGCCGAGCGC AAACACCGAC
1021 ACCTGCCCGT AGCTGACGCT GTGATTCACG CGTCGGGCAA GCAGATGTGG CAGGCGCGTC
1081 TCACGGTCTC GGGACTGGCC TGGACGCGTC AGCAGAACCA GTGGAAAGAG CCCGACGTCT
1141 ACTACACGTC AGCGTTCGTG TTTCCCACCA AGGACGTGGC ACTGCGGCAC GTGGTGTGCG
1201 CGCACGAGCT GGTTTGCTCC ATGGAGAACA CGCGCGCAAC CAAGATGCAG GTGATAGGTG
1261 ACCAGTACGT CAAGGTGTAC CTGGAGTCCT TCTGCGAGGA CGTGCCCTCC GGCAAGCTCT
1321 TTATGCACGT CACGCTGGGC TCTGACGTGG AAGAGGACCT GACGATGACC CGCAACCCGC
1381 AACCCTTCAT GCGCCCCAC GAGCGCAACG GCTTTACGGT GTTGTGTCCC AAAAATATGA
1441 TAATCAAACC GGGCAAGATC TCGCACATCA TGCTGGATGT GGCTTTTACC TCACACGAGC
1501 ATTTTGGGCT GCTGTGTCCC AAGAGCATCC CGGGCCTGAG CATCTCAGGT AACCTATTGA
1561 TGAACGGGCA GCAGATCTTC CTGGAGGTGC AAGCGATACG CGAGACCGTG GAACTGCGTC
1621 AGTACGATCC CGTGGCTGCG CTCTTCTTTT TCGATATCGA CTTGCTGCTG CAGCGCGGGC
1681 CTCAGTACAG CGAACACCCC ACCTTCACCA GCCAGTATCG CATCCAGGGC AAGCTTGAGT
1741 ACCGACACAC CTGGGACCGG CACGACGAGG GTGCCGCCCA GGGCGACGAC GACGTCTGGA
1801 CCAGCGGATC GGACTCCGAC GAGGAACTCG TAACCACCGA GCGCAAGACG CCCCGCGTTA
1861 CCGGCGGCGG CGCCATGGCG GGCGCCTCCA CTTCCGCGGG CCGCAAACGC AAATCAGCAT
1921 CCTCGGCGAC GGCGTGCACG GCGGGCGTTA TGACACGCGG CCGCCTTAAG GCCGAGTCCA
1981 CCGTCGCGCC CGAAGAGGAC ACCGACGAGG ATTCCGACAA CGAAATCCAC AATCCGGCCG
2041 TGTTCACCTG GCCGCCCTGG CAGGCCGGCA TCCTGGCCCG CAACCTGGTG CCCATGGTGG
2101 CTACGGTTCA GGGTCAGAAT CTGAAGTACC AGGAGTTCTT CTGGGACGCC AACGACATCT
2161 ACCGCATCTT CGCCGAATTG GAAGGCGTAT GGCAGCCCGC TGCGCAACCC AAACGTCGCC
2221 GCCACCGGCA AGACGCCTTG CCCGGGCCAT GCATCGCCTC GACGCCCAAA AAGCACCGAG
2281 GTTGATTTTT ATGGATCCCC CGGGTAGCTA GCTAATTTTT CTTTTACGTA TTATATATGT
2341 AATAAACGTT CACGTAAATA CAAAACAGAG AACAAAGTCT AGATTTTTGA CTTACATAAA
2401 TGTCTGGGAT AGTAAAATCT ATCATATTGA GCGGACCATC TGGTTCAGGA AAGACAGCCA
2461 TAGCCAAAAG ACTATGGGAA TATATTTGGA TTTGTGGTGT CCCATACCAC TAGATTTCCT
2521 CGTCCTATGG AACGAGAAGG TGTCGATTAC CATTACGTTA ACAGAGAGGC CATCTGGAAG
2581 GGAATAGCCG CCGGAAACTT TCTAGAACAT ACTGAGTTTT TAGGAAATAT TTACGGAACT
2641 TCTAAAACTG CTGTGAATAC AGCGGCTATT AATAATCGTA TTTGTGTGAT GGATTTAAAC
2701 ATCGACGGTG TTAGAAGTTT TAAAAATACT TACCTGCAGA AGCTT
```

FIG. 38A

```
   1 AAGCTTCTAT CAAAAGTCTT AATGAGTTAG GTGTAGATAG TATAGATATT ACTACAAAGG
  61 TATTCATATT TCCTATCAAT TCTAAAGTAG ATGATATTAA TAACTCAAAG ATGATGATAG
 121 TAGATAATAG ATACGCTCAT ATAATGACTG CAAATTTGGA CGGTTCACAT TTTAATCATC
 181 ACGCGTTCAT AAGTTTCAAC TGCATAGATC AAAATCTCAC TAAAAAGATA GCCGATGTAT
 241 TTGAGAGAGA TTGGACATCT AACTACGCTA AAGAAATTAC AGTTATAAAT AATACATAAT
 301 GGATTTGTT ATCATCAGTT ATATTTAACA TAAGTACAAT AAAAAGTATT AAATAAAAAT
 361 ACTTACTTAC GAAAAAATGT CATTATTACA AAAACTATAT TTTACAGAAC AATCTATAGT
 421 AGAGTCCTTT AAGAGTTATA ATTTAAAAGA TAACCATAAT GTAATATTTA CCACATCAGA
 481 TGTTGATACT GTTGTAGTAA TAAATGAAGA TAATGTACTG TTATCTACAA GATTATTATC
 541 ATTTGATAAA ATTCTGTTTT TTAACTCCTT TAATAACGGT TTATCAAAAT ACGAAACTAT
 601 TAGTGATACA ATATTAGATA TAGATACTCA TAATTATTAT ATACCTAGTT CTTCTTCTTT
 661 GTTAGATATT CTAAAAAAAA GAGCGTGTGA TTTAGAATTA GAAGATCTAA ATTATGCGTT
 721 AATAGGAGAC AATAGTAACT TATATTATAA AGATATGACT TACATGAATA ATTGGTTATT
 781 TACTAAAGGA TTATTAGATT ACAAGTTTGT ATTATTGCGC GATGTAGATA AATGTTACAA
 841 ACAGTATAAT AAAAAGAATA CTATAATAGA TATAATACAT CGCGATAACA GACAGTATAA
 901 CATATGGGTT AAAAATGTTA TAGAATACTG TTCTCCTGGC TATATATTAT GGTTACATGA
 961 TCTAAAAGCC GCTGCTGAAG ATGATTGGTT AAGATACGAT AACCGTATAA ACGAATTATC
1021 TGCGGATAAA TTATACACTT TCGAGTTCAT AGTTATATTA GAAAATAATA TAAAACATTT
1081 ACGAGTAGGT ACAATAATTG TACATCCAAA CAAGATAATA GCTAATGGTA CATCTAATAA
1141 TATACTTACT GATTTTCTAT CTTACGTAGA AGAACTAATA TATCATCATA ATTCATCTAT
1201 AATATTGGCC GGATATTTTT TAGAATTCTT TGAGACCACT ATTTTATCAG AATTTATTTC
1261 TTCATCTTCT GAATGGGTAA TGAATAGTAA CTGTTTAGTA CACCTGAAAA CAGGGTATGA
1321 AGCTATACTC TTTGATGCTA GTTTATTTTT CCAACTCTCT ACTAAAAGCA ATTATGTAAA
1381 ATATTGGACA AAGAAAACTT TGCAGTATAA GAACTTTTTT AAAGACGGTA AACAGTTAGC
1441 AAAATATATA ATTAAGAAAG ATAGTCAGGT GATAGATAGA GTATGTTATT TACACGCAGC
1501 TGTATATAAT CACGTAACTT ACTTAATGGA TACGTTTAAA ATTCCTGGTT TTGATTTTAA
1561 ATTCTCCGGA ATGATAGATA TACTACTGTT TGGAATATTG CATAAGGATA ATGAGAATAT
1621 ATTTTATCCG AAACGTGTTT CTGTAACTAA TATAATATCA GAATCTATCT ATGCAGATTT
1681 TTACTTTATA TCAGATGTTA ATAAATTCAG TAAAAAGATA GAATATAAAA CTATGTTTCC
1741 TATACTCGCA GAAAACTACT ATCCAAAAGG AAGGCCCTAT TTTACACATA CATCTAACGA
1801 AGATCTTCTG TCTATCTGTT TATGCGAAGT AACAGTTTGT AAAGATATAA AAAATCCATT
1861 ATTATATTCT AAAAAGGATA TATCAGCAAA ACGATTCATA GGTTTATTTA CATCTGTCGA
1921 TATAAATACG GCTGTTGAGT TAAGAGGATA TAAAATAAGA GTAATAGGAT GTTTAGAATG
1981 GCCTGAAAAG ATAAAAATAT TTAATTCTAA TCCTACATAC ATTAGATTAT TACTAACAGA
2041 AAGACGTTTA GATATTCTAC ATTCCTATCT GCTTAAATTT AATATAACAG AGGATATAGC
2101 TACCAGAGAT GGAGTCAGAA ATAATTTACC TATAATTTCT TTTATCGTCA GTTATTGTAG
2161 ATCGTATACT TATAAATTAC TAAATTGCCA TATGTACAAT TCGTGTAAGA TAACAAAGTG
2221 TAAATATAAT CAGGTAATAT ATAATCCTAT ATAGGAGTAT ATATAATTGA AAAAGTAAAA
2281 ATAAATCATA TAATAATGAA ACGAAATATC AGTAATAGAC AGGAACTGGC AGATTCTTCT
2341 TCTAATGAAG TAAGTACTGC TAAATCTCCA AAATTAGATA AAAATGATAC AGCAAATACA
2401 GCTTCATTCA ACGAATTACC TTTTAATTTT TTCAGACACA CCTTATTACA AACTAACTAA
2461 GTCAGATGAT GAGAAAGTAA ATATAAATTT AACTTATGGG TATAATATAA TAAAGATTCA
2521 TGATATTAAT AATTTACTTA ACGATGTTAA TAGACTTATT CCATCAACCC CTTCAAACCT
2581 TTCTGGATAT TATAAAATAC CAGTTAATGA TATTAAAATA GATTGTTTAA GAGATGTAAA
2641 TAATTATTTG GAGGTAAAGG ATATAAAATT AGTCTATCTT TCACATGGAA ATGAATTACC
2701 TAATATTAAT AATTATGATA GGAATTTTTT AGGATTTACA GCTGTTATAT GTATCAACAA
2761 TACAGGCAGA TCTATGGTTA TGGTAAAACA CTGTAACGGG AAGCAGCATT CTATGGTAAC
2821 TGGCCTATGT TTAATAGCCA GATCATTTTA CTCTATAAAC ATTTTACCAC AAATAATAGG
2881 ATCCTCTAGA TATTTAATAT TATATCTAAC AACAACAAAA AAATTTAACG ATGTATGGCC
2941 AGAAGTATTT TCTACTAATA AAGATAAAGA TAGTCTATCT TATCTACAAG ATATGAAAGA
3001 AGATAATCAT TTAGTAGTAG CTACTAATAT GGAAAGAAAT GTATACAAAA ACGTGGAAGC
3061 TTTTATATTA AATAGCATAT TACTAGAAGA TTTAAAATCT AGACTTAGTA TAACAAAACA
```

```
3121 GTTAAATGCC AATATCGATT CTATATTTCA TCATAACAGT AGTACATTAA TCAGTGATAT
3181 ACTGAAACGA TCTACAGACT CAACTATGCA AGGAATAAGC AATATGCCAA TTATGTCTAA
3241 TATTTTAACT TTAGAACTAA AACGATTCTA CCAATACTAA AAATAGGATA CGTGATAGGC
3301 TGTTAAAAGC TGCAATAAAT AGTAAGGATG TAGAAGAAAT ACTTTGTTCT ATACCTTCGG
3361 AGGAAAGAAC TTTAGAACAA CTTAAGTTTA ATCAAACTTG TATTTATGAA CACTATAAAA
3421 AAATTATGGA AGATACAAGT AAAAGAATGG ATGTTGAATG TCGTAGTTTA GAACATAACT
3481 ATACGGCTAA CTTATATAAA GTGTACGGAC AAAACGAATA TATGATTACT TATATACTAG
3541 CTCTCATAAG TAGGATTAAT AATATTATAG AAACTTTAAA ATATAATCTG GTGGGCTAG
3601 ACGAATCTAC AATACGTAAT ATAAATTATA TAATTTCACA AAGAACAAAA AAAAATCAGT
3661 TTCTAATACC TTATAGATAA ACTATATTTT TTACCACTGA CAACAC
```

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTGTTAT CATCAGTTAT ATTTAACATA AGTACAATAA AAAGTATTAA
 361 ATAAAAATAC TTACTTACGA AAAAATGACT AATTAGCTAT AAAAACCCAA CAAAAACTAA
 421 TCAGCTATCG GGGTTAATTA ATTAGTTATT AGACAAGGTG AAAACGAAAC TATTTGTAGC
 481 TTAATTAATT AGAGCTTCTT TATTCTATAC TTAAAAAGTG AAAATAAATA CAAAGGTTCT
 541 TGAGGGTTGT GTTAAATTGA AAGCGAGAAA TAATCATAAA TTATTTCATT ATCGCGATAT
 601 CCGTTAAGTT TGTATCGTAA TGGAGTCGCG CGGTCGCCGT TGTCCCGAAA TGATATCCGT
 661 ACTGGGTCCC ATTTCGGGGC ACGTGCTGAA AGCCGTGTTT AGTCGCGGCG ACACGCCGGT
 721 GCTGCCGCAC GAGACGCGAC TCCTGCAGAC GGGTATCCAC GTGCGCGTGA GCCAGCCCTC
 781 GCTGATCCTG GTGTCGCAGT ACACGCCCGA CTCGACGCCA TGCCACCGCG GCGACAATCA
 841 GCTGCAGGTG CAGCACACGT ACTTTACGGG CAGCGAGGTG GAGAACGTGT CGGTCAACGT
 901 GCACAACCCC ACGGGCCGGA GCATCTGCCC CAGCCAAGAG CCCATGTCGA TCTATGTGTA
 961 CGCGCTGCCG CTCAAGATGC TGAACATCCC CAGCATCAAC GTGCACCACT ACCCGTCGGC
1021 GGCCGAGCGC AAACACCGAC ACCTGCCCGT AGCTGACGCT GTGATTCACG CGTCGGGCAA
1081 GCAGATGTGG CAGGCGCGTC TCACGGTCTC GGGACTGGCC TGGACGCGTC AGCAGAACCA
1141 GTGGAAAGAG CCCGACGTCT ACTACACGTC AGCGTTCGTG TTTCCCACCA AGGACGTGGC
1201 ACTGCGGCAC GTGGTGTGCG CGCACGAGCT GGTTTGCTCC ATGGAGAACA CGCGCGCAAC
1261 CAAGATGCAG GTGATAGGTG ACCAGTACGT CAAGGTGTAC CTGGAGTCCT TCTGCGAGGA
1321 CGTGCCCTCC GGCAAGCTCT TTATGCACGT CACGCTGGGC TCTGACGTGG AAGAGGACCT
1381 GACGATGACC CGCAACCCGC AACCCTTCAT GCGCCCCCAC GAGCGCAACG GCTTTACGGT
1441 GTTGTGTCCC AAAAATATGA TAATCAAACC GGGCAAGATC TCGCACATCA TGCTGGATGT
1501 GGCTTTTACC TCACACGAGC ATTTTGGGCT GCTGTGTCCC AAGAGCATCC CGGGCCTGAG
1561 CATCTCAGGT AACCTATTGA TGAACGGGCA GCAGATCTTC CTGGAGGTGC AAGCGATACG
1621 CGAGACCGTG GAACTGCGTC AGTACGATCC CGTGGCTGCG CTCTTCTTTT TCGATATCGA
1681 CTTGCTGCTG CAGCGCGGGC TCAGTACAG CGAACACCCC ACCTTCACCA GCCAGTATCG
1741 CATCCAGGGC AAGCTTGAGT ACCGACACAC CTGGGACCGG CACGACGAGG GTGCCGCCCA
1801 GGGCGACGAC GACGTCTGGA CCAGCGGATC GGACTCCGAC GAGGAACTCG TAACCACCGA
1861 GCGCAAGACG CCCCGCGTTA CCGGCGGCGG CGCCATGGCG GGCGCCTCCA CTTCCGCGGG
1921 CCGCAAACGC AAATCAGCAT CCTCGGCGAC GGCGTGCACG GCGGGCGTTA TGACACGCGG
1981 CCGCCTTAAG GCCGAGTCCA CCGTCGCGCC CGAAGAGGAC ACCGACGAGG ATTCCGACAA
2041 CGAAATCCAC AATCCGGCCG TGTTCACCTG GCCGCCCTGG CAGGCCGGCA TCCTGGCCCG
2101 CAACCTGGTG CCCATGGTGG CTACGGTTCA GGGTCAGAAT CTGAAGTACC AGGAGTTCTT
2161 CTGGGACGCC AACGACATCT ACCGCATCTT CGCCGAATTG GAAGGCGTAT GGCAGCCCGC
2221 TGCGCAACCC AAACGTCGCC GCCACCGGCA AGACGCCTTG CCCGGGCCAT GCATCGCCTC
2281 GACGCCCAAA AAGCACCGAG GTTGATTTTT ATGGATCCGG TACCCTCGAG GAATTCTTTT
2341 TATTGATTAA CTAGTCAAAT GAGTATATAT AATTGAAAAA GTAAATATA AATCATATAA
2401 TAATGAAACG AAATATCAGT AATAGACAGG AACTGGCAGA TTCTTCTTCT AATGAAGTAA
2461 GTACTGCTAA ATCTCCAAAA TTAGATAAAA ATGATACAGC AAATACAGCT TCATTCAACG
2521 AATTACCTTT TAATTTTTC AGACACACCT TATTACAAAC TAACTAAGTC AGATGATGAG
2581 AAAGTAAATA TAAATTTAAC TTATGGGTAT AATATAATAA AGATTCATGA TATTAATAAT
2641 TTACTTAACG ATGTTAATAG ACTTATTCCA TCAACCCCTT CAAACCTTTC TGGATATTAT
2701 AAAATACCAG TTAATGATAT TAAAATAGAT TGTTTAAGAG ATGTAAATAA TTATTTGGAG
2761 GTAAGGATA TAAAATTAGT CTATCTTTCA CATGGAAATG AATTACCTAA TATTAATAAT
2821 TATGATAGGA ATTTTTTAGG ATTTACAGCT GTTATATGTA TCAACAATAC AGGCAGATCT
2881 ATGGTTATGG TAAAACACTG TAACGGGAAG CAGCATTCTA TGGTAACTGG CCTATGTTTA
2941 ATAGCCAGAT CATTTTACTC TATAAACATT TTACCACAAA TAATAGGATC CTCTAGATAT
3001 TTAATATTAT ATCTAACAAC AACAAAAAAA TTTAACGATG TATGGCCAGA AGTATTTTCT
3061 ACTAATAAAG ATAAAGATAG TCTATCTTAT CTACAAGATA TGAAAGAAGA TAATCATTTA
```

```
3121 GTAGTAGCTA CTAATATGGA AAGAAATGTA TACAAAAACG TGGAAGCTTT TATATTAAAT
3181 AGCATATTAC TAGAAGATTT AAAATCTAGA CTTAGTATAA CAAAACAGTT AAATGCCAAT
3241 ATCGATTCTA TATTTCATCA TAACAGTAGT ACATTAATCA GTGATATACT GAAACGATCT
3301 ACAGACTCAA CTATGCAAGG AATAAGCAAT ATGCCAATTA TGTCTAATAT TTTAACTTTA
3361 GAACTAAAAC GTTCTACCAA TACTAAAAAT AGGATACGTG ATAGGCTGTT AAAAGCTGCA
3421 ATAAATAGTA AGGATGTAGA AGAAATACTT TGTTCTATAC CTTCGGAGGA AAGAACTTTA
3481 GAACAACTTA AGTTTAATCA AACTTGTATT TATGAAGGTA C
```

FIG. 39B

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGCCCCC TCGAAGCTTC TTTATTCTAT
 181 ACTTAAAAAG TGAAAATAAA TACAAAGGTT CTTGAGGGTT GTGTTAAATT TTTATTCTAT
 241 AATAATCATA AATTATTTCA TTATCGCGAT ATCCGTTAAG TTTGTATCGT GAAAGCGAGA
 301 CGCGGTCGCC GTTGTCCCGA AATGATATCC GTACTGGGTC CCATTTCGGG AATGGAGTCG
 361 AAAGCCGTGT TTAGTCGCGG CGACACGCCG GTGCTGCCGC ACGAGACGCG GCACGTGCTG
 421 ACGGGTATCC ACGTGCGCGT GAGCCAGCCC TCGCTGATCC TGGTGTCGCA ACTCCTGCAG
 481 GACTCGACGC CATGCCACCG CGGCGACAAT CAGCTGCAGG TGCAGCACAC GTACACGCCC
 541 GGCAGCGAGG TGGAGAACGT GTCGGTCAAC GTGCACAACC CCACGGGCCG GTACTTTACG
 601 CCCAGCCAAG AGCCCATGTC GATCTATGTG TACGCGCTGC CGCTCAAGAT GAGCATCTGC
 661 CCCAGCATCA ACGTGCACCA CTACCCGTCG GCGGCCGAGC GCAAACACCG ACACCTGCCC
 721 GTAGCTGACG CTGTGATTCA CGCGTCGGGC AAGCAGATGT GGCAGGCGCG TCTCACGGTC
 781 TCGGGACTGG CCTGGACGCG TCAGCAGAAC CAGTGGAAAG AGCCCGACGT CTACTACACG
 841 TCAGCGTTCG TGTTTCCCAC CAAGGACGTG GCACTGCGGC ACGTGGTGTG CGCGCACGAG
 901 CTGGTTTGCT CCATGGAGAA CACGCGCGCA ACCAAGATGC AGGTGATAGG TGACCAGTAC
 961 GTCAAGGTGT ACCTGGAGTC CTTCTGCGAG GACGTGCCCT CCGGCAAGCT CTTTATGCAC
1021 GTCACGCTGG GCTCTGACGT GGAAGAGGAC CTGACGATGA CCCGCAACCC GCAACCCTTC
1081 ATGCGCCCCC ACGAGCGCAA CGGCTTTACG GTGTTGTGTC CAAAAAATAT GATAATCAAA
1141 CCGGGCAAGA TCTCGCACAT CATGCTGGAT GTGGCTTTTA CCTCACACGA GCATTTTGGG
1201 CTGCTGTGTC CAAGAGCAT CCCGGGCCTG AGCATCTCAG GTAACCTATT GATGAACGGG
1261 CAGCAGATCT TCCTGGAGGT GCAAGCGATA CGCGAGACCG TGGAACTGCG TCAGTACGAT
1321 CCCGTGGCTG CGCTCTTCTT TTTCGATATC GACTTGCTGC TGCAGCGCGG GCCTCAGTAC
1381 AGCGAACACC CCACCTTCAC CAGCCAGTAT CGCATCCAGG GCAAGCTTGA GTACCGACAC
1441 ACCTGGGACC GGCACGACGA GGGTGCCGCC CAGGGCGACG ACGACGTCTG GACCAGCGGA
1501 TCGGACTCCG ACGAGGAACT CGTAACCACC GAGCGCAAGA CGCCCCGCGT TACCGGCGGC
1561 GGCGCCATGG CGGGCGCCTC CACTTCCGCG GGCCGCAAAC GCAAATCAGC ATCCTCGGCG
1621 ACGGCGTGCA CGGCGGGCGT TATGACACGC GGCCGCCTTA AGGCCGAGTC CACCGTCGCG
1681 CCCGAAGAGG ACACCGACGA GGATTCCGAC AACGAAATCC ACAATCCGGC CGTGTTCACC
1741 TGGCCGCCCT GGCAGGCCGG CATCCTGGCC CGCAACCTGG TGCCCATGGT GGCTACGGTT
1801 CAGGGTCAGA ATCTGAAGTA CCAGGAGTTC TTCTGGGACG CCAACGACAT CTACCGCATC
1861 TTCGCCGAAT GGAAGGCGT ATGGCAGCCC GCTGCGCAAC CCAAACGTCG CCGCCACCGG
1921 CAAGACGCCT TGCCCGGGCC ATGCATCGCC TCGACGCCCA AAAAGCACCG AGGTTGATTT
1981 TTATGGATCC TCGCGACTGC AGGGTACCTG AGTAGCTAAT TTTTAAACAA AAATGTGGGA
2041 GAATCTAATT AGTTTTTCTT TACACAATTG ACGTACATGA GTCTGAGTTC CTTGTTTTTG
2101 CTAATTATTT CATCCAATTT ATTATTCTTG ACGATATCGA GATCTTTTGT ATAGGAGTCA
```

```
   1 ATGAGTTTGC AGTTTATCGG TCTACAGCGG CGCGATGTGG TGGCCCTGGT CAACTTTCTG
  61 CGCCATCTCA CGCAAAAGCC CGACGTGGAT CTCGAGGCAC ACCCCAAGAT CCTGAAAAAA
 121 TGTGGCGAAA AACGCCTGCA CCGGCGTACG GTGCTGTTCA ACGAGCTCAT GCTTTGGTTG
 181 GGATACTACC GCGAGCTGCG TTTCCACAAC CCCGACCTCT CCTCGGTTCT CGAGGAGTTC
 241 GAGGTGCGTT GCGCGGCCGT GGCGCGTCGC GGCTACACTT ACCCGTTCGG TGATCGTGGT
 301 AAGGCGCGTG ACCACCTGGC TGTGCTAGAC CGTACCGAAT TCGATACGGA CGTACGCCAC
 361 GATGCTGAGA TTGTGGAGCG CGCGCTCGTA AGCGCGGTCA TTCTGGCCAA GATGTCGGTG
 421 CGCGAGACGC TGGTCACAGC CATCGGCCAG ACGGAACCCA TCGCTTTTGT GCACCTCAAG
 481 GATACGGAGG TGCAGCGCAT TGAAGAAAAC CTGGAGGGTG TGCGCCGTAA CATGTTCTGC
 541 GTGAAACCGC TCGACCTTAA CCTGGACCGG CACGCCAACA CGGCGCTGGT CAACGCCGTC
 601 AACAAGCTCG TGTACACGGG CCGTCTCATC ATGAACGTGC GCAGGTCTTG GGAGGAGCTG
 661 GAGCGCAAAT GTCTGGCGCG CATTCAGGAG CGCTGCAAGC TGCTGGTCAA GGAGCTGCGC
 721 ATGTGCCTTT CCTTTGATTC CAACTACTGT CGCAATATCC TCAAACACGC CGTGGAAAAC
 781 GGTGACTCGG CCGACACGCT GCTGGAGCTG CTCATCGAGG ACTTTGACAT CTACGTGGAC
 841 AGCTTCCCGC AGTCGGCGCA CACCTTTTTG GGCGCGCGCC CGCCGTCGTT GGAGTTTGAC
 901 GATGACGCCA ATCTCCTCTC GCTCGGCGGC GGTTCAGCCT CTCGTCGGT ACCCAAGAA
 961 CATGTCCCCA CGCAGCCGCT GGACGGCTGG AGCTGGATCG CCAGTCCCTG GAAGGGACAC
1021 AAACCGTTCC GCTTCGAGGC CCATGGTTCT CTGGCACCGG CCGCCGACGC CCACGCCGCC
1081 CGTTCGGCGC GCGTCGGCTA TTACGACGAA GAGGAAAAGC GTCGCGAGCG GCAGAAACGG
1141 GTGGACGACG AGGTGGTGCA GCGTGAGAAA CAGCAGCTGA AGGCTTGGGA GGAGAGGCAG
1201 CAGAACCTGC AGCAACGTCA GCAGCAACCG CCGCCCCCGA CACGTAAACC GGGCGCCTCC
1261 CGGAGGCTCT TTGGCTCCAG TGCCGATGAG GACGACGACG ATGATGATGA CGAGAAAAAC
1321 ATCTTTACGC CCATCAAGAA ACCGGGAACT AGCGGCAAGG GCGCCGCTAG TGGCAACGGT
1381 GTTTCCAGCA TTTTCAGCGG CATGTTATCC TCGGGCAGTC AGAAACCGAC CAGCGGTCCC
1441 TTGAACATCC CGCAGCAACA ACAGCGTCAC GCGGCTTTCA GTCTCGTCTC CCCGCAGGTA
1501 ACCAAGGCCA GCCCGGGAAG GGTCCGTCGG ACAGCGCGT GGGACGTGAG GCCGCTCACG
1561 GAGACAAGAG GGGATCTTTT CTCGGGCGAC GAGGATTCCG ACAGCTCGGA TGGCTATCCC
1621 CCCAACCGTC AAGATCCGCG TTTCACCGAC ACGCTGGTGG ACATCACGGA TACCGAGACG
1681 AGCGCCAAAC CGCCCGTCAC CACCGCGTAC AAGTTCGAGC AACCGACGTT GACGTTCGGC
1741 GCCGGAGTTA ACGTCCCTGC TGGCGCCGGC GCTGCCATCC TCACGCCGAC GCCTGTCAAT
1801 CCTTCCACGG CCCCCGCTCC GGCCCCGACA CCTACCTTCG CGGGTACCCA AACCCCGGTC
1861 AACGGTAACT CGCCCTGGGC TCCGACGGCG CCGTTGCCCG GGGATATGAA CCCCGCCAAC
1921 TGGCCGCGCG AACGCGCGTG GGCCCTCAAG AATCCTCACC TGGCTTACAA TCCCTTCAGG
1981 ATGCCTACGA CTTCCACGAC TTCTCAAAAC AACGTGTCCA CCACCCCTCG GAGGCCGTCG
2041 ACTCCACGCG CCGCGGTGAC ACAAACAGCG TCTCAGAACG CCGCTGATGA GGTTTGGGCT
2101 TTAAGGGACC AAACTGCAGA GTCACCGGTC GAAGACAGCG AGGAGGAAGA CGACGACTCC
2161 TCGGACACCG GCTCCGTCGT CAGCCTGGGA CACACAACAC CGTCGTCCGA TTACAACGAC
2221 GTCATTTCGC CTCCCAGTCA GACGCCCGAG CAGTCGACGC CGTCCAGAAT ACGTAAAGCT
2281 AAGTTATCGT CTCCAATGAC GACGACATCC ACGAGCCAGA AACCGGTGCT GGGCAAGCGA
2341 GTCGCGACGC CGCACGCGTC CGCCCGAGCG CAGACGGTGA CGTCGACACC GGTTCAGGGA
2401 AGGGTAGAGA AACAGGTATC GGGCACGCCG TCGACGGTAC CCGCCACGCT GTTGCAACCT
2461 CAACCGGCTT CGTCTAAAAC AACGTCATCA AGGAACGTGA CTTCTGGCGC GAGAACCTCT
2521 TCCGCTTCGG CTCGACAGCC GTCAGCCTCG GCGTCCGTTT TGTCGCCCAC GGAGGATGAT
2581 GTCGTGTCCC CCGTCACGTC GCCGCTGTCC ATGCTTTCGT CAGCCTCTCC GTCCCGGCC
2641 AAGAGTGCCC CTCCGTCTCC GGTGAAAGGT CGGGGCAGCC GCGTCGGTGT TCCTTCTTTG
2701 AAACCTACTT TGGGCGGCAA GGCGGTGGTA GGTCGACCGC CCTCGGTCCC CGTGAGCGGT
2761 AGCGCGCCGG GTCGCCTGTC CGGCACCAGC CGGGCCGCCT CGACCACGCC GACGTATCCC
2821 GCGGTAACCA CCGTTTACCC ACCGTCGTCT ACGGCCAAAA GCAGCGTATC GAATGCGCCG
2881 CCTGTGGCCT CCCCCTCCAT CCTGAAACCG GGGGCGAGCG CGGCTTTGCA ATCACGCCGC
2941 TCGACGGGGA CCGCCGCCGT AGGTTCCCCC GTCAAGAGCA CGACGGGCAT GAAAACGGTG
3001 GCTTTCGACC TATCGTCGCC CCAGAAGAGC GGTACGGGGC CGCAACCGGG TTCTGCCGGC
3061 ATGGGGGGCG CCAAAACGCC GTCGGACGCC GTGCAGAACA TCCTCCAAAA GATCGAGAAG
3121 ATTAAGAACA CGGAGGAATA G
```

FIG. 42A

```
   1 AAGCTTGCGG CCGCTCATTA GACAAGCGAA TGAGGGACGA AAACGTGGAG GAGGTATTAA
  61 GTTTGGAGAA ATGGAGAGAG ACTGTTTAAT AGCGCATGGC GCAGCCAATA CTATTACAGA
 121 AGTTTTGAAA GATTCGGAAG AAGATTATCA AGATGTGTAT GTTTGTGAAA ATTGTGGAGA
 181 CATAGCAGCA CAAATCAAGG GTATTAATAC ATGTCTTAGA TGTTCAAAAC TTAATCTCTC
 241 TCCTCTCTTA ACAAAAATTG ATACCACGCA CGTATCTAAA GTATTTCTTA CTCAAATGAA
 301 CGCCAGAGGC GTAAAAGTCA AATTAGATTT CGAACGAAGG CCTCCTTCGT TTTATAAACC
 361 ATTAGATAAA GTTGATCTCA AGCCGTCTTT TCTGGTGTAA TAAAAATTAA TTAATTACTC
 421 GAGCCCCTAG CAATAAAAAC TATTCCTCCG TGTTCTTAAT CTTCTCGATC TTTTGGAGGA
 481 TGTTCTGCAC GGCGTCCGAC GGCGTTTTGG CGCCCCCCAT GCCGGCAGAA CCCGGTTGCG
 541 GCCCCGTACC GCTCTTCTGG GGCGACGATA GGTCGAAAGC CACCGTTTTC ATGCCCGTCG
 601 TGCTCTTGAC GGGGGAACCT ACGGCGGCGG TCCCCGTCGA GCGGCGTGAT TGCAAAGCCG
 661 CGCTCGCCCC CGGTTTCAGG ATGGAGGGGG AGGCCACAGG CGGCGCATTC GATACGCTGC
 721 TTTTGGCCGT AGACGACGGT GGGTAAACGG TGGTTACCGC GGGATACGTC GGCGTGGTCG
 781 AGGCGGCCCG GCTGGTGCCG GACAGGCGAC CCGGCGCGCT ACCGCTCACG GGTACCGAGG
 841 GCGGTCGACC TACCACCGCC TTGCCGCCCA AAGTAGGTTT CAAAGAAGGA ACACCGACGC
 901 GGCTGCCCCG ACCTTTCACC GGAGACGGAG GGGCACTCTT GGCCGGGGAC GGAGAGGCTG
 961 ACGAAAGCAT GGACAGCGGC GACGTGACGG GGGACACGAC ATCATCCTCC GTGGGCGACA
1021 AAACGGACGC CGAGGCTGAC GGCTGTCGAG CCGAAGCGGA AGAGGTTCTC GCGCCAGAAG
1081 TCACGTTCCT TGATGACGTT GTTTTAGACG AAGCCGGTTG AGGTTGCAAC AGCGTGGCGG
1141 GTACCGTCGA CGGCGTGCCC GATACCTGTT TCTCTACCCT TCCCTGAACC GGTGTCGACG
1201 TCACCGTCTG CGCTCGGGCG GACGCGTGCG GCGTCGCGAC TCGCTTGCCC AGCACCGGTT
1261 TCTGGCTCGT GGATGTCGTC GTCATTGGAG ACGATAACTT AGCTTTACGT ATTCTGGACG
1321 GCGTCGACTG CTCGGGCGTC TGACTGGGAG GCGAAATGAC GTCGTTGTAA TCGGACGACG
1381 GTGTTGTGTG TCCCAGGCTG ACGACGGAGC CGGTGTCCGA GGAGTCGTCG TCTTCCTCCT
1441 CGCTGTCTTC GACCGGTGAC TCTGCAGTTT GGTCCCTTAA AGCCCAAACC TCATCAGCGG
1501 CGTTCTGAGA CGCTGTTTGT GTCACCGCGG CGCGTGGAGT CGACGGCCTC CGAGGGGTGG
1561 TGGACACGTT GTTTTGAGAA GTCGTGGAAG TCGTAGGCAT CCTGAAGGGA TTGTAAGCCA
1621 GGTGAGGATT CTTGAGGGCC CACGCGCGTT CGCGCGGCCA GTTGGCGGGG TTCATATCCC
1681 CGGGCAACGG CGCCGTCGGA GCCCAGGGCG AGTTACCGTT GACCGGGGTT TGGGTACCCG
1741 CGAAGGTAGG TGTCGGGGCC GGAGCGGGGG CCGTGGAAGG ATTGACAGGC GTCGGCGTGA
1801 GGATGGCAGC GCCGGCGCCA GCAGGGACGT TAACTCCGGC GCCGAACGTC AACGTCGGTT
1861 GCTCGAACTT GTACGCGGTG GTGACGGGCG GTTTGGCGCT CGTCTCGGTA TCCGTGATGT
1921 CCACCAGCGT GTCGGTGAAA CGCGGATCTT GACGGTTGGG GGGATAGCCA TCCGAGCTGT
1981 CGGAATCCTC GTCGCCCGAG AAAAGATCCC CTCTTGTCTC CGTGAGCGGC CTCACGTCCC
2041 ACGCGCTGTC CCGACGGACC CTTCCCGGGC TGGCCTTGGT TACCTGCGGG GAGACGAGAC
2101 TGAAAGCCGC GTGACGCTGT TGTTGCTGCG GGATGTTCAA GGGACCGCTG GTCGGTTTCT
2161 GACTGCCCGA GGATAACATG CCGCTGAAAA TGCTGGAAAC ACCGTTGCCA CTAGCGGCGC
2221 CCTTGCCGCT AGTTCCCGGT TTCTTGATGG GCGTAAAGAT GTTTTTCTCG TCATCATCAT
2281 CGTCGTCGTC CTCATCGGCA CTGGAGCCAA AGAGCCTCCG GGAGGCGCCC GGTTTACGTG
2341 TCGGGGCGG CGGTTGCTGC TGACGTTGCT GCAGGTTCTG CTGCCTCTCC TCCCAAGCCT
2401 TCAGCTGCTG TTTCTCACGC TGCACCACCT CGTCGTCCAC CCGTTTCTGC CGCTCGCGAC
2461 GCTTTTCCTC TTCGTCGTAA TAGCCGACGC GCGCCGAACG GGCGGCGTGG GCGTCGGCGG
2521 CCGGTGCCAG AGAACCATGG GCCTCGAAGC GGAACGGTTT GTGTCCCTTC CAGGGACTGG
2581 CGATCCAGCT CCAGCCGTCC AGCGGCTGCG TGGGGACATG TTTCTTGGGT ACCGACGAGA
2641 AGGCTGAACC GCCGCCAGC GAGAGGAGAT TGGCGTCATC GTCAAACTCC AACGACGGCG
2701 GGCGCGCGCC CAAAAAGGTG TGCGCCGACT GCGGGAAGCT GTCCACGTAG ATGTCAAAGT
2761 CCTCGATGAG CAGCTCCAGC AGCGTGTCGG CCGAGTCACC GTTTTCCACG GCGTGTTTGA
2821 GGATATTGCG ACAGTAGTTG GAATCAAAGG AAAGGCACAT GCGCAGCTCC TTGACCAGCA
2881 GCTTGCAGCG CTCCTGAATG CGCGCCAGAC ATTTGCGCTC CAGCTCCTCC AAGACCTGC
2941 GCACGTTCAT GATGAGACGG CCCGTGTACA CGAGCTTGTT GACGGCGTTG ACCAGCGCCG
3001 TGTTGGCGTG CCGGTCCAGG TTAAGGTCGA GCGGTTTCAC GCAGAACATG TTACGGCGCA
3061 CACCCTCCAG GTTTTCTTCA ATGCGCTGCA CCTCCGTATC CTTGAGGTGC ACAAAAGCGA
```

```
3121 TGGGTTCCGT CTGGCCGATG GCTGTGACCA GCGTCTCGCG CACCGACATC TTGGCCAGAA
3181 TGACCGCGCT TACGAGCGCG CGCTCCACAA TCTCAGCATC GTGGCGTACG TCCGTATCGA
3241 ATTCGGTACG GTCTAGCACA GCCAGGTGGT CACGCGCCTT ACCACGATCA CCGAACGGGT
3301 AAGTGTAGCC GCGACGCGCC ACGGCCGCGC AACGCACCTC GAACTCCTCG AGAACCGAGG
3361 AGAGGTCGGG GTTGTGGAAA CGCAGCTCGC GGTAGTATCC CAACCAAAGC ATGAGCTCGT
3421 TGAACAGCAC CGTACGCCGG TGCAGGCGTT TTTCGCCACA TTTTTTCAGG ATCTTGGGGT
3481 GTGCCTCGAG ATCCACGTCG GGCTTTTGCG TGAGATGGCG CAGAAAGTTG ACCAGGGCCA
3541 CCACATCGCG CCGCTGTAGA CCGATAAACT GCAAACTCAT TTTATATTGT AATTATATAT
3601 TTTCAATTTT GAAATCCCAA AATATTATCA TATCTTCCCA ATAAAGCTAG GGGAGATCTA
3661 ATTTAATTTA ATTTATATAA CTTATTTTTT GAATATACTT TTAATTAACA AAAGAGTTAA
3721 GTTACTCATA TGGACGCCGT CCAGTCTGAA CATCAATCTT TTTAGCCAGA GATATCATAG
3781 CCGCTCTTAG AGTTTCAGCG TGATTTTCCA ACCTAAATAG AACTTCATCG TTGCGTTTAC
3841 AACACTTTTC TATTTGTTCA AACTTTGTTG TTACATTAGT AATCTTTTTT TCCAAATTAG
3901 TTAGCCGTTG TTTGAGAGTT TCCTCATTGT CGTCTTCATC GGCTTTAACA ATTGCTTCGC
3961 GTTTAGCCTC CTGGCTGTTC TTATCAGCCT TGTAGAAAA AAATTCAGTT GCTGGAATTG
4021 CAAGATCGTC ATCTCCGGGG AAAAGAGTTC CGTCCATTTA AAGCCGCGGG AATTC
```

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCGG GGGATCCTTA
 421 ATTAATTAGT TATTAGACAA GGTGAAAACG AAACTATTTG TAGCTTAATT AATTAGCTGC
 481 AGGGCTGCAG GAATTCTAGC AATAAAAACT ATTCCTCCGT GTTCTTAATC TTTCTCGATCT
 541 TTTGGAGGAT GTTCTGCACG GCGTCCGACG GCGTTTTGGC GCCCCCCATG CCGGCAGAAC
 601 CCGGTTGCGG CCCCGTACCG CTCTTCTGGG GCGACGATAG GTCGAAAGCC ACCGTTTTCA
 661 TGCCCGTCGT GCTCTTGACG GGGGAACCTA CGGCGGCGGT CCCCGTCGAG CGGCGTGATT
 721 GCAAAGCCGC GCTCGCCCCC GGTTTCAGGA TGGAGGGGGA GGCCACAGGC GGCGCATTCG
 781 ATACGCTGCT TTTGGCCGTA GACGACGGTG GGTAAACGGT GGTTACCGCG GGATACGTCG
 841 GCGTGGTCGA GGCGGCCCGG CTGGTGCCGG ACAGGCGACC CGGCGCGCTA CCGCTCACGG
 901 GTACCGAGGG CGGTCGACCT ACCACCGCCT TGCCGCCCAA AGTAGGTTTC AAAGAAGGAA
 961 CACCGACGCG GCTGCCCCGA CCTTTCACCG GAGACGGAGG GGCACTCTTG GCCGGGGACG
1021 GAGAGGCTGA CGAAAGCATG GACAGCGGCG ACGTGACGGG GGACACGACA TCATCCTCCG
1081 TGGGCGACAA AACGGACGCC GAGGCTGACG GCTGTCGAGC CGAAGCGGAA GAGGTTCTCG
1141 CGCCAGAAGT CACGTTCCTT GATGACGTTG TTTTAGACGA AGCCGGTTGA GGTTGCAACA
1201 GCGTGGCGGG TACCGTCGAC GGCGTGCCCG ATACCTGTTT CTCTACCCTT CCCTGAACCG
1261 GTGTCGACGT CACCGTCTGC GCTCGGGCGG ACGCGTGCGG CGTCGCGACT CGCTTGCCCA
1321 GCACCGGTTT CTGGCTCGTG GATGTCGTCG TCATTGGAGA CGATAACTTA GCTTTACGTA
1381 TTCTGGACGG CGTCGACTGC TCGGGCGTCT GACTGGGAGG CGAAATGACG TCGTTGTAAT
1441 CGGACGACGG TGTTGTGTGT CCCAGGCTGA CGACGGAGCC GGTGTCCGAG GAGTCGTCGT
1501 CTTCCTCCTC GCTGTCTTCG ACCGGTGACT CTGCAGTTTG GTCCCTTAAA GCCCAAACCT
1561 CATCAGCGGC GTTCTGAGAC GCTGTTTGTG TCACCGCGGC GCGTGGAGTC GACGGCCTCC
1621 GAGGGGTGGT GGACACGTTG TTTTGAGAAG TCGTGGAAGT CGTAGGCATC CTGAAGGGAT
1681 TGTAAGCCAG GTGAGGATTC TTGAGGGCCC ACGCGCGTTC GCGCGGCCAG TTGGCGGGGT
1741 TCATATCCCC GGGCAACGGC GCCGTCGGAG CCCAGGGCGA GTTACCGTTG ACCGGGGTTT
1801 GGGTACCCGC GAAGGTAGGT GTCGGGGCCG GAGCGGGGGC CGTGGAAGGA TTGACAGGCG
1861 TCGGCGTGAG GATGGCAGCG CCGGCGCCAG CAGGGACGTT AACTCCGGCG CCGAACGTCA
1921 ACGTCGGTTG CTCGAACTTG TACGCGGTGG TGACGGGCGG TTTGGCGCTC GTCTCGGTAT
1981 CCGTGATGTC CACCAGCGTG TCGGTGAAAC GCGGATCTTG ACGGTTGGGG GGATAGCCAT
2041 CCGAGCTGTC GGAATCCTCG TCGCCCGAGA AAAGATCCCC TCTTGTCTCC GTGAGCGGCC
2101 TCACGTCCCA CGCGCTGTCC CGACGGACCC TTCCCGGGCT GGCCTTGGTT ACCTGCGGGG
2161 AGACGAGACT GAAAGCCGCG TGACGCTGTT GTTGCTGCGG GATGTTCAAG GGACCGCTGG
2221 TCGGTTTCTG ACTGCCCGAG GATAACATGC CGCTGAAAAT GCTGGAAACA CCGTTGCCAC
2281 TAGCGGCGCC CTTGCCGCTA GTTCCGGTT TCTTGATGGG CGTAAAGATG TTTTTCTCGT
2341 CATCATCATC GTCGTCGTCC TCATCGGCAC TGGAGCCAAA GAGCCTCCGG GAGGCGCCCG
2401 GTTTACGTGT CGGGGGCGGC GGTTGCTGCT GACGTTGCTG CAGGTTCTGC TGCCTCTCCT
2461 CCCAAGCCTT CAGCTGCTGT TTCTCACGCT GCACCACCTC GTCGTCCACC CGTTTCTGCC
2521 GCTCGCGACG CTTTTCCTCT TCGTCGTAAT AGCCGACGCG CGCCAACGG GCGGCGTGGG
2581 CGTCGGCGGC CGGTGCCAGA GAACCATGGG CCTCGAAGCG AACGGTTTG TGTCCCTTCC
2641 AGGGACTGGC GATCCAGCTC CAGCCGTCCA GCGGCTGCGT GGGGACATGT TTCTTGGGTA
2701 CCGACGAGAA GGCTGAACCG CCGCCGAGCG AGAGGAGATT GGCGTCATCG TCAAACTCCA
2761 ACGACGGCGG GCGCGCGCCC AAAAAGGTGT GCGCCGACTG CGGGAAGCTG TCCACGTAGA
2821 TGTCAAAGTC CTCGATGAGC AGCTCCAGCA GCGTGTCGGC CGAGTCACCG TTTTCCACGG
2881 CGTGTTTGAG GATATTGCGA CAGTAGTTGG AATCAAAGGA AAGGCACATG CGCAGCTCCT
2941 TGACCAGCAG CTTGCAGCGC TCCTGAATGC GCGCCAGACA TTTGCGCTCC AGCTCCTCCC
3001 AAGACCTGCG CACGTTCATG ATGAGACGGC CCGTGTACAC GAGCTTGTTG ACGGCGTTGA
3061 CCAGCGCCGT GTTGGCGTGC CGGTCCAGGT TAAGGTCGAG CGGTTTCACG CAGAACATGT
```

```
3121 TACGGCGCAC ACCCTCCAGG TTTTCTTCAA TGCGCTGCAC CTCCGTATCC TTGAGGTGCA
3181 CAAAAGCGAT GGGTTCCGTC TGGCCGATGG CTGTGACCAG CGTCTCGCGC ACCGACATCT
3241 TGGCCAGAAT GACCGCGCTT ACGAGCGCGC GCTCCACAAT CTCAGCATCG TGGCGTACGT
3301 CCGTATCGAA TTCGGTACGG TCTAGCACAG CCAGGTGGTC ACGCGCCTTA CCACGATCAC
3361 CGAACGGGTA AGTGTAGCCG CGACGCGCCA CGGCCGCGCA ACGCACCTCG AACTCCTCGA
3421 GAACCGAGGA GAGGTCGGGG TTGTGGAAAC GCAGCTCGCG GTAGTATCCC AACCAAAGCA
3481 TGAGCTCGTT GAACAGCACC GTACGCCGGT GCAGGCGTTT TTCGCCACAT TTTTTCAGGA
3541 TCTTGGGGTG TGCCTCGAGA TCCACGTCGG GCTTTTGCGT GAGATGGCGC AGAAAGTTGA
3601 CCAGGGCCAC CACATCGCGC CGCTGTAGAC CGATAAACTG CAAACTCATT TTATATTGTA
3661 ATTATATATT TTCAATTTTG AAATCCCAAA ATATTATCAT ATCTTCCCAA TAAAGCTAGA
3721 TTCTTTTTAT TGATTAACTA GTCAAATGAG TATATATAAT TGAAAAAGTA AAATATAAAT
3781 CATATAATAA TGAAACGAAA TATCAGTAAT AGACAGGAAC TGGCAGATTC TTCTTCTAAT
3841 GAAGTAAGTA CTGCTAAATC TCCAAAATTA GATAAAAATG ATACAGCAAA TACAGCTTCA
3901 TTCAACGAAT TACCTTTTAA TTTTTTCAGA CACACCTTAT TACAAACTAA CTAAGTCAGA
3961 TGATGAGAAA GTAAATATAA ATTTAACTTA TGGGTATAAT ATAATAAAGA TTCATGATAT
4021 TAATAATTTA CTTAACGATG TTAATAGACT TATTCCATCA ACCCCTTCAA ACCTTTCTGG
4081 ATATTATAAA ATACCAGTTA ATGATATTAA AATAGATTGT TTAAGAGATG TAAATAATTA
4141 TTTGGAGGTA AAGGATATAA AATTAGTCTA TCTTTCACAT GGAAATGAAT TACCTAATAT
4201 TAATAATTAT GATAGGAATT TTTTAGGATT TACAGCTGTT ATATGTATCA ACAATACAGG
4261 CAGATCTATG GTTATGGTAA AACACTGTAA CGGGAAGCAG CATTCTATGG TAACTGGCCT
4321 ATGTTTAATA GCCAGATCAT TTTACTCTAT AAACATTTTA CCACAAATAA TAGGATCCTC
4381 TAGATATTTA ATATTATATC TAACAACAAC AAAAAAATTT AACGATGTAT GGCCAGAAGT
4441 ATTTTCTACT AATAAAGATA AAGATAGTCT ATCTTATCTA CAAGATATGA AAGAAGATAA
4501 TCATTTAGTA GTAGCTACTA ATATGGAAAG AAATGTATAC AAAAACGTGG AAGCTTTTAT
4561 ATTAAATAGC ATATTACTAG AAGATTTAAA ATCTAGACTT AGTATAACAA AACAGTTAAA
4621 TGCCAATATC GATTCTATAT TTCATCATAA CAGTAGTACA TTAATCAGTG ATATACTGAA
4681 ACGATCTACA GACTCAACTA TGCAAGGAAT AAGCAATATG CCAATTATGT CTAATATTTT
4741 AACTTTAGAA CTAAACGTT CTACCAATAC TAAAAATAGG ATACGTGATA GGCTGTTAAA
4801 AGCTGCAATA AATAGTAAGG ATGTAGAAGA AATACTTTGT TCTATACCTT CGGAGGAAAG
4861 AACTTTAGAA CAACTTAAGT TTAATCAAAC TTGTATTTAT GAAGGTACC
```

```
   1 AAGACTAATT TGTAAACCAT CTTACTCAAA ATATGTAACA ATAGTACGAT GCAATGAGTA
  61 AGACAATAGG AAATCTATCT TATATACACA TAATTATTCT ATCAATTTTA CCAATTAGTT
 121 AGTGTAATGT TATAAAAACT AATTAATCAC TCGAGCCCCT AGCAATAAAA ACTATTCCTC
 181 CGTGTTCTTA ATCTTCTCGA TCTTTTGGAG GATGTTCTGC ACGGCGTCCG ACGGCGTTTT
 241 GGCGCCCCCC ATGCCGGCAG AACCCGGTTG CGGCCCCGTA CCGCTCTTCT GGGGCGACGA
 301 TAGGTCGAAA GCCACCGTTT TCATGCCCGT CGTGCTCTTG ACGGGGAAC CTACGGCGGC
 361 GGTCCCCGTC GAGCGGCGTG ATTGCAAAGC CGCGCTCGCC CCCGGTTTCA GGATGGAGGG
 421 GGAGGCCACA GGCGGCGCAT TCGATACGCT GCTTTTGGCC GTAGACGACG GTGGGTAAAC
 481 GGTGGTTACC GCGGGATACG TCGGCGTGGT CGAGGCGGCC CGGCTGGTGC GGACAGGCG
 541 ACCCGGCGCG CTACCGCTCA CGGGTACCGA GGGCGGTCGA CCTACCACCG CCTTGCCGCC
 601 CAAAGTAGGT TTCAAAGAAG GAACACCGAC GCGGCTGCCC CGACCTTTCA CCGGAGACGG
 661 AGGGGCACTC TTGGCCGGGG ACGGAGAGGC TGACGAAAGC ATGGACAGCG GCGACGTGAC
 721 GGGGGACACG ACATCATCCT CCGTGGGCGA CAAAACGGAC GCCGAGGCTG ACGGCTGTCG
 781 AGCCGAAGCG GAAGAGGTTC TCGCGCCAGA AGTCACGTTC CTTGATGACG TTGTTTTAGA
 841 CGAAGCCGGT TGAGGTTGCA ACAGCGTGGC GGGTACCGTC GACGGCGTGC CCGATACCTG
 901 TTTCTCTACC CTTCCCTGAA CCGGTGTCGA CGTCACCGTC TGCGCTCGGG CGGACGCGTG
 961 CGGCGTCGCG ACTCGCTTGC CCAGCACCGG TTTCTGGCTC GTGGATGTCG TCGTCATTGG
1021 AGACGATAAC TTAGCTTTAC GTATTCTGGA CGGCGTCGAC TGCTCGGGCG TCTGACTGGG
1081 AGGCGAAATG ACGTCGTTGT AATCGGACGA CGGTGTTGTG TGTCCCAGGC TGACGACGGA
1141 GCCGGTGTCC GAGGAGTCGT CGTCTTCCTC CTCGCTGTCT TCGACCGGTG ACTCTGCAGT
1201 TTGGTCCCTT AAAGCCCAAA CCTCATCAGC GGCGTTCTGA GACGCTGTTT GTGTCACCGC
1261 GGCGCGTGGA GTCGACGGCC TCCGAGGGGT GGTGGACACG TTGTTTTGAG AAGTCGTGGA
1321 AGTCGTAGGC ATCCTGAAGG GATTGTAAGC CAGGTGAGGA TTCTTGAGGG CCCACGCGCG
1381 TTCGCGCGGC CAGTTGGCGG GGTTCATATC CCCGGGCAAC GGCGCCGTCG GAGCCCAGGG
1441 CGAGTTACCG TTGACCGGGG TTTGGGTACC CGCGAAGGTA GGTGTCGGGG CCGGAGCGGG
1501 GGCCGTGGAA GGATTGACAG GCGTCGGCGT GAGGATGGCA GCGCCGGCGC CAGCAGGGAC
1561 GTTAACTCCG GCGCCGAACG TCAACGTCGG TTGCTCGAAC TTGTACGCGG TGGTGACGGG
1621 CGGTTTGGCG CTCGTCTCGG TATCCGTGAT GTCCACCAGC GTGTCGGTGA AACGCGGATC
1681 TTGACGGTTG GGGGATAGC CATCCGAGCT GTCGGAATCC TCGTCGCCCG AGAAAAGATC
1741 CCCTCTTGTC TCCGTGAGCG GCCTCACGTC CCACGCGCTG TCCCGACGGA CCCTTCCCGG
1801 GCTGGCCTTG GTTACCTGCG GGGAGACGAG ACTGAAAGCC GCGTGACGCT GTTGTTGCTG
1861 CGGGATGTTC AAGGGACCGC TGGTCGGTTT CTGACTGCCC GAGGATAACA TGCCGCTGAA
1921 AATGCTGGAA ACACCGTTGC CACTAGCGGC GCCCTTGCCG CTAGTTCCCG GTTTCTTGAT
1981 GGGCGTAAAG ATGTTTTTCT CGTCATCATC ATCGTCGTCG TCCTCATCGG CACTGGAGCC
2041 AAAGAGCCTC CGGGAGGCGC CCGGTTTACG TGTCGGGGGC GGCGGTTGCT GCTGACGTTG
2101 CTGCAGGTTC TGCTGCCTCT CCTCCCAAGC CTTCAGCTGC TGTTTCTCAC GCTGCACCAC
2161 CTCGTCGTCC ACCCGTTTCT GCCGCTCGCG ACGCTTTTCC TCTTCGTCGT AATAGCCGAC
2221 GCGCGCCGAA CGGGCGGCGT GGGCGTCGGC GGCCGGTGCC AGAGAACCAT GGGCCTCGAA
2281 GCGGAACGGT TTGTGTCCCT TCCAGGGACT GGCGATCCAG CTCCAGCCGT CCAGCGGCTG
2341 CGTGGGGACA TGTTTCTTGG GTACCGACGA GAAGGCTGAA CCGCCGCCGA GCGAGAGGAG
2401 ATTGGCGTCA TCGTCAAACT CCAACGACGG CGGGCGCGCG CCCAAAAAGG TGTGCGCCGA
2461 CTGCGGGAAG CTGTCCACGT AGATGTCAAA GTCCTCGATG AGCAGCTCCA GCAGCGTGTC
2521 GGCCGAGTCA CCGTTTTCCA CGGCGTGTTT GAGGATATTG CGACAGTAGT TGGAATCAAA
2581 GGAAAGGCAC ATGCGCAGCT CCTTGACCAG CAGCTTGCAG CGCTCCTGAA TGCGCGCCAG
2641 ACATTTGCGC TCCAGCTCCT CCCAAGACCT GCGCACGTTC ATGATGAGAC GGCCCGTGTA
2701 CACGAGCTTG TTGACGGCGT TGACCAGCGC CGTGTTGGCG TGCCGGTCCA GGTTAAGGTC
2761 GAGCGGTTTC ACGCAGAACA TGTTACGGCG CACACCCTCG AGGTTTTCTT CAATGCGCTG
2821 CACCTCCGTA TCCTTGAGGT GCACAAAAGC GATGGGTTCC GTCTGGCCGA TGGCTGTGAC
2881 CAGCGTCTCG CGCACCGACA TCTTGGCCAG AATGACCGCG CTTACGAGCG CGCGCTCCAC
2941 AATCTCAGCA TCGTGGCGTA CGTCCGTATC GAATTCGGTA CGGTCTAGCA CAGCCAGGTG
3001 GTCACGCGCC TTACCACGAT CACCGAACGG GTAAGTGTAG CCGCGACGCG CCACGGCCGC
3061 GCAACGCACC TCGAACTCCT CGAGAACCGA GGAGAGGTCG GGTTGTGGA AACGCAGCTC
```

```
3121 GCGGTAGTAT CCCAACCAAA GCATGAGCTC GTTGAACAGC ACCGTACGCC GGTGCAGGCG
3181 TTTTTCGCCA CATTTTTTCA GGATCTTGGG GTGTGCCTCG AGATCCACGT CGGGCTTTTG
3241 CGTGAGATGG CGCAGAAAGT TGACCAGGGC CACCACATCG CGCCGCTGTA GACCGATAAA
3301 CTGCAAACTC ATTTTATATT GTAATTATAT ATTTTCAATT TTGAAATCCC AAAATATTAT
3361 CATATCTTCC CAATAAAGCT AGGGGGAATT CGGATCCTCG CGACTGCAGG GTACCTGAGT
3421 AGCTAATTTT TAAACAAAAA TGTGGGAGAA TCTAATTAGT TTTTCTTTAC ACAATTGACG
3481 TACATGAGTC TGAGTTCCTT GTTTTTGCTA ATTATTTCAT CCAATTTATT ATTCTTGACG
3541 ATATCGAGAT CTTTTGTATA GGAGTCA
```

```
   1 CTGCAGGTCG ACGGATCTGA GAATGGATGA TTCTCCAGCC GAAACATATT CTACCATGGC
  61 TCCGTTTAAT TTGTTGATGA AGATGGATTC ATCCTTAAAT GTTTTCTCTG TAATAGTTTC
 121 CACCGAAAGA CTATGCAAAG AATTTGGAAT GCGTTCCTTG TGCTTAATGT TTCCATAGAC
 181 GGCTTCTAGA AGTTGATACA ACATAGGACT AGCCGCGGTA ACTTTTATTT TTAGAAAGTA
 241 TCCATCGCTT CTATCTTGTT TAGATTTATT TTTATAAAGT TTAGTCTCTC CTTCCAACAT
 301 AATAAAAGTG GAAGTCATTT GACTAGATAA ACTATCAGTA AGTTTTATAG AGATAGACGA
 361 ACAATTAGCG TATTGAGAAG CATTTAGTGT AACGTATTCG ATACATTTTG CATTAGATTT
 421 ACTAATCGAT TTTGCATACT CTATAACACC CGCACAAGTC TGTAGAGAAT CGCTAGATGC
 481 AGTAGGTCTT GGTGAAGTTT CAACTCTCTT CTTGATTACC TTACTCATGA TTAAACCTAA
 541 ATAATTGTAC TTTGTAATAT AATGATATAT ATTTTCACTT TATCTCATTT GAGAATAAAA
 601 AGATCACAAA AATTAACTAA TCAGGATCTC GAGATAAAAA TCAGCATGTC TTGAGCATGC
 661 GGTAGAGCAG ATAGATGCCG ATGATGGCCG ATAGCGCGTA GACGGACATC ATGAGGAGAC
 721 GACTGTCGGT AGCGTCCACG ACGACGTCAG TTACTTCTAG GACCGTACCG TTTTTCAAAA
 781 GCATGAGGTA GTGAGTTCGC GGAGATGAGA CCACCACTTC GTTGTAGGGA TCCAGGGCGA
 841 AAAGGACGTC GTCCGAGTCG TGCATGTACA TGATGTTGAT GACGCCTTGC GTGTCGTCGT
 901 ATTCTAGTAG GGCGCTTTGG CAAAAGGCGC AGTTTTCTAG GGAAATGTTG AGCGCCGCTG
 961 TGATGCTGTG TGTGGTATGC ATGTTGCGCG TCAGTTCGCA TTTAGTTTGA CTGTCCGTCT
1021 GGGTGATGAT GAGGCTCTGG CCTACGACGG TGGTGGAGAC AGGGTAGGAG ATACCTTTGA
1081 TCAGGTACTG GTTTGTTACG ACATAACTGA CGTGTTCGGA GACGGTCAGC GCGGAGAAGG
1141 ATTCGCCGAG CGGCAGACAA AACAGGTCGG GGAAGGTTTC TAGCGTGCTT GGTTGCATGG
1201 TAGATAGGAT GGAGAGGGCG GCGGGAACGG TAGTGGGGAC GGTGGCATCG GGGAAGAGAC
1261 GTGTGAGGCG TTCGAGCGAG TGATCGCGTC GCCCGCTACT GGAACAGGGT GTGTACAGGT
1321 CGCTGAGGTA TTCGTGGTGC GGATGAGCTA GCAACTGCGT AAAGTGTGAT AGCTCGGCTA
1381 ATGAACAGAG GCCCGTTTCT ACGATGAAGA TTTCGCGTCT CTCCGTCGTA TGTACTAGCA
1441 TGGAGTGGAC GAGGCTGCCC ATGAGGTAGA GTTCTTGACG CGCGAAGGCT GAAAGAAAAG
1501 AGGCCAGGTG CGTTTTGTGT AGTTTTAGGG CAAAGTCGGC GATCTGTCGT AGTGCCCACT
1561 GGGGGATGAG ATGTTGCTGA TTCTGTTTAG AGAGTATGTA GACCAGGCGT ACGAGGCTGG
1621 TGATGTCGGT GATCTGATTC GGTGTCCAAA GGGCTCGTTT GGCCAGGTCC ACGGCCGTGG
1681 GATACAGCAG CAACGTGGTG CGTGGTGGTG TTTGTGAGAG GCAGGTGATC ATAAATTCTT
1741 GTATTTGTAA GAGTGCGGCC TGGCGGTCTA GGGCCCGTGG GACGGAGACT TGGGCGCCGG
1801 CCTCTTCTTG TCGGGCTGCT GCGAACAGTG CTAATGCGTA GGCGAAGGCC ATTTCTACCG
1861 TGCGGCGGTC CAGCATCTGA CATCGACCGC TTTTGAGTAC ATCCACGGCG TAACGGTGAA
1921 AGCTGTTACG TAGTAGTGCG CTGAGGTCCA GGTAGTTGAA GTCAAGTGCG GCGTCAAGAA
1981 AGTCCGGGTC TTTGAGATAA GAGTGACGGT TCAGTTGATC TTTCTTAACT AGCACCAGGA
2041 GCTCGTGTTT TTCAGTTTGT CGTAGTATAA AGTTGTCGCG TTGATAGGGC GCTTTAAAGA
2101 GTACGCGTGG AAGTGGCCG AAGATAAGCA GCATGGGTGT GTCGTCGTCT ATGGACACCG
2161 TAACTACGAA GAAGTCCTCG GTCAGTGTTA TTTTAACGTA ACGTAGTTCG TCGATGAGGT
2221 AAAAGCTTTG GTGCAAACAA GGTGTGACGG TGCTGAATAG TAGATCGTGT CCATCAAAGA
2281 GGATACAGGT CTGGTTAAAG TGTGGTCGGT GTAGTCCTGA GGTGGTATGT GATTCTGTCC
2341 AGCCGTGTGG AGTGGTTTGC GGTGGCATCC AAACGTGAGG TATTGACAGG TCAATGGGTG
2401 GTGGCACAGT GGTGGCTGT TCACCTAGGC TGTCCTGTGC CTTTAGCTGC TGCGAAAAAG
2461 ATCGGTAGCT GGCCAGGTCT TTGGATACCA GCGCGTAAGT GTTAAGTCTC TGTTGGTATC
2521 TTTCCAGGGT TTCGGTCAGA TCTACCTGGT TCAGAAACTG CTCCGCCAGA GGACCCGCAA
2581 AAAGACATCG AGGCATATGG AATACATAGT ATTGATTATA GCTTTGGAAA AAGTTGAAAC
2641 TGATGGCGTT TTCCCTGACG ACCGTGCTGT TACGGAGGCT GCTATTGTAG GTACACTGGG
2701 TGGTGTTTTC ACGCAGGAAG CGGATGGGTC TCCCGTAGGT GTTGAGCAGT AGGTGAAACG
2761 CTTTGTCCAG CGGTTCGGAT ATGGCTTCTG CGCCATATCG TGACGAAAGT AGGTGGCTGA
2821 GGAGACAGAC GGCGAGGACG ATGAGGTAGG AGGGGAGCCC GGGCCGCATT TTATATTGTA
2881 ATTATATATT TTCAATTTTG AAATCCCAAA ATATTATCAT ATTCTTCCCA ATAAACTCGA
2941 GATCCTTCTT TATTCTATAC TTAAAAGTG AAAATAAATA CAAAGGTTCT TGAGGGTTGT
3001 GTTAAATTGA AAGCGAGAAA TAATCATAAA TTATTTCATT ATCGCGATAT CCGTTAAGTT
3061 TGTATCGTAA TGAAACAGAT TAAGGTTCGA GTGGACATGG TGCGGCATAG AATCAAGGAG
```

```
3121 CACATGCTGA AAAAATATAC CCAGACGGAA GAGAAATTCA CTGGCGCCTT TAATATGATG
3181 GGAGGATGTT TGCAGAATGC CTTAGATATC TTAGATAAGG TTCATGAGCC TTTCGAGGAG
3241 ATGAAGTGTA TTGGGCTAAC TATGCAGAGC ATGTATGAGA ACTACATTGT ACCTGAGGAT
3301 AAGCGGGAGA TGTGGATGGC TTGTATTAAG GAGCTGCATG ATGTGAGCAA GGGCGCCGCT
3361 AACAAGTTGG GGGTGCACT GCAGGCTAAG GCCCGTGCTA AAAAGGATGA ACTTAGGAGA
3421 AAGATGATGT ATATGTGCTA CAGGAATATA GAGTTCTTTA CCAAGAACTC AGCCTTCCCT
3481 AAGACCACCA ATGGCTGCAG TCAGGCCATG GCGGCACTGC AGAACTTGCC TCAGTGCTCC
3541 CCTGATGAGA TTATGGCTTA TGCCCAGAAA ATATTTAAGA TTTTGGATGA GGAGAGAGAC
3601 AAGGTGCTCA CGCACATTGA TCACATATTT ATGGATATCC TCACTACATG TGTGGAAACA
3661 ATGTGTAATG AGTACAAGGT CACTAGTGAC GCTTGTATGA TGACCATGTA CGGGGGCATC
3721 TCTCTCTTAA GTGAGTTCTG TCGGGTGCTG TGCTGCTATG TCTTAGAGGA GACTAGTGTG
3781 ATGCTGGCCA AGCGGCCTCT GATAACCAAG CCTGAGGTTA TCAGTGTAAT GAAGCGCCGC
3841 ATTGAGGAGA TCTGCATGAA GGTCTTTGCC CAGTACATTC TGGGGGCCGA TCCTCTGAGA
3901 GTCTGCTCTC CTAGTGTGGA TGACCTACGG GCCATCGCCG AGGAGTCAGA TGAGGAAGAG
3961 GCTATTGTAG CCTACACTTT GGCCACCGCT GGTGTCAGCT CCTCTGATTC TCTGGTGTCA
4021 CCCCCAGAGT CCCCTGTACC CGCGACTATC CCTCTGTCCT CAGTAATTGT GGCTGAGAAC
4081 AGTGATCAGG AAGAAGTGA GCAGAGTGAT GAGGAAGAGG AGGAGGGTGC TCAGGAGGAG
4141 CGGGAGGACA CTGTGTCTGT CAAGTCTGAG CCAGTGTCTG AGATAGAGGA AGTTGCCCCA
4201 GAGGAAGAGG AGGATGGTGC TGAGGAACCC ACCGCCTCTG GAGGTAAGAG TACCCACCCT
4261 ATGGTGACTA GAAGCAAGGC TGACCAGTAA TTTTTATCTC GAGCCCGGGA GATCTTAGCT
4321 AACTGATTTT TCTGGGAAAA AAATTATTTA ACTTTTCATT AATAGGGATT TGACGTATGT
4381 AGCGTACAAA ATTATCGTTC CTGGTATATA GATAAAGAGT CCTATATATT TGAAAATCGT
4441 TACGGCTCGA TTAAACTTTA ATGATTGCAT AGTAATATA TCATTAGGAT TTAACTCCTT
4501 GACTATCATG GCGGCGCCAG AAATTACCAT CAAAAGCATT AATACAGTTA TGCCGATCGC
4561 AGTTAGAACG GTTATAGCAT CCACCATTTA TATCTAAAAA TTAGATCAAA GAATATGTGA
4621 CAAAGTCCTA GTTGTATACT GAGAATTGAC GAAACAATGT TCTTACATA TTTTTTTCTT
4681 ATTAGTAACT GACTTAATAG TAGGAACTGG AAAGCTAGAC TTGATTATTC TATAAGTATA
4741 GATACCCTTC CAGATAATGT TCTCTTTGAT AAAAGTTCCA GAAAATGTAG AATTTTTTAA
4801 AAAGTTATCT TTTGCTATTA CCAAGATTGT GTTTAGACGC TTATTATTAA TATGAGTAAT
4861 GAAATCCACA CCGCCTCTAG ATATGGGGAA TTC
```

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAA CAAAAACTAA
 421 TCAGCTATCG GGGTTAATTA ATTAGTTATT AGACAAGGTG AAAACGAAAC TATTTGTAGC
 481 TTAATTAATT AGAGCTTCTT TATTCTATAC TTAAAAAGTG AAAATAAATA CAAAGGTTCT
 541 TGAGGGTTGT GTTAAATTGA AAGCGAGAAA TAATCATAAA TTATTTCATT ATGGCGATAT
 601 CCGTTAAGTT TGTATCGTAA TGGAGTCGCG CGGTCGCCGT TGTCCCGAAA TGATATCCGT
 661 ACTGGGTCCC ATTTCGGGGC ACGTGCTGAA AGCCGTGTTT AGTCGCGGCG ACACGCCGGT
 721 GCTGCCGCAC GAGACGCGAC TCCTGCAGAC GGGTATCCAC GTGCGCGTGA GCCAGCCCTC
 781 GCTGATCCTG GTGTCGCAGT ACACGCCCGA CTCGACGCCA TGCCACCGCG GCGACAATCA
 841 GCTGCAGGTG CAGCACACGT ACTTTACGGG CAGCGAGGTG GAGAACGTGT CGGTCAACGT
 901 GCACAACCCC ACGGGCCGGA GCATCTGCCC CAGCCAAGAG CCCATGTCGA TCTATGTGTA
 961 CGCGCTGCCG CTCAAGATGC TGAACATCCC CAGCATCAAC GTGCACCACT ACCCGTCGGC
1021 GGCCGAGCGC AAACACCGAC ACCTGCCCGT AGCTGACGCT GTGATTCACG CGTCGGGCAA
1081 GCAGATGTGG CAGGCGCGTC TCACGGTCTC GGGACTGGCC TGGACGCGTC AGCAGAACCA
1141 GTGGAAAGAG CCCGACGTCT ACTACGTC AGCGTTCGTG TTTCCCACCA AGGACGTGGC
1201 ACTGCGGCAC GTGGTGTGCG CGCACGAGCT GGTTTGCTCC ATGGAGAACA CGCGCGCAAC
1261 CAAGATGCAG GTGATAGGTG ACCAGTACGT CAAGGTGTAC CTGGAGTCCT TCTGCGAGGA
1321 CGTGCCCTCC GGCAAGCTCT TTATGCACGT CACGCTGGGC TCTGACGTGG AAGAGGACCT
1381 GACGATGACC CGCAACCCGC AACCCTTCAT GCGCCCCAC GAGCGCAACG GCTTTACGGT
1441 GTTGTGTCCC AAAAATATGA TAATCAAACC GGGCAAGATC TCGCACATCA TGCTGGATGT
1501 GGCTTTTACC TCACACGAGC ATTTTGGGCT GCTGTGTCCC AAGAGCATCC CGGGCCTGAG
1561 CATCTCAGGT AACCTATTGA TGAACGGGCA GCAGATCTTC CTGGAGGTGC AAGCGATACG
1621 CGAGACCGTG GAACTGCGTC AGTACGATCC CGTGGCTGCG CTCTTCTTTT TCGATATCGA
1681 CTTGCTGCTG CAGCGCGGGC CTCAGTACAG CGAACACCCC ACCTTCACCA GCCAGTATCG
1741 CATCCAGGGC AAGCTTGAGT ACCGACACAC CTGGGACCGG CACGACGAGG GTGCCGCCCA
1801 GGGCGACGAC GACGTCTGGA CCAGCGGATC GGACTCCGAC GAGGAACTCG TAACCACCGA
1861 GCGCAAGACG CCCCGCGTTA CCGGCGGCGG CGCCATGGCG GGCGCCTCCA CTTCCGCGGG
1921 CCGCAAACGC AAATCAGCAT CCTCGGCGAC GGCGTGCACG GCGGGCGTTA TGACACGCGG
1981 CCGCCTTAAG GCCGAGTCCA CCGTCGCGCC CGAAGAGGAC ACCGACGAGG ATTCCGACAA
2041 CGAAATCCAC AATCCGGCCG TGTTCACCTG GCCGCCCTGG CAGGCCGGCA TCCTGGCCCG
2101 CAACCTGGTG CCCATGGTGG CTACGGTTCA GGGTCAGAAT CTGAAGTACC AGGAGTTCTT
2161 CTGGGACGCC AACGACATCT ACCGCATCTT CGCCGAATTG AAGGCGTAT GGCAGCCCGC
2221 TGCGCAACCC AAACGTCGCC GCCACCGGCA AGACGCCTTG CCCGGGCCAT GCATCGCCTC
2281 GACGCCCAAA AAGCACCGAG GTTGATTTTT ATGGATCCGG TACCCTCGAG GAATTCTAGC
2341 AATAAAAACT ATTCCTCCGT GTTCTTAATC TTCTCGATCT TTTGGAGGAT GTTCTGCACG
2401 GCGTCCGACG GCGTTTTGGC GCCCCCATG CCGGCAGAAC CCGGTTGCGG CCCCGTACCG
2461 CTCTTCTGGG GCGACGATAG GTCGAAAGCC ACCGTTTTCA TGCCCGTCGT GCTCTTGACG
2521 GGGGAACCTA CGGCGGCGGT CCCCGTCGAG CGGCGTGATT GCAAAGCCGC GCTCGCCCCC
2581 GGTTTCAGGA TGGAGGGGGA GGCCACAGGC GGCGCATTCG ATACGCTGCT TTTGGCCGTA
2641 GACGACGGTG GGTAAACGGT GGTTACCGCG GGATACGTCG GCGTGGTCGA GGCGGCCCGG
2701 CTGGTGCCGG ACAGGCGACC CGGCGCGCTA CCGCTCACGG GTACCGAGGG CGGTCGACCT
2761 ACCACCGCCT TGCCGCCCAA AGTAGGTTTC AAAGAAGGAA CACCGACGCG GCTGCCCCGA
2821 CCTTTCACCG GAGACGGAGG GGCACTCTTG GCCGGGACG GAGAGGCTGA CGAAAGCATG
2881 GACAGCGGCG ACGTGACGGG GGACACGACA TCATCCTCCG TGGGCGACAA AACGGACGCC
2941 GAGGCTGACG GCTGTCGAGC CGAAGCGGAA GAGGTTCTCG CGCCAGAAGT CACGTTCCTT
3001 GATGACGTTG TTTTAGACGA AGCCGGTTGA GGTTGCAACA GCGTGGCGGG TACCGTCGAC
3061 GGCGTGCCCG ATACCTGTTT CTCTACCCTT CCCTGAACCG GTGTCGACGT CACCGTCTGC
```

FIG. 46B

```
3121 GCTCGGGCGG ACGCGTGCGG CGTCGCGACT CGCTTGCCCA GCACCGGTTT CTGGCTCGTG
3181 GATGTCGTCG TCATTGGAGA CGATAACTTA GCTTTACGTA TTCTGGACGG CGTCGACTGC
3241 TCGGGCGTCT GACTGGGAGG CGAAATGACG TCGTTGTAAT CGGACGACGG TGTTGTGTGT
3301 CCCAGGCTGA CGACGGAGCC GGTGTCCGAG GAGTCGTCGT CTTCCTCCTC GCTGTCTTCG
3361 ACCGGTGACT CTGCAGTTTG GTCCCTTAAA GCCCAAACCT CATCAGCGGC GTTCTGAGAC
3421 GCTGTTTGTG TCACCGCGGC GCGTGGAGTC GACGGCCTCC GAGGGGTGGT GGACACGTTG
3481 TTTTGAGAAG TCGTGGAAGT CGTAGGCATC CTGAAGGGAT TGTAAGCCAG GTGAGGATTC
3541 TTGAGGGCCC ACGCGCGTTC GCGCGGCCAG TTGGCGGGGT TCATATCCCC GGGCAACGGC
3601 GCCGTCGGAG CCCAGGGCGA GTTACCGTTG ACCGGGGTTT GGGTACCCGC GAAGGTAGGT
3661 GTCGGGCCG GAGCGGGGGC CGTGGAAGGA TTGACAGGCG TCGGCGTGAG GATGGCAGCG
3721 CCGGCGCCAG CAGGGACGTT AACTCCGGCG CCGAACGTCA ACGTCGGTTG CTCGAACTTG
3781 TACGCGGTGG TGACGGGCGG TTTGGCGCTC GTCTCGGTAT CCGTGATGTC CACCAGCGTG
3841 TCGGTGAAAC GCGGATCTTG ACGGTTGGGG GGATAGCCAT CCGAGCTGTC GGAATCCTCG
3901 TCGCCCGAGA AAAGATCCCC TCTTGTCTCC GTGAGCGGCC TCACGTCCCA CGCGCTGTCC
3961 CGACGGACCC TTCCCGGGCT GGCCTTGGTT ACCTGCGGGG AGACGAGACT GAAAGCCGCG
4021 TGACGCTGTT GTTGCTGCGG GATGTTCAAG GGACCGCTGG TCGGTTTCTG ACTGCCCGAG
4081 GATAACATGC CGCTGAAAAT GCTGGAAACA CCGTTGCCAC TAGCGGCGCC CTTGCCGCTA
4141 GTTCCCGGTT TCTTGATGGG CGTAAAGATG TTTTTCTCGT CATCATCATC GTCGTCGTCC
4201 TCATCGGCAC TGGAGCCAAA GAGCTCCGG GAGGCGCCCG GTTTACGTGT CGGGGGCGGC
4261 GGTTGCTGCT GACGTTGCTG CAGGTTCTGC TGCCTCTCCT CCCAAGCCTT CAGCTGCTGT
4321 TTCTCACGCT GCACCACCTC GTCGTCCACC CGTTTCTGCC GCTCGCGACG CTTTTCCTCT
4381 TCGTCGTAAT AGCCGACGCG CGCCGAACGG GCGGCGTGGG CGTCGGCGGC CGGTGCCAGA
4441 GAACCATGGG CCTCGAAGCG AACGGTTTG TGTCCCTTCC AGGGACTGGC GATCCAGCTC
4501 CAGCCGTCCA GCGGCTGCGT GGGGACATGT TTCTTGGGTA CCGACGAGAA GGCTGAACCG
4561 CCGCCGAGCG AGAGGAGATT GGCGTCATCG TCAAACTCCA ACGACGGCGG GCGCGCGCCC
4621 AAAAAGGTGT GCGCCGACTG CGGGAAGCTG TCCACGTAGA TGTCAAAGTC CTCGATGAGC
4681 AGCTCCAGCA GCGTGTCGGC CGAGTCACCG TTTTCCACGG CGTGTTTGAG GATATTGCGA
4741 CAGTAGTTGG AATCAAAGGA AAGGCACATG CGCAGCTCCT TGACCAGCAG CTTGCAGCGC
4801 TCCTGAATGC GCGCCAGACA TTTGCGCTCC AGCTCCTCCC AAGACCTGCG CACGTTCATG
4861 ATGAGACGGC CCGTGTACAC GAGCTTGTTG ACGGCGTTGA CCAGCGCCGT GTTGGCGTGC
4921 CGGTCCAGGT TAAGGTCGAG CGGTTTCACG CAGAACATGT TACGGCGCAC ACCCTCCAGG
4981 TTTTCTTCAA TGCGCTGCAC CTCCGTATCC TTGAGGTGCA CAAAAGCGAT GGGTTCCGTC
5041 TGGCCGATGG CTGTGACCAG CGTCTCGCGC ACCGACATCT TGGCCAGAAT GACCGCGCTT
5101 ACGAGCGCGC GCTCCACAAT CTCAGCATCG TGGCGTACGT CCGTATCGAA TTCGGTACGG
5161 TCTAGCACAG CCAGGTGGTC ACGCGCCTTA CCACGATCAC CGAACGGGTA AGTGTAGCCG
5221 CGACGCGCCA CGGCCGCGCA ACGCACCTCG AACTCCTCGA GAACCGAGGA GAGGTCGGGG
5281 TTGTGAAAAC GCAGCTCGCG GTAGTATCCC AACCAAAGCA TGAGCTCGTT GAACAGCACC
5341 GTACGCCGGT GCAGGCGTTT TTCGCCACAT TTTTTCAGGA TCTTGGGGTG TGCCTCGAGA
5401 TCCACGTCGG GCTTTTGCGT GAGATGGCGC AGAAAGTTGA CCAGGGCCAC CACATCGCGC
5461 CGCTGTAGAC CGATAAACTG CAAACTCATT TTATATTGTA ATTATATATT TTCAATTTTG
5521 AAATCCCAAA ATATTATCAT ATCTTCCCAA TAAAGCTAGA ATTCTTTTA TTGATTAACT
5581 AGTCAAATGA GTATATATAA TTGAAAAAGT AAAATATAAA TCATATAATA ATGAAACGAA
5641 ATATCAGTAA TAGACAGGAA CTGGCAGATT CTTCTTCTAA TGAAGTAAGT ACTGCTAAAT
5701 CTCCAAAATT AGATAAAAAT GATACAGCAA ATACAGCTTC ATTCAACGAA TTACCTTTTA
5761 ATTTTTTCAG ACACACCTTA TTACAAACTA ACTAAGTCAG ATGATGAGAA AGTAAATATA
5821 AATTTAACTT ATGGGTATAA TATAATAAAG ATTCATGATA TTAATAATTT ACTTAACGAT
5881 GTTAATAGAC TTATTCCATC AACCCCTTCA AACCTTTCTG GATATTATAA AATACCAGTT
5941 AATGATATTA AAATAGATTG TTTAAGAGAT GTAAATAATT ATTTGGAGGT AAAGGATATA
6001 AAATTAGTCT ATCTTTCACA TGGAAATGAA TTACCTAATA TTAATAATTA TGATAGGAAT
6061 TTTTAGGAT TTACAGCTGT TATATGTATC AACAATACAG GCAGATCTAT GGTTATGGTA
6121 AAACACTGTA ACGGGAAGCA GCATTCTATG GTAACTGGCC TATGTTTAAT AGCCAGATCA
6181 TTTTACTCTA TAAACATTTT ACCACAAATA ATAGGATCCT CTAGATATTT AATATTATAT
```

```
6241 CTAACAACAA CAAAAAAATT TAACGATGTA TGGCCAGAAG TATTTTCTAC TAATAAAGAT
6301 AAAGATAGTC TATCTTATCT ACAAGATATG AAAGAAGATA ATCATTTAGT AGTAGCTACT
6361 AATATGGAAA GAAATGTATA CAAAAACGTG GAAGCTTTTA TATTAAATAG CATATTACTA
6421 GAAGATTTAA AATCTAGACT TAGTATAACA AAACAGTTAA ATGCCAATAT CGATTCTATA
6481 TTTCATCATA ACAGTAGTAC ATTAATCAGT GATATACTGA AACGATCTAC AGACTCAACT
6541 ATGCAAGGAA TAAGCAATAT GCCAATTATG TCTAATATTT TAACTTTAGA ACTAAAACGT
6601 TCTACCAATA CTAAAAATAG GATACGTGAT AGGCTGTTAA AAGCTGCAAT AAATAGTAAG
6661 GATGTAGAAG AAATACTTTG TTCTATACCT TCGGAGGAAA GAACTTTAGA ACAACTTAAG
6721 TTTAATCAAA CTTGTATTTA TGAAGGTAC
```

FIG.46C

```
  1 ATGTGCCGCC GCCCGGATTG CGGCTTCTCT TTCTCACCTG GACCGGTGGC ACTGCTGTGG
 61 TGTTGCCTTC TGCTGCCCAT CGTTTCCTCA GCCACCGTCA GCGTCGCTCC TACCGTCGCC
121 GAGAAAGTTC CCGCGGAGTG CCCCGAACTA ACGCGTCGAT GCCTGTTGGG TGAGGTGTTT
181 CAGGGTGACA AGTATGAAAG TTGGCTGCGC CCGTTGGTGA ATGTTACCAG ACGCGATGGC
241 CCGCTATCGC AACTTATTCG TTACCGTCCC GTTACGCCGG AGGCCGCCAA CTCCGTGCTG
301 TTGGACGATG CTTTCCTGGA CACTCTGGCC CTGCTGTACA ACAATCCGGA TCAATTGCGG
361 GCCTTGCTGA CGCTGTTGAG CTCGGACACA GCGCCGCGCT GGATGACGGT GATGCGCGGT
421 TACAGCGAGT GCGGCGATGG CTCGCCGGCC GTGTACACGT GCGTGGACGA CCTGTGCCGC
481 GGCTACGACC TCACGCGACT GTCATACGGG CGCAGCATCT TCACGGAACA CGTGTTAGGC
541 TTCGAGCTGG TGCCACCGTC TCTCTTTAAC GTGGTGGTGG CCATACGCAA CGAAGCCACG
601 CGTACCAACC GCGCCGTGCG TCTGCCCGTG AGCACCGCTG CCGCGCCCGA GGGCATCACG
661 CTCTTTTACG GCCTGTACAA CGCAGTGAAG GAATTCTGCC TGCGTCACCA GCTGGACCCG
721 CCGCTGCTAC GCCACCTAGA TAAATACTAC GCCGGACTGC CGCCCGAGCT GAAGCAGACG
781 CGCGTCAACC TGCCGGCTCA CTCGCGCTAT GGCCCTCAAG CAGTGGATGC TCGCTAA
```

```
   1 AAGCTTTTGC GATCAATAAA TGGATCACAA CCAGTATCTC TTAACGATGT TCTTCGCAGA
  61 TGATGATTCA TTTTTAAGT ATTTGGCTAG TCAAGATGAT GAATCTTCAT TATCTGATAT
 121 ATTGCAAATC ACTCAATATC TAGACTTTCT GTTATTATTA TTGATCCAAT CAAAAAATAA
 181 ATTAGAAGCC GTGGGTCATT GTTATGAATC TCTTTCAGAG GAATACAGAC AATTGACAAA
 241 ATTCACAGAC TCTCAAGATT TTAAAAAACT GTTTAACAAG GTCCCTATTG TTACAGATGG
 301 AAGGGTCAAA CTTAATAAAG GATATTTGTT CGACTTTGTG ATTAGTTTGA TGCGATTCAA
 361 AAAAGAATCC TCTCTAGCTA CCACCGCAAT AGATCCTATT AGATACATAG ATCCTCGTCG
 421 CGATATCGCA TTTTCTAACG TGATGGATAT ATTAAAGTCG AATAAAGTGA ACAATAATTA
 481 ATTCTTTATT GTCATCATGT AATTAACTAG CTACCCGGGA GATCTCTCGA GCTGCAGAAG
 541 CTTATAAAAA TCACAAGTCT CTGTCACTTT TTTTGTCTAG TTTTTTTTTC TCCTCTTGGT
 601 TCAGACGTTC TCTTCTTCGT CGGAGTCTTT CAAGTGTCGG TAGCCGTTTT TGCGGTGTCG
 661 CAGTCGGTCT AGCAGGTTGG GCTTCTGTCC CTTGTCCTGC GTGCCAGTCT GTCCGTCCAA
 721 AGAATCTGTA CCGTTCTCGT GCGCTCGCTG CTCTGCGTCC AGACGGACCA GGGCCAGAAG
 781 CATCTGGTAA GCCTGCTCGT TGGTGTAAGG CGGAGCCGCC GTGGATGCAT CAGACGACGG
 841 TGGTCCCGGT CCTTTGCGAC CAGAATTATA AACACTTTCC TCGTAGGAAG GCGGAGCCTG
 901 TAACGACGTG TCTTTGGTGT TGCCCGACGT CACGGTGGTC CCGTCGGCGG ACACCAGATA
 961 GGGAAAGAGG TTCTGCAGCG GCTGCATGCA GAGACGCCGC TGTCGAGTAT AGATCAAATA
1021 AATGATAATG ACGACGGCTA TGGCCACGAG GATGATGGTG AAGGCTCCGA AGGGGTTTTT
1081 GAGGAAGGTG GCAACGCCTT CGACCACGGA GGCCACCGCG CCACCCACGG CCCCAATGGC
1141 TACGCCAACG GCCTTTCCCG CGGCGCCCAG GCCGCTCATG AGGTCGTCCA GACCCTTGAG
1201 GTAGGGCGGC AGCGGGTCGA CTACCTTGTC CTCCACGTAC TTTACCCGCT GCTTATACGA
1261 ATTGAACTCG CGCATGATCT CCTCGAGATC AAAAACGTTG CTGGAACGCA ATTCTTTCTG
1321 CGAGTAAAGT TCCAGTACCC TGAAGTCGGT GTTTTCCAGC GGGTCGATGT CTAGGGCGAT
1381 CATGCTGTCG ACGGTGGAGA TGCTGCTGAG GTCAATCATG CGTTTGAAGA GGTAGTCCAC
1441 GTACTCGTAG GCCGAGTTGC CGGCGATGAA GATCTTGAGG CTGGGAAGCT GACATTCCTC
1501 AGTGCGGTGG TTGCCCAACA GGATTTCGTT ATCCTCGCCC AGTTGACCGT ACTGCACGTA
1561 CGAGCTGTTG GCGAAATTAA AGATGACCAC TGGTCGTGAG TAGCAGCGTC CTGGCGATTC
1621 CTTCACATTC ATATCACGCA GCACCTTGAC GCTGGTTTGG TTAATGGTCA CGCAGCTGGC
1681 CAGACCCAGG ACATCACCCA TGAAACGCGC GGCAATCGGT TTGTTGTAGA TGGCCGAGAG
1741 AATAGCTGAC GGGTTGATCT TGCTAAGTTC CTTGAAGACC TCTAGGGTGC GCCGTTGATC
1801 CACACACCAG GCTTCTGCGA TTTCGGCCAG CGCCCGGTTG ATGTAACCGC GCAACGTGTC
1861 ATAGGTGAAC TGCAGCTGGG CGTAGACCAG ATTGTGCACC GACTCCATGT TGGATAAATG
1921 AGTTGCATTG TTGCCATCTG TACTTCTTTT GGTTCTATTA TGAGTAAGAT TCAGACTGGA
1981 GCGGTTGGCC AAACGTTCGA GTTCCACCAG AGATTTTGC TTGATACCTT GCCAGAACAC
2041 CACCAAACCA CCAGTGGTTT CAAAGACGGA CACGTTTCCA TATTTTTCAT ATGTTTGATT
2101 GTATGAAGTA TTGAAAATCT GCTGTAACTT ATTTATGGCC TCATCACGTA CACAGTCCAG
2161 CGCAGAGTCG GACATGTTCA CCTCTTGCTT CTTAGATAAG AAAGTGGCGG TCATTTTGGC
2221 AGAAGAAAAG TGATACGAGT CCTCGGCTTC GGAACGAATG GTGCGTTCCG AGGCTTCCCA
2281 GAAAGTGAGT TGACAAGTAA CATTCTTCTC GTCCTGTATA TCCCAGGAGA TCACTGAGTC
2341 CGCACGTTCA AGAAAGCCA CCAACCTGTG GGTCTCTAAC GCAGAATTCG GTCTTTCAAA
2401 GTCGGAGACG ATAGTGTAGT TCGGAAAAAT GAAAAACTTG TCGGCGTTTT CTCCAAAATA
2461 GCTGGCATTG CGATTAGTTC CGTTGTAGAA AGGAGAAATG TCAACCACAT CACCCGTGGA
2521 AGTTGCAAAA AAATGATAGG GATACTTGGA GCGCGCAGTA GTGATGGTCA CCATACAATT
2581 CAGATTACAG GTCTCACGAT AGAGCCAGGT GCTGCCGCGG CTGTGCCATT GATCCTTGAC
2641 CGTCACGTAA CGGGTACTGT GGGTGTTGGA ATAATCGTCG GCATTAATT GCATGGTTTT
2701 GTTTTCATAG CTGTCCCTAT GATAAGCCAC GAAAACCGTG CCTGCTATAA CGCGGCTGTA
2761 GGAACTGTAG CACTGACTGT GACTGTTGAT ATGATGAATC TCCCACATAG GAGGCGCCAC
2821 GTATTCCGTG TTGCTGCCCA GCAGATAAGT GGTGTGGATG TAAGCGTAGC TACGACGAAA
2881 CGTCAAAACC TTCTGGTAGA CTCGTACCTT AAAGGTGTGC GCGACGATGT TGCGTTTGTA
2941 GACCACCATG ATGCCCTCGT CCAGGTCTTC ATTGATGGGC TTCATCGAGG TGCAGACGAT
3001 ATTACGTTCA AAGCGAATAA GATCCGTACC CTGTGCCATA AACACACGC GATAGGGGTA
3061 CTTGGTGGTG TTGACCCCCA CCACATCTCC GTACTTGAGG GTAGTGTTGT AGATGGTCTC
```

3121 GTTAACACCA TGGCTGACCG TTTGGGAAGA AGTTACGCGT TGAGAGACTG AACCGGATCG
3181 AGAATGAGCA GCAGACGTCG TATGAGAGGA ATGGTGACTG TGAGTAGCAG AAGTTCCACG
3241 AGTAGAAGAT GAGGAAACCG CAGCACCCAG ACAGACGATA CACAAGTTAA CGCAGACTAC
3301 CAGGCACCAG ATCCTGGATT CCATTACGAT ACAAACTTAA CGGATATCGC GATAATGAAA
3361 TAATTTATGA TTATTTCTCG CTTTCAATTT AACACAACCC TCAAGAACCT TTGTATTTAT
3421 TTTCACTTTT AAGTATAGAA TAAAGAAGCT TGCATGCCAC GCGTCTCGAG GGCCCCTGCA
3481 GGTCGACTCT AGAGGATCCT TCTTTATTCT ATACTTAAAA AGTGAAAATA AATACAAAGG
3541 TTCTTGAGGG TTGTGTTAAA TTGAAAGCGA GAAATAATCA TAAATTATTT CATTATCGCG
3601 ATATCCGTTA AGTTTGTATC GTAATGTGCC GCCGCCCGGA TTGCGGCTTC TCTTTCTCAC
3661 CTGGACCGGT GGCACTGCTG TGGTGTTGCC TTCTGCTGCC CATCGTTTCC TCAGCCACCG
3721 TCAGCGTCGC TCCTACCGTC GCCGAGAAAG TTCCCGCGGA GTGCCCCGAA CTAACGCGTC
3781 GATGCCTGTT GGGTGAGGTG TTTCAGGGTG ACAAGTATGA AAGTTGGCTG CGCCCGTTGG
3841 TGAATGTTAC CAGACGCGAT GGCCCGCTAT CGCAACTTAT TCGTTACCGT CCCGTTACGC
3901 CGGAGGCCGC CAACTCCGTG CTGTTGGACG ATGCTTTCCT GGACACTCTG GCCCTGCTGT
3961 ACAACAATCC GGATCAATTG CGGGCCTTGC TGACGCTGTT GAGCTCGGAC ACAGCGCCGC
4021 GCTGGATGAC GGTGATGCGC GGTTACAGCG AGTGCGGCGA TGGCTCGCCG GCCGTGTACA
4081 CGTGCGTGGA CGACCTGTGC CGCGGCTACG ACCTCACGCG ACTGTCATAC GGGCGCAGCA
4141 TCTTCACGGA ACACGTGTTA GGCTTCGAGC TGGTGCCACC GTCTCTCTTT AACGTGGTGG
4201 TGGCCATACG CAACGAAGCC ACGCGTACCA ACCGCGCCGT GCGTCTGCCC GTGAGCACCG
4261 CTGCCGCGCC CGAGGGCATC ACGCTCTTTT ACGGCCTGTA CAACGCAGTG AAGGAATTCT
4321 GCCTGCGTCA CCAGCTGGAC CCGCCGCTGC TACGCCACCT AGATAAATAC TACGCCGGAC
4381 TGCCGCCCGA GCTGAAGCAG ACGCGCGTCA ACCTGCCGGC TCACTCGCGC TATGGCCCTC
4441 AAGCAGTGGA TGCTCGCTAA TTTTTATAGA TCCTGATCCT TTTTCTGGGT AAGTAATACG
4501 TCAAGGAGAA AACGAAACGA TCTGTAGTTA GCGGCCGCCT AATTAACTAA TATTATATTT
4561 TTTATCTAAA AAACTAAAAA TAAACATTGA TTAAATTTTA ATATAATACT TAAAAATGGA
4621 TGTTGTGTCG TTAGATAAAC CGTTTATGTA TTTTGAGGAA ATTGATAATG AGTTAGATTA
4681 CGAACCAGAA AGTGCAAATG AGGTCGCAAA AAAACTGCCG TATCAAGGAC AGTTAAAACT
4741 ATTACTAGGA GAATTATTTT TTCTTAGTAA GTTACAGCGA CACGGTATAT TAGATGGTGC
4801 CACCGTAGTG TATATAGGAT CGGCTCCTGG TACACATATA CGTTATTTGA GAGATCATTT
4861 CTATAATTTA GGAATGATTA TCAAATGGAT GCTAATTGAC GGACGCCATC ATGATCCTAT
4921 TTTAAATGGA TTGCGTGATG TGACTCTAGT GACTCGGTTC GTTGATGAGG AATATCTACG
4981 ATCCATCAAA AAACAACTGC ATCCTTCTAA GATTATTTTA ATTTCTGATG TGAGATCCAA
5041 ACGAGGAGGA AATGAACCTA GTACGGCGGA TTTACTAAGT AATTACGCTC TACAAAATGT
5101 CATGATTAGT ATTTTAAACC CCGTGGCGTC TAGTCTTAAA TGGAGATGCC CGTTTCCAGA
5161 TCAATGGATC AAGGACTTTT ATATCCCACA CGGTAATAAA ATGTTACAAC CTTTTGCTCC
5221 TTCATATTCA GCTG

FIG. 48B

SEQUENCE LISTING (1) GENERAL INFORMATION:

(iii) NUMBER OF SEQUENCES: 176

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TAATTAACTA GCTACCCGGG                                          20

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

AATTCCCGGG TAGCTAGTTA ATTACATG                            28

(2) INFORMATION FOR SEQ ID NO:3:

(i) SEQUENCE CHARACTERISTICS:
      (A) LENGTH: 73 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

AGCTTCCCGG GTAAGTAATA CGTCAAGGAG AAAACGAAAC GATCTGTAGT TAGCGGCCGC    60

CTAATTAACT AAT                                                             73

(2) INFORMATION FOR SEQ ID NO:4:

(i) SEQUENCE CHARACTERISTICS:
      (A) LENGTH: 69 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

ATTAGTTAAT TAGGCGGCCG CTAACTACAG ATCGTTTCGT TTTCTCCTTG ACGTATTACT    60

TACCCGGGA                                                                                 69

(2) INFORMATION FOR SEQ ID NO:5:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:5:

TTAGTTAATT AGGCGGCCGC                                                    20

(2) INFORMATION FOR SEQ ID NO:6:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:6:

CGATTACTAT GAAGGATCCG TT                                                 22

(2) INFORMATION FOR SEQ ID NO:7:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:7:

AACGGATCCT TCATAGTAAT                                                    20

(2) INFORMATION FOR SEQ ID NO:8:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:8:

CGATTACTAG ATCTGAGCTC CCCGGGCTCG AGGGATCCGT T                             41

(2) INFORMATION FOR SEQ ID NO:9:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:9:

AACGGATCCC TCGAGCCCGG GGAGCTCAGA TCTAGTAAT                                39

(2) INFORMATION FOR SEQ ID NO:10:

(i) SEQUENCE CHARACTERISTICS:
                (A) LENGTH: 16 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:10:

```
GATCCGAATT CTAGCT                                                          16

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTAGAATT CG                                                              12

(2) INFORMATION FOR SEQ ID NO:12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TATGAGTAAC TTAACTCTTT TGTTAATTAA AAGTATATTC AAAAAATAAG TTATATAAAT          60

AGATCTGAAT TCGTT                                                           75

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AACGAATTCA GATCTATTTA TATAACTTAT TTTTTGAATA TACTTTTAAT TAACAAAAGA          60

GTTAAGTTAC TCA                                                             73

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AAAATGGGCG TGGATTGTTA ACTTTATATA ACTTATTTTT TGAATATAC                      49

(2) INFORMATION FOR SEQ ID NO:15:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:
```

ACACGAATGA TTTTCTAAAG TATTTGGAAA GTTTTATAGG TAGTTGATAG AACAAAATAC    60

ATAATTT    67

(2) INFORMATION FOR SEQ ID NO:16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TCTATCAACT ACCTATAAAA CTTTCCAAAT ACTTTAGAAA ATCATTCGTG T    51

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TGTAAAAATA AATCACTTTT TATACTAAGA TCTCCCGGGC TGCAGC    46

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GGCCGCTGCA GCCCGGGAGA TCTTAGTATA AAAAGTGATT TATTTTTACA AAATTATGTA    60

TTTTGT    66

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TTTCTGTATA TTTGCACCAA TTTAGATCTT ACTCAAAATA TGTAACAATA    50

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TGTCATTTAA CACTATACTC ATATTAATAA AAATAATATT TATT          44

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GATCCTGAGT ACTTTGTAAT ATAATGATAT ATATTTTCAC TTTATCTCAT TTGAGAATAA          60

AAAGATCTTA GG          72

(2) INFORMATION FOR SEQ ID NO:22:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AATTCCTAAG ATCTTTTTAT TCTCAAATGA GATAAAGTGA AAATATATAT CATTATATTA          60

CAAAGTACTC AG          72

(2) INFORMATION FOR SEQ ID NO:23:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GATCCAGATC TCCCGGGAAA AAAATTATTT AACTTTTCAT TAATAGGGAT TTGACGTATG          60

TAGCGTACTA GG          72

(2) INFORMATION FOR SEQ ID NO:24:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AATTCCTAGT ACGCATCATA CGTCAAATCC CTATTAATGA AAAGTTAAAT AATTTTTTTC          60

CCGGGAGATC TG          72

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGGAGATCTC TCGAGCTGCA GGGCGCCGGA TCCTTTTTCT                          40

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AGAAAAAGGA TCCGGCGCCC TGCAGCTCGA GAGATCTCCC                          40

(2) INFORMATION FOR SEQ ID NO:27:

(i) SEQUENCE CHARACTERISTICS:
        (A) LENGTH: 3209 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TGAATGTTAA ATGTTATACT TTGGATGAAG CTATAAATAT GCATTGGAAA AATAATCCAT     60

TTAAAGAAAG GATTCAAATA CTACAAAACC TAAGCGATAA TATGTTAACT AAGCTTATTC    120

TTAACGACGC TTTAAATATA CACAAATAAA CATAATTTTT GTATAACCTA ACAAATAACT    180

AAAACATAAA AATAATAAAA GGAAATGTAA TATCGTAATT ATTTTACTCA GGAATGGGGT    240

TAAATATTTA TATCACGTGT ATATCTATAC TGTTATCGTA TACTCTTTAC AATTACTATT    300

ACGAATATGC AAGAGATAAT AAGATTACGT ATTTAAGAGA ATCTTGTCAT GATAATTGGG    360

TACGACATAG TGATAAATGC TATTTCGCAT CGTTACATAA AGTCAGTTGG AAAGATGGAT    420

TTGACAGATG TAACTTAATA GGTGCAAAAA TGTTAAATAA CAGCATTCTA TCGGAAGATA    480

GGATACCAGT TATATTATAC AAAAATCACT GGTTGGATAA AACAGATTCT GCAATATTCG    540

TAAAAGATGA AGATTACTGC GAATTTGTAA ACTATGACAA TAAAAAGCCA TTTATCTCAA    600

CGACATCGTG TAATTCTTCC ATGTTTTATG TATGTGTTTC AGATATTATG AGATTACTAT    660

AAACTTTTTG TATACTTATA TTCCGTAAAC TATATTAATC ATGAAGAAAA TGAAAAAGTA    720

TAGAAGCTGT TCACGAGCGG TTGTTGAAAA CAACAAAATT ATACATTCAA GATGGCTTAC    780

ATGTACGTCT GTGAGGCTAT CATGGATAAT GACAATGCAT CTCTAAATAG GTTTTTGGAC    840

AATGGATTCG ACCCTAACAC GGAATATGGT ACTCTACAAT CTCCTCTTGA AATGGCTGTA    900

ATGTTCAAGA ATACCGAGGC TATAAAAATC TTGATGAGGT ATGGAGCTAA ACCTGTAGTT    960

ACTGAATGCA CAACTTCTTG TCTGCATGAT GCGGTGTTGA GAGACGACTA CAAAATAGTA   1020

AAAGATCTGT TGAAGAATAA CTATGTAAAC AATGTTCTTT ACAGCGGAGG CTTTACTCCT   1080

TTGTGTTTGG CAGCTTACCT TAACAAAGTT AATTTGGTTA AACTTCTATT GGCTCATTCG   1140

GCGGATGTAG ATATTTCAAA CACGGATCGG TTAACTCCTC TACATATAGC CGTATCAAAT   1200

AAAAATTTAA CAATGGTTAA ACTTCTATTG AACAAAGGTG CTGATACTGA CTTGCTGGAT   1260

AACATGGGAC GTACTCCTTT AATGATCGCT GTACAATCTG GAAATATTGA AATATGTAGC   1320

```
ACACTACTTA AAAAAAATAA AATGTCCAGA ACTGGGAAAA ATTGATCTTG CCAGCTGTAA    1380

TTCATGGTAG AAAAGAAGTG CTCAGGCTAC TTTTCAACAA AGGAGCAGAT GTAAACTACA    1440

TCTTTGAAAG AAATGGAAAA TCATATACTG TTTTGGAATT GATTAAAGAA AGTTACTCTG    1500

AGACACAAAA GAGGTAGCTG AAGTGGTACT CTCAAAATGC AGAACGATGA CTGCGAAGCA    1560

AGAAGTAGAG AAATAACACT TTATGACTTT CTTAGTTGTA GAAAGATAG ATATAATG    1620

ATGGTCATAG ATAACTCTGA TATTGCAAGT AAATGCAATA ATAAGTTAGA TTTATTTAAA    1680

AGGATAGTTA AAAATAGAAA AAAAGAGTTA ATTTGTAGGG TTAAAATAAT ACATAAGATC    1740

TTAAAATTTA TAAATACGCA TAATAATAAA AATAGATTAT ACTTATTACC TTCAGAGATA    1800

AAATTTAAGA TATTTACTTA TTTAACTTAT AAAGATCTAA AATGCATAAT TTCTAAATAA    1860

TGAAAAAAAA GTACATCATG AGCAACGCGT TAGTATATTT TACAATGGAG ATTAACGCTC    1920

TATACCGTTC TATGTTTATT GATTCAGATG ATGTTTTAGA AAAGAAAGTT ATTGAATATG    1980

AAAACTTTAA TGAAGATGAA GATGACGACG ATGATTATTG TTGTAAATCT GTTTTAGATG    2040

AAGAAGATGA CGCGCTAAAG TATACTATGG TTACAAAGTA TAACTCTATA CTACTAATGG    2100

CGACTTCTGC AAGAAGGTAT AGTATAGTGA AAATGTTGTT AGATTATGAT TATGAAAAAC    2160

CAAATAAATC AGATCCATAT CTAAAGGTAT CTCCTTTGCA CATAATTTCA TCTATTCCTA    2220

GTTTAGAATA CTTTTCATTA TATTTGTTTA CAGCTGAAGA CGAAAAAAAT ATATCGATAA    2280

TAGAAGATTA TGTTAACTCT GCTAATAAGA TGAAATTGAA TGAGTCTGTG ATAATAGCTA    2340

TAATCAGAGA AGTTCTAAAA GGAAATAAAA ATCTAACTGA TCAGGATATA AAAACATTGG    2400

CTGATGAAAT CAACAAGGAG GAACTGAATA TAGCTAAACT ATTGTTAGAT AGAGGGCCA    2460

AAGTAAATTA CAAGGATGTT TACGGTTCTT CAGCTCTCCA TAGAGCTGCT ATTGGTAGGA    2520

AACAGGATAT GATAAAGCTG TTAATCGATC ATGGAGCTGA TGTAAACTCT TTAACTATTG    2580

CTAAAGATAA TCTTATTAAA AAAAAATAAT ATCACGTTTA GTAATATTAA AATATATTAA    2640

TAACTCTATT ACTAATAACT CCAGTGGATA TGAACATAAT ACGAAGTTTA TACATTCTCA    2700

TCAAAATCTT ATTGACATCA AGTTAGATTG TGAAAATGAG ATTATGAAAT TAAGGAATAC    2760

AAAAATAGGA TGTAAGAACT TACTAGAATG TTTTATCAAT AATGATATGA ATACAGTATC    2820

TAGGGCTATA AACAATGAAA CGATTAAAAA TTATAAAAAT CATTTCCCTA TATATAATAC    2880

GCTCATAGAA AAATTCATTT CTGAAAGTAT ACTAAGACAC GAATTATTGG ATGGAGTTAT    2940

AAATTCTTTT CAAGGATTCA ATAATAAATT GCCTTACGAG ATTCAGTACA TTATACTGGA    3000

GAATCTTAAT AACCATGAAC TAAAAAAAAT TTTAGATAAT ATACATTAAA AAGGTAAATA    3060

GATCATCTGT TATTATAAGC AAAGATGCTT GTTGCCAATA ATATACAACA GGTATTTGTT    3120

TTTATTTTTA ACTACATATT TGATGTTCAT TCTCTTTATA TAGTATACAC AGAAAATTCA    3180

TAATCCACTT AGAATTTCTA GTTATCTAG                                      3209
```

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
GCTTCCCGGG AATTCTAGCT AGCTAGTTT                                      29
```

(2) INFORMATION FOR SEQ ID NO:29:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ACTCTCAAAA GCTTCCCGGG AATTCTAGCT AGCTAGTTTT TATAAA                46

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GATCTTTATA AAAACTAGCT AGCTAGAATT CCCGGGAAGC TTTTGAGAGT            50

(2) INFORMATION FOR SEQ ID NO:31:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CTGAAATTAT TTCATTATCG CGATATCCGT TAAGTTTGTA TCGTAATGGT TCCTCAGGCT 60

CTCCTGTTTG T                                                      71

(2) INFORMATION FOR SEQ ID NO:32:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CATTACGATA CAAACTTAAC GGATATCGCG ATAATGAAAT AATTTCAG              48

(2) INFORMATION FOR SEQ ID NO:33:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

ACCCCTTCTG GTTTTTCCGT TGTGTTTTGG GAAATTCCCT ATTTACACGA TCCCAGACAA 60

GCTTAGATCT CAG                                                    73

(2) INFORMATION FOR SEQ ID NO:34:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
CTGAGATCTA AGCTTGTCTG GGATCGTGTA AATAGGGAAT TTCCCAAAAC A          51
```

(2) INFORMATION FOR SEQ ID NO:35:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
CAACGGAAAA ACCAGAAGGG GTACAAACAG GAGAGCCTGA GGAAC                 45
```

(2) INFORMATION FOR SEQ ID NO:36:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
GGATCCCCGG G                                                     11
```

(2) INFORMATION FOR SEQ ID NO:37:

(i) SEQUENCE CHARACTERISTICS:
        (A) LENGTH: 2724 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
ATGGAATCCA GGATCTGGTG CCTGGTAGTC TGCGTTAACT TGTGTATCGT CTGTCTGGGT    60
GCTGCGGTTT CCTCATCTTC TACTCGTGGA ACTTCTGCTA CTCACAGTCA CCATTCCTCT   120
CATACGACGT CTGCTGCTCA TTCTCGATCC GGTTCAGTCT CTCAACGCGT AACTTCTTCC   180
CAAACGGTCA GCCATGGTGT TAACGAGACC ATCTACAACA CTACCCTCAA GTACGGAGAT   240
GTGGTGGGGG TCAACACCAC CAAGTACCCC TATCGCGTGT GTTCTATGGC ACAGGGTACG   300
GATCTTATTC GCTTTGAACG TAATATCGTC TGCACCTCGA TGAAGCCCAT CAATGAAGAC   360
CTGGACGAGG GCATCATGGT GGTCTACAAA CGCAACATCG TCGCGCACAC CTTTAAGGTA   420
CGAGTCTACC AGAAGGTTTT GACGTTTCGT CGTAGCTACG CTTACATCCA CACCACTTAT   480
CTGCTGGGCA GCAACACGGA ATACGTGGCG CCTCCTATGT GGGAGATTCA TCATATCAAC   540
AGTCACAGTC AGTGCTACAG TTCCTACAGC CGCGTTATAG CAGGCACGGT TTTCGTGGCT   600
TATCATAGGG ACAGCTATGA AAACAAAACC ATGCAATTAA TGCCCGACGA TTATTCCAAC   660
```

```
ACCCACAGTA CCCGTTACGT GACGGTCAAG GATCAATGGC ACAGCCGCGG CAGCACCTGG      720

CTCTATCGTG AGACCTGTAA TCTGAATTGT ATGGTGACCA TCACTACTGC GCGCTCCAAG      780

TATCCCTATC ATTTTTTCGC AACTTCCACG GGTGATGTGG TTGACATTTC TCCTTTCTAC      840

AACGGAACTA ATCGCAATGC CAGCTATTTT GGAGAAAACG CCGACAAGTT TTTCATTTTT      900

CCGAACTACA CTATCGTCTC CGACTTTGAA AGACCGAATT CTGCGTTAGA GACCCACAGG      960

TTGGTGGCTT TTCTTGAACG TGCGGACTCA GTGATCTCCT GGGATATACA GGACGAGAAG     1020

AATGTTACTT GTCAACTCAC TTTCTGGGAA GCCTCGGAAC GCACCATTCG TTCCGAAGCC     1080

GAGGACTCGT ATCACTTTTC TTCTGCCAAA ATGACCGCCA CTTTCTTATC TAAGAAGCAA     1140

GAGGTGAACA TGTCCGACTC TGCGCTGGAC TGTGTACGTG ATGAGGCCAT AAATAAGTTA     1200

CAGCAGATTT TCAATACTTC ATACAATCAA ACATATGAAA AATATGGAAA CGTGTCCGTC     1260

TTTGAAACCA CTGGTGGTTT GGTGGTGTTC TGGCAAGGTA TCAAGCAAAA ATCTCTGGTG     1320

GAACTCGAAC GTTTGGCCAA CCGCTCCAGT CTGAATCTTA CTCATAATAG AACCAAAAGA     1380

AGTACAGATG GCAACAATGC AACTCATTTA TCCAACATGG AGTCGGTGCA CAATCTGGTC     1440

TACGCCCAGC TGCAGTTCAC CTATGACACG TTGCGCGGTT ACATCAACCG GGCGCTGGCC     1500

GAAATCGCAG AAGCCTGGTG TGTGGATCAA CGGCGCACCC TAGAGGTCTT CAAGGAACTT     1560

AGCAAGATCA ACCCGTCAGC TATTCTCTCG GCCATCTACA ACAAACCGAT TGCCGCGCGT     1620

TTCATGGGTG ATGTCCTGGG TCTGGCCAGC TGCGTGACCA TTAACCAAAC CAGCGTCAAG     1680

GTGCTGCGTG ATATGAATGT GAAGGAATCG CCAGGACGCT GCTACTCACG ACCAGTGGTC     1740

ATCTTTAATT TCGCCAACAG CTCGTACGTG CAGTACGGTC AACTGGGCGA GGATAACGAA     1800

ATCCTGTTGG GCAACCACCG CACTGAGGAA TGTCAGCTTC CCAGCCTCAA GATCTTCATC     1860

GCCGGCAACT CGGCCTACGA GTACGTGGAC TACCTCTTCA AACGCATGAT TGACCTCAGC     1920

AGCATCTCCA CCGTCGACAG CATGATCGCC CTAGACATCG ACCCGCTGGA AAACACCGAC     1980

TTCAGGGTAC TGGAACTTTA CTCGCAGAAA GAATTGCGTT CCAGCAACGT TTTTGATCTC     2040

GAGGAGATCA TGCGCGAGTT CAATTCGTAT AAGCAGCGGG TAAAGTACGT GGAGGACAAG     2100

GTAGTCGACC CGCTGCCGCC CTACCTCAAG GGTCTGGACG ACCTCATGAG CGGCCTGGGC     2160

GCCGCGGGAA AGGCCGTTGG CGTAGCCATT GGGGCCGTGG GTGGCGCGGT GGCCTCCGTG     2220

GTCGAAGGCG TTGCCACCTT CCTCAAAAAC CCCTTCGGAG CCTTCACCAT CATCCTCGTG     2280

GCCATAGCCG TCGTCATTAT CATTTATTTG ATCTATATCC GACAGCGGCG TCTCTGCATG     2340

CAGCCGCTGC AGAACCTCTT TCCCTATCTG GTGTCCGCCG ACGGGACCAC CGTGACGTCG     2400

GGCAACACCA AAGACACGTC GTTACAGGCT CCGCCTTCCT ACGAGGAAAG TGTTTATAAT     2460

TCTGGTCGCA AAGGACCGGG ACCACCGTCG TCTGATGCAT CCACGGCGGC TCCGCCTTAC     2520

ACCAACGAGC AGGCTTACCA GATGCTTCTG GCCCTGGTCC GTCTGGACGC AGAGCAGCGA     2580

GCGCACGAGA ACGGTACAGA TTCTTTGGAC GGACAGACTG GCACGCAGGA CAAGGGACAG     2640

AAGCCCAACC TGCTAGACCG ACTGCGACAC CGCAAAAACG GCTACCGACA CTTGAAAGAC     2700

TCCGACGAAG AAGAGAACGT CTGA                                           2724
```

(2) INFORMATION FOR SEQ ID NO:38:

(i) SEQUENCE CHARACTERISTICS:
        (A) LENGTH: 4260 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

| | | | | | |
|---|---|---|---|---|---|
| AAGCTTTTGC | GATCAATAAA | TGGATCACAA | CCAGTATCTC | TTAACGATGT | TCTTCGCAGA | 60
| TGATGATTCA | TTTTTTAAGT | ATTTGGCTAG | TCAAGATGAT | GAATCTTCAT | TATCTGATAT | 120
| ATTGCAAATC | ACTCAATATC | TAGACTTTCT | GTTATTATTA | TTGATCCAAT | CAAAAAATAA | 180
| ATTAGAAGCC | GTGGGTCATT | GTTATGAATC | TCTTTCAGAG | GAATACAGAC | AATTGACAAA | 240
| ATTCACAGAC | TCTCAAGATT | TTAAAAAACT | GTTTAACAAG | GTCCCTATTG | TTACAGATGG | 300
| AAGGGTCAAA | CTTAATAAAG | GATATTTGTT | CGACTTTGTG | ATTAGTTTGA | TGCGATTCAA | 360
| AAAAGAATCC | TCTCTAGCTA | CCACCGCAAT | AGATCCTATT | AGATACATAG | ATCCTCGTCG | 420
| CGATATCGCA | TTTTCTAACG | TGATGGATAT | ATTAAAGTCG | AATAAAGTGA | ACAATAATTA | 480
| ATTCTTTATT | GTCATCATGT | AATTAACTAG | CTACCCGGGA | GATCTCTCGA | GCTGCAGAAG | 540
| CTTATAAAAA | TCACAAGTCT | CTGTCACTTT | TTTTGTCTAG | TTTTTTTTTC | TCCTCTTGGT | 600
| TCAGACGTTC | TCTTCTTCGT | CGGAGTCTTT | CAAGTGTCGG | TAGCCGTTTT | TGCGGTGTCG | 660
| CAGTCGGTCT | AGCAGGTTGG | GCTTCTGTCC | CTTGTCCTGC | GTGCCAGTCT | GTCCGTCCAA | 720
| AGAATCTGTA | CCGTTCTCGT | GCGCTCGCTG | CTCTGCGTCC | AGACGGACCA | GGGCCAGAAG | 780
| CATCTGGTAA | GCCTGCTCGT | TGGTGTAAGG | CGGAGCCGCC | GTGGATGCAT | CAGACGACGG | 840
| TGGTCCCGGT | CCTTTGCGAC | CAGAATTATA | AACACTTTCC | TCGTAGGAAG | GCGGAGCCTG | 900
| TAACGACGTG | TCTTTGGTGT | TGCCCGACGT | CACGGTGGTC | CCGTCGGCGG | ACACCAGATA | 960
| GGGAAAGAGG | TTCTGCAGCG | GCTGCATGCA | GAGACGCCGC | TGTCGAGTAT | AGATCAAATA | 1020
| AATGATAATG | ACGACGGCTA | TGGCCACGAG | GATGATGGTG | AAGGCTCCGA | AGGGGTTTTT | 1080
| GAGGAAGGTG | GCAACGCCTT | CGACCACGGA | GGCCACCGCG | CCACCCACGG | CCCCAATGGC | 1140
| TACGCCAACG | GCCTTTCCCG | CGGCGCCCAG | GCCGCTCATG | AGGTCGTCCA | GACCCTTGAG | 1200
| GTAGGGCGGC | AGCGGGTCGA | CTACCTTGTC | CTCCACGTAC | TTTACCCGCT | GCTTATACGA | 1260
| ATTGAACTCG | CGCATGATCT | CCTCGAGATC | AAAAACGTTG | CTGGAACGCA | ATTCTTTCTG | 1320
| CGAGTAAAGT | TCCAGTACCC | TGAAGTCGGT | GTTTTCCAGC | GGGTCGATGT | CTAGGGCGAT | 1380
| CATGCTGTCG | ACGGTGGAGA | TGCTGCTGAG | GTCAATCATG | CGTTTGAAGA | GGTAGTCCAC | 1440
| GTACTCGTAG | GCCGAGTTGC | CGGCGATGAA | GATCTTGAGG | CTGGGAAGCT | GACATTCCTC | 1500
| AGTGCGGTGG | TTGCCCAACA | GGATTTCGTT | ATCCTCGCCC | AGTTGACCGT | ACTGCACGTA | 1560
| CGAGCTGTTG | GCGAAATTAA | AGATGACCAC | TGGTCGTGAG | TAGCAGCGTC | CTGGCGATTC | 1620
| CTTCACATTC | ATATCACGCA | GCACCTTGAC | GCTGGTTTGG | TTAATGGTCA | CGCAGCTGGC | 1680
| CAGACCCAGG | ACATCACCCA | TGAAACGCGC | GGCAATCGGT | TGTTGTAGA | TGGCCGAGAG | 1740
| AATAGCTGAC | GGGTTGATCT | TGCTAAGTTC | CTTGAAGACC | TCTAGGGTGC | GCCGTTGATC | 1800
| CACACACCAG | GCTTCTGCGA | TTTCGGCCAG | CGCCCGGTTG | ATGTAACCGC | GCAACGTGTC | 1860
| ATAGGTGAAC | TGCAGCTGGG | CGTAGACCAG | ATTGTGCACC | GACTCCATGT | TGGATAAATG | 1920
| AGTTGCATTG | TTGCCATCTG | TACTTCTTTT | GGTTCTATTA | TGAGTAAGAT | TCAGACTGGA | 1980
| GCGGTTGGCC | AAACGTTCGA | GTTCCACCAG | AGATTTTTGC | TTGATACCTT | GCCAGAACAC | 2040
| CACCAAACCA | CCAGTGGTTT | CAAAGACGGA | CACGTTTCCA | TATTTTTCAT | ATGTTTGATT | 2100
| GTATGAAGTA | TTGAAAATCT | GCTGTAACTT | ATTTATGGCC | TCATCACGTA | CACAGTCCAG | 2160
| CGCAGAGTCG | GACATGTTCA | CCTCTTGCTT | CTTAGATAAG | AAAGTGGCGG | TCATTTTGGC | 2220

```
AGAAGAAAAG TGATACGAGT CCTCGGCTTC GGAACGAATG GTGCGTTCCG AGGCTTCCCA    2280

GAAAGTGAGT TGACAAGTAA CATTCTTCTC GTCCTGTATA TCCCAGGAGA TCACTGAGTC    2340

CGCACGTTCA AGAAAAGCCA CCAACCTGTG GGTCTCTAAC GCAGAATTCG GTCTTTCAAA    2400

GTCGGAGACG ATAGTGTAGT TCGGAAAAAT GAAAAACTTG TCGGCGTTTT CTCCAAAATA    2460

GCTGGCATTG CGATTAGTTC CGTTGTAGAA AGGAGAAATG TCAACCACAT CACCCGTGGA    2520

AGTTGCGAAA AAATGATAGG GATACTTGGA GCGCGCAGTA GTGATGGTCA CCATACAATT    2580

CAGATTACAG GTCTCACGAT AGAGCCAGGT GCTGCCGCGG CTGTGCCATT GATCCTTGAC    2640

CGTCACGTAA CGGGTACTGT GGGTGTTGGA ATAATCGTCG GCATTAATT GCATGGTTTT    2700

GTTTTCATAG CTGTCCCTAT GATAAGCCAC GAAAACCGTG CCTGCTATAA CGCGGCTGTA    2760

GGAACTGTAG CACTGACTGT GACTGTTGAT ATGATGAATC TCCCACATAG GAGGCGCCAC    2820

GTATTCCGTG TTGCTGCCCA GCAGATAAGT GGTGTGGATG TAAGCGTAGC TACGACGAAA    2880

CGTCAAAACC TTCTGGTAGA CTCGTACCTT AAAGGTGTGC GCGACGATGT TGCGTTTGTA    2940

GACCACCATG ATGCCCTCGT CCAGGTCTTC ATTGATGGGC TTCATCGAGG TGCAGACGAT    3000

ATTACGTTCA AAGCGAATAA GATCCGTACC CTGAGCCATA GAACACACGC GATAGGGTA    3060

CTTGGTGGTG TTGACCCCCA CCACATCTCC GTACTTGAGG GTAGTGTTGT AGATGGTCTC    3120

GTTAACACCA TGGCTGACCG TTTGGGAAGA AGTTACGCGT TGAGAGACTG AACCGGATCG    3180

AGAATGAGCA GCAGACGTCG TATGAGAGGA ATGGTGACTG TGAGTAGCAG AAGTTCCACG    3240

AGTAGAAGAT GAGGAAACCG CAGCACCCAG ACAGACGATA CACAAGTTAA CGCAGACTAC    3300

CAGGCACCAG ATCCTGGATT CCATTACGAT ACAAACTTAA CGGATATCGC GATAATGAAA    3360

TAATTTATGA TTATTTCTCG CTTTCAATTT AACACAACCC TCAAGAACCT TTGTATTTAT    3420

TTTCACTTTT AAGTATAGAA TAAAGAAGCT TGCATGCCAC GCGTCTCGAG GGCCCCTGCA    3480

GGTCGACTCT AGAGGATCCT GATCCTTTTT CTGGGTAAGT AATACGTCAA GGAGAAAACG    3540

AAACGATCTG TAGTTAGCGG CCGCCTAATT AACTAATATT ATATTTTTTA TCTAAAAAAC    3600

TAAAAATAAA CATTGATTAA ATTTTAATAT AATACTTAAA AATGGATGTT GTGTCGTTAG    3660

ATAAACCGTT TATGTATTTT GAGGAAATTG ATAATGAGTT AGATTACGAA CCAGAAAGTG    3720

CAAATGAGGT CGCAAAAAAA CTGCCGTATC AAGGACAGTT AAAACTATTA CTAGGAGAAT    3780

TATTTTTTCT TAGTAAGTTA CAGCGACACG GTATATTAGA TGGTGCCACC GTAGTGTATA    3840

TAGGATCGGC TCCTGGTACA CATATACGTT ATTTGAGAGA TCATTTCTAT AATTTAGGAA    3900

TGATTATCAA ATGGATGCTA ATTGACGGAC GCCATCATGA TCCTATTTTA AATGGATTGC    3960

GTGATGTGAC TCTAGTGACT CGGTTCGTTG ATGAGGAATA TCTACGATCC ATCAAAAAAC    4020

AACTGCATCC TTCTAAGATT ATTTTAATTT CTGATGTGAG ATCCAAACGA GGAGGAAATG    4080

AACCTAGTAC GGCGGATTTA CTAAGTAATT ACGCTCTACA AAATGTCATG ATTAGTATTT    4140

TAAACCCCGT GGCGTCTAGT CTTAAATGGA GATGCCCGTT TCCAGATCAA TGGATCAAGG    4200

ACTTTTATAT CCCACACGGT AATAAAATGT TACAACCTTT TGCTCCTTCA TATTCAGCTG    4260
```

(2) INFORMATION FOR SEQ ID NO:39:

(i) SEQUENCE CHARACTERISTICS:
  (A) LENGTH: 7351 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:39:

```
AGATATTTGT TAGCTTCTGC CGGAGATACC GTGAAAATCT ATTTTCTGGA AGGAAAGGGA      60
GGTCTTATCT ATTCTGTCAG CAGAGTAGGT TCCTCTAATG ACGAAGACAA TAGTGAATAC     120
TTGCATGAAG GTCACTGTGT AGAGTTCAAA ACTGATCATC AGTGTTTGAT AACTCTAGCG     180
TGTACGAGTC CTTCTAACAC TGTGGTTTAT TGGCTGGAAT AAAAGGATAA AGACACCTAT     240
ACTGATTCAT TTTCATCTGT CAACGTTTCT CTAAGAGATT CATAGGTATT ATTATTACAT     300
CGATCTAGAA GTCTAATAAC TGCTAAGTAT ATTATTGGAT TTAACGCGCT ATAAACGCAT     360
CCAAAACCTA CAAATATAGG AGAAGCTTCT CTTATGAAAC TTCTTAAAGC TTTACTCTTA     420
CTATTACTAC TCAAAAGAGA TATTACATTA ATTATGTGAT GAGGCATCCA ACATATAAAG     480
AAGACTAAAG CTGTAGAAGC TGTTATGAAG AATATCTTAT CAGATATATT AGATGCATTG     540
TTAGTTCTGT AGATCAGTAA CGTATAGCAT ACGAGTATAA TTATCGTAGG TAGTAGGTAT     600
CCTAAAATAA ATCTGATACA GATAATAACT TTGTAAATCA ATTCAGCAAT TTCTCTATTA     660
TCATGATAAT GATTAATACA CAGCGTGTCG TTATTTTTTG TTACGATAGT ATTTCTAAAG     720
TAAAGAGCAG GAATCCCTAG TATAATAGAA ATAATCCATA TGAAAAATAT AGTAATGTAC     780
ATATTTCTAA TGTTAACATA TTTATAGGTA AATCCAGGAA GGGTAATTTT TACATATCTA     840
TATACGCTTA TTACAGTTAT TAAAAATATA CTTGCAAACA TGTTAGAAGT AAAAAAGAAA     900
GAACTAATTT TACAAAGTGC TTTACCAAAA TGCCAATGGA AATTACTTAG TATGTATATA     960
ATGTATAAAG GTATGAATAT CACAAACAGC AAATCGGCTA TTCCCAAGTT GAGAAACGGT    1020
ATAATAGATA TATTTCTAGA TACCATTAAT AACCTTATAA GCTTGACGTT TCCTATAATG    1080
CCTACTAAGA AAACTAGAAG ATACATACAT ACTAACGCCA TACGAGAGTA ACTACTCATC    1140
GTATAACTAC TGTTGCTAAC AGTGACACTG ATGTTATAAC TCATCTTTGA TGTGGTATAA    1200
ATGTATAATA ACTATATTAC ACTGGTATTT TATTTCAGTT ATATACTATA TAGTATTAAA    1260
AATTATATTT GTATAATTAT ATTATTATAT TCAGTGTAGA AAGTAAAATA CTATAAATAT    1320
GTATCTCTTA TTTATAACTT ATTAGTAAAG TATGTACTAT TCAGTTATAT TGTTTTATAA    1380
AAGCTAAATG CTACTAGATT GATATAAATG AATATGTAAT AAATTAGTAA TGTAGTATAC    1440
TAATATTAAC TCACATTATG AATACTACTA ATCACGAAGA ATGCAGTAAA ACATATGATA    1500
CAAACATGTT AACAGTTTTA AAAGCCATTA GTAATAAACA GTACAATATA ATTAAGTCTT    1560
TACTTAAAAA AGATATTAAT GTTAATAGAT TATTAACTAG TTATTCTAAC GAAATATATA    1620
AACATTTAGA CATTACATTA TGTAATATAC TTATAGAACG TGCAGCAGAC ATAAACATTA    1680
TAGATAAGAA CAATCGTACA CCGTTGTTTT ATGCGGTAAA GAATAATGAT TATGATATGG    1740
TTAAACTCCT ATTAAAAAAT GGCGCGAATG TAAATTTACA AGATAGTATA GGATATTCAT    1800
GTCTTCACAT CGCAGGTATA CATAAATAGTA ACATAGAAAT AGTAGATGCA TTGATATCAT    1860
ACAAACCAGA TTTAAACTCC CGCGATTGGG TAGGTAGAAC ACCGCTACAT ATCTTCGTGA    1920
TAGAATCTAA CTTTGAAGCT GTGAAATTAT TATTAAAGTC AGGTGCATAT GTAGGTTTGA    1980
AAGACAAATG TAAGCATTTT CCTATACACC ATTCTGTAAT GAAATTAGAT CACTTAATAT    2040
CAGGATTGTT ATTAAAATAT GGAGCAAATC CAAATACAAT TAACGGCAAT GGAAAAACAT    2100
TATTAAGCAT TGCTGTAACA TCTAATAATA CACTACTGGT AGAACAGCTG CTGTTATATG    2160
GAGCAGAAGT TAATAATGGT GGTTATGATG TTCCAGCTCC TATTATATCC GCTGTCAGTG    2220
TTAACAATTA TGATATTGTT AAGATACTGA TACATAATGG TGCGAATATA AATGTATCCA    2280
CGGAAGATGG TAGAACGTCT TTACATACAG CTATGTTTTG GAATAACGCT AAAATAATAG    2340
```

```
ATGAGTTGCT TAACTATGGA AGTGACATAA ACAGCGTAGA TACTTATGGT AGAACTCCGT    2400

TATCTTGTTA TCGTAGCTTA AGTTATGATA TCGCTACTAA ACTAATATCA CGTATCATTA    2460

TAACAGATGT CTATCGTGAA GCACCAGTAA ATATCAGCGG ATTTATAATT AATTTAAAAA    2520

CTATAGAAAA TAATGATATA TTCAAATTAA TTAAAGATGA TTGTATTAAA GAGATAAACA    2580

TACTTAAAAG TATAACCCTT AATAAATTTC ATTCATCTGA CATATTTATA CGATATAATA    2640

CTGATATATG TTTATTAACG AGATTTATTC AACATCCAAA GATAATGAAA CTAACAAAAA    2700

ACTCTACGCT TATAAATCTA TAGTCAACGA GAGAAAAATC AAAGCTACTT ACAGGTATTA    2760

TCAAATAAAA AAGTATTAA CTGTACTACC TTTTTCAGGA TATTTCTCTA TATTGCCGTT     2820

TGATGTGTTA GTATATATAC TTGAATTCAT CTATGATAAT AATATGTTGG TACTTATGAG    2880

AGCGTTATCA TTAAAATGAA ATAAAAAGCA TACAAGCTAT TGCTTCGCTA TCGTTACAAA    2940

ATGGCAGGAA TTTTGTGTAA ACTAAGCCAC ATACTTGCCA ATGAAAAAAA TAGTAGAAAG    3000

GATACTATTT TAATGGGATT AGATGTTAAG GTTCCTTGGG ATTATAGTAA CTGGGCATCT    3060

GTTAACTTTT ACGACGTTAG GTTAGATACT GATGTTACAG ATTATAATAA TGTTACAATA    3120

AAATACATGA CAGGATGTGA TATTTTTCCT CATATAACTC TTGGAATAGC AAATATGGAT    3180

CAATGTGATA GATTTGAAAA TTTCAAAAAG CAAATAACTG ATCAAGATTT ACAGACTATT    3240

TCTATAGTCT GTAAAGAAGA GATGTGTTTT CCTCAGAGTA ACGCCTCTAA ACAGTTGGGA    3300

GCGAAAGGAT GCGCTGTAGT TATGAAACTG GAGGTATCTG ATGAACTTAG AGCCCTAAGA    3360

AATGTTCTGC TGAATGCGGT ACCCTGTTCG AAGGACGTGT TTGGTGATAT CACAGTAGAT    3420

AATCCGTGGA ATCCTCACAT AACAGTAGGA TATGTTAAGG AGGACGATGT CGAAAACAAG    3480

AAACGCCTAA TGGAGTGCAT GTCCAAGTTT AGGGGGCAAG AAATACAAGT TCTAGGATGG    3540

TATTAATAAG TATCTAAGTA TTTGGTATAA TTTATTAAAT AGTATAATTA TAACAAATAG    3600

ATAAATAACA TGATAACGGT TTTTATTAGA ATAAAATAGA GATAATATCA TAATGATATA    3660

TAATACTTCA TTACCAGAAA TGAGTAATGG AAGACTTATA AATGAACTGC ATAAAGCTAT    3720

AAGGTATAGA GATATAAATT TAGTAAGGTA TATACTTAAA AAATGCAAAT ACAATAACGT    3780

AAATATACTA TCAACGTCTT TGTATTTAGC CGTAAGTATT TCTGATATAG AAATGGTAAA    3840

ATTATTACTA GAACACGGTG CCGATATTTT AAAATGTAAA AATCCTCCTC TTCATAAAGC    3900

TGCTAGTTTA GATAATACAG AAATTGCTAA ACTACTAATA GATTCTGGCG CTGACATAGA    3960

ACAGATACAT TCTGGAAATA GTCCGTTATA TATTTCTGTA TATAGAAACA ATAAGTCATT    4020

AACTAGATAT TTATTAAAAA AAGGTGTTAA TTGTAATAGA TTCTTTCTAA ATTATTACGA    4080

TGTACTGTAT GATAAGATAT CTGATGATAT GTATAAAATA TTTATAGATT TTAATATTGA    4140

TCTTAATATA CAAACTAGAA ATTTTGAAAC TCCGTTACAT TACGCTATAA AGTATAAGAA    4200

TATAGATTTA ATTAGGATAT TGTTAGATAA TAGTATTAAA ATAGATAAAA GTTTATTTTT    4260

GCATAAACAG TATCTCATAA AGGCACTTAA AATAATTGT AGTTACGATA TAATAGCGTT     4320

ACTTATAAAT CACGGAGTGC CTATAAACGA ACAAGATGAT TTAGGTAAAA CCCCATTACA    4380

TCATTCGGTA ATTAATAGAA GAAAAGATGT AACAGCACTT CTGTTAAATC TAGGAGCTGA    4440

TATAAACGTA ATAGATGACT GTATGGGCAG TCCCTTACAT TACGCTGTTT CACGTAACGA    4500

TATCGAAACA ACAAAGACAC TTTTAGAAAG AGGATCTAAT GTTAATGTGG TTAATAATCA    4560

TATAGATACC GTTCTAAATA TAGCTGTTGC ATCTAAAAAC AAAACTATAG TAAACTTATT    4620

ACTGAAGTAC GGTACTGATA CAAAGTTGGT AGGATTAGAT AAACATGTTA TTCACATAGC    4680
```

```
TATAGAAATG AAAGATATTA ATATACTGAA TGCGATCTTA TTATATGGTT GCTATGTAAA    4740

CGTCTATAAT CATAAAGGTT TCACTCCTCT ATACATGGCA GTTAGTTCTA TGAAAACAGA    4800

ATTTGTTAAA CTCTTACTTG ACCACGGTGC TTACGTAAAT GCTAAAGCTA AGTTATCTGG    4860

AAATACTCCT TTACATAAAG CTATGTTATC TAATAGTTTT AATAATATAA AATTACTTTT    4920

ATCTTATAAC GCCGACTATA ATTCTCTAAA TAATCACGGT AATACGCCTC TAACTTGTGT    4980

TAGCTTTTTA GATGACAAGA TAGCTATTAT GATAATATCT AAAATGATGT TAGAAATATC    5040

TAAAAATCCT GAAATAGCTA ATTCAGAAGG TTTTATAGTA AACATGGAAC ATATAAACAG    5100

TAATAAAAGA CTACTATCTA TAAAGAATC ATGCGAAAAA GAACTAGATG TTATAACACA    5160

TATAAAGTTA AATTCTATAT ATTCTTTTAA TATCTTTCTT GACAATAACA TAGATCTTAT    5220

GGTAAAGTTC GTAACTAATC CTAGAGTTAA TAAGATACCT GCATGTATAC GTATATATAG    5280

GGAATTAATA CGGAAAAATA AATCATTAGC TTTTCATAGA CATCAGCTAA TAGTTAAAGC    5340

TGTAAAAGAG AGTAAGAATC TAGGAATAAT AGGTAGGTTA CCTATAGATA TCAAACATAT    5400

AATAATGGAA CTATTAAGTA ATAATGATTT ACATTCTGTT ATCACCAGCT GTTGTAACCC    5460

AGTAGTATAA AGTGATTTTA TTCAATTACG AAGATAAACA TTAAATTTGT TAACAGATAT    5520

GAGTTATGAG TATTTAACTA AAGTTACTTT AGGTACAAAT AAAATATTAT GTAATATAAT    5580

AGAAAATTAT CTTGAGTCTT CATTTCCATC ACCGTCTAAA TTTATTATTA AAACCTTATT    5640

ATATAAGGCT GTTGAGTTTA GAAATGTAAA TGCTGTAAAA AAAATATTAC AGAATGATAT    5700

TGAATATGTT AAAGTAGATA GTCATGGTGT CTCGCCTTTA CATATTATAG CTATGCCTTC    5760

AAATTTTTCT CTCATAGACG CTGACATGTA TTCAGAATTT AATGAAATTA GTAATAGACT    5820

TCAAAAATCT AAAGATAGTA ACGAATTTCA ACGAGTTAGT CTACTAAGGA CAATTATAGA    5880

ATATGGTAAT GATAGTGATA TTAATAAGTG TCTAACATTA GTAAAAACGG ATATACAGAG    5940

TAACGAAGAG ATAGATATTA TAGATCTTTT GATAAATAAA GGAATAGATA TAAATATTAA    6000

AGACGATTTA GGAAACACAG CTTTGCATTA CTCGTGTGAT TATGCTAAGG GATCAAAGAT    6060

AGCTAAAAAG TTACTAGATT GTGGAGCAGA TCCTAACATA GTTAATGATT TAGGTGTTAC    6120

ACCACTAGCG TGTGCCGTTA ATACTTGCAA CGAGATACTA GTAGATATTC TGTTAAATAA    6180

TGATGCGAAT CCTGATTCAT CTTCCTCATA TTTTTTAGGT ACTAATGTGT TACATACAGC    6240

CGTAGGTACC GGTAATATAG ATATTGTAAG ATCTTTACTT ACGGCTGGTG CCAATCCTAA    6300

TGTAGGAGAT AAATCTGGAG TTACTCCTTT GCACGTTGCT GCAGCTGATA AGACAGTTA    6360

TCTGTTAATG GAGATGCTAC TAGATAGCGG GGCAGATCCA AATATAAAAT GCGCAAACGG    6420

TTTTACTCCT TTGTTTAATG CAGTATATGA TCATAACCGT ATAAAGTTAT TATTTCTTTA    6480

CGGGGCTGAT ATCAATATTA CTGACTCTTA CGGAAATACT CCTCTTACTT ATATGACTAA    6540

TTTTGATAAT AAATATGTAA ATTCAATAAT TATCTTACAA ATATATCTAC TTAAAAAAGA    6600

ATATAACGAT GAAAGATTGT TTCCACCTGG TATGATAAAA AATTTAAACT TTATAGAATC    6660

AAACGATAGT CTTAAAGTTA TAGCTAAAAA GTGTAATTCG TTAATACGCT ATAAGAAAAA    6720

TAAAGACATA GATGCAGATA ACGTATTATT GGAGCTTTTA GAGGAAGAGG AAGAAGATGA    6780

AATAGACAGA TGGCATACTA CATGTAAAAT ATCTTAAATA GTAATTAAAT CATTGAAATA    6840

TTAACTTACA AGATGATCGA GGTCACTTAT TATACTCTTT AATAATGGGT ACAAAGAGTA    6900

TTCATACGTT AGTTAAATCT AACGATGTAA TACGTGTTCG TGAATTAATA AAGGATGATA    6960

GATGTTTGAT AAATAAAAGA AATAGAAGAA ATCAGTCACC TGTATATATA GCTATATACA    7020

AAGGACTTTA TGAAATGACT GAAATGTTAT TGCTAAATAA TGCAAGTCTA GATACTAAAA    7080
```

```
TACCTTCTTT AATTATAGCA GCTAAAAATA ATGACTTACC TATGATAAAA TTATTGATAC      7140

AATACGGGGC AAAATTAAAT GATATTTATT TAAGGGACAC AGCATTAATG ATAGCTCTCA      7200

GAAATGGTTA CCTAGATATA GCTGAATATT TACTTTCATT AGGAGCAGAA TTTGTTAAAT      7260

ACAGACATAA GGTAATATAT AAATATCTAT CAAAAGATGC GTATGAATTA CTTTTTAGAT      7320

TTAATTATGA CGTTAATATA ATAGATTGAG A                                    7351

(2) INFORMATION FOR SEQ ID NO:40:

(i) SEQUENCE CHARACTERISTICS:
        (A) LENGTH: 7091 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

AGATATTTGT TAGCTTCTGC CGGAGATACC GTGAAAATCT ATTTTCTGGA AGGAAAGGGA        60

GGTCTTATCT ATTCTGTCAG CAGAGTAGGT TCCTCTAATG ACGAAGACAA TAGTGAATAC       120

TTGCATGAAG GTCACTGTGT AGAGTTCAAA ACTGATCATC AGTGTTTGAT AACTCTAGCG       180

TGTACGAGTC CTTCTAACAC TGTGGTTTAT TGGCTGGAAT AAAAGGATAA AGACACCTAT       240

ACTGATTCAT TTTCATCTGT CAACGTTTCT CTAAGAGATT CATAGGTATT ATTATTACAT       300

CGATCTAGAA GTCTAATAAC TGCTAAGTAT ATTATTGGAT TTAACGCGCT ATAAACGCAT       360

CCAAAACCTA CAAATATAGG AGAAGCTTCT CTTATGAAAC TTCTTAAAGC TTTACTCTTA       420

CTATTACTAC TCAAAAGAGA TATTCACATTA ATTATGTGAT GAGGCATCCA ACATATAAAG      480

AAGACTAAAG CTGTAGAAGC TGTTATGAAG AATATCTTAT CAGATATATT AGATGCATTG       540

TTAGTTCTGT AGATCAGTAA CGTATAGCAT ACGAGTATAA TTATCGTAGG TAGTAGGTAT       600

CCTAAAATAA ATCTGATACA GATAATAACT TTGTAAATCA ATTCAGCAAT TTCTCTATTA       660

TCATGATAAT GATTAATACA CAGCGTGTCG TTATTTTTTG TTACGATAGT ATTTCTAAAG       720

TAAAGAGCAG GAATCCCTAG TATAATAGAA ATAATCCATA TGAAAAATAT AGTAATGTAC       780

ATATTTCTAA TGTTAACATA TTTATAGGTA AATCCAGGAA GGGTAATTTT TACATATCTA       840

TATACGCTTA TTACAGTTAT TAAAAATATA CTTGCAAACA TGTTAGAAGT AAAAAAGAAA       900

GAACTAATTT TACAAAGTGC TTTACCAAAA TGCCAATGGA AATTACTTAG TATGTATATA       960

ATGTATAAAG GTATGAATAT CACAAACAGC AAATCGGCTA TTCCCAAGTT GAGAAACGGT      1020

ATAATAGATA TATTTCTAGA TACCATTAAT AACCTTATAA GCTTGACGTT TCCTATAATG      1080

CCTACTAAGA AAACTAGAAG ATACATACAT ACTAACGCCA TACGAGAGTA ACTACTCATC      1140

GTATAACTAC TGTTGCTAAC AGTGACACTG ATGTTATAAC TCATCTTTGA TGTGGTATAA      1200

ATGTATAATA ACTATATTAC ACTGGTATTT TATTTCAGTT ATATACTATA TAGTATTAAA      1260

AATTATATTT GTATAATTAT ATTATTATAT TCAGTGTAGA AAGTAAAATA CTATAAATAT      1320

GTATCTCTTA TTTATAACTT ATTAGTAAAG TATGTACTAT TCAGTTATAT TGTTTTATAA      1380

AAGCTAAATG CTACTAGATT GATATAAATG AATATGTAAT AAATTAGTAA TGTAGTATAC      1440

TAATATTAAC TCACATTTGA CTAATTAGCT ATAAAAACCC GGGCTGCAGG AATTCCTCGA      1500

GACGCGTGGC ATGCAAGCTT ATAAAAATCA CAAGTCTCTG TCACTTTTTT TGTCTAGTTT      1560

TTTTTTCTCC TCTTGGTTCA GACGTTCTCT TCTTCGTCGG AGTCTTTCAA GTGTCGGTAG      1620

CCGTTTTTGC GGTGTCGCAG TCGGTCTAGC AGGTTGGGCT TCTGTCCCTT GTCCTGCGTG      1680
```

-continued

```
CCAGTCTGTC CGTCCAAAGA ATCTGTACCG TTCTCGTGCG CTCGCTGCTC TGCGTCCAGA    1740

CGGACCAGGG CCAGAAGCAT CTGGTAAGCC TGCTCGTTGG TGTAAGGCGG AGCCGCCGTG    1800

GATGCATCAG ACGACGGTGG TCCCGGTCCT TTGCGACCAG AATTATAAAC ACTTTCCTCG    1860

TAGGAAGGCG GAGCCTGTAA CGACGTGTCT TTGGTGTTGC CCGACGTCAC GGTGGTCCCG    1920

TCGGCGGACA CCAGATAGGG AAAGAGGTTC TGCAGCGGCT GCATGCAGAG ACGCCGCTGT    1980

CGAGTATAGA TCAAATAAAT GATAATGACG ACGGCTATGG CCACGAGGAT GATGGTGAAG    2040

GCTCCGAAGG GGTTTTTGAG GAAGGTGGCA ACGCCTTCGA CCACGGAGGC CACCGCGCCA    2100

CCCACGGCCC CAATGGCTAC GCCAACGGCC TTTCCCGCGG CGCCCAGGCC GCTCATGAGG    2160

TCGTCCAGAC CCTTGAGGTA GGGCGGCAGC GGGTCGACTA CCTTGTCCTC CACGTACTTT    2220

ACCCGCTGCT TATACGAATT GAACTCGCGC ATGATCTCCT CGAGATCAAA AACGTTGCTG    2280

GAACGCAATT CTTTCTGCGA GTAAAGTTCC AGTACCCTGA AGTCGGTGTT TTCCAGCGGG    2340

TCGATGTCTA GGGCGATCAT GCTGTCGACG GTGGAGATGC TGCTGAGGTC AATCATGCGT    2400

TTGAAGAGGT AGTCCACGTA CTCGTAGGCC GAGTTGCCGG CGATGAAGAT CTTGAGGCTG    2460

GGAAGCTGAC ATTCCTCAGT GCGGTGGTTG CCCAACAGGA TTTCGTTATC CTCGCCCAGT    2520

TGACCGTACT GCACGTACGA GCTGTTGGCG AAATTAAAGA TGACCACTGG TCGTGAGTAG    2580

CAGCGTCCTG GCGATTCCTT CACATTCATA TCACGCAGCA CCTTGACGCT GGTTTGGTTA    2640

ATGGTCACGC AGCTGGCCAG ACCCAGGACA TCACCCATGA AACGCGCGGC AATCGGTTTG    2700

TTGTAGATGG CCGAGAGAAT AGCTGACGGG TTGATCTTGC TAAGTTCCTT GAAGACCTCT    2760

AGGGTGCGCC GTTGATCCAC ACACCAGGCT TCTGCGATTT CGGCCAGCGC CCGGTTGATG    2820

TAACCGCGCA ACGTGTCATA GGTGAACTGC AGCTGGGCGT AGACCAGATT GTGCACCGAC    2880

TCCATGTTTA ATAAATGAGT TGCATTGTTG CCATCTGTAC TTCTTTTGGT TCTATTATGA    2940

GTAAGATTCA GACTGGAGCG GTTGGCCAAA CGTTCGAGTT CCACCAGAGA TTTTTGCTTG    3000

ATACCTTGCC AGAACACCAC CAAACCACCA GTGGTTTCAA AGACGGACAC GTTTCCATAT    3060

TTTTCATATG TTTGATTGTA TGAAGTATTG AAAATCTGCT GTAACTTATT TATGGCCTCA    3120

TCACGTACAC AGTCCAGCGC AGAGTCGGAC ATGTTCACCT CTTGCTTCTT AGATAAGAAA    3180

GTGGCGGTCA TTTTGGCAGA AGAAAAGTGA TACGAGTCCT CGGCTTCGGA ACGAATGGTG    3240

CGTTCCGAGG CTTCCCAGAA AGTGAGTTGA CAAGTAACAT TCTTCTCGTC CTGTATATCC    3300

CAGGAGATCA CTGAGTCCGC ACGTTCAAGA AAAGCCACCA ACCTGTGGGT CTCTAACGCA    3360

GAATTCGGTC TTTCAAAGTC GGAGACGATA GTGTAGTTCG GAAAAATGAA AAACTTGTCG    3420

GCGTTTTCTC CAAAATAGCT GGCATTGCGA TTAGTTCCGT TGTAGAAAGG AGAAATGTCA    3480

ACCACATCAC CCGTGGAAGT TGCGAAAAAA TGATAGGGAT ACTTGGAGCG CGCAGTAGTG    3540

ATGGTCACCA TACAATTCAG ATTACAGGTC TCACGATAGA GCCAGGTGCT GCCGCGGCTG    3600

TGCCATTGAT CCTTGACCGT CACGTAACGG GTACTGTGGG TGTTGGAATA ATCGTCGGGC    3660

ATTAATTGCA TGGTTTTGTT TTCATAGCTG TCCCTATGAT AAGCCACGAA AACCGTGCCT    3720

GCTATAACGC GGCTGTAGGA ACTGTAGCAC TGACTGTGAC TGTTGATATG ATGAATCTCC    3780

CACATAGGAG GCGCCACGTA TTCCGTGTTG CTGCCCAGCA GATAAGTGGT GTGGATGTAA    3840

GCGTAGCTAC GACGAAACGT CAAAACCTTC TGGTAGACTC GTACCTTAAA GGTGTGCGCG    3900

ACGATGTTGC GTTTGTAGAC CACCATGATG CCCTCGTCCA GGTCTTCATT GATGGGCTTC    3960

ATCGAGGTGC AGACGATATT ACGTTCAAAG CGAATAAGAT CCGTACCCTG AGCCATAGAA    4020
```

-continued

| | | | | |
|---|---|---|---|---|
| CACACGCGAT | AGGGGTACTT | GGTGGTGTTG | ACCCCCACCA | CATCTCCGTA CTTGAGGGTA | 4080 |
| GTGTTGTAGA | TGGTCTCGTT | AACACCATGG | CTGACCGTTT | GGGAAGAAGT TACGCGTTGA | 4140 |
| GAGACTGAAC | CGGATCGAGA | ATGAGCAGCA | GACGTCGTAT | GAGAGGAATG GTGACTGTGA | 4200 |
| GTAGCAGAAG | TTCCACGAGT | AGAAGATGAG | GAAACCGCAG | CACCCAGACA GACGATACAC | 4260 |
| AAGTTAACGC | AGACTACCAG | GCACCAGATC | CTGGATTCCA | TTACGATACA AACTTAACGG | 4320 |
| ATATCGCGAT | AATGAAATAA | TTTATGATTA | TTTCTCGCTT | TCAATTTAAC ACAACCCTCA | 4380 |
| AGAACCTTTG | TATTTATTTT | CACTTTTTAA | GTATAGAATA | AAGAAGCTCT AATTAATTAA | 4440 |
| GCTACAAATA | GTTTCGTTTT | CACCTTGTCT | AATAACTAAT | TAATTAACCC GGATCCCGAT | 4500 |
| TTTTATGACT | AGTTAATCAA | ATAAAAAGCA | TACAAGCTAT | TGCTTCGCTA TCGTTACAAA | 4560 |
| ATGGCAGGAA | TTTTGTGTAA | ACTAAGCCAC | ATACTTGCCA | ATGAAAAAAA TAGTAGAAAG | 4620 |
| GATACTATTT | TAATGGGATT | AGATGTTAAG | GTTCCTTGGG | ATTATAGTAA CTGGGCATCT | 4680 |
| GTTAACTTTT | ACGACGTTAG | GTTAGATACT | GATGTTACAG | ATTATAATAA TGTTACAATA | 4740 |
| AAATACATGA | CAGGATGTGA | TATTTTTCCT | CATATAACTC | TTGGAATAGC AAATATGGAT | 4800 |
| CAATGTGATA | GATTTGAAAA | TTTCAAAAAG | CAAATAACTG | ATCAAGATTT ACAGACTATT | 4860 |
| TCTATAGTCT | GTAAAGAAGA | GATGTGTTTT | CCTCAGAGTA | ACGCCTCTAA ACAGTTGGGA | 4920 |
| GCGAAAGGAT | GCGCTGTAGT | TATGAAACTG | GAGGTATCTG | ATGAACTTAG AGCCCTAAGA | 4980 |
| AATGTTCTGC | TGAATGCGGT | ACCCTGTTCG | AAGGACGTGT | TTGGTGATAT CACAGTAGAT | 5040 |
| AATCCGTGGA | ATCCTCACAT | AACAGTAGGA | TATGTTAAGG | AGGACGATGT CGAAAACAAG | 5100 |
| AAACGCCTAA | TGGAGTGCAT | GTCCAAGTTT | AGGGGGCAAG | AAATACAAGT TCTAGGATGG | 5160 |
| TATTAATAAG | TATCTAAGTA | TTTGGTATAA | TTTATTAAAT | AGTATAATTA TAACAAATAA | 5220 |
| TAAATAACAT | GATAACGGTT | TTTATTAGAA | TAAAATAGAG | ATAATATCAT AATGATATAT | 5280 |
| AATACTTCAT | TACCAGAAAT | GAGTAATGGA | AGACTTATAA | ATGAACTGCA TAAAGCTATA | 5340 |
| AGGTATAGAG | ATATAAATTT | AGTAAGGTAT | ATACTTAAAA | AATGCAAATA CAATAACGTA | 5400 |
| AATATACTAT | CAACGTCTTT | GTATTTAGCC | GTAAGTATTT | CTGATATAGA AATGGTAAAA | 5460 |
| TTATTACTAG | AACACGGTGC | CGATATTTTA | AAATGTAAAA | ATCCTCCTCT TCATAAAGCT | 5520 |
| GCTAGTTTAG | ATAATACAGA | AATTGCTAAA | CTACTAATAG | ATTCTGGCGC TGACATAGAA | 5580 |
| CAGATACATT | CTGGAAATAG | TCCGTTATAT | ATTTCTGTAT | ATAGAAACAA TAAGTCATTA | 5640 |
| ACTAGATATT | TATTAAAAAA | AGGTGTTAAT | TGTAATAGAT | TCTTTCTAAA TTATTACGAT | 5700 |
| GTACTGTATG | ATAAGATATC | TGATGATATG | TATAAAATAT | TTATAGATTT TAATATTGAT | 5760 |
| CTTAATATAC | AAACTAGAAA | TTTTGAAACT | CCGTTACATT | ACGCTATAAA GTATAAGAAT | 5820 |
| ATAGATTTAA | TTAGGATATT | GTTAGATAAT | AGTATTAAAA | TAGATAAAAG TTTATTTTTG | 5880 |
| CATAAACAGT | ATCTCATAAA | GGCACTTAAA | AATAATTGTA | GTTACGATAT AATAGCGTTA | 5940 |
| CTTATAAATC | ACGGAGTGCC | TATAAACGAA | CAAGATGATT | TAGGTAAAAC CCCATTACAT | 6000 |
| CATTCGGTAA | TTAATAGAAG | AAAAGATGTA | ACAGCACTTC | TGTTAAATCT AGGAGCTGAT | 6060 |
| ATAAACGTAA | TAGATGACTG | TATGGGCAGT | CCCTTACATT | ACGCTGTTTC ACGTAACGAT | 6120 |
| ATCGAAACAA | CAAAGACACT | TTTAGAAAGA | GGATCTAATG | TTAATGTGGT TAATAATCAT | 6180 |
| ATAGATACCG | TTCTAAATAT | AGCTGTTGCA | TCTAAAAACA | AAACTATAGT AAACTTATTA | 6240 |
| CTGAAGTACG | GTACTGATAC | AAAGTTGGTA | GGATTAGATA | AACATGTTAT TCACATAGCT | 6300 |
| ATAGAAATGA | AAGATATTAA | TATACTGAAT | GCGATCTTAT | TATATGGTTG CTATGTAAAC | 6360 |
| GTCTATAATC | ATAAAGGTTT | CACTCCTCTA | TACATGGCAG | TTAGTTCTAT GAAAACAGAA | 6420 |

```
TTTGTTAAAC TCTTACTTGA CCACGGTGCT TACGTAAATG CTAAAGCTAA GTTATCTGGA      6480

AATACTCCTT TACATAAAGC TATGTTATCT AATAGTTTTA ATAATATAAA ATTACTTTTA      6540

TCTTATAACG CCGACTATAA TTCTCTAAAT AATCACGGTA ATACGCCTCT AACTTGTGTT      6600

AGCTTTTTAG ATGACAAGAT AGCTATTATG ATAATATCTA AAATGATGTT AGAAATATCT      6660

AAAAATCCTG AAATAGCTAA TTCAGAAGGT TTTATAGTAA ACATGGAACA TATAAACAGT      6720

AATAAAAGAC TACTATCTAT AAAAGAATCA TGCGAAAAAG AACTAGATGT TATAACACAT      6780

ATAAAGTTAA ATTCTATATA TTCTTTTAAT ATCTTTCTTG ACAATAACAT AGATCTTATG      6840

GTAAAGTTCG TAACTAATCC TAGAGTTAAT AAGATACCTG CATGTATACG TATATATAGG      6900

GAATTAATAC GGAAAAATAA ATCATTAGCT TTTCATAGAC ATCAGCTAAT AGTTAAAGCT      6960

GTAAAAGAGA GTAAGAATCT AGGAATAATA GGTAGGTTAC CTATAGATAT CAAACATATA      7020

ATAATGGAAC TATTAAGTAA TAATGATTTA CATTCTGTTA TCACCAGCTG TTGTAACCCA      7080

GTAGTATAAA G                                                          7091
```

(2) INFORMATION FOR SEQ ID NO:41:

(i) SEQUENCE CHARACTERISTICS:
        (A) LENGTH: 4768 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
AAGCTTGCGG CCGCTCATTA GACAAGCGAA TGAGGGACGA AAACGTGGAG GAGGTATTAA        60

GTTTGGAGAA ATGGAGAGAG ACTGTTTAAT AGCGCATGGC GCAGCCAATA CTATTACAGA       120

AGTTTTGAAA GATTCGGAAG AAGATTATCA AGATGTGTAT GTTTGTGAAA ATTGTGGAGA       180

CATAGCAGCA CAAATCAAGG GTATTAATAC ATGTCTTAGA TGTTCAAAAC TTAATCTCTC       240

TCCTCTCTTA ACAAAAATTG ATACCACGCA CGTATCTAAA GTATTTCTTA CTCAAATGAA       300

CGCCAGAGGC GTAAAAGTCA AATTAGATTT CGAACGAAGG CCTCCTTCGT TTTATAAACC       360

ATTAGATAAA GTTGATCTCA AGCCGTCTTT TCTGGTGTAA TAAAAATTAA TTAATTACTC       420

GAGGGTACCG GATCCCCCAG CTTATAAAAA TCACAAGTCT CTGACACTTT TTTTGTCTAG       480

TTTTTTTTTC TCCTCTTGGT TCAGACGTTC TCTTCTTCGT CGGAGTCTTT CAAGTGTCGG       540

TAGCCGTTTT TGCGGTGTCG CAGTCGGTCT AGCAGGTTGG GCTTCTGTCC CTTGTCCTGC       600

GTGCCAGTCT GTCCGTCCAA AGAATCTGTA CCGTTCTCGT GCGCTCGCTG CTCTGCGTCC       660

AGACGGACCA GGGCCAGAAG CATCTGGTAA GCCTGCTCGT TGGTGTAAGG CGGAGCCGCC       720

GTGGATGCAT CAGACGACGG TGGTCCCGGT CCTTTGCGAC CAGAATTATA AACACTTTCC       780

TCGTAGGAAG GCGGAGCCTG TAACGACGTG TCTTTGGTGT TGCCCGACGT CACGGTGGTC       840

CCGTCGGCGG ACACCAGATA GGGAAAGAGG TTCTGCAGCG GCTGCATGCA GAGACGCCGC       900

TGTCGAGTAT AGATCAAATA AATGATAATG ACGACGGCTA TGGCCACGAG GATGATGGTG       960

AAGGCTCCGA AGGGGTTTTT GAGGAAGGTG GCAACGCCTT CGACCACGGA GGCCACCGCG      1020

CCACCCACGG CCCCAATGGC TACGCCAACG GCCTTTCCCG CGGCGCCCAG GCCGCTCATG      1080

AGGTCGTCCA GACCCTTGAG GTAGGGCGGC AGCGGGTCGA CTACCTTGTC CTCCACGTAC      1140

TTTACCCGCT GCTTATACGA ATTGAACTCG CGCATGATCT CCTCGAGATC AAAAACGTTG      1200

CTGGAACGCA ATTCTTTCTG CGAGTAAAGT TCCAGTACCC TGAAGTCGGT GTTTTCCAGC      1260
```

-continued

```
GGGTCGATGT CTAGGGCGAT CATGCTGTCG ACGGTGGAGA TGCTGCTGAG GTCAATCATG    1320

CGTTTGAAGA GGTAGTCCAC GTACTCGTAG GCCGAGTTGC CGGCGATGAA GATCTTGAGG    1380

CTGGGAAGCT GACATTCCTC AGTGCGGTGG TTGCCCAACA GGATTTCGTT ATCCTCGCCC    1440

AGTTGACCGT ACTGCACGTA CGAGCTGTTG GCGAAATTAA AGATGACCAC TGGTCGTGAG    1500

TAGCAGCGTC CTGGCGATTC CTTCACATTC ATATCACGCA GCACCTTGAC GCTGGTTTGG    1560

TTAATGGTCA CGCAGCTGGC CAGACCCAGG ACATCACCCA TGAAACGCGC GGCAATCGGT    1620

TTGTTGTAGA TGGCCGAGAG AATAGCTGAC GGGTTGATCT TGCTAAGTTC CTTGAAGACC    1680

TCTAGGGTGC GCCGTTGATC CACACACCAG GCTTCTGCGA TTTCGGCCAG CGCCCGGTTG    1740

ATGTAACCGC GCAACGTGTC ATAGGTGAAC TGCAGCTGGG CGTAGACCAG ATTGTGCACC    1800

GACTCCATGT TGGATAAATG AGTTGCATTG TTGCCATCTG TACTTCTTTT GGTTCTATTA    1860

TGAGTAAGAT TCAGACTGGA GCGGTTGGCC AAACGTTCGA GTTCCACCAG AGATTTTTGC    1920

TTGATACCTT GCCAGAACAC CACCAAACCA CCAGTGGTTT CAAAGACGGA CACGTTTCCA    1980

TATTTTTCAT ATGTTTGATT GTATGAAGTA TTGAAAATCT GCTGTAACTT ATTTATGGCC    2040

TCATCACGTA CACAGTCCAG CGCAGAGTCG GACATGTTCA CCTCTTGCTT CTTAGATAAG    2100

AAAGTGGCGG TCATTTTGGC AGAAGAAAAG TGATACGAGT CCTCGGCTTC GGAACGAATG    2160

GTGCGTTCCG AGGCTTCCCA GAAAGTGAGT TGACAAGTAA CATTCTTCTC GTCCTGTATA    2220

TCCCAGGAGA TCACTGAGTC CGCACGTTCA AGAAAAGCCA CCAACCTGTG GGTCTCTAAC    2280

GCAGAATTCG GTCTTTCAAA GTCGGAGACG ATAGTGTAGT TCGGAAAAAT GAAAAACTTG    2340

TCGGCGTTTT CTCCAAAATA GCTGGCATTG CGATTAGTTC CGTTGTAGAA AGGAGAAATG    2400

TCAACCACAT CACCCGTGGA AGTTGCGAAA AAATGATAGG GATACTTGGA GCGCGCAGTA    2460

GTGATGGTCA CCATACAATT CAGATTACAG GTCTCACGAT AGAGCCAGGT GCTGCCGCGG    2520

CTGTGCCATT GATCCTTGAC CGTCACGTAA CGGGTACTGT GGGTGTTGGA ATAATCGTCG    2580

GGCATTAATT GCATGGTTTT GTTTTCATAG CTGTCCCTAT GATAAGCCAC GAAAACCGTG    2640

CCTGCTATAA CGCGGCTGTA GGAACTGTAG CACTGACTGT GACTGTTGAT ATGATGAATC    2700

TCCCACATAG GAGGCGCCAC GTATTCCGTG TTGCTGCCCA GCAGATAAGT GGTGTGGATG    2760

TAAGCGTAGC TACGACGAAA CGTCAAAACC TTCTGGTAGA CTCGTACCTT AAAGGTGTGC    2820

GCGACGATGT TGCGTTTGTA GACCACCATG ATGCCCTCGT CCAGGTCTTC ATTGATGGGC    2880

TTCATCGAGG TGCAGACGAT ATTACGTTCA AAGCGAATAA GATCCGTACC CTGAGCCATA    2940

GAACACACGC GATAGGGGTA CTTGGTGGTG TTGACCCCCA CCACATCTCC GTACTTGAGG    3000

GTAGTGTTGT AGATGGTCTC GTTAACACCA TGGCTGACCG TTTGGGAAGA AGTTACGCGT    3060

TGAGAGACTG AACCGGATCG AGAATGAGCA GCAGACGTCG TATGAGAGGA ATGGTGACTG    3120

TGAGTAGCAG AAGTTCCACG AGTAGAAGAT GAGGAAACCG CAGCACCCAG ACAGACGATA    3180

CACAAGTTAA CGCAGACTAC CAGGCACCAG ATCCTGGATT CCATTACGAT ACAAACTTAA    3240

CGGATATCGC GATAATGAAA TAATTTATGA TTATTTCTCG CTTTCAATTT AACACAACCC    3300

TCAAGAACCT TTGTATTTAT TTTCACTTTT TAAGTATAGA ATAAAGAAGC TGGGAATCGA    3360

TTCGCGATAG CTGATTAGTT TTTGTTAACA AAAATGTGGG AGAATCTAAT TAGTTTTTCT    3420

TTACACAATT GACGTACATG AGTCTGAGTT CCTTGTTTTT GCTAATTATT TCATCCAATT    3480

TATTATTCTT GACGATATCG AGATCTTTTG TATAGGAGTC AGACTTGTAT TCAACATGCT    3540

TTTCTATAAT CATCTTAGTT ATTTCGGCAT CATCCAATAG TACATTTTCC AGATTAACAG    3600
```

-continued

```
AGTAGATATT AATGTCGTAT TTGAACAGAG CCTGTAACAT CTCAATGTCT TTATTATCTA      3660

TAGCCAATTT AATGTCCGGA ATGAAGAGAA GGGAATTATT GGTGTTTGTC GACGTCATAT      3720

AGTCGAGCAA GAGAATCATC ATATCCACGT GTCCATTTTT TATAGTGGTG TGAATACAAC      3780

TAAGGAGAAT AGCCAGATCA AAAGTAGATG GTATTTCTGA AGAAAGTAT GATACAATAC       3840

TTACATCATT AAGCATGACG GCATGATAAA ATGAAGTTTT CCATCCAGTT TTCCCATAGA      3900

ACATCAGTCT CCAATTTTTC TTAAACAGTT TCACCGTTTG CATGTTACCA CTATCAACCG      3960

CATAATACAA TGCGGTGTTT CCTTTGTCAT CAAATTGTGA ATCATCCATT CCACTGAATA      4020

GCAAAATCTT TACTATTTTG GTATCTTCTA ATGTGGCTGC CTGATGTAAT GGAAATTCAT      4080

TCTCTAGAAG ATTTTTCAAT GCTCCAGCGT TCAACAACGT ACATACTAGA CGCACGTTAT      4140

TATCAGCTAT TGCATAATAC AAGGCACTAT GTCCATGGAC ATCCGCCTTA AATGTATCTT      4200

TACTAGAGAG AAAGCTTTTC AGCTGCTTAG ACTTCCAAGT ATTAATTCGT GACAGATCCA      4260

TGTCTGAAAC GAGACGCTAA TTAGTGTATA TTTTTTCATT TTTTATAATT TTGTCATATT      4320

GCACCAGAAT TAATAATATC TCTAATAGAT CTAATTTAAT TTAATTTATA TAACTTATTT      4380

TTTGAATATA CTTTTAATTA ACAAAAGAGT TAAGTTACTC ATATGGACGC CGTCCAGTCT      4440

GAACATCAAT CTTTTTAGCC AGAGATATCA TAGCCGCTCT TAGAGTTTCA GCGTGATTTT      4500

CCAACCTAAA TAGAACTTCA TCGTTGCGTT TACAACACTT TTCTATTTGT TCAAACTTTG      4560

TTGTTACATT AGTAATCTTT TTTTCCAAAT TAGTTAGCCG TTGTTTGAGA GTTTCCTCAT      4620

TGTCGTCTTC ATCGGCTTTA ACAATTGCTT CGCGTTTAGC CTCCTGGCTG TTCTTATCAG      4680

CCTTTGTAGA AAAAAATTCA GTTGCTGGAA TTGCAAGATC GTCATCTCCG GGGAAAAGAG      4740

TTCCGTCCAT TTAAAGCCGC GGGAATTC                                        4768
```

(2) INFORMATION FOR SEQ ID NO:42:

(i) SEQUENCE CHARACTERISTICS:
        (A) LENGTH: 2550 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
ATGGAATCCA GGATCTGGTG CCTGGTAGTC TGCGTTAACT TGTGTATCGT CTGTCTGGGT       60

GCTGCGGTTT CCTCATCTTC TACTCGTGGA ACTTCTGCTA CTCACAGTCA CCATTCCTCT      120

CATACGACGT CTGCTGCTCA TTCTCGATCC GGTTCAGTCT CTCAACGCGT AACTTCTTCC      180

CAAACGGTCA GCCATGGTGT TAACGAGACC ATCTACAACA CTACCCTCAA GTACGGAGAT      240

GTGGTGGGGG TCAACACCAC CAAGTACCCC TATCGCGTGT GTTCTATGGC TCAGGGTACG      300

GATCTTATTC GCTTTGAACG TAATATCGTC TGCACCTCGA TGAAGCCCAT CAATGAAGAC      360

CTGGACGAGG GCATCATGGT GGTCTACAAA CGCAACATCG TCGCGCACAC CTTTAAGGTA      420

CGAGTCTACC AGAAGGTTTT GACGTTTCGT CGTAGCTACG CTTACATCCA CACCACTTAT      480

CTGCTGGGCA GCAACACGGA ATACGTGGCG CCTCCTATGT GGGAGATTCA TCATATCAAC      540

AGTCACAGTC AGTGCTACAG TTCCTACAGC CGCGTTATAG CAGGCACGGT TTTCGTGGCT      600

TATCATAGGG ACAGCTATGA AAACAAAACC ATGCAATTAA TGCCCGACGA TTATTCCAAC      660

ACCCACAGTA CCCGTTACGT GACGGTCAAG GATCAATGGC ACAGCCGCGG CAGCACCTGG      720

CTCTATCGTG AGACCTGTAA TCTGAATTGT ATGGTGACCA TCACTACTGC GCGCTCCAAG      780
```

```
TATCCCTATC ATTTTTTCGC AACTTCCACG GGTGATGTGG TTGACATTTC TCCTTTCTAC      840

AACGGAACTA ATCGCAATGC CAGCTATTTT GGAGAAAACG CCGACAAGTT TTTCATTTTT      900

CCGAACTACA CTATCGTCTC CGACTTTGAA AGACCGAATT CTGCGTTAGA GACCCACAGG      960

TTGGTGGCTT TTCTTGAACG TGCGGACTCA GTGATCTCCT GGGATATACA GGACGAGAAG     1020

AATGTTACTT GTCAACTCAC TTTCTGGGAA GCCTCGGAAC GCACCATTCG TTCCGAAGCC     1080

GAGGACTCGT ATCACTTTTC TTCTGCCAAA ATGACCGCCA CTTTCTTATC TAAGAAGCAA     1140

GAGGTGAACA TGTCCGACTC TGCGCTGGAC TGTGTACGTG ATGAGGCCAT AAATAAGTTA     1200

CAGCAGATTT TCAATACTTC ATACAATCAA ACATATGAAA AATATGGAAA CGTGTCCGTC     1260

TTTGAAACCA CTGGTGGTTT GGTGGTGTTC TGGCAAGGTA TCAAGCAAAA ATCTCTGGTG     1320

GAACTCGAAC GTTTGGCCAA CCGCTCCAGT CTGAATCTTA CTCATAATAG AACCAAAAGA     1380

AGTACAGATG GCAACAATGC AACTCATTTA TCCAACATGG AGTCGGTGCA CAATCTGGTC     1440

TACGCCCAGC TGCAGTTCAC CTATGACACG TTGCGCGGTT ACATCAACCG GGCGCTGGCC     1500

GAAATCGCAG AAGCCTGGTG TGTGGATCAA CGGCGCACCC TAGAGGTCTT CAAGGAACTT     1560

AGCAAGATCA ACCCGTCAGC TATTCTCTCG GCCATCTACA ACAAACCGAT TGCCGCGCGT     1620

TTCATGGGTG ATGTCCTGGG TCTGGCCAGC TGCGTGACCA TTAACCAAAC CAGCGTCAAG     1680

GTGCTGCGTG ATATGAATGT GAAGGAATCG CCAGGACGCT GCTACTCACG ACCAGTGGTC     1740

ATCTTTAATT TCGCCAACAG CTCGTACGTG CAGTACGGTC AACTGGGCGA GGATAACGAA     1800

ATCCTGTTGG GCAACCACCG CACTGAGGAA TGTCAGCTTC CCAGCCTCAA GATCTTCATC     1860

GCCGGCAACT CGGCCTACGA GTACGTGGAC TACCTCTTCA AACGCATGAT TGACCTCAGC     1920

AGCATCTCCA CCGTCGACAG CATGATCGCC CTAGACATCG ACCCGCTGGA AAACACCGAC     1980

TTCAGGGTAC TGGAACTTTA CTCGCAGAAA GAATTGCGTT CCAGCAACGT TTTTGATCTC     2040

GAGGAGATCA TGCGCGAGTT CAATTCGTAT AAGCAGCGGG TAAAGTACGT GGAGGACAAG     2100

GTAGTCGACC CGCTGCCGCC CTACCTCAAG GGTCTGGACG ACACTCGACA GCGGCGTCTC     2160

TGCATGCAGC CGCTGCAGAA CCTCTTTCCC TATCTGGTGT CCGCCGACGG GACCACCGTG     2220

ACGTCGGGCA ACACCAAAGA CACGTCGTTA CAGGCTCCGC CTTCCTACGA GGAAAGTGTT     2280

TATAATTCTG GTCGCAAAGG ACCGGGACCA CCGTCGTCTG ATGCATCCAC GGCGGCTCCG     2340

CCTTACACCA ACGAGCAGGC TTACCAGATG CTTCTGGCCC TGGTCCGTCT GGACGCAGAG     2400

CAGCGAGCGC ACGAGAACGG TACAGATTCT TTGGACGGAC AGACTGGCAC GCAGGACAAG     2460

GGACAGAAGC CCAACCTGCT AGACCGACTG CGACACCGCA AAAACGGCTA CCGACACTTG     2520

AAAGACTCCG ACGAAGAAGA GAACGTCTGA                                       2550

(2) INFORMATION FOR SEQ ID NO:43:

(i) SEQUENCE CHARACTERISTICS:
        (A) LENGTH: 4594 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

AAGCTTGCGG CCGCTCATTA GACAAGCGAA TGAGGGACGA AAACGTGGAG GAGGTATTAA       60

GTTTGGAGAA ATGGAGAGAG ACTGTTTAAT AGCGCATGGC GCAGCCAATA CTATTACAGA      120

AGTTTTGAAA GATTCGGAAG AAGATTATCA AGATGTGTAT GTTTGTGAAA ATTGTGGAGA      180
```

-continued

| | |
|---|---|
| CATAGCAGCA CAAATCAAGG GTATTAATAC ATGTCTTAGA TGTTCAAAAC TTAATCTCTC | 240 |
| TCCTCTCTTA ACAAAAATTG ATACCACGCA CGTATCTAAA GTATTTCTTA CTCAAATGAA | 300 |
| CGCCAGAGGC GTAAAAGTCA AATTAGATTT CGAACGAAGG CCTCCTTCGT TTTATAAACC | 360 |
| ATTAGATAAA GTTGATCTCA AGCCGTCTTT TCTGGTGTAA TAAAAATTAA TTAATTACTC | 420 |
| GAGGGTACCG GATCCCCCAG CTTATAAAAA TCACAAGACT CTGTCACTTT TTTTGACTAG | 480 |
| TTTTTTTTTC TCCTCTTGGT TCAGACGTTC TCTTCTTCGT CGGAGTCTTT CAAGTGTCGG | 540 |
| TAGCCGTTTT TGCGGTGTCG CAGTCGGTCT AGCAGGTTGG GCTTCTGTCC CTTGTCCTGC | 600 |
| GTGCCAGTCT GTCCGTCCAA AGAATCTGTA CCGTTCTCGT GCGCTCGCTG CTCTGCGTCC | 660 |
| AGACGGACCA GGGCCAGAAG CATCTGGTAA GCCTGCTCGT TGGTGTAAGG CGGAGCCGCC | 720 |
| GTGGATGCAT CAGACGACGG TGGTCCCGGT CCTTTGCGAC CAGAATTATA AACACTTTCC | 780 |
| TCGTAGGAAG GCGGAGCCTG TAACGACGTG TCTTTGGTGT TGCCCGACGT CACGGTGGTC | 840 |
| CCGTCGGCGG ACACCAGATA GGGAAAGAGG TTCTGCAGCG GCTGCATGCA GAGACGCCGC | 900 |
| TGTCGAGTGT CGTCCAGACC CTTGAGGTAG GGCGGCAGCG GGTCGACTAC CTTGTCCTCC | 960 |
| ACGTACTTTA CCCGCTGCTT ATACGAATTG AACTCGCGCA TGATCTCCTC GAGATCAAAA | 1020 |
| ACGTTGCTGG AACGCAATTC TTTCTGCGAG TAAAGTTCCA GTACCCTGAA GTCGGTGTTT | 1080 |
| TCCAGCGGGT CGATGTCTAG GGCGATCATG CTGTCGACGG TGGAGATGCT GCTGAGGTCA | 1140 |
| ATCATGCGTT TGAAGAGGTA GTCCACGTAC TCGTAGGCCG AGTTGCCGGC GATGAAGATC | 1200 |
| TTGAGGCTGG GAAGCTGACA TTCCTCAGTG CGGTGGTTGC CCAACAGGAT TTCGTTATCC | 1260 |
| TCGCCCAGTT GACCGTACTG CACGTACGAG CTGTTGGCGA AATTAAAGAT GACCACTGGT | 1320 |
| CGTGAGTAGC AGCGTCCTGG CGATTCCTTC ACATTCATAT CACGCAGCAC CTTGACGCTG | 1380 |
| GTTTGGTTAA TGGTCACGCA GCTGGCCAGA CCCAGGACAT CACCCATGAA ACGCGCGGCA | 1440 |
| ATCGGTTTGT TGTAGATGGC CGAGAGAATA GCTGACGGGT TGATCTTGCT AAGTTCCTTG | 1500 |
| AAGACCTCTA GGGTGCGCCG TTGATCCACA CACCAGGCTT CTGCGATTTC GGCCAGCGCC | 1560 |
| CGGTTGATGT AACCGCGCAA CGTGTCATAG GTGAACTGCA GCTGGGCGTA GACCAGATTG | 1620 |
| TGCACCGACT CCATGTTGGA TAAATGAGTT GCATTGTTGC CATCTGTACT TCTTTTGGTT | 1680 |
| CTATTATGAG TAAGATTCAG ACTGGAGCGG TTGGCCAAAC GTTCGAGTTC CACCAGAGAT | 1740 |
| TTTTGCTTGA TACCTTGCCA GAACACCACC AAACCACCAG TGGTTTCAAA GACGGACACG | 1800 |
| TTTCCATATT TTTCATATGT TTGATTGTAT GAAGTATTGA AAATCTGCTG TAACTTATTT | 1860 |
| ATGGCCTCAT CACGTACACA GTCCAGCGCA GAGTCGGACA TGTTCACCTC TTGCTTCTTA | 1920 |
| GATAAGAAAG TGGCGGTCAT TTTGGCAGAA GAAAAGTGAT ACGAGTCCTC GGCTTCGGAA | 1980 |
| CGAATGGTGC GTTCCGAGGC TTCCCAGAAA GTGAGTTGAC AAGTAACATT CTTCTCGTCC | 2040 |
| TGTATATCCC AGGAGATCAC TGAGTCCGCA CGTTCAAGAA AAGCCACCAA CCTGTGGGTC | 2100 |
| TCTAACGCAG AATTCGGTCT TTCAAAGTCG GAGACGATAG TGTAGTTCGG AAAAATGAAA | 2160 |
| AACTTGTCGG CGTTTTCTCC AAAATAGCTG GCATTGCGAT TAGTTCCGTT GTAGAAAGGA | 2220 |
| GAAATGTCAA CCACATCACC CGTGGAAGTT GCGAAAAAAT GATAGGGATA CTTGGAGCGC | 2280 |
| GCAGTAGTGA TGGTCACCAT ACAATTCAGA TTACAGGTCT CACGATAGAG CCAGGTGCTG | 2340 |
| CCGCGGCTGT GCCATTGATC CTTGACCGTC ACGTAACGGG TACTGTGGGT GTTGGAATAA | 2400 |
| TCGTCGGGCA TTAATTGCAT GGTTTTGTTT TCATAGCTGT CCCTATGATA AGCCACGAAA | 2460 |
| ACCGTGCCTG CTATAACGCG GCTGTAGGAA CTGTAGCACT GACTGTGACT GTTGATATGA | 2520 |
| TGAATCTCCC ACATAGGAGG CGCCACGTAT TCCGTGTTGC TGCCCAGCAG ATAAGTGGTG | 2580 |

```
TGGATGTAAG CGTAGCTACG ACGAAACGTC AAAACCTTCT GGTAGACTCG TACCTTAAAG      2640

GTGTGCGCGA CGATGTTGCG TTTGTAGACC ACCATGATGC CCTCGTCCAG GTCTTCATTG      2700

ATGGGCTTCA TCGAGGTGCA GACGATATTA CGTTCAAAGC GAATAAGATC CGTACCCTGA      2760

GCCATAGAAC ACACGCGATA GGGGTACTTG GTGGTGTTGA CCCCCACCAC ATCTCCGTAC      2820

TTGAGGGTAG TGTTGTAGAT GGTCTCGTTA ACACCATGGC TGACCGTTTG GGAAGAAGTT      2880

ACGCGTTGAG AGACTGAACC GGATCGAGAA TGAGCAGCAG ACGTCGTATG AGAGGAATGG      2940

TGACTGTGAG TAGCAGAAGT TCCACGAGTA GAAGATGAGG AAACCGCAGC ACCCAGACAG      3000

ACGATACACA AGTTAACGCA GACTACCAGG CACCAGATCC TGGATTCCAT TACGATACAA      3060

ACTTAACGGA TATCGCGATA ATGAAATAAT TTATGATTAT TTCTCGCTTT CAATTTAACA      3120

CAACCCTCAA GAACCTTTGT ATTTATTTTC ACTTTTTAAG TATAGAATAA GAAGCTGGG       3180

AATCGATTCG CGATAGCTGA TTAGTTTTTG TTAACAAAAA TGTGGGAGAA TCTAATTAGT      3240

TTTTCTTTAC ACAATTGACG TACATGAGTC TGAGTTCCTT GTTTTTGCTA ATTATTTCAT      3300

CCAATTTATT ATTCTTGACG ATATCGAGAT CTTTTGTATA GGAGTCAGAC TTGTATTCAA      3360

CATGCTTTTC TATAATCATC TTAGTTATTT CGGCATCATC CAATAGTACA TTTTCCAGAT      3420

TAACAGAGTA GATATTAATG TCGTATTTGA ACAGAGCCTG TAACATCTCA ATGTCTTTAT      3480

TATCTATAGC CAATTTAATG TCCGGAATGA AGAGAAGGGA ATTATTGGTG TTTGTCGACG      3540

TCATATAGTC GAGCAAGAGA ATCATCATAT CCACGTGTCC ATTTTTTATA GTGGTGTGAA      3600

TACAACTAAG GAGAATAGCC AGATCAAAAG TAGATGGTAT TTCTGAAAGA AAGTATGATA      3660

CAATACTTAC ATCATTAAGC ATGACGGCAT GATAAAATGA AGTTTTCCAT CCAGTTTTCC      3720

CATAGAACAT CAGTCTCCAA TTTTTCTTAA ACAGTTTCAC CGTTTGCATG TTACCACTAT      3780

CAACCGCATA ATACAATGCG GTGTTTCCTT TGTCATCAAA TTGTGAATCA TCCATTCCAC      3840

TGAATAGCAA AATCTTTACT ATTTTGGTAT CTTCTAATGT GGCTGCCTGA TGTAATGGAA      3900

ATTCATTCTC TAGAAGATTT TTCAATGCTC CAGCGTTCAA CAACGTACAT ACTAGACGCA      3960

CGTTATTATC AGCTATTGCA TAATACAAGG CACTATGTCC ATGGACATCC GCCTTAAATG      4020

TATCTTTACT AGAGAGAAAG CTTTTCAGCT GCTTAGACTT CCAAGTATTA ATTCGTGACA      4080

GATCCATGTC TGAAACGAGA CGCTAATTAG TGTATATTTT TTCATTTTTT ATAATTTTGT      4140

CATATTGCAC CAGAATTAAT AATATCTCTA ATAGATCTAA TTTAATTTAA TTTATATAAC      4200

TTATTTTTTG AATATACTTT TAATTAACAA AAGAGTTAAG TTACTCATAT GGACGCCGTC      4260

CAGTCTGAAC ATCAATCTTT TTAGCCAGAG ATATCATAGC CGCTCTTAGA GTTTCAGCGT      4320

GATTTTCCAA CCTAAATAGA ACTTCATCGT TGCGTTTACA ACACTTTTCT ATTTGTTCAA      4380

ACTTTGTTGT TACATTAGTA ATCTTTTTTT CCAAATTAGT TAGCCGTTGT TTGAGAGTTT      4440

CCTCATTGTC GTCTTCATCG GCTTTAACAA TTGCTTCGCG TTTAGCCTCC TGGCTGTTCT      4500

TATCAGCCTT TGTAGAAAAA AATTCAGTTG CTGGAATTGC AAGATCGTCA TCTCCGGGGA      4560

AAAGAGTTCC GTCCATTTAA AGCCGCGGGA ATTC                                 4594
```

(2) INFORMATION FOR SEQ ID NO:44:

(i) SEQUENCE CHARACTERISTICS:
        (A) LENGTH: 2550 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
ATGGAATCCA GGATCTGGTG CCTGGTAGTC TGCGTTAACT TGTGTATCGT CTGTCTGGGT      60
GCTGCGGTTT CCTCATCTTC TACTCGTGGA ACTTCTGCTA CTCACAGTCA CCATTCCTCT     120
CATACGACGT CTGCTGCTCA TTCTCGATCC GGTTCAGTCT CTCAACGCGT AACTTCTTCC     180
CAAACGGTCA GCCATGGTGT TAACGAGACC ATCTACAACA CTACCCTCAA GTACGGAGAT     240
GTGGTGGGGG TCAACACCAC CAAGTACCCC TATCGCGTGT GTTCTATGGC TCAGGGTACG     300
GATCTTATTC GCTTTGAACG TAATATCGTC TGCACCTCGA TGAAGCCCAT CAATGAAGAC     360
CTGGACGAGG GCATCATGGT GGTCTACAAA CGCAACATCG TCGCGCACAC CTTTAAGGTA     420
CGAGTCTACC AGAAGGTTTT GACGTTTCGT CGTAGCTACG CTTACATCCA CACCACTTAT     480
CTGCTGGGCA GCAACACGGA ATACGTGGCG CCTCCTATGT GGGAGATTCA TCATATCAAC     540
AGTCACAGTC AGTGCTACAG TTCCTACAGC CGCGTTATAG CAGGCACGGT TTTCGTGGCT     600
TATCATAGGG ACAGCTATGA AAACAAAACC ATGCAATTAA TGCCCGACGA TTATTCCAAC     660
ACCCACAGTA CCCGTTACGT GACGGTCAAG GATCAATGGC ACAGCCGCGG CAGCACCTGG     720
CTCTATCGTG AGACCTGTAA TCTGAATTGT ATGGTGACCA TCACTACTGC GCGCTCCAAG     780
TATCCCTATC ATTTTTTCGC AACTTCCACG GGTGATGTGG TTGACATTTC TCCTTTCTAC     840
AACGGAACTA ATCGCAATGC CAGCTATTTT GGAGAAAACG CCGACAAGTT TTTCATTTTT     900
CCGAACTACA CTATCGTCTC CGACTTTGAA AGACCGAATT CTGCGTTAGA GACCCACAGG     960
TTGGTGGCTT TTCTTGAACG TGCGGACTCA GTGATCTCCT GGGATATACA GGACGAGAAG    1020
AATGTTACTT GTCAACTCAC TTTCTGGGAA GCCTCGGAAC GCACCATTCG TTCCGAAGCC    1080
GAGGACTCGT ATCACTTTTC TTCTGCCAAA ATGACCGCCA CTTTCTTATC TAAGAAGCAA    1140
GAGGTGAACA TGTCCGACTC TGCGCTGGAC TGTGTACGTG ATGAGGCCAT AAATAAGTTA    1200
CAGCAGATTT TCAATACTTC ATACAATCAA ACATATGAAA AATATGGAAA CGTGTCCGTC    1260
TTTGAAACCA CTGGTGGTTT GGTGGTGTTC TGGCAAGGTA TCAAGCAAAA ATCTCTGGTG    1320
GAACTCGAAC GTTTGGCCAA CCGCTCCAGT CTGAATCTTA CTCATAATAG AACCATAAGA    1380
TCTACAGATG GCAACAATGC AACTCATTTA TCCAACATGG AGTCGGTGCA CAATCTGGTC    1440
TACGCCCAGC TGCAGTTCAC CTATGACACG TTGCGCGGTT ACATCAACCG GGCGCTGGCC    1500
GAAATCGCAG AAGCCTGGTG TGTGGATCAA CGGCGCACCC TAGAGGTCTT CAAGGAACTT    1560
AGCAAGATCA ACCCGTCAGC TATTCTCTCG GCCATCTACA ACAAACCGAT TGCCGCGCGT    1620
TTCATGGGTG ATGTCCTGGG TCTGGCCAGC TGCGTGACCA TTAACCAAAC CAGCGTCAAG    1680
GTGCTGCGTG ATATGAATGT GAAGGAATCG CCAGGACGCT GCTACTCACG ACCAGTGGTC    1740
ATCTTTAATT TCGCCAACAG CTCGTACGTG CAGTACGGTC AACTGGGCGA GGATAACGAA    1800
ATCCTGTTGG GCAACCACCG CACTGAGGAA TGTCAGCTTC CCAGCCTCAA GATCTTCATC    1860
GCCGGCAACT CGGCCTACGA GTACGTGGAC TACCTCTTCA AACGCATGAT TGACCTCAGC    1920
AGCATCTCCA CCGTCGACAG CATGATCGCC CTAGACATCG ACCCGCTGGA AAACACCGAC    1980
TTCAGGGTAC TGGAACTTTA CTCGCAGAAA GAATTGCGTT CCAGCAACGT TTTTGATCTC    2040
GAGGAGATCA TGCGCGAGTT CAATTCGTAT AAGCAGCGGG TAAAGTACGT GGAGGACAAG    2100
GTAGTCGACC CGCTGCCGCC CTACCTCAAG GGTCTGGACG ACACTCGACA GCGGCGTCTC    2160
TGCATGCAGC CGCTGCAGAA CCTCTTTCCC TATCTGGTGT CCGCCGACGG GACCACCGTG    2220
ACGTCGGGCA ACACCAAAGA CACGTCGTTA CAGGCTCCGC CTTCCTACGA GGAAAGTGTT    2280
```

-continued

| | |
|---|---|
| TATAATTCTG GTCGCAAAGG ACCGGGACCA CCGTCGTCTG ATGCATCCAC GGCGGCTCCG | 2340 |
| CCTTACACCA ACGAGCAGGC TTACCAGATG CTTCTGGCCC TGGTCCGTCT GGACGCAGAG | 2400 |
| CAGCGAGCGC ACGAGAACGG TACAGATTCT TTGGACGGAC AGACTGGCAC GCAGGACAAG | 2460 |
| GGACAGAAGC CCAACCTGCT AGACCGACTG CGACACCGCA AAAACGGCTA CCGACACTTG | 2520 |
| AAAGACTCCG ACGAAGAAGA GAACGTCTGA | 2550 |

(2) INFORMATION FOR SEQ ID NO:45:

(i) SEQUENCE CHARACTERISTICS:
        (A) LENGTH: 4594 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

| | |
|---|---|
| AAGCTTGCGG CCGCTCATTA GACAAGCGAA TGAGGGACGA AAACGTGGAG GAGGTATTAA | 60 |
| GTTTGGAGAA ATGGAGAGAG ACTGTTTAAT AGCGCATGGC GCAGCCAATA CTATTACAGA | 120 |
| AGTTTTGAAA GATTCGGAAG AAGATTATCA AGATGTGTAT GTTTGTGAAA ATTGTGGAGA | 180 |
| CATAGCAGCA CAAATCAAGG GTATTAATAC ATGTCTTAGA TGTTCAAAAC TTAATCTCTC | 240 |
| TCCTCTCTTA ACAAAAATTG ATACCACGCA CGTATCTAAA GTATTTCTTA CTCAAATGAA | 300 |
| CGCCAGAGGC GTAAAAGTCA AATTAGATTT CGAACGAAGG CCTCCTTCGT TTTATAAACC | 360 |
| ATTAGATAAA GTTGATCTCA AGCCGTCTTT TCTGGTGTAA TAAAAATTAA TTAATTACTC | 420 |
| GAGGGTACCG GATCCCCCAG CTTATAAAAA TCACAAGTCT CTGACACTTT TTTTGTCTAG | 480 |
| TTTTTTTTTC TCCTCTTGGT TCAGACGTTC TCTTCTTCGT CGGAGTCTTT CAAGTGTCGG | 540 |
| TAGCCGTTTT TGCGGTGTCG CAGTCGGTCT AGCAGGTTGG GCTTCTGTCC CTTGTCCTGC | 600 |
| GTGCCAGTCT GTCCGTCCAA AGAATCTGTA CCGTTCTCGT GCGCTCGCTG CTCTGCGTCC | 660 |
| AGACGGACCA GGGCCAGAAG CATCTGGTAA GCCTGCTCGT TGGTGTAAGG CGGAGCCGCC | 720 |
| GTGGATGCAT CAGACGACGG TGGTCCCGGT CCTTTGCGAC CAGAATTATA AACACTTTCC | 780 |
| TCGTAGGAAG GCGGAGCCTG TAACGACGTG TCTTTGGTGT TGCCCGACGT CACGGTGGTC | 840 |
| CCGTCGGCGG ACACCAGATA GGGAAAGAGG TTCTGCAGCG GCTGCATGCA GAGACGCCGC | 900 |
| TGTCGAGTGT CGTCCAGACC CTTGAGGTAG GGCGGCAGCG GGTCGACTAC CTTGTCCTCC | 960 |
| ACGTACTTTA CCCGCTGCTT ATACGAATTG AACTCGCGCA TGATCTCCTC GAGATCAAAA | 1020 |
| ACGTTGCTGG AACGCAATTC TTTCTGCGAG TAAAGTTCCA GTACCCTGAA GTCGGTGTTT | 1080 |
| TCCAGCGGGT CGATGTCTAG GGCGATCATG CTGTCGACGG TGGAGATGCT GCTGAGGTCA | 1140 |
| ATCATGCGTT TGAAGAGGTA GTCCACGTAC TCGTAGGCCG AGTTGCCGGC GATGAAGATC | 1200 |
| TTGAGGCTGG GAAGCTGACA TTCCTCAGTG CGGTGGTTGC CCAACAGGAT TTCGTTATCC | 1260 |
| TCGCCCAGTT GACCGTACTG CACGTACGAG CTGTTGGCGA AATTAAAGAT GACCACTGGT | 1320 |
| CGTGAGTAGC AGCGTCCTGG CGATTCCTTC ACATTCATAT CACGCAGCAC CTTGACGCTG | 1380 |
| GTTTGGTTAA TGGTCACGCA GCTGGCCAGA CCCAGGACAT CACCCATGAA ACGCGCGGCA | 1440 |
| ATCGGTTTGT TGTAGATGGC CGAGAGAATA GCTGACGGGT TGATCTTGCT AAGTTCCTTG | 1500 |
| AAGACCTCTA GGGTGCGCCG TTGATCCACA CACCAGGCTT CTGCGATTTC GGCCAGCGCC | 1560 |
| CGGTTGATGT AACCGCGCAA CGTGTCATAG GTGAACTGCA GCTGGGCGTA GACCAGATTG | 1620 |
| TGCACCGACT CCATGTTGGA TAAATGAGTT GCATTGTTGC CATCTGTAGA TCTTATGGTT | 1680 |

-continued

```
CTATTATGAG TAAGATTCAG ACTGGAGCGG TTGGCCAAAC GTTCGAGTTC CACCAGAGAT      1740

TTTTGCTTGA TACCTTGCCA GAACACCACC AAACCACCAG TGGTTTCAAA GACGGACACG      1800

TTTCCATATT TTTCATATGT TTGATTGTAT GAAGTATTGA AAATCTGCTG TAACTTATTT      1860

ATGGCCTCAT CACGTACACA GTCCAGCGCA GAGTCGGACA TGTTCACCTC TTGCTTCTTA      1920

GATAAGAAAG TGGCGGTCAT TTTGGCAGAA GAAAAGTGAT ACGAGTCCTC GGCTTCGGAA      1980

CGAATGGTGC GTTCCGAGGC TTCCCAGAAA GTGAGTTGAC AAGTAACATT CTTCTCGTCC      2040

TGTATATCCC AGGAGATCAC TGAGTCCGCA CGTTCAAGAA AAGCCACCAA CCTGTGGGTC      2100

TCTAACGCAG AATTCGGTCT TTCAAAGTCG GAGACGATAG TGTAGTTCGG AAAAATGAAA      2160

AACTTGTCGG CGTTTTCTCC AAAATAGCTG GCATTGCGAT TAGTTCCGTT GTAGAAAGGA      2220

GAAATGTCAA CCACATCACC CGTGGAAGTT GCGAAAAAAT GATAGGGATA CTTGGAGCGC      2280

GCAGTAGTGA TGGTCACCAT ACAATTCAGA TTACAGGTCT CACGATAGAG CCAGGTGCTG      2340

CCGCGGCTGT GCCATTGATC CTTGACCGTC ACGTAACGGG TACTGTGGGT GTTGGAATAA      2400

TCGTCGGGCA TTAATTGCAT GGTTTTGTTT TCATAGCTGT CCCTATGATA AGCCACGAAA      2460

ACCGTGCCTG CTATAACGCG GCTGTAGGAA CTGTAGCACT GACTGTGACT GTTGATATGA      2520

TGAATCTCCC ACATAGGAGG CGCCACGTAT TCCGTGTTGC TGCCCAGCAG ATAAGTGGTG      2580

TGGATGTAAG CGTAGCTACG ACGAAACGTC AAAACCTTCT GGTAGACTCG TACCTTAAAG      2640

GTGTGCGCGA CGATGTTGCG TTTGTAGACC ACCATGATGC CCTCGTCCAG GTCTTCATTG      2700

ATGGGCTTCA TCGAGGTGCA GACGATATTA CGTTCAAAGC GAATAAGATC CGTACCCTGA      2760

GCCATAGAAC ACACGCGATA GGGGTACTTG GTGGTGTTGA CCCCCACCAC ATCTCCGTAC      2820

TTGAGGGTAG TGTTGTAGAT GGTCTCGTTA ACACCATGGC TGACCGTTTG GGAAGAAGTT      2880

ACGCGTTGAG AGACTGAACC GGATCGAGAA TGAGCAGCAG ACGTCGTATG AGAGGAATGG      2940

TGACTGTGAG TAGCAGAAGT TCCACGAGTA GAAGATGAGG AAACCGCAGC ACCCAGACAG      3000

ACGATACACA AGTTAACGCA GACTACCAGG CACCAGATCC TGGATTCCAT TACGATACAA      3060

ACTTAACGGA TATCGCGATA ATGAAATAAT TTATGATTAT TTCTCGCTTT CAATTTAACA      3120

CAACCCTCAA GAACCTTTGT ATTTATTTTC ACTTTTTAAG TATAGAATAA AGAAGCTGGG      3180

AATCGATTCG CGATAGCTGA TTAGTTTTTG TTAACAAAAA TGTGGGAGAA TCTAATTAGT      3240

TTTTCTTTAC ACAATTGACG TACATGAGTC TGAGTTCCTT GTTTTTGCTA ATTATTTCAT      3300

CCAATTTATT ATTCTTGACG ATATCGAGAT CTTTTGTATA GGAGTCAGAC TTGTATTCAA      3360

CATGCTTTTC TATAATCATC TTAGTTATTT CGGCATCATC CAATAGTACA TTTTCCAGAT      3420

TAACAGAGTA GATATTAATG TCGTATTTGA ACAGAGCCTG TAACATCTCA ATGTCTTTAT      3480

TATCTATAGC CAATTTAATG TCCGGAATGA AGAGAAGGGA ATTATTGGTG TTTGTCGACG      3540

TCATATAGTC GAGCAAGAGA ATCATCATAT CCACGTGTCC ATTTTTTATA GTGGTGTGAA      3600

TACAACTAAG GAGAATAGCC AGATCAAAAG TAGATGGTAT TTCTGAAAGA AGTATGATA      3660

CAATACTTAC ATCATTAAGC ATGACGGCAT GATAAAATGA AGTTTTCCAT CCAGTTTTCC      3720

CATAGAACAT CAGTCTCCAA TTTTTCTTAA ACAGTTTCAC CGTTTGCATG TTACCACTAT      3780

CAACCGCATA ATACAATGCG GTGTTTCCTT TGTCATCAAA TTGTGAATCA TCCATTCCAC      3840

TGAATAGCAA AATCTTTACT ATTTTGGTAT CTTCTAATGT GGCTGCCTGA TGTAATGGAA      3900

ATTCATTCTC TAGAAGATTT TTCAATGCTC CAGCGTTCAA CAACGTACAT ACTAGACGCA      3960

CGTTATTATC AGCTATTGCA TAATACAAGG CACTATGTCC ATGGACATCC GCCTTAAATG      4020

TATCTTTACT AGAGAGAAAG CTTTTCAGCT GCTTAGACTT CCAAGTATTA ATTCGTGACA      4080
```

| | |
|---|---|
| GATCCATGTC TGAAACGAGA CGCTAATTAG TGTATATTTT TTCATTTTTT ATAATTTTGT | 4140 |
| CATATTGCAC CAGAATTAAT AATATCTCTA ATAGATCTAA TTTAATTTAA TTTATATAAC | 4200 |
| TTATTTTTTG AATATACTTT TAATTAACAA AAGAGTTAAG TTACTCATAT GGACGCCGTC | 4260 |
| CAGTCTGAAC ATCAATCTTT TTAGCCAGAG ATATCATAGC CGCTCTTAGA GTTTCAGCGT | 4320 |
| GATTTTCCAA CCTAAATAGA ACTTCATCGT TGCGTTTACA ACACTTTCT ATTTGTTCAA | 4380 |
| ACTTTGTTGT TACATTAGTA ATCTTTTTTT CCAAATTAGT TAGCCGTTGT TTGAGAGTTT | 4440 |
| CCTCATTGTC GTCTTCATCG GCTTTAACAA TTGCTTCGCG TTTAGCCTCC TGGCTGTTCT | 4500 |
| TATCAGCCTT TGTAGAAAAA AATTCAGTTG CTGGAATTGC AAGATCGTCA TCTCCGGGGA | 4560 |
| AAAGAGTTCC GTCCATTTAA AGCCGCGGGA ATTC | 4594 |

(2) INFORMATION FOR SEQ ID NO:46:

(i) SEQUENCE CHARACTERISTICS:
        (A) LENGTH: 2229 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

| | |
|---|---|
| ATGCGGCCAG GCCTCCCCTC CTACCTCATC GTCCTCGCCG TCTGTCTCCT CAGCCACCTA | 60 |
| CTTTCGTCAC GATATGGCGC AGAAGCCATA TCCGAACCGC TGGACAAAGC GTTTCACCTA | 120 |
| CTGCTCAACA CCTACGGGAG ACCCATCCGC TTCCTGCGTG AAAACACCAC CCAGTGTACC | 180 |
| TACAATAGCA GCCTCCGTAA CAGCACGGTC GTCAGGGAAA ACGCCATCAG TTTCAACTTT | 240 |
| TTCCAAAGCT ATAATCAATA CTATGTATTC CATATGCCTC GATGTCTTTT TGCGGGTCCT | 300 |
| CTGGCGGAGC AGTTTCTGAA CCAGGTAGAT CTGACCGAAA CCCTGGAAAG ATACCAACAG | 360 |
| AGACTTAACA CTTACGCGCT GGTATCCAAA GACCTGGCCA GCTACGATC TTTTTCGCAG | 420 |
| CAGCTAAAGG CACAGGACAG CCTAGGTGAA CAGCCCACCA CTGTGCCACC ACCCATTGAC | 480 |
| CTGTCAATAC CTCACGTTTG GATGCCACCG CAAACCACTC CACACGGCTG GACAGAATCA | 540 |
| CATACCACCT CAGGACTACA CCGACCACAC TTTAACCAGA CCTGTATCCT CTTTGATGGA | 600 |
| CACGATCTAC TATTCAGCAC CGTCACACCT TGTTTGCACC AAGGCTTTTA CCTCATCGAC | 660 |
| GAACTACGTT ACGTTAAAAT AACACTGACC GAGGACTTCT TCGTAGTTAC GGTGTCCATA | 720 |
| GACGACGACA CACCCATGCT GCTTATCTTC GGCCATCTTC CACGCGTACT CTTTAAAGCG | 780 |
| CCCTATCAAC GCGACAACTT TATACTACGA CAAACTGAAA AACACGAGCT CCTGGTGCTA | 840 |
| GTTAAGAAAG ATCAACTGAA CCGTCACTCT TATCTCAAAG ACCCGGACTT TCTTGACGCC | 900 |
| GCACTTGACT TCAACTACCT GGACCTCAGC GCACTACTAC GTAACAGCTT TCACCGTTAC | 960 |
| GCCGTGGATG TACTCAAAAG CGGTCGATGT CAGATGCTGG ACCGCCGCAC GGTAGAAATG | 1020 |
| GCCTTCGCCT ACGCATTAGC ACTGTTCGCA GCAGCCCGAC AAGAAGAGGC CGGCGCCCAA | 1080 |
| GTCTCCGTCC CACGGGCCCT AGACCGCCAG GCCGCACTCT TACAAATACA AGAATTTATG | 1140 |
| ATCACCTGCC TCTCACAAAC ACCACCAGCG ACCACGTTGC TGCTGTATCC CACGGCCGTG | 1200 |
| GACCTGGCCA AACGAGCCCT TTGGACACCG AATCAGATCA CCGACATCAC CAGCCTCGTA | 1260 |
| CGCCTGGTCT ACATACTCTC TAAACAGAAT CAGCAACATC TCATCCCCCA GTGGGCACTA | 1320 |
| CGACAGATCG CCGACTTTGC CCTAAAACTA CACAAAACGC ACCTGGCCTC TTTTCTTTCA | 1380 |
| GCCTTCGCGC GTCAAGAACT CTACCTCATG GGCAGCCTCG TCCACTCCAT GCTAGTACAT | 1440 |

-continued

```
ACGACGGAGA GACGCGAAAT CTTCATCGTA GAAACGGGCC TCTGTTCATT AGCCGAGCTA    1500

TCACACTTTA CGCAGTTGCT AGCTCATCCG CACCACGAAT ACCTCAGCGA CCTGTACACA    1560

CCCTGTTCCA GTAGCGGGCG ACGCGATCAC TCGCTCGAAC GCCTCACACG TCTCTTCCCC    1620

GATGCCACCG TCCCCACTAC CGTTCCCGCC GCCCTCTCCA TCCTATCTAC CATGCAACCA    1680

AGCACGCTAG AAACCTTCCC CGACCTGTTT TGTCTGCCGC TCGGCGAATC CTTCTCCGCG    1740

CTGACCGTCT CCGAACACGT CAGTTATGTC GTAACAAACC AGTACCTGAT CAAAGGTATC    1800

TCCTACCCTG TCTCCACCAC CGTCGTAGGC CAGAGCCTCA TCATCACCCA GACGGACAGT    1860

CAAACTAAAT GCGAACTGAC GCGCAACATG CATACCACAC ACAGCATCAC AGCGGCGCTC    1920

AACATTTCCC TAGAAAACTG CGCCTTTTGC CAAAGCGCCC TACTAGAATA CGACGACACG    1980

CAAGGCGTCA TCAACATCAT GTACATGCAC GACTCGGACG ACGTCCTTTT CGCCCTGGAT    2040

CCCTACAACG AAGTGGTGGT CTCATCTCCG CGAACTCACT ACCTCATGCT TTTGAAAAAC    2100

GGTACGGTCC TAGAAGTAAC TGACGTCGTC GTGGACGCTA CCGACAGTCG TCTCCTCATG    2160

ATGTCCGTCT ACGCGCTATC GGCCATCATC GGCATCTATC TGCTCTACCG CATGCTCAAG    2220

ACATGCTGA                                                            2229
```

(2) INFORMATION FOR SEQ ID NO:47:

(i) SEQUENCE CHARACTERISTICS:
        (A) LENGTH: 3539 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
CTGCAGGTCG ACGGATCTGA GAATGGATGA TTCTCCAGCC GAAACATATT CTACCATGGC      60

TCCGTTTAAT TTGTTGATGA AGATGGATTC ATCCTTAAAT GTTTTCTCTG TAATAGTTTC     120

CACCGAAAGA CTATGCAAAG AATTTGGAAT GCGTTCCTTG TGCTTAATGT TTCCATAGAC     180

GGCTTCTAGA AGTTGATACA ACATAGGACT AGCCGCGGTA ACTTTTATTT TTAGAAAGTA     240

TCCATCGCTT CTATCTTGTT TAGATTTATT TTTATAAAGT TTAGTCTCTC CTTCCAACAT     300

AATAAAAGTG GAAGTCATTT GACTAGATAA ACTATCAGTA AGTTTATAG AGATAGACGA      360

ACAATTAGCG TATTGAGAAG CATTTAGTGT AACGTATTCG ATACATTTTG CATTAGATTT     420

ACTAATCGAT TTTGCATACT CTATAACACC CGCACAAGTC TGTAGAGAAT CGCTAGATGC     480

AGTAGGTCTT GGTGAAGTTT CAACTCTCTT CTTGATTACC TTACTCATGA TTAAACCTAA     540

ATAATTGTAC TTTGTAATAT AATGATATAT ATTTTCACTT TATCTCATTT GAGAATAAAA     600

AGATCACAAA AATTAACTAA TCAGGATCCG GTACCCTCGA GTTTATTGGG AAGAATATGA     660

TAATATTTTG GGATTTCAAA ATTGAAAATA TATAATTACA ATATAAAATG CGGCCCGGGC     720

TCCCCTCCTA CCTCATCGTC CTCGCCGTCT GTCTCCTCAG CCACCTACTT TCGTCACGAT     780

ATGGCGCAGA AGCCATATCC GAACCGCTGG ACAAAGCGTT TCACCTACTG CTCAACACCT     840

ACGGGAGACC CATCCGCTTC CTGCGTGAAA ACACCACCCA GTGTACCTAC AATAGCAGCC     900

TCCGTAACAG CACGGTCGTC AGGGAAAACG CCATCAGTTT CAACTTTTTC CAAAGCTATA     960

ATCAATACTA TGTATTCCAT ATGCCTCGAT GTCTTTTTGC GGGTCCTCTG GCGGAGCAGT    1020

TTCTGAACCA GGTAGATCTG ACCGAAACCC TGGAAAGATA CCAACAGAGA CTTAACACTT    1080

ACGCGCTGGT ATCCAAAGAC CTGGCCAGCT ACCGATCTTT TTCGCAGCAG CTAAAGGCAC    1140
```

```
AGGACAGCCT AGGTGAACAG CCCACCACTG TGCCACCACC CATTGACCTG TCAATACCTC    1200

ACGTTTGGAT GCCACCGCAA ACCACTCCAC ACGGCTGGAC AGAATCACAT ACCACCTCAG    1260

GACTACACCG ACCACACTTT AACCAGACCT GTATCCTCTT TGATGGACAC GATCTACTAT    1320

TCAGCACCGT CACACCTTGT TTGCACCAAG GCTTTTACCT CATCGACGAA CTACGTTACG    1380

TTAAAATAAC ACTGACCGAG GACTTCTTCG TAGTTACGGT GTCCATAGAC GACGACACAC    1440

CCATGCTGCT TATCTTCGGC CATCTTCCAC GCGTACTCTT TAAAGCGCCC TATCAACGCG    1500

ACAACTTTAT ACTACGACAA ACTGAAAAAC ACGAGCTCCT GGTGCTAGTT AAGAAAGATC    1560

AACTGAACCG TCACTCTTAT CTCAAAGACC CGGACTTTCT TGACGCCGCA CTTGACTTCA    1620

ACTACCTGGA CCTCAGCGCA CTACTACGTA ACAGCTTTCA CCGTTACGCC GTGGATGTAC    1680

TCAAAAGCGG TCGATGTCAG ATGCTGGACC GCCGCACGGT AGAAATGGCC TTCGCCTACG    1740

CATTAGCACT GTTCGCAGCA GCCCGACAAG AAGAGGCCGG CGCCCAAGTC TCCGTCCCAC    1800

GGGCCCTAGA CCGCCAGGCC GCACTCTTAC AAATACAAGA ATTTATGATC ACCTGCCTCT    1860

CACAAACACC ACCACGCACC ACGTTGCTGC TGTATCCCAC GGCCGTGGAC CTGGCCAAAC    1920

GAGCCCTTTG GACACCGAAT CAGATCACCG ACATCACCAG CCTCGTACGC CTGGTCTACA    1980

TACTCTCTAA ACAGAATCAG CAACATCTCA TCCCCCAGTG GGCACTACGA CAGATCGCCG    2040

ACTTTGCCCT AAAACTACAC AAAACGCACC TGGCCTCTTT TCTTTCAGCC TTCGCGCGTC    2100

AAGAACTCTA CCTCATGGGC AGCCTCGTCC ACTCCATGCT AGTACATACG ACGGAGAGAC    2160

GCGAAATCTT CATCGTAGAA ACGGGCCTCT GTTCATTAGC CGAGCTATCA CACTTTACGC    2220

AGTTGCTAGC TCATCCGCAC CACGAATACC TCAGCGACCT GTACACACCC TGTTCCAGTA    2280

GCGGGCGACG CGATCACTCG CTCGAACGCC TCACACGTCT CTTCCCCGAT GCCACCGTCC    2340

CCACTACCGT TCCCGCCGCC CTCTCCATCC TATCTACCAT GCAACCAAGC ACGCTAGAAA    2400

CCTTCCCCGA CCTGTTTTGT CTGCCGCTCG GCGAATCCTT CTCCGCGCTG ACCGTCTCCG    2460

AACACGTCAG TTATGTCGTA ACAAACCAGT ACCTGATCAA AGGTATCTCC TACCCTGTCT    2520

CCACCACCGT CGTAGGCCAG AGCCTCATCA TCACCCAGAC GGACAGTCAA ACTAAATGCG    2580

AACTGACGCG CAACATGCAT ACCACACACA GCATCACAGC GGCGCTCAAC ATTTCCCTAG    2640

AAAACTGCGC CTTTTGCCAA AGCGCCCTAC TAGAATACGA CGACACGCAA GGCGTCATCA    2700

ACATCATGTA CATGCACGAC TCGGACGACG TCCTTTTCGC CCTGGATCCC TACAACGAAG    2760

TGGTGGTCTC ATCTCCGCGA ACTCACTACC TCATGCTTTT GAAAAACGGT ACGGTCCTAG    2820

AAGTAACTGA CGTCGTCGTG GACGCTACCG ACAGTCGTCT CCTCATGATG TCCGTCTACG    2880

CGCTATCGGC CATCATCGGC ATCTATCTGC TCTACCGCAT GCTCAAGACA TGCTGATTTT    2940

TATCTCGAGC CCGGGAGATC TTAGCTAACT GATTTTTCTG GGAAAAAAAT TATTTAACTT    3000

TTCATTAATA GGGATTTGAC GTATGTAGCG TACAAAATTA TCGTTCCTGG TATATAGATA    3060

AAGAGTCCTA TATATTTGAA AATCGTTACG GCTCGATTAA ACTTTAATGA TTGCATAGTG    3120

AATATATCAT TAGGATTTAA CTCCTTGACT ATCATGGCGG CGCCAGAAAT TACCATCAAA    3180

AGCATTAATA CAGTTATGCC GATCGCAGTT AGAACGGTTA TAGCATCCAC CATTTATATC    3240

TAAAAATTAG ATCAAAGAAT ATGTGACAAA GTCCTAGTTG TATACTGAGA ATTGACGAAA    3300

CAATGTTTCT TACATATTTT TTTCTTATTA GTAACTGACT TAATAGTAGG AACTGGAAAG    3360

CTAGACTTGA TTATTCTATA AGTATAGATA CCCTTCCAGA TAATGTTCTC TTTGATAAAA    3420

GTTCCAGAAA ATGTAGAATT TTTTAAAAAG TTATCTTTTG CTATTACCAA GATTGTGTTT    3480
```

| | |
|---|---|
| AGACGCTTAT TATTAATATG AGTAATGAAA TCCACACCGC CTCTAGATAT GGGGAATTC | 3539 |

(2) INFORMATION FOR SEQ ID NO:48:

(i) SEQUENCE CHARACTERISTICS:
        (A) LENGTH: 4427 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

| | |
|---|---|
| GAATTGCGGC CGCTGAATGT TAAATGTTAT ACTTTGGATG AAGCTATAAA TATGCATTGG | 60 |
| AAAAATAATC CATTTAAAGA AAGGATTCAA ATACTACAAA ACCTAAGCGA TAATATGTTA | 120 |
| ACTAAGCTTA TTCTTAACGA CGCTTTAAAT ATACACAAAT AAACATAATT TTTGTATAAC | 180 |
| CTAACAAATA ACTAAAACAT AAAAATAATA AAAGGAAATG TAATATCGTA ATTATTTTAC | 240 |
| TCAGGAATGG GGTTAAATAT TTATATCACG TGTATATCTA TACTGTTATC GTATACTCTT | 300 |
| TACAATTACT ATTACGAATA TGCAAGAGAT AATAAGATTA CGTATTTAAG AGAATCTTGT | 360 |
| CATGATAATT GGGTACGACA TAGTGATAAA TGCTATTTCG CATCGTTACA TAAAGTCAGT | 420 |
| TGGAAAGATG GATTTGACAG ATGTAACTTA ATAGGTGCAA AAATGTTAAA TAACAGCATT | 480 |
| CTATCGGAAG ATAGGATACC AGTTATATTA TACAAAAATC ACTGGTTGGA TAAAACAGAT | 540 |
| TCTGCAATAT TCGTAAAAGA TGAAGATTAC TGCGAATTTG TAAACTATGA CAATAAAAAG | 600 |
| CCATTTATCT CAACGACATC GTGTAATTCT TCCATGTTTT ATGTATGTGT TTCAGATATT | 660 |
| ATGAGATTAC TATAAACTTT TTGTATACTT ATATTCCGTA AACTATATTA ATCATGAAGA | 720 |
| AAATGAAAAA GTATAGAAGC TGTTCACGAG CGGTTGTTGA AAACAACAAA ATTATACATT | 780 |
| CAAGATGGCT TACATATACG TCTGTGAGGC TATCATGGAT AATGACAATG CATCTCTAAA | 840 |
| TAGGTTTTTG GACAATGGAT TCGACCCTAA CACGGAATAT GGTACTCTAC AATCTCCTCT | 900 |
| TGAAATGGCT GTAATGTTCA AGAATACCGA GGCTATAAAA ATCTTGATGA GGTATGGAGC | 960 |
| TAAACCTGTA GTTACTGAAT GCACAACTTC TTGTCTGCAT GATGCGGTGT TGAGAGACGA | 1020 |
| CTACAAAATA GTGAAAGATC TGTTGAAGAA TAACTATGTA AACAATGTTC TTTACAGCGG | 1080 |
| AGGCTTTACT CCTTTGTGTT TGGCAGCTTA CCTTAACAAA GTTAATTTGG TTAAACTTCT | 1140 |
| ATTGGCTCAT TCGGCGGATG TAGATATTTC AAACACGGAT CGGTTAACTC CTCTACATAT | 1200 |
| AGCCGTATCA AATAAAAATT TAACAATGGT TAAACTTCTA TTGAACAAAG GTGCTGATAC | 1260 |
| TGACTTGCTG GATAACATGG GACGTACTCC TTTAATGATC GCTGTACAAT CTGGAAATAT | 1320 |
| TGAAATATGT AGCACACTAC TTAAAAAAAA TAAAATGTCC AGAACTGGGA AAAATTGATC | 1380 |
| TTGCCAGCTG TAATTCATGG TAGAAAAGAA GTGCTCAGGC TACTTTTCAA CAAAGGAGCA | 1440 |
| GATGTAAACT ACATCTTTGA AAGAAATGGA AAATCATATA CTGTTTTGGA ATTGATTAAA | 1500 |
| GAAAGTTACT CTGAGACACA AAAGAGGTAG CTGAAGTGGT ACTCTCAAAG GTACGTGACT | 1560 |
| AATTAGCTAT AAAAAGGATC TTAATTAATT AGTCATCAGG CAGGGCGAGA ACGAGACTAT | 1620 |
| CTGCTCGTTA ATTAATTAGG TCGACGGATC CGGTACCCTC GAGTTTATTG GGAAGAATAT | 1680 |
| GATAATATTT TGGGATTTCA AAATTGAAAA TATATAATTA CAATATAAAA TGCGGCCCGG | 1740 |
| GCTCCCCTCC TACCTCATCG TCCTCGCCGT CTGTCTCCTC AGCCACCTAC TTTCGTCACG | 1800 |
| ATATGGCGCA GAAGCCATAT CCGAACCGCT GGACAAAGCG TTTCACCTAC TGCTCAACAC | 1860 |
| CTACGGGAGA CCCATCCGCT TCCTGCGTGA AACACCACC CAGTGTACCT ACAATAGCAG | 1920 |

-continued

| | | | | |
|---|---|---|---|---|
| CCTCCGTAAC | AGCACGGTCG | TCAGGGAAAA | CGCCATCAGT | TTCAACTTTT TCCAAAGCTA | 1980 |
| TAATCAATAC | TATGTATTCC | ATATGCCTCG | ATGTCTTTTT | GCGGGTCCTC TGGCGGAGCA | 2040 |
| GTTTCTGAAC | CAGGTAGATC | TGACCGAAAC | CCTGGAAAGA | TACCAACAGA GACTTAACAC | 2100 |
| TTACGCGCTG | GTATCCAAAG | ACCTGGCCAG | CTACCGATCT | TTTTCGCAGC AGCTAAAGGC | 2160 |
| ACAGGACAGC | CTAGGTGAAC | AGCCCACCAC | TGTGCCACCA | CCCATTGACC TGTCAATACC | 2220 |
| TCACGTTTGG | ATGCCACCGC | AAACCACTCC | ACACGGCTGG | ACAGAATCAC ATACCACCTC | 2280 |
| AGGACTACAC | CGACCACACT | TTAACCAGAC | CTGTATCCTC | TTTGATGGAC ACGATCTACT | 2340 |
| ATTCAGCACC | GTCACACCTT | GTTTGCACCA | AGGCTTTTAC | CTCATCGACG AACTACGTTA | 2400 |
| CGTTAAAATA | ACACTGACCG | AGGACTTCTT | CGTAGTTACG | GTGTCCATAG ACGACGACAC | 2460 |
| ACCCATGCTG | CTTATCTTCG | GCCATCTTCC | ACGCGTACTC | TTTAAAGCGC CCTATCAACG | 2520 |
| CGACAACTTT | ATACTACGAC | AAACTGAAAA | ACACGAGCTC | CTGGTGCTAG TTAAGAAAGA | 2580 |
| TCAACTGAAC | CGTCACTCTT | ATCTCAAAGA | CCCGGACTTT | CTTGACGCCG CACTTGACTT | 2640 |
| CAACTACCTG | GACCTCAGCG | CACTACTACG | TAACAGCTTT | CACCGTTACG CCGTGGATGT | 2700 |
| ACTCAAAAGC | GGTCGATGTC | AGATGCTGGA | CCGCCGCACG | GTAGAAATGG CCTTCGCCTA | 2760 |
| CGCATTAGCA | CTGTTCGCAG | CAGCCCGACA | AGAAGAGGCC | GGCGCCCAAG TCTCCGTCCC | 2820 |
| ACGGGCCCTA | GACCGCCAGG | CCGCACTCTT | ACAAATACAA | GAATTTATGA TCACCTGCCT | 2880 |
| CTCACAAACA | CCACCACGCA | CCACGTTGCT | GCTGTATCCC | ACGGCCGTGG ACCTGGCCAA | 2940 |
| ACGAGCCCTT | TGGACACCGA | ATCAGATCAC | CGACATCACC | AGCCTCGTAC GCCTGGTCTA | 3000 |
| CATACTCTCT | AAACAGAATC | AGCAACATCT | CATCCCCCAG | TGGGCACTAC GACAGATCGC | 3060 |
| CGACTTTGCC | CTAAAACTAC | ACAAAACGCA | CCTGGCCTCT | TTTCTTTCAG CCTTCGCGCG | 3120 |
| TCAAGAACTC | TACCTCATGG | GCAGCCTCGT | CCACTCCATG | CTAGTACATA CGACGGAGAG | 3180 |
| ACGCGAAATC | TTCATCGTAG | AAACGGGCCT | CTGTTCATTA | GCCGAGCTAT CACACTTTAC | 3240 |
| GCAGTTGCTA | GCTCATCCGC | ACCACGAATA | CCTCAGCGAC | CTGTACACAC CCTGTTCCAG | 3300 |
| TAGCGGGCGA | CGCGATCACT | CGCTCGAACG | CCTCACACGT | CTCTTCCCCG ATGCCACCGT | 3360 |
| CCCCACTACC | GTTCCCGCCG | CCCTCTCCAT | CCTATCTACC | ATGCAACCAA GCACGCTAGA | 3420 |
| AACCTTCCCC | GACCTGTTTT | GTCTGCCGCT | CGGCGAATCC | TTCTCCGCGC TGACCGTCTC | 3480 |
| CGAACACGTC | AGTTATGTCG | TAACAAACCA | GTACCTGATC | AAAGGTATCT CCTACCCTGT | 3540 |
| CTCCACCACC | GTCGTAGGCC | AGAGCCTCAT | CATCACCCAG | ACGGACAGTC AAACTAAATG | 3600 |
| CGAACTGACG | CGCAACATGC | ATACCACACA | CAGCATCACA | GCGGCGCTCA ACATTTCCCT | 3660 |
| AGAAAACTGC | GCCTTTTGCC | AAAGCGCCCT | ACTAGAATAC | GACGACACGC AAGGCGTCAT | 3720 |
| CAACATCATG | TACATGCACG | ACTCGGACGA | CGTCCTTTTC | GCCCTGGATC CCTACAACGA | 3780 |
| AGTGGTGGTC | TCATCTCCGC | GAACTCACTA | CCTCATGCTT | TTGAAAAACG GTACGGTCCT | 3840 |
| AGAAGTAACT | GACGTCGTCG | TGGACGCTAC | CGACAGTCGT | CTCCTCATGA TGTCCGTCTA | 3900 |
| CGCGCTATCG | GCCATCATCG | GCATCTATCT | GCTCTACCGC | ATGCTCAAGA CATGCTGATT | 3960 |
| TTTATCTCGA | GTCTAGAATC | GATCCCGGGT | TTTTATGACT | AGTTAATCAC GGCCGCTTAT | 4020 |
| AAAGATCTAA | AATGCATAAT | TTCTAAATAA | TGAAAAAAA | GTACATCATG AGCAACGCGT | 4080 |
| TAGTATATTT | TACAATGGAG | ATTAACGCTC | TATACCGTTC | TATGTTTATT GATTCAGATG | 4140 |
| ATGTTTTAGA | AAAGAAAGTT | ATTGAATATG | AAAACTTTAA | TGAAGATGAA GATGACGACG | 4200 |
| ATGATTATTG | TTGTAAATCT | GTTTTAGATG | AAGAAGATGA | CGCGCTAAAG TATACTATGG | 4260 |
| TTACAAAGTA | TAAGTCTATA | CTACTAATGG | CGACTTGTGC | AAGAAGGTAT AGTATAGTGA | 4320 |

```
AAATGTTGTT AGATTATGAT TATGAAAAAC CAAATAAATC AGATCCATAT CTAAAGGTAT      4380

CTCCTTTGCA CATAATTTCA TCTATTCCTA GTTTAGAATA CCTGCAG                   4427

(2) INFORMATION FOR SEQ ID NO:49:

(i) SEQUENCE CHARACTERISTICS:
        (A) LENGTH: 2651 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AAGACTAATT TGTAAACCAT CTTACTCAAA ATATGTAACA ATAGTACGAT GCAATGAGTA        60

AGACAATAGG AAATCTATCT TATATACACA TAATTATTCT ATCAATTTTA CCAATTAGTT       120

AGTGTAATGT TATAAAAACT AATTAATCAC TCGAGATAAA AATCAGCATG TCTTGAGCAT       180

GCGGTAGAGC AGATAGATGC CGATGATGGC CGATAGCGCG TAGACGGACA TCATGAGGAG       240

ACGACTGTCG GTAGCGTCCA CGACGACGTC AGTTACTTCT AGGACCGTAC CGTTTTTCAA      300

AAGCATGAGG TAGTGAGTTC GCGGAGATGA GACCACCACT TCGTTGTAGG GATCCAGGGC       360

GAAAAGGACG TCGTCCGAGT CGTGCATGTA CATGATGTTG ATGACGCCTT GCGTGTCGTC       420

GTATTCTAGT AGGGCGCTTT GGCAAAAGGC GCAGTTTTCT AGGGAAATGT TGAGCGCCGC       480

TGTGATGCTG TGTGTGGTAT GCATGTTGCG CGTCAGTTCG CATTTAGTTT GACTGTCCGT       540

CTGGGTGATG ATGAGGCTCT GGCCTACGAC GGTGGTGGAG ACAGGGTAGG AGATACCTTT      600

GATCAGGTAC TGGTTTGTTA CGACATAACT GACGTGTTCG GAGACGGTCA GCGCGGAGAA       660

GGATTCGCCG AGCGGCAGAC AAAACAGGTC GGGGAAGGTT TCTAGCGTGC TTGGTTGCAT       720

GGTAGATAGG ATGGAGAGGG CGGCGGGAAC GGTAGTGGGG ACGGTGGCAT CGGGGAAGAG       780

ACGTGTGAGG CGTTCGAGCG AGTGATCGCG TCGCCCGCTA CTGGAACAGG GTGTGTACAG       840

GTCGCTGAGG TATTCGTGGT GCGGATGAGC TAGCAACTGC GTAAAGTGTG ATAGCTCGGC       900

TAATGAACAG AGGCCCGTTT CTACGATGAA GATTTCGCGT CTCTCCGTCG TATGTACTAG       960

CATGGAGTGG ACGAGGCTGC CCATGAGGTA GAGTTCTTGA CGCGCGAAGG CTGAAAGAAA      1020

AGAGGCCAGG TGCGTTTTGT GTAGTTTTAG GGCAAAGTCG GCGATCTGTC GTAGTGCCCA      1080

CTGGGGATG AGATGTTGCT GATTCTGTTT AGAGAGTATG TAGACCAGGC GTACGAGGCT      1140

GGTGATGTCG GTGATCTGAT TCGGTGTCCA AAGGGCTCGT TTGGCCAGGT CCACGGCCGT      1200

GGGATACAGC AGCAACGTGG TGCGTGGTGG TGTTTGTGAG AGGCAGGTGA TCATAAATTC      1260

TTGTATTTGT AAGAGTGCGG CCTGGCGGTC TAGGGCCCGT GGGACGGAGA CTTGGGCGCC      1320

GGCCTCTTCT TGTCGGGCTG CTGCGAACAG TGCTAATGCG TAGGCGAAGG CCATTTCTAC      1380

CGTGCGGCGG TCCAGCATCT GACATCGACC GCTTTTGAGT ACATCCACGG CGTAACGGTG      1440

AAAGCTGTTA CGTAGTAGTG CGCTGAGGTC CAGGTAGTTG AAGTCAAGTG CGGCGTCAAG      1500

AAAGTCCGGG TCTTTGAGAT AAGAGTGACG GTTCAGTTGA TCTTTCTTAA CTAGCACCAG      1560

GAGCTCGTGT TTTTCAGTTT GTCGTAGTAT AAAGTTGTCG CGTTGATAGG GCGCTTTAAA      1620

GAGTACGCGT GGAAGATGGC CGAAGATAAG CAGCATGGGT GTGTCGTCGT CTATGGACAC      1680

CGTAACTACG AAGAAGTCCT CGGTCAGTGT TATTTTAACG TAACGTAGTT CGTCGATGAG      1740

GTAAAAGCCT TGGTGCAAAC AAGGTGTGAC GGTGCTGAAT AGTAGATCGT GTCCATCAAA      1800

GAGGATACAG GTCTGGTTAA AGTGTGGTCG GTGTAGTCCT GAGGTGGTAT GTGATTCTGT      1860
```

-continued

| | | | | |
|---|---|---|---|---|
| CCAGCCGTGT | GGAGTGGTTT | GCGGTGGCAT | CCAAACGTGA | GGTATTGACA | GGTCAATGGG | 1920 |
| TGGTGGCACA | GTGGTGGGCT | GTTCACCTAG | GCTGTCCTGT | GCCTTTAGCT | GCTGCGAAAA | 1980 |
| AGATCGGTAG | CTGGCCAGGT | CTTTGGATAC | CAGCGCGTAA | GTGTTAAGTC | TCTGTTGGTA | 2040 |
| TCTTTCCAGG | GTTTCGGTCA | GATCTACCTG | GTTCAGAAAC | TGCTCCGCCA | GAGGACCCGC | 2100 |
| AAAAAGACAT | CGAGGCATAT | GGAATACATA | GTATTGATTA | TAGCTTTGGA | AAAAGTTGAA | 2160 |
| ACTGATGGCG | TTTTCCCTGA | CGACCGTGCT | GTTACGGAGG | CTGCTATTGT | AGGTACACTG | 2220 |
| GGTGGTGTTT | TCACGCAGGA | AGCGGATGGG | TCTCCCGTAG | GTGTTGAGCA | GTAGGTGAAA | 2280 |
| CGCTTTGTCC | AGCGGTTCGG | ATATGGCTTC | TGCGCCATAT | CGTGACGAAA | GTAGGTGGCT | 2340 |
| GAGGAGACAG | ACGGCGAGGA | CGATGAGGTA | GGAGGGGAGC | CCGGGCCGCA | TTTTATATTG | 2400 |
| TAATTATATA | TTTTCAATTT | TGAAATCCCA | AAATATTATC | ATATTCTTCC | CAATAAACTC | 2460 |
| GAGCCCGGGG | AATTCGGATC | CTCGCGACTG | CAGGGTACCT | GAGTAGCTAA | TTTTTAAACA | 2520 |
| AAAATGTGGG | AGAATCTAAT | TAGTTTTTCT | TTACACAATT | GACGTACATG | AGTCTGAGTT | 2580 |
| CCTTGTTTTT | GCTAATTATT | TCATCCAATT | TATTATTCTT | GACGATATCG | AGATCTTTTG | 2640 |
| TATAGGAGTC | A | | | | | 2651 |

(2) INFORMATION FOR SEQ ID NO:50:

(i) SEQUENCE CHARACTERISTICS:
        (A) LENGTH: 1476 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

| | | | | | | |
|---|---|---|---|---|---|---|
| ATGGAGTCCT | CTGCCAAGAG | AAAGATGGAC | CCTGATAATC | CTGACGAGGG | CCCTTCCTCC | 60 |
| AAGGTGCCAC | GGCCCGAGAC | ACCCGTGACC | AAGGCCACGA | CGTTCCTGCA | GACTATGTTG | 120 |
| AGGAAGGAGG | TTAACAGTCA | GCTGAGTCTG | GGAGACCCGC | TGTTTCCAGA | GTTGGCCGAA | 180 |
| GAATCCCTCA | AAACTTTTGA | CAAGTGACC | GAGGATTGCA | ACGAGAACCC | CGAGAAAGAT | 240 |
| GTCCTGGCAG | AACTCGTCAA | ACAGATTAAG | GTTCGAGTGG | ACATGGTGCG | GCATAGAATC | 300 |
| AAGGAGCACA | TGCTGAAAAA | ATATACCCAG | ACGGAAGAGA | AATTCACTGG | CGCCTTTAAT | 360 |
| ATGATGGGAG | GATGTTTGCA | GAATGCCTTA | GATATCTTAG | ATAAGGTTCA | TGAGCCTTTC | 420 |
| GAGGAGATGA | AGTGTATTGG | GCTAACTATG | CAGAGCATGT | ATGAGAACTA | CATTGTACCT | 480 |
| GAGGATAAGC | GGGAGATGTG | GATGGCTTGT | ATTAAGGAGC | TGCATGATGT | GAGCAAGGGC | 540 |
| GCCGCTAACA | AGTTGGGGGG | TGCACTGCAG | GCTAAGGCCC | GTGCTAAAAA | GGATGAACTT | 600 |
| AGGAGAAAGA | TGATGTATAT | GTGCTACAGG | AATATAGAGT | TCTTTACCAA | GAACTCAGCC | 660 |
| TTCCCTAAGA | CCACCAATGG | CTGCAGTCAG | GCCATGGCGG | CACTGCAGAA | CTTGCCTCAG | 720 |
| TGCTCCCCTG | ATGAGATTAT | GGCTTATGCC | CAGAAAATAT | TTAAGATTTT | GGATGAGGAG | 780 |
| AGAGACAAGG | TGCTCACGCA | CATTGATCAC | ATATTTATGG | ATATCCTCAC | TACATGTGTG | 840 |
| GAAACAATGT | GTAATGAGTA | CAAGGTCACT | AGTGACGCTT | GATGATGAC | CATGTACGGG | 900 |
| GGCATCTCTC | TCTTAAGTGA | GTTCTGTCGG | GTGCTGTGCT | GCTATGTCTT | AGAGGAGACT | 960 |
| AGTGTGATGC | TGGCCAAGCG | GCCTCTGATA | ACCAAGCCTG | AGGTTATCAG | TGTAATGAAG | 1020 |
| CGCCGCATTG | AGGAGATCTG | CATGAAGGTC | TTTGCCCAGT | ACATTCTGGG | GGCCGATCCT | 1080 |
| CTGAGAGTCT | GCTCTCCTAG | TGTGGATGAC | CTACGGGCCA | TCGCCGAGGA | GTCAGATGAG | 1140 |

```
GAAGAGGCTA TTGTAGCCTA CACTTTGGCC ACCGCTGGTG TCAGCTCCTC TGATTCTCTG      1200

GTGTCACCCC CAGAGTCCCC TGTACCCGCG ACTATCCCTC TGTCCTCAGT AATTGTGGCT      1260

GAGAACAGTG ATCAGGAAGA AAGTGAGCAG AGTGATGAGG AAGAGGAGGA GGGTGCTCAG      1320

GAGGAGCGGG AGGACACTGT GTCTGTCAAG TCTGAGCCAG TGTCTGAGAT AGAGGAAGTT      1380

GCCCCAGAGG AAGAGGAGGA TGGTGCTGAG GAACCCACCG CCTCTGGAGG TAAGAGTACC      1440

CACCCTATGG TGACTAGAAG CAAGGCTGAC CAGTAA                                1476
```

(2) INFORMATION FOR SEQ ID NO:51:

(i) SEQUENCE CHARACTERISTICS:
        (A) LENGTH: 1975 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
ATATAATCCT CCACCAAAAT AGAGAATATA TATATCATCA TTTCATGATG TATACTACTG        60

ACATAGTTTC AATGTGAACT TTTCACTTTC TTGCCGGTTA TGAAGAATAT TTTTTATTTT       120

AATGGTCATT ACTAATCGTA TATTATAATT GAAAATGAAT TAGTTTAATA TGACGCTCGT       180

CATGGGATCC ATAAAAATTA CTGGTCAGCC TTGCTTCTAG TCACCATAGG GTGGGTACTC       240

TTACCTCCAG AGGCGGTGGG TTCCTCAGCA CCATCCTCCT CTTCCTCTGG GGCAACTTCC       300

TCTATCTCAG ACACTGGCTC AGACTTGACA GACACAGTGT CCTCCCGCTC CTCCTGAGCA       360

CCCTCCTCCT CTTCCTCATC ACTCTGCTCA CTTTCTTCCT GATCACTGTT CTCAGCCACA       420

ATTACTGAGG ACAGAGGGAT AGTCGCGGGT ACAGGGGACT CTGGGGGTGA CACCAGAGAA       480

TCAGAGGAGC TGACACCAGC GGTGGCCAAA GTGTAGGCTA CAATAGCCTC TTCCTCATCT       540

GACTCCTCGG CGATGGCCCG TAGGTCATCC ACACTAGGAG AGCAGACTCT CAGAGGATCG       600

GCCCCCAGAA TGTACTGGGC AAAGACCTTC ATGCAGATCT CCTCAATGCG GCGCTTCATT       660

ACACTGATAA CCTCAGGCTT GGTTATCAGA GGCCGCTTGG CCAGCATCAC ACTAGTCTCC       720

TCTAAGACAT AGCAGCACAG CACCCGACAG AACTCACTTA AGAGAGAGAT GCCCCCGTAC       780

ATGGTCATCA TACAAGCGTC ACTAGTGACC TTGTACTCAT TACACATTGT TTCCACACAT       840

GTAGTGAGGA TATCCATAAA TATGTGATCA ATGTGCGTGA GCACCTTGTC TCTCTCCTCA       900

TCCAAAATCT TAAATATTTT CTGGGCATAA GCCATAATCT CATCAGGGGA GCACTGAGGC       960

AAGTTCTGCA GTGCCGCCAT GGCCTGACTG CAGCCATTGG TGGTCTTAGG GAAGGCTGAG      1020

TTCTTGGTAA AGAACTCTAT ATTCCTGTAG CACATATACA TCATCTTTCT CCTAAGTTCA      1080

TCCTTTTTAG CACGGGCCTT AGCCTGCAGT GCACCCCCCA ACTTGTTAGC GGCGCCCTTG      1140

CTCACATCAT GCAGCTCCTT AATACAAGCC ATCCACATCT CCCGCTTATC CTCAGGTACA      1200

ATGTAGTTCT CATACATGCT CTGCATAGTT AGCCCAATAC ACTTCATCTC CTCGAAAGGC      1260

TCATGAACCT TATCTAAGAT ATCTAAGGCA TTCTGCAAAC ATCCTCCCAT CATATTAAAG      1320

GCGCCAGTGA ATTTCTCTTC CGTCTGGGTA TATTTTTTCA GCATGTGCTC CTTGATTCTA      1380

TGCCGCACCA TGTCCACTCG AACCTTAATC TGTTTGACGA GTTCTGCCAG GACATCTTTC      1440

TCGGGGTTCT CGTTGCAATC CTCGGTCACT TGTTCAAAAG TTTTGAGGGA TTCTTCGGCC      1500

AACTCTGGAA ACAGCGGGTC TCCCAGACTC AGCTGACTGT TAACCTCCTT CCTCAACATA      1560

GTCTGCAGGA ACGTCGTGGC CTTGGTCACG GGTGTCTCGG GCCGTGGCAC CTTGGAGGAA      1620
```

```
GGGCCCTCGT CAGGATTATC AGGGTCCATC TTTCTCTTGG CAGAGGACTC CATTACGATA    1680

CAAACTTAAC GGATATCGCG ATAATGAAAT AATTTATGAT TATTTCTCGC TTTCAATTTA    1740

ACACAACCCT CAAGAACCTT TGTATTTATT TTCACTTTTT AAGTATAGAA TAAAGAGATC    1800

CTGCTGTGGT AGATTCTGTG ACGCTAAGAA TAAGAATAAG AAGGAAGATG TAGAAGAGGG    1860

AAGAGAAGGA TGTTACAATT ATAAGAACCT TAATGATCTG GATGAATCCG AAGCACGTGT    1920

AGAATTTGGA CCATTATATA TGATAAATGA AGAAAAATCA GACATAAATA CATTG         1975
```

(2) INFORMATION FOR SEQ ID NO:52:

(i) SEQUENCE CHARACTERISTICS:
        (A) LENGTH: 3499 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
AAGCTTGCGG CCGCTCATTA GACAAGCGAA TGAGGGACGA AAACGTGGAG GAGGTATTAA      60

GTTTGGAGAA ATGGAGAGAG ACTGTTTAAT AGCGCATGGC GCAGCCAATA CTATTACAGA     120

AGTTTTGAAA GATTCGGAAG AAGATTATCA AGATGTGTAT GTTTGTGAAA ATTGTGGAGA     180

CATAGCAGCA CAAATCAAGG GTATTAATAC ATGTCTTAGA TGTTCAAAAC TTAATCTCTC     240

TCCTCTCTTA ACAAAAATTG ATACCACGCA CGTATCTAAA GTATTTCTTA CTCAAATGAA     300

CGCCAGAGGC GTAAAAGTCA AATTAGATTT CGAACGAAGG CCTCCTTCGT TTTATAAACC     360

ATTAGATAAA GTTGATCTCA AGCCGTCTTT TCTGGTGTAA TAAAAATTAA TTAATTACTC     420

GAGATAAAAA TTACTGGTCA GCCTTGCTTC TAGTCACCAT AGGGTGGGTA CTCTTACCTC     480

CAGAGGCGGT GGGTTCCTCA GCACCATCCT CCTCTTCCTC TGGGGCAACT TCCTCTATCT     540

CAGACACTGG CTCAGACTTG ACAGACACAG TGTCCTCCCG CTCCTCCTGA GCACCCTCCT     600

CCTCTTCCTC ATCACTCTGC TCACTTTCTT CCTGATCACT GTTCTCAGCC ACAATTACTG     660

AGGACAGAGG GATAGTCGCG GGTACAGGGG ACTCTGGGGG TGACACCAGA GAATCAGAGG     720

AGCTGACACC AGCGGTGGCC AAAGTGTAGG CTACAATAGC CTCTTCCTCA TCTGACTCCT     780

CGGCGATGGC CCGTAGGTCA TCCACACTAG GAGAGCAGAC TCTCAGAGGA TCGGCCCCCA     840

GAATGTACTG GGCAAAGACC TTCATGCAGA TCTCCTCAAT GCGGCGCTTC ATTACACTGA     900

TAACCTCAGG CTTGGTTATC AGAGGCCGCT TGGCCAGCAT CACACTAGTC TCCTCTAAGA     960

CATAGCAGCA CAGCACCCGA CAGAACTCAC TTAAGAGAGA GATGCCCCCG TACATGGTCA    1020

TCATACAAGC GTCACTAGTG ACCTTGTACT CATTACACAT TGTTTCCACA CATGTAGTGA    1080

GGATATCCAT AAATATGTGA TCAATGTGCG TGAGCACCTT GTCTCTCTCC TCATCCAAAA    1140

TCTTAAATAT TTTCTGGGCA TAAGCCATAA TCTCATCAGG GGAGCACTGA GGCAAGTTCT    1200

GCAGTGCCGC CATGGCCTGA CTGCAGCCAT TGGTGGTCTT AGGGAAGGCT GAGTTCTTGG    1260

TAAAGAACTC TATATTCCTG TAGCACATAT ACATCATCTT TCTCCTAAGT TCATCCTTTT    1320

TAGCACGGGC CTTAGCCTGC AGTGCACCCC CCAACTTGTT AGCGGCGCCC TTGCTCACAT    1380

CATGCAGCTC CTTAATACAA GCCATCCACA TCTCCCGCTT ATCCTCAGGT ACAATGTAGT    1440

TCTCATACAT GCTCTGCATA GTTAGCCCAA TACACTTCAT CTCCTCGAAA GGCTCATGAA    1500

CCTTATCTAA GATATCTAAG GCATTCTGCA AACATCCTCC CATCATATTA AAGGCGCCAG    1560

TGAATTTCTC TTCCGTCTGG GTATATTTTT TCAGCATGTG CTCCTTGATT CTATGCCGCA    1620
```

```
CCATGTCCAC TCGAACCTTA ATCTGTTTGA CGAGTTCTGC CAGGACATCT TTCTCGGGGT    1680

TCTCGTTGCA ATCCTCGGTC ACTTGTTCAA AAGTTTTGAG GGATTCTTCG GCCAACTCTG    1740

GAAACAGCGG GTCTCCCAGA CTCAGCTGAC TGTTAACCTC CTTCCTCAAC ATAGTCTGCA    1800

GGAACGTCGT GGCCTTGGTC ACGGGTGTCT CGGGCCGTGG CACCTTGGAG GAAGGGCCCT    1860

CGTCAGGATT ATCAGGGTCC ATCTTTCTCT TGGCAGAGGA CTCCATTACG ATACAAACTT    1920

AACGGATATC GCGATAATGA AATAATTTAT GATTATTTCT CGCTTTCAAT TAACACAAC     1980

CCTCAAGAAC CTTTGTATTT ATTTTCACTT TTTAAGTATA GAATAAAGAA GCTCTAATTA    2040

ATTAAGCTAC AAATAGTTTC GTTTTCACCT TGTCTAATAA CTAATTAATT AACCCCGATA    2100

GCTGATTAGT TTTTGTTAAC AAAAATGTGG GAGAATCTAA TTAGTTTTTC TTTACACAAT    2160

TGACGTACAT GAGTCTGAGT TCCTTGTTTT TGCTAATTAT TTCATCCAAT TTATTATTCT    2220

TGACGATATC GAGATCTTTT GTATAGGAGT CAGACTTGTA TTCAACATGC TTTTCTATAA    2280

TCATCTTAGT TATTTCGGCA TCATCCAATA GTACATTTTC CAGATTAACA GAGTAGATAT    2340

TAATGTCGTA TTTGAACAGA GCCTGTAACA TCTCAATGTC TTTATTATCT ATAGCCAATT    2400

TAATGTCCGG AATGAAGAGA AGGGAATTAT TGGTGTTTGT CGACGTCATA TAGTCGAGCA    2460

AGAGAATCAT CATATCCACG TGTCCATTTT TTATAGTGGT GTGAATACAA CTAAGGAGAA    2520

TAGCCAGATC AAAAGTAGAT GGTATTTCTG AAAGAAAGTA TGATACAATA CTTACATCAT    2580

TAAGCATGAC GGCATGATAA AATGAAGTTT TCCATCCAGT TTTCCCATAG AACATCAGTC    2640

TCCAATTTTT CTTAAACAGT TTCACCGTTT GCATGTTACC ACTATCAACC GCATAATACA    2700

ATGCGGTGTT TCCTTTGTCA TCAAATTGTG AATCATCCAT TCCACTGAAT AGCAAAATCT    2760

TTACTATTTT GGTATCTTCT AATGTGGCTG CCTGATGTAA TGGAAATTCA TTCTCTAGAA    2820

GATTTTTCAA TGCTCCAGCG TTCAACAACG TACATACTAG ACGCACGTTA TTATCAGCTA    2880

TTGCATAATA CAAGGCACTA TGTCCATGGA CATCCGCCTT AAATGTATCT TTACTAGAGA    2940

GAAAGCTTTT CAGCTGCTTA GACTTCCAAG TATTAATTCG TGACAGATCC ATGTCTGAAA    3000

CGAGACGCTA ATTAGTGTAT ATTTTTTCAT TTTTTATAAT TTTGTCATAT TGCACCAGAA    3060

TTATAATATC TCTAATAGAT CTAATTTAAT TTAATTTATA TAACTTATTT TTTGAATATA    3120

CTTTTAATTA ACAAAAGAGT TAAGTTACTC ATATGGACGC CGTCCAGTCT GAACATCAAT    3180

CTTTTTAGCC AGAGATATCA TAGCCGCTCT TAGAGTTTCA GCGTGATTTT CCAACCTAAA    3240

TAGAACTTCA TCGTTGCGTT TACAACACTT TTCTATTTGT TCAAACTTTG TTGTTACATT    3300

AGTAATCTTT TTTTCCAAAT TAGTTAGCCG TTGTTTGAGA GTTTCCTCAT TGTCGTCTTG    3360

CATCGGCTTT AACAATTGCT TCGCGTTTAG CCTCCTGGCT GTTCTTATCA GCCTTTGTAG    3420

AAAAAAATTC AGTTGCTGGA ATTGCAAGAT CGTCATCTCC GGGGAAAAGA GTTCCGTCCA    3480

TTTAAAGCCG CGGGAATTC                                                3499
```

(2) INFORMATION FOR SEQ ID NO:53:

(i) SEQUENCE CHARACTERISTICS:
        (A) LENGTH: 1386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
ATGGAGTCCT CTGCCAAGAG AAAGATGGAC CCTGATAATC CTGACGAGGG CCCTTCCTCC      60
```

```
AAGGTGCCAC GGCCCGAGAC ACCCGTGACC AAGGCCACGA CGTTCCTGCA GACTATGTTG      120

AGGAAGGAGG TTAACAGTCA GCTGAGTCTG GGAGACCCGC TGTTTCCAGA GTTGGCCGAA      180

GAATCCCTCA AAACTTTTGA ACAAGTGACC GAGGATTGCA ACGAGAACCC CGAGAAAGAT      240

GTCCTGGCAG AACTCGTCAA ACAGATTAAG GTTCGAGTGG ACATGGTGCG GCATAGAATC      300

AAGGAGCACA TGCTGAAAAA ATATACCCAG ACGGAAGAGA AATTCACTGG CGCCTTTAAT      360

ATGATGGGAG GATGTTTGCA GAATGCCTTA GATATCTTAG ATAAGGTTCA TGAGCCTTTC      420

GAGGAGATGA AGTGTATTGG GCTAACTATG CAGAGCATGT ATGAGAACTA CATTGTACCT      480

GAGGATAAGC GGGAGATGTG GATGGCTTGT ATTAAGGAGC TGCATGATGT GAGCAAGGGC      540

GCCGCTAACA AGTTGGGGGG TGCACTGCAG GCTAAGGCCC GTGCTAAAAA GGATGAACTT      600

AGGAGAAAGA TGATGTATAT GTGCTACAGG AATATAGAGT TCTTTACCAA GAACTCAGCC      660

TTCCCTAAGA CCACCAATGG CTGCAGTCAG GCCATGGCGG CACTGCAGAA CTTGCCTCAG      720

TGCTCCCCTG ATGAGATTAT GGCTTATGCC CAGAAAATAT TTAAGATTTT GGATGAGGAG      780

AGAGACAAGG TGCTCACGCA CATTGATCAC ATATTTATGG ATATCCTCAC TACATGTGTG      840

GAAACAATGT GTAATGAGTA CAAGGTCACT AGTGTGATGC TGGCCAAGCG GCCTCTGATA      900

ACCAAGCCTG AGGTTATCAG TGTAATGAAG CGCCGCATTG AGGAGATCTG CATGAAGGTC      960

TTTGCCCAGT ACATTCTGGG GGCCGATCCT CTGAGAGTCT GCTCTCCTAG TGTGGATGAC     1020

CTACGGGCCA TCGCCGAGGA GTCAGATGAG GAAGAGGCTA TTGTAGCCTA CACTTTGGCC     1080

ACCGCTGGTG TCAGCTCCTC TGATTCTCTG GTGTCACCCC CAGAGTCCCC TGTACCCGCG     1140

ACTATCCCTC TGTCCTCAGT AATTGTGGCT GAGAACAGTG ATCAGGAAGA AAGTGAGCAG     1200

AGTGATGAGG AAGAGGAGGA GGGTGCTCAG GAGGAGCGGG AGGACACTGT GTCTGTCAAG     1260

TCTGAGCCAG TGTCTGAGAT AGAGGAAGTT GCCCCAGAGG AAGAGGAGGA TGGTGCTGAG     1320

GAACCCACCG CCTCTGGAGG TAAGAGTACC CACCCTATGG TGACTAGAAG CAAGGCTGAC     1380

CAGTAA                                                                 1386

(2) INFORMATION FOR SEQ ID NO:54:

(i) SEQUENCE CHARACTERISTICS:
         (A) LENGTH: 3409 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:54:

AAGCTTGCGG CCGCTCATTA GACAAGCGAA TGAGGGACGA AAACGTGGAG GAGGTATTAA       60

GTTTGGAGAA ATGGAGAGAG ACTGTTTAAT AGCGCATGGC GCAGCCAATA CTATTACAGA      120

AGTTTTGAAA GATTCGGAAG AAGATTATCA AGATGTGTAT GTTTGTGAAA ATTGTGGAGA      180

CATAGCAGCA CAAATCAAGG GTATTAATAC ATGTCTTAGA TGTTCAAAAC TTAATCTCTC      240

TCCTCTCTTA ACAAAAATTG ATACCACGCA CGTATCTAAA GTATTTCTTA CTCAAATGAA      300

CGCCAGAGGC GTAAAAGTCA AATTAGATTT CGAACGAAGG CCTCCTTCGT TTTATAAACC      360

ATTAGATAAA GTTGATCTCA AGCCGTCTTT TCTGGTGTAA TAAAAATTAA TTAATTACTC      420

GAGATAAAAA TTACTGGTCA GCCTTGCTTC TAGTCACCAT AGGGTGGGTA CTCTTACCTC      480

CAGAGGCGGT GGGTTCCTCA GCACCATCCT CCTCTTCCTC TGGGGCAACT TCCTCTATCT      540

CAGACACTGG CTCAGACTTG ACAGACACAG TGTCCTCCCG CTCCTCCTGA GCACCCTCCT      600
```

-continued

```
CCTCTTCCTC ATCACTCTGC TCACTTTCTT CCTGATCACT GTTCTCAGCC ACAATTACTG     660

AGGACAGAGG GATAGTCGCG GGTACAGGGG ACTCTGGGGG TGACACCAGA GAATCAGAGG     720

AGCTGACACC AGCGGTGGCC AAAGTGTAGG CTACAATAGC CTCTTCCTCA TCTGACTCCT     780

CGGCGATGGC CCGTAGGTCA TCCACACTAG GAGAGCAGAC TCTCAGAGGA TCGGCCCCCA     840

GAATGTACTG GGCAAAGACC TTCATGCAGA TCTCCTCAAT GCGGCGCTTC ATTACACTGA     900

TAACCTCAGG CTTGGTTATC AGAGGCCGCT TGGCCAGCAT CACACTAGTG ACCTTGTACT     960

CATTACACAT TGTTTCCACA CATGTAGTGA GGATATCCAT AAATATGTGA TCAATGTGCG    1020

TGAGCACCTT GTCTCTCTCC TCATCCAAAA TCTTAAATAT TTTCTGGGCA TAAGCCATAA    1080

TCTCATCAGG GGAGCACTGA GGCAAGTTCT GCAGTGCCGC CATGGCCTGA CTGCAGCCAT    1140

TGGTGGTCTT AGGGAAGGCT GAGTTCTTGG TAAAGAACTC TATATTCCTG TAGCACATAT    1200

ACATCATCTT TCTCCTAAGT TCATCCTTTT TAGCACGGGC CTTAGCCTGC AGTGCACCCC    1260

CCAACTTGTT AGCGGCGCCC TTGCTCACAT CATGCAGCTC CTTAATACAA GCCATCCACA    1320

TCTCCCGCTT ATCCTCAGGT ACAATGTAGT TCTCATACAT GCTCTGCATA GTTAGCCCAA    1380

TACACTTCAT CTCCTCGAAA GGCTCATGAA CCTTATCTAA GATATCTAAG GCATTCTGCA    1440

AACATCCTCC CATCATATTA AAGGCGCCAG TGAATTTCTC TTCCGTCTGG GTATATTTTT    1500

TCAGCATGTG CTCCTTGATT CTATGCCGCA CCATGTCCAC TCGAACCTTA ATCTGTTTGA    1560

CGAGTTCTGC CAGGACATCT TTCTCGGGGT TCTCGTTGCA ATCCTCGGTC ACTTGTTCAA    1620

AAGTTTTGAG GGATTCTTCG GCCAACTCTG GAAACAGCGG GTCTCCCAGA CTCAGCTGAC    1680

TGTTAACCTC CTTCCTCAAC ATAGTCTGCA GGAACGTCGT GGCCTTGGTC ACGGGTGTCT    1740

CGGGCCGTGG CACCTTGGAG GAAGGGCCCT CGTCAGGATT ATCAGGGTCC ATCTTTCTCT    1800

TGGCAGAGGA CTCCATTACG ATACAAACTT AACGGATATC GCGATAATGA AATAATTTAT    1860

GATTATTTCT CGCTTTCAAT TTAACACAAC CCTCAAGAAC CTTTGTATTT ATTTTCACTT    1920

TTTAAGTATA GAATAAAGAA GCTCTAATTA ATTAAGCTAC AAATAGTTTC GTTTTCACCT    1980

TGTCTAATAA CTAATTAATT AACCCCGATA GCTGATTAGT TTTTGTTAAC AAAAATGTGG    2040

GAGAATCTAA TTAGTTTTTC TTTACACAAT TGACGTACAT GAGTCTGAGT TCCTTGTTTT    2100

TGCTAATTAT TTCATCCAAT TTATTATTCT TGACGATATC GAGATCTTTT GTATAGGAGT    2160

CAGACTTGTA TTCAACATGC TTTTCTATAA TCATCTTAGT TATTTCGGCA TCATCCAATA    2220

GTACATTTTC CAGATTAACA GAGTAGATAT TAATGTCGTA TTTGAACAGA GCCTGTAACA    2280

TCTCAATGTC TTTATTATCT ATAGCCAATT TAATGTCCGG AATGAAGAGA AGGGAATTAT    2340

TGGTGTTTGT CGACGTCATA TAGTCGAGCA AGAGAATCAT CATATCCACG TGTCCATTTT    2400

TTATAGTGGT GTGAATACAA CTAAGGAGAA TAGCCAGATC AAAAGTAGAT GGTATTTCTG    2460

AAAGAAAGTA TGATACAATA CTTACATCAT TAAGCATGAC GGCATGATAA AATGAAGTTT    2520

TCCATCCAGT TTTCCCATAG AACATCAGTC TCCAATTTTT CTTAAACAGT TTCACCGTTT    2580

GCATGTTACC ACTATCAACC GCATAATACA ATGCGGTGTT TCCTTTGTCA TCAAATTGTG    2640

AATCATCCAT TCCACTGAAT AGCAAAATCT TTACTATTTT GGTATCTTCT AATGTGGCTG    2700

CCTGATGTAA TGGAAATTCA TTCTCTAGAA GATTTTTCAA TGCTCCAGCG TTCAACAACG    2760

TACATACTAG ACGCACGTTA TTATCAGCTA TTGCATAATA CAAGGCACTA TGTCCATGGA    2820

CATCCGCCTT AAATGTATCT TTACTAGAGA GAAAGCTTTT CAGCTGCTTA GACTTCCAAG    2880

TATTAATTCG TGACAGATCC ATGTCTGAAA CGAGACGCTA ATTAGTGTAT ATTTTTTCAT    2940
```

```
TTTTTATAAT TTTGTCATAT TGCACCAGAA TTAATAATAT CTCTAATAGA TCTAATTTAA    3000

TTTAATTTAT ATAACTTATT TTTTGAATAT ACTTTTAATT AACAAAAGAG TTAAGTTACT    3060

CATATGGACG CCGTCCAGTC TGAACATCAA TCTTTTTAGC CAGAGATATC ATAGCCGCTC    3120

TTAGAGTTTC AGCGTGATTT TCCAACCTAA ATAGAACTTC ATCGTTGCGT TTACAACACT    3180

TTTCTATTTG TTCAAACTTT GTTGTTACAT TAGTAATCTT TTTTTCCAAA TTAGTTAGCC    3240

GTTGTTTGAG AGTTTCCTCA TTGTCGTCTT CATCGGCTTT AACAATTGCT TCGCGTTTAG    3300

CCTCCTGGCT GTTCTTATCA GCCTTTGTAG AAAAAAATTC AGTTGCTGGA ATTGCAAGAT    3360

CGTCATCTCC GGGGAAAAGA GTTCCGTCCA TTTAAAGCCG CGGGAATTC              3409

(2) INFORMATION FOR SEQ ID NO:55:

(i) SEQUENCE CHARACTERISTICS:
        (A) LENGTH: 1221 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

ATGAAACAGA TTAAGGTTCG AGTGGACATG GTGCGGCATA GAATCAAGGA GCACATGCTG      60

AAAAAATATA CCCAGACGGA AGAGAAATTC ACTGGCGCCT TAATATGAT GGGAGGATGT     120

TTGCAGAATG CCTTAGATAT CTTAGATAAG GTTCATGAGC CTTTCGAGGA GATGAAGTGT    180

ATTGGGCTAA CTATGCAGAG CATGTATGAG AACTACATTG TACCTGAGGA TAAGCGGGAG    240

ATGTGGATGG CTTGTATTAA GGAGCTGCAT GATGTGAGCA AGGCGCCGC TAACAAGTTG     300

GGGGGTGCAC TGCAGGCTAA GGCCCGTGCT AAAAAGGATG AACTTAGGAG AAAGATGATG    360

TATATGTGCT ACAGGAATAT AGAGTTCTTT ACCAAGAACT CAGCCTTCCC TAAGACCACC    420

AATGGCTGCA GTCAGGCCAT GGCGGCACTG CAGAACTTGC CTCAGTGCTC CCCTGATGAG    480

ATTATGGCTT ATGCCCAGAA AATATTTAAG ATTTTGGATG AGGAGAGAGA CAAGGTGCTC    540

ACGCACATTG ATCACATATT TATGGATATC CTCACTACAT GTGTGGAAAC AATGTGTAAT    600

GAGTACAAGG TCACTAGTGA CGCTTGTATG ATGACCATGT ACGGGGGCAT CTCTCTCTTA    660

AGTGAGTTCT GTCGGGTGCT GTGCTGCTAT GTCTTAGAGG AGACTAGTGT GATGCTGGCC    720

AAGCGGCCTC TGATAACCAA GCCTGAGGTT ATCAGTGTAA TGAAGCGCCG CATTGAGGAG    780

ATCTGCATGA AGGTCTTTGC CCAGTACATT CTGGGGGCCG ATCCTCTGAG AGTCTGCTCT    840

CCTAGTGTGG ATGACCTACG GGCCATCGCC GAGGAGTCAG ATGAGGAAGA GGCTATTGTA    900

GCCTACACTT TGGCCACCGC TGGTGTCAGC TCCTCTGATT CTCTGGTGTC ACCCCCAGAG    960

TCCCCTGTAC CCGCGACTAT CCCTCTGTCC TCAGTAATTG TGGCTGAGAA CAGTGATCAG    1020

GAAGAAAGTG AGCAGAGTGA TGAGGAAGAG GAGGAGGGTG CTCAGGAGGA GCGGGAGGAC    1080

ACTGTGTCTG TCAAGTCTGA GCCAGTGTCT GAGATAGAGG AAGTTGCCCC AGAGGAAGAG    1140

GAGGATGGTG CTGAGGAACC CACCGCCTCT GGAGGTAAGA GTACCCACCC TATGGTGACT    1200

AGAAGCAAGG CTGACCAGTA A                                              1221

(2) INFORMATION FOR SEQ ID NO:56:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:56:

| | | | | | |
|---|---|---|---|---|---|
| CTGCAGGTCG | ACGGATCTGA | GAATGGATGA | TTCTCCAGCC | GAAACATATT | CTACCATGGC | 60
| TCCGTTTAAT | TTGTTGATGA | AGATGGATTC | ATCCTTAAAT | GTTTTCTCTG | TAATAGTTTC | 120
| CACCGAAAGA | CTATGCAAAG | AATTTGGAAT | GCGTTCCTTG | TGCTTAATGT | TTCCATAGAC | 180
| GGCTTCTAGA | AGTTGATACA | ACATAGGACT | AGCCGCGGTA | ACTTTTATTT | TTAGAAAGTA | 240
| TCCATCGCTT | CTATCTTGTT | TAGATTTATT | TTTATAAAGT | TTAGTCTCTC | CTTCCAACAT | 300
| AATAAAAGTG | GAAGTCATTT | GACTAGATAA | ACTATCAGTA | AGTTTTATAG | AGATAGACGA | 360
| ACAATTAGCG | TATTGAGAAG | CATTTAGTGT | AACGTATTCG | ATACATTTTG | CATTAGATTT | 420
| ACTAATCGAT | TTTGCATACT | CTATAACACC | CGCACAAGTC | TGTAGAGAAT | CGCTAGATGC | 480
| AGTAGGTCTT | GGTGAAGTTT | CAACTCTCTT | CTTGATTACC | TTACTCATGA | TTAAACCTAA | 540
| ATAATTGTAC | TTTGTAATAT | AATGATATAT | ATTTTCACTT | TATCTCATTT | GAGAATAAAA | 600
| AGATCACAAA | AATTAACTAA | TCAGGATCCT | TCTTTATTCT | ATACTTAAAA | AGTGAAAATA | 660
| AATACAAAGG | TTCTTGAGGG | TTGTGTTAAA | TTGAAAGCGA | GAAATAATCA | TAAATTATTT | 720
| CATTATCGCG | ATATCCGTTA | AGTTTGTATC | GTAATGAAAC | AGATTAAGGT | TCGAGTGGAC | 780
| ATGGTGCGGC | ATAGAATCAA | GGAGCACATG | CTGAAAAAAT | ATACCCAGAC | GGAAGAGAAA | 840
| TTCACTGGCG | CCTTTAATAT | GATGGGAGGA | TGTTTGCAGA | ATGCCTTAGA | TATCTTAGAT | 900
| AAGGTTCATG | AGCCTTTCGA | GGAGATGAAG | TGTATTGGGC | TAACTATGCA | GAGCATGTAT | 960
| GAGAACTACA | TTGTACCTGA | GGATAAGCGG | GAGATGTGGA | TGGCTTGTAT | TAAGGAGCTG | 1020
| CATGATGTGA | GCAAGGGCGC | CGCTAACAAG | TTGGGGGGTG | CACTGCAGGC | TAAGGCCCGT | 1080
| GCTAAAAAGG | ATGAACTTAG | GAGAAAGATG | ATGTATATGT | GCTACAGGAA | TATAGAGTTC | 1140
| TTTACCAAGA | ACTCAGCCTT | CCCTAAGACC | ACCAATGGCT | GCAGTCAGGC | CATGGCGGCA | 1200
| CTGCAGAACT | TGCCTCAGTG | CTCCCCTGAT | GAGATTATGG | CTTATGCCCA | GAAAATATTT | 1260
| AAGATTTTGG | ATGAGGAGAG | AGACAAGGTG | CTCACGCACA | TTGATCACAT | ATTTATGGAT | 1320
| ATCCTCACTA | CATGTGTGGA | AACAATGTGT | AATGAGTACA | AGGTCACTAG | TGACGCTTGT | 1380
| ATGATGACCA | TGTACGGGGG | CATCTCTCTC | TTAAGTGAGT | TCTGTCGGGT | GCTGTGCTGC | 1440
| TATGTCTTAG | AGGAGACTAG | TGTGATGCTG | GCCAAGCGGC | CTCTGATAAC | CAAGCCTGAG | 1500
| GTTATCAGTG | TAATGAAGCG | CCGCATTGAG | GAGATCTGCA | TGAAGGTCTT | TGCCCAGTAC | 1560
| ATTCTGGGGG | CCGATCCTCT | GAGAGTCTGC | TCTCCTAGTG | TGGATGACCT | ACGGGCCATC | 1620
| GCCGAGGAGT | CAGATGAGGA | AGAGGCTATT | GTAGCCTACA | CTTTGGCCAC | CGCTGGTGTC | 1680
| AGCTCCTCTG | ATTCTCTGGT | GTCACCCCCA | GAGTCCCCTG | TACCCGCGAC | TATCCCTCTG | 1740
| TCCTCAGTAA | TTGTGGCTGA | GAACAGTGAT | CAGGAAGAAA | GTGAGCAGAG | TGATGAGGAA | 1800
| GAGGAGGAGG | GTGCTCAGGA | GGAGCGGGAG | GACACTGTGT | CTGTCAAGTC | TGAGCCAGTG | 1860
| TCTGAGATAG | AGGAAGTTGC | CCCAGAGGAA | GAGGAGGATG | GTGCTGAGGA | ACCCACCGCC | 1920
| TCTGGAGGTA | AGAGTACCCA | CCCTATGGTG | ACTAGAAGCA | AGGCTGACCA | GTAATTTTTA | 1980
| TCTCGAGCCC | GGGAGATCTT | AGCTAACTGA | TTTTTCTGGG | AAAAAAATTA | TTTAACTTTT | 2040
| CATTAATAGG | GATTTGACGT | ATGTAGCGTA | CAAAATTATC | GTTCCTGGTA | TATAGATAAA | 2100
| GAGTCCTATA | TATTTGAAAA | TCGTTACGGC | TCGATTAAAC | TTTAATGATT | GCATAGTGAA | 2160
| TATATCATTA | GGATTTAACT | CCTTGACTAT | CATGGCGGCG | CCAGAAATTA | CCATCAAAAG | 2220

```
CATTAATACA GTTATGCCGA TCGCAGTTAG AACGGTTATA GCATCCACCA TTTATATCTA      2280

AAAATTAGAT CAAAGAATAT GTGACAAAGT CCTAGTTGTA TACTGAGAAT TGACGAAACA      2340

ATGTTTCTTA CATATTTTTT TCTTATTAGT AACTGACTTA ATAGTAGGAA CTGGAAAGCT      2400

AGACTTGATT ATTCTATAAG TATAGATACC CTTCCAGATA ATGTTCTCTT TGATAAAAGT      2460

TCCAGAAAAT GTAGAATTTT TTAAAAAGTT ATCTTTTGCT ATTACCAAGA TTGTGTTTAG      2520

ACGCTTATTA TTAATATGAG TAATGAAATC CACACCGCCT CTAGATATGG GGAATTC        2577
```

(2) INFORMATION FOR SEQ ID NO:57:

(i) SEQUENCE CHARACTERISTICS:
        (A) LENGTH: 3460 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

```
GAATTGCGGC CGCTGAATGT TAAATGTTAT ACTTTGGATG AAGCTATAAA TATGCATTGG        60

AAAAATAATC CATTTAAAGA AAGGATTCAA ATACTACAAA ACCTAAGCGA TAATATGTTA       120

ACTAAGCTTA TTCTTAACGA CGCTTTAAAT ATACACAAAT AAACATAATT TTTGTATAAC       180

CTAACAAATA ACTAAAACAT AAAAATAATA AAAGGAAATG TAATATCGTA ATTATTTTAC       240

TCAGGAATGG GGTTAAATAT TTATATCACG TGTATATCTA TACTGTTATC GTATACTCTT       300

TACAATTACT ATTACGAATA TGCAAGAGAT AATAAGATTA CGTATTTAAG AGAATCTTGT       360

CATGATAATT GGGTACGACA TAGTGATAAA TGCTATTTCG CATCGTTACA TAAAGTCAGT       420

TGGAAAGATG GATTTGACAG ATGTAACTTA ATAGGTGCAA AAATGTTAAA TAACAGCATT       480

CTATCGGAAG ATAGGATACC AGTTATATTA TACAAAAATC ACTGGTTGGA TAAAACAGAT       540

TCTGCAATAT TCGTAAAAGA TGAAGATTAC TGCGAATTTG TAAACTATGA CAATAAAAAG       600

CCATTTATCT CAACGACATC GTGTAATTCT TCCATGTTTT ATGTATGTGT TCAGATATT        660

ATGAGATTAC TATAAACTTT TTGTATACTT ATATTCCGTA AACTATATTA ATCATGAAGA       720

AAATGAAAAA GTATAGAAGC TGTTCACGAG CGGTTGTTGA AAACAACAAA ATTATACATT       780

CAAGATGGCT TACATATACG TCTGTGAGGC TATCATGGAT AATGACAATG CATCTCTAAA       840

TAGGTTTTTG GACAATGGAT TCGACCCTAA CACGGAATAT GGTACTCTAC AATCTCCTCT       900

TGAAATGGCT GTAATGTTCA AGAATACCGA GGCTATAAAA ATCTTGATGA GGTATGGAGC       960

TAAACCTGTA GTTACTGAAT GCACAACTTC TTGTCTGCAT GATGCGGTGT TGAGAGACGA      1020

CTACAAAATA GTGAAAGATC TGTTGAAGAA TAACTATGTA AACAATGTTC TTTACAGCGG      1080

AGGCTTTACT CCTTTGTGTT TGGCAGCTTA CCTTAACAAA GTTAATTTGG TTAAACTTCT      1140

ATTGGCTCAT TCGGCGGATG TAGATATTTC AAACACGGAT CGGTTAACTC CTCTACATAT      1200

AGCCGTATCA AATAAAAATT TAACAATGGT TAAACTTCTA TTGAACAAAG GTGCTGATAC      1260

TGACTTGCTG GATAACATGG GACGTACTCC TTTAATGATC GCTGTACAAT CTGGAAATAT      1320

TGAAATATGT AGCACACTAC TTAAAAAAAA TAAAATGTCC AGAACTGGGA AAAATTGATC      1380

TTGCCAGCTG TAATTCATGG TAGAAAAGAA GTGCTCAGGC TACTTTTCAA CAAGGAGCA      1440

GATGTAAACT ACATCTTTGA AAGAAATGGA AAATCATATA CTGTTTTGGA ATTGATTAAA      1500

GAAAGTTACT CTGAGACACA AAAGAGGTAG CTGAAGTGGT ACTCTCAAAG GTACGTGACT      1560

AATTAGCTAT AAAAAGGATC CGGGTTAATT AATTAGTCAT CAGGCAGGGC GAGAACGAGA      1620
```

-continued

```
CTATCTGCTC GTTAATTAAT TAGAGCTTCT TTATTCTATA CTTAAAAAGT GAAAATAAAT    1680

ACAAAGGTTC TTGAGGGTTG TGTTAAATTG AAAGCGAGAA ATAATCATAA ATTATTTCAT    1740

TATCGCGATA TCCGTTAAGT TTGTATCGTA ATGAAACAGA TTAAGGTTCG AGTGGACATG    1800

GTGCGGCATA GAATCAAGGA GCACATGCTG AAAAAATATA CCCAGACGGA AGAGAAATTC    1860

ACTGGCGCCT TTAATATGAT GGGAGGATGT TTGCAGAATG CCTTAGATAT CTTAGATAAG    1920

GTTCATGAGC CTTTCGAGGA GATGAAGTGT ATTGGGCTAA CTATGCAGAG CATGTATGAG    1980

AACTACATTG TACCTGAGGA TAAGCGGGAG ATGTGGATGG CTTGTATTAA GGAGCTGCAT    2040

GATGTGAGCA AGGGCGCCGC TAACAAGTTG GGGGGTGCAC TGCAGGCTAA GGCCCGTGCT    2100

AAAAAGGATG AACTTAGGAG AAAGATGATG TATATGTGCT ACAGGAATAT AGAGTTCTTT    2160

ACCAAGAACT CAGCCTTCCC TAAGACCACC AATGGCTGCA GTCAGGCCAT GGCGGCACTG    2220

CAGAACTTGC CTCAGTGCTC CCCTGATGAG ATTATGGCTT ATGCCAGAA AATATTTAAG    2280

ATTTTGGATG AGGAGAGAGA CAAGGTGCTC ACGCACATTG ATCACATATT TATGGATATC    2340

CTCACTACAT GTGTGGAAAC AATGTGTAAT GAGTACAAGG TCACTAGTGA CGCTTGTATG    2400

ATGACCATGT ACGGGGGCAT CTCTCTCTTA AGTGAGTTCT GTCGGGTGCT GTGCTGCTAT    2460

GTCTTAGAGG AGACTAGTGT GATGCTGGCC AAGCGGCCTC TGATAACCAA GCCTGAGGTT    2520

ATCAGTGTAA TGAAGCGCCG CATTGAGGAG ATCTGCATGA AGGTCTTTGC CCAGTACATT    2580

CTGGGGGCCG ATCCTCTGAG AGTCTGCTCT CCTAGTGTGG ATGACCTACG GGCCATCGCC    2640

GAGGAGTCAG ATGAGGAAGA GGCTATTGTA GCCTACACTT TGGCCACCGC TGGTGTCAGC    2700

TCCTCTGATT CTCTGGTGTC ACCCCCAGAG TCCCCTGTAC CCGCGACTAT CCCTCTGTCC    2760

TCAGTAATTG TGGCTGAGAA CAGTGATCAG GAAGAAAGTG AGCAGAGTGA TGAGGAAGAG    2820

GAGGAGGGTG CTCAGGAGGA GCGGGAGGAC ACTGTGTCTG TCAAGTCTGA GCCAGTGTCT    2880

GAGATAGAGG AAGTTGCCCC AGAGGAAGAG GAGGATGGTG CTGAGGAACC CACCGCCTCT    2940

GGAGGTAAGA GTACCCACCC TATGGTGACT AGAAGCAAGG CTGACCAGTA ATTTTTATCT    3000

CGAGTCTAGA ATCGATCCCG GGTTTTTATG ACTAGTTAAT CACGGCCGCT TATAAAGATC    3060

TAAAATGCAT AATTTCTAAA TAATGAAAAA AAAGTACATC ATGAGCAACG CGTTAGTATA    3120

TTTTACAATG GAGATTAACG CTCTATACCG TTCTATGTTT ATTGATTCAG ATGATGTTTT    3180

AGAAAAGAAA GTTATTGAAT ATGAAAACTT TAATGAAGAT GAAGATGACG ACGATGATTA    3240

TTGTTGTAAA TCTGTTTTAG ATGAAGAAGA TGACGCGCTA AAGTATACTA TGGTTACAAA    3300

GTATAAGTCT ATACTACTAA TGGCGACTTG TGCAAGAAGG TATAGTATAG TGAAAATGTT    3360

GTTAGATTAT GATTATGAAA AACCAAATAA ATCAGATCCA TATCTAAAGG TATCTCCTTT    3420

GCACATAATT TCATCTATTC CTAGTTTAGA ATACCTGCAG                          3460
```

(2) INFORMATION FOR SEQ ID NO:58:

(i) SEQUENCE CHARACTERISTICS:
        (A) LENGTH: 1383 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
ATGACGACGT TCCTGCAGAC TATGTTGAGG AAGGAGGTTA ACAGTCAGCT GAGTCTGGGA      60

GACCCGCTGT TTCCAGAGTT GGCCGAAGAA TCCCTCAAAA CTTTTGAACA AGTGACCGAG     120
```

```
GATTGCAACG AGAACCCCGA GAAAGATGTC CTGGCAGAAC TCGTCAAACA GATTAAGGTT    180

CGAGTGGACA TGGTGCGGCA TAGAATCAAG GAGCACATGC TGAAAAAATA TACCCAGACG    240

GAAGAGAAAT TCACTGGCGC CTTTAATATG ATGGGAGGAT GTTTGCAGAA TGCCTTAGAT    300

ATCTTAGATA AGGTTCATGA GCCTTTCGAG GAGATGAAGT GTATTGGGCT AACTATGCAG    360

AGCATGTATG AGAACTACAT TGTACCTGAG GATAAGCGGG AGATGTGGAT GGCTTGTATT    420

AAGGAGCTGC ATGATGTGAG CAAGGGCGCC GCTAACAAGT TGGGGGGTGC ACTGCAGGCT    480

AAGGCCCGTG CTAAAAAGGA TGAACTTAGG AGAAAGATGA TGTATATGTG CTACAGGAAT    540

ATAGAGTTCT TTACCAAGAA CTCAGCCTTC CCTAAGACCA CCAATGGCTG CAGTCAGGCC    600

ATGGCGGCAC TGCAGAACTT GCCTCAGTGC TCCCCTGATG AGATTATGGC TTATGCCCAG    660

AAAATATTTA AGATTTTGGA TGAGGAGAGA GACAAGGTGC TCACGCACAT TGATCACATA    720

TTTATGGATA TCCTCACTAC ATGTGTGGAA ACAATGTGTA ATGAGTACAA GGTCACTAGT    780

GACGCTTGTA TGATGACCAT GTACGGGGGC ATCTCTCTCT TAAGTGAGTT CTGTCGGGTG    840

CTGTGCTGCT ATGTCTTAGA GGAGACTAGT GTGATGCTGG CCAAGCGGCC TCTGATAACC    900

AAGCCTGAGG TTATCAGTGT AATGAAGCGC CGCATTGAGG AGATCTGCAT GAAGGTCTTT    960

GCCCAGTACA TTCTGGGGGC CGATCCTCTG AGAGTCTGCT CTCCTAGTGT GGATGACCTA    1020

CGGGCCATCG CCGAGGAGTC AGATGAGGAA GAGGCTATTG TAGCCTACAC TTTGGCCACC    1080

GCTGGTGTCA GCTCCTCTGA TTCTCTGGTC TCACCCCCAG AGTCCCCTGT ACCCGCGACT    1140

ATCCCTCTGT CCTCAGTAAT TGTGGCTGAG AACAGTGATC AGGAAGAAAG TGAGCAGAGT    1200

GATGAGGAAG AGGAGGAGGG TGCTCAGGAG GAGCGGGAGG ACACTGTGTC TGTCAAGTCT    1260

GAGCCAGTGT CTGAGATAGA GGAAGTTGCC CCAGAGGAAG AGGAGGATGG TGCTGAGGAA    1320

CCCACCGCCT CTGGAGGTAA GAGTACCCAC CCTATGGTGA CTAGAAGCAA GGCTGACCAG    1380

TAA                                                                 1383

(2) INFORMATION FOR SEQ ID NO:59:

(i) SEQUENCE CHARACTERISTICS:
        (A) LENGTH: 2739 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

CTGCAGGTCG ACGGATCTGA GAATGGATGA TTCTCCAGCC GAAACATATT CTACCATGGC     60

TCCGTTTAAT TTGTTGATGA AGATGGATTC ATCCTTAAAT GTTTTCTCTG TAATAGTTTC    120

CACCGAAAGA CTATGCAAAG AATTTGGAAT GCGTTCCTTG TGCTTAATGT TTCCATAGAC    180

GGCTTCTAGA AGTTGATACA ACATAGGACT AGCCGCGGTA ACTTTTATTT TTAGAAAGTA    240

TCCATCGCTT CTATCTTGTT TAGATTTATT TTTATAAAGT TTAGTCTCTC CTTCCAACAT    300

AATAAAAGTG GAAGTCATTT GACTAGATAA ACTATCAGTA AGTTTTATAG AGATAGACGA    360

ACAATTAGCG TATTGAGAAG CATTTAGTGT AACGTATTCG ATACATTTTG CATTAGATTT    420

ACTAATCGAT TTTGCATACT CTATAACACC CGCACAAGTC TGTAGAGAAT CGCTAGATGC    480

AGTAGGTCTT GGTGAAGTTT CAACTCTCTT CTTGATTACC TTACTCATGA TTAAACCTAA    540

ATAATTGTAC TTTGTAATAT AATGATATAT ATTTTCACTT TATCTCATTT GAGAATAAAA    600

AGATCACAAA AATTAACTAA TCAGGATCCT TCTTTATTCT ATACTTAAAA AGTGAAAATA    660
```

```
AATACAAAGG TTCTTGAGGG TTGTGTTAAA TTGAAAGCGA GAAATAATCA TAAATTATTT      720

CATTATCGCG ATATCCGTTA AGTTTGTATC GTAATGACGA CGTTCCTGCA GACTATGTTG      780

AGGAAGGAGG TTAACAGTCA GCTGAGTCTG GGAGACCCGC TGTTTCCAGA GTTGGCCGAA      840

GAATCCCTCA AAACTTTTGA ACAAGTGACC GAGGATTGCA ACGAGAACCC CGAGAAAGAT      900

GTCCTGGCAG AACTCGTCAA ACAGATTAAG GTTCGAGTGG ACATGGTGCG GCATAGAATC      960

AAGGAGCACA TGCTGAAAAA ATATACCCAG ACGGAAGAGA AATTCACTGG CGCCTTTAAT     1020

ATGATGGGAG GATGTTTGCA GAATGCCTTA GATATCTTAG ATAAGGTTCA TGAGCCTTTC     1080

GAGGAGATGA AGTGTATTGG GCTAACTATG CAGAGCATGT ATGAGAACTA CATTGTACCT     1140

GAGGATAAGC GGGAGATGTG GATGGCTTGT ATTAAGGAGC TGCATGATGT GAGCAAGGGC     1200

GCCGCTAACA AGTTGGGGGG TGCACTGCAG GCTAAGGCCC GTGCTAAAAA GGATGAACTT     1260

AGGAGAAAGA TGATGTATAT GTGCTACAGG AATATAGAGT TCTTTACCAA GAACTCAGCC     1320

TTCCCTAAGA CCACCAATGG CTGCAGTCAG GCCATGGCGG CACTGCAGAA CTTGCCTCAG     1380

TGCTCCCCTG ATGAGATTAT GGCTTATGCC CAGAAAATAT TTAAGATTTT GGATGAGGAG     1440

AGAGACAAGG TGCTCACGCA CATTGATCAC ATATTTATGG ATATCCTCAC TACATGTGTG     1500

GAAACAATGT GTAATGAGTA CAAGGTCACT AGTGACGCTT GATGATGAC CATGTACGGG      1560

GGCATCTCTC TCTTAAGTGA GTTCTGTCGG GTGCTGTGCT GCTATGTCTT AGAGGAGACT     1620

AGTGTGATGC TGGCCAAGCG GCCTCTGATA ACCAAGCCTG AGGTTATCAG TGTAATGAAG     1680

CGCCGCATTG AGGAGATCTG CATGAAGGTC TTTGCCCAGT ACATTCTGGG GGCCGATCCT     1740

CTGAGAGTCT GCTCTCCTAG TGTGGATGAC CTACGGGCCA TCGCCAGGA GTCAGATGAG      1800

GAAGAGGCTA TTGTAGCCTA CACTTTGGCC ACCGCTGGTG TCAGCTCCTC TGATTCTCTG     1860

GTGTCACCCC CAGAGTCCCC TGTACCCGCG ACTATCCCTC TGTCCTCAGT AATTGTGGCT     1920

GAGAACAGTG ATCAGGAAGA AAGTGAGCAG AGTGATGAGG AAGAGGAGGA GGGTGCTCAG     1980

GAGGAGCGGG AGGACACTGT GTCTGTCAAG TCTGAGCCAG TGTCTGAGAT AGAGGAAGTT     2040

GCCCCAGAGG AAGAGGAGGA TGGTGCTGAG GAACCCACCG CCTCTGGAGG TAAGAGTACC     2100

CACCCTATGG TGACTAGAAG CAAGGCTGAC CAGTAATTTT TATCTCGAGC CCGGGAGATC     2160

TTAGCTAACT GATTTTTCTG GGAAAAAAAT TATTTAACTT TTCATTAATA GGGATTTGAC     2220

GTATGTAGCG TACAAAATTA TCGTTCCTGG TATATAGATA AAGAGTCCTA TATATTTGAA     2280

AATCGTTACG GCTCGATTAA ACTTTAATGA TTGCATAGTG AATATATCAT TAGGATTTAA     2340

CTCCTTGACT ATCATGGCGG CGCCAGAAAT TACCATCAAA AGCATTAATA CAGTTATGCC     2400

GATCGCAGTT AGAACGGTTA TAGCATCCAC CATTTATATC TAAAAATTAG ATCAAAGAAT     2460

ATGTGACAAA GTCCTAGTTG TATACTGAGA ATTGACGAAA CAATGTTTCT TACATATTTT     2520

TTTCTTATTA GTAACTGACT TAATAGTAGG AACTGGAAAG CTAGACTTGA TTATTCTATA     2580

AGTATAGATA CCCTTCCAGA TAATGTTCTC TTTGATAAAA GTTCCAGAAA ATGTAGAATT     2640

TTTTAAAAAG TTATCTTTTG CTATTACCAA GATTGTGTTT AGACGCTTAT TATTAATATG     2700

AGTAATGAAA TCCACACCGC CTCTAGATAT GGGGAATTC                            2739
```

(2) INFORMATION FOR SEQ ID NO:60:

(i) SEQUENCE CHARACTERISTICS:
        (A) LENGTH: 3622 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

| | | | | | |
|---|---|---|---|---|---|
| GAATTGCGGC | CGCTGAATGT | TAAATGTTAT | ACTTTGGATG | AAGCTATAAA | TATGCATTGG | 60 |
| AAAAATAATC | CATTTAAAGA | AAGGATTCAA | ATACTACAAA | ACCTAAGCGA | TAATATGTTA | 120 |
| ACTAAGCTTA | TTCTTAACGA | CGCTTTAAAT | ATACACAAAT | AAACATAATT | TTTGTATAAC | 180 |
| CTAACAAATA | ACTAAAACAT | AAAAATAATA | AAAGGAAATG | TAATATCGTA | ATTATTTTAC | 240 |
| TCAGGAATGG | GGTTAAATAT | TTATATCACG | TGTATATCTA | TACTGTTATC | GTATACTCTT | 300 |
| TACAATTACT | ATTACGAATA | TGCAAGAGAT | AATAAGATTA | CGTATTTAAG | AGAATCTTGT | 360 |
| CATGATAATT | GGGTACGACA | TAGTGATAAA | TGCTATTTCG | CATCGTTACA | TAAAGTCAGT | 420 |
| TGGAAAGATG | GATTTGACAG | ATGTAACTTA | ATAGGTGCAA | AAATGTTAAA | TAACAGCATT | 480 |
| CTATCGGAAG | ATAGGATACC | AGTTATATTA | TACAAAAATC | ACTGGTTGGA | TAAAACAGAT | 540 |
| TCTGCAATAT | TCGTAAAAGA | TGAAGATTAC | TGCGAATTTG | TAAACTATGA | CAATAAAAAG | 600 |
| CCATTTATCT | CAACGACATC | GTGTAATTCT | TCCATGTTTT | ATGTATGTGT | TTCAGATATT | 660 |
| ATGAGATTAC | TATAAACTTT | TTGTATACTT | ATATTCCGTA | AACTATATTA | ATCATGAAGA | 720 |
| AAATGAAAAA | GTATAGAAGC | TGTTCACGAG | CGGTTGTTGA | AAACAACAAA | ATTATACATT | 780 |
| CAAGATGGCT | TACATATACG | TCTGTGAGGC | TATCATGGAT | AATGACAATG | CATCTCTAAA | 840 |
| TAGGTTTTTG | GACAATGGAT | TCGACCCTAA | CACGGAATAT | GGTACTCTAC | AATCTCCTCT | 900 |
| TGAAATGGCT | GTAATGTTCA | AGAATACCGA | GGCTATAAAA | ATCTTGATGA | GGTATGGAGC | 960 |
| TAAACCTGTA | GTTACTGAAT | GCACAACTTC | TTGTCTGCAT | GATGCGGTGT | TGAGAGACGA | 1020 |
| CTACAAAATA | GTGAAAGATC | TGTTGAAGAA | TAACTATGTA | AACAATGTTC | TTTACAGCGG | 1080 |
| AGGCTTTACT | CCTTTGTGTT | TGGCAGCTTA | CCTTAACAAA | GTTAATTTGG | TTAAACTTCT | 1140 |
| ATTGGCTCAT | TCGGCGGATG | TAGATATTTC | AAACACGGAT | CGGTTAACTC | CTCTACATAT | 1200 |
| AGCCGTATCA | ATAAAAATT | TAACAATGGT | TAAACTTCTA | TTGAACAAAG | GTGCTGATAC | 1260 |
| TGACTTGCTG | GATAACATGG | GACGTACTCC | TTTAATGATC | GCTGTACAAT | CTGGAAATAT | 1320 |
| TGAAATATGT | AGCACACTAC | TTAAAAAAAA | TAAAATGTCC | AGAACTGGGA | AAAATTGATC | 1380 |
| TTGCCAGCTG | TAATTCATGG | TAGAAAAGAA | GTGCTCAGGC | TACTTTTCAA | CAAAGGAGCA | 1440 |
| GATGTAAACT | ACATCTTTGA | AAGAAATGGA | AAATCATATA | CTGTTTTGGA | ATTGATTAAA | 1500 |
| GAAAGTTACT | CTGAGACACA | AAAGAGGTAG | CTGAAGTGGT | ACTCTCAAAG | GTACGTGACT | 1560 |
| AATTAGCTAT | AAAAAGGATC | CGGGTTAATT | AATTAGTCAT | CAGGCAGGGC | GAGAACGAGA | 1620 |
| CTATCTGCTC | GTTAATTAAT | TAGAGCTTCT | TTATTCTATA | CTTAAAAAGT | GAAAATAAAT | 1680 |
| ACAAAGGTTC | TTGAGGGTTG | TGTTAAATTG | AAAGCGAGAA | ATAATCATAA | ATTATTTCAT | 1740 |
| TATCGCGATA | TCCGTTAAGT | TTGTATCGTA | ATGACGACGT | TCCTGCAGAC | TATGTTGAGG | 1800 |
| AAGGAGGTTA | ACAGTCAGCT | GAGTCTGGGA | GACCCGCTGT | TTCCAGAGTT | GGCCGAAGAA | 1860 |
| TCCCTCAAAA | CTTTTGAACA | AGTGACCGAG | GATTGCAACG | AGAACCCCGA | GAAAGATGTC | 1920 |
| CTGGCAGAAC | TCGTCAAACA | GATTAAGGTT | CGAGTGGACA | TGGTGCGGCA | TAGAATCAAG | 1980 |
| GAGCACATGC | TGAAAAAATA | TACCCAGACG | GAAGAGAAAT | TCACTGGCGC | CTTTAATATG | 2040 |
| ATGGGAGGAT | GTTTGCAGAA | TGCCTTAGAT | ATCTTAGATA | AGGTTCATGA | GCCTTTCGAG | 2100 |
| GAGATGAAGT | GTATTGGGCT | AACTATGCAG | AGCATGTATG | AGAACTACAT | TGTACCTGAG | 2160 |
| GATAAGCGGG | AGATGTGGAT | GGCTTGTATT | AAGGAGCTGC | ATGATGTGAG | CAAGGGCGCC | 2220 |
| GCTAACAAGT | TGGGGGGTGC | ACTGCAGGCT | AAGGCCCGTG | CTAAAAAGGA | TGAACTTAGG | 2280 |

-continued

```
AGAAAGATGA TGTATATGTG CTACAGGAAT ATAGAGTTCT TTACCAAGAA CTCAGCCTTC      2340

CCTAAGACCA CCAATGGCTG CAGTCAGGCC ATGGCGGCAC TGCAGAACTT GCCTCAGTGC      2400

TCCCCTGATG AGATTATGGC TTATGCCCAG AAAATATTTA AGATTTTGGA TGAGGAGAGA      2460

GACAAGGTGC TCACGCACAT TGATCACATA TTTATGGATA TCCTCACTAC ATGTGTGGAA      2520

ACAATGTGTA ATGAGTACAA GGTCACTAGT GACGCTTGTA TGATGACCAT GTACGGGGGC      2580

ATCTCTCTCT TAAGTGAGTT CTGTCGGGTG CTGTGCTGCT ATGTCTTAGA GGAGACTAGT      2640

GTGATGCTGG CCAAGCGGCC TCTGATAACC AAGCCTGAGG TTATCAGTGT AATGAAGCGC      2700

CGCATTGAGG AGATCTGCAT GAAGGTCTTT GCCCAGTACA TTCTGGGGGC CGATCCTCTG      2760

AGAGTCTGCT CTCCTAGTGT GGATGACCTA CGGGCCATCG CCGAGGAGTC AGATGAGGAA      2820

GAGGCTATTG TAGCCTACAC TTTGGCCACC GCTGGTGTCA GCTCCTCTGA TTCTCTGGTG      2880

TCACCCCCAG AGTCCCCTGT ACCCGCGACT ATCCCTCTGT CCTCAGTAAT TGTGGCTGAG      2940

AACAGTGATC AGGAAGAAAG TGAGCAGAGT GATGAGGAAG AGGAGGAGGG TGCTCAGGAG      3000

GAGCGGGAGG ACACTGTGTC TGTCAAGTCT GAGCCAGTGT CTGAGATAGA GGAAGTTGCC      3060

CCAGAGGAAG AGGAGGATGG TGCTGAGGAA CCCACCGCCT CTGGAGGTAA GAGTACCCAC      3120

CCTATGGTGA CTAGAAGCAA GGCTGACCAG TAATTTTTAT CTCGAGTCTA GAATCGATCC      3180

CGGGTTTTTA TGACTAGTTA ATCACGGCCG CTTATAAAGA TCTAAAATGC ATAATTTCTA      3240

AATAATGAAA AAAAGTACA TCATGAGCAA CGCGTTAGTA TATTTTACAA TGGAGATTAA      3300

CGCTCTATAC CGTTCTATGT TTATTGATTC AGATGATGTT TTAGAAAAGA AAGTTATTGA      3360

ATATGAAAAC TTTAATGAAG ATGAAGATGA CGACGATGAT TATTGTTGTA AATCTGTTTT      3420

AGATGAAGAA GATGACGCGC TAAAGTATAC TATGGTTACA AAGTATAAGT CTATACTACT      3480

AATGGCGACT TGTGCAAGAA GGTATAGTAT AGTGAAAATG TTGTTAGATT ATGATTATGA      3540

AAAACCAAAT AAATCAGATC CATATCTAAA GGTATCTCCT TTGCACATAA TTTCATCTAT      3600

TCCTAGTTTA GAATACCTGC AG                                               3622
```

(2) INFORMATION FOR SEQ ID NO:61:

(i) SEQUENCE CHARACTERISTICS:
        (A) LENGTH: 1686 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
ATGGAGTCGC GCGGTCGCCG TTGTCCCGAA ATGATATCCG TACTGGGTCC CATTTCGGGG        60

CACGTGCTGA AAGCCGTGTT TAGTCGCGGC GACACGCCGG TGCTGCCGCA CGAGACGCGA       120

CTCCTGCAGA CGGGTATCCA CGTGCGCGTG AGCCAGCCCT CGCTGATCCT GGTGTCGCAG       180

TACACGCCCG ACTCGACGCC ATGCCACCGC GGCGACAATC AGCTGCAGGT GCAGCACACG       240

TACTTTACGG GCAGCGAGGT GGAGAACGTG TCGGTCAACG TGCACAACCC CACGGGCCGG       300

AGCATCTGCC CCAGCCAAGA GCCCATGTCG ATCTATGTGT ACGCGCTGCC GCTCAAGATG       360

CTGAACATCC CCAGCATCAA CGTGCACCAC TACCCGTCGG CGGCCGAGCG CAAACACCGA       420

CACCTGCCCG TAGCTGACGC TGTGATTCAC GCGTCGGGCA AGCAGATGTG GCAGGCGCGT       480

CTCACGGTCT CGGGACTGGC CTGGACGCGT CAGCAGAACC AGTGGAAAGA GCCCGACGTC       540

TACTACACGT CAGCGTTCGT GTTTCCCACC AAGGACGTGG CACTGCGGCA CGTGGTGTGC       600
```

-continued

```
GCGCACGAGC TGGTTTGCTC CATGGAGAAC ACGCGCGCAA CCAAGATGCA GGTGATAGGT    660

GACCAGTACG TCAAGGTGTA CCTGGAGTCC TTCTGCGAGG ACGTGCCCTC CGGCAAGCTC    720

TTTATGCACG TCACGCTGGG CTCTGACGTG GAAGAGGACC TGACGATGAC CCGCAACCCG    780

CAACCCTTCA TGCGCCCCCA CGAGCGCAAC GGCTTTACGG TGTTGTGTCC CAAAAATATG    840

ATAATCAAAC CGGGCAAGAT CTCGCACATC ATGCTGGATG TGGCTTTTAC CTCACACGAG    900

CATTTTGGGC TGCTGTGTCC CAAGAGCATC CCGGGCCTGA GCATCTCAGG TAACCTATTG    960

ATGAACGGGC AGCAGATCTT CCTGGAGGTG CAAGCGATAC GCGAGACCGT GGAACTGCGT   1020

CAGTACGATC CCGTGGCTGC GCTCTTCTTT TTCGATATCG ACTTGCTGCT GCAGCGCGGG   1080

CCTCAGTACA GCGAACACCC CACCTTCACC AGCCAGTATC GCATCCAGGG CAAGCTTGAG   1140

TACCGACACA CCTGGGACCG GCACGACGAG GGTGCCGCCC AGGGCGACGA CGACGTCTGG   1200

ACCAGCGGAT CGGACTCCGA CGAGGAACTC GTAACCACCG AGCGCAAGAC GCCCCGCGTT   1260

ACCGGCGGCG GCGCCATGGC GGGCGCCTCC ACTTCCGCGG GCCGCAAACG CAAATCAGCA   1320

TCCTCGGCGA CGGCGTGCAC GGCGGGCGTT ATGACACGCG GCCGCCTTAA GGCCGAGTCC   1380

ACCGTCGCGC CCGAAGAGGA CACCGACGAG GATTCCGACA ACGAAATCCA CAATCCGGCC   1440

GTGTTCACCT GGCCGCCCTG GCAGGCCGGC ATCCTGGCCC GCAACCTGGT GCCCATGGTG   1500

GCTACGGTTC AGGGTCAGAA TCTGAAGTAC CAGGAGTTCT CTGGGACGC CAACGACATC    1560

TACCGCATCT TCGCCGAATT GGAAGGCGTA TGGCAGCCCG CTGCGCAACC CAAACGTCGC   1620

CGCCACCGGC AAGACGCCTT GCCCGGGCCA TGCATCGCCT CGACGCCCAA AAAGCACCGA   1680

GGTTGA                                                              1686
```

(2) INFORMATION FOR SEQ ID NO:62:

(i) SEQUENCE CHARACTERISTICS:
        (A) LENGTH: 2745 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
GTCGACGATT GTTCATGATG GCAAGATTTA TATATCTGGA GGTTACAACA ATAGTAGTGT     60

AGTTAATGTA ATATCGAATC TAGTCCTTAG CTATAATCCG ATATATGATG AATGGACCAA    120

ATTATCATCA TTAAACATTC CTAGAATTAA TCCCGCTCTA TGGTCAGCGC ATAATAAATT    180

ATATGTAGGA GGAGGAATAT CTGATGATGT TCGAACTAAT ACATCTGAAA CATACGATAA    240

AGAAAAAGAT TGTTGGACAT TGGATAATGG TCACGTGTTA CCACGCAATT ATATAATGTA    300

TAAATGCGAA CCGATTAAAC ATAAATATCC ATTGGAAAAA ACACAGTACA CGAATGATTT    360

TCTAAAGTAT TTGGAAAGTT TTATAGGTAG TTGATAGAAC AAAATACATA ATTTTGTAAA    420

AATAAATCAC TTTTTATACT AATATTTAAT TAATTAAGCT TGGTACCCTC GAAGCTTCTT    480

TATTCTATAC TTAAAAAGTG AAAATAAATA CAAAGGTTCT TGAGGGTTGT GTTAAATTGA    540

AAGCGAGAAA TAATCATAAA TTATTTCATT ATCGCGATAT CCGTTAAGTT TGTATCGTAA    600

TGGAGTCGCG CGGTCGCCGT TGTCCCGAAA TGATATCCGT ACTGGGTCCC ATTTCGGGGC    660

ACGTGCTGAA AGCCGTGTTT AGTCGCGGCA CACGCCGGT GCTGCCGCAC GAGACGCGAC     720

TCCTGCAGAC GGGTATCCAC GTGCGCGTGA GCCAGCCCTC GCTGATCCTG GTGTCGCAGT    780

ACACGCCCGA CTCGACGCCA TGCCACCGCG GCGACAATCA GCTGCAGGTG CAGCACACGT    840
```

```
ACTTTACGGG CAGCGAGGTG GAGAACGTGT CGGTCAACGT GCACAACCCC ACGGGCCGGA      900
GCATCTGCCC CAGCCAAGAG CCCATGTCGA TCTATGTGTA CGCGCTGCCG CTCAAGATGC      960
TGAACATCCC CAGCATCAAC GTGCACCACT ACCCGTCGGC GGCCGAGCGC AAACACCGAC     1020
ACCTGCCCGT AGCTGACGCT GTGATTCACG CGTCGGGCAA GCAGATGTGG CAGGCGCGTC     1080
TCACGGTCTC GGGACTGGCC TGGACGCGTC AGCAGAACCA GTGGAAAGAG CCCGACGTCT     1140
ACTACACGTC AGCGTTCGTG TTTCCCACCA AGGACGTGGC ACTGCGGCAC GTGGTGTGCG     1200
CGCACGAGCT GGTTTGCTCC ATGGAGAACA CGCGCGCAAC CAAGATGCAG GTGATAGGTG     1260
ACCAGTACGT CAAGGTGTAC CTGGAGTCCT TCTGCGAGGA CGTGCCCTCC GGCAAGCTCT     1320
TTATGCACGT CACGCTGGGC TCTGACGTGG AAGAGGACCT GACGATGACC CGCAACCCGC     1380
AACCCTTCAT GCGCCCCCAC GAGCGCAACG GCTTTACGGT GTTGTGTCCC AAAAATATGA     1440
TAATCAAACC GGGCAAGATC TCGCACATCA TGCTGGATGT GGCTTTTACC TCACACGAGC     1500
ATTTTGGGCT GCTGTGTCCC AAGAGCATCC CGGGCCTGAG CATCTCAGGT AACCTATTGA     1560
TGAACGGGCA GCAGATCTTC CTGGAGGTGC AAGCGATACG CGAGACCGTG GAACTGCGTC     1620
AGTACGATCC CGTGGCTGCG CTCTTCTTTT TCGATATCGA CTTGCTGCTG CAGCGCGGGC     1680
CTCAGTACAG CGAACACCCC ACCTTCACCA GCCAGTATCG CATCCAGGGC AAGCTTGAGT     1740
ACCGACACAC CTGGGACCGG CACGACGAGG GTGCCGCCCA GGGCGACGAC GACGTCTGGA     1800
CCAGCGGATC GGACTCCGAC GAGGAACTCG TAACCACCGA GCGCAAGACG CCCCGCGTTA     1860
CCGGCGGCGG CGCCATGGCG GGCGCCTCCA CTTCCGCGGG CCGCAAACGC AAATCAGCAT     1920
CCTCGGCGAC GGCGTGCACG GCGGGCGTTA TGACACGCGG CCGCCTTAAG GCCGAGTCCA     1980
CCGTCGCGCC CGAAGAGGAC ACCGACGAGG ATTCCGACAA CGAAATCCAC AATCCGGCCG     2040
TGTTCACCTG GCCGCCCTGG CAGGCCGGCA TCCTGGCCCG CAACCTGGTG CCCATGGTGG     2100
CTACGGTTCA GGGTCAGAAT CTGAAGTACC AGGAGTTCTT CTGGGACGCC AACGACATCT     2160
ACCGCATCTT CGCCGAATTG GAAGGCGTAT GGCAGCCCGC TGCGCAACCC AAACGTCGCC     2220
GCCACCGGCA AGACGCCTTG CCCGGGCCAT GCATCGCCTC GACGCCCAAA AAGCACCGAG     2280
GTTGATTTTT ATGGATCCCC CGGGTAGCTA GCTAATTTTT CTTTTACGTA TTATATATGT     2340
AATAAACGTT CACGTAAATA CAAAACAGAG AACAAAGTCT AGATTTTTGA CTTACATAAA     2400
TGTCTGGGAT AGTAAAATCT ATCATATTGA GCGGACCATC TGGTTCAGGA AAGACAGCCA     2460
TAGCCAAAAG ACTATGGGAA TATATTTGGA TTTGTGGTGT CCCATACCAC TAGATTTCCT     2520
CGTCCTATGG AACGAGAAGG TGTCGATTAC CATTACGTTA ACAGAGAGGC CATCTGGAAG     2580
GGAATAGCCG CCGGAAACTT TCTAGAACAT ACTGAGTTTT TAGGAAATAT TTACGGAACT     2640
TCTAAAACTG CTGTGAATAC AGCGGCTATT AATAATCGTA TTTGTGTGAT GGATTTAAAC     2700
ATCGACGGTG TTAGAAGTTT TAAAAATACT TACCTGCAGA AGCTT                     2745
```

(2) INFORMATION FOR SEQ ID NO:63:

(i) SEQUENCE CHARACTERISTICS:
        (A) LENGTH: 3706 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
AAGCTTCTAT CAAAGTCTT AATGAGTTAG GTGTAGATAG TATAGATATT ACTACAAAGG       60
```

| | |
|---|---|
| TATTCATATT TCCTATCAAT TCTAAAGTAG ATGATATTAA TAACTCAAAG ATGATGATAG | 120 |
| TAGATAATAG ATACGCTCAT ATAATGACTG CAAATTTGGA CGGTTCACAT TTTAATCATC | 180 |
| ACGCGTTCAT AAGTTTCAAC TGCATAGATC AAAATCTCAC TAAAAAGATA GCCGATGTAT | 240 |
| TTGAGAGAGA TTGGACATCT AACTACGCTA AAGAAATTAC AGTTATAAAT AATACATAAT | 300 |
| GGATTTTGTT ATCATCAGTT ATATTAACA TAAGTACAAT AAAAAGTATT AAATAAAAAT | 360 |
| ACTTACTTAC GAAAAAATGT CATTATTACA AAAACTATAT TTTACAGAAC AATCTATAGT | 420 |
| AGAGTCCTTT AAGAGTTATA ATTTAAAAGA TAACCATAAT GTAATATTTA CCACATCAGA | 480 |
| TGTTGATACT GTTGTAGTAA TAAATGAAGA TAATGTACTG TTATCTACAA GATTATTATC | 540 |
| ATTTGATAAA ATTCTGTTTT TTAACTCCTT TAATAACGGT TTATCAAAAT ACGAAACTAT | 600 |
| TAGTGATACA ATATTAGATA TAGATACTCA TAATTATTAT ATACCTAGTT CTTCTTCTTT | 660 |
| GTTAGATATT CTAAAAAAAA GAGCGTGTGA TTTAGAATTA GAAGATCTAA ATTATGCGTT | 720 |
| AATAGGAGAC AATAGTAACT TATATTATAA AGATATGACT TACATGAATA ATTGGTTATT | 780 |
| TACTAAAGGA TTATTAGATT ACAAGTTTGT ATTATTGCGC GATGTAGATA AATGTTACAA | 840 |
| ACAGTATAAT AAAAAGAATA CTATAATAGA TATAATACAT CGCGATAACA GACAGTATAA | 900 |
| CATATGGGTT AAAAATGTTA TAGAATACTG TTCTCCTGGC TATATATTAT GGTTACATGA | 960 |
| TCTAAAAGCC GCTGCTGAAG ATGATTGGTT AAGATACGAT AACCGTATAA ACGAATTATC | 1020 |
| TGCGGATAAA TTATACACTT TCGAGTTCAT AGTTATATTA GAAAATAATA TAAAACATTT | 1080 |
| ACGAGTAGGT ACAATAATTG TACATCCAAA CAAGATAATA GCTAATGGTA CATCTAATAA | 1140 |
| TATACTTACT GATTTCTAT CTTACGTAGA AGAACTAATA TATCATCATA ATTCATCTAT | 1200 |
| AATATTGGCC GGATATTTTT TAGAATTCTT TGAGACCACT ATTTTATCAG AATTTATTTC | 1260 |
| TTCATCTTCT GAATGGGTAA TGAATAGTAA CTGTTTAGTA CACCTGAAAA CAGGGTATGA | 1320 |
| AGCTATACTC TTTGATGCTA GTTTATTTTT CCAACTCTCT ACTAAAAGCA ATTATGTAAA | 1380 |
| ATATTGGACA AAGAAAACTT TGCAGTATAA GAACTTTTTT AAAGACGGTA ACAGTTAGC | 1440 |
| AAAATATATA ATTAAGAAAG ATAGTCAGGT GATAGATAGA GTATGTTATT TACACGCAGC | 1500 |
| TGTATATAAT CACGTAACTT ACTTAATGGA TACGTTAAAA ATTCCTGGTT TTGATTTTAA | 1560 |
| ATTCTCCGGA ATGATAGATA TACTACTGTT TGGAATATTG CATAAGGATA ATGAGAATAT | 1620 |
| ATTTTATCCG AAACGTGTTT CTGTAACTAA TATAATATCA GAATCTATCT ATGCAGATTT | 1680 |
| TTACTTTATA TCAGATGTTA ATAAATTCAG TAAAAAGATA GAATATAAAA CTATGTTTCC | 1740 |
| TATACTCGCA GAAAACTACT ATCCAAAAGG AAGGCCCTAT TTTACACATA CATCTAACGA | 1800 |
| AGATCTTCTG TCTATCTGTT TATGCGAAGT AACAGTTTGT AAAGATATAA AAAATCCATT | 1860 |
| ATTATATTCT AAAAAGGATA TATCAGCAAA ACGATTCATA GGTTTATTTA CATCTGTCGA | 1920 |
| TATAAATACG GCTGTTGAGT TAAGAGGATA TAAAATAAGA GTAATAGGAT GTTTAGAATG | 1980 |
| GCCTGAAAAG ATAAAAATAT TTAATTCTAA TCCTACATAC ATTAGATTAT TACTAACAGA | 2040 |
| AAGACGTTTA GATATTCTAC ATTCCTATCT GCTTAAATTT AATATAACAG AGGATATAGC | 2100 |
| TACCAGAGAT GGAGTCAGAA ATAATTTACC TATAATTTCT TTTATCGTCA GTTATTGTAG | 2160 |
| ATCGTATACT TATAAATTAC TAAATTGCCA TATGTACAAT TCGTGTAAGA TAACAAAGTG | 2220 |
| TAAATATAAT CAGGTAATAT ATAATCCTAT ATAGGAGTAT ATATAATTGA AAAAGTAAAA | 2280 |
| ATAAATCATA TAATAATGAA ACGAAATATC AGTAATAGAC AGGAACTGGC AGATTCTTCT | 2340 |
| TCTAATGAAG TAAGTACTGC TAAATCTCCA AAATTAGATA AAAATGATAC AGCAAATACA | 2400 |

```
GCTTCATTCA ACGAATTACC TTTTAATTTT TTCAGACACA CCTTATTACA AACTAACTAA      2460

GTCAGATGAT GAGAAAGTAA ATATAAATTT AACTTATGGG TATAATATAA TAAAGATTCA      2520

TGATATTAAT AATTTACTTA ACGATGTTAA TAGACTTATT CCATCAACCC CTTCAAACCT      2580

TTCTGGATAT TATAAAATAC CAGTTAATGA TATTAAAATA GATTGTTTAA GAGATGTAAA      2640

TAATTATTTG GAGGTAAAGG ATATAAAATT AGTCTATCTT TCACATGGAA ATGAATTACC      2700

TAATATTAAT AATTATGATA GGAATTTTTT AGGATTTACA GCTGTTATAT GTATCAACAA      2760

TACAGGCAGA TCTATGGTTA TGGTAAAACA CTGTAACGGG AAGCAGCATT CTATGGTAAC      2820

TGGCCTATGT TTAATAGCCA GATCATTTTA CTCTATAAAC ATTTTACCAC AAATAATAGG      2880

ATCCTCTAGA TATTTAATAT TATATCTAAC AACAACAAAA AAATTTAACG ATGTATGGCC      2940

AGAAGTATTT TCTACTAATA AAGATAAAGA TAGTCTATCT TATCTACAAG ATATGAAAGA      3000

AGATAATCAT TTAGTAGTAG CTACTAATAT GGAAAGAAAT GTATACAAAA ACGTGGAAGC      3060

TTTTATATTA AATAGCATAT TACTAGAAGA TTTAAAATCT AGACTTAGTA TAACAAAACA      3120

GTTAAATGCC AATATCGATT CTATATTTCA TCATAACAGT AGTACATTAA TCAGTGATAT      3180

ACTGAAACGA TCTACAGACT CAACTATGCA AGGAATAAGC AATATGCCAA TTATGTCTAA      3240

TATTTTAACT TTAGAACTAA AACGATTCTA CCAATACTAA AAATAGGATA CGTGATAGGC      3300

TGTTAAAAGC TGCAATAAAT AGTAAGGATG TAGAAGAAAT ACTTTGTTCT ATACCTTCGG      3360

AGGAAAGAAC TTTAGAACAA CTTAAGTTTA ATCAAACTTG TATTTATGAA CACTATAAAA      3420

AAATTATGGA AGATACAAGT AAAAGAATGG ATGTTGAATG TCGTAGTTTA GAACATAACT      3480

ATACGGCTAA CTTATATAAA GTGTACGGAC AAAACGAATA TATGATTACT TATATACTAG      3540

CTCTCATAAG TAGGATTAAT AATATTATAG AAACTTTAAA ATATAATCTG GTGGGGCTAG      3600

ACGAATCTAC AATACGTAAT ATAAATTATA TAATTTCACA AGAACAAAA AAAAATCAGT      3660

TTCTAATACC TTATAGATAA ACTATATTTT TTACCACTGA CAACAC                    3706

(2) INFORMATION FOR SEQ ID NO:64:

(i) SEQUENCE CHARACTERISTICS:
        (A) LENGTH: 3521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GAGCTCGCGG CCGCCTATCA AAAGTCTTAA TGAGTTAGGT GTAGATAGTA TAGATATTAC        60

TACAAAGGTA TTCATATTTC CTATCAATTC TAAAGTAGAT GATATTAATA ACTCAAAGAT       120

GATGATAGTA GATAATAGAT ACGCTCATAT AATGACTGCA AATTTGGACG GTTCACATTT       180

TAATCATCAC GCGTTCATAA GTTTCAACTG CATAGATCAA AATCTCACTA AAAGATAGC        240

CGATGTATTT GAGAGAGATT GGACATCTAA CTACGCTAAA GAAATTACAG TTATAAATAA       300

TACATAATGG ATTTTGTTAT CATCAGTTAT ATTTAACATA AGTACAATAA AAGTATTAA        360

ATAAAAATAC TTACTTACGA AAAAATGACT AATTAGCTAT AAAAACCCAA CAAAAACTAA       420

TCAGCTATCG GGGTTAATTA ATTAGTTATT AGACAAGGTG AAAACGAAAC TATTTGTAGC       480

TTAATTAATT AGAGCTTCTT TATTCTATAC TTAAAAAGTG AAAATAAATA CAAAGGTTCT       540

TGAGGGTTGT GTTAAATTGA AAGCGAGAAA TAATCATAAA TTATTTCATT ATCGCGATAT       600

CCGTTAAGTT TGTATCGTAA TGGAGTCGCG CGGTCGCCGT TGTCCCGAAA TGATATCCGT       660
```

-continued

| | |
|---|---|
| ACTGGGTCCC ATTTCGGGGC ACGTGCTGAA AGCCGTGTTT AGTCGCGGCG ACACGCCGGT | 720 |
| GCTGCCGCAC GAGACGCGAC TCCTGCAGAC GGGTATCCAC GTGCGCGTGA GCCAGCCCTC | 780 |
| GCTGATCCTG GTGTCGCAGT ACACGCCCGA CTCGACGCCA TGCCACCGCG GCGACAATCA | 840 |
| GCTGCAGGTG CAGCACACGT ACTTTACGGG CAGCGAGGTG GAGAACGTGT CGGTCAACGT | 900 |
| GCACAACCCC ACGGGCCGGA GCATCTGCCC CAGCCAAGAG CCCATGTCGA TCTATGTGTA | 960 |
| CGCGCTGCCG CTCAAGATGC TGAACATCCC CAGCATCAAC GTGCACCACT ACCCGTCGGC | 1020 |
| GGCCGAGCGC AAACACCGAC ACCTGCCCGT AGCTGACGCT GTGATTCACG CGTCGGGCAA | 1080 |
| GCAGATGTGG CAGGCGCGTC TCACGGTCTC GGGACTGGCC TGGACGCGTC AGCAGAACCA | 1140 |
| GTGGAAAGAG CCCGACGTCT ACTACACGTC AGCGTTCGTG TTTCCCACCA AGGACGTGGC | 1200 |
| ACTGCGGCAC GTGGTGTGCG CGCACGAGCT GGTTTGCTCC ATGGAGAACA CGCGCGCAAC | 1260 |
| CAAGATGCAG GTGATAGGTG ACCAGTACGT CAAGGTGTAC CTGGAGTCCT TCTGCGAGGA | 1320 |
| CGTGCCCTCC GGCAAGCTCT TTATGCACGT CACGCTGGGC TCTGACGTGG AAGAGGACCT | 1380 |
| GACGATGACC CGCAACCCGC AACCCTTCAT GCGCCCCCAC GAGCGCAACG GCTTTACGGT | 1440 |
| GTTGTGTCCC AAAAATATGA TAATCAAACC GGGCAAGATC TCGCACATCA TGCTGGATGT | 1500 |
| GGCTTTTACC TCACACGAGC ATTTTGGGCT GCTGTGTCCC AAGAGCATCC CGGGCCTGAG | 1560 |
| CATCTCAGGT AACCTATTGA TGAACGGGCA GCAGATCTTC CTGGAGGTGC AAGCGATACG | 1620 |
| CGAGACCGTG GAACTGCGTC AGTACGATCC CGTGGCTGCG CTCTTCTTTT TCGATATCGA | 1680 |
| CTTGCTGCTG CAGCGCGGGC TCAGTACAG CGAACACCCC ACCTTCACCA GCCAGTATCG | 1740 |
| CATCCAGGGC AAGCTTGAGT ACCGACACAC CTGGGACCGG CACGACGAGG GTGCCGCCCA | 1800 |
| GGGCGACGAC GACGTCTGGA CCAGCGGATC GGACTCCGAC GAGGAACTCG TAACCACCGA | 1860 |
| GCGCAAGACG CCCCGCGTTA CCGGCGGCGG CGCCATGGCG GGCGCCTCCA CTTCCGCGGG | 1920 |
| CCGCAAACGC AAATCAGCAT CCTCGGCGAC GGCGTGCACG GCGGGCGTTA TGACACGCGG | 1980 |
| CCGCCTTAAG GCCGAGTCCA CCGTCGCGCC CGAAGAGGAC ACCGACGAGG ATTCCGACAA | 2040 |
| CGAAATCCAC AATCCGGCCG TGTTCACCTG GCCGCCCTGG CAGGCCGGCA TCCTGGCCCG | 2100 |
| CAACCTGGTG CCCATGGTGG CTACGGTTCA GGGTCAGAAT CTGAAGTACC AGGAGTTCTT | 2160 |
| CTGGGACGCC AACGACATCT ACCGCATCTT CGCCGAATTG GAAGGCGTAT GGCAGCCCGC | 2220 |
| TGCGCAACCC AAACGTCGCC GCCACCGGCA AGACGCCTTG CCCGGGCCAT GCATCGCCTC | 2280 |
| GACGCCCAAA AAGCACCGAG GTTGATTTTT ATGGATCCGG TACCCTCGAG GAATTCTTTT | 2340 |
| TATTGATTAA CTAGTCAAAT GAGTATATAT AATTGAAAAA GTAAAATATA AATCATATAA | 2400 |
| TAATGAAACG AAATATCAGT AATAGACAGG AACTGGCAGA TTCTTCTTCT AATGAAGTAA | 2460 |
| GTACTGCTAA ATCTCCAAAA TTAGATAAAA ATGATACAGC AAATACAGCT TCATTCAACG | 2520 |
| AATTACCTTT TAATTTTTTC AGACACACCT TATTACAAAC TAACTAAGTC AGATGATGAG | 2580 |
| AAAGTAAATA TAAATTTAAC TTATGGGTAT AATATAATAA AGATTCATGA TATTAATAAT | 2640 |
| TTACTTAACG ATGTTAATAG ACTTATTCCA TCAACCCCTT CAAACCTTTC TGGATATTAT | 2700 |
| AAAATACCAG TTAATGATAT TAAAATAGAT TGTTTAAGAG ATGTAAATAA TTATTTGGAG | 2760 |
| GTAAAGGATA TAAAATTAGT CTATCTTTCA CATGGAAATG AATTACCTAA TATTAATAAT | 2820 |
| TATGATAGGA ATTTTTTAGG ATTTACAGCT GTTATATGTA TCAACAATAC AGGCAGATCT | 2880 |
| ATGGTTATGG TAAAACACTG TAACGGGAAG CAGCATTCTA TGGTAACTGG CCTATGTTTA | 2940 |
| ATAGCCAGAT CATTTTACTC TATAAACATT TTACCACAAA TAATAGGATC CTCTAGATAT | 3000 |
| TTAATATTAT ATCTAACAAC AACAAAAAAA TTTAACGATG TATGGCCAGA AGTATTTTCT | 3060 |

```
ACTAATAAAG ATAAAGATAG TCTATCTTAT CTACAAGATA TGAAAGAAGA TAATCATTTA    3120

GTAGTAGCTA CTAATATGGA AAGAAATGTA TACAAAAACG TGGAAGCTTT TATATTAAAT    3180

AGCATATTAC TAGAAGATTT AAAATCTAGA CTTAGTATAA CAAAACAGTT AAATGCCAAT    3240

ATCGATTCTA TATTTCATCA TAACAGTAGT ACATTAATCA GTGATATACT GAAACGATCT    3300

ACAGACTCAA CTATGCAAGG AATAAGCAAT ATGCCAATTA TGTCTAATAT TTTAACTTTA    3360

GAACTAAAAC GTTCTACCAA TACTAAAAAT AGGATACGTG ATAGGCTGTT AAAAGCTGCA    3420

ATAAATAGTA AGGATGTAGA AGAAATACTT TGTTCTATAC CTTCGGAGGA AAGAACTTTA    3480

GAACAACTTA AGTTTAATCA AACTTGTATT TATGAAGGTA C                       3521

(2) INFORMATION FOR SEQ ID NO:65:

(i) SEQUENCE CHARACTERISTICS:
        (A) LENGTH: 2160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

AAGACTAATT TGTAAACCAT CTTACTCAAA ATATGTAACA ATAGTACGAT GCAATGAGTA      60

AGACAATAGG AAATCTATCT TATATACACA TAATTATTCT ATCAATTTTA CCAATTAGTT     120

AGTGTAATGT TATAAAAACT AATTAATCAC TCGAGCCCCC TCGAAGCTTC TTTATTCTAT     180

ACTTAAAAAG TGAAAATAAA TACAAAGGTT CTTGAGGGTT GTGTTAAATT GAAAGCGAGA     240

AATAATCATA AATTATTTCA TTATCGCGAT ATCCGTTAAG TTTGTATCGT AATGGAGTCG     300

CGCGGTCGCC GTTGTCCCGA AATGATATCC GTACTGGGTC CCATTTCGGG GCACGTGCTG     360

AAAGCCGTGT TTAGTCGCGG CGACACGCCG GTGCTGCCGC ACGAGACGCG ACTCCTGCAG     420

ACGGGTATCC ACGTGCGCGT GAGCCAGCCC TCGCTGATCC TGGTGTCGCA GTACACGCCC     480

GACTCGACGC CATGCCACCG CGGCGACAAT CAGCTGCAGG TGCAGCACAC GTACTTTACG     540

GGCAGCGAGG TGGAGAACGT GTCGGTCAAC GTGCACAACC CCACGGGCCG GAGCATCTGC     600

CCCAGCCAAG AGCCCATGTC GATCTATGTG TACGCGCTGC CGCTCAAGAT GCTGAACATC     660

CCCAGCATCA ACGTGCACCA CTACCCGTCG GCGGCCGAGC GCAAACACCG ACACCTGCCC     720

GTAGCTGACG CTGTGATTCA CGCGTCGGGC AAGCAGATGT GGCAGGCGCG TCTCACGGTC     780

TCGGGACTGG CCTGGACGCG TCAGCAGAAC CAGTGGAAAG AGCCCGACGT CTACTACACG     840

TCAGCGTTCG TGTTTCCCAC CAAGGACGTG GCACTGCGGC ACGTGGTGTG CGCGCACGAG     900

CTGGTTTGCT CCATGGAGAA CACGCGCGCA ACCAAGATGC AGGTGATAGG TGACCAGTAC     960

GTCAAGGTGT ACCTGGAGTC CTTCTGCGAG GACGTGCCCT CCGGCAAGCT CTTTATGCAC    1020

GTCACGCTGG GCTCTGACGT GGAAGAGGAC CTGACGATGA CCCGCAACCC GCAACCCTTC    1080

ATGCGCCCCC ACGAGCGCAA CGGCTTTACG GTGTTGTGTC CAAAAATAT GATAATCAAA     1140

CCGGGCAAGA TCTCGCACAT CATGCTGGAT GTGGCTTTTA CCTCACACGA GCATTTGGG     1200

CTGCTGTGTC CCAAGAGCAT CCCGGGCCTG AGCATCTCAG GTAACCTATT GATGAACGGG    1260

CAGCAGATCT TCCTGGAGGT GCAAGCGATA CGCGAGACCG TGGAACTGCG TCAGTACGAT    1320

CCCGTGGCTG CGCTCTTCTT TTTCGATATC GACTTGCTGC TGCAGCGCGG GCCTCAGTAC    1380

AGCGAACACC CCACCTTCAC CAGCCAGTAT CGCATCCAGG GCAAGCTTGA GTACCGACAC    1440

ACCTGGGACC GGCACGACGA GGGTGCCGCC CAGGGCGACG ACGACGTCTG GACCAGCGGA    1500
```

```
TCGGACTCCG ACGAGGAACT CGTAACCACC GAGCGCAAGA CGCCCCGCGT TACCGGCGGC      1560

GGCGCCATGG CGGGCGCCTC CACTTCCGCG GGCCGCAAAC GCAAATCAGC ATCCTCGGCG      1620

ACGGCGTGCA CGGCGGGCGT TATGACACGC GGCCGCCTTA AGGCCGAGTC CACCGTCGCG      1680

CCCGAAGAGG ACACCGACGA GGATTCCGAC AACGAAATCC ACAATCCGGC CGTGTTCACC      1740

TGGCCGCCCT GGCAGGCCGG CATCCTGGCC CGCAACCTGG TGCCCATGGT GGCTACGGTT      1800

CAGGGTCAGA ATCTGAAGTA CCAGGAGTTC TTCTGGGACG CCAACGACAT CTACCGCATC      1860

TTCGCCGAAT TGGAAGGCGT ATGGCAGCCC GCTGCGCAAC CCAAACGTCG CCGCCACCGG      1920

CAAGACGCCT TGCCCGGGCC ATGCATCGCC TCGACGCCCA AAAAGCACCG AGGTTGATTT      1980

TTATGGATCC TCGCGACTGC AGGGTACCTG AGTAGCTAAT TTTTAAACAA AAATGTGGGA      2040

GAATCTAATT AGTTTTTCTT TACACAATTG ACGTACATGA GTCTGAGTTC CTTGTTTTTG      2100

CTAATTATTT CATCCAATTT ATTATTCTTG ACGATATCGA GATCTTTTGT ATAGGAGTCA      2160

(2) INFORMATION FOR SEQ ID NO:66:

(i) SEQUENCE CHARACTERISTICS:
        (A) LENGTH: 3141 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

ATGAGTTTGC AGTTTATCGG TCTACAGCGG CGCGATGTGG TGGCCCTGGT CAACTTTCTG        60

CGCCATCTCA CGCAAAAGCC CGACGTGGAT CTCGAGGCAC ACCCCAAGAT CCTGAAAAAA       120

TGTGGCGAAA AACGCCTGCA CCGGCGTACG GTGCTGTTCA ACGAGCTCAT GCTTTGGTTG       180

GGATACTACC GCGAGCTGCG TTTCCACAAC CCCGACCTCT CCTCGGTTCT CGAGGAGTTC       240

GAGGTGCGTT GCGCGGCCGT GGCGCGTCGC GGCTACACTT ACCCGTTCGG TGATCGTGGT       300

AAGGCGCGTG ACCACCTGGC TGTGCTAGAC CGTACCGAAT CGATACGGA CGTACGCCAC        360

GATGCTGAGA TTGTGGAGCG CGCGCTCGTA AGCGCGGTCA TTCTGGCCAA GATGTCGGTG       420

CGCGAGACGC TGGTCACAGC CATCGGCCAG ACGGAACCCA TCGCTTTTGT GCACCTCAAG       480

GATACGGAGG TGCAGCGCAT TGAAGAAAAC CTGGAGGGTG TGCGCCGTAA CATGTTCTGC       540

GTGAAACCGC TCGACCTTAA CCTGGACCGG CACGCCAACA CGGCGCTGGT CAACGCCGTC       600

AACAAGCTCG TGTACACGGG CCGTCTCATC ATGAACGTGC GCAGGTCTTG GGAGGAGCTG       660

GAGCGCAAAT GTCTGGCGCG CATTCAGGAG CGCTGCAAGC TGCTGGTCAA GGAGCTGCGC       720

ATGTGCCTTT CCTTTGATTC CAACTACTGT CGCAATATCC TCAAACACGC CGTGGAAAAC       780

GGTGACTCGG CCGACACGCT GCTGGAGCTG CTCATCGAGG ACTTTGACAT CTACGTGGAC       840

AGCTTCCCGC AGTCGGCGCA CACCTTTTTG GGCGCGCGCC CGCCGTCGTT GGAGTTTGAC       900

GATGACGCCA ATCCTCCTCT GCTCGGCGGC GGTTCAGCCT TCTCGTCGGT ACCCAAGAAA       960

CATGTCCCCA CGCAGCCGCT GGACGGCTGG AGCTGGATCG CCAGTCCCTG GAAGGGACAC      1020

AAACCGTTCC GCTTCGAGGC CCATGGTTCT CTGGCACCGG CCGCCGACGC CCACGCCGCC      1080

CGTTCGGCGC GCGTCGGCTA TTACGACGAA GAGGAAAAGC GTCGCGAGCG GCAGAAACGG      1140

GTGGACGACG AGGTGGTGCA GCGTGAGAAA CAGCAGCTGA AGGCTTGGGA GGAGAGGCAG      1200

CAGAACCTGC AGCAACGTCA GCAGCAACCG CCGCCCCCGA CACGTAAACC GGGCGCCTCC      1260

CGGAGGCTCT TTGGCTCCAG TGCCGATGAG GACGACGACG ATGATGATGA CGAGAAAAAC      1320
```

```
ATCTTTACGC CCATCAAGAA ACCGGGAACT AGCGGCAAGG GCGCCGCTAG TGGCAACGGT      1380

GTTTCCAGCA TTTTCAGCGG CATGTTATCC TCGGGCAGTC AGAAACCGAC CAGCGGTCCC      1440

TTGAACATCC CGCAGCAACA ACAGCGTCAC GCGGCTTTCA GTCTCGTCTC CCCGCAGGTA      1500

ACCAAGGCCA GCCCGGGAAG GGTCCGTCGG GACAGCGCGT GGGACGTGAG GCCGCTCACG      1560

GAGACAAGAG GGGATCTTTT CTCGGGCGAC GAGGATTCCG ACAGCTCGGA TGGCTATCCC      1620

CCCAACCGTC AAGATCCGCG TTTCACCGAC ACGCTGGTGG ACATCACGGA TACCGAGACG      1680

AGCGCCAAAC CGCCCGTCAC CACCGCGTAC AAGTTCGAGC AACCGACGTT GACGTTCGGC      1740

GCCGGAGTTA ACGTCCCTGC TGGCGCCGGC GCTGCCATCC TCACGCCGAC GCCTGTCAAT      1800

CCTTCCACGG CCCCCGCTCC GGCCCCGACA CCTACCTTCG CGGGTACCCA AACCCCGGTC      1860

AACGGTAACT CGCCCTGGGC TCCGACGGCG CCGTTGCCCG GGGATATGAA CCCCGCCAAC      1920

TGGCCGCGCG AACGCGCGTG GGCCCTCAAG AATCCTCACC TGGCTTACAA TCCCTTCAGG      1980

ATGCCTACGA CTTCCACGAC TTCTCAAAAC AACGTGTCCA CCACCCCTCG GAGGCCGTCG      2040

ACTCCACGCG CCGCGGTGAC ACAAACAGCG TCTCAGAACG CCGCTGATGA GGTTTGGGCT      2100

TTAAGGGACC AAACTGCAGA GTCACCGGTC GAAGACAGCG AGGAGGAAGA CGACGACTCC      2160

TCGGACACCG GCTCCGTCGT CAGCCTGGGA CACACAACAC CGTCGTCCGA TTACAACGAC      2220

GTCATTTCGC CTCCCAGTCA GACGCCCGAG CAGTCGACGC CGTCCAGAAT ACGTAAAGCT      2280

AAGTTATCGT CTCCAATGAC GACGACATCC ACGAGCCAGA AACCGGTGCT GGGCAAGCGA      2340

GTCGCGACGC CGCACGCGTC CGCCCGAGCG CAGACGGTGA CGTCGACACC GGTTCAGGGA      2400

AGGGTAGAGA AACAGGTATC GGGCACGCCG TCGACGGTAC CCGCCACGCT GTTGCAACCT      2460

CAACCGGCTT CGTCTAAAAC AACGTCATCA AGGAACGTGA CTTCTGGCGC GAGAACCTCT      2520

TCCGCTTCGG CTCGACAGCC GTCAGCCTCG GCGTCCGTTT TGTCGCCCAC GGAGGATGAT      2580

GTCGTGTCCC CCGTCACGTC GCCGCTGTCC ATGCTTTCGT CAGCCTCTCC GTCCCCGGCC      2640

AAGAGTGCCC CTCCGTCTCC GGTGAAAGGT CGGGGCAGCC GCGTCGGTGT TCCTTCTTTG      2700

AAACCTACTT TGGGCGGCAA GGCGGTGGTA GGTCGACCGC CCTCGGTCCC CGTGAGCGGT      2760

AGCGCGCCGG GTCGCCTGTC CGGCACCAGC CGGGCCGCCT CGACCACGCC GACGTATCCC      2820

GCGGTAACCA CCGTTTACCC ACCGTCGTCT ACGGCCAAAA GCAGCGTATC GAATGCGCCG      2880

CCTGTGGCCT CCCCCTCCAT CCTGAAACCG GGGGCGAGCG CGGCTTTGCA ATCACGCCGC      2940

TCGACGGGGA CCGCCGCCGT AGGTTCCCCC GTCAAGAGCA CGACGGGCAT GAAAACGGTG      3000

GCTTTCGACC TATCGTCGCC CCAGAAGAGC GGTACGGGGC CGCAACCGGG TTCTGCCGGC      3060

ATGGGGGCG CCAAAACGCC GTCGGACGCC GTGCAGAACA TCCTCCAAAA GATCGAGAAG      3120

ATTAAGAACA CGGAGGAATA G                                                3141
```

(2) INFORMATION FOR SEQ ID NO:67:

(i) SEQUENCE CHARACTERISTICS:
        (A) LENGTH: 4075 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

```
AAGCTTGCGG CCGCTCATTA GACAAGCGAA TGAGGGACGA AAACGTGGAG GAGGTATTAA       60

GTTTGGAGAA ATGGAGAGAG ACTGTTTAAT AGCGCATGGC GCAGCCAATA CTATTACAGA      120
```

```
AGTTTTGAAA GATTCGGAAG AAGATTATCA AGATGTGTAT GTTTGTGAAA ATTGTGGAGA    180

CATAGCAGCA CAAATCAAGG GTATTAATAC ATGTCTTAGA TGTTCAAAAC TTAATCTCTC    240

TCCTCTCTTA ACAAAAATTG ATACCACGCA CGTATCTAAA GTATTTCTTA CTCAAATGAA    300

CGCCAGAGGC GTAAAAGTCA AATTAGATTT CGAACGAAGG CCTCCTTCGT TTTATAAACC    360

ATTAGATAAA GTTGATCTCA AGCCGTCTTT TCTGGTGTAA TAAAAATTAA TTAATTACTC    420

GAGCCCCTAG CAATAAAAAC TATTCCTCCG TGTTCTTAAT CTTCTCGATC TTTTGGAGGA    480

TGTTCTGCAC GGCGTCCGAC GGCGTTTTGG CGCCCCCCAT GCCGGCAGAA CCCGGTTGCG    540

GCCCCGTACC GCTCTTCTGG GGCGACGATA GGTCGAAAGC CACCGTTTTC ATGCCCGTCG    600

TGCTCTTGAC GGGGGAACCT ACGGCGGCGG TCCCCGTCGA GCGGCGTGAT TGCAAAGCCG    660

CGCTCGCCCC CGGTTTCAGG ATGGAGGGGG AGGCCACAGG CGGCGCATTC GATACGCTGC    720

TTTTGGCCGT AGACGACGGT GGGTAAACGG TGGTTACCGC GGGATACGTC GGCGTGGTCG    780

AGGCGGCCCG GCTGGTGCCG GACAGGCGAC CCGGCGCGCT ACCGCTCACG GGTACCGAGG    840

GCGGTCGACC TACCACCGCC TTGCCGCCCA AGTAGGTTT CAAAGAAGGA ACACCGACGC    900

GGCTGCCCCG ACCTTTCACC GGAGACGGAG GGGCACTCTT GGCCGGGGAC GGAGAGGCTG    960

ACGAAAGCAT GGACAGCGGC GACGTGACGG GGGACACGAC ATCATCCTCC GTGGGCGACA    1020

AAACGGACGC CGAGGCTGAC GGCTGTCGAG CCGAAGCGGA AGAGGTTCTC GCGCCAGAAG    1080

TCACGTTCCT TGATGACGTT GTTTTAGACG AAGCCGGTTG AGGTTGCAAC AGCGTGGCGG    1140

GTACCGTCGA CGGCGTGCCC GATACCTGTT TCTCTACCCT TCCCTGAACC GGTGTCGACG    1200

TCACCGTCTG CGCTCGGGCG GACGCGTGCG GCGTCGCGAC TCGCTTGCCC AGCACCGGTT    1260

TCTGGCTCGT GGATGTCGTC GTCATTGGAG ACGATAACTT AGCTTTACGT ATTCTGGACG    1320

GCGTCGACTG CTCGGGCGTC TGACTGGGAG GCGAAATGAC GTCGTTGTAA TCGGACGACG    1380

GTGTTGTGTG TCCCAGGCTG ACGACGGAGC CGGTGTCCGA GGAGTCGTCG TCTTCCTCCT    1440

CGCTGTCTTC GACCGGTGAC TCTGCAGTTT GGTCCCTTAA AGCCCAAACC TCATCAGCGG    1500

CGTTCTGAGA CGCTGTTTGT GTCACCGCGG CGCGTGGAGT CGACGGCCTC CGAGGGGTGG    1560

TGGACACGTT GTTTTGAGAA GTCGTGGAAG TCGTAGGCAT CCTGAAGGGA TTGTAAGCCA    1620

GGTGAGGATT CTTGAGGGCC CACGCGCGTT CGCGCGGCCA GTTGGCGGGG TTCATATCCC    1680

CGGGCAACGG CGCCGTCGGA GCCCAGGGCG AGTTACCGTT GACCGGGGTT TGGGTACCCG    1740

CGAAGGTAGG TGTCGGGGCC GGAGCGGGGG CCGTGGAAGG ATTGACAGGC GTCGGCGTGA    1800

GGATGGCAGC GCCGGCGCCA GCAGGGACGT TAACTCCGGC GCCGAACGTC AACGTCGGTT    1860

GCTCGAACTT GTACGCGGTG GTGACGGGCG GTTTGGCGCT CGTCTCGGTA TCCGTGATGT    1920

CCACCAGCGT GTCGGTGAAA CGCGGATCTT GACGGTTGGG GGGATAGCCA TCCGAGCTGT    1980

CGGAATCCTC GTCGCCCGAG AAAAGATCCC CTCTTGTCTC CGTGAGCGGC CTCACGTCCC    2040

ACGCGCTGTC CCGACGGACC CTTCCCGGGC TGGCCTTGGT TACCTGCGGG GAGACGAGAC    2100

TGAAAGCCGC GTGACGCTGT TGTTGCTGCG GGATGTTCAA GGGACCGCTG GTCGGTTTCT    2160

GACTGCCCGA GGATAACATG CCGCTGAAAA TGCTGGAAAC ACCGTTGCCA CTAGCGGCGC    2220

CCTTGCCGCT AGTTCCCGGT TTCTTGATGG GCGTAAAGAT GTTTTTCTCG TCATCATCAT    2280

CGTCGTCGTC CTCATCGGCA CTGGAGCCAA AGAGCCTCCG GGAGGCGCCC GGTTTACGTG    2340

TCGGGGGCGG CGGTTGCTGC TGACGTTGCT GCAGGTTCTG CTGCCTCTCC TCCCAAGCCT    2400

TCAGCTGCTG TTTCTCACGC TGCACCACCT CGTCGTCCAC CCGTTTCTGC CGCTCGCGAC    2460
```

```
GCTTTTCCTC TTCGTCGTAA TAGCCGACGC GCGCCGAACG GGCGGCGTGG GCGTCGGCGG      2520

CCGGTGCCAG AGAACCATGG GCCTCGAAGC GGAACGGTTT GTGTCCCTTC CAGGGACTGG      2580

CGATCCAGCT CCAGCCGTCC AGCGGCTGCG TGGGGACATG TTTCTTGGGT ACCGACGAGA      2640

AGGCTGAACC GCCGCCGAGC GAGAGGAGAT TGGCGTCATC GTCAAACTCC AACGACGGCG      2700

GGCGCGCGCC CAAAAAGGTG TGCGCCGACT GCGGGAAGCT GTCCACGTAG ATGTCAAAGT      2760

CCTCGATGAG CAGCTCCAGC AGCGTGTCGG CCGAGTCACC GTTTTCCACG GCGTGTTTGA      2820

GGATATTGCG ACAGTAGTTG GAATCAAAGG AAAGGCACAT GCGCAGCTCC TTGACCAGCA      2880

GCTTGCAGCG CTCCTGAATG CGCGCCAGAC ATTTGCGCTC CAGCTCCTCC AAGACCTGC       2940

GCACGTTCAT GATGAGACGG CCCGTGTACA CGAGCTTGTT GACGGCGTTG ACCAGCGCCG      3000

TGTTGGCGTG CCGGTCCAGG TTAAGGTCGA GCGGTTTCAC GCAGAACATG TTACGGCGCA      3060

CACCCTCCAG GTTTTCTTCA ATGCGCTGCA CCTCCGTATC CTTGAGGTGC ACAAAAGCGA      3120

GTGGGTTCCG TCTGGCCGAT GGCTGTGACC AGCGTCTCGC GCACCGACAT CTTGGCCAGA      3180

ATGACCGCGC TTACGAGCGC GCGCTCCACA ATCTCAGCAT CGTGGCGTAC GTCCGTATCG      3240

AATTCGGTAC GGTCTAGCAC AGCCAGGTGG TCACGCGCCT TACCACGATC ACCGAACGGG      3300

TAAGTGTAGC CGCGACGCGC CACGGCCGCG CAACGCACCT CGAACTCCTC GAGAACCGAG      3360

GAGAGGTCGG GGTTGTGGAA ACGCAGCTCG CGGTAGTATC CCAACCAAAG CATGAGCTCG      3420

TTGAACAGCA CCGTAGCCGG TGCAGGCGTT TTTCGCCACA TTTTTTCAGG ATCTTGGGGT      3480

GTGCCTCGAG ATCCACGTCG GGCTTTTGCG TGAGATGGCG CAGAAAGTTG ACCAGGGCCA      3540

CCACATCGCG CCGCTGTAGA CCGATAAACT GCAAACTCAT TTTATATTGT AATTATATAT      3600

TTTCAATTTT GAAATCCCAA AATATTATCA TATCTTCCCA ATAAAGCTAG GGGAGATCTA      3660

ATTTAATTTA ATTTATATAA CTTATTTTTT GAATATACTT TTAATTAACA AAAGAGTTAA      3720

GTTACTCATA TGGACGCCGT CCAGTCTGAA CATCAATCTT TTTAGCCAGA GATATCATAG      3780

CCGCTCTTAG AGTTTCAGCG TGATTTTCCA ACCTAAATAG AACTTCATCG TTGCGTTTAC      3840

AACACTTTTC TATTTGTTCA AACTTTGTTG TTACATTAGT AATCTTTTTT TCCAAATTAG      3900

TTAGCCGTTG TTTGAGAGTT TCCTCATTGT CGTCTTCATC GGCTTTAACA ATTGCTTCGC      3960

GTTTAGCCTC CTGGCTGTTC TTATCAGCCT TTGTAGAAAA AAATTCAGTT GCTGGAATTG      4020

CAAGATCGTC ATCTCCGGGG AAAAGAGTTC CGTCCATTTA AAGCCGCGGG AATTC          4075

(2) INFORMATION FOR SEQ ID NO:68:

(i) SEQUENCE CHARACTERISTICS:
        (A) LENGTH: 4909 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GAGCTCGCGG CCGCCTATCA AAAGTCTTAA TGAGTTAGGT GTAGATAGTA TAGATATTAC        60

TACAAAGGTA TTCATATTTC CTATCAATTC TAAAGTAGAT GATATTAATA ACTCAAAGAT       120

GATGATAGTA GATAATAGAT ACGCTCATAT AATGACTGCA AATTTGGACG TTCACATTT        180

TAATCATCAC GCGTTCATAA GTTTCAACTG CATAGATCAA AATCTCACTA AAAAGATAGC       240

CGATGTATTT GAGAGAGATT GGACATCTAA CTACGCTAAA GAAATTACAG TTATAAATAA       300

TACATAATGG ATTTTGTTAT CATCAGTTAT ATTTAACATA AGTACAATAA AAAGTATTAA       360
```

-continued

| | |
|---|---|
| ATAAAAATAC TTACTTACGA AAAAATGACT AATTAGCTAT AAAAACCCGG GGGATCCTTA | 420 |
| ATTAATTAGT TATTAGACAA GGTGAAAACG AAACTATTTG TAGCTTAATT AATTAGCTGC | 480 |
| AGGGCTGCAG GAATTCTAGC AATAAAAACT ATTCCTCCGT GTTCTTAATC TTCTCGATCT | 540 |
| TTTGGAGGAT GTTCTGCACG GCGTCCGACG GCGTTTTGGC GCCCCCCATG CCGGCAGAAC | 600 |
| CCGGTTGCGG CCCCGTACCG CTCTTCTGGG GCGACGATAG GTCGAAAGCC ACCGTTTTCA | 660 |
| TGCCCGTCGT GCTCTTGACG GGGGAACCTA CGGCGGCGGT CCCCGTCGAG CGGCGTGATT | 720 |
| GCAAAGCCGC GCTCGCCCCC GGTTTCAGGA TGGAGGGGGA GGCCACAGGC GGCGCATTCG | 780 |
| ATACGCTGCT TTTGGCCGTA GACGACGGTG GGTAAACGGT GGTTACCGCG GGATACGTCG | 840 |
| GCGTGGTCGA GGCGGCCCGG CTGGTGCCGG ACAGGCGACC CGGCGCGCTA CCGCTCACGG | 900 |
| GTACCGAGGG CGGTCGACCT ACCACCGCCT TGCCGCCCAA AGTAGGTTTC AAAGAAGGAA | 960 |
| CACCGACGCG GCTGCCCCGA CCTTTCACCG GAGACGGAGG GGCACTCTTG GCCGGGGACG | 1020 |
| GAGAGGCTGA CGAAAGCATG GACAGCGGCG ACGTGACGGG GGACACGACA TCATCCTCCG | 1080 |
| TGGGCGACAA AACGGACGCC GAGGCTGACG GCTGTCGAGC CGAAGCGGAA GAGGTTCTCG | 1140 |
| CGCCAGAAGT CACGTTCCTT GATGACGTTG TTTTAGACGA AGCCGGTTGA GGTTGCAACA | 1200 |
| GCGTGGCGGG TACCGTCGAC GGCGTGCCCG ATACCTGTTT CTCTACCCTT CCCTGAACCG | 1260 |
| GTGTCGACGT CACCGTCTGC GCTCGGGCGG ACGCGTGCGG CGTCGCGACT CGCTTGCCCA | 1320 |
| GCACCGGTTT CTGGCTCGTG GATGTCGTCG TCATTGGAGA CGATAACTTA GCTTTACGTA | 1380 |
| TTCTGGACGG CGTCGACTGC TCGGGCGTCT GACTGGGAGG CGAAATGACG TCGTTGTAAT | 1440 |
| CGGACGACGG TGTTGTGTGT CCCAGGCTGA CGACGGAGCC GGTGTCCGAG GAGTCGTCGT | 1500 |
| CTTCCTCCTC GCTGTCTTCG ACCGGTGACT CTGCAGTTTG GTCCCTTAAA GCCCAAACCT | 1560 |
| CATCAGCGGC GTTCTGAGAC GCTGTTTGTG TCACCGCGGC GCGTGGAGTC GACGGCCTCC | 1620 |
| GAGGGGTGGT GGACACGTTG TTTTGAGAAG TCGTGGAAGT CGTAGGCATC CTGAAGGGAT | 1680 |
| TGTAAGCCAG GTGAGGATTC TTGAGGGCCC ACGCGCGTTC GCGCGGCCAG TTGGCGGGGT | 1740 |
| TCATATCCCC GGGCAACGGC GCCGTCGGAG CCCAGGGCGA GTTACCGTTG ACCGGGGTTT | 1800 |
| GGGTACCCGC GAAGGTAGGT GTCGGGGCCG GAGCGGGGGC CGTGGAAGGA TTGACAGGCG | 1860 |
| TCGGCGTGAG GATGGCAGCG CCGGCGCCAG CAGGGACGTT AACTCCGGCG CCGAACGTCA | 1920 |
| ACGTCGGTTG CTCGAACTTG TACGCGGTGG TGACGGGCGG TTTGGCGCTC GTCTCGGTAT | 1980 |
| CCGTGATGTC CACCAGCGTG TCGGTGAAAC GCGGATCTTG ACGGTTGGGG GGATAGCCAT | 2040 |
| CCGAGCTGTC GGAATCCTCG TCGCCCGAGA AAAGATCCCC TCTTGTCTCC GTGAGCGGCC | 2100 |
| TCACGTCCCA CGCGCTGTCC CGACGGACCC TTCCCGGGCT GGCCTTGGTT ACCTGCGGGG | 2160 |
| AGACGAGACT GAAAGCCGCG TGACGCTGTT GTTGCTGCGG GATGTTCAAG GGACCGCTGG | 2220 |
| TCGGTTTCTG ACTGCCCGAG GATAACATGC CGCTGAAAAT GCTGGAAACA CCGTTGCCAC | 2280 |
| TAGCGGCGCC CTTGCCGCTA GTTCCCGGTT TCTTGATGGG CGTAAAGATG TTTTTCTCGT | 2340 |
| CATCATCATC GTCGTCGTCC TCATCGGCAC TGGAGCCAAA GAGCCTCCGG GAGGCGCCCG | 2400 |
| GTTTACGTGT CGGGGGCGGC GGTTGCTGCT GACGTTGCTG CAGGTTCTGC TGCCTCTCCT | 2460 |
| CCCAAGCCTT CAGCTGCTGT TTCTCACGCT GCACCACCTC GTCGTCCACC CGTTTCTGCC | 2520 |
| GCTCGCGACG CTTTTCCTCT TCGTCGTAAT AGCCGACGCG CGCCGAACGG GCGGCGTGGG | 2580 |
| CGTCGGCGGC CGGTGCCAGA GAACCATGGG CCTCGAAGCG GAACGGTTTG TGTCCCTTCC | 2640 |
| AGGGACTGGC GATCCAGCTC CAGCCGTCCA GCGGCTGCGT GGGGACATGT TCTTGGGTA | 2700 |
| CCGACGAGAA GGCTGAACCG CCGCCGAGCG AGAGGAGATT GGCGTCATCG TCAAACTCCA | 2760 |

```
ACGACGGCGG GCGCGCGCCC AAAAAGGTGT GCGCCGACTG CGGGAAGCTG TCCACGTAGA    2820

TGTCAAAGTC CTCGATGAGC AGCTCCAGCA GCGTGTCGGC CGAGTCACCG TTTTCCACGG    2880

CGTGTTTGAG GATATTGCGA CAGTAGTTGG AATCAAAGGA AAGGCACATG CGCAGCTCCT    2940

TGACCAGCAG CTTGCAGCGC TCCTGAATGC GCGCCAGACA TTTGCGCTCC AGCTCCTCCC    3000

AAGACCTGCG CACGTTCATG ATGAGACGGC CCGTGTACAC GAGCTTGTTG ACGGCGTTGA    3060

CCAGCGCCGT GTTGGCGTGC CGGTCCAGGT TAAGGTCGAG CGGTTTCACG CAGAACATGT    3120

TACGGCGCAC ACCCTCCAGG TTTTCTTCAA TGCGCTGCAC CTCCGTATCC TTGAGGTGCA    3180

CAAAAGCGAT GGGTTCCGTC TGGCCGATGG CTGTGACCAG CGTCTCGCGC ACCGACATCT    3240

TGGCCAGAAT GACCGCGCTT ACGAGCGCGC GCTCCACAAT CTCAGCATCG TGGCGTACGT    3300

CCGTATCGAA TTCGGTACGG TCTAGCACAG CCAGGTGGTC ACGCGCCTTA CCACGATCAC    3360

CGAACGGGTA AGTGTAGCCG CGACGCGCCA CGGCCGCGCA ACGCACCTCG AACTCCTCGA    3420

GAACCGAGGA GAGGTCGGGG TTGTGGAAAC GCAGCTCGCG GTAGTATCCC AACCAAAGCA    3480

TGAGCTCGTT GAACAGCACC GTACGCCGGT GCAGGCGTTT TTCGCCACAT TTTTTCAGGA    3540

TCTTGGGGTG TGCCTCGAGA TCCACGTCGG GCTTTTGCGT GAGATGGCGC AGAAAGTTGA    3600

CCAGGGCCAC CACATCGCGC CGCTGTAGAC CGATAAACTG CAAACTCATT TTATATTGTA    3660

ATTATATATT TTCAATTTTG AAATCCCAAA ATATTATCAT ATCTTCCCAA TAAAGCTAGA    3720

TTCTTTTTAT TGATTAACTA GTCAAATGAG TATATATAAT TGAAAAAGTA AAATATAAAT    3780

CATATAATAA TGAAACGAAA TATCAGTAAT AGACAGGAAC TGGCAGATTC TTCTTCTAAT    3840

GAAGTAAGTA CTGCTAAATC TCCAAAATTA GATAAAAATG ATACAGCAAA TACAGCTTCA    3900

TTCAACGAAT TACCTTTTAA TTTTTTCAGA CACACCTTAT TACAAACTAA CTAAGTCAGA    3960

TGATGAGAAA GTAAATATAA ATTTAACTTA TGGGTATAAT ATAATAAAGA TTCATGATAT    4020

TAATAATTTA CTTAACGATG TTAATAGACT TATTCCATCA ACCCCTTCAA ACCTTTCTGG    4080

ATATTATAAA ATACCAGTTA ATGATATTAA AATAGATTGT TTAAGAGATG TAAATAATTA    4140

TTTGGAGGTA AAGGATATAA AATTAGTCTA TCTTTCACAT GGAAATGAAT TACCTAATAT    4200

TAATAATTAT GATAGGAATT TTTTAGGATT TACAGCTGTT ATATGTATCA ACAATACAGG    4260

CAGATCTATG GTTATGGTAA AACACTGTAA CGGGAAGCAG CATTCTATGG TAACTGGCCT    4320

ATGTTTAATA GCCAGATCAT TTTACTCTAT AAACATTTTA CCACAAATAA TAGGATCCTC    4380

TAGATATTTA ATATTATATC TAACAACAAC AAAAAAATTT AACGATGTAT GGCCAGAAGT    4440

ATTTTCTACT AATAAAGATA AAGATAGTCT ATCTTATCTA CAAGATATGA AAGAAGATAA    4500

TCATTTAGTA GTAGCTACTA ATATGGAAAG AAATGTATAC AAAAACGTGG AAGCTTTTAT    4560

ATTAAATAGC ATATTACTAG AAGATTTAAA ATCTAGACTT AGTATAACAA AACAGTTAAA    4620

TGCCAATATC GATTCTATAT TTCATCATAA CAGTAGTACA TTAATCAGTG ATATACTGAA    4680

ACGATCTACA GACTCAACTA TGCAAGGAAT AAGCAATATG CCAATTATGT CTAATATTTT    4740

AACTTTAGAA CTAAAACGTT CTACCAATAC TAAAAATAGG ATACGTGATA GGCTGTTAAA    4800

AGCTGCAATA AATAGTAAGG ATGTAGAAGA AATACTTTGT TCTATACCTT CGGAGGAAAG    4860

AACTTTAGAA CAACTTAAGT TTAATCAAAC TTGTATTTAT GAAGGTACC               4909
```

(2) INFORMATION FOR SEQ ID NO:69:

(i) SEQUENCE CHARACTERISTICS:
        (A) LENGTH: 3567 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:69:

| | | | | | |
|---|---|---|---|---|---|
| AAGACTAATT | TGTAAACCAT | CTTACTCAAA | ATATGTAACA | ATAGTACGAT | GCAATGAGTA | 60 |
| AGACAATAGG | AAATCTATCT | TATATACACA | TAATTATTCT | ATCAATTTTA | CCAATTAGTT | 120 |
| AGTGTAATGT | TATAAAAACT | AATTAATCAC | TCGAGCCCCT | AGCAATAAAA | ACTATTCCTC | 180 |
| CGTGTTCTTA | ATCTTCTCGA | TCTTTTGGAG | GATGTTCTGC | ACGGCGTCCG | ACGGCGTTTT | 240 |
| GGCGCCCCCC | ATGCCGGCAG | AACCCGGTTG | CGGCCCCGTA | CCGCTCTTCT | GGGGCGACGA | 300 |
| TAGGTCGAAA | GCCACCGTTT | TCATGCCCGT | CGTGCTCTTG | ACGGGGAAC | CTACGGCGGC | 360 |
| GGTCCCCGTC | GAGCGGCGTG | ATTGCAAAGC | CGCGCTCGCC | CCCGGTTTCA | GGATGGAGGG | 420 |
| GGAGGCCACA | GGCGGCGCAT | TCGATACGCT | GCTTTTGGCC | GTAGACGACG | GTGGGTAAAC | 480 |
| GGTGGTTACC | GCGGGATACG | TCGGCGTGGT | CGAGGCGGCC | CGGCTGGTGC | CGGACAGGCG | 540 |
| ACCCGGCGCG | CTACCGCTCA | CGGGTACCGA | GGGCGGTCGA | CCTACCACCG | CCTTGCCGCC | 600 |
| CAAAGTAGGT | TTCAAAGAAG | GAACACCGAC | GCGGCTGCCC | CGACCTTTCA | CCGGAGACGG | 660 |
| AGGGGCACTC | TTGGCCGGGG | ACGGAGAGGC | TGACGAAAGC | ATGGACAGCG | GCGACGTGAC | 720 |
| GGGGGACACG | ACATCATCCT | CCGTGGGCGA | CAAAACGGAC | GCCGAGGCTG | ACGGCTGTCG | 780 |
| AGCCGAAGCG | GAAGAGGTTC | TTGCGCCAGA | AGTCACGTTC | CTTGATGACG | TTGTTTTAGA | 840 |
| CGAAGCCGGT | TGAGGTTGCA | ACAGCGTGGC | GGGTACCGTC | GACGGCGTGC | CCGATACCTG | 900 |
| TTTCTCTACC | CTTCCCTGAA | CCGGTGTCGA | CGTCACCGTC | TGCGCTCGGG | CGGACGCGTG | 960 |
| CGGCGTCGCG | ACTCGCTTGC | CCAGCACCGG | TTTCTGGCTC | GTGGATGTCG | TCGTCATTGG | 1020 |
| AGACGATAAC | TTAGCTTTAC | GTATTCTGGA | CGGCGTCGAC | TGCTCGGGCG | TCTGACTGGG | 1080 |
| AGGCGAAATG | ACGTCGTTGT | AATCGGACGA | CGGTGTTGTG | TGTCCCAGGC | TGACGACGGA | 1140 |
| GCCGGTGTCC | GAGGAGTCGT | CGTCTTCCTC | CTCGCTGTCT | TCGACCGGTG | ACTCTGCAGT | 1200 |
| TTGGTCCCTT | AAAGCCCAAA | CCTCATCAGC | GGCGTTCTGA | GACGCTGTTT | GTGTCACCGC | 1260 |
| GGCGCGTGGA | GTCGACGGCC | TCCGAGGGGT | GGTGGACACG | TTGTTTTGAG | AAGTCGTGGA | 1320 |
| AGTCGTAGGC | ATCCTGAAGG | GATTGTAAGC | CAGGTGAGGA | TTCTTGAGGG | CCCACGCGCG | 1380 |
| TTCGCGCGGC | CAGTTGGCGG | GGTTCATATC | CCCGGGCAAC | GGCGCCGTCG | GAGCCCAGGG | 1440 |
| CGAGTTACCG | TTGACCGGGG | TTTGGGTACC | CGCGAAGGTA | GGTGTCGGGG | CCGGAGCGGG | 1500 |
| GGCCGTGGAA | GGATTGACAG | GCGTCGGCGT | GAGGATGGCA | GCGCCGGCGC | CAGCAGGGAC | 1560 |
| GTTAACTCCG | GCGCCGAACG | TCAACGTCGG | TTGCTCGAAC | TTGTACGCGG | TGGTGACGGG | 1620 |
| CGGTTTGGCG | CTCGTCTCGG | TATCCGTGAT | GTCCACCAGC | GTGTCGGTGA | AACGCGGATC | 1680 |
| TTGACGGTTG | GGGGGATAGC | CATCCGAGCT | GTCGGAATCC | TCGTCGCCCG | AGAAAAGATC | 1740 |
| CCCTCTTGTC | TCCGTGAGCG | GCCTCACGTC | CCACGCGCTG | TCCCGACGGA | CCCTTCCCGG | 1800 |
| GCTGGCCTTG | GTTACCTGCG | GGGAGACGAG | ACTGAAAGCC | GCGTGACGCT | GTTGTTGCTG | 1860 |
| CGGGATGTTC | AAGGGACCGC | TGGTCGGTTT | CTGACTGCCC | GAGGATAACA | TGCCGCTGAA | 1920 |
| AATGCTGGAA | ACACCGTTGC | CACTAGCGGC | GCCCTTGCCG | CTAGTTCCCG | GTTTCTTGAT | 1980 |
| GGGCGTAAAG | ATGTTTTTCT | CGTCATCATC | ATCGTCGTCG | TCCTCATCGG | CACTGGAGCC | 2040 |
| AAAGAGCCTC | CGGGAGGCGC | CCGGTTTACG | TGTCGGGGGC | GGCGGTTGCT | GCTGACGTTG | 2100 |
| CTGCAGGTTC | TGCTGCCTCT | CCTCCCAAGC | CTTCAGCTGC | TGTTTCTCAC | GCTGCACCAC | 2160 |

```
CTCGTCGTCC ACCCGTTTCT GCCGCTCGCG ACGCTTTTCC TCTTCGTCGT AATAGCCGAC    2220

GCGCGCCGAA CGGGCGGCGT GGGCGTCGGC GGCCGGTGCC AGAGAACCAT GGGCCTCGAA    2280

GCGGAACGGT TTGTGTCCCT TCCAGGGACT GGCGATCCAG CTCCAGCCGT CCAGCGGCTG    2340

CGTGGGACA TGTTTCTTGG GTACCGACGA GAAGGCTGAA CCGCCGCCGA GCGAGAGGAG     2400

ATTGGCGTCA TCGTCAAACT CCAACGACGG CGGGCGCGCG CCCAAAAAGG TGTGCGCCGA    2460

CTGCGGGAAG CTGTCCACGT AGATGTCAAA GTCCTCGATG AGCAGCTCCA GCAGCGTGTC    2520

GGCCGAGTCA CCGTTTTCCA CGGCGTGTTT GAGGATATTG CGACAGTAGT TGGAATCAAA    2580

GGAAAGGCAC ATGCGCAGCT CCTTGACCAG CAGCTTGCAG CGCTCCTGAA TGCGCGCCAG    2640

ACATTTGCGC TCCAGCTCCT CCCAAGACCT GCGCACGTTC ATGATGAGAC GGCCCGTGTA    2700

CACGAGCTTG TTGACGGCGT TGACCAGCGC CGTGTTGGCG TGCCGGTCCA GGTTAAGGTC    2760

GAGCGGTTTC ACGCAGAACA TGTTACGGCG CACACCCTCC AGGTTTTCTT CAATGCGCTG    2820

CACCTCCGTA TCCTTGAGGT GCACAAAAGC GATGGGTTCC GTCTGGCCGA TGGCTGTGAC    2880

CAGCGTCTCG CGCACCGACA TCTTGGCCAG AATGACCGCG CTTACGAGCG CGCGCTCCAC    2940

AATCTCAGCA TCGTGGCGTA CGTCCGTATC GAATTCGGTA CGGTCTAGCA CAGCCAGGTG    3000

GTCACGCGCC TTACCACGAT CACCGAACGG GTAAGTGTAG CCGCGACGCG CCACGGCCGC    3060

GCAACGCACC TCGAACTCCT CGAGAACCGA GGAGAGGTCG GGGTTGTGGA AACGCAGCTC    3120

GCGGTAGTAT CCCAACCAAA GCATGAGCTC GTTGAACAGC ACCGTACGCC GGTGCAGGCG    3180

TTTTTCGCCA CATTTTTTCA GGATCTTGGG GTGTGCCTCG AGATCCACGT CGGGCTTTTG    3240

CGTGAGATGG CGCAGAAAGT TGACCAGGGC CACCACATCG CGCCGCTGTA GACCGATAAA    3300

CTGCAAACTC ATTTTATATT GTAATTATAT ATTTTCAATT TTGAAATCCC AAAATATTAT    3360

CATATCTTCC CAATAAAGCT AGGGGGAATT CGGATCCTCG CGACTGCAGG GTACCTGAGT    3420

AGCTAATTTT TAAACAAAAA TGTGGGAGAA TCTAATTAGT TTTTCTTTAC ACAATTGACG    3480

TACATGAGTC TGAGTTCCTT GTTTTTGCTA ATTATTTCAT CCAATTTATT ATTCTTGACG    3540

ATATCGAGAT CTTTTGTATA GGAGTCA                                       3567
```

(2) INFORMATION FOR SEQ ID NO:70:

(i) SEQUENCE CHARACTERISTICS:
        (A) LENGTH: 4893 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

```
CTGCAGGTCG ACGGATCTGA GAATGGATGA TTCTCCAGCC GAAACATATT CTACCATGGC     60

TCCGTTTAAT TTGTTGATGA AGATGGATTC ATCCTTAAAT GTTTTCTCTG TAATAGTTTC    120

CACCGAAAGA CTATGCAAAG AATTTGGAAT GCGTTCCTTG TGCTTAATGT TTCCATAGAC    180

GGCTTCTAGA AGTTGATACA ACATAGGACT AGCCGCGGTA ACTTTTATTT TTAGAAAGTA    240

TCCATCGCTT CTATCTTGTT TAGATTTATT TTTATAAAGT TTAGTCTCTC CTTCCAACAT    300

AATAAAAGTG GAAGTCATTT GACTAGATAA ACTATCAGTA AGTTTTATAG AGATAGACGA    360

ACAATTAGCG TATTGAGAAG CATTTAGTGT AACGTATTCG ATACATTTTG CATTAGATTT    420

ACTAATCGAT TTTGCATACT CTATAACACC CGCACAAGTC TGTAGAGAAT CGCTAGATGC    480

AGTAGGTCTT GGTGAAGTTT CAACTCTCTT CTTGATTACC TTACTCATGA TTAAACCTAA    540
```

-continued

| | | | | |
|---|---|---|---|---|
| ATAATTGTAC | TTTGTAATAT | AATGATATAT | ATTTTCACTT | TATCTCATTT | GAGAATAAAA | 600 |
| AGATCACAAA | AATTAACTAA | TCAGGATCTC | GAGATAAAAA | TCAGCATGTC | TTGAGCATGC | 660 |
| GGTAGAGCAG | ATAGATGCCG | ATGATGGCCG | ATAGCGCGTA | GACGGACATC | ATGAGGAGAC | 720 |
| GACTGTCGGT | AGCGTCCACG | ACGACGTCAG | TTACTTCTAG | GACCGTACCG | TTTTTCAAAA | 780 |
| GCATGAGGTA | GTGAGTTCGC | GGAGATGAGA | CCACCACTTC | GTTGTAGGGA | TCCAGGGCGA | 840 |
| AAAGGACGTC | GTCCGAGTCG | TGCATGTACA | TGATGTTGAT | GACGCCTTGC | GTGTCGTCGT | 900 |
| ATTCTAGTAG | GGCGCTTTGG | CAAAAGGCGC | AGTTTTCTAG | GGAAATGTTG | AGCGCCGCTG | 960 |
| TGATGCTGTG | TGTGGTATGC | ATGTTGCGCG | TCAGTTCGCA | TTTAGTTTGA | CTGTCCGTCT | 1020 |
| GGGTGATGAT | GAGGCTCTGG | CCTACGACGG | TGGTGGAGAC | AGGGTAGGAG | ATACCTTTGA | 1080 |
| TCAGGTACTG | GTTTGTTACG | ACATAACTGA | CGTGTTCGGA | GACGGTCAGC | GCGGAGAAGG | 1140 |
| ATTCGCCGAG | CGGCAGACAA | AACAGGTCGG | GGAAGGTTTC | TAGCGTGCTT | GGTTGCATGG | 1200 |
| TAGATAGGAT | GGAGAGGGCG | GCGGGAACGG | TAGTGGGAC | GGTGGCATCG | GGGAAGAGAC | 1260 |
| GTGTGAGGCG | TTCGAGCGAG | TGATCGCGTC | GCCCGCTACT | GGAACAGGGT | GTGTACAGGT | 1320 |
| CGCTGAGGTA | TTCGTGGTGC | GGATGAGCTA | GCAACTGCGT | AAAGTGTGAT | AGCTCGGCTA | 1380 |
| ATGAACAGAG | GCCCGTTTCT | ACGATGAAGA | TTTCGCGTCT | CTCCGTCGTA | TGTACTAGCA | 1440 |
| TGGAGTGGAC | GAGGCTGCCC | ATGAGGTAGA | GTTCTTGACG | CGCGAAGGCT | GAAAGAAAAG | 1500 |
| AGGCCAGGTG | CGTTTGTGT | AGTTTTAGGG | CAAAGTCGGC | GATCTGTCGT | AGTGCCCACT | 1560 |
| GGGGGATGAG | ATGTTGCTGA | TTCTGTTTAG | AGAGTATGTA | GACCAGGCGT | ACGAGGCTGG | 1620 |
| TGATGTCGGT | GATCTGATTC | GGTGTCCAAA | GGGCTCGTTT | GGCCAGGTCC | ACGGCCGTGG | 1680 |
| GATACAGCAG | CAACGTGGTG | CGTGGTGGTG | TTTGTGAGAG | GCAGGTGATC | ATAAATTCTT | 1740 |
| GTATTTGTAA | GAGTGCGGCC | TGGCGGTCTA | GGGCCCGTGG | GACGGAGACT | TGGGCGCCGG | 1800 |
| CCTCTTCTTG | TCGGGCTGCT | GCGAACAGTG | CTAATGCGTA | GGCGAAGGCC | ATTTCTACCG | 1860 |
| TGCGGCGGTC | CAGCATCTGA | CATCGACCGC | TTTTGAGTAC | ATCCACGGCG | TAACGGTGAA | 1920 |
| AGCTGTTACG | TAGTAGTGCG | CTGAGGTCCA | GGTAGTTGAA | GTCAAGTGCG | GCGTCAAGAA | 1980 |
| AGTCCGGGTC | TTTGAGATAA | GAGTGACGGT | TCAGTTGATC | TTTCTTAACT | AGCACCAGGA | 2040 |
| GCTCGTGTTT | TCAGTTTGT | CGTAGTATAA | AGTTGTCGCG | TTGATAGGGC | GCTTTAAAGA | 2100 |
| GTACGCGTGG | AAGATGGCCG | AAGATAAGCA | GCATGGGTGT | GTCGTCGTCT | ATGGACACCG | 2160 |
| TAACTACGAA | GAAGTCCTCG | GTCAGTGTTA | TTTTAACGTA | ACGTAGTTCG | TCGATGAGGT | 2220 |
| AAAAGCCTTG | GTGCAAACAA | GGTGTGACGG | TGCTGAATAG | TAGATCGTGT | CCATCAAAGA | 2280 |
| GGATACAGGT | CTGGTTAAAG | TGTGGTCGGT | GTAGTCCTGA | GGTGGTATGT | GATTCTGTCC | 2340 |
| AGCCGTGTGG | AGTGGTTTGC | GGTGGCATCC | AAACGTGAGG | TATTGACAGG | TCAATGGGTG | 2400 |
| GTGGCACAGT | GGTGGGCTGT | TCACCTAGGC | TGTCCTGTGC | CTTTAGCTGC | TGCGAAAAAG | 2460 |
| ATCGGTAGCT | GGCCAGGTCT | TTGGATACCA | GCGCGTAAGT | GTTAAGTCTC | TGTTGGTATC | 2520 |
| TTTCCAGGGT | TTCGGTCAGA | TCTACCTGGT | TCAGAAACTG | CTCCGCCAGA | GGACCCGCAA | 2580 |
| AAAGACATCG | AGGCATATGG | AATACATAGT | ATTGATTATA | GCTTTGGAAA | AAGTTGAAAC | 2640 |
| TGATGGCGTT | TTCCCTGACG | ACCGTGCTGT | TACGGAGGCT | GCTATTGTAG | GTACACTGGG | 2700 |
| TGGTGTTTTC | ACGCAGGAAG | CGGATGGGTC | TCCCGTAGGT | GTTGAGCAGT | AGGTGAAACG | 2760 |
| CTTTGTCCAG | CGGTTCGGAT | ATGGCTTCTG | CGCCATATCG | TGACGAAAGT | AGGTGGCTGA | 2820 |
| GGAGACAGAC | GGCGAGGACG | ATGAGGTAGG | AGGGGAGCCC | GGGCCGCATT | TTATATTGTA | 2880 |
| ATTATATATT | TTCAATTTTG | AAATCCCAAA | ATATTATCAT | ATTCTTCCCA | ATAAACTCGA | 2940 |

```
GATCCTTCTT TATTCTATAC TTAAAAAGTG AAAATAAATA CAAAGGTTCT TGAGGGTTGT    3000

GTTAAATTGA AAGCGAGAAA TAATCATAAA TTATTTCATT ATCGCGATAT CCGTTAAGTT    3060

TGTATCGTAA TGAAACAGAT TAAGGTTCGA GTGGACATGG TGCGGCATAG AATCAAGGAG    3120

CACATGCTGA AAAATATAC CCAGACGGAA GAGAAATTCA CTGGCGCCTT TAATATGATG    3180

GGAGGATGTT TGCAGAATGC CTTAGATATC TTAGATAAGG TTCATGAGCC TTTCGAGGAG    3240

ATGAAGTGTA TTGGGCTAAC TATGCAGAGC ATGTATGAGA ACTACATTGT ACCTGAGGAT    3300

AAGCGGGAGA TGTGGATGGC TTGTATTAAG GAGCTGCATG ATGTGAGCAA GGGCGCCGCT    3360

AACAAGTTGG GGGGTGCACT GCAGGCTAAG GCCCGTGCTA AAAAGGATGA ACTTAGGAGA    3420

AAGATGATGT ATATGTGCTA CAGGAATATA GAGTTCTTTA CCAAGAACTC AGCCTTCCCT    3480

AAGACCACCA ATGGCTGCAG TCAGGCCATG GCGGCACTGC AGAACTTGCC TCAGTGCTCC    3540

CCTGATGAGA TTATGGCTTA TGCCCAGAAA ATATTTAAGA TTTTGGATGA GGAGAGAGAC    3600

AAGGTGCTCA CGCACATTGA TCACATATTT ATGGATATCC TCACTACATG TGTGGAAACA    3660

ATGTGTAATG AGTACAAGGT CACTAGTGAC GCTTGTATGA TGACCATGTA CGGGGGCATC    3720

TCTCTCTTAA GTGAGTTCTG TCGGGTGCTG TGCTGCTATG TCTTAGAGGA GACTAGTGTG    3780

ATGCTGGCCA AGCGGCCTCT GATAACCAAG CCTGAGGTTA TCAGTGTAAT GAAGCGCCGC    3840

ATTGAGGAGA TCTGCATGAA GGTCTTTGCC CAGTACATTC TGGGGGCCGA TCCTCTGAGA    3900

GTCTGCTCTC CTAGTGTGGA TGACCTACGG GCCATCGCCG AGGAGTCAGA TGAGGAAGAG    3960

GCTATTGTAG CCTACACTTT GGCCACCGCT GGTGTCAGCT CCTCTGATTC TCTGGTGTCA    4020

CCCCCAGAGT CCCCTGTACC CGCGACTATC CCTCTGTCCT CAGTAATTGT GGCTGAGAAC    4080

AGTGATCAGG AAGAAAGTGA GCAGAGTGAT GAGGAAGAGG AGGAGGGTGC TCAGGAGGAG    4140

CGGGAGGACA CTGTGTCTGT CAAGTCTGAG CCAGTGTCTG AGATAGAGGA AGTTGCCCCA    4200

GAGGAAGAGG AGGATGGTGC TGAGGAACCC ACCGCCTCTG GAGGTAAGAG TACCCACCCT    4260

ATGGTGACTA GAAGCAAGGC TGACCAGTAA TTTTTATCTC GAGCCCGGGA GATCTTAGCT    4320

AACTGATTTT TCTGGGAAAA AAATTATTTA ACTTTTCATT AATAGGGATT TGACGTATGT    4380

AGCGTACAAA ATTATCGTTC CTGGTATATA GATAAAGAGT CCTATATATT TGAAAATCGT    4440

TACGGCTCGA TTAAACTTTA ATGATTGCAT AGTGAATATA TCATTAGGAT TTAACTCCTT    4500

GACTATCATG GCGGCGCCAG AAATTACCAT CAAAAGCATT AATACAGTTA TGCCGATCGC    4560

AGTTAGAACG GTTATAGCAT CCACCATTTA TATCTAAAAA TTAGATCAAA GAATATGTGA    4620

CAAAGTCCTA GTTGTATACT GAGAATTGAC GAAACAATGT TTCTTACATA TTTTTTTCTT    4680

ATTAGTAACT GACTTAATAG TAGGAACTGG AAAGCTAGAC TTGATTATTC TATAAGTATA    4740

GATACCCTTC CAGATAATGT TCTCTTTGAT AAAAGTTCCA GAAATGTAG AATTTTTTAA    4800

AAAGTTATCT TTTGCTATTA CCAAGATTGT GTTTAGACGC TTATTATTAA TATGAGTAAT    4860

GAAATCCACA CCGCCTCTAG ATATGGGAA TTC                                 4893
```

(2) INFORMATION FOR SEQ ID NO:71:

(i) SEQUENCE CHARACTERISTICS:
        (A) LENGTH: 6749 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

-continued

```
GAGCTCGCGG CCGCCTATCA AAAGTCTTAA TGAGTTAGGT GTAGATAGTA TAGATATTAC    60
TACAAAGGTA TTCATATTTC CTATCAATTC TAAAGTACAT GATATTAATA ACTCAAAGAT   120
GATGATAGTA GATAATAGAT ACGCTCATAT AATGACTGCA AATTTGGACG GTTCACATTT   180
TAATCATCAC GCGTTCATAA GTTTCAACTG CATAGATCAA AATCTCACTA AAAGATAGC    240
CGATGTATTT GAGAGAGATT GGACATCTAA CTACGCTAAA GAAATTACAG TTATAAATAA   300
TACATAATGG ATTTTGTTAT CATCAGTTAT ATTTAACATA AGTACAATAA AAAGTATTAA   360
ATAAAAATAC TTACTTACGA AAAAATGACT AATTAGCTAT AAAAACCCAA CAAAAACTAA   420
TCAGCTATCG GGGTTAATTA ATTAGTTATT AGACAAGGTG AAAACGAAAC TATTTGTAGC   480
TTAATTAATT AGAGCTTCTT TATTCTATAC TTAAAAAGTG AAAATAAATA CAAAGGTTCT   540
TGAGGGTTGT GTTAAATTGA AAGCGAGAAA TAATCATAAA TTATTTCATT ATGGCGATAT   600
CCGTTAAGTT TGTATCGTAA TGGAGTCGCG CGGTCGCCGT TGTCCCGAAA TGATATCCGT   660
ACTGGGTCCC ATTTCGGGGC ACGTGCTGAA AGCCGTGTTT AGTCGCGGCG ACACGCCGGT   720
GCTGCCGCAC GAGACGCGAC TCCTGCAGAC GGGTATCCAC GTGCGCGTGA GCCAGCCCTC   780
GCTGATCCTG GTGTCGCAGT ACACGCCCGA CTCGACGCCA TGCCACCGCG GCGACAATCA   840
GCTGCAGGTG CAGCACACGT ACTTTACGGG CAGCGAGGTG GAGAACGTGT CGGTCAACGT   900
GCACAACCCC ACGGGCCGGA GCATCTGCCC CAGCCAAGAG CCCATGTCGA TCTATGTGTA   960
GCGCGCTGCC GCTCAAGATG CTGAACATCC CCAGCATCAA CGTGCACCAC TACCCGTCGG  1020
CGGCCGAGCG CAAACACCGA CACCTGCCCG TAGCTGACGC TGTGATTCAC GCGTCGGGCA  1080
AGCAGATGTG GCAGGCGCGT CTCACGGTCT CGGGACTGGC CTGGACGCGT CAGCAGAACC  1140
AGTGGAAAGA GCCCGACGTC TACTACACGT CAGCGTTCGT GTTTCCCACC AAGGACGTGG  1200
CACTGCGGCA CGTGGTGTGC GCGCACGAGC TGGTTTGCTC CATGGAGAAC ACGCGCGCAA  1260
CCAAGATGCA GGTGATAGGT GACCAGTACG TCAAGGTGTA CCTGGAGTCC TTCTGCGAGG  1320
ACGTGCCCTC CGGCAAGCTC TTTATGCACG TCACGCTGGG CTCTGACGTG GAAGAGGACC  1380
TGACGATGAC CCGCAACCCG CAACCCTTCA TGCGCCCCCA CGAGCGCAAC GGCTTTACGG  1440
TGTTGTGTCC CAAAAATATG ATAATCAAAC CGGGCAAGAT CTCGCACATC ATGCTGGATG  1500
TGGCTTTTAC CTCACACGAG CATTTTGGGC TGCTGTGTCC CAAGAGCATC CCGGGCCTGA  1560
GCATCTCAGG TAACCTATTG ATGAACGGGC AGCAGATCTT CCTGGAGGTG CAAGCGATAC  1620
GCGAGACCGT GGAACTGCGT CAGTACGATC CCGTGGCTGC GCTCTTCTTT TTCGATATCG  1680
AGCTTGCTGC TGCAGCGCGG GCCTCAGTAC AGCGAACACC CCACCTTCAC CAGCCAGTAT  1740
CGCATCCAGG GCAAGCTTGA GTACCGACAC ACCTGGGACC GGCACGACGA GGGTGCCGCC  1800
CAGGGCGACG ACGACGTCTG GACCAGCGGA TCGGACTCCG ACGAGGAACT CGTAACCACC  1860
GAGGCGCAAG ACGCCCGCG TTACCGGCGG CGGCGCCATG GCGGGCGCCT CCACTTCCGC  1920
GGGCCGCAAA CGCAAATCAG CATCCTCGGC GACGGCGTGC ACGGCGGGCG TTATGACACG  1980
CGGCCGCCTT AAGGCCGAGT CCACCGTCGC GCCCGAAGAG GACACCGACG AGGATTCCGA  2040
CAACGAAATC CACAATCCGG CCGTGTTCAC CTGGCCGCCC TGGCAGGCCG GCATCCTGGC  2100
CCGCAACCTG GTGCCCATGG TGGCTACGGT TCAGGGTCAG AATCTGAAGT ACCAGGAGTT  2160
CTTCTGGGAC GCCAACGACA TCTACCGCAT CTTCGCCGAA TTGGAAGGCG TATGGCAGCC  2220
CGCTGCGCAA CCCAAACGTC GCCGCCACCG GCAAGACGCC TTGCCCGGGC CATGCATCGC  2280
CTCGACGCCC AAAAAGCACC GAGGTTGATT TTTATGGATC CGGTACCCTC GAGGAATTCT  2340
```

```
AGCAATAAAA ACTATTCCTC CGTGTTCTTA ATCTTCTCGA TCTTTTGGAG GATGTTCTGC    2400

ACGGCGTCCG ACGGCGTTTT GGCGCCCCCC ATGCCGGCAG AACCCGGTTG CGGCCCCGTA    2460

CCGCTCTTCT GGGGCGACGA TAGGTCGAAA GCCACCGTTT TCATGCCCGT CGTGCTCTTG    2520

ACGGGGAAC CTACGGCGGC GGTCCCCGTC GAGCGGCGTG ATTGCAAAGC CGCGCTCGCC     2580

CCCGGTTTCA GGATGGAGGG GGAGGCCACA GGCGGCGCAT TCGATACGCT GCTTTTGGCC    2640

GTAGACGACG GTGGGTAAAC GGTGGTTACC GCGGGATACG TCGGCGTGGT CGAGGCGGCC    2700

CGGCTGGTGC CGGACAGGCG ACCCGGCGCG CTACCGCTCA CGGGTACCGA GGGCGGTCGA    2760

CCTACCACCG CCTTGCCGCC CAAAGTAGGT TTCAAAGAAG GAACACCGAC GCGGCTGCCC    2820

CGACCTTTCA CCGGAGACGG AGGGGCACTC TTGGCCGGGG ACGAGAGGC TGACGAAAGC     2880

ATGGACAGCG GCGACGTGAC GGGGGACACG ACATCATCCT CCGTGGGCGA CAAAACGGAC    2940

GCCGAGGCTG ACGGCTGTCG AGCCGAAGCG GAAGAGGTTC TCGCGCCAGA AGTCACGTTC    3000

CTTGATGACG TTGTTTTAGA CGAAGCCGGT TGAGGTTGCA ACAGCGTGGC GGGTACCGTC    3060

GACGGCGTGC CCGATACCTG TTTCTCTACC CTTCCCTGAA CCGGTGTCGA CGTCACCGTC    3120

TGCGCTCGGG CGGACGCGTG CGGCGTCGCG ACTCGCTTGC CCAGCACCGG TTTCTGGCTC    3180

GTGGATGTCG TCGTCATTGG AGACGATAAC TTAGCTTTAC GTATTCTGGA CGGCGTCGAC    3240

TGCTCGGGCG TCTGACTGGG AGGCGAAATG ACGTCGTTGT AATCGGACGA CGGTGTTGTG    3300

TGTCCCAGGC TGACGACGGA GCCGGTGTCC GAGGAGTCGT CGTCTTCCTC CTCGCTGTCT    3360

TCGACCGGTG ACTCTGCAGT TTGGTCCCTT AAAGCCCAAA CCTCATCAGC GGCGTTCTGA    3420

GACGCTGTTT GTGTCACCGC GGCGCGTGGA GTCGACGGCC TCCGAGGGGT GGTGGACACG    3480

TTGTTTTGAG AAGTCGTGGA AGTCGTAGGC ATCCTGAAGG GATTGTAAGC CAGGTGAGGA    3540

TTCTTGAGGG CCCACGCGCG TTCGCGCGGC CAGTTGGCGG GGTTCATATC CCCGGGCAAC    3600

GGCGCCGTCG GAGCCCAGGG CGAGTTACCG TTGACCGGGG TTTGGGTACC CGCGAAGGTA    3660

GGTGTCGGGG CCGGAGCGGG GGCCGTGGAA GGATTGACAG GCGTCGGCGT GAGGATGGCA    3720

GCGCCGGCGC CAGCAGGGAC GTTAACTCCG GCGCCGAACG TCAACGTCGG TTGCTCGAAC    3780

TTGTACGCGG TGGTGACGGG CGGTTTGGCG CTCGTCTCGG TATCCGTGAT GTCCACCAGC    3840

GTGTCGGTGA AACGCGGATC TTGACGGTTG GGGGATAGC CATCCGAGCT GTCGGAATCC     3900

TCGTCGCCCG AGAAAAGATC CCCTCTTGTC TCCGTGAGCG GCCTCACGTC CCACGCGCTG    3960

TCCCGACGGA CCCTTCCCGG GCTGGCCTTG GTTACCTGCG GGGAGACGAG ACTGAAAGCC    4020

GCGTGACGCT GTTGTTGCTG CGGGATGTTC AAGGGACCGC TGGTCGGTTT CTGACTGCCC    4080

GAGGATAACA TGCCGCTGAA AATGCTGAAA ACACCGTTGC CACTAGCGGC GCCCTTGCCG    4140

CTAGTTCCCG GTTTCTTGAT GGGCGTAAAG ATGTTTTTCT CGTCATCATC ATCGTCGTCG    4200

TCCTCATCGG CACTGGAGCC AAAGAGCCTC CGGGAGGCGC CCGGTTTACG TGTCGGGGGC    4260

GGCGGTTGCT GCTGACGTTG CTGCAGGTTC TGCTGCCTCT CCTCCCAAGC CTTCAGCTGC    4320

TGTTTCTCAC GCTGCACCAC CTCGTCGTCC ACCCGTTTCT GCCGCTCGCG ACGCTTTTCC    4380

TCTTCGTCGT AATAGCCGAC GCGCGCCGAA CGGGCGGCGT GGGCGTCGGC GGCCGGTGCC    4440

AGAGAACCAT GGGCCTCGAA GCGGAACGGT TTGTGTCCCT TCCAGGGACT GGCGATCCAG    4500

CTCCAGCCGT CCAGCGGCTG CGTGGGGACA TGTTTCTTGG GTACCGACGA GAAGGCTGAA    4560

CCGCCGCCGA GCGAGAGGAG ATTGCGTCA TCGTCAAACT CCAACGACGG CGGGCGCGCG     4620

CCCAAAAAGG TGTGCGCCGA CTGCGGGAAG CTGTCCACGT AGATGTCAAA GTCCTCGATG    4680

AGCAGCTCCA GCAGCGTGTC GGCCGAGTCA CCGTTTTCCA CGGCGTGTTT GAGGATATTG    4740
```

```
CGACAGTAGT TGGAATCAAA GGAAAGGCAC ATGCGCAGCT CCTTGACCAG CAGCTTGCAG      4800

CGCTCCTGAA TGCGCGCCAG ACATTTGCGC TCCAGCTCCT CCCAAGACCT GCGCACGTTC      4860

ATGATGAGAC GGCCCGTGTA CACGAGCTTG TTGACGGCGT TGACCAGCGC CGTGTTGGCG      4920

TGCCGGTCCA GGTTAAGGTC GAGCGGTTTC ACGCAGAACA TGTTACGGCG CACACCCTCC      4980

AGGTTTTCTT CAATGCGCTG CACCTCCGTA TCCTTGAGGT GCACAAAAGC GATGGGTTCC      5040

GTCTGGCCGA TGGCTGTGAC CAGCGTCTCG CGCACCGACA TCTTGGCCAG AATGACCGCG      5100

CTTACGAGCG CGCGCTCCAC AATCTCACCA TCGTGGCGTA CGTCCGTATC GAATTCGGTA      5160

CGGTCTAGCA CAGCCAGGTG GTCACGCGCC TTACCACGAT CACCGAACGG GTAAGTGTAG      5220

CCGCGACGCG CCACGGCCGC GCAACGCACC TCGAACTCCT CGGAACCGAG GAGAGGTCGG      5280

GGTTGTGGAA ACGCAGCTCG CGGTAGTATC CCAACCAAAG CATGAGCTCG TTGAACAGCA      5340

CCGTACGCCG GTGCAGGCGT TTTTCGCCAC ATTTTTTCAG GATCTTGGGG TGTGCCTCGA      5400

GATCCACGTC GGGCTTTTGC GTGAGATGGC GCAGAAAGTT GACCAGGGCC ACCACATCGC      5460

GCCGCTGTAG ACCGATAAAC TGCAAACTCA TTTTATATTG TAATTATATA TTTTCAATTT      5520

TGAAATCCCA AAATATTATC ATATCTTCCC AATAAAGCTA GAATTCTTTT TATTGATTAA      5580

CTAGTCAAAT GAGTATATAT AATTGAAAAA GTAAATATA  AATCATATAA TAATGAAACG      5640

AAATATCAGT AATAGACAGG AACTGGCAGA TTCTTCTTCT AATGAAGTAA GTACTGCTAA      5700

ATCTCCAAAA TTAGATAAAA ATGATACACC AAATACAGCT TCATTCAACG AATTACCTTT      5760

TAATTTTTTC AGACACACCT TATTACAAAC TAACTAAGTC AGATGATGAG AAAGTAAATA      5820

TAAATTTAAC TATGGGTATA ATATAATAAA GATTCATGAT ATTAATAATT TACTTAACGA      5880

TGTTAATAGA CTTATTCCAT CAACCCCTTC AAACCTTTCT GGATATTATA AATACCAGT      5940

AATGATATTA AAATAGATTG TTTAAGAGAT GTAAATAATT ATTTGGAGGT AAAGGATATA      6000

AAATTAGTCT ATCTTTCACA TGGAAATGAA TTACCTAATA TTAATAATTA TGATAGGAAT      6060

TTTTTAGGAT TTACAGCTGT TATATGTATC AACAATACAG GCAGATCTAT GGTTATGGTA      6120

AAACACTGTA ACGGGAAGCA GCATTCTATG GTAACTGGCC TATGTTTAAT AGCCAGATCA      6180

TTTTACTCTA TAAACATTTT ACCACAAATA ATAGGATCCT CTAGATATTT AATATTTATAT    6240

CTAACAACAA CAAAAAAATT TAACGATGTA TGGCCAGAAG TATTTTCTAC TAATAAAGAT     6300

AAAGATAGTC TATCTTATCT ACAAGATATG AAAGAAGATA ATCATTTAGT AGTAGCTACT    6360

AATATGGAAA GAAATGTATA CAAAAACGTG GAAGCTTTTA TATTAAATAG CATATTACTA    6420

GAAGATTTAA AATCTAGACT TAGTATAACA AAACAGTTAA ATGCCAATAT CGATTCTATA    6480

TTTCATCATA ACAGTAGTAC ATTAATCAGT GATATACTGA AACGATCTAC AGACTCAACT    6540

ATGCAAGGAA TAAGCAATAT GCCAATTATG TCTAATATTT TAACTTTAGA ACTAAAACGT    6600

TCTACCAATA CTAAAAATAG GATACGTGAT AGGCTGTTAA AAGCTGCAAT AAATAGTAAG    6660

GATGTAGAAG AAATACTTTG TTCTATACCT TCGGAGGAAA GAACTTTAGA ACAACTTAAG    6720

TTTAATCAAA CTTGTATTTA TGAAGGTAC                                      6749
```

(2) INFORMATION FOR SEQ ID NO:72:

(i) SEQUENCE CHARACTERISTICS:
        (A) LENGTH: 837 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

```
ATGTGCCGCC GCCCGGATTG CGGCTTCTCT TTCTCACCTG GACCGGTGGC ACTGCTGTGG      60
TGTTGCCTTC TGCTGCCCAT CGTTTCCTCA GCCACCGTCA GCGTCGCTCC TACCGTCGCC     120
GAGAAAGTTC CCGCGGAGTG CCCCGAACTA ACGCGTCGAT GCCTGTTGGG TGAGGTGTTT     180
CAGGGTGACA AGTATGAAAG TTGGCTGCGC CCGTTGGTGA ATGTTACCAG ACGCGATGGC     240
CCGCTATCGC AACTTATTCG TTACCGTCCC GTTACGCCGG AGGCCGCCAA CTCCGTGCTG     300
TTGGACGATG CTTTCCTGGA CACTCTGGCC CTGCTGTACA ACAATCCGGA TCAATTGCGG     360
GCCTTGCTGA CGCTGTTGAG CTCGGACACA GCGCCGCGCT GGATGACGGT GATGCGCGGT     420
TACAGCGAGT GCGGCGATGG CTCGCCGGCC GTGTACACGT GCGTGGACGA CCTGTGCCGC     480
GGCTACGACC TCACGCGACT GTCATACGGG CGCAGCATCT TCACGGAACA CGTGTTAGGC     540
TTCGAGCTGG TGCCACCGTC TCTCTTTAAC GTGGTGGTGG CCATACGCAA CGAAGCCACG     600
CGTACCAACC GCGCCGTGCG TCTGCCCGTG AGCACCGCTG CCGCGCCCGA GGGCATCACG     660
CTCTTTTACG GCCTGTACAA CGCAGTGAAG GAATTCTGCC TGCGTCACCA GCTGGACCCG     720
CCGCTGCTAC GCCACCTAGA TAAATACTAC GCCGGACTGC CGCCCGAGCT GAAGCAGACG     780
CGCGTCAACC TGCCGGCTCA CTCGCGCTAT GGCCCTCAAG CAGTGGATGC TCGCTAA       837
```

(2) INFORMATION FOR SEQ ID NO:73:

(i) SEQUENCE CHARACTERISTICS:
        (A) LENGTH: 5234 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

```
AAGCTTTTGC GATCAATAAA TGGATCACAA CCAGTATCTC TTAACGATGT TCTTCGCAGA      60
TGATGATTCA TTTTTTAAGT ATTTGGCTAG TCAAGATGAT GAATCTTCAT TATCTGTATAT    120
ATTGCAAATC ACTCAATATC TAGACTTTCT GTTATTATTA TTGATCCAAT CAAAAAATAA    180
ATTAGAAGCC GTGGGTCATT GTTATGAATC TCTTTCAGAG GAATACAGAC AATTGACAAA    240
ATTCACAGAC TCTCAAGATT TTAAAAAACT GTTTAACAAG GTCCCTATTG TTACAGATGG    300
AAGGGTCAAA CTTAATAAAG GATATTTGTT CGACTTTGTG ATTAGTTTGA TGCGATTCAA    360
AAAAGAATCC TCTCTAGCTA CCACCGCAAT AGATCCTATT AGATACATAG ATCCTCGTCG    420
CGATATCGCA TTTTCTAACG TGATGGATAT ATTAAAGTCG AATAAAGTGA ACAATAATTA    480
ATTCTTTATT GTCATCATGT AATTAACTAG CTACCCGGGA GATCTCTCGA GCTGCAGAAG    540
CTTATAAAAA TCACAAGTCT CTGTCACTTT TTTTGTCTAG TTTTTTTTTC TCCTCTTGGT    600
TCAGACGTTC TCTTCTTCGT CGGAGTCTTT CAAGTGTCGG TAGCCGTTTT TGCGGTGTCG    660
CAGTCGGTCT AGCAGGTTGG GCTTCTGTCC CTTGTCCTGC GTGCCAGTCT GTCCGTCCAA    720
AGAATCTGTA CCGTTCTCGT GCGCTCGCTG CTCTGCGTCC AGACGGACCA GGGCCAGAAG    780
CATCTGGTAA GCCTGCTCGT TGGTGTAAGG CGGAGCCGCC GTGGATGCAT CAGACGACGG    840
TGGTCCCGGT CCTTTGCGAC CAGAATTATA AACACTTTCC TCGTAGGAAG GCGGAGCCTG    900
TAACGACGTG TCTTTGGTGT GCCCGACGT CACGGTGGTC CCGTCGGCGG ACACCAGATA    960
GGGAAAGAGG TTCTGCAGCG GCTGCATGCA GAGACGCCGC TGTCGAGTAT AGATCAAATA   1020
AATGATAATG ACGACGGCTA TGGCCACGAG GATGATGGTG AAGGCTCCGA AGGGGTTTTT   1080
```

```
GAGGAAGGTG GCAACGCCTT CGACCACGGA GGCCACCGCG CCACCCACGG CCCCAATGGC    1140

TACGCCAACG GCCTTTCCCG CGGCGCCCAG GCCGCTCATG AGGTCGTCCA GACCCTTGAG    1200

GTAGGGCGGC AGCGGGTCGA CTACCTTGTC CTCCACGTAC TTTACCCGCT GCTTATACGA    1260

ATTGAACTCG CGCATGATCT CCTCGAGATC AAAAACGTTG CTGGAACGCA ATTCTTTCTG    1320

CGAGTAAAGT TCCAGTACCC TGAAGTCGGT GTTTTCCAGC GGGTCGATGT CTAGGGCGAT    1380

CATGCTGTCG ACGGTGGAGA TGCTGCTGAG GTCAATCATG CGTTTGAAGA GGTAGTCCAC    1440

GTACTCGTAG GCCGAGTTGC CGGCGATGAA GATCTTGAGG CTGGGAAGCT GACATTCCTC    1500

AGTGCGGTGG TTGCCCAACA GGATTTCGTT ATCCTCGCCC AGTTGACCGT ACTGCACGTA    1560

CGAGCTGTTG GCGAAATTAA AGATGACCAC TGGTCGTGAG TAGCAGCGTC CTGGCGATTC    1620

CTTCACATTC ATATCACGCA GCACCTTGAC GCTGGTTTGG TTAATGGTCA CGCAGCTGGC    1680

CAGACCCAGG ACATCACCCA TGAAACGCGC GGCAATCGGT TTGTTGTAGA TGGCCGAGAG    1740

AATAGCTGAC GGGTTGATCT TGCTAAGTTC CTTGAAGACC TCTAGGGTGC GCCGTTGATC    1800

CACACACCAG GCTTCTGCGA TTTCGGCCAG CGCCCGGTTG ATGTAACCGC GCAACGTGTC    1860

ATAGGTGAAC TGCAGCTGGG CGTAGACCAG ATTGTGCACC GACTCCATGT TGGATAAATG    1920

AGTTGCATTG TTGCCATCTG TACTTCTTTT GGTTCTATTA TGAGTAAGAT TCAGACTGGA    1980

GCGGTTGGCC AAACGTTCGA GTTCCACCAG AGATTTTTGC TTGATACCTT GCCAGAACAC    2040

CACCAAACCA CCAGTGGTTT CAAAGACGGA CACGTTCCA TATTTTTCAT ATGTTTGATT    2100

GTATGAAGTA TTGAAAATCT GCTGTAACTT ATTTATGGCC TCATCACGTA CACAGTCCAG    2160

CGCAGAGTCG GACATGTTCA CCTCTTGCTT CTTAGATAAG AAAGTGGCGG TCATTTTGGC    2220

AGAAGAAAAG TGATACGAGT CCTCGGCTTC GGAACGAATG GTGCGTTCCG AGGCTTCCCA    2280

GAAAGTGAGT TGACAAGTAA CATTCTTCTC GTCCTGTATA TCCCAGGAGA TCACTGAGTC    2340

CGCACGTTCA AGAAAAGCCA CCAACCTGTG GGTCTCTAAC GCAGAATTCG GTCTTTCAAA    2400

GTCGGAGACG ATAGTGTAGT TCGGAAAAAT GAAAAACTTG TCGGCGTTTT CTCCAAAATA    2460

GCTGGCATTG CGATTAGTTC CGTTGTAGAA AGGAGAAATG TCAACCACAT CACCCGTGGA    2520

AGTTGCGAAA AAATGATAGG GATACTTGGA GCGCGCAGTA GTGATGGTCA CCATACAATT    2580

CAGATTACAG GTCTCACGAT AGAGCCAGGT GCTGCCGCGG CTGTGCCATT GATCCTTGAC    2640

CGTCACGTAA CGGGTACTGT GGGTGTTGGA ATAATCGTCG GGCATTAATT GCATGGTTTT    2700

GTTTTCATAG CTGTCCCTAT GATAAGCCAC GAAAACCGTG CCTGCTATAA CGCGGCTGTA    2760

GGAACTGTAG CACTGACTGT GACTGTTGAT ATGATGAATC TCCCACATAG GAGGCGCCAC    2820

GTATTCCGTG TTGCTGCCCA GCAGATAAGT GGTGTGGATG TAAGCGTAGC TACGACGAAA    2880

CGTCAAAACC TTCTGGTAGA CTCGTACCTT AAAGGTGTGC GCGACGATGT TGCGTTTGTA    2940

GACCACCATG ATGCCCTCGT CCAGGTCTTC ATTGATGGGC TTCATCGAGG TGCAGACGAT    3000

ATTACGTTCA AAGCGAATAA GATCCGTACC CTGTGCCATA GAACACACGC GATAGGGTA    3060

CTTGGTGGTG TTGACCCCCA CCACATCTCC GTACTTGAGG GTAGTGTTGT AGATGGTCTC    3120

GTTAACACCA TGGCTGACCG TTTGGGAAGA AGTTACGCGT TGAGAGACTG AACCGGATCG    3180

AGAATGAGCA GCAGACGTCG TATGAGAGGA ATGGTGACTG TGAGTAGCAG AAGTTCCACG    3240

AGTAGAAGAT GAGGAAACCG CAGCACCCAG ACAGACGATA CACAAGTTAA CGCAGACTAC    3300

CAGGCACCAG ATCCTGGATT CCATTACGAT ACAAACTTAA CGGATATCGC GATAATGAAA    3360

TAATTTATGA TTATTTCTCG CTTTCAATTT AACACAACCC TCAAGAACCT TTGTATTTAT    3420
```

```
TTTCACTTTT AAGTATAGAA TAAAGAAGCT TGCATGCCAC GCGTCTCGAG GGCCCCTGCA    3480

GGTCGACTCT AGAGGATCCT TCTTTATTCT ATACTTAAAA AGTGAAAATA AATACAAAGG    3540

TTCTTGAGGG TTGTGTTAAA TTGAAAGCGA GAAATAATCA TAAATTATTT CATTATCGCG    3600

ATATCCGTTA AGTTTGTATC GTAATGTGCC GCCGCCCGGA TTGCGGCTTC TCTTTCTCAC    3660

CTGGACCGGT GGCACTGCTG TGGTGTTGCC TTCTGCTGCC CATCGTTTCC TCAGCCACCG    3720

TCAGCGTCGC TCCTACCGTC GCCGAGAAAG TTCCCGCGGA GTGCCCCGAA CTAACGCGTC    3780

GATGCCTGTT GGGTGAGGTG TTTCAGGGTG ACAAGTATGA AAGTTGGCTG CGCCCGTTGG    3840

TGAATGTTAC CAGACGCGAT GGCCCGCTAT CGCAACTTAT TCGTTACCGT CCCGTTACGC    3900

CGGAGGCCGC CAACTCCGTG CTGTTGGACG ATGCTTTCCT GGACACTCTG GCCCTGCTGT    3960

ACAACAATCC GGATCAATTG CGGGCCTTGC TGACGCTGTT GAGCTCGGAC ACAGCGCCGC    4020

GCTGGATGAC GGTGATGCGC GGTTACAGCG AGTGCGGCGA TGGCTCGCCG GCCGTGTACA    4080

CGTGCGTGGA CGACCTGTGC CGCGGCTACG ACCTCACGCG ACTGTCATAC GGGCGCAGCA    4140

TCTTCACGGA ACACGTGTTA GGCTTCGAGC TGGTGCCACC GTCTCTCTTT AACGTGGTGG    4200

TGGCCATACG CAACGAAGCC ACGCGTACCA ACCGCGCCGT GCGTCTGCCC GTGAGCACCG    4260

CTGCCGCGCC CGAGGGCATC ACGCTCTTTT ACGGCCTGTA CAACGCAGTG AAGGAATTCT    4320

GCCTGCGTCA CCAGCTGGAC CCGCCGCTGC TACGCCACCT AGATAAATAC TACGCCGGAC    4380

TGCCGCCCGA GCTGAAGCAG ACGCGCGTCA ACCTGCCGGC TCACTCGCGC TATGGCCCTC    4440

AAGCAGTGGA TGCTCGCTAA TTTTTATAGA TCCTGATCCT TTTTCTGGGT AAGTAATACG    4500

TCAAGGAGAA AACGAAACGA TCTGTAGTTA GCGGCCGCCT AATTAACTAA TATTATATTT    4560

TTTATCTAAA AAACTAAAAA TAAACATTGA TTAAATTTTA ATATAATACT TAAAAATGGA    4620

TGTTGTGTCG TTAGATAAAC CGTTTATGTA TTTTGAGGAA ATTGATAATG AGTTAGATTA    4680

CGAACCAGAA AGTGCAAATG AGGTCGCAAA AAAACTGCCG TATCAAGGAC AGTTAAAACT    4740

ATTACTAGGA GAATTATTTT TTCTTAGTAA GTTACAGCGA CACGGTATAT TAGATGGTGC    4800

CACCGTAGTG TATATAGGAT CGGCTCCTGG TACACATATA CGTTATTTGA GAGATCATTT    4860

CTATAATTTA GGAATGATTA TCAAATGGAT GCTAATTGAC GGACGCCATC ATGATCCTAT    4920

TTTAAATGGA TTGCGTGATG TGACTCTAGT GACTCGGTTC GTTGATGAGG AATATCTACG    4980

ATCCATCAAA AAACAACTGC ATCCTTCTAA GATTATTTTA ATTTCTGATG TGAGATCCAA    5040

ACGAGGAGGA AATGAACCTA GTACGGCGGA TTTACTAAGT AATTACGCTC TACAAAATGT    5100

CATGATTAGT ATTTTAAACC CCGTGGCGTC TAGTCTTAAA TGGAGATGCC CGTTTCCAGA    5160

TCAATGGATC AAGGACTTTT ATATCCCACA CGGTAATAAA ATGTTACAAC CTTTTGCTCC    5220

TTCATATTCA GCTG                                                     5234
```

(2) INFORMATION FOR SEQ ID NO:74:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

```
GCCTCATCGC TGCTGGATAT CCGTTAAGTT TGTATCGTAA TGGAATCCAG GATCTG       56
```

(2) INFORMATION FOR SEQ ID NO:75:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

GACAGAGACT TGTGATTTTT ATAAGCTTCG TAAGCTGTCA                              40

(2) INFORMATION FOR SEQ ID NO:76:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

AGCTTCTTTA TTCTATACTT AAAAAGTGAA AATAAATACA AAGGTTCTTG AGGGT            55

(2) INFORMATION FOR SEQ ID NO:77:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

TGTGTTAAAT TGAAAGCGAG AAATAATCAT AAATTATTTC ATTATCGCGA TATCCGTTAA       60

GTTTGTATCG TAC                                                          73

(2) INFORMATION FOR SEQ ID NO:78:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

TTATTAGTAT TTAATAAAGT AATAGCGCTA TAGGCAATTC AAACATAGCA TGAGCT           56

(2) INFORMATION FOR SEQ ID NO:79:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

AGAAATAAGA TATGAATTTT TCACTTTTAT TTATGTTTCC AAGAACTCCC AACACAATTT       60

AACTTTCGCT CT                                                           72

(2) INFORMATION FOR SEQ ID NO:80:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

GGTCGACGGA TCCT                                                           14

(2) INFORMATION FOR SEQ ID NO:81:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:81:

GATCAGGATC CGTCGACCTG CA                                                  22

(2) INFORMATION FOR SEQ ID NO:82:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

CAGTTGGTAC CACTGGTATT TTATTTCAG                                           29

(2) INFORMATION FOR SEQ ID NO:83:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

TATCTGAATT CCTGCAGCCC GGGTTTTTAT AGCTAATTAG TCAAATGTGA GTTAATATTA         60

G                                                                         61

(2) INFORMATION FOR SEQ ID NO:84:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

TCGCTGAATT CGATATCAAG CTTATCGATT TTTATGACTA GTTAATCAAA TAAAAAGCAT         60

ACAAGC                                                                    66

(2) INFORMATION FOR SEQ ID NO:85:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:85:

TTATCGAGCT CTGTAACATC AGTATCTAAC                                30

(2) INFORMATION FOR SEQ ID NO:86:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

TCCGGTACCG CGGCCGCAGA TATTTGTTAG CTTCTGC                         37

(2) INFORMATION FOR SEQ ID NO:87:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

TCGCTCGAGT AGGATACCTA CCTACTACCT ACG                             33

(2) INFORMATION FOR SEQ ID NO:88:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

TCGCTCGAGC TTTCTTGACA ATAACATAG                                  29

(2) INFORMATION FOR SEQ ID NO:89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:89:

TAGGAGCTCT TTATACTACT GGGTTACAAC                                 30

(2) INFORMATION FOR SEQ ID NO:90:

(i) SEQUENCE CHARACTERISTICS:
        (A) LENGTH: 17 base pairs
        (B) TYPE: nucleic acid (C) STRANDEDNESS: single
         (D) TOPOLOGY: linear (ii) MOLECULE TYPE: DNA (genomic)

(xi) SEQUENCE DESCRIPTION: SEQ ID NO:90:

AATTCCTCGA GGGATCC                                                      17

(2) INFORMATION FOR SEQ ID NO:91:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

CGGGATCCCT CGAGG                                                        15

(2) INFORMATION FOR SEQ ID NO:92:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

TCGGGATCCG GGTTAATTAA TTAGTTATTA GACAAGGTG                              39

(2) INFORMATION FOR SEQ ID NO:93:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:93:

TAGGAATTCC TCGAGTACGA TACAAACTTA AGCGGATATC G                           41

(2) INFORMATION FOR SEQ ID NO:94:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:94:

GGGCTGAAGC TTGCTGGCCG CTCATTAGAC AAGCGAATGA GGGAC                       45

(2) INFORMATION FOR SEQ ID NO:95:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:95:

AGATCTCCCG GGCTCGAGTA ATTAATTAAT TTTTATTACA CCAGAAAAGA CGGCTTGAGA    60

TC                                                                  62

(2) INFORMATION FOR SEQ ID NO:96:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:96:

TAATTACTCG AGCCCGGGAG ATCTAATTTA ATTTAATTTA TATAACTCAT TTTTTGAATA    60

TACT                                                                64

(2) INFORMATION FOR SEQ ID NO:97:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:97:

TATCTCGAAT TCCCGCGGCT TTAAATGGAC GGAACTCTTT TCCCCC                   46

(2) INFORMATION FOR SEQ ID NO:98:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:98:

GATCTTTTGT TAACAAAAAC TAATCAGCTA TCGCGAATCG ATTCCCGGGG GATCCGGTAC    60

CC                                                                  62

(2) INFORMATION FOR SEQ ID NO:99:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:99:

TCGAGGGTAC CGGATCCCCC GGGAATCGAT TCGCGATAGC TGATTAGTTT TGTTAACAA    60

AA                                                                  62

(2) INFORMATION FOR SEQ ID NO:100:

(i) SEQUENCE CHARACTERISTICS:
        (A) LENGTH: 46 base pairs
        (B) TYPE: nucleic acid (C) STRANDEDNESS: single
                (D) TOPOLOGY: linear (ii) MOLECULE TYPE: DNA (genomic)

(xi) SEQUENCE DESCRIPTION: SEQ ID NO:100:

GATCCATGGA CTCGACAGCG GCGTCTCTGC ATGCAGCCGC TGCAGA         46

(2) INFORMATION FOR SEQ ID NO:101:

(i) SEQUENCE CHARACTERISTICS:
                (A) LENGTH: 46 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:101:

AGCTTCTGCA GCGGCTGCAT GCAGAGACGC CGCTGTCGAG TCCATG         46

(2) INFORMATION FOR SEQ ID NO:102:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:102:

TACGAATTCT GCAGTTCACC TATGACACGT TGC         33

(2) INFORMATION FOR SEQ ID NO:103:

(i) SEQUENCE CHARACTERISTICS:
                (A) LENGTH: 37 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:103:

ATAGGATCCA TGGTCGTCCA GACCCTTGAG GTAGGGC         37

(2) INFORMATION FOR SEQ ID NO:104:

(i) SEQUENCE CHARACTERISTICS:
                (A) LENGTH: 48 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:104:

GCCCTACCTC AAGGGTCTGG ACGACACTCG ACAGCGGCGT CTCTGCAT         48

(2) INFORMATION FOR SEQ ID NO:105:

(i) SEQUENCE CHARACTERISTICS:
                (A) LENGTH: 12 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:105:

AATTGGTGAC CG                                                                    12

(2) INFORMATION FOR SEQ ID NO:106:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:106:

GATCCGGTCA CC                                                                    12

(2) INFORMATION FOR SEQ ID NO:107:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:107:

TGAAAGACCG AATTCTGCGT                                                            20

(2) INFORMATION FOR SEQ ID NO:108:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:108:

TGCGATTCAT CGGTTTGTTG TAGAT                                                      25

(2) INFORMATION FOR SEQ ID NO:109:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:109:

GACCCTTGAG GTAGGGCGGC                                                            20

(2) INFORMATION FOR SEQ ID NO:110:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:110:

ACTCATAATA GAACCATAAG ATCTACAGAT GGCAACAAT                                       39

(2) INFORMATION FOR SEQ ID NO:111:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

TATCTGCAGA TGCGGCCAGG CCTCCCCTCC TAC                            33

(2) INFORMATION FOR SEQ ID NO:112:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:112:

CCGAAGCTTT CAGCATGTCT TGAGCATGC                                29

(2) INFORMATION FOR SEQ ID NO:113:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:113:

CTCAAGACAT GCTGATTTTT ATCTCGAGA                                29

(2) INFORMATION FOR SEQ ID NO:114:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

AGCTTCTCGA GATAAAAATC AGCATGTCTT GAGCATG                      37

(2) INFORMATION FOR SEQ ID NO:115:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

AATTCTCGAG TTTATTGGGA AGAATATGAT AATATTTTGG GATTTC           46

(2) INFORMATION FOR SEQ ID NO:116:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:116:

AAAATTGAAA ATATATAATT ACAATATAAA ATGCGGCCCG GG                              42

(2) INFORMATION FOR SEQ ID NO:117:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:117:

GATCCCCGGG CCGCATTTTA TATTGTAATT ATAT                                      34

(2) INFORMATION FOR SEQ ID NO:118:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:118:

ATTTTCAATT TTGAAATCCC AAAATATTAT CATATTCTTC CCAATAAACT CGAG                 54

(2) INFORMATION FOR SEQ ID NO:119:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:119:

TTAGAATTCC CCGGGCTCCC CTCCTACCTC ATCGT                                     35

(2) INFORMATION FOR SEQ ID NO:120:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:120:

TTACTGCAGT AAGTGTTAAG TCTCTGTTGG TATC                                      34

(2) INFORMATION FOR SEQ ID NO:121:

(i) SEQUENCE CHARACTERISTICS:
        (A) LENGTH: 66 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:121:

AGAAAAATCA GTTAGCTAAG ATCTCCCGGG CTCGAGGGTA CCGGATCCTG ATTAGTTAAT    60

TTTTGT    66

(2) INFORMATION FOR SEQ ID NO:122:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:122:

GATCACAAAA ATTAACTAAT CAGGATCCGG TACCCTCGAG CCCGGGAGAT CTTAGCTAAC    60

TGATTTTTCT    70

(2) INFORMATION FOR SEQ ID NO:123:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:123:

ATCATCGAAT TCTGAATGTT AAATGTTATA CTTTG    35

(2) INFORMATION FOR SEQ ID NO:124:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:124:

GGGGGTACCT TTGAGAGTAC CACTTCAG    28

(2) INFORMATION FOR SEQ ID NO:125:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:125:

GGGTCTAGAG CGGCCGCTTA TAAAGATCTA AAATGCATAA TTTC    44

(2) INFORMATION FOR SEQ ID NO:126:

(i) SEQUENCE CHARACTERISTICS:
        (A) LENGTH: 35 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:126:

ATCATCCTGC AGGTATTCTA AACTAGGAAT AGATG                                   35

(2) INFORMATION FOR SEQ ID NO:127:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

GTACGTGACT AATTAGCTAT AAAAAGGATC CGGTACCCTC GAGTCTAGAA TCGATCCCGG         60

GTTTTTATGA CTAGTTAATC AC                                                 82

(2) INFORMATION FOR SEQ ID NO:128:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

GGCCGTGATT AACTAGTCAT AAAAACCCGG GATCGATTCT AGACTCGAGG GTACCGGATC         60

CTTTTTATAG CTAATTAGTC AC                                                 82

(2) INFORMATION FOR SEQ ID NO:129:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

GATCTTAATT AATTAGTCAT CAGGCAGGGC GAGAACGAGA CTATCTGCTC GTTAATTAAT         60

TAGGTCGACG                                                               70

(2) INFORMATION FOR SEQ ID NO:130:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

GATCCGTCGA CCTAATTAAT TAACGAGCAG ATAGTCTCGT TCTCGCCCTG CCTGATGACT         60

AATTAATTAA                                                               70

(2) INFORMATION FOR SEQ ID NO:131:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:131:

AATTGCGGCC GC                                                              12

(2) INFORMATION FOR SEQ ID NO:132:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:132:

ATAAAAATTA GCTACTCAGG TACCCTGCAG TCGCGAGGAT CCGAATTCCC CGGGCTCGAG          60

TGATTAATTA GTTTTTAT                                                        78

(2) INFORMATION FOR SEQ ID NO:133:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:133:

ATAAAAACTA ATTAATCACT CGAGCCCGGG GAATTCGGAT CCTCGCGACT GCAGGGTACC          60

TGAGTAGCTA ATTTTTAT                                                        78

(2) INFORMATION FOR SEQ ID NO:134:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:134:

ACGGATCCAT AAAAATTACT GGTCAGCCTT GCTTC                                     35

(2) INFORMATION FOR SEQ ID NO:135:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:135:

ATCCGTTAAG TTTGTATCGT AATGGAGTCC TCTGCCAAGA GA                             42

(2) INFORMATION FOR SEQ ID NO:136:

```
    (i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:136:

CGCGAATTCT CGCGATATCC GTTAAGTTTG TATCGTAATG GAGT                44

(2) INFORMATION FOR SEQ ID NO:137:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:137:

GCCTCTAGAG TTAACCTCCT TCCTCAACAT                                30

(2) INFORMATION FOR SEQ ID NO:138:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:138:

CGGTCTAGAG GTTATCAGTG TAATGAAGC                                 29

(2) INFORMATION FOR SEQ ID NO:139:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:139:

CCGAAGCTTC TCGAGATAAA AATTACTGGT CAGCCTTGCT TCTAGT              46

(2) INFORMATION FOR SEQ ID NO:140:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:140:

CGATATCCGT TAAGTTTGTA TCGTAATCTG CAGCCCGGGG GGG                 43

(2) INFORMATION FOR SEQ ID NO:141:

(i) SEQUENCE CHARACTERISTICS:
        (A) LENGTH: 44 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:141:

GATCCCCCGG GCTGCAGATT ACGATACAAA CTTAACGGAT ATCG 44

(2) INFORMATION FOR SEQ ID NO:142:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:142:

CGCGAATTCT CGCGATATCC GTTAAGTTTG TATCGTAATG AAACAGATTA AGGTTCGAGT 60

(2) INFORMATION FOR SEQ ID NO:143:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:143:

GCCTCTAGAT GCCGCCATGG CCTGACT 27

(2) INFORMATION FOR SEQ ID NO:144:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:144:

TCGGGATCCG GGTTAATTAA TTAGTCATCA GGCAGGGCG 39

(2) INFORMATION FOR SEQ ID NO:145:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:145:

TAGCTCGAGG GTACCTACGA TACAAACTTA ACGGATATCG 40

(2) INFORMATION FOR SEQ ID NO:146:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:146:

TCGGGATCCT TCTTTATTCT ATACTTA                                              27

(2) INFORMATION FOR SEQ ID NO:147:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:147:

AATTCTCGCG ATATCCGTTA AGTTTGTATC GTAATGACGA CGTTCCTGCA GACTATGTTG          60

AGGAAGGAGG TT                                                              72

(2) INFORMATION FOR SEQ ID NO:148:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:148:

AACCTCCTTC CTCAACATAG TCTGCAGGAA CGTCGTCATT ACGATACAAA CTTAACGGAT          60

ATCGCGAG                                                                   68

(2) INFORMATION FOR SEQ ID NO:149:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:149:

CCCCCCGAAT TCGTCGACGA TTGTTCATGA TGGCAAGAT                                 39

(2) INFORMATION FOR SEQ ID NO:150:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:150:

CCCGGGGAT CCCTCGAGGG TACCAAGCTT AATTAATTAA ATATTAGTAT AAAAAGTGAT           60

TTATTTTT                                                                   68

(2) INFORMATION FOR SEQ ID NO:151:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:151:

AAGCTTGGTA CCCTCGAGGG ATCCCCCGGG TAGCTAGCTA ATTTTTCTTT TACGTATTAT    60

ATATGTAATA AACGTTC    77

(2) INFORMATION FOR SEQ ID NO:152:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:152:

TTTTTTCTGC AGGTAAGTAT TTTTAAAACT TCTAACACC    39

(2) INFORMATION FOR SEQ ID NO:153:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:153:

GATTATCGCG ATATCCGTTA AGTTTGTATC GTAATGGCAT CCGTACTGGG TCCCATTTCG    60

GG    62

(2) INFORMATION FOR SEQ ID NO:154:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:154:

GCATAGGTAC CGGATCCATA AAAATCAACC TCGGTGCTTT TTGGGCG    47

(2) INFORMATION FOR SEQ ID NO:155:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:155:

TAGTTCGGAT CCCCGCTCAG TCGCCTACA    29

(2) INFORMATION FOR SEQ ID NO:156:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:156:

ATCAAGGGAT CCATCGAAAA AGAAGAGCG                                        29

(2) INFORMATION FOR SEQ ID NO:157:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:157:

GATTATCGCG ATATCCGTTA AGTTTGTATC GTAATGGAGT CGCGCGGTCG CCGTTGTCCC        60

G                                                                      61

(2) INFORMATION FOR SEQ ID NO:158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:158:

ACCTGCATCT TGGTTGC                                                     17

(2) INFORMATION FOR SEQ ID NO:159:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:159:

ATCATCGAGC TCGCGGCCGC CTATCAAAAG TCTTAATGAG TT                          42

(2) INFORMATION FOR SEQ ID NO:160:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:160:

GAATTCCTCG AGCTGCAGCC CGGGTTTTTA TAGCTAATTA GTCATTTTTT CGTAAGTAAG        60

TATTTTATTT AA                                                          72

(2) INFORMATION FOR SEQ ID NO:161:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:161:

CCCGGGCTGC AGCTCGAGGA ATTCTTTTTA TTGATTAACT AGTCAAATGA GTATATATAA      60

TTGAAAAAGT AA      72

(2) INFORMATION FOR SEQ ID NO:162:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:162:

GATGATGGTA CCTTCATAAA TACAAGTTTG ATTAAACTTA AGTTG      45

(2) INFORMATION FOR SEQ ID NO:163:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:163:

TTCGGATCCG GTTCTGGAGA AAAGCC      26

(2) INFORMATION FOR SEQ ID NO:164:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:164:

GCTTCCAAGC TTTCCTGAAG GGATTGTAAG CC      32

(2) INFORMATION FOR SEQ ID NO:165:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:165:

TTCGGATCCG GCTTTCAGTC TCGTCTCC      28

(2) INFORMATION FOR SEQ ID NO:166:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:166:

TTCGGATCCA TGCAATTGCC CGCGGACAAC                                    30

(2) INFORMATION FOR SEQ ID NO:167:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:167:

TTCGAATTCG CTAGCTTTAT TGGGAAGAAT ATGATAATAT TTTGGGATTT CAAAATTGAA    60

AATATATAAT TACAATATAA AATGAGTTTG CAGTTTATC                          99

(2) INFORMATION FOR SEQ ID NO:168:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:168:

TTCTCTAGAT GAGCTCGTTG AACAGCAC                                      28

(2) INFORMATION FOR SEQ ID NO:169:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:169:

CCGAAGCTTG CTAGCAATAA AAACTATTCC TCCGTGTTCT TAAT                     44

(2) INFORMATION FOR SEQ ID NO:170:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:170:

GCCTCTAGAT ACGTAAAGCT AAGTTATC                                      28

(2) INFORMATION FOR SEQ ID NO:171:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:171:

```
GCCTCTAGAA TGTGCCGCCG CCCGGATTGC                                          30

(2) INFORMATION FOR SEQ ID NO:172:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:172:

CGCAAGCTTA GCGAGCATCC ACTGCTTGAG GGC                                      33

(2) INFORMATION FOR SEQ ID NO:173:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:173:

TCCAAGCTTA GATCTATAAA AATTAGCGAG CATCCACTGC TTGAGGGCCA TAGC               54

(2) INFORMATION FOR SEQ ID NO:174:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:174:

GCCTCTAGAT GCTGACGCTG TTGAGCTCGG AC                                       32

(2) INFORMATION FOR SEQ ID NO:175:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:175:

CGCGAATTCT CGCGATATCC GTTAAGTTTG TATCGTAATG TGCCGCCGCC CGGATTGC           58

(2) INFORMATION FOR SEQ ID NO:176:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:176:

GCCTCTAGAT TCCAGCGCGG CGCTGTGTCC GAGC                                     34
```

RECOMBINANT POXVIRUS—CYTOMEGALOVIRUS COMPOSITIONS AND USES

RELATED APPLICATIONS

This application is a continuation of application Ser. No. 08/471,014, filed Jun. 6, 1995 now abandoned, which in turn is a continuation-in-part of application Ser. No. 08/105,483, filed Aug. 12, 1993 and issued Feb. 27, 1996 as U.S. Pat. No. 5,494,807, which in turn is a continuation of application Ser. No. 07/847,951, filed Mar. 6, 1992 now abandoned, which in turn is a continuation-in-part of application Ser. No. 07/713,967 filed Jun. 11, 1991 now abandoned, which in turn is a continuation-in-part of application Ser. No. 07/666,056, filed Mar. 7, 1991 now abandoned; application Ser. No. 08/036,217, filed Mar. 24, 1993, was a continuation of application Ser. No. 07/666,056 and issued Nov. 15, 1994 as U.S. Pat. No. 5,364,773. This application is also a continuation-in-part of U.S. application Ser. No. 08/124,668, filed Sep. 21, 1993, U.S. Pat. No. 5,482,713,which was a divisional of application Ser. No. 07/502,834, filed Apr. 4, 1990, now U.S. Pat. No. 5,338,683; application Ser. No. 07/502,834 was a continuation-in-part of application Ser. No. 07/394,488, filed Aug. 16, 1989, now abandoned which was a continuation-in-part of application Ser. No. 07/339,004, filed Apr. 17, 1989 now abandoned; and, a continuation-in-part of application Ser. No. 07/090,209, filed Aug. 27, 1987 now abandoned, which was a division of application Ser. No. 06/622, 135, filed Jun. 19, 1984, now U.S. Pat. No. 4,722,848, which was a continuation-in-part of application Ser. No. 06/446,824, filed Dec. 8, 1982, now U.S. Pat. No. 4,603,112, which was a continuation-in-part of U.S. application Ser. No. 06/334,456, filed Dec. 24, 1981, now U.S. Pat. No. 4,769,330. Each of the aforementioned and above-referenced application and patents are hereby incorporated herein by reference.

FIELD OF THE INVENTION

The present invention relates to a modified poxvirus and to methods of making and using the same; for instance, a vaccinia virus or avipox (e.g. canarypox or fowlpox), e.g., modified recombinant poxvirus-cytomegalovirus (CMV), e.g, human cytomegalovirus (HCMV) such as an attenuated recombinant, especially a NYVAC or ALVAC CMV or HCMV recombinant. More in particular, the invention relates to improved vectors for the insertion and expression of foreign genes for use as safe immunization vehicles to elicit an immune response against CMV or HCMV virus. Thus, the invention relates to a recombinant poxvirus, which virus expresses gene products of CMV or HCMV and to immunogenic compositions which induce an immunological response against CMV or HCMV infections when administered to a host, or in vitro (e.g., ex vivo modalities) as well as to the products of expression of the poxvirus which by themselves are useful for eliciting an immune response e.g., raising antibodies, which antibodies are useful against CMV or HCMV infection, in either seropositive or seronegative individuals, or which expression products or antibodies elicited thereby, isolated from an animal or human or cell culture as the case may be, are useful for preparing a diagnostic kit, test or assay for the detection of the virus, or of infected cells, or, of the expression of the antigens or products in other systems. The isolated expression products are especially useful in kits, tests or assays for detection of antibodies in a system, host, serum or sample, or for generation of antibodies. The poxvirus recombinants preferably contain DNA coding for any or all of CMV or HCMVgB, gH, gL, pp105, pp65 and IE1, including recombinants expressing truncated versions of IE1; and, the recombinant poxvirus DNA is useful for probes for CMV or HCMV or for preparing PCR primers for detecting the presence or absence of CMV or HCMV or antigens thereof.

Several publications are referenced in this application. Full citation to these references is found at the end of the specification immediately preceding the claims or where the publication is mentioned; and each of these publications is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,762,330, 4,723,848, 4,603,112, 5,110,587, and 5,174, 993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, $TK^-$ recombinant vaccinia generated equivalent anti-vaccinia neutralizing antibodies as compared with the parental $TK^+$ vaccinia virus, indicating that in this test system the loss of TK function does not significantly decrease immunogenicity of the vaccinia virus vector. Following intranasal inoculation of mice with $TK^-$ and $TK^+$recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSv deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant $HA^-$ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation The u gene is present in WR strain of vaccinia virus (Kotwal et al., 1989b). Nice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine NIL and a 35 kDa protein (C3L, by the terminology reported in Goebel et al., 1990a,b). Insertional inactivation of NIL reduces virulence by intracranial inoculation for both normal and nude mice (Kotwal et al., 1989a). The 35 kDa protein is secreted like NiL into the medium of vaccinia virus infected cells. The protein contains homology to the family of complement control proteins, particularly the complement 4B binding protein (C4 bp) (Kotwal et al., 1988a). Like the cellular C4 bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipox viruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

Human cytomegalovirus (HCMV) is a member of the betaherpesviridae subfamily (family Herpesviridae). HCMV is ubiquitous in humans, with usually mild or inapparent acute infection followed by persistence or latency. However, HCMV is a significant cause of morbidity and mortality in infants infected in-utero (Stagno et al., 1983). HCMV is the most common infectious complication of organ transplantation (Glenn et al., 1981) and in immunocompromised hosts (Weller et al., 1971). In AIDS patients, CMV retinitis is the leading cause of blindness (Roarty et al., 1993; Gallant et al., 1992; Gross et al., 1990) A potential role of HCMV in coronary restinosis has recently been described (Speir et al., 1994). The live attenuated Towne strain of HCMV has been shown to protect seronegative renal transplant recipients from severe clinical symptoms of HCMV infection (Plotkin et al., 1976, 1984 and 1989) and to protect initially seronegative healthy individuals from infection and clinical symptoms after subcutaneous challenge with a wild-type strain of HCMV (Plotkin et al., 1989). Concerns remain about the use of a live HCMV vaccine because of the latency reactivation phenomenon characteristic of herpesvirus infections in humans and because of the capability of certain strains of HCMV to transform cells malignantly in vitro (Albrecht and Rapp, 1973; Galloway et al., 1986). For these reasons, a recombinant subunit CMV vaccine may be more acceptable for human immunization.

The role of individual HCMV proteins in protective immunity is unclear. Three immunologically distinct families of glycoproteins associated with the HCMV envelope have been described (Gretch et al., 1988b); gCI (gp55 and gp93–130); gCII (gp47–52); and gCIII (gp85–pl45). Neutralization of HCMV has been demonstrated in vitro with antibodies specific for each of these glycoprotein families (Pachl et al., 1989; Rasmussen et al., 1988; Kari et al., 1986).

The gene coding for gCI is homologous to HSV I gB (Cranage et al., 1986). HCMVgB is synthesized as a glycosylated uncleaved precursor of apparent molecular weight 130–140 kDa which is processed by cellular proteinase into N-terminal 90–110 kDa and C-terminal 55–58 kDa products which remain associated in a disulfide linked complex (Britt and Auger, 1986; Britt and Vugler, 1989; Reis et al., 1993). Monoclonal antibodies capable of neutralizing HCMV have been obtained from mice immunized with lysates of HCMV infected cells or HCMV virions, these monoclonals were predominantly reactive with the C-terminal 55–58 kDa fragment (Britt, 1984; Kari et al., 1986; Pereira et al., 1984; Rasmussen et al., 1988). However, immunization with biochemically purified gP93 resulted in the development of gp93-specific neutralizing mAbs (Kari et al., 1990).

HCMV-gB may serve to elicit protective immunity in humans: immunization with the purified gB protein induces neutralizing antibody (Gönczöl et al., 1990) and human anti-gB monoclonal antibodies neutralize the virus (Masuho et al., 1987). Following natural infection neutralizing antibody specific for HCMV-gB is observed. When gB specific antibody is absorbed from human sera, HCMV neutralizing antibody titer is reduced significantly (50–88%, Gönczöl al., 1991; 0–98% median 48%, Marshall et al., 1992). There is also evidence for activation of helper T cells by the gB protein in naturally seropositive humans (Liu et al., 1991) and gB specific CTL has been detected in humans in some studies (Borysiewicz et al., 1988; Liu et al., 1991; Riddell, et al., 1991).

The gCII glycoproteins are encoded by a gene or genes in the US6 gene family (US6 through US11, Gretch et al., 1988a). These glycoproteins are recognized by human anti-HCMV antibody in sera from convalescent adults. However, sera from congenitally infected infants with persistent infection failed to react with gCII glycoproteins (Kari and Gehrz, 1990), suggesting that gCII may be important to human protective immune responses to HCMV.

The gP86 component of the gCIII complex is encoded by a gene that is homologous to HSV-I gH (Cranage et al., 1988; Pachl et al., 1989). The HCMV gH protein is capable of inducing a neutralizing immune response in humans (10% of HCMV infected individuals have a detectable level of circulating gH specific antibody (Rasmussen et al., 1991) as well as in laboratory animals (Baboonian et al., 1989; Cranage et al., 1988; Ehrlich et al., 1988; Rasmussen et al., 1984). Murine gH-specific monoclonal antibodies neutralize virus infectivity in a complement-independent manner (Baboonian et al., 1989; Cranage et al., 1988; Rasmussen et al., 1984) and inhibit viral spread (Pachl et al., 1989) suggesting that gH may be responsible for virus attachment, penetration and or spread.

Although gH is found on the surface of HCMV infected cells (Cranage et al., 1988), when expressed by a variety of recombinant systems it is restricted to the endoplasmic reticulum (Spaete et al., 1991). Coexpression of the HCMV UL115 gene product (glycoprotein gL) results in the formation of a stable complex of these two proteins and the transport of gH to the cell surface (Spaete et al., 1993; Kaye et al., 1992).

HCMV synthesizes a number of matrix tegument phosphoproteins. The pp150 phosphoprotein is highly immunogenic apparently more so than any other of the HCMV structural proteins (Jahn et al., 1987). A second matrix phosphoprotein, pp65, elicits a variable humoral response in humans (Jahn et al., 1987; Plachter et al., 1990). This protein can stimulate lymphoproliferation, IL-2 and interferon production, B-cell stimulation of antibody and natural killer cell activity (Forman et al., 1985). It also serves as a target antigen for HCMV-specific, HLA-restricted cytotoxic T cells (CTLs) (Pande et al., 1991; Gilbert et al., 1993).

Additional structural proteins may be required for eliciting a protective immune response to HCMV. The major capsid protein (UL86) is known to induce specific antibodies during natural infection and has been considered as the CMV-group common antigen (Spaete et al., 1994). The tegument phosphoprotein, pp28 (UL99), is also known to elicit persistent antibody responses during a natural infection. Further, this protein has also been implicated as a CTL target immunogen (Charpentier et al., 1986). The immune response to the upper tegument phosphoprotein, pp71 (UL82), is not as well characterized as the other tegument phosphoproteins (pp28, pp65), but as a known tegument protein requires further attention.

In addition to these structural proteins, some non-structural proteins may also be candidates for inclusion in a recombinant subunit vaccine. Immunization of mice with a recombinant vaccinia virus expressing murine cytomegalovirus (MCMV) pp89 (functional homolog of HCMV IE 1) induces $CD8^+$ T-cell responses that mediate protective immunity from challenge with MCMV (Jonjic et al., 1988). The human CMV major immediate early protein (IE 1) has been shown to be a target for CTLs isolated from HCMV seropositive individuals (Borysiewicz et al., 1988). Since IE 1 is among the initial viral proteins expressed and is necessary for inducing the expression of other CMV genes and initiating the viral life cycle in latently infected cells (Blanton and Tevethia, 1981; Cameron and Preston, 1981; DeMarchi et al., 1980: McDonough and Spector, 1983; Wathen et al., 1981), CTL responses directed against IE 1 may be important for controlling and/or eliminating HCMV infection. Recently Gilbert et al., (1993) have suggested that HCMV has evolved a mechanism by which other viral encoded proteins selectively interfere with the presentation of IE-derived peptides in association with Class I major histocompatibility complex (MHC) molecules.

Some additional nonstructural proteins may also be candidates for inclusion in a recombinant subunit HCMV vaccine candidate. The immediate early protein, IE2 (UL122), and the regulatory protein UL69 are known to contain human T-helper epitopes (Beninga et al., 1995).

One approach to the development of a subunit HCMV vaccine is the use of live viral vectors to express relevant HCMV gene products.

It can thus be appreciated that provision of a CMV or an HCMV recombinant poxvirus, and of compositions and products therefrom particularly NYVAC or ALVAC based CMV or HCMV recombinants and compositions and products therefrom, especially such recombinants containing coding for any or all of HCMVgB, gH, gL, pp150, pp65 and IE1, including recombinants expressing altered or truncated versions of IE1 and/or gB and compositions and products therefrom would be a highly desirable advance over the current state of technology.

OBJECTS AND SUMMARY OF THE INVENTION

It is therefore an object of this invention to provide modified recombinant viruses, which viruses have enhanced safety, and to provide a method of making such recombinant viruses.

It is an additional object of this invention to provide a recombinant poxvirus antigenic vaccine or immunological composition having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

In one aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus or canarypox virus. The modified recombinant virus can include, within a nonessential region of the virus genome, a heterologous DNA sequence which encodes an antigen or epitope derived from HCMV, such as any or all of HCMVgB, gH, gL, pp150, pp65, IE1, including altered or truncated versions of IE1, and/or gB.

In another aspect, the present invention relates to an antigenic, immunological or vaccine composition or a therapeutic composition for inducing an antigenic or immunological response in a host animal inoculated with the composition, said vaccine including a carrier and a modified recombinant virus having inactivated nonessential virus-encoded genetic functions so that the recombinant virus has attenuated virulence and enhanced safety. The virus used in the composition according to the present invention is advantageously a poxvirus, particularly a vaccinia virus or an avipox virus, such as fowlpox virus and canarypox virus. The modified recombinant virus can include, within a nonessential region of the virus genome, a heterologous DNA sequence which encodes an antigenic protein, e.g., derived from HCMV, such as any or all of HCMVgB, gH, gL, pp150, pp65, IE1, including altered or truncated versions of IE1, and/or gB.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein (e.g., derived from HCMV, such as any or all of HCMVgB, gH, gL, pp150, pp65, IE1, including altered or truncated versions of IE1, and/or gB) wherein the composition, when administered to a host, is capable of inducing an immunological response specific to the antigen.

In a further aspect, the present invention relates to a method for expressing a gene product in a cell in vitro by introducing into the cell a modified recombinant virus having attenuated virulence and enhanced safety. The modified recombinant virus can include, within a nonessential region of the virus genome, a heterologous DNA sequence which encodes an antigenic protein, e.g. derived from HCMV such as any or all of HCMVgB, gH, gL, pp150, pp65, IE1, including altered or truncated versions of IE1, and/or gB. The cells can then be reinfused directly into the individual or used to amplify specific reactivities for reinfusion (Ex vivo therapy).

In a further aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., derived from HCMV such as any or all of HCMVgB, gH, gL, pp150, pp65, IE1, including altered or truncated versions of IE1, and/or gB. The product can then be administered to individuals or animals to stimulate an immune response. The antibodies raised can be useful in individuals for the prevention or treatment of HCMV and, the antibodies from individuals or animals or the isolated in vitro expression products can be used in diagnostic kits, assays or tests to determine the presence or absence in a sample such as sera of HCMV or antigens therefrom or antibodies thereto (and therefore the absence or presence of the virus or of the products, or of an immune response to the virus or antigens).

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for HCMV such as any or all of HCMVgB, gH, gL, pp150, pp65, IE1, including altered or truncated versions of IE1, and/or gB. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus or canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. A suitable modified Copenhagen strain of vaccinia virus is identified as NYVAC (Tartaglia et al., 1992), or a vaccinia virus from which has been deleted J2R, B13R+B14R, A26L, A56R, C7L-K11 and I4L or a thymidine kinase gene, a hemorrhagic region, an A type inclusion body region, a hemagglutinin gene, a host range region, and a large subunit, ribonucleotide reductase (See also U.S. Pat. No. 5,364,773). Alternatively, a suitable poxvirus is an ALVAC or, a canarypox virus (Rentschler vaccine strain) which was attenuated, for instance, through more than 200 serial passages on chick embryo fibroblasts, a master seed therefrom was subjected to four successive plaque purifications under agar from which a plaque clone was amplified through five additional passages.

The invention in yet a further aspect relates to the product of expression of the inventive recombinant poxvirus and uses therefor, such as to form antigenic, immunological or vaccine compositions for treatment, prevention, diagnosis or testing; and, to DNA from the recombinant poxvirus which is useful in constructing DNA probes and PCR primers.

These and other embodiments are disclosed or are obvious from and encompassed by the following detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 8 shows the DNA sequence of a 3209 base pair fragment of canarypox DNA containing the C5 ORF (SEQ ID NO:27) (the C5 ORF initiates at position 1537 and terminates at position 1857);

FIGS. 9A and 9B schematically show a method for the construction of recombinant canarypox virus vCP65 (ALVAC-RG);

FIGS. 11A to 11D show graphs of rabies neutralizing antibody titers (RFFIT, IU/ml), booster effect of HDC and vCP65 ($10^{5.5}$ $TCID_{50}$) in volunteers previously immunized with either the same or the alternate vaccine (vaccines given at days 0, 28 and 180, antibody titers measured at days 0, 7, 28, 35, 56, 173, 187 and 208);

FIG. 12 shows the DNA sequence of HCMVgB (Towne strain) (SEQ ID NO:37);

FIGS. 13A and B show the DNA sequence of the H6 promoted HCMVgB and NYVAC sequences flanking the TK locus (SEQ ID NO:38) (the 5' end of the H6 promoted CMVgB is at position 3447; the CMVgB coding sequence is from position 3324 through position 606);

FIGS. 14A to C show the DNA sequence of a 7351 base pair fragment of canarypox DNA containing the C3 ORF (SEQ ID NO:39) (the C3 ORF is initiated at position 1458 and terminates at position 2897);

FIG. 15A to C show the DNA sequence of the H6 promoted HCMVgB and ALVAC sequences flanking the C3 locus (SEQ ID NO:40) (the 5' end of the H6 promoted CMVgB is at position 4425; the CMVgB coding sequence is from position 4301 through position 1581);

FIGS. 16A and B show the DNA sequence of the H6 promoted HCMVgB and NYVAC sequences flanking the ATI locus (SEQ ID NO:41) (the 5' end of the H6 promoted CMVgB is at position 3348; the CMVgB coding sequence is from position 3224 through position 504);

FIG. 17 shows the DNA sequence of HCMVgB (Towne strain) deleted of its transmembrane region (SEQ ID NO:42);

FIGS. 18A and B show the DNA sequence of the H6 promoted HCMVgB lacking its transmembrane region and NYVAC sequences flanking the ATI locus (SEQ ID NO:43) (the 5' end of the H6 promoted CMVgB is at position 3173; the CMVgB coding sequence is from position 3050 through position 504);

FIG. 19 shows the DNA sequence of HCMVgB (Towne strain) deleted of its transmembrane region and containing an altered cleavage site (SEQ ID NO:44);

FIGS. 20A and B show the DNA sequence of the H6 promoted HCMVgB lacking its transmembrane region and containing an altered cleavage site plus NYVAC sequences flanking the ATI locus (SEQ ID NO:45) (the 5' end of the H6 promoted CMVgB is at position 3173; the CMVgB coding sequence is from position 3050 through position 504);

FIG. 21 shows the DNA sequence of HCMVgH (Towne strain) (SEQ ID NO:46);

FIGS. 22A and B show the DNA sequence of the 42K promoted HCMVgH plus NYVAC sequences flanking the I4L locus (SEQ ID NO:47) (the 5' end of the 42K promoted CMVgH is at position 641; the CMVgH coding sequence is from position 708 through position 2933);

FIGS. 23A and B show the DNA sequence of the 42K promoted CMVgH and ALVAC sequences flanking the C5 locus (SEQ ID NO:48) (the 5' end of the 42K promoted CMVgH is at position 1664; the CMVgH coding sequence is from position 1730 through position 3955);

FIG. 24 shows the DNA sequence of the 42K promoted CMVgH and WR flanking sequences (SEQ ID NO:49) (the 5' end of the 42K promoted CMVgH is at position 2457; the CMVgH coding sequence is from position 2391 through 166);

FIG. 25 shows the DNA sequence of HCMV IE1 (AD169 strain) (SEQ ID NO:50);

FIG. 26 shows the DNA sequence of the H6 promoted CMVIE1 and WR flanking sequences (SEQ ID NO:51) (the 5' end of the H6 promoted CMVIE1 is at position 1796; the CMVIE1 coding sequence is from position 1673 through 201);

FIGS. 27A and B show the DNA sequence of the H6 promoted CMVIE1 and NYVAC sequences flanking the ATI locus (SEQ ID NO:52) (the 5' end of the H6 promoted CMVIE1 is at position 2030; the CMVIE1 coding sequence is from position 1906 through position 434);

FIG. 28 shows the DNA sequence of HCMVIE1 (AD169 strain) lacking amino acids 292–319 (SEQ ID NO:53);

FIGS. 29A and B show the DNA sequence of the H6 promoted CMVIE1 lacking amino acids 292–319 and NYVAC sequences flanking the ATI locus (SEQ ID NO:54) (the 5' end of the H6 promoted CMVIE1 is at position 1940; the CMVIE1 coding sequence is from position 1816 through position 434);

FIG. 30 shows the DNA sequence of the Exon 4 segment of HCMVIE1 (AD169 strain) (SEQ ID NO:55);

FIG. 31 shows the DNA sequence of the H6 promoted CMVIE1 Exon 4 segment and NYVAC sequences flanking the I4L locus (SEQ ID NO:56) (the 5' end of the H6 promoted I1 Exon 4 is at position 630; the CMVIE1 Exon 4 coding sequence is from position 754 through position 1971).

FIGS. 32A and B show the DNA sequence of the H6 promoted CMVIE1 Exon 4 segment and ALVAC sequences flanking the C5 locus (SEQ ID NO:57) (the 5' end of the H6 promoted IE1 Exon 4 is at position 1647; the CMVIE1Exon 4 coding sequence is from position 1771 through position 2988).

FIG. 33 shows the DNA sequence of HCMVIE1 (AD169 strain) lacking amino acids 2–32 (SEQ ID NO:58);

FIG. 34 shows the DNA sequence of the H6 promoted CMVIE1 lacking amino acids 2–32 and NYVAC sequences flanking the I4L locus (SEQ ID NO:59) (the 5' end of the H6 promoted IE1 lacking amino acids 2–32 is at position 630; the coding sequence for CMVIE1 lacking amino acids 2–32 is from position 754 through position 2133);

FIGS. 35A and B show the DNA sequence of the H6 promoted CMVIE1 lacking amino acids 2–32 and ALVAC sequences flanking the C5 locus (SEQ ID NO:60) (the 5' end of the H6 promoted IE1 lacking amino acids 2–32 is at position 1647; the CMVIE1 coding sequence for CMVIE1 lacking amino acids 2–32 is from position 1771 through position 3150);

FIG. 36 shows the DNA sequence of HCMV pp65 (Towne strain) (SEQ ID NO:61);

FIG. 37 shows the DNA sequence of the H6 promoted CMVpp65 and NYVAC sequences flanking the HA locus (SEQ ID NO:62) (the 5' end of the H6 promoted pp65 is at position 476; the CMVpp65 coding sequence is from position 600 through 2282);

FIGS. 38A and B show the DNA sequence of a 3706 base pair fragment of canarypox DNA containing the C6 ORF (SEQ ID NO:63) (the C6 ORF is initiated at position 377 and terminated at position 2254);

FIGS. 39A and B show the DNA sequence of the H6 promoted CVVpp65 and ALVAC sequences flanking the C6 locus (SEQ ID NO:64) (the 5' end of the H6 promoted pp65 is at position 496; the CMVpp65 coding sequence is from position 620 through 2302);

FIG. 40 shows the DNA sequence of the H6 promoted CMVpp65 and WR flanking sequences (SEQ ID NO:65) (the 5' end of the H6 promoted pp65 is at position 168; the CMVpp65 coding sequence is from position 292 through 1974);

FIG. 41 shows the DNA sequence of HCMVpp150 (Towne strain) (SEQ ID NO:66);

FIGS. 42A and B show the DNA sequence of the 42K promoted CMVpp150 and NYVAC sequences flanking the ATI locus (SEQ ID NO:67) (the 5' end of the 42K promoted pp150 is at position 3645; the CMVpp150 coding sequence is from position 3580 through 443);

FIGS. 43A and B show the DNA sequence of the 42K promoted CMVpp150 and ALVAC sequences flanking the C6 locus (SEQ ID NO:68) (the 5' end of the 42K promoted pp150 is at position 3714; the CMVpp150 coding sequence is from position 3649 through 512);

FIGS. 44A and B show the DNA sequence of the 42K promoted CMVpp150 gene and WR flanking sequences (SEQ ID NO:69) (the 5' end of the H6 promoted pp150 is at position 3377; the CMVpp150 coding sequence is from position 3312 through 175);

FIGS. 45A and B show the DNA sequence of the 42K promoted HCMVgH and H6 promoted HCMVIE Exon 4 and NYVAC sequences flanking the I4L locus (SEQ ID NO:70) (the 5' end of the 42K promoted CMVgH is at position 2935; the CMVgH coding sequence is from position 2869 through 644; the 5' end of the H6 promoted CMVIE Exon 4 is at position 2946; the CMVIE Exon 4 coding sequence is from position 3070 through position 4287);

FIGS. 46A to C show the DNA sequence of the H6 promoted HCMV pp65 and 42K promoted HCMVpp150 and ALVAC sequences flanking the C6 locus (SEQ ID NO:71) (the 5' end of the H6 promoted CMVpp65 is at position 496; the CMVpp65 coding sequence is from position 620 through 2302; the 5' end of the 42K promoted CMVpp150 is at position 5554; the CMVpp150 coding sequence is from position 5489 through position 2352);

FIG. 47 shows the DNA sequence of HCMVgL (Towne strain) (SEQ ID NO:72);

FIGS. 48A and B show the DNA sequence of the H6 promoted HCMVgB and H6 promoted HCMVgL and NYVAC sequences flanking the TK locus (SEQ ID NO:73) (the 5' end of the H6 promoted CMVgB is at position 3447; the CMVgB coding sequence is from position 3324 through position 606; the 5' end of the H6 promoted CMVgL is at position 3500; the CMVgL coding sequence is from position 3624 through position 4460);

DETAILED DESCRIPTION OF THE INVENTION

Figure 1:
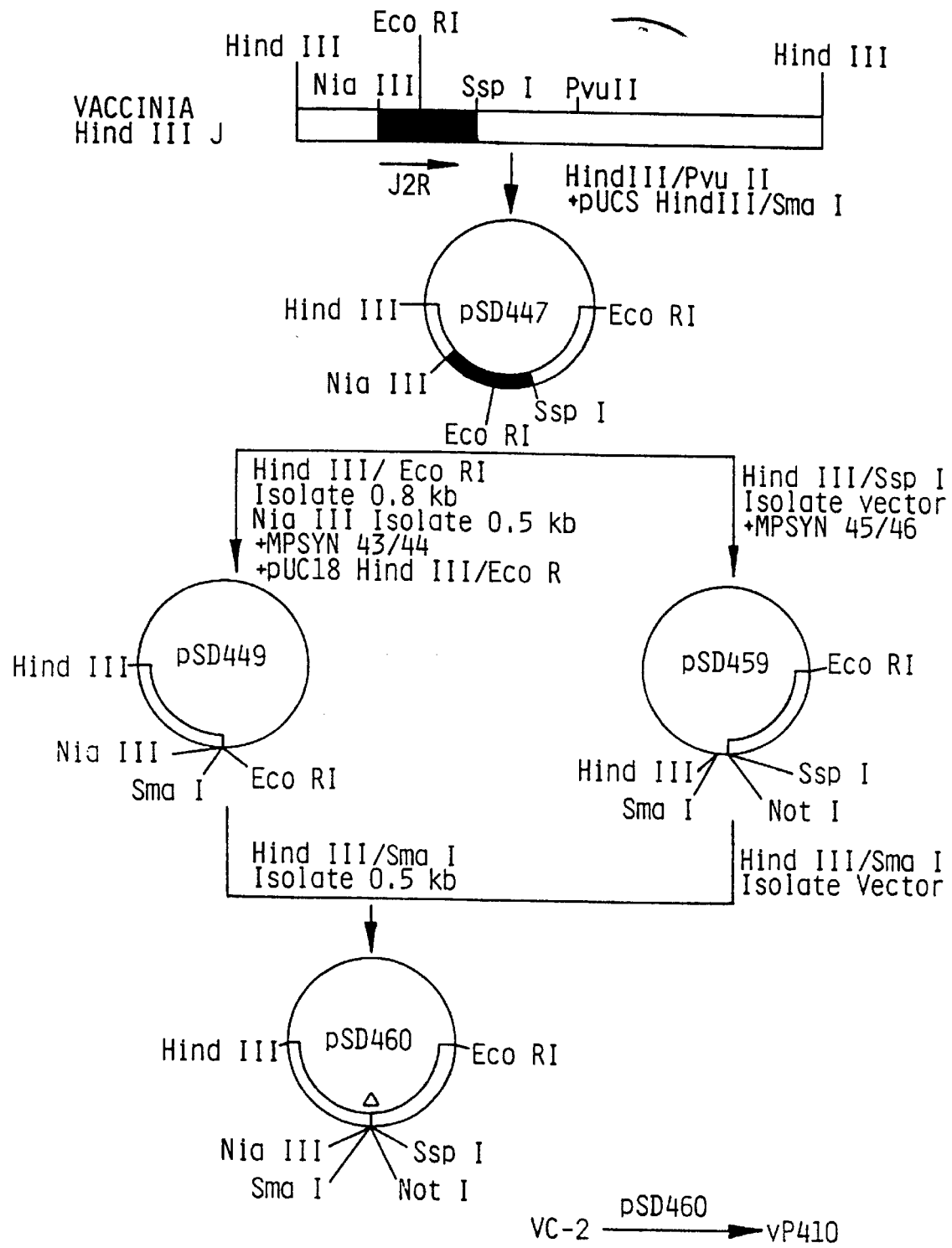
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below (See U.S. Pat. No. 5,364,773). All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410,
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products some of which associated with virulence and host range (Tartaglia et al., 1992; Goebel et al., 1990a,b). The deletion of host range genes diminishes the ability of the virus to replicate in tissue culture cell derived from certain species such as swine and humans (Tartaglia et al., 1992; Perkus et al., 1990). In addition to reduced replication competency, NYVAC was shown to be highly attenuated by a number of criteria including (a) lack of induration or ulceration on rabbit skin, (b) rapid clearance from the site of inoculation, (c) high avirulence by intracranial inoculation into newborn mice when compared with other vaccinia strains including WYETH, and (d) failure to cause death, secondary lesions or disseminated infection when inoculated intraperitoneally in immunocompromised animals (Tartaglia et al., 1992). In spite of the highly attenuated characteristics of NYVAC, NYVAC based recombinants were effective in protecting mice from rabies challenge (Tartaglia et al., 1992), swine from challenge with Japanese encephalitis virus and pseudorabies virus challenge (Brockmeier et al., 1993; Konishi et al., 1992) and horses from equine influenza virus challenge (Taylor et al., 1993).

NYVAC is also highly attenuated by a number of criteria including i) decreased virulence after intracerebral inoculation in newborn mice, ii) inocuity in genetically ($nu^+$/$nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

Avipoxvirus-based recombinants as live vectors provide an additional approach to develop recombinant subunit vaccines. These viruses are naturally restricted by their ability to replicate only in avian species. TROVAC refers to an attenuated fowlpox that was a plaque-cloned isolate derived from the FP-1 vaccine strain of fowlpoxvirus which is licensed for vaccination of 1 day old chicks.

ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). For instance, mice immunized with an ALVAC recombinant expressing the rabies virus glycoprotein were protected from lethal challenge with rabies virus (Tartaglia et al., 1992) demonstrating the potential for ALVAC as a vaccine vector. ALVAC-based recombinants have also proven efficacious in dogs challenged with canine distemper virus (Taylor et al., 1992) and rabies virus (Perkus et al., 1994), in cats challenged with feline leukemia virus (Tartaglia et al., 1993b), and in horses challenged with equine influenza virus (Taylor et al., 1993).

This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991b). Recent Phase I clinical trials in both Europe and the United States of a canarypox/rabies glycoprotein recombinant (ALVAC-RG; vCP65) demonstrated that the experimental vaccine was well tolerated and induced protective levels of rabiesvirus neutralizing antibody titers (Cadoz et al., 1992; Fries et al., 1992). Indeed, reactogenicity in volunteers following administration of ALVAC-RG was minimal; and following two administrations of ALVAC-RG at a dose of $10^{5.5}$ TCID$_{50}$, all vaccinees developed rabies neutralizing antibody. Additionally, peripheral blood mononuclear cells (PBMCs) derived from the ALVAC-RG vaccinates demonstrated significant levels of lymphocyte proliferation when stimulated with purified rabies virus (Fries et al., 1992).

An ALVAC recombinant expressing the HIV envelope glycoprotein gp160 (ALVAC-HIV; vCP125) has been tested in phase I human clinical trial in a prime/boost protocol with recombinant gp160 (Pialoux et al., 1995). Reactogenicity in volunteers following administration of ALVAC-HIV was minimal and this vaccine candidate primed both HIV-I envelope-specific humoral and cell-mediated immune responses.

Recent studies have indicated that a prime/boost protocol, whereby immunization with a poxvirus recombinant expressing a foreign gene product is followed by a boost using a purified subunit preparation form of that gene product, elicits an enhanced immune response relative to the response elicited with either product alone. Human volunteers immunized with a vaccinia recombinant expressing the HIV-1 envelope glycoprotein and boosted with purified HIV-1 envelope glycoprotein subunit preparation exhibit higher HIV-1 neutralizing antibody titers than individuals immunized with just the vaccinia recombinant or purified envelope glycoprotein alone (Graham et al., 1993; Cooney et al., 1993). Humans immunized with two injections of an ALVAC-HIV-1 env recombinant (vCP125) failed to develop HIV specific antibodies. Boosting with purified rgp160 from a vaccinia virus recombinant resulted in detectable HIV-1 neutralizing antibodies. Furthermore, specific lymphocyte T cell proliferation to rgp160 was clearly increased by the boost with rgp160. Envelope specific cytotoxic lymphocyte activity was also detected with this vaccination regimen (Pialoux et al., 1995). Macaques immunized with a vaccinia recombinant expressing the simian immunodeficiency virus (SIV) envelope glycoprotein and boosted with SIV envelope glycoprotein from a baculovirus recombinant are protected against a SIV challenge (Hu et al., 1991; 1992). In the same fashion, purified HCMVgB protein can be used in prime/boost protocols with NYVAC or ALVAC-gB recombinants.

NYVAC, ALVAC and TROVAC have also been recognized as unique among all poxviruses in that the National Institutes of Health ("NIH") (U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

ALVAC, TROVAC, and NYVAC were deposited under the terms of the Budapest Treaty with the American Type Culture Collection (ATCC), 10801 University Blvd., Manassas, VA 20110–2209, USA: NYVAC under ATCC accession number VR-2559 on Mar. 6, 1997; TROVAC under ATCC accession number VR-2553 on Feb. 6, 1997; and ALVAC under ATCC accession number VR-2547 on Nov. 14, 1996.

CMV is a frequent cause of morbidity and mortality in AIDS patients, bone marrow transplant recipients, and patients undergoing immunosuppressive therapies for neoplastic diseases. There is no effective, well-tolerated, pharmaceutical therapy for CMV infection. One approach might be the ex vivo stimulation of donor CMV-specific CTLs for the treatment and control of the often fatal pneumonia caused by CMV infection in the bone marrow transplant recipient. In fact, the treatment and control of CMV infection in man by adoptive transfer of CMV CTL clones has been successfully demonstrated (Riddell et al., 1992). However, in this instance, CMV was used to stimulate and maintain the CMV-specific CTL clones used in this therapeutic protocol. The use of CMV for the purpose of ex vivo stimulation of CTL clones has its drawbacks, the most obvious being the possibility of introducing additional CMV into an immunosuppressed patient. The availability of immunotherapeutic agents that provide a safe and acceptable means for stimulating antigen-specific cellular immune effector activities seems to be a major shortcoming in the field of adoptive immunotherapy. Protein subunits, although potentially safe, are notoriously poor at stimulating CTLs. Peptides, generally considered safe yet effective at stimulating a CTL response, are highly restrictive in their abilities to stimulate CTL responses. Peptides are typically capable of inducing a CTL response to only one CTL epitope of many possible CTL epitopes contained within a single protein. Furthermore, peptides typically stimulate CTL responses from only a restricted portion of the population, being restricted to only those individuals expressing a particular allele of the human major histocompatibility complex (MHC). Recombinant virus vectors are considered excellent inducers of CTL reactivities since they are capable of expressing the entire antigen, thus not restricted to a single epitope for a single segment of the population. However, most of these virus vectors, such as adenovirus, are capable of replication and are not considered safe for use in this type of protocol. Since ALVAC recombinants do not replicate in mammalian cells, yet are capable of stimulating antigen-specific CTL responses, as demonstrated by data contained within this application, ALVAC recombinants represent a uniquely safe and effective method for the ex vivo stimulation of virus-specific CTL clones for utilization in immunotherapeutic applications.

This invention pertains to NYVAC, ALVAC and vaccinia (WR strain) recombinants containing the HCMV genes encoding for gB, gH, gL, pp150, pp65 and IE 1, including truncated versions thereof, which are further described in the Examples below.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

The administration procedure for recombinant virus or expression product thereof, compositions of the invention such as immunological, antigenic or vaccine compositions or therapeutic compositions can be via a parenteral route (intradermal, intramuscular or subcutaneous). Such an administration enables a systemic immune response.

More generally, the inventive antigenic, immunological or vaccine compositions or therapeutic compositions (compositions containing the poxvirus recombinants of the invention) can be prepared in accordance with standard techniques well known to those skilled in the pharmaceutical art. Such compositions can be administered in dosages and by techniques well known to those skilled in the medical arts taking into consideration such factors as the age, sex, weight, and condition of the particular patient and the route of administration. The compositions can be administered alone, or can be co-administered or sequentially administered with compositions of the invention or with other immunological, antigenic or vaccine or therapeutic compositions in seropositive individuals. The compositions can be administered alone, or can be co-administered or sequentially administered with compositions of the invention or with other antigenic, immunological, vaccine or therapeutic compositions in seronegative individuals. Such other compositions can include purified antigens from HCMV or from the expression of such antigens by a recombinant poxvirus or other vector system or, such other compositions can include a recombinant poxvirus which expresses other HCMV antigens or biological response modifiers again taking into consideration such factors as the age, sex, weight, and condition of the particular patient, and, the route of administration.

Examples of compositions of the invention include liquid preparations for orifice, e.g., oral, nasal, anal, vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus may be in admixture with a suitable carrier, diluent, or excipient such as sterile water, physiological saline, glucose or the like.

Further, the products of expression of the inventive recombinant poxviruses can be used directly to stimulate an immune response in either seronegative or seropositive individuals or in animals. Thus, the expression products can be used in compositions of the invention instead or in addition to the inventive recombinant poxvirus in the aforementioned compositions.

Additionally, the inventive recombinant poxvirus and the expression products therefrom stimulate an immune or antibody response in humans and animals and therefore those products are antigens. From those antibodies or antigens, by techniques well-known in the art, monoclonal antibodies can be prepared and, those monoclonal antibodies or the antigens, can be employed in well known antibody binding assays, diagnostic kits or tests to determine the presence or absence of particular HCMV antigen(s) and therefore the presence or absence of the virus or expression of the antigen(s) (in HCMV or other systems), or to determine whether an immune response to the virus or antigen(s) has simply been stimulated. Those monoclonal antibodies or the antigens can also be employed in immunoadsorption chromatography to recover or isolate HCMV or expression products of the inventive recombinant poxvirus.

More in particular, the inventive recombinants and compositions have numerous utilities, including:

(i) inducing an immunological response in seronegative individuals (use as or as part of a vaccine regimen);

(ii) therapy in seropositive individuals; and (iii) a means for generating HCMV protein in vitro without the risk of virus infection.

The products of expression of the inventive recombinant poxvirus can be used directly to stimulate an immune response in either seronegative or seropositive individuals or in animals. Thus, the expression products can be used in compositions of the invention instead of or in addition to the inventive recombinant poxvirus.

Additionally, the inventive recombinant poxvirus and the expression products therefrom stimulate an immune or antibody response in humans and animals. From those antibodies, by techniques well-known in the art, monoclonal antibodies can be prepared and, those monoclonal antibodies or the expression products of the inventive poxvirus and composition can be employed in well known antibody binding assays, diagnostic kits or tests to determine the presence or absence of particular HCMV antigen(s) or antibody(ies) and therefore the presence or absence of the virus, or to determine whether an immune response to the virus or antigen(s) has simply been stimulated. Those monoclonal antibodies can also be employed in immunoadsorption chromatography to recover, isolate or detect HCMV or expression products of the inventive recombinant poxvirus. Methods for producing monoclonal antibodies and for uses of monoclonal antibodies, and, of uses and methods for HCMV antigens—the expression products of the inventive poxvirus and composition—are well known to those of ordinary skill in the art. They can be used in diagnostic methods, kits, tests or assays, as well as to recover materials by immunoadsorption chromatography or by immunoprecipitation.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Furthermore, the inventive recombinant poxvirus or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against HCMV.

Accordingly, the inventive recombinant poxvirus has several utilities: In antigenic, immunological or vaccine compositions such as for administration to seronegative individuals. In therapeutic compositions in seropositive individuals in need of therapy to stimulate or boost the immune system against HCMV. In vitro to produce antigens which can be further used in antigenic, immunological or vaccine compositions or in therapeutic compositions. To generate antibodies (either by direct administration or by administration of an expression product of the inventive recombinant poxvirus) or expression products or antigens which can be further used: in diagnosis, tests or kits to ascertain the presence or absence of antigens in a sample such as sera, for instance, to ascertain the presence or absence of HCMV in a sample such as sera or, to determine whether an immune response has elicited to the virus or, to particular antigen(s); or, in immunoadsorption chromatography, immunoprecipitation and the like.

Furthermore, the recombinant poxviruses of the invention are useful for generating DNA for probes or for PCR primers which can be used to detect the presence or absence of hybridizable DNA or to amplify DNA, e.g., to detect HCMV in a sample or for amplifying HCMV DNA.

Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

As to NYVAC and especially Examples 1 to 6, reference's made to U.S. Pat. No. 5,364,773, incorporated herein by reference.

Example 1

Construction OF Plasmid pSD460 for Deletion of Thymidine Kinase Gene (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII /SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII /EcoRI fragment was isolated from pSD447, then digested with NlaIII and a 0.5 kb HindIII /NlaIII fragment isolated. Annealed synthetic oligonucleotides MPSYN43/MPSYN44 (SEQ ID NO:1/SEQ ID NO:2)

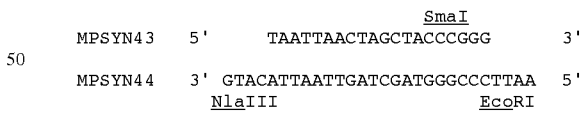

were ligated with the 0.5 kb HindIII /NlaIII fragment into pUC18 vector plasmid cut with HindIII /EcoRI, generating plasmid pSD449.

To obtain a restriction fragment containing a vaccinia right flanking arm and pUC vector sequences, pSD447 was cut with SsI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

-continued

```
MPSYN46  3'      AGGGCCCATTCATTATGCAGTTCCTCTTTTGCTT

NotI         SspI
         ACGATCTGTAGTTAGCGGCCGCCTAATTAACTAAT 3'   MPSYN45

TGCTAGACATCAATCGCCGGCGGATTAATTGATTA 5'   MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20 mer oligonucleotide MPSYN47 (SEQ ID NO:5)

(5' TTAGTTAATTAGGCGGCCGC 3') as primer. Recombinant virus vP410 was identified by plaque hybridization.

Example 2

Construction of Plasmid pSD486 for Deletion of Hemorrhagic Region (B13R+B14R)

Figure 2:
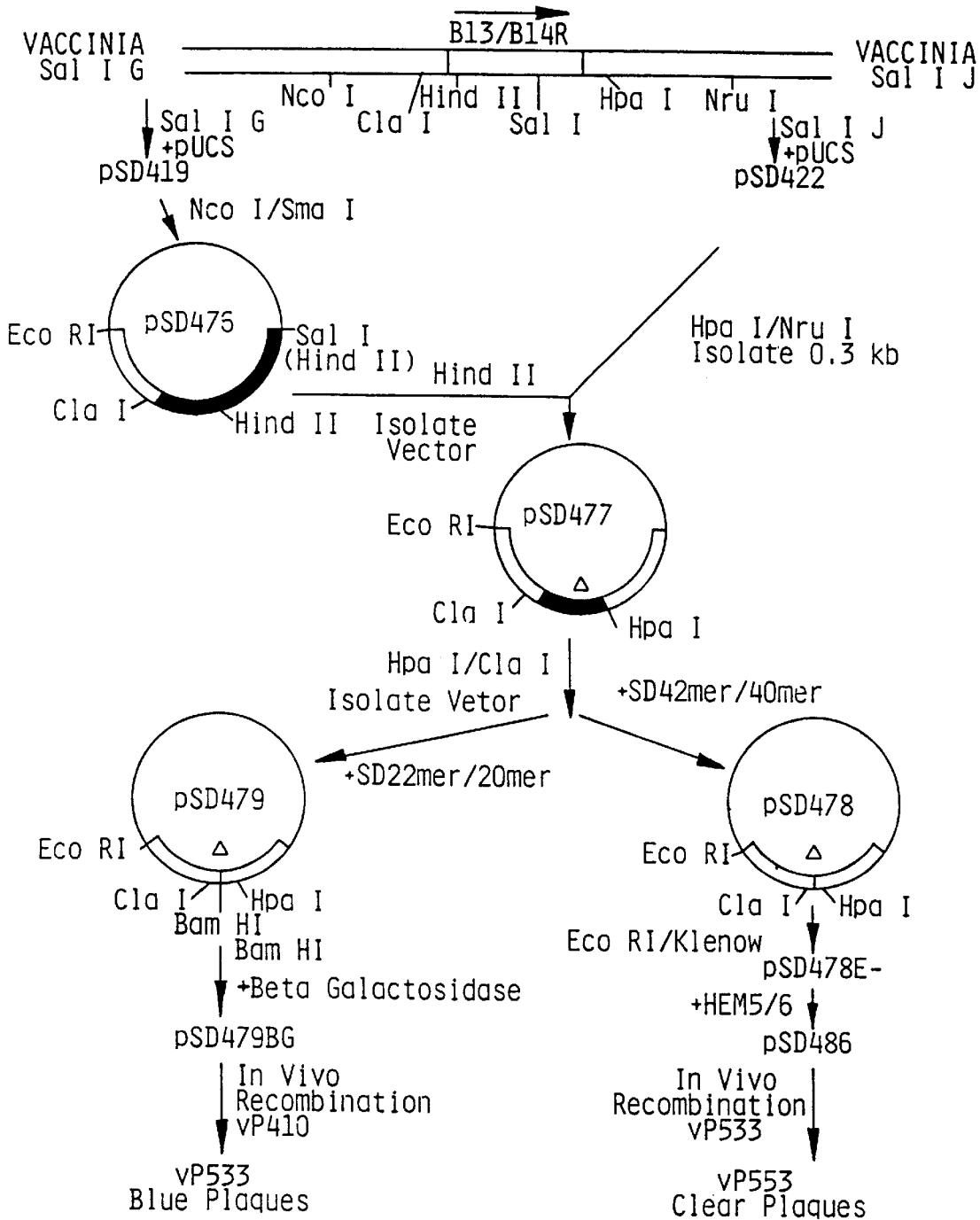
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with CaI/HpaI, and the resulting vector fragment was ligated with annealed synthetic oligonucleotides SD22mer/SD20mer (SEQ ID NO:6/SEQ ID NO:7)

```
                ClaI          BamHI HpaI
   SD22mer  5'  CGATTACTATGAAGGATCCGTT      3'

SD20mer  3'      TAATGATACTTCCTAGGCAA    5'
``` generating pSD479. pSD479 contains an initiation codon (underlined) followed by a BamHI site. To place E. coli Beta-galactosidase in the B13–14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the udeletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
                ClaI       SacI         XhoI        HpaI
   SD42mer  5'  CGATTACTAGATCTGAGCTCCCCGGGCTCGAGGGATCCGTT    3'

SD40mer  3'     TAATGATCTAGACTCGAGGGGCCCGAGCTCCCTAGGCAA    5'
                    BglII        SmaI         BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E$^{31}$. pSD478E$^-$ was digested with BamHI and HpaI and ligated with annealed synthetic oligonucleotides HEM5/HEM6 (SEQ ID NO:10/SEQ ID NO:11)

```
              BamHI EcoRI   HpaI
   HEM5   5'  GATCCGAATTCTAGCT   3'

HEM6   3'        GCTTAAGATCGA 5'
``` generating plasmid pSD486. pSD486 was used as donor plasmid for recombination with recombinant vaccinia virus vP533, generating vP553, which was isolated as a clear plaque in the presence of X-gal.

Example 3

Construction of Plasmid pMP494Δfor Deletion of ATI Region (A26L) for Deletion of ATI Region (A26L)

Figure 3:
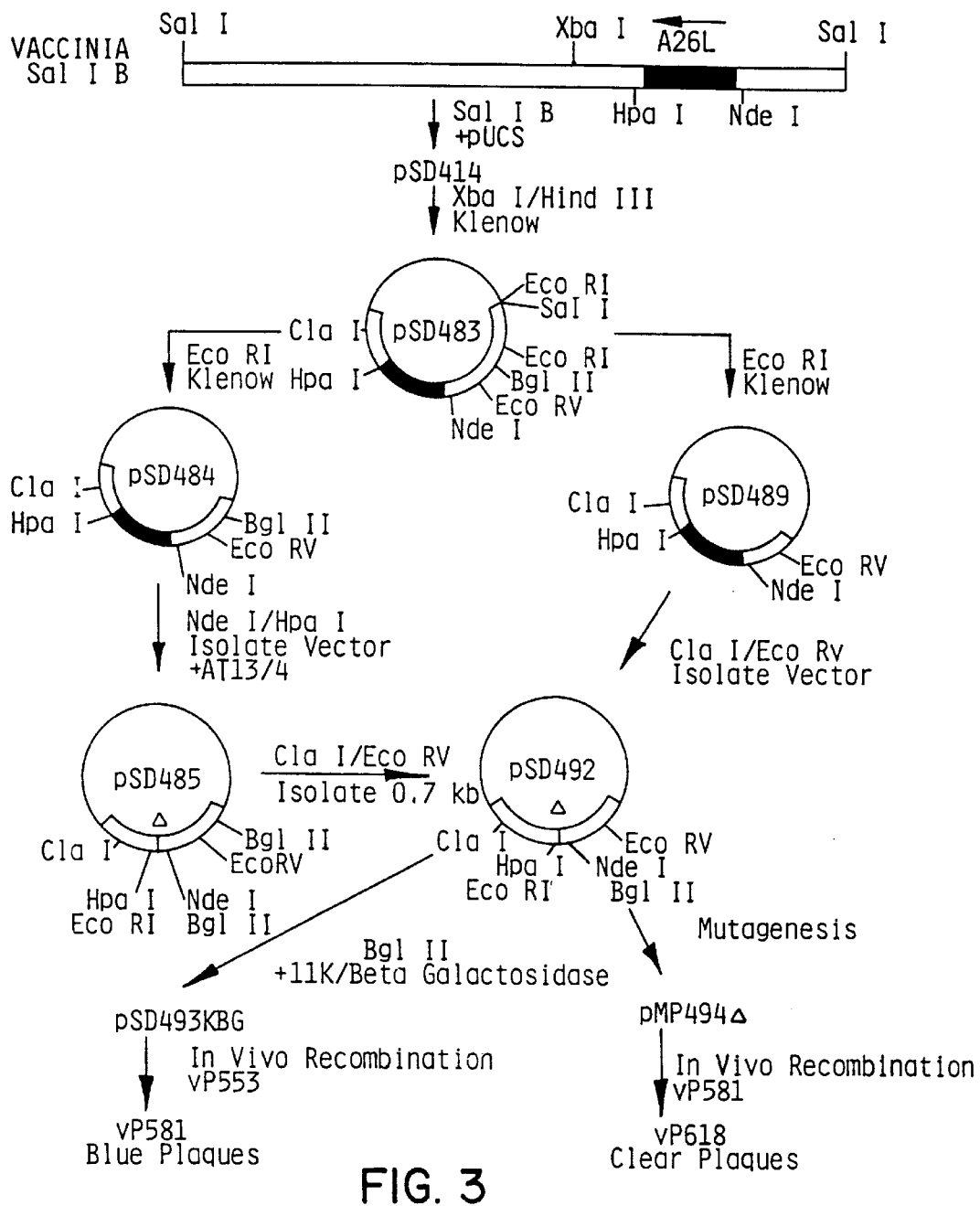
FIG. 3 schematically shows a method for the construction of plasmid pMP494Δfor deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
             NdeI
ATI3    5'  TATGAGTAACTTAACTCTTTTGTTAATTAAAAGTATATTCAAAAAATAAGT

ATI4    3'      ACTCATTGAATTGAGAAAACAATTAATTTTCATATAAGTTTTTTATTCA

BglII EcoRI HpaI
          TATATAAATAGATCTGAATTCGTT    3'  ATI3

ATATATTTATCTAGACTTAAGCAA    5'  ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5'AAAATGGGCGTGGATTGTTAACTTTATATAACTT-ATTTTTTGAATATAC 3'). In the resulting plasmid, pMP494Δ, vaccinia DNA encompassing positions [137, 889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 4

Construction of Plasmid pSD467 for Deletion of Hemagglutinin Gene (A56R)

Figure 4:
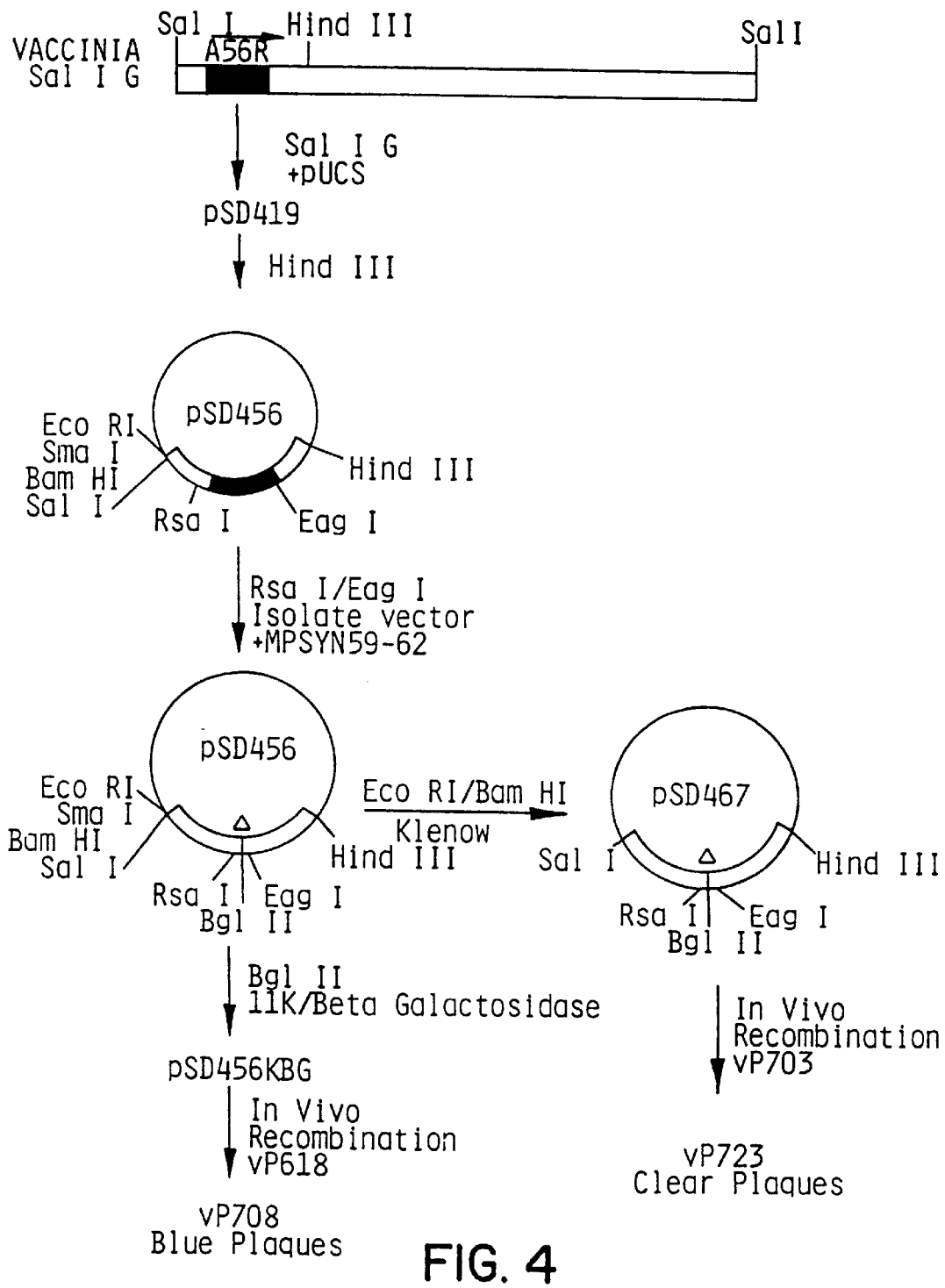
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the puC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

```
              RsaI
MPSYN59   5' ACACGAATGATTTTCTAAAGTATTTGGAAAGTTTTATAGGT-

MPSYN62   3' TGTGCTTACTAAAAGATTTCATAAACCTTTCAAAATATCCA-

MPSYN59      AGTTGATAGAACAAAATACATAATTT 3'

MPSYN62      TCAACTATCT 5'

MPSYN60   5'                        TGTAAAAATAAATCACTTTTTATA-

MPSYN61   3' TGTTTTATGTATTAAAACATTTTTATTTAGTGAAAAATAT-

BalII SmaI  PstI  EagI
MPSYN60      CTAAGATCTCCCGGGCTGCAGC           3'

MPSYN61      GATTCTAGAGGGCCCGACGTCGCCGG       5'
``` reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Example 5

Construction of Plasmid pMPCSK1Δ for Deletion of Open Reading Frames [C7L–K1L]

Figure 5:
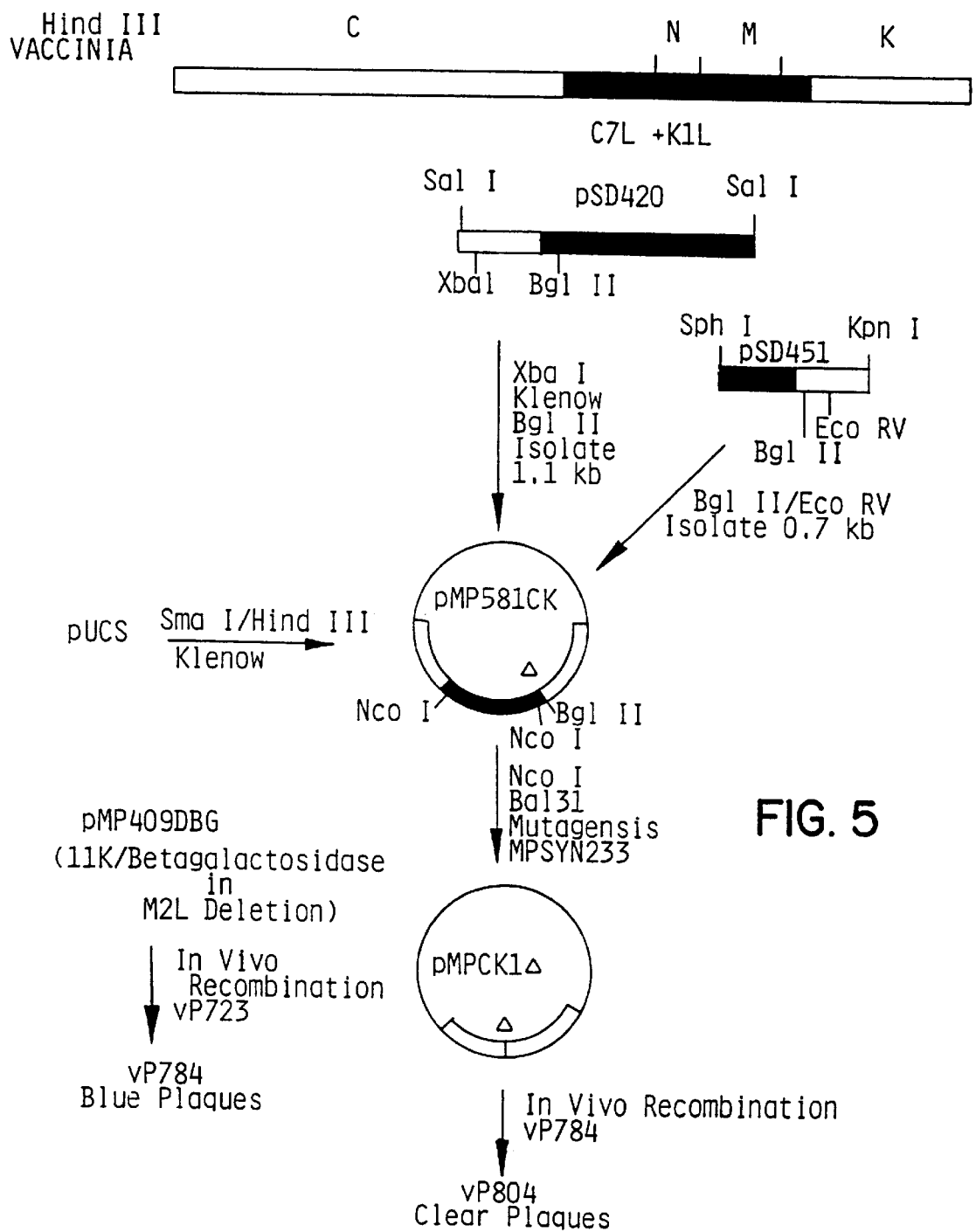
FIG. 5 schematically shows a method for the construction of plasmid pMPCK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide (SEQ ID NO:19)

```
                   BglII
MPSYN82    5' TTTCTGTATATTTGCACCAATTTAGATCTT-
           ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTTAACACTATACTCATATTAATAAAAAT-AATATTTATT-3'. The resulting plasmid, pMPCSK1Δ, is deleted for vaccinia sequences positions 18,805–29,108, encompassing 12 vaccinia open reading frames [IC7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Example 6

Construction of Plasmid pSD548 for Deletion of Large Subunit, Ribonucleotide Reductase (I4L)

Figure 6:
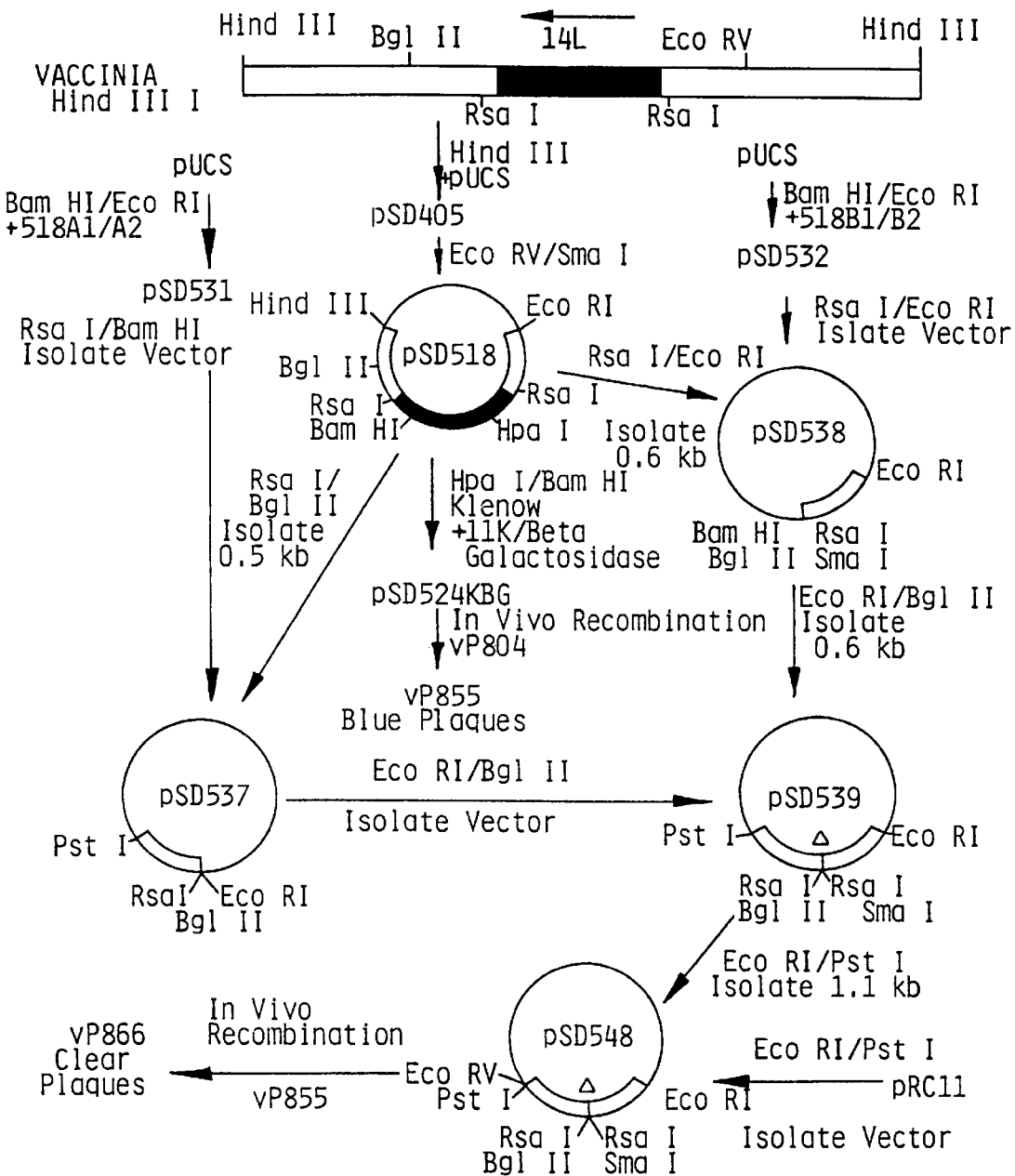
FIG. 6 schematically shows a method for the construction of plasmid pSD548 for deletion of large subunit, ribonucleotide reductase and generation of recombinant vaccinia virus vP866 (NYVAC)
Figure 7:
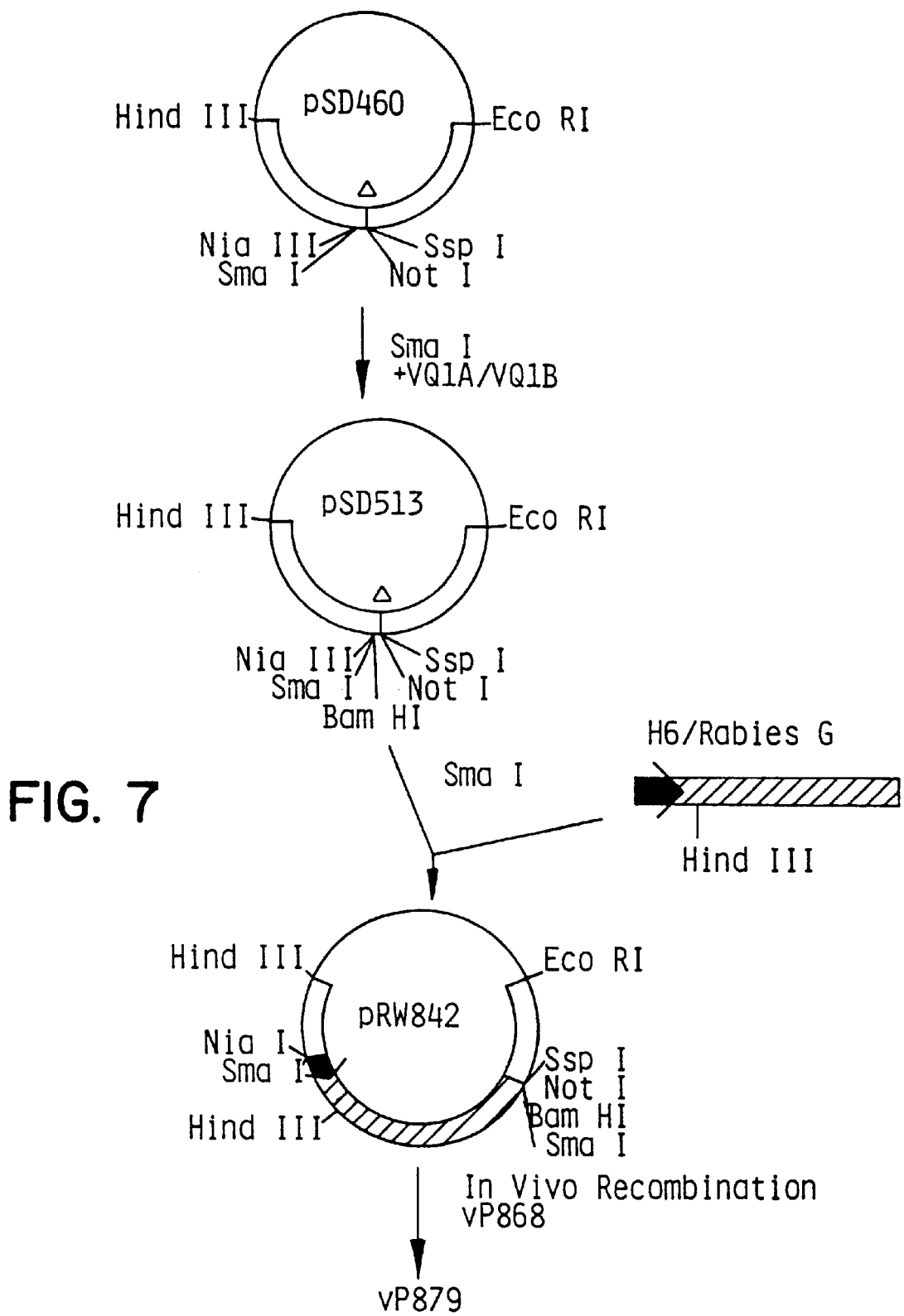
FIG. 7 schematically shows a method for the construction of plasmid pRW842 for insertion of rabies glycoprotein G gene into the TK deletion locus and generation of recombinant vaccinia virus vP879.

Referring now to FIG. 6, plasmid pSD405 contains vaccinia HindIII (pos. 63,875-70,367) cloned in pUC8. pSD405 was digested with EcoRV within vaccinia sequences (pos. 67,933) and with SmaI at the pUC/vaccinia junction, and ligated, forming plasmid pSD518. psD518 was used as the source of all the vaccinia restriction fragments used in the construction of pSD548.

The vaccinia I4L gene extends from position 67,371-65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, PUC8 was cut with BamHI/EcoRI and ligated with annealed synthetic oligonucleotides 518A1/518A2 (SEQ ID NO:21/SEQ ID NO:22)

```
              BamHI    RsaI
518A1    5' GATCCTGAGTACTTTGTAATATAATGATATATATTTTCACTTTATCTCAT
518A2    3'     GACTCATGAAACATTATATTACTATATATAAAAGTGAAATAGAGTA
                                                    BglII    EcoRI
```

-continued

```
TTGAGAATAAAAAGATCTTAGG      3'    518A1

AACTCTTATTTTTCTAGAATCCTTAA  5'    518A2
``` forming plasmid pSD531. pSD531 was cut with RsaI (partial) and BamHI and a 2.7 kb vector fragment isolated. pSD518 was cut with BglII (pos. 64,459)/ RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
                  BamHI BglII SmaI
518B1    5'  GATCCAGATCTCCCGGGAAAAAAATTATTTAACTTTTCATTAATAG-

518B2    3'      GTCTAGAGGGCCCTTTTTTTAATAAATTGAAAAGTAATTATC-

RsaI    EcoRI
             GGATTTGACGTATGTAGCGTACTAGG       3'    518B1

CCTAAACTGCATACTACGCATGATCCTTAA   5'    518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/Bglfragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 7

Insertion of a Rabies Glycoprotein G Gene Into NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
       SmaI BglII XhoI  PstI  NarI  BamHI
VQ1A 5' GGGAGATCTCTCGAGCTGCAGGGCGCCGGATCCTTTTTCT3'

VQ1B 3' CCCTCTAGAGAGCTCGACGTCCCGCGGCCTAGGAAAAAGA5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}P$-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 8

Construction of ALVAC Recombinants Expressing Rabies Virus Glycoprotein G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 8 (SEQ ID NO. 27) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:28) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides: RW145 (SEQ ID NO:29): ACTCT-CAAAAGCTTCCCGGGAAT-TCTAGCTAGCTAGTTTTTATAAA RW146 (SEQ ID NO:30): GATCTTTATAAAAACTAGCTAGCTA-GAATTCCCGGGAAGCTTTTGAGAGT Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G. were cloned into pUC9 as pRW737. Oligonucleotides A through E contain the H6 promoter, starting at NruI, through the HindIII site of rabies G followed by BglII. Sequences of oligonucleotides A through E ((SEQ ID NO:31)–(SEQ ID NO:35)) are:

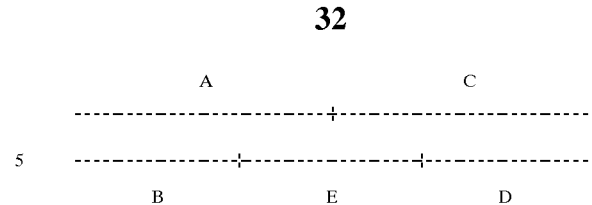

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI , completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:36): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 9A and 9B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previ-

```
A (SEQ ID NO:31):  CTGAAATTATTTCATTATCGCGATATCCGTTAAGTTTGTATCGTAATGGTTCCTCAGGCTCTCCTGTTTGT

B (SEQ ID NO:32):  CATTACGATACAAACTTAACGGATATCGCGATAATGAAATAATTTCAG

C (SEQ ID NO:33):  ACCCCTTCTGGTTTTTCCGTTGTGTTTTGGGAAATTCCCTATTTACACGATCCCAGACAAGCTTAGATCTCAG

D (SEQ ID NO:34):  CTGAGATCTAAGCTTGTCTGGGATCGTGTAAATAGGGAATTTCCCAAAACA

E (SEQ ID NO:35):  CAACGGAAAAACCAGAAGGGGTACAAACAGGAGAGCCTGAGGAAC
```

The diagram of annealed oligonucleotides A through E is as follows:

ously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell substrates:
(1) Primary chick embryo fibroblast (CEF) cells produced from 11 day old white leghorn embryos;
(2) Vero cells—a continuous line of African Green monkey kidney cells (ATCC # CCL81); and
(3) MRC-5 cells—a diploid cell line derived from human fetal lung tissue (ATCC # CCL171).

The initial inoculation was performed at an m.o.i. of 0.1 pfu per cell using three 60mm dishes of each cell substrate containing $2 \times 10^6$ cells per dish. One dish was inoculated in the presence of 40 μg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5ml of EMEM+2% NBCS on two dishes (samples to and t0) and 5 ml of EMEM+2% NBCS containing 40 μg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell substrate was inoculated undiluted onto three dishes of the same cell substrate (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-S and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell substrate was inoculated onto a permissive CEF monolayer and harvested at cytopathic effect (CPE) or at 7 days if no CPE was evident. The results of this experiment are shown in Table 3. Even after amplification through a permissive cell substrate, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1 \times 10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 μl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 log10 mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 μl instilled on the surface of the right eye without scarification; (2) 100 μl as several droplets in the mouth; (3) 100 μl in each of two intradermal injection sites in the shaven skin of the external face of the right arm; and (4) 100 μl in the anterior muscle of the right thigh.

Four monkeys were inoculated with each virus, two with a total of 5.0 $\log_{10}$ pfu and two with a total of 7.0 $\log_{10}$ pfu.

Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;

(b) MRC-5, human embryonic lung, ATCC # CCL 171;

(c) WISH human amnion, ATCC # CCL 25;

(d) Detroit-532, human foreskin, Downs's syndrome, ATCC # CCL 54; and (e) Primary CEF cells.

Chicken embryo fibroblast cells produced from 11 day old white leghorn embryos were included as a positive control. All inoculations were performed on preformed monolayers of $2\times10^6$ cells as discussed below.

A. Methods for DNA analysis.

Three dishes of each cell line were inoculated at 5 pfu/cell of the virus under test, allowing one extra dish of each cell line un-inoculated. One dish was incubated in the presence of 40 µg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2\times10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 µg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene.

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 $\mu$l of dilutions inoculated into the footpad of four to six week old mice. Mice were challenged 14 days later by the intracranial route with 300 $\mu$l of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 6. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 $\mu$l of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 $\log_{10}$ mouse LD$_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ TCID$_{50}$ had antibody titers on day 14 post-vaccination and all dogs had titers at 29 days. All dogs were protected from a challenge which killed three out of four controls. In cats, three of five cats receiving 6.7 $\log_{10}$ TCID$_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ TCID$_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An anamnestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

Sequential Passage of ALVAC in Avian and non-Avian Cells

| | | CEF | Vero | MRC-5 |
|---|---|---|---|---|
| Pass 1 | | | | |
| Sample | t0[a] | 2.4 | 3.0 | 2.6 |
| | t7[b] | 7.0 | 1.4 | 0.4 |
| | t7A[c] | 1.2 | 1.2 | 0.4 |
| Pass 2 | | | | |
| Sample | t0 | 5.0 | 0.4 | N.D.[d] |
| | t7 | 7.3 | 0.4 | N.D. |
| | t7A | 3.9 | N.D. | N.D. |
| Pass 3 | | | | |
| Sample | t0 | 5.4 | 0.4 | N.D. |
| | t7 | 7.4 | N.D. | N.D. |
| | t7A | 3.8 | N.D. | N.D. |
| Pass 4 | | | | |
| Sample | t0 | 5.2 | N.D. | N.D. |
| | t7 | 7.1 | N.D. | N.D. |
| | t7A | 3.9 | N.D. | N.D. |

[a] This sample was harvested at zero time and represents the residual input virus. The titer is expressed as $\log_{10}$ pfu per ml.
[b] This sample was harvested at 7 days post-infection.
[c] This sample was inoculated in the presence of 40 µg/ml of Cytosine arabinoside and harvested at 7 days post infection.
[d] Not detectable

TABLE 2

Sequential Passage of ALVAC-RG in Avian and non-Avian Cells

| | | CEF | Vero | MRC-5 |
|---|---|---|---|---|
| Pass 1 | | | | |
| Sample | t0[a] | 3.0 | 2.9 | 2.9 |
| | t7[b] | 7.1 | 1.0 | 1.4 |
| | t7A[c] | 1.8 | 1.4 | 1.2 |
| Pass 2 | | | | |
| Sample | t0 | 5.1 | 0.4 | 0.4 |
| | t7 | 7.1 | N.D.[d] | N.D. |
| | t7A | 3.8 | N.D. | N.D. |
| Pass 3 | | | | |
| Sample | t0 | 5.1 | 0.4 | N.D. |
| | t7 | 7.2 | N.D. | N.D. |
| | t7A | 3.6 | N.D. | N.D. |
| Pass 4 | | | | |
| Sample | t0 | 5.1 | N.D. | N.D. |
| | t7 | 7.0 | N.D. | N.D. |
| | t7A | 4.0 | N.D. | N.D |

[a] This sample was harvested at zero time and represents the residual input virus. The titer is expressed as $\log_{10}$ pfu per ml.
[b] This sample was harvested at 7 days post-infection.
[c] This sample was inoculated in the presence of 40 µg/ml of Cytosine arabinoside and harvested at 7 days post-infection.
[d] Not detectable.

TABLE 3

Amplification of residual virus by passage in CEF cells

| | | CEF | Vero | MRC-5 |
|---|---|---|---|---|
| a) ALVAC | | | | |
| Pass | 2[a] | 7.0[b] | 6.0 | 5.2 |
| | 3 | 7.5 | 4.1 | 4.9 |
| | 4 | 7.5 | N.D.[c] | N.D. |
| | 5 | 7.1 | N.D. | N.D. |
| b) ALVAC-RG | | | | |
| Pass | 2[a] | 7.2 | 5.5 | 5.5 |
| | 3 | 7.2 | 5.0 | 5.1 |
| | 4 | 7.2 | N.D. | N.D. |
| | 5 | 7.2 | N.D. | N.D. |

[a] Pass 2 represents the amplification in CEF cells of the 7 day sample from Pass 1.
[b] Titer expressed as $\log_{10}$ pfu per ml
[c] Not Detectable

TABLE 4

Schedule of inoculation of rhesus macaques with ALVAC-RG (vCP65)

| Animal | | Inoculation |
|---|---|---|
| 176L | Primary: | $1 \times 10^8$ pfu of vCP65 orally in TANG |
| | Secondary: | $1 \times 10^7$ pfu of vCP65 plus $1 \times 10^7$ pfu of vCP82[a] by SC route |
| 185 L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177 L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP6S by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Priinary | $1 \times 10^7$ pfu of vCP65 orally |

[a] vCP82 is a canarypox virus recombinant expressing the measles virus fusion and hemagglutinin genes.

TABLE 5

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a] Titer expressed as $\log_{10}$ pfu per ml
[b] Culture incubated in the presence of 40 µg/ml of Cytosine arabinoside

TABLE 6

Potency of ALVAC-RG as tested in mice

| Test | Challenge Dose[a] | $PD_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse $LD_{50}$
[b]Expressed as $\log_{10} TCID_{50}$

TABLE 7

Efficacy of ALVAC-RG in dogs and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 8

Anti-rabies serological response of squirrel monkeys inoculated with canarypox recombinants

| Monkey # | Previous Exposure | Rabies serum-neutralizing antibody[a] | | | | | |
|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10} TCID_{50}$ of ALVAC
[d]Animals received 5.0 $\log_{10} TCID_{50}$ of vCP37
[e]Animals received 5.0 $\log_{10} TCID_{50}$ of ALVAC-RG
[f]Animals received 7.0 $\log_{10} TCID_{50}$ of ALVAC-RG
[g]Not tested.

TABLE 9

Inoculation of rhesus macaques with ALVAC-RG[a]

| | Route of Primary Inoculation | | | | | | | | | |
|---|---|---|---|---|---|---|---|---|---|---|
| Days post-Inoculation | or/Tang 176L[b] | SC 185L | SC 177L | SC 186L | IM 178L | SC 182L | IM 179L | SC 183L | IM 180L | OR 184L | 187L[b] |
| −84 | — | — | — | — | | | | | | | |
| −9 | — | — | — | — | — | — | | | | | |
| 3 | — | — | — | — | | | | | | | |
| 6 | — | — | ± | ± | | | | | | | |
| 11 | — | — | 16[d] | 128 | | | | | | | |
| 19 | — | — | 32 | 128 | — | — | | | | | |
| 35 | — | — | 32 | 512 | | | | | | | |
| 59 | — | — | 64 | 256 | | | | | | | |
| 75 | — | — | 64 | 128 | | | | | | | |
| 99[c] | — | — | 64 | 256 | — | — | — | — | — | — | |
| 2 | — | — | 32 | 256 | — | — | — | — | — | — | |
| 6 | — | — | 512 | 512 | — | — | — | — | — | — | |
| 15 | 16 | 16 | 512 | 512 | 64 | 32 | 64 | 128 | 32 | — | — |
| 29 | 16 | 32 | 256 | 256 | 64 | 64 | 32 | 128 | 32 | — | — |
| 55 | | 32 | | | | 32 | | 32 | 16 | | |
| 57 | 16 | | 128 | 128 | 16 | | 16 | | | | — |

[a]See Table 9 for schedule of inoculations.
[b]Animals 176L and 185L received 8.0 $\log_{10}$ pfu by the oral route in 5 ml Tang. Animal 187L received 7.0 $\log_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |

TABLE 10-continued

Inoculation of chimpanzees with ALVAC-RG

| Weeks post-<br>Inoculation | Animal 431<br>I.M. | Animal 457<br>S.C. |
|---|---|---|
| 20/8 | 64 | 128 |
| 26/12 | 32 | 128 |

[a]Titer expressed as reciprocal of last dilution showing inhibition of fluorescence in an RFFI test
[b]Day of re-inoculation Example 9

Immunization of Humans Using Canarypox Expressing Rabies Glycoprotein (ALVAC-RG: vCP65)

Figure 9A:
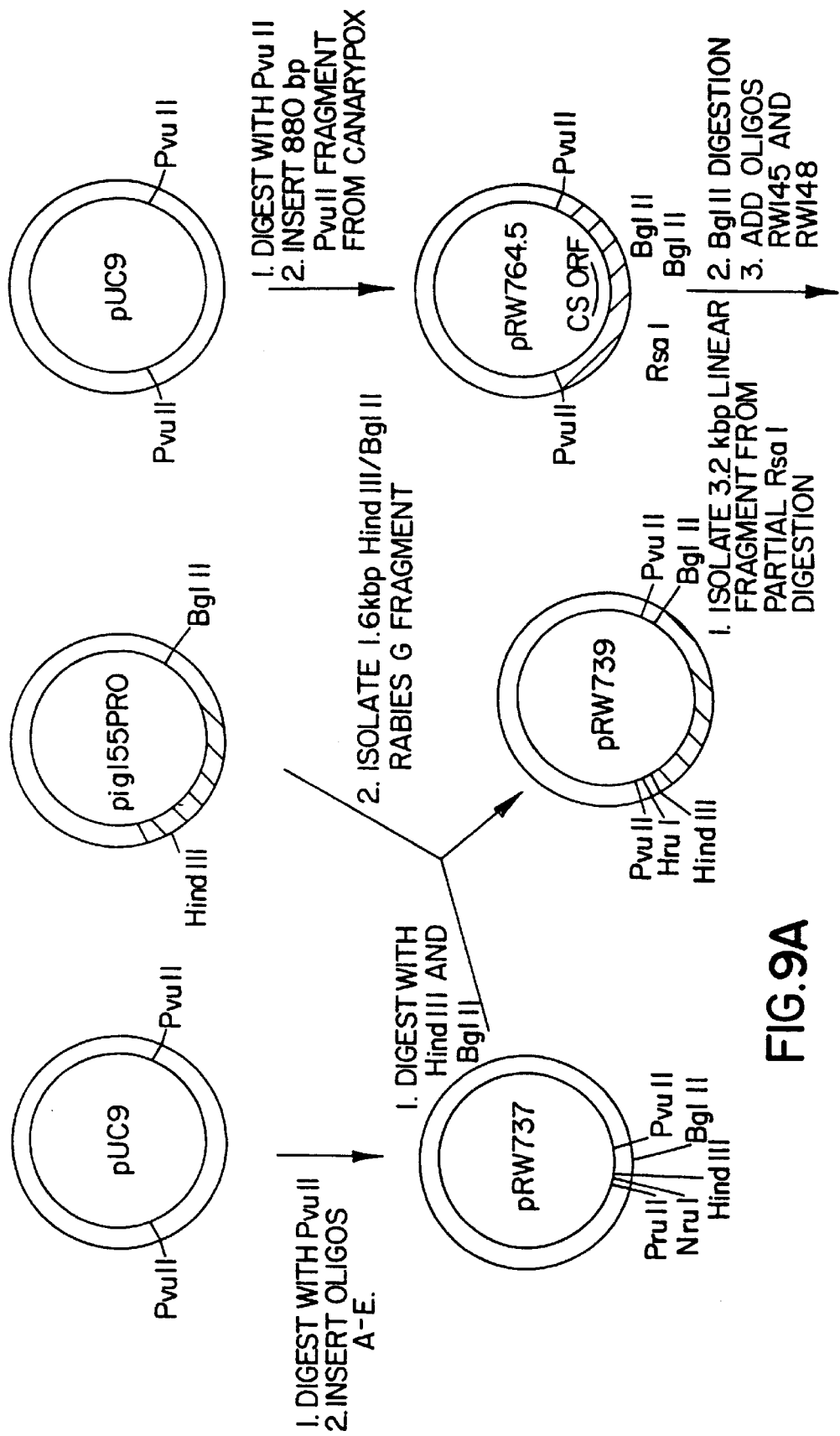

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.1 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and inocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC-HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith et al., 1973). Canarypox antibodies were measured by direct ELISA. The antigen, a suspension of purified canarypox virus disrupted with 0.1% Triton ×100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.7° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 12). Twenty eight days after the first injection all the HDC recipients had protective titers ($\geq 0.5$ IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIGS. 11A–11D show graphs of rabies neutralizing antibody titers (Rapid Fluorescent Focus Inhibition Test or RFFIT, IU/ml): Booster effect of HDC and vCP65 ($10^{5.5}$ $TCID_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 11A to 11D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)-ALVAC-RG (vCP65) group had significantly lower titers than the three other groups. Similarly, the ALVAC-RG (VCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ $TCID_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Geneva, 1981; Kuwert et al., 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., 1991; Etinger et al., 1991).

Thus, this Example clearly demonstrates that a non-replicating poxvirus can serve as an immunizing vector in humans, with all of the advantages that replicating agents confer on the immune response, but without the safety problem created by a fully permissive virus. And, from this disclosure such as this Example and other Examples suitable dosages and modes or routes for administration or immunization of recombinants containing either rabies or other coding, or expression products thereof, are within the ambit of the skilled artisan as well modes for in vitro expression.

TABLE 11

Reactions in the 5 days following vaccination

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp > 37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 12

Rabies neutralizing antibodies (REFIT; IU/ml)
Individual titers and geometric mean titers (GMT)

| | | Days | | | | |
|---|---|---|---|---|---|---|
| No. | TCID50/dose | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| | G.M.T. | <0.1 | <0.1 | 2.96 | 9.0 | 11.5* |

*p = 0.007 student t test

TABLE 13

Canarypox antibodies: ELISA Geometric Mean Titers*

| vCP65 dosage | | Days | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 10

Comparison of the $LD_{50}$ of ALVAC and NYVAC with Various Vaccinia Virus Strains Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated for plaque forming units in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench (Reed and Muench, 1938).

Comparison of the $LD_{50}$ of ALVAC and NYVAC with Various Vaccinia Virus Strains for Normal. Young Outbred Mice by the ic Route. In young, normal mice, the virulence of NYVAC and ALVAC were several orders of magnitude lower than the other vaccinia virus strains tested (Table 14). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses (3.85×10$^8$ PFUs, ALVAC and 3×10$^8$ PFUS, NYVAC) by an undetermined mechanism by this route of inoculation.

Comparison of the $LD_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3 \times 10^7$ PFUs, 100% mortality resulted. Mortality rates of 33.3% were observed at $6.3 \times 10^6$ PFUS. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, $6 \times 10^8$ and $6 \times 10^7$ PFUs, caused 100% mortality. However, the MST of mice challenged with the highest dose, corresponding to 380 $LD_{50}$, was only 2 days (9 deaths on day 2 and 1 on day 4). In contrast, all mice challenged with the highest dose of WR-L, equivalent to 500 $LD_{50}$, survived to day 4.

TABLE 14

Calculated 50% Lethal Dose for mice by various vaccinia virus strains and for canarypox virus (ALVAC) by the ic route

| POXVIRUS STRAIN | CALCULATED $LD_{50}$ (PFUs) |
|---|---|
| WR(L) | 2.5 |
| VC-2 | $1.26 \times 10^4$ |
| WYETH | $5.00 \times 10^4$ |
| NYVAC | $1.58 \times 10^8$ |
| ALVAC | $1.58 \times 10^8$ |

TABLE 15

Calculated 50% Lethal Dose for newborn mice by various vaccinia virus strains and for canarypox virus (ALVAC) by the ic route

| POXVIRUS STRAIN | CALCULATED $LD_{50}$ (PFUs) |
|---|---|
| WR(L) | 0.4 |
| VC-2 | 0.1 |
| WYETH | 1.6 |
| NYVAC | $1.58 \times 10^6$ |
| ALVAC | $1.00 \times 10^7$ |

Example 11

Evaluation of NYVAC (vP866) and NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, New York, and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test. virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites with 0.1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day -2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per µl for untreated mice (n=4) and 4,220 cells per µl for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 µl of a range of dilutions (2.0–8.0 $\log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Figure 10:
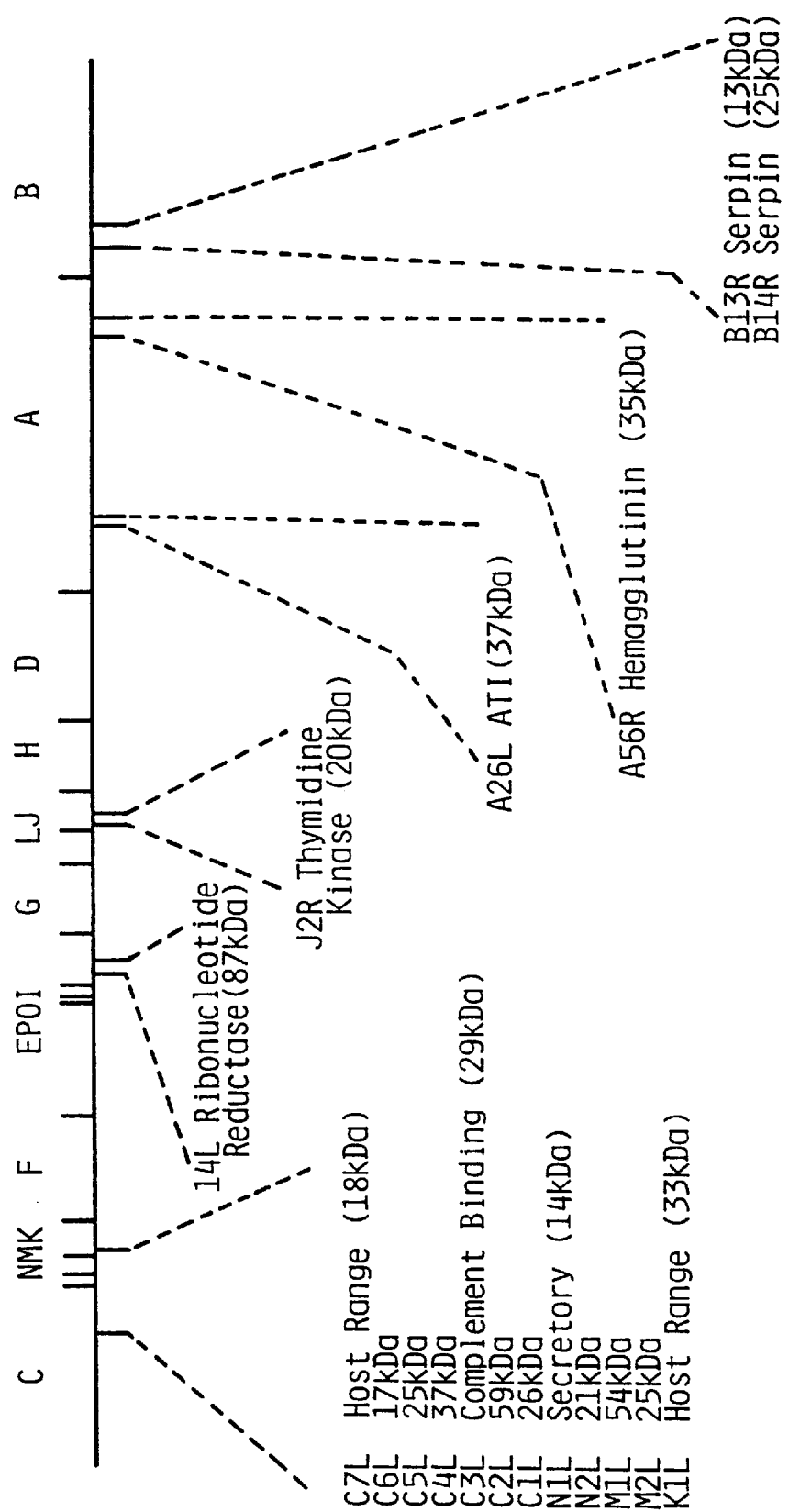
FIG. 10 shows schematically the ORFs deleted to generate NYVAC.
Figure 11A:
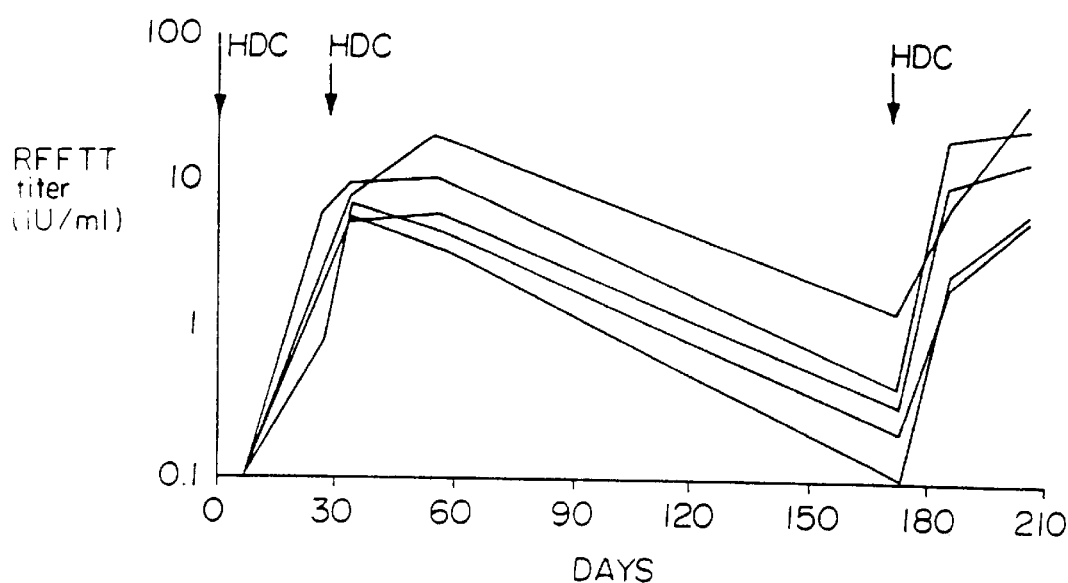
Figure 11C:
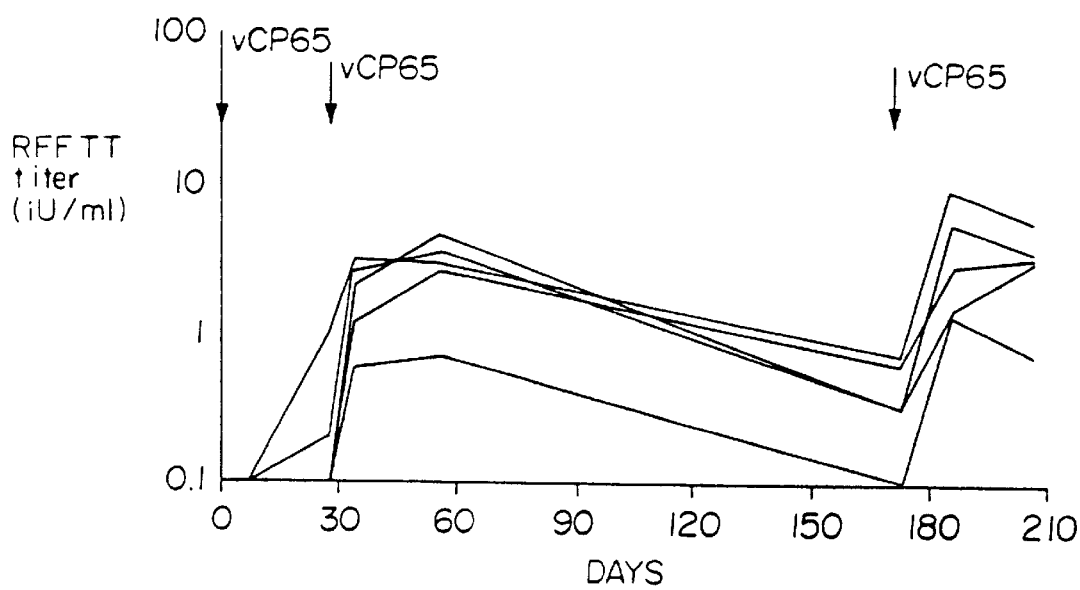

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contrast, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70-151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained. in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells.

The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5\times10^4$ to $9.5\times10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65\times10^5$ to $1.65\times10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the inocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of specific virulence-associated genes in NYVAC prevents lesion occurrence.

Together, the results in this Example and in foregoing Examples, including Example 10, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human, animal, medical and veterinary applications (Tartaglia et al., 1992). Furthermore, the use of NYVAC as a general laboratory expression vector system may greatly reduce the biological hazards associated with using vaccinia virus.

By the following criteria, the results of this Example and the Examples herein, including Example 10, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] | | | % Yield |
|---|---|---|---|---|---|
| | | VC-2 | NYVAC | ALVAC | |
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 µg/ml of cytosine arabinoside.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION | | ULCERATION | |
|---|---|---|---|---|---|
| | | Size[b] | Days[c] | Size | Days |
| WR | 10[4] | 386 | 30 | 88 | 30 |
| | 10[5] | 622 | 35 | 149 | 32 |
| | 10[6] | 1057 | 34 | 271 | 34 |
| | 10[7] | 877 | 35 | 204 | 35 |
| | 10[8] | 581 | 25 | 88 | 26 |
| WYETH | 10[4] | 32 | 5 | —[d] | — |
| | 10[5] | 116 | 15 | — | — |
| | 10[6] | 267 | 17 | 3 | 15 |
| | 10[7] | 202 | 17 | 3 | 24 |
| | 10[8] | 240 | 29 | 12 | 31 |
| VC-2 | 10[4] | 64 | 7 | — | — |
| | 10[5] | 86 | 8 | — | — |
| | 10[6] | 136 | 17 | — | — |
| | 10[7] | 167 | 21 | 6 | 10 |
| | 10[8] | 155 | 32 | 6 | 8 |
| NYVAC | 10[4] | — | — | — | — |
| | 10[5] | — | — | — | — |
| | 10[6] | — | — | — | — |
| | 10[7] | — | — | — | — |
| | 10[8] | — | — | — | — |

[a]pfu of indicated vaccinia virus in 0.1 ml PBS inoculated intradermally into one site.
[b]mean maximum size of lesions ($mm^2$)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0[a] | 6.14 |
|  | 7.0 | 6.26 |
|  | 6.0 | 6.21 |
| WYETH | 8.0 | 3.66 |
|  | 7.0 | 4.10 |
|  | 6.0 | 3.59 |
| VC-2 | 8.0 | 4.47 |
|  | 7.0 | 4.74 |
|  | 6.0 | 3.97 |
| NYVAC | 8.0 | 0 |
|  | 7.0 | 0 |
|  | 6.0 | 0 |

[a]expressed as $\log_{10}$ pfu.

TABLE 19

Virulence studies in immunocompromised mice

| Poxvirus Strain | $LD_{50}$[a] Nude mice | Cyclophosphamide treated mice |
|---|---|---|
| WR | 422 | 42 |
| VC-2 | >10$^9$ | <1.65 × 10$^5$ |
| WYETH | 1.58 × 10$^7$ | 1.83 × 10$^6$ |
| NYVAC | >5.50 × 10$^8$ | 7.23 × 10$^8$ |
| ALVAC | >10$^9$ | ≥5.00 × 10$^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of 5 × 10$^8$ pfu.

TABLE 20

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]Four to six week old mice were inoculated in the footpad with 50–100 μl of range of dilutions (2.0–8.0 $\log_{10}$ tissue culture infection dose 50% ($TCID_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% ($LD_{50}$) per mouse. At day 28, surviving mice were counted and a protective dose 50% ($PD_{50}$) was calculated.

Example 12

Cloning of HCMV gB in Poxvirus Vectors

Cloning of the HCMV gB gene into vaccinia donor Plasmid, pMP22BHP. The 4800 bp HindIII-BamHI fragment of the HindIII D fragment of the HCMV DNA (Towne strain) was cloned into the 2800 bp HindIII-BamHI fragment of the plasmid pIBI24 (International Biotechnologies, Inc., New Haven, Conn.). By in vitro mutagenesis (Kunkel, 1985) using the oligonucleotides CMVM5 (SEQ ID NO:74) (5-GCCTCATCGCTGCTGGATATCCGTTAAGTTTGTA-TCGTAATGGAATCCAGGATCTG-3') and CMVM3 (SEQ ID NO:75) (5"-GACAGAGACTTGTGATTTTTATAAGCTTCGTAAGC-TGTCA-3'), the gB gene was modified to be expressed under the control of the vaccinia H6 promoter (Taylor et al., 1988a,b; Perkus et al., 1989). The plasmid containing the modified gB was designated 24CMVgB (5+3). The DNA sequence of the CMVgB gene is shown in FIG. 12 (SEQ ID NO:37).

Plasmid pMP2VCL (containing a polylinker region with vaccinia sequences upstream of the K1L host range gene) was digested within the polylinker with HindIII and XhoI and ligated to annealed oligonucleotides SPHPRHA A through D generating SP131 containing a HindIII site, H6 promoter −124 through −1 (Perkus et al., 1989) and a polylinker region. SPHPRHA A(SEQ ID NO:76) (5'-AGCTTCTTTATTCTATACTTAAAAAGTGAAAATAAA-TACAAAGGTTCTTGAGGGT-3') SPHPRHA B(SEQ ID NO:77) (5'-TGTGTTAAATTGAAAGCGAGAAATAAT-CATAAATTATTTCATTATCGCGATATCCGTTAA GTTTGTATCGTAC-3') SPHPRHA C (SEQ ID NO:78) (3'-TTATTAGTATTTAATAAAGTAATAGCGCTATA-GGCAATTCAAACATAGCATGAGCT-5') SPHPRHA D (SEQ ID NO:79) (3'-AGAAATAAGATATGAATTTTTCACTTT-TATTTATGTTTCCAAGAACTCCCAACACAATTT AACTTTCGCTCT-5').

The 2900 bp EcoRV-BamHI fragment of 24CMVgB (5+3) was cloned into the 3100 bp EcoRV-BglII fragment of SP131. This cloning step put the gB gene under the control of the H6 promoter. The resulting plasmid was designated SP131CMVgB.

Plasmid pSD22-H contains a 2.9 kb BglII fragment derived from the HindIII F region of the WR strain of vaccinia virus ligated into the BamHI site of pUC8. The unique BamHI site in pSD22-H is a nonessential site used as an insertion locus for foreign genes (Panicali and Paoletti, 1982). Plasmid pMP22BHP is a derivative of pSD22-H in which the unique BamHI site was modified by the addition of an expanded polylinker region for the insertion of foreign DNA. Plasmid pMP22BHP was digested with HindIII and ligated to a 2.9 kb HindIII fragment from SP131CMVgB (containing the H6 promoted gB gene) generating plasmid SAg22CMVgB. To modify the polylinker region in sAg22CMVgB, the plasmid was digested with BamHI followed by partial digestion with HindIII and purified. Ligation to a 50 bp BamHI/HindIII polylinker derived from IBI24 resulted in plasmid 22CMVgB.

Cloning of the HCMVgB gene into NYVAC donor plasmid pSD542. Plasmid pSD542 (a NYVAC TK locus donor plasmid) was derived from plasmid pSD513 (Tartaglia et al., 1992). The polylinker region in pSD513 was modified by cutting with PstI/BamHI and ligating to annealed synthetic oligonucleotides MPSYN288 (SEQ ID NO:80) (5'-GGTCGACGGATCCT -3') and MPSYN289 (SEQ ID NO:81) (5'-GATCAGGATCCGTCGACCTGCA -3') resulting in plasmid pSD542.

22CMVgB was digested with BamHI and NsiI to generate a fragment containing the H6 promoter and part of the gB gene, and with NsiI and PstI to generate a fragment containing the remainder of the gB gene. These two fragments were ligated to pSD542 that had been digested with BamHI and PstI within its' polylinker creating the NYVAC donor plasmid 542CMVgB. The DNA sequence of the CMVgB gene and flanking sequences contained in 542CMVgB is shown in FIG. 13A and B (SEQ ID NO:38).

Cloning of the HCMV gB gene into the ALVAG donor plasmid CP3LVOH6. An 8.5 kb canarypox BglII fragment was cloned in the BamHI site of pBS-SK plasmid vector (Stratagene, La Jolla, Calif.) to form pWW5. Nucleotide sequence analysis revealed a reading frame designated C3 initiated at position 1458 and terminated at position 2897 in the sequence in FIGS. 14A—C (SEQ ID NO:39). In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:82) (5'-CAGTTGGTACCACTGGTATTTTATTTCAG -3') and RG278 (SEQ ID NO:83) (5'-TATCTGAATTCCTGCAGCCCGGGTTTT-TATAGCTAATTAGTCAAATGTGAGTTAATATTA G -3').

Primers for the 3" sequences were RG279 (SEQ ID NO:84) TCGCTGAATTCGATATCAAGCTTATC-GATTTTTATGACTAGTTAATCAAATAAAAAGCAT ACAAGC-3') and RG280 (SEQ ID NO:85) (5'-TTATCGAGCTCTGTAACATCAGTATCTAAC-3'). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

A 908 bp fragment of canarypox DNA, immediately upstream of the C3 locus was obtained by digestion of plasmid pWW5 with NsiI and SspI. A 604 bp fragment of canarypox DNA was derived by PCR (Engelke et al., 1988) using plasmid PWW5 as template and oligonucleotides CP16 (SEQ ID NO:86) (5'-TCCGG-TACCGCGGCCGCAGATATTTGTTAGCTTCTGC-3') and CP17 (SEQ ID NO:87) (5'-TCGCTCGAGTAGGATACCTACCTACTACCTACG-3'). The 604 bp fragment was digested with Asp718 and XhoI (sites present at the 5' ends of oligonucleotides CP16 and CP17, respectively) and cloned into Asp718 -XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI and ligated to the 908 bp NsiI-SspI fragment generating SPCPLAX which contains 1444 bp of canarypox DNA upstream of the C3 locus.

A 2178 bp BglII-StyI fragment of canarypox DNA was isolated from plasmids pXX4 (which contains a 6.5 kb NsiI fragment of canarypox DNA cloned into the PstI site of pBS-SK). A 279 bp fragment of canarypox DNA was isolated by PCR (Engelke et al., 1988) using plasmid pXX4 as template and oligonucleotides CP19 (SEQ ID NO:88) (5'-TCGCTCGAGCTTTCTTGACAATAACATAG-3') and CP20 (SEQ ID NO:89) (5'-TAGGAGCTCTTTATACT ACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA.

To add additional unique sites to the polylinker, pC3I was digested within the polylinker region with EcoRI and ClaI, treated with alkaline phosphatase and ligated to kinased and annealed oligonucleotides CP12 (SEQ ID NO:90) (5'-AATTCCTCGAGGGATCC-3') and CP13 (SEQ ID NO:91) (5'-CGGGATCCCTCGAGG-3') (containing an EcoRI sticky end, XhoI site, BamHI site and a sticky end compatible with ClaI) generating plasmid SPCP3S. SPCP3S was digested within the canarypox sequences downstream of the C3 locus with StyI and SacI (pBS-SK) and ligated to a 261 bp BglII-SacI fragment from SPC3RA and the 2178 bp BglII-StyI fragment from pXX4 generating plasmid CPRAL containing 2572 bp of canarypox DNA downstream of the C3 locus. SPCP3S was digested within the canarypox sequences upstream of the C3 locus with Asp718 (in pBS-SK) and AccI and ligated to a 1436 bp Asp718-AccI fragment from SPCPLAX generating plasmid CPLAL containing 1457 bp of canarypox DNA upstream of the C3 locus. CPLAL was digested within the canarypox sequences downstream of the C3 locus with StyI and SacI (in pBS-SK) and ligated to a 2438 bp StyI-SacI fragment from CPRAL generating plasmid CP3L containing 1457 bp of canarypox DNA upstream of the C3 locus, stop codons in six reading frames, early transcription termination signal, a polylinker region, early transcription termination signal, stop codons in six reading frames, and 2572 bp of canarypox DNA downstream of the C3 locus.

The early/late H6 vaccinia virus promoter (Taylor et al., 1988a,b; Perkus et al., 1989) was derived by PCR (Engelke et al., 1988) using pRW838 (a plasmid containing the rabies glycoprotein gene (Kieny et al., 1984) linked to the H6 promoter) as template and oligonucleotides CP21 (SEQ ID NO:92) (5'-TCGGGATCCGGGTTAATTAATTAGTT-ATTAGACAAGGTG-3') and CP22 (SEQ ID NO:93) (5'-TAGGAATTCCTCGAGTACGATACAAACTTAAGCGG-ATATCG-3'). The PCR product was digested with BamHI and EcoRI (sites present at the 5' ends of oligonucleotides CP21 and CP22, respectively) and ligated to CP3L that was digested with BamHI and EcoRI in the polylinker generating plasmid VQH6CP3L.

ALVAC donor plasmid VQH6CP3L was digested within the polylinker with XhoI and within the H6 promoter with NruI and ligated to a NruI/HindIII fragment from 22CMVgB containing part of the H6 promoter and gB gene and a polylinker derived from pIBI24 by XhoI and HindIII digestion generating the ALVAC donor plasmid CP3LCMVgB. The DNA sequence of the CMVgB gene plus additional flanking DNA sequences in plasmid CP3LCMVgB is shown in FIGS. 15A–C (SEQ ID NO:40).

Cloning of the HCMV gB gene deleted of its transmembrane region into the NYVAC donor plasmid pSD553. Plasmid pSD553 is a vaccinia deletion/insertion plasmid of the COPAK series. It contains the vaccinia K1pL host range gene (Gillard et al., 1986; Perkus et al., 1990) within flanking Copenhagen vaccinia arms, replacing the ATI region (ORFs A25L, A26L; Goebel et al., 1990a,b). pSD553 was constructed as follows.

Left and right vaccinia flanking arms were constructed by polymerase chain reaction (PCR) using pSD414, a pUC8-based clone of vaccinia SalI B (Goebel et al., 1990a,b) as template. The left arm was synthesized using synthetic deoxyoligonucleotides MPSYN267 (SEQ ID NO:94) (5'-GGGCTGAAGCTTGCTGGCCGCTCATTAGACAAGC-GAATGAGGGAC-3') and MPSYN268 (SEQ ID NO:95) (5'-AGATCTCCCGGGCTCGAGTAATT- AATTAATTTT-TATTACACCAGAAAAGACGGCTTGAGA T C-3') as primers. The right arm was synthesized using synthetic deoxyoligonucleotides MPSYN269 (SEQ ID NO:96) (5'-TAATTACTCGAGCCCGGGAGATCTAATT-TAATTTAATTTATATAACTCATTTTTTGAATA T ACT-3') and MPSYN270 (SEQ ID NO:97) (5'-TATCTCGAATTCCCGCGGCTTTAAATGGACGGAAC-TCTTTTCCCCC-3') as primers. The two PCR-derived DNA fragments containing the left and right arms were combined in a further PCR reaction. The resulting product was cut with EcoRI/HindIII and a 0.9 kb fragment isolated. The 0.9 kb fragment was ligated with pUC8 cut with EcoRI/

HindIII, resulting in plasmid pSD541. The polylinker region located at the vaccinia ATI deletion locus was expanded as follows. pSD541 was cut with BglII/XhoI and ligated with annealed complementary synthetic oligonucleotides MPSYN333 (SEQ ID NO:98) (5'-GATCTTTTGTTAACAAAAACTAATCAGC-TATCGCGAATCGATTCCCGGGGGATCCGGTAC CC-3') and MPSYN334 (SEQ ID NO:99) (5'-TCGAGGGTACCGGATCCCCCGGGAATC-GATTCGCGATAGCTGATTAGTTTTTGTTAACAA AA-3') generating plasmid pSD552. The K1L host range gene was isolated as a 1 kb BglII (partial)/HpaI fragment from plasmid pSD452 (Perkus et al., 1990). pSD552 was cut with BglII/HpaI and ligated with the K1L containing fragment, generating pSD553.

A HindIII fragment from SP131CMVgB (containing the HCMVgB gene under the control of the H6 promoter) was filled in with the klenow fragment of DNA polymerase I and ligated into plasmid pSD553 which had been SmaI digested and alkaline phosphatase treated. The resulting NYVAC donor plasmid (in which the H6 promoted gB is in the same orientation as K1L) was designated 553H6CMVgB. The DNA sequence of the CMVgB gene plus additional flanking DNA sequences in plasmid 553H6CMVgB is shown in FIGS. 16A and B (SEQ ID NO:41).

The sequence of CMVgB deleted of its transmembrane region is presented in FIG. 17 (SEQ ID NO:42). The nucleotides encoding the transmembrane region were deleted in the following manner. Oligonucleotides SPgB3 (SEQ ID NO:100) (5'-GATCCATGGACTCGACAGCGGCGTCTCT-GCATGCAGCCGCTGCAGA -3') and SPgB4 (SEQ ID NO:101) (5'-AGCTTCTGCAGCGGCTGCATGCAGAGA-CGCCGCTGTCGAGTCCATG-3') were kinased, annealed and cloned into BamHI/HindIII digested and alkaline phosphatase treated IBI24 generating plasmid SPCMVgB2. Oligonucleotides SPgB1 (SEQ ID NO:102) (5'-TACGAATTCTGCAGTTCACCTATGACACGTTGC-3') and SPgB2 (SEQ ID NO:103) (5'-ATAGGATCCATGGTCGTCCAGACCCTTGAGGTA-GGGC-3') were used in PCR with plasmid SP131CMVgB as template to generate a 0.7 kb fragment. This fragment was digested with EcoRI/BamHI and cloned into EcoRI/BamHI digested and alkaline phosphase treated IBI24 generating plasmid SPCMVgB1. A 0.7 kb EcoRI/NcoI fragment from SPCMVgB1 was ligated to EcoRI/NcoI digested and phosphatase treated SPCMVgB2 generating plasmid SPCMVgB3. The unique NcoI site in SPCMVgB3 was deleted by mutagenesis (Mandecki, 1986) using oligonucleotide SPgB5 (SEQ ID NO:104) (5'-GCCCTACCTCAAGGGTCTGGACG-ACACTCGACAGCGGCGTCTCTGCAT-3') generating plasmid SPCMVgB4. A 0.7 kb PstI fragment from SPCM-VgB4 was ligated to a 6.6 kb PstI fragment from 553H6CMVgB generating NYVAC donor plasmid 553H6CMVgBTM[31]. This plasmid contains the gB gene under the control of the H6 promoter with its transmembrane region deleted (amino acids 715–772; Spaete et al., 1988). The DNA sequence of the transmembrane deleted CMVgB gene plus additional flanking DNA sequences in plasmid 553H6CMVgBTM⁻ is shown in FIGS. 18A and B (SEQ ID NO:43).

Cloning the HCMVgB gene deleted of its transmembrane region and containing an altered cleavage site into NYVAC donor plasmid pSD553. The sequence of CMVgB deleted of its transmembrane region and containing an altered cleavage site is presented in FIG. 19 (SEQ ID NO:44). The alteration of the cleavage site was accomplished in the following manner. Oligonucleotides SPgB8 (SEQ ID NO:105) (5'-AATTGGTGACCG-3') and SPgB9 (SEQ ID NO:106) (5'-GATCCGGTCACC-3') were kinased, annealed and cloned into EcoRI/BamHI digested and alkaline phosphatase treated IBI24 generating plasmid BstIBI. A 1.4 kb BstEII/SphI fragment from 553H6CMVgBTM⁻ was cloned into BstEII/SphI digested and alkaline phosphatase treated BstIBI. generating plasmid SPCMVgB5.

Oligonucleotides SPgB10 (SEQ ID NO:107) (5'-TGAAAGACCGAATTCTGCGT-3') plus SPgB11 (SEQ ID NO:108) (5'-TGCGATTCATCGGTTTGTTGTAGAT-3') and SPgB12 (SEQ ID NO:109) (5'-GACCCTTGAGGTAGGGCGGC-3') plus SPgB13 (SEQ ID NO:110) (5'-ACTCATAATAGAACCATAAGATCTA-CAGATGGCAACAAT-3') were used in PCR with plasmid 553H6CMVgBTM- to generate 0.7 and 0.8 kb fragments. These two fragments were combined in a PCR with oligonucleotides SPgB10 plus SPgB12 to generate a 1.2 kb fragment. The 1.2 kb fragment was digested with EcoRI and PstI and a 0.5 kb fragment isolated and cloned into EcoRI/PstI digested and alkaline phosphatase treated IBI24 generating plasmid SPCMVgB6. The 0.5 kb EcoRI/PstI fragment from SPCMVgB6 was used to replace the corresponding fragment in SPCMVgB5 generating plasmid SPCMVgB7. A 1.4 kb BstEII/SphI fragment from SPCMVgB7 was used to replace the corresponding fragment in 553H6CMVgB generating NYVAC donor plasmid 553H6gBC⁻ TM⁻. This plasmid contains the gB gene under the control of the H6 promoter with its transmembrane region deleted (amino acids 715–772) and an alteration at the cleavage site (RTKR*ST modified to RTIRST where the asterisk indicated where cleavage normally occurs (Spaete et al., 1988) the S codon was modified to create a BglII restriction site). The DNA sequence of the cleavage site altered and transmembrane deleted CMVgB gene plus additional flanking DNA sequences in plasmid 553H6gBC⁻ TM⁻ is shown in FIGS. 20A and B (SEQ ID NO:45).

Example 13

Construction of Recombinant Poxviruses Containing HCMVgB

Procedures for transfection of recombinant donor plasmids into tissue culture cells infected with a rescuing poxvirus and identification of recombinants by in situ hybridization on nitrocellulose filters have been described (Guo et al., 1989; Panicali and Paoletti, 1982; Piccini et al., 1987; Perkus et al., 1993). Plasmid 542CMVgB was transfected into NYVAC (vP866) infected Vero cells (ATCC CCL#81) to generate the recombinant vP10001 (NYVAC-gB). Plasmid CP3LCMVgB was transfected into ALVAC infected primary chicken embryo fibroblast (CEF) cells to generate the recombinant vCP139 (ALVAC-gB). Plasmids 553H6CMVgB, 553H6CMVgBTM⁻ and 553H6gBC⁻ TM⁻ were transfected into NYVAC infected Vero cells to generate the recombinants vP1126, vP1128 and vP1145, respectively. Plasmid 22CMVgB was transfected into Vero cells infected with the WR L variant vaccinia virus (Panicali et al., 1981) to generate the recombinant vP992.

Example 14

Immunopecipitation of HCMVgB Expressed by Poxvirus Recombinants

Immunoprecipitation assays were performed as described previously (Taylor et al., 1990) using gB specific guinea pig polyclonal serum (Gönczöl et al., 1990). The apparent molecular weights of the gB specific bands corresponded to previously published results (Britt and Auger, 1986; Britt and Vugler, 1989; Reis et al., 1993). The intracellular fraction from vP992, vP1001, vCP139, vP1126, vP1128 and vP1145 contained a major band of apparent molecular weight 130–140 kDa, identifiable as the glycosylated uncleaved gB precursor. Fainter bands at approximately 110 kDa and 55 kDa, representing the N-terminal and C-terminal processed fragments were also seen in the cell fractions. The extracellular medium from vP1128 and vP1145 infected cells contained the uncleaved precursor and N-terminal and C-terminal processed fragments.

Example 15

Humeral Response of Laboratory Animals Inoculaated with ACVAC-gB MYVAC-gBR

Following a single immunization of CBA mice with vP1001 (NYVAC-gB), neutralizing antibody titers of the sera of inoculated mice were assessed (Gönczöl et al., 1986). Antibodies capable of neutralizing HCMV were detected (Table 21) in the sera of mice 14–21 days later (geometric mean titers of 1:16) and between 28–60 days post-immunization (gmt=1:26). A single immunization of CBA mice with vCP139 (ALVAC-gB) generated HCMV neutralizing antibody titers of 1:64 gmt (14–21 days pi) and 1:111 gmt (between 28 and 60 days pi). Thus, immunization of mice with NYVAC and ALVAC recombinants expressing HCMV gB elicited antibodies able to neutralize the infectivity of HCMV.

ALVAC-gB (vCP139) was evaluated for safety and immunogenicity in human volunteers. After two inoculations with $10^{6.3}$ TCID$_{50}$ of this recombinant, no serious reactions were noted.

TABLE 21

HCMV Neutralizing Antibodies in CBA mice

| Immunization | Days After Immunization | | |
|---|---|---|---|
| | 14–21 | 21–28 | 28–60 |
| NYVAC-gB | 16 | | |
| | 16 | | |
| | | | 32 |
| | | | 24 |
| | | | 32 |
| | | | 24 |
| ALVAC-gB | 32 | | |
| | 64 | | |
| | 128 | | |
| | 64 | | |
| | | 64 | |
| | | 28 | |
| | | | 128 |
| | | | 96 |

Immunization was i.p. with 2–4 × $10^8$ PFU of recombinant viruses.

Guinea pigs were immunized twice with ALVAC-gB (days 0 and 28) and sera were tested for the presence of HCMV neutralizing antibody. HCNV neutralizing antibody was detected (Table 22) in the sera on day 34 (gmt=60), day 42 (gmt=60) and day 56(gmt=60). Thus, immunization of guinea pigs with ALVAC-gB elicited antibodies able to neutralize the infectivity of HCMV.

TABLE 22

HCMV Neutralizing Antibodies in Guinea Pigs Inoculated with ALVAC-gB

| | Days | | | | | |
|---|---|---|---|---|---|---|
| Guinea Pig # | 0 | 14 | 28 | 34 | 42 | 56 |
| 19 | <4 | <4 | <4 | 64 | 64 | 64 |
| 20 | <4 | <4 | <4 | 32 | 64 | 64 |
| 21 | <4 | <4 | <4 | 12 | 32 | 64 |
| 22 | <4 | <4 | <4 | 48 | 48 | 32 |
| 23 | <4 | <4 | 4 | 96 | 46 | 46 |
| 24 | <4 | <4 | <4 | 46 | 46 | 32 |

Guinea pigs were inoculated by intramuscular route on days 0 and 28 with $10^{6.3}$ TCID$_{50}$ Example 16

Cloning of HCMVgH in Poxvirus Vectors

Cloning of the HCMVgh gene into the NYVAC donor plasmid pSD550. The HCMVH gene was isolated from genomic DNA (Town strain) by PCR using oligonucleotides SPgH1 (SEQ ID No:111) (5'-TATCTGCAGATGCGGCCAGGCCTCCCCTCCTAC-3') and SPgH2 (SEQ ID NO:112) (5'-CCGAAGCTTTCAGCATGTCTTGAGCATGC-3'). The resulting 2.3 kb fragment was digested with PstI (site at 5' end of SPgH1) and HindIII (site at the 5' end of SPgH2) and cloned into PstI/HindIII digested and alkaline phosphatase treated IBI24 generating plasmid SPgH1. The sequence of CMVGH is presented in FIG. 21 (SEQ ID NO:46).

The 3' end of the gH gene in SPgH1 was modified to contain a vaccinia virus early transcription termination signal (Yuen and Moss, 1987) and a unique XhoI restriction site in the following manner. SPgH1 was digested within the 3' end of the gH gene with SPH1 and within IBI24 with HindIII and the fragment containing gH was purified and ligated to kinased and annealed oligonucleotides SPgH16 (SEQ ID NO:113) (5'-CTCAAGACATGCTGATTTTTATCTCGAGA-31') and SPgH17 (SEQ ID NO:114) (5'-AGCTTCTCGAGATAAAAATCAGCAT-GTCTTGAGCATG -3') generating plasmid SPgH2.

Kinased and annealed oligonucleotides SPgH12 (SEQ ID NO:115) (5'-AATTCTCGAGTTTATTGGGAAGAATAT-GATAATATTTTGGGATTTC -3'), SPgH13 (SEQ ID NO:116) (5'-AAAATTGAAAATATATAATTA-CAATATAAAATGCGGCCCGGG-3'), SPgH14 (SEQ ID NO:117) (5'-GATCCCC GGGCCGCATTTTATATTGTAATTATAT-3') and SPgH15 (SEQ ID NO:118) (5'-ATTTTCAATTTTGAAATCCCAAAATATTATCATATTC-TTCCCAATAAACTCGAG-3') were ligated to EcoRI/BamHI digested and alkaline phosphatase treated IBI24 generating plasmid SPgH3 which contains a unique XhoI site, the entomopox 42K promoter and nucleotide sequences encoding the first four amino acids of HCMVgH (underlined bases in codons three and four in oligonucleotides SPgH13 (SEQ ID NO:116) and SPgH14 (SEQ ID NO:117) were modified to create a SmaI site without altering the amino acid sequence). Oligonucleotides SPgH18 (SEQ ID NO:119) (5'-TTAGAATTCCCCGGGCTCCCCTCCTACCTCATCGT-3') and SPgH19 (SEQ ID NO:120) (5'-

TTACTGCAGTAAGTGTTAAGTCTCTGTTGGTATC-3') were used in PCR with plasmid SPgH1 as template to derive a 0.4 kb fragment. This fragment was digested with SmaI and PstI and cloned into SmaI/PstI digested and alkaline phosphatase treated SPgH3 generating plasmid SPgH5 which contains a unique XhoI site, the 42K promoter and 5' 15% of the HCMVgH gene. A 0.4 kb EcoRI/BglII fragment from SPgH5 was ligated to a 4.7 kb EcoRI/BglII fragment from SPgH3 generating plasmid SPgH6 which contains the 42K promoted gH gene flanked by XhoI sites.

Plasmid pSD550 (an I4L locus donor plasmid) was derived from plasmid pSD548 (Tartaglia et al., 1992). The polylinker region in pSD548 was modified by cutting with BglII and SmaI and ligating to annealed synthetic oligonucleotides 539A (SEQ ID NO:121) (5'-AGAAAAATCAGTTAGCTAAGATCTC-CCGGGCTCGAGGGTACCGGATCCTGATTAGTTAAT T TTTGT-3') and 539B (SEQ ID NO:122) (5'-GATCACAAAAATTAACTAATCAGGATC-CGGTACCCTCGAGCCCGGGAGATCTTAGCTAAC T GATTTTTCT-3') resulting in plasmid pSD550. The 2.3 kb XhoI fragment from SPgH6 was cloned into XhoI digested and alkaline phosphatase treated pSD550 generating the NYVAC donor plasmid I4L42KgH in which the orientation of gH is in the same direction as the replaced 14L gene. The DNA sequence of CMVgH plus additional flanking DNA sequences in plasmid I4L42KgH are shown in FIGS. 22A and B (SEQ ID NO:47).

Cloning of the HCMVqH gene into the ALVAC donor plasmid NVQC5LSP. A C5 insertion vector containing 1535 bp upstream of C5, polylinker containing KpnI/SmaI/XbaI and NotI sites and 404 bp of canarypox DNA (31 base pairs of C5 coding sequence and 373 bp of downstream sequence) was derived in the following manner. A genomic library of canarypox DNA was constructed in the cosmid vector puK102 (Knauf and Nester, 1982) probed with pRW764.5 (a PuC9 based plasmid containing an 880 bp canarypox PvuII fragment which includes the C5 ORF Nucleotides 1372 to 2251 in FIG. 8 (SEQ ID NO:27)) and a clone containing a 29 kb insert identified (pHCOS1). A 3.3 kb ClaI fragment from pHCOS1 containing the C5 region was identified. The C5 open reading frame is initiated at position 1537 and terminated at position 1857 in the sequence shown in FIG. 8 (SEQ ID NO:27).

The C5 insertion vector was constructed in two steps. The 1535 bp upstream sequence was generated by PCR amplification using oligonucleotides C5A (SEQ ID NO:123) (5'-ATCATCGAATTCTGAATGTTAAATGTTATACTTTG-3') and C5B (SEQ ID NO:124) (5'-GGGGGTACCTTTGAGAGTACCACTTCAG-3') and purified genomic canarypox DNA as template. This fragment was digested with EcoRI (within oligoC5A) and cloned into EcoRI/SmaI digested pUC8 generating C5LAB. The 404 bp arm was generated by PCR amplification using oligonucleotides C5C (SEQ ID NO:125) (5'-GGGTCTAGAGCGGCCGCTTATAAAGATCTAAAATG-CATAATTTC-3') and C5DA (SEQ ID NO:126) (5'-ATCATCCTGCAGGTATTCTAAACTAGGAATAGATG-3'). This fragment was digested with PstI (within oligoC5DA) and cloned into SmaI/PstI digested C5LAB generating pC5L.

pC5L was digested within the polylinker with AsP718 and NotI, treated with alkaline phosphatase and ligated to kinased and annealed oligonucleotides CP26 (SEQ ID NO:127) (51'-GTACGTGACTAATTAGCTATAAAAAG-GATCCGGTACCCTCGAGTCTAGAATCGATCCCGG GTTTTTATGA CTAGTTAATCAC-3') and CP27 (SEQ ID NO:128) (5'-GGCCGTGATTAACTAGTCATAAAAAC-CCGGGATCGATTCTAGACTCGAGGGTACCGGATC C TTTTTATAGCTAATTAGTCAC-3') (containing a disabled Asp718 site, translation stop codons in six reading frames, vaccinia early transcription termination signal (Yuen and Moss, 1987), BamHI KpnI XhoI XbaI ClaI and SmaI restriction sites, vaccinia early transcription termination signal, translation stop codons in six reading frames, and a disabled NotI site) generating plasmid C5LSP. The polylinker region in C5LSP was further modified by digesting with BamHI and ligating to annealed oligonucleotides CP32 (SEQ ID NO:129) (5'-GATCTTAATTAATTAGTCATCAG-GCAGGGCGAGAACGAGACTATCT-GCTCGTTAATTAAT TAGGTCGACG-3') and CP33 (SEQ ID NO:130) (5'-GATCCGTCGACCTAATTAATTAACGAG-CAGATAGTCTCGTTCTCGCCCTGCCTGATGACT A ATTAATTAA-3'0 generating plasmid VQC5LSP. VQC5LSP was digested with EcoRI, treated with alkaline phosphatase, ligated with kinased and annealed oligonucleotide CP29 (SEQ ID NO:131) (5'-AATTGCGGCCGC-3') and digested with NotI. The linearized plasmid was purified and self ligated to generate plasmid NVQC5LSP. The 2.3 kb XhoI fragment from SPgH6 was cloned into XhoI digested and alkaline phosphatase treated NVQC5LSP generating the ALVAC donor plasmid NVQC5L42KgH in which the orientation of gH is in the same direction as the deleted C5 gene. The DNA sequence of CMVgH plus additional flanking DNA sequences in plasmid NVQC5L42KgH are shown in FIGS. 23A and B (SEQ ID NO:27).

Cloning of the HCMVgH gene into the vaccinia donor plasmid pSD157K1LINS. Plasmid pHK (which contains the WR vaccinia HindIII K fragment cloned in pBR322) was digested with HindIII/BglII and a 1.2 kb fragment isolated and cloned into BamHI/HindIII digested pBS-SK+ yielding plasmid pBS-HKARM. pBS-HKARM was digested with Asp718 in the polylinker region, blunt ended with the klenow fragment of E. Coli DNA polymerase, and digested with HindIII at the pBS/vaccinia junction. The resulting 4.1 kb vector fragment was ligated to a 2.0 kb NruI/HindIII fragment from pHM-1 (pHM-1 contains the WR vaccinia virus HindIII M fragment cloned in pBR322) resulting in plasmid pMPWRMK. pMPWRMK was cut with HpaI and ligated with annealed synthetic oligonucleotides MPSYN527 (SEQ ID NO:132) (5'-ATAAAAATTAGCTACTCAGGTACCCTG-CAGTCGCGAGGATCCGAATTCCCCGGGCTCGAG T GATTAATTAGTTTTTAT-3') and MPSYN528 (SEQ ID NO:133) (5'-ATAAAAACTAATTAATCACTCGAGC-CCGGGGAATTCGGATCCTCGCGACTGCAGGGTACC T GAGTAGCTAATTTTTAT-3'). The resulting plasmid is pSD157K1LINS. pSD157K1LINS was digested within its polylinker region with XhoI, treated with alkaline phosphatase and ligated to the 2.3 kb XhoI fragment from SPgH6 yielding plasmid MP804-42KgH (which contains the HCM-VgH gene and vaccinia K1L gene both in the same orientation.) The DNA sequence of CMVgH plus additional flanking DNA sequences in plasmid MP804-42KgH are shown in FIG. 24 (SEQ ID NO:49).

Example 17

Construction of Recombinant Poxviruses Containing HCMVgH

Plasmid I4L42kgH was transfected into NYVAC infected CEF cells to generate the recombinant vP1173 (containing HCMVgH). The same plasmid was transfected into vP1001 infected Vero cells to generate the recombinant vP1183 (containing HCMVgB and gH).

Plasmid NVQC5L42KgH was transfected into ALVAC infected CEF cells to generate the recombinant vCP236 (containing HCMVgH). The same plasmid was transfected into vCP139 infected CEF cells to generate the recombinant vCP233 (containing HCMVgB and gH). Vaccinia virus vP11170 (which contains Ecogpt under the transcriptional control of the entomopoxvirus 42K promoter in place of the deleted K1L gene) was used to infect Vero cells transfected with plasmid MP804-42KgH to generate the recombinant vP1205B.

Example 18

Immunoprecipitation of HCMVgH Expressed by Poxvirus Recombinants

Immunoprecipitation performed with a monoclonal antibody specific for HCMVgH demonstrated the expression of an 86 kDa gH protein (Pachl et al., 1989) by recombinants vP1173, vP1183, vP1205B, vCP233 and vCP236. Immunoprecipitation with the gB specific guinea pig polyclonal serum demonstrated correct expression of gB by recombinants vP1183 and vCP233.

The HCMV 72-kDa immediate early 1 protein (IE1) is a target for $CD^+$ cytotoxic T cells in humans (Borysiewicz et al., 1988) and is recognized by $CD4^+$ T cells (Alp et al., 1991). For one individual the peptide specificities of proliferative and MHC-class I-restricted cytotoxic determinants on IE1 were determined and found to be spatially distinct segments of the exon 4 coding region (Alp et al., 1991).

The IE1 protein has been shown to up-regulate expression from its own promoter (Cherrington and Mocarski, 1989) as well as expression from the HIV LTR (Biegalke and Geballe, 1991; Ghazal et al., 1991) and expression of the promoters for the cellular genes c-myc, c-fos and hsp70 (Hagemeier et al., 1992; Santomenna and Colberg-Poley, 1990; Colberg-Poley et al., 1992). Lafemina et al., (1989) reported that the IE1 protein expressed in stable cell lines preferentially associates with metaphase chromosomes and proposed that this protein may be involved in maintenance of a putative plasmid state for HCMV DNA during latency.

In the following Examples 19–30, the development of poxvirus recombinants expressing the entire IE1 gene, IE1 deleted of amino acids 2–32, IE1 deleted of amino acids 292–319 or the exon 4 segment of IE1 are provided. These studies were performed in order to develop a form of the IE1 gene product that would be incapable of translocation to the nucleus, thus decreasing its potential to act as a transactivator, while maintaining its ability to be recognized by $CD8^+$ cytotoxic T cells. Example 45 demonstrates that an ALVAC recombinant expressing an altered form of the IE1 protein (deleted of amino acids 2–32) which unlike the full length gene product is found in both the nucleus and cytomplasm of infected cells, can re-stimulate cytotoxic effector cells from HCMV seropositive individuals.

Example 19

Cloning of the Entire HCMV IE1 Gene in Poxvirus Vectors

Cloning of the HCMV IE1gene into the vaccinia donor plasmid pSD22-H. The entire HCMV IE1 gene (AD169 strain) was derived as a 1.5 kb fragment by PCR using plasmid pJD083 as template (Akrigg et al., 1985) along with oligonucleotides IE3 (SEQ ID NO:134) (5'-ACGGATCCATAAAAATTACTGGTCAGCCTTGCTTC-3') and IE5 (SEQ ID NO:135) (5'-ATCCGTTAAGTTTGTATCGTAATGGAGTCCTCTGC-CAAGAGA-3'). The DNA sequence of CMV IE1 is presented in FIG. 25 (SEQ ID NO:50). Plasmid pSD486H6340 (which contains an irrelevant gene linked precisely to H6 promoter) was digested (within the H6 promoter) with NruI and (at the 3' end of the irrelevant gene) with BamHI and ligated to the BamHI digested 1.5 kb PCR fragment (BamHI site located at the 5' end of oligonucleotide IE3) generating plasmid pSD486H6HCMVIE1.

The H6 promoted IE1 gene was obtained from pSD486H6HCMVIE1 as a 1.6 kb fragment by digestion with BamHI followed by partial BglII digestion and ligated to BamHI digested pSD22-H yielding plasmid pSD22-HCMVIE1. The DNA sequence of CMV IE1 plus additional flanking DNA sequences in plasmid pSD22-HCMVIE1are shown in FIG. 26 (SEQ ID NO:51).

Cloning of the HCMVIE1 gene into the vaccinia donor plasmid pSD554. Oligonucleotides SPIE1(SEQ ID NO:136) (5'-CGCGAATTCTCGCGATATCCGTTAAGTTTGT-ATCGTAATGGAGT-3') and SPIE2 (SEQ ID NO:137) (5'-GCCTCTAGAGTTAACCTCCTTCCTCAACAT-3') were used in PCR with plasmid pSD486H6HCMVIE1 as template to generate a 181 bp fragment. This fragment was digested with EcoRI and XbaI and cloned into EcoRI/XbaI digested and alkaline phosphatase treated IBI24 generating plasmid SPIE1 containing part of the H6 promoter and the first 135 bp of the IE1 gene. Oligonucleotides SPIE3 (SEQ ID NO:138) (5'-CGGTCTAGAGGTTATCAGTGTAATGAAGC-3') and SPIE4 (SEQ ID NO:139) (5'-CCGAAGCTTCTCGAGATAAAAATTACTGGTCAGC-CTTGCTTCTAGT-3') were used in PCR with plasmid pSD486H6HCMVIE1as template to generate a 506 bp fragment. This fragment was digested with XbaI and HindIII and cloned into XbaI/HindIII digested and alkaline phosphatase treated IBI24 generating plasmid SPIE2 containing the 3' end of the IE1 gene, a vaccinia early transcription termination signal and an XhoI site. SPIE1 was digested at the 3' end of the inserted fragment of the IE1 gene with HindII and within the IBI24 polylinker with HindIII, alkaline phosphatase treated and ligated to a 903 bp HindII-BglII fragment from pSD486H6HCMVIE1and a 464 bp BglII-HindIII fragment from SPIE2 generating plasmid SPIE3 containing the entire IE1 gene linked to part of the H6 promoter.

Plasmid pSD553 was cut with NruI and ligated with a SmaI/NruI fragment containing the synthetic H6 promoter (Perkus et al., 1989) upstream from the NruI site located at −26 relative to the translation initiation codon. The resulting plasmid, pMP553H6, was digested with NruI and BamHI and ligated to annealed oligonucleotides MPSYN347 (SEQ ID NO:140) (5'-CGATATCCGTTAAGTTTGTATCG-TAATCTGCAGCCCGGGGGGG -3') and MPSYN348 (SEQ ID NO:141) (5'-GATCCCCCCGGGCTGCAGATTACGATACAAACTTAA-CGGATATCG-3'). The resulting plasmid, pSD554, contains the entire H6 promoter region through nucleotide −1 relative to the initiation codon, followed by a polylinker region. pSD554 was digested with NruI and XhoI and ligated to a 1.5 kb NruI/XhoI fragment from SPIE3 generating plasmid COPAKH6IE. The DNA sequence of CMV IE1 plus flanking DNA sequences in plasmid COPAKH6IE are shown in FIGS. 27A and B (SEQ ID NO:52).

Example 20

Construction of Recombinant Poxviruses Containing the Entire HCMVIE1 Gene

Plasmid pSD22-HCMVIE1 was transfected into Vero cells infected with the WR L variant to generate the recombinant vP893. Plasmid COPAKH6IE was transfected into NYVAC infected Vero cells to generate the recombinant vP1161.

Example 21

Expression of the Entire IE1 Gene by Poxvirus Recombinants

Immunoprecipitation studies performed with a monoclonal antibody specific for HCMVIE1 demonstrated the expression of a 72 kDa IE1 protein (Blanton and Tevethia, 1981; Cameron and Preston, 1981) by recombinants vP893 and vP116. Immunofluorescence studies (performed as described in Taylor et al., 1990) revealed nuclear localization of the IE1 gene product.

Example 22

Cloning of the HCMVIE1 Gene (Lacking Amino Acides 292–319) Vaccinia Donor Plasmid pSD554

The DNA sequence of CMVIE1 lacking amino acids 292–319 is shown in FIG. 28 (SEQ ID NO:53). This deletion was made in the following manner. Plasmid SPIE3 was digested with SpeI and a 4239 bp fragment isolated (which lacks nucleotides 868–958 encoding amino acids 292–319). This fragment was self ligated generating plasmid SPIE4. A 1.4 kb NruI/XhoI fragment from SPIE4 was ligated to NruI/XhoI digested pSD554 generating plasmid COPAKH6IEN⁻. The DNA sequence of CMVIE1 lacking amino acids 292–319 plus flanking DNA sequences in plasmid COPAKH6IEN⁻ are shown in FIGS. 29A and B (SEQ ID NO:54).

Example 23

Construction of a Recombinant Poxvirus Containing The HCMV IE1 Gene Lacking Amino Acides 292–319

Plasmid COPAKH6IEN⁻ was transfected into NYVAC infected Vero cells to generate the recombinant vP1160.

Example 24

Expression of the HCMVIE1 Gene Lacking Amino Acids 292–319

Immunoprecipitation assays demonstrated the expression of a 69 kDa protein in cells infected with vP1160 consistent with the deletion of amino acids 292–319. Immunofluorescence studies revealed nuclear localization of this gene product.

Example 25

Cloning of the Exon 4 Segment of HCMVIE1 in Poxvirus Vectors

Cloning of the Exon 4 segment of HCMVIE1 in NYVAC donor plasmid SPI4LH6. The DNA sequence of the Exon 4 segment of HCMVIE1 is shown in FIG. 30 (SEQ ID NO:55). This segment of the gene was obtained in the following manner. Oligonucleotides SPIE5 (SEQ ID NO:142) (5'-CGCGAATTCTCGCGATATCCGT-TAAGTTTGTATCGTAATGAAACAGAT-TAAGGTTCGAGT-3') and SPIE6 (SEQ ID NO:143) (5'-GCCTCTAGATGCCGCCATGGCCTGACT-3') were used in PCR with plasmid pSD486H6HCMVIE1 to generate a 0.5 kb fragment. This fragment was digested with EcoRI and XbaI and cloned into EcoRI/XbaI digested and alkaline phosphatase treated IBI24 generating plasmid SPIE5. Plasmid SPIE3 was digested with EcoRI and NcoI and a 3.6 kb fragment purified and ligated to a 0.47 kb EcoRI-NcoI fragment from SPIES generating plasmid SPIE6 which contains the Exon 4 segment of IE1 linked to part of the H6 promoter.

The early/late H6 vaccinia virus promoter (Guo et al., 1989; Perkus et al., 1989) was derived by PCR using PRW823 as template (a plasmid containing the H6 promoter linked to an irrelevant gene) and oligonucleotides CP30 (SEQ ID NO:144) (5'-TCGGGATCCGGGTTAATTAATTAGTCATCAGGCA-GGGCG-3') and CP31 (SEQ ID NO:145) (5'-TAGCTCGAGGGTACCTACGATACAAACTTAACGGA-TATCG-3'). The PCR product was digested with BanHI and XhoI (sites present at the 5' end of CP30 and CP31, respectively) and ligated to BamHI/XhoI digested C5LSP generating plasmid VQH6C5LSP. This plasmid was used as template in PCR with oligonucleotides CP31 and RUB1 (SEQ ID NO:146) (5'-TCGGGATCCTTCTTTATTCTATACTTA-3'). The PCR product was digested with BamHI and XhoI (site present at the 5' ends of RUB1 and CP31, respectively) and ligated to BamHI/XhoI digested pSD550 generating plasmid SPI4LH6. A 1.3 kb NruI/XhoI fragment isolated from SPIE6 was cloned into NruI/XhoI digested and alkaline phosphatase treated SPI4LH6 generating plasmid I4LH6IE-Ex4 (in which the H6 promoted IE1 Exon 4 gene is in the same orientation as the replaced I4L gene). The DNA sequence of the Exon 4 segment of HCMVIE1 plus flanking DNA sequences in plasmid I4LH6IE-Ex4 are shown in FIG. 31 (SEQ ID NO:56).

Cloning of the Exon 4 fragment of HCMVIE1 in ALVAC donor plasmid NVQH6C5LSP. Plasmid VQH6C5LSP was digested with EcoRI, treated with alkaline phosphatase, ligated with kinased and annealed oligonucleotide CP29 and digested with NotI. The linearized plasmid was purified and self ligated generating plasmid NVQH6C5LSP. The 1,3 kb NruI/XhoI fragment from SPIE6 was cloned into NruI/XhoI digested and alkaline phosphatase treated NVQH6C5LSP generating plasmid NVQH6IE-Ex4 (in which the H6 promoted IE1 Exon 4 gene is in the same orientation as the replaced C5 gene). The DNA sequence of the Exon 4 segment of HCMVIE1 plus flanking DNA sequences in plasmid NVQH6IE-Ex4 are shown in FIG. 32A and B (SEQ ID NO:57).

Example 26

Construction of Recombinant of Poxviruses Containing the Exon 4 Segment of IE1

Plasmid I4LH6IE-Ex4 was transfected into NYVAC infected CEF cells to generate the recombinant vP1186. Plasmid NVQH6IE-Ex4 was transfected into ALVAC infected CEF cells to generate the recombinant vCP244.

Example 27

Expression of the Exon 4 Segment of HCMVIE1 by Poxvirus Recombinants

Immunofluorescence experiments revealed cytoplasmic localization of the IE-Exon 4 protein expressed by recombinants vP1186 and vCP244. Immunoprecipitation experiments with a monoclonal antibody specific for IE-Exon 4 demonstrated the expression of a 60 kDa protein in cells infected with vCP244 consistent with the predicted size of the exon 4 segment. Immunoprecipitation with a polyclonal rabbit serum raised against a bacterial Exon 4 fusion protein revealed the expression of a 60 kDa protein in cells infected with vP1186 and VCP244.

Example 28

Cloning of the HCMVIE1 Gene (Lacking Amino Acids 2–32) in Poxvirus Vectors

Cloning of the HCMVIE1 gene (lacking amino acids 2–32) in NYVAC donor plasmid SPI4LH6. The DNA sequence of HCMVIE1lacking amino acids 2–32 is shown in FIG. 33 (SEQ ID NO:58). This segment was obtained in the following manner. Oligonucleotides SPIE9 (SEQ ID NO:147) (5'-AATTCTCGCGATATCCGTTAAGTTTG-TATCGTAATGACGACGTTCCTGCAGACTATGTTG A GGAAGGAGGTT-3') and SPIE10 (SEQ ID NO:148) (5'-AACCTCCTTCCTCAACATAGTCTGCAG-GAACGTCGTCATTACGATACAAACTTAACGGAT ATCGC GAG-3') were kinased, annealed and ligated to a 4.2 kb HindII/EcoRI digested and alkaline phosphatase treated fragment from SPIE3 generating plasmid SPIE8. A 1.4 kb NruI/XhoI fragment from SPIE8 (containing part of the H6 promoter and IE1 lacking amino acids 2–32) was ligated to NruI/XhoI digested and alkaline phosphatase treated SPI4LH6 generating plasmid I4LH6IEd32. The DNA sequence of HCMVIE1 lacking amino acids 2–32 plus flanking DNA sequences in plasmid I4LH6IEd32 are shown in FIG. 34 (SEQ ID NO:59).

Cloning of the HCMVIE1 gene (lacking amino acids 2–32) in ALVAC donor plasmid NVQH6C5LSP. The 1.4 kb NruI/XhoI fragment from SPIE8 was cloned into NruI/XhoI digested and alkaline phosphatase treated NVQH6C5LSP generating plasmid NVQH6IEd32. The DNA sequence of HCMVIE1 lacking amino acids 2–32 plus flanking DNA sequences in plasmid NVQH6IEd32 are shown in FIGS. 35A and B (SEQ ID NO:60).

Example 29

Construction of Poxvirus Recombinants Containing the IE1 Gene Lacking Amino Acids 2–32

Plasmid I4LH6IEd32 was transfected into NYVAC infected CEF cells to generate the recombinant vP1201. Plasmid NVQH6IEd32 was transfected into ALVAC infected CEF cells to generate the recombinant vCP256.

Example 30

Expression of IE1Lacking Amino Acides 2–32 by Poxvirus Recombinants

Immunofluorescence experiments revealed both nuclear and cytoplasmic localization of the IE1 protein lacking amino acids 2–32 by recombinants vP1201 and vCP256. Immunoprecipitation with a polyclonal rabbit serum raised against a bacterial exon 4 fusion protein revealed the expression of a 68 kDa protein in cells infected with vP1201 consistent with the predicted size.

Example 31

Cloning of the HCMV pp65 Gene in Poxvirus Vectors

Cloning of the HCMV pp65 gene in NYVAC donor plasmid SPHA-H6. pSD456 is a subclone of Copenhagen vaccinia DNA containing the HA gene (A56R; Goebel et al., 1990a,b) and surrounding regions. pSD456 was used as a template in PCR for synthesis of left and right vaccinia arms flanking the A56R ORF. The left arm was synthesized using oligonucleotides MPSYN279. (SEQ ID NO:149) (5'-CCCCCCGAATTCGTCGACGATTGTTCATGATGGC-AAGAT-3') and MPSYN280 (SEQ ID NO:150) (5'-CCCGGGGGATCCCTCGAGGGTAC-CAAGCTTAATTAATTAAATATTAGTATAAAAAGTGAT TTATTTT-3'). The right arm was synthesized using oligonucleotides MPSYN281 (SEQ ID NO:151) (5'-AAGCTTGGTACCCTCGAGGGATC-CCCCGGGTAGCTAGCTAATTTTTCTTTTACGTATTAT A TATGTAATAAACGTTC-3') and MSYN312 (SEQ ID NO:152) (5'-TTTTTTCTGCAGGTAAGTATTTTTAAAACTTCTAA-CACC-3'). The purified PCR fragments for the left and right arms were combined in a further PCR reaction. The resulting product was digested with EcoRI/HindIII. The resulting 0.9 kb fragment was cloned into EcoRI/HindIII digested pUC8 resulting in plasmid pSD544.

pSD544 was digested within its polylinker with XhoI, filled in with klenow and treated with alkaline phosphatase. Plasmid SP126 (equivalent to SP131) was digested with HindIII, treated with klenow and the H6 promoter isolated by digestion with SmaI. Ligation of the H6 promoter fragment to pSD544 generated SPHA-H6.

The HCMV pp65 gene was PCR amplified using HCMV genomic DNA as template (Towne strain) and oligonucleotides pp65I (SEQ ID NO:153) (5'-GATTATCGCGATATCCGTTAAGTTTG-TATCGTAATGGCATCCGTACTGGGTCCCATTTCG GG-3') and pp651R (SEQ ID NO:154) (5'-GCATAGGTACCGGATCCATAAAAATCAACCTCGGT-GCTTTTTGGGCG-3). The DNA sequence of CMVpp65 is shown in FIG. 36 (SEQ ID NO:61). The 1.6 kb product was digested with NruI and BamHI (site present at the 5' end of oligonucleotides pp651 and pp651R, respectively) and cloned into NruI/BamHI digested SPHA-H6 generating plasmid CMV65.1. This plasmid contained the pp65 gene linked to the H6 promoter, however, the first 30 bp of the pp65 gene were missing.

To derive a plasmid containing the first 30 bp of the pp65 gene oligonucleotides RNApp65I (SEQ ID NO:155) (5'-TAGTTCGGATCCCCGCTCAGTCGCCTACA-3') and pp65R4 (SEQ ID NO:156) (5'-ATCAAGGGATCCATCGAAAAAGAAGAGCG-3') were used in PCR with genomic DNA. The resulting 1 kb fragment was digested with BamHI (BamHI sites present at the 5' ends of both oligonucleotides) and cloned into BamHI digested IBI24 generating plasmid pp65.7. Plasmid pp65.7 was used in PCR with oligonucleotides pp651B (SEQ ID NO:157) (5'-GATTATCGCGATATCCGTTAAGTTTG-TATCGTAATGGAGTCGCGCGGTCGCCGTTGTCCC G -3') and pp65BstXI (SEQ ID NO:158) (5'-ACCTGCATCTTGGTTGC-3') to generate a 0.5 kb fragment. This fragment was digested with NruI and BstXI (sites at the 5' ends of oligonucleotides pp651B and pp65BstXI, respectively) and ligated to a 4.8 kb NruI/BstXI fragment of CMV65.1 generating plasmid pCMV65.2. This plasmid contains the entire pp65 gene linked precisely to the H6 promoter oriented in the same direction as the replaced HA gene. The DNA sequence of CMVpp65 plus flanking DNA sequences in plasmid pCMV65.2 are shown in FIG. 37 (SEQ ID NO:62).

Cloning of the HCMV pp65 gene in ALVAC donor plasmid pMPC616E6VQ. FIGS. 38A and B (SEQ ID NO:63) is the sequence of a 3.7 kb segment of canarypox DNA. Analysis of the sequence revealed a reading frame designate C6L initiated at position 377 and terminated at position 2254. A C6 insertion vector containing 370 bp upstream of C6, polylinker containing SmaI, PstI, XhoI and EcoRI sites, and 1156 bp of downstream sequence was derived in the following manner. The 0.4 bp upstream sequence was generated by PCR amplification of a cosmid clone derived from purified genomic canarypox DNA using oligonucleotides C6A1SG (SEQ ID NO:159) (5'-ATCATCGAGCTCGCGGCCGCCTATCAAAAGTCTT-AATGAGTT-3') and C6B1SG (SEQ ID NO:160) (5'-GAATTCCTCGAGCTGCAGCCCGGGTTTT-TATAGCTAATTAGTCATTTTTTCGTAAGTAAG T ATTTTATTTAA-3'). The 1.2 kb downstream arm was generated by PCR amplification of the same template using oligonucleotides C6C1SG (SEQ ID NO:161) (5'-CCCGGGCTGCAGCTCGAGGAATTCTTTT-TATTGATTAACTAGTCAAATGAGTATATATAA T TGAAAAAGTAA-3') and C6D1SG (SEQ ID NO:162) (5'-GATGATGGTACCTTCATAAATACAAGTTTGA-TTAAACTTAAGTTG-3'). These fragments were fused by a third PCR employing 4gel purified 0.4 and 1.2 kb fragments as template for primers C6A1SG (SEQ ID NO:159) and C6D1SG (SEQ ID NO:162). The resulting 1.6 kb fragment was isolated from an agarose gel, digested with SacI and KpnI and ligated to similarly digested pBS generating C6 insertion plasmid pC6L.

Plasmid pMPC616E6VQ was derived by cloning a HpaI-XhoI fragment containing the H6 promoter precisely linked to an irrelevant gene into Sma-XhoI digested pC6L. pMPC616E6VQ was digested with NruI and BamHI and the 4 kb vector fragment (NruI-BamHI) and 0.6 kb C6 flanking arm fragment (BamHI-BamHI) isolated. These two fragments were combined in a ligation with a 1.7 kb NruI-BamHI fragment from pCMV65.2 (containing part of the H6 promoter linked to the p65 gene) generating plasmid CMV65C6.1 which contained a C6 flanking arm, H6 promoter and the pp65 gene but lacked the 0.6 kb C6 flanking arm. CMV65C6.1 was digested with BamHI, treated with alkaline phosphatase and ligated to the 0.6 kb C6 flanking arm generating plasmid CMV65C6.2 in which C6 flanking arms are present on both sides of the H6-pp65 insert. The DNA sequence of CMVpp65 plus flanking DNA sequences in plasmid CMV65C6.2 are shown in FIGS. 39A and B (SEQ ID NO:64).

Cloning of the HCMVpp65 gene into the vaccinia donor plasmid pSD157 K1LINS. Plasmid pCMV65.2 was digested with KpnI, treated with Mung Bean Nuclease and digested with BamHI generating a 1.7 kb fragment containing H6-pp65. PSD157K1LINS was digested with BamHI and SmaI and ligated to the 1.7 kb fragment generating plasmid CMV65.WR. The DNA sequence of CMVpp65 plus flanking DNA sequences in plasmid CMV65.WR are shown in FIG. 40 (SEQ ID NO:65).

Example 32

Construction of Recombinant Poxviruses Containing HCMVpp65

Plasmid pCMV65.2 was transfected into NYVAC infected Vero cells to generate the recombinant vP1184 (containing HCMVpp65), into vP1001 infected Vero cells to generate the recombinant vP1196 (containing HCMVgB and pp65) and into vP1183 infected Vero cells to generate the recombinant vP1210 (containing HCMVgB, gH and pp65).

Plasmid CMV65C6.2 was transfected into ALVAC infected CEF cells to generate the recombinant vCP260 (containing HCMVpp65).

Plasmid CMV65.WR was transfected into vP1170 infected Vero cells to generate the recombinant vP1214 (WR-pp65).

Example 33

Expression of HCMVpp65 by Poxvirus Recombinants

Immunoprecipitation experiments with a monoclonal antibody specific for HCMV pp65 demonstrated the expression of a 65 kDa protein (Pande et al., 1991) by recombinants vP1184, vP1214, vCP260, vP1196 and vP210. In addition, immunoprecipitation with gB specific guinea pig polyclonal sera demonstrated correct expression of gB by recombinants vP1196 and vP1210 and immunoprecipitation with a gH specific monoclonal antibody demonstrated correct expression of gH by recombinant vP1210.

Example 34

Cloning of the HCMV pp150 Gene in Poxvirus Vectors

Cloning of the pp150 gene into the NYVAC donor plasmid pSD541. The DNA sequence of CMVpp150 is shown in FIG. 41 (SEQ ID NO:66). Oligonucleotides pp150. 1B (SEQ ID NO:163) (5'-TTCGGATCCGGTTCTGGAGAAAAGCC-3') and pp150R6 (SEQ ID NO:164) (5'-GCTTCCAAGCTTTCCTGAAGGGATTGTAAGCC-3') were used in PCR with Towne genomic DNA to generate a 2 kb fragment from the 5' end of pp150. This fragment was digested with BamHI and Hin dIII and cloned into BamHI/HindIII digested and alkaline phosphatase treated IBI24 generating plasmid pp150.5.

Oligonucleotides pp150.9 (SEQ ID NO:165) (5'-TTCGGATCCGGCTTTCAGTCTCGTCTCC-3') and pp150END2 (SEQ ID NO:166) (5'-TTCGGATCCATGCAATTGCCCGCGGACAAC-3') were used in PCR with Towne DNA to generated a 1.8 kb fragment which includes the 3' end of the gene. This fragment was digested with BamHI and cloned into BamHI digested and alkaline phosphatase treated PUC8 yielding pp150.3.

Oligonucleotides SP150-3 (SEQ ID NO:167) (5'-TTCGAATTCGCTAGCTTTATTGGGAA-GAATATGATAATATTTTGGGATTTCAAAATTGAA A ATATATAATTACAATATAAAATGAGTTTGCAGTTTA-TC-3') and SP150-4 (SEQ ID NO:168) (5'-TTCTCTAGATGAGCTCGTTGAACAGCAC-3') were used in PCR with plasmid pp150.5 as template to generate a 259 bp fragment. This fragment was digested with EcoRI and XbaI and cloned into EcoRI/XbaI digested and alkaline phosphatase treated IBI24 generating plasmid 150.5MP. This plasmid contains a NheI site, 65 bp entomopoxvirus 42K promoter and bases 1–170 from the 5' end of the pp150 gene. The underlined base in the sequence of oligonucleotide SP150-3 (position −53 of the promoter) is missing in this clone.

Oligonucleotides SP150-1 (SEQ ID NO:169) (5'-CCGAAGCTTGCTAGCAATAAAAACTATTCCTCCGT-GTTCTTAAT-3') and SP150-2 (SEQ ID NO:170) (5'-GCCTCTAGATACGTAAAGCTAAGTTATC-3') were used in PCR with plasmid pp150.3 as template to generate a 907 bp fragment. This fragment was digested with XbaI and HindIII and cloned into XbaI/HindIII digested and alkaline phosphatase treated IBI24 yielding plasmid 150.3MP. This plasmid contains nucleotides 2273–3141 from pp150 followed by a vaccinia early transcription termination signal (T$_5$ATT) (Yuen and Moss, 1987) and a NheI site. pp150 nucleotide 2748 (FIG. 41; SEQ ID NO:66) in this clone is an A not a C as in pp150.3, this change is silent.

Plasmid pp150.3 was digested with SnaBI and HindIII and a 3451 bp fragment isolated. Plasmid 150.3MP was digested with SnaBI and HindIII and 873 bp fragment isolated. Ligation of these two fragments yielded plasmid 150.3MC which contains pp150 nucleotides 1473–3141 followed by T$_5$ATT and a NheI site.

Plasmid 150.5MP was digested with SacI and HindIII and a 3056 bp fragment isolated. Plasmid pp150.5 was digested with SacI and HindIII and a 1816 bp fragment isolated. Ligation of these two fragments yielded plasmid 150.5MC which contains a NheI site, 65 bp 42K promoter and pp150 nucleotides 1–1981.

Plasmid 150.5 MC was digested with SpaI and HindIII and a 4634 bp fragment isolated. Plasmid 150.3MC was digested with HpaI and HindIII and a 1412 bp fragment isolated. Ligation of these two fragments yielded plasmid 150.1 which contains a NheI site, 65 bp 42K promoter, nucleotides 1–3141 pp150, T$_5$ATT and a NheI site.

Plasmid pSD541 is a vaccinia insertion plasmid which is deleted for vaccinia sequences encompassing the A25L and A26L ORFs (Goebel et al., 1990a,b). The deletion junction consists of a polylinker region containing XhoI, SmaI and BglII restriction sites, flanked on both sides by stop codons and early vaccinia transcriptional terminators (Yuen and Moss, 1987). pSD541 was constructed by polymerase chain reaction (PCR) using cloned vaccinia SalI E plasmid pSD414 as template. Synthetic oligonucleotides MPSYN267 (SEQ ID NO:94) (5'-GGGCTCAAGCTTGCGGCCGCTCATTAGACAAGCG-AATGAGGGAC-3') and MPSYN268 (SEQ ID NO:95) (5'-AGATCTCCCGGGCTCGAGTAATTAAT-TAATTTTATTACACCAGAAAAGACGGCTTGAGA T C-3') were used as primers to generate the left vaccinia arm and synthetic oligonucleotides MPSYN269 (SEQ ID NO:96) (5'-TAATTACTCGAGCCCGGGAGATCTAATT-TAATTTAATTTATATAACTCATTTTTTGAATA T ACT-3') and MPSYN270 (SEQ ID NO:97) (5'-TATCTCGAATTCCCGCGGCTTTAAATGGACGGAAC-TCTTTTCCCC-3') were used to generate the right vaccinia arm. PCR products consisting of the left and right vaccinia arms were combined, and subjected to PCR amplification. The PCR product was digested with EcoRI and HindIII and electrophoresed on a agarose gel. The 0.8 kb fragment was isolated and ligated into pUC8 cut with EcoRI/HindIII, resulting in plasmid pSD541.

Plasmid pSD541 was digested in its polylinker region with SmaI and alkaline phosphatase treated. Plasmid 150.1 was digested with NheI, treated with klenow and a 3224 bp fragment (containing 42K-pp150) isolated. Ligation of these two fragments yielded plasmid 150.7. The DNA sequence of CMVpp150 plus flanking DNA sequences in plasmid 150.7 are shown in FIGS. 42A and B (SEQ ID NO:68).

Cloning of the pp150 gene into ALVAC donor plasmid PMM117. Plasmid PMM117 is a derivative of pC6L with a modified polylinker region. PMM117 was digested in its polylinker with EcoRI filled in with klenow and treated with alkaline phosphatase. Plasmid 150.1 was digested with NheI, treated with klenow and a 3224 bp fragment (containing 42K-pp150) isolated. Ligation of these two fragments generated plasmid 150.6. The DNA sequence of CMVpp150 plus flanking DNA sequences in plasmid 150.6 are shown in FIGS. 43A and B (SEQ ID NO:68).

Cloning of the pp150 gene into vaccinia donor plasmid pSD157K1LINS. Plasmid pSD1571LINS was digested in its polylinker region with SmaI and alkaline phosphatase treated. Plasmid 150.1 was digested with NheI, treated with klenow and a 3224 bp fragment (containing 42K-pp150) isolated. Ligation of these two fragments generated plasmid 150.4. The DNA sequence of CMVpp150 plus flanking DNA sequences in plasmid 150.4 are shown in FIGS. 44A and B (SEQ ID NO:69).

Example 35

Construction of Recombinant Poxviruses Containing HCMVpp50

Plasmid 150.4 was transfected into vP1170 infected CEF cells to generate the recombinant vP1238 (WR-pp150 ).

Plasmid 150.7 was transfected into NYVAC infected CEF cells to generate the recombinant vP1247 (NYVAC-pp150).

Plasmid 150.6 was transfected into ALVAC infected CEF cells to generate the recombinant vCP284 (ALVAC-pp150).

Example 36

Expression of HCMVpp150 by poxvirus Recombinants

Western blot (Harlow and Lane, 1988) with a monoclonal antibody specific for HCMVpp150 demonstrated the expression of a 150 kDa protein in cells infected with vP1238 which comigrated with a protein present in HCMV infected cells. Expression of a 150 kDa protein was observed in vP1247 and vCP284 infected cells by immunoprecipitation with the pp105 specific monoclonal antibody.

Example 37

Developing a NYVAC Donor Plasmid Containing the HCMVgH and IE1 Exon 4 Genes

Plasmid I4LH6IE-Ex4 was linearized with BamHI, filled in with klenow and treated with alkaline phosphatase yielding a 4.9 kb fragment. Plasmid gH6-3 was digested with XhoI, filled in with klenow and a 2.3 kb fragment (containing 42K-gH) isolated. These two fragments were ligated to generate plasmid I4L42KgHH6IE -Ex4. The DNA sequence of CMVgH and IE-Exon4 plus additional flanking sequences in plasmid I4L42KgHH6IE-Ex4 are shown in FIGS. 45A and B (SEQ ID NO:70).

Example 38

Construction of NYVAC Recombinants Containing HCMVgB.$^+$ gH.$^+$ pp65.$^+$ IE-Exon 4, HCMVgB.$^+$ gh.$^+$ pp65.$^+$ pp150 or HCMVgB.$^+$ gh.+pp65.$^+$ IE-Exon 4 and pp150

Plasmid I4L42KgHH6IE-Ex 4 was transfected into vP1196 infected Vero cells to generate the recombinant vP1216 (containing HCMVgB, gH, pp65, IE-Exon 4). Plasmid 150.7 was transfected into vP1216 infected CEF cells to generate the recombinant vP1251 (containing HCMVgB, gH, IE-Exon 4, pp65, pp150). Plasmid 150.7 was transfected into vP1210 infected Vero cells to generate the recombinant vP1262 (containing HCMV-gB, gH, pp65, pp150).

Example 39

Expression of the HCMV Genes in vP1216, vP1251, vP1262

Immunoprecipitation with monoclonal antibodies specific for gB, gH, pp65 and IE-Exon 4 demonstrated the correct expression of all four genes by recombinant vP1216. Immunoprecipitation with monoclonal antibodies specific for gB, gH, pp65 and IE-Exon 4 demonstrated the correct expression of these four genes by recombinant vP1251. Immunoprecipitation with monoclonal antibodies specific for gB, gH and pp65 demonstrated the correct expression of these three genes by recombinant vP1262. Western blot with a monoclonal antibody specific for pp150 demonstrated the correct expression of this gene by recombinants vP1251 and vP1262.

Example 40

Developing an ALVAC Doner Plasmid Containing the HCMV pp65 and pp150 Genes

Plasmid CMV65C6.2 was linearized with EcoRI, filled in with klenow and treated with alkaline phosphatase generating a 6.3 kb fragment. Plasmid 150.1 was digested with NheI, filled in with klenow and a 3.2 kb fragment (42K-pp150) isolated. Ligation of these two fragments yielded plasmid 150.8. The DNA sequence of CMVpp65 and pp150 plus additional flanking sequences in plasmid 150.8 are shown in FIGS. 46A to C (SEQ ID NO:71).

Example 41

Construction of an ALVAC Recombinant Containing HCMVgB, gH, pp65 and pp150

Plasmid 150.8 was transfected into vPC233 infected CEF cells to generate an ALVAC-gB, gH, pp65, pp150 recombinant (vCP280).

Example 42

Expression of the HCMV Genes in vCP280

Immunoprecipitation with monoclonal antibodies specific for gB, gH and pp65 demonstrated the correct expression of these three genes by recombinant vCP280.

Example 43

Cloning of HCMVgL in Poxvirus Vectors Deriving a NYVAC Doner Plasmid Containing gB AND gL Oligonucleotides UL115A (SEQ ID NO:171) (5'-GCCTCTAGAATGTGCCGCCGCCCGGATTGC-3') and UL115B (SEQ ID NO:172) (5'-CGCAAGCTTAGCGAGCATCCACTGCTTGAGGGC-3') were used in PCR with Towne DNA as template to generate a 853 bp fragment. This fragment was digested with XbaI and HindIII and cloned into XbaI/HindIII digested and alkaline phosphatase treated IBI24 generating plasmid UL115.1. The sequence of CMVgL is presented in FIG. 47 (SEQ ID NO:72).

Oligonucleotides UL115M (SEQ ID NO:173) (5'-TCCAAGCTTAGATCTATAAAAATTAGCGAGCATCC-ACTGCTTGAGGGCCATAGC-3') and UL115N (SEQ ID NO:174) (5'-GCCTCTAGATGCTGACGCTGTTGAGCTCGGAC-3') were used in PCR with plasmid UL115.1 as template to generate a 498 bp fragment. This fragment was digested with HindIII and XbaI and cloned into HindIII/XbaI digested and alkaline phosphatase treated IBI24 generating plasmid UL115.2.

Oligonucleotides UL115G2 (SEQ ID NO:175) (5'-CGCGAATTCTCGCGATATCCGTTAAGTTTGTATCGT-AATGTGCCGCCGCCCGGATTGC-3') and UL115H2 (SEQ ID NO:176) (5'-GCCTCTAGATTCCAGCGCGGCGCTGTGTCCGAGC-3') were used in PCR with plasmid UL115.1 as template to generate a 450 bp fragment. This fragment was digested with EcoRI and XbaI and cloned into EcoRI/XbaI digested and alkaline phosphatase treated IBI24 generating plasmid UL115.3.

Plasmid UL115.3 was digested with HindIII and SacI and a 3226 bp fragment isolated. Plasmid UL115.2 was digested with HindIII and SacI and a 469 bp fragment isolated. Ligation of these two fragments yielded plasmid UL115.4.

Plasmid UL115.4 was digested with NruI and BglII and a 865 bp fragment isolated. Plasmid I4LH6 was digested with NruI and BglII and a 3683 bp fragment isolated. Ligation of these two fragments yielded plasmid I4LH6gL.

To correct a one base deletion in the H6 promoter in I4LH6gL this plasmid was digested with EcoRV treated with alkaline phosphatase and a 3805 bp fragment isolated. Plasmid I4LH6 was digested with EcoRV and a 736 bp fragment isolated. Ligation of thise two fragments yielded plasmid I4LH6CgL.

Plasmid 542CMVgB was linearized with BamHI and treated with alkaline phosphatase. Plasmid I4LH6CgL was digested with BamHI and BglII and a 968 bp fragment (contianing the H6 promoted gL gene) isolated. Ligation of thise two fragments generated plasmid 542CMVgBgL. The DNA sequence of CMVgL and CMVgB plus additional flanking DNA sequences in plasmid 542CMVgBgL are shown in FIGS. 48A and B (SEQ. ID NO:73).

Example 44

Developing a NYVAC Recombinant containing gB. gH, gL, pp65, pp150, IE1-Exon 4 or gB, gH, aL, pp65, pp150

Plasmid 542CMVgBgL was transfected into vP1251 infected CEF cells to generate a NYVAC gB, gH, gL, pp65, pp150, IE1-Exon 4 recombinant (vP1302).

Plasmid 542CMVgBgL is transfected into 1262 infected cells to generate a NYVAC gB, gH, gL pp65, pp150recombinant.

Example 45

Human Cytotocix T Lymphocyte Responses to HCMV Proteins

Lymphocytes comprising the antigen-specific segment of the immune system may functionally react to antigen by producing antibodies (B-lymphocytes) or by becoming cytotoxic T lymphocytes (CD8+ T-lymphocytes). ALVAC recombinants expressing HCMV proteins that are known to be recognized by human cytotoxic T lymphocytes (CTLs) are capable of re-stimulating human cellular immune responses with characteristics of classical CTLs.

Thirteen individuals for which there was previously established EBV-transformed B-cell lines (LBCL) for use as CTL targets were screened for CTL responses to HCMV gB, IE1, and pp65. Although only one of these volunteer blood donos had an established clinical history of HCMV infection, seven were found to be HCMV seropositive by virtue of their sera containing antibodies which neutralized HCMV.

Stimulation of HCMV 1E1 CTLs by ALVAC-1E1 (vCP256): Whole blood was collected into heparinized Vacutainer tubes from each volunteer donor by venipuncture. The mononuclear cell fraction was separated from the remainder of the blood components by centrifugation over Leucoprep gradients, washed several times by centrifugation in Stim Medium (MEM containing 5% fetal bovine serum [FBS], 2 mM L-glutamine, $10^{-4}$ M 2-mercaptoethanol, 100 IU/ml penicillin, and 100 µg/ml streptomycin), counted for viable cells with trypan blue, and resuspended at $5 \times 10^6$ cells/ml in Stim Medium (responder cells). A portion of the mononuclear cells were resuspended at $10^7$ cells/ml in MEM containing 2% FBS and infected with recombinant ALVAC expressing HCMV 1E1(vCP256) at a multiplicity of infection of 25 for approximately 1 hour at 37 C. Following incubation, sufficient Stim Medium was added to dilute the infected cells to $5 \times 10^5$ cells/ml (stimulator cells). Equal volumes of responder cells and stimulator cells were added to upright 25 cm$^2$ tissue culture flasks or to the wells of 24-well tissue culture plates and incubated in 5% $C_2$/95% air at 37° C. for 6 days. Target cells were prepared by infecting LBCLs with recombinant WR vaccinia virus expressing HCMV 1E1 (vP893) similarly to the infection of stimulator cells except the target cells were incubated overnight at $4 \times 10^5$ cells/ml in RPMI 1640 medium containing 20% FBS. Following incubation, the mononuclear cells and the target cells were washed by centrifugation in Assay Medium (RPMI 1640 medium containing 10% FBS, 2 mM L-glutamine, $5 \times 10^{-5}$ M 2-mercaptoethanol, 100 IU/ml penicillin, and 100 µg/ml streptomycin). Target cells were incubated in Na$_2$$^{51}$CrO$_4$ for 1 hour, washed by centrifugation in Assay Medium, resuspended to $10^5$ cells/ml in Assay Medium, and held on ice until use. Following centrifugation, the mononuclear cells were diluted to $2 \times 10^6$ cells/ml in Assay Medium. One tenth ml of mononuclear cells and 0.1 ml of $^{51}$Cr labelled, infected target cells were added to the wells of 96-well round bottom tissue culture plates. These volumes and cell densities resulted in an effector to target ratio (E:T) of 20:1. The tissue culture plates were centrifuged at 250 g for 2 minutes and incubated in 5% CO$_2$/95% air at 37 C. for 4 to 5 hours. Following incubation, 0.1 ml of supernatant fluid from each well was collected using Skatron filter wicks and counted for released radioactivity. Percent cytotoxicity was calculated as:

(EXPERIMENTAL $^{51}$CR RELEASE-SPONTANEOUS $^{51}$CR RELEASE) (MAXIMUM $^5$CR RELEASE-SPONTANEOUS $^{51}$ CR RELEASE)×100.

Maximum release was determined by the addition of 5% sodium dodecyl sulfate to target cells while spontaneous release was determined by incubating target cells in the absence of effector cells. In none of the experiments presented did spontaneous release of $^{51}$Cr from target cells exceed 20% of maximum $^{51}$Cr release.

Figure 49:
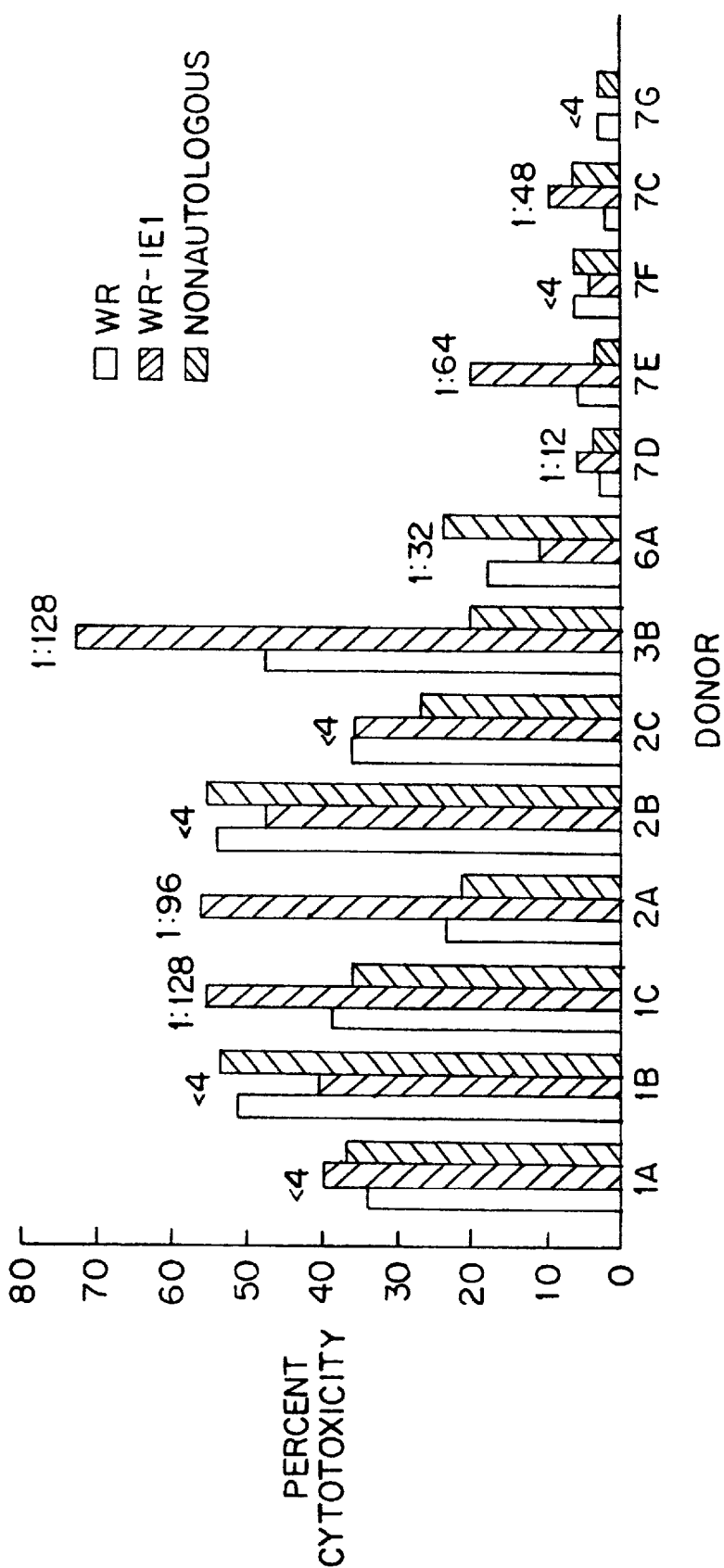
FIG. 49 shows the results of HCMV IE1 CTL stimulation by ALVAC-IE1 (vCP256) (percent cytotoxicity; white bars= WR, black bars=WRIE1, striped bars=nonautologous)
Figure 50:
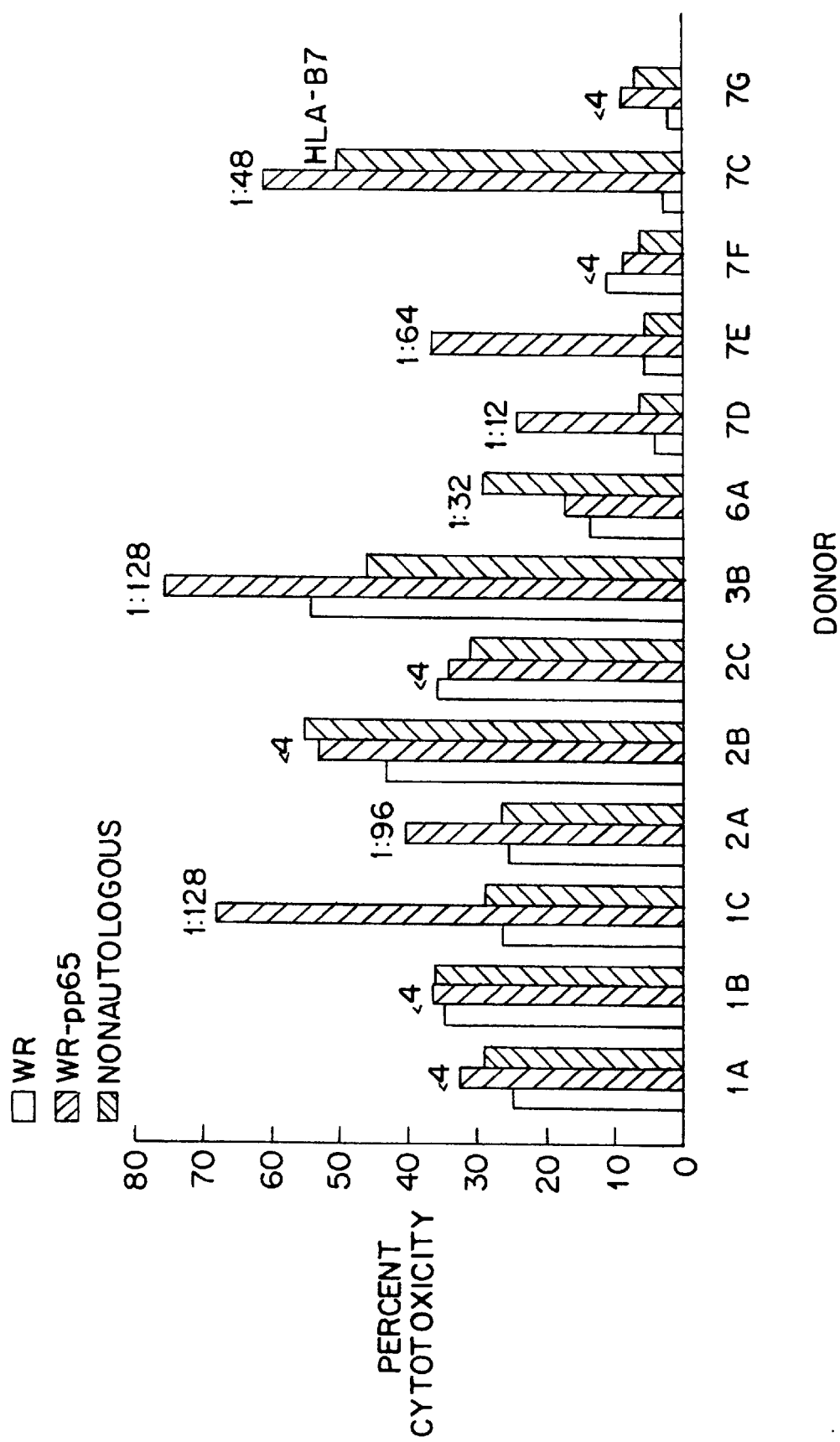
FIG. 50 shows the results of stimulation of HCMV pp65-CTLs by ALVAC-pp65 (vCP260) (human CTLs stimulated in vitro and assayed for HCMV pp65 CTLs using methodology similar to that used for FIG. 49; percent cytotoxicity; white bars=WR, black bars=WR-pp65, striped bars=nonautologous)

Following in vitro stimulation with ALVAC recombinants expressing a single HCMV protein, mononuclear cells from four of the seven seropositive volunteer donors lysed autologous targets expressing HCMV IE1 (FIG. 49) and mononuclear cells from six of the seven seropositive donors lysed autologous targets expressing HCMV pp65 (FIG. 50). Re-stimulated mononuclear cells from none of the HCMV seropositive donors lysed autologous targets expressing HCMV gB.

The mononuclear cells from HCMV seronegative volunteer donors, when re-stimulated similarly to the mononuclear cells of the HCMV seropositive donors, failed to lyse autologous target cells expressing HCMV IE1 or HCMV pp65 (FIG. 49 and FIG. 50, respectively).

In all cases except one, the cytotoxic effector cells only lysed autologous, but not nonautologous, target cells expressing the appropriate HCMV protein. The single exception, mononuclear cells from Donor 7C, following re-stimulation with ALVAC pp65 (vCP260), was capable of lysing nonautologous target cells expressing HCMV pp65. However, it was later demonstrated that Donor 7C and the donor for the nonautologous target cell line share HLA-B7 of the human major histocompatibility complex (MHC).

Stimulation of HCMV IE1 CTLs by ALVAC-IE1 (vCP256): Human CTLs were stimulated in vitro and assayed for HCMV 1E1 CTLs using similar methodology as in FIG. 49 except that following 6 days incubation for restimulation, the responder mononuclear cells were incubated with immunomagnetic beads coupled to monoclonal anti-human CD3, CD4, or CD8. Following incubation, the beads were removed by a magnet and therefore the CD3+, CD4+ or CD8+ cells. The cells adhering to the magnetic beads were uncoupled, washed and used in the cytotoxicity assay.

Figure 51:
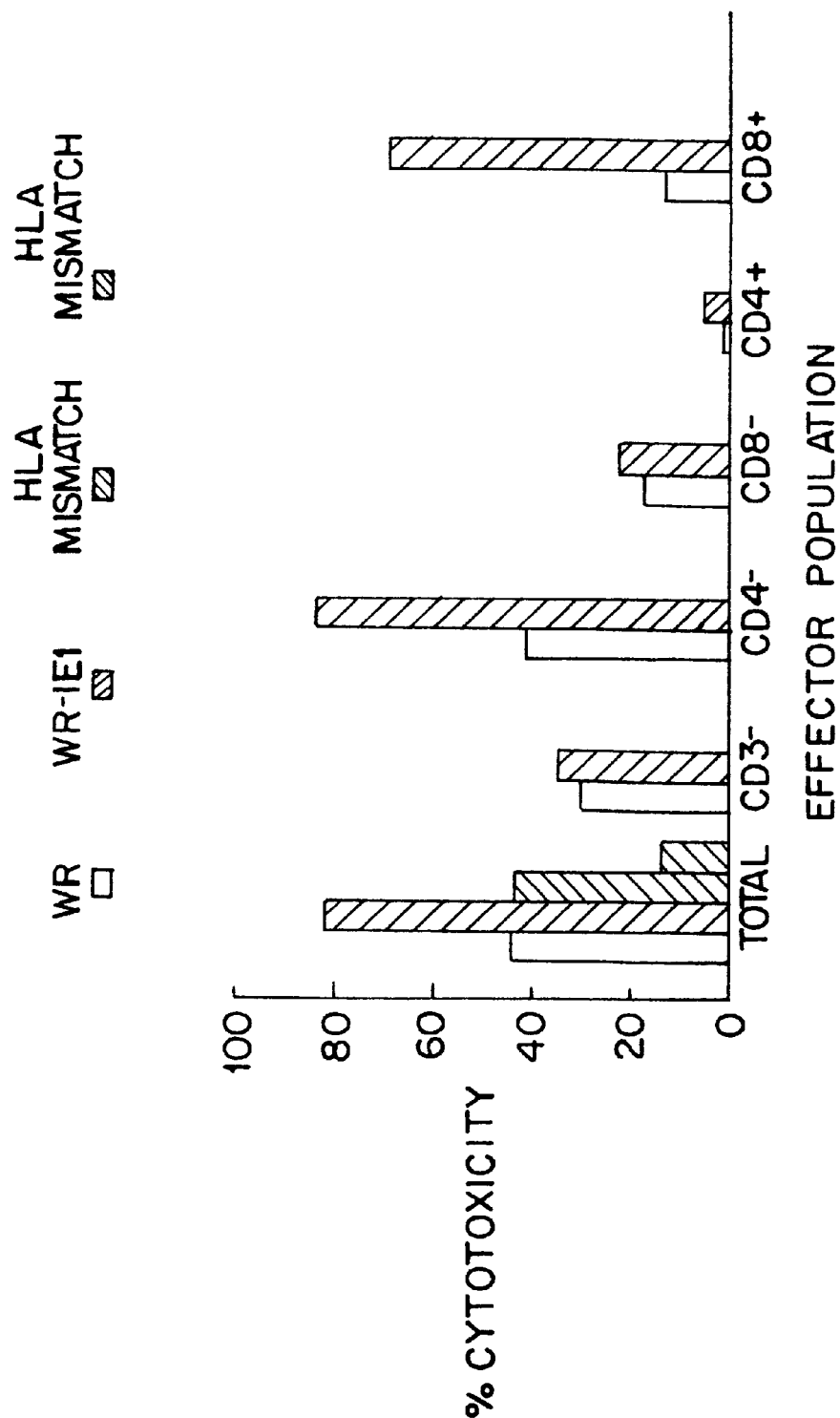
FIG. 51 shows the results of stimulation of HCMV IE1 CTLs by ALVAC-IE1 (vCP256) (methodology similar to that used for FIG. 49, except that following 6 days incubation for restimulation, the responder mononuclear cells were incubated with immunomagnetic beads coupled to monoclonal anti-human CD3, CD4 or CD8; percent cytotoxicity; white bars=WR, black bars=WR-IE1, striped bars=HLA mismatch)

Representative of the phenotype of the cytotoxic responses of this HCMV seropositive cohort, the ALVAC-IE1 (vCP256) re-stimulated mononuclear cells from Donor 2A failed to lyse IE1-expressing targets following depletion of lymphocytes expressing CD3 and CD8, but not CD4 (FIG. 51). Furthermore, re-stimulated mononuclear cells that had been enriched for CD8, but not CD4, retained cytotoxic activity.

Thus, the cytotoxic effector cells derived from HCMV seropositive volunteer donors by re-stimulation in vitro with ALVAC recombinants expressing HCMV IE1 (vCP256) or HCMV pp65 (vCP260) were antigen specific, MHC-restricted, and expressed CD3 and CD8. These characteristics are consistent with those of classical cytotoxic T lymphocytes (CTLs).

These results show that ALVAC recombinants expressing HCMV proteins can serve as vaccines for the purpose of eliciting human cytotoxic T lymphocytes capable of mediating the destruction of HCMV-infected human cells. Furthermore, these data also show that these recombinant viruses can serve as reagents for the ex vivo stimulation and expansion of cytotoxic T lymphocyte clones for the purpose of immunotherapeutic applications (Riddell et al., 1992).

As discussed earlier, HCMV-gB can serve to elicit protective immunity in humans since 1) HCMV neutralizing antibody titer is reduced significantly when gB specific antibody is absorbed from human sera (Gönczöl et al., 1991; Marshall et al., 1992) and 2) there is evidence for the activation of helper T cells by the gB protein in seropositive individuals (Liu et al., 1991). Gönczöl et al., (1990) reported the immunoaffinity purified gB was immunogenic in human volunteers. In this study a single injection of the purified gB was able to induce high titers of HCMV neutralizing antibodies and lymphocyte proliferation in naturally seropositive individuals. In seronegative individuals three injections of the gB preparation induced transient HCMV neutralizing antibodies, a fourth injection induced a rapid reappearance and increase in titer of HCMV neutralizing antibodies.

These studies show the use of purified gB as a subunit vaccine. Additionally purified gB can also be used in prime/boost protocols in combination with NYVAC or ALVAC-gB recombinants. Recent studies have indicated that a prime/boost protocol, whereby immunization with a poxvirus recombinant expressing a foreign gene product is followed by a boost with a purified form of that gene product, elicits an enhanced immune response relative to the response elicited with either product alone. For example, humans immunized with a vaccinia recombinant expressing the HIV-1 envelope glycoprotein and boosted with purified HIV-1 envelope glycoprotein from a baculovirus recombinant exhibit higher HIV-1 neutralizing antibody titers than individuals immunized with just the vaccinia recombinant or purified envelope glycoprotein alone (Graham et al., 1993; Cooney et al., 1993). Humans immunized with two injections of ALVAC-HIV (vCP125) failed to develop HIV specific antibodies. Boosting with purified rgp160 from a vaccinia virus recombinant resulted in detectable HIV-1 neutralizing antibodies. Furthermore, specific lymphocyte T cell proliferation to rgp160 was clearly increased by the boost with rgp160. Envelope specific cytotoxic lymphocyte activity was also detected with this vaccination regimen (Pialoux et al., 1995). Macaques immunized with a vaccinia recombinant expressing the simian immunodeficiency virus (SIV) envelope glycoprotein and boosted with SIV envelope glycoprotein from a baculovirus recombinant are protected against a SIV challenge (Hu et al., 1991; 1992).

Example 46

Purification of HCMV Glycoprotein B

This Example involves purification of CMV glycoprotein B produced by a vaccinia recombinant, and the testing of its immunogenicity in laboratory animals in combination with ALVAC-CMV gB (vCP139).

COPAK recombinants vP1126, vP1128, and vP1145, each expressing a different form of gB, elicit CMV neutralizing antibodies in mice (Table 23) and therefore express gB in an immunogenic form. To select a virus and cell system, and an immunological reagent for CMV gB purification, gB expression by the three COPAK recombinants was compared by an immunoprecipitation assay, utilizing 5 different gB-specific monoclonal antibodies. Based on the assay results, a scheme was developed to purify gB from the medium of vP1145-infected VERO cells.

Immunoaffinity column bed material was prepared by crosslinking CMV gB-specific monoclonal antibody (mAb) CH380 to Protein A-agarose. This material was used to purify gB in a one-step procedure. Batches of gB were produced and evaluated for purity, as described in section III.

Immunoprecipitation Assay. Vero and HeLa cell monolayers in 60 mm dishes were infected with vP1126, vP1128, vP1145, or vP993 (described below) at an moi of 5 pfu/cell in serum-free medium. Medium and cells were harvested separately at 24 hours post infection. Immunoprecipitation (IP) assays were performed (Taylor et al., 1990) using the reagents described below, with rat anti-mouse IgG as a bridge to protein A for the monoclonals.

Virus:
vP1126: COPAK-CMV gB (entire). Full length wild type gB
vP1128: COPAK-CMV gB (TM⁻). Lacks transmembrane region
vP1145: COPAK-CMV gB (TM⁻, Cl⁻ lacks transmembrane region and has an altered cleavage site.
vP993: COPAK control
Reagents:
Guinea pig anti-CMV gB: Obtained from Eva Gönczöl (Wistar Institute)
Monoclonal CH380: Obtained from PMs&v (Pereria and Hoffman, 1986)
Monoclonal 13-127 Advanced Biotechnologies, Inc.
Monoclonal 13-128 Advanced Biotechnologies, Inc., neutralizing, conformationally dependent
Monoclonal HCMV-34 Cogent Diagnostics, neutralizing
Monoclonal HCMV-37 Cogent Diagnostics, neutralizing
Rabbit anti-p25 (Vaccinia E3L) (obtained from Bert Jacobs, U. Arizona)

Preparation of immunoaffinity chromatography bed material. One ml of immunoaffinity column bed material consisting of approximately 2.4 mg of mAb CH380 coupled to Protein A-agarose with the crosslinking agent dimethylpimelimidate was provided by Stephen Cockle, Connaught Laboratories, Limited (Willowdale, Ontario, Canada). mAb CH380 (Pereria and Hoffman, 1986) was used previously to purify CMV gB from a CMV viral envelope preparation (Gönczöl et.al., 1990). The material from S. Cockle was used in preliminary experiments to further determine its utility in gB purification. To scale up gB production, additional bed material was prepared by the same method used by S. Cockle, as described below.

Preparation of monoclonal ch380. Four vials of lyophilized monoclonal CH380 (lot S1705, obtained from PMsv) were reconstituted in PBS (137 mM NaCl, 2.7 mM KCl, 1.5 mM KH$_2$PO$_4$, 8.1 mM Na$_2$HPO$_4$, pH 7.4) (1 ml each) and dialysed overnight versus PBS (final volume 3.5 ml). Protein concentration was determined to be 4.9 mg/ml by bicinchoninic acid assay (BCA assay, reagents obtained from Pierce, Rockford, Ill.). This preparation was then diluted in an equal volume of MAPS binding buffer (Bio-Rad cat# 153-6161; 31.4% w/v in milli-Q water, adjusted to pH 9, and filtered through a 22 mm membrane). To remove particulate material, the antibody preparation in MAPS buffer was centrifuged at 16,000×g for 30 min, and the protein concentration of the supernate was calculated from the absorbence at 280 nm, using 1.44 as the absorbence coefficient for IgG.

Preparation of Protein a-agarose beads. Three ml of protein A-agarose beads (Bio-Rad cat # 153-6153) were washed 4 times with 2 volumes of MAPS binding buffer by gentle mixing in a closed tube and centrifugation for 5 min at 1000 x g (1400 rpm in Beckman GPKR centrifuge, GH 3.7 rotor). The supernate was discarded after the last wash.

Binding of monoclonal antibody to the beads. All of the mAb antibody from step 1 was added to the washed beads from step 2 and the mixture was rotated in a closed tube at 4° C. The amount of mAb bound to the beads was determined at 6–12 hour intervals by pelleting the beads (1000 g/5 min) and determining concentration of IgG in the supernatant by reading OD at 280 nm, as described above. Approximately 48 hour of incubation at 4° C. were required to reach 90% depletion of IgG from the supernate.

Covalent crosslinking of monoclonal antibody to the beads. After binding was 90% complete, the beads were washed 4 times with 6 ml (2 volumes) of 50 mM borate, 3M NaCl, pH9. The beads were then resuspended in 30 ml (10 volumes) of 200 mM borate, 3M NaCl, pH9, and the pH adjusted to 9±0.1. A sample of beads (100 µl) was removed for later evaluation of cross-linking. Cross linking reagent dimethylpimelimidate (DMP) was prepared immediately before use at a concentration of 500 mM in 200 mM borate, 3M NaCl, pH9. DMP was added to the beads to produce a final concentration of 20 mM, and the beads were mixed in a closed tube, end-over-end, for 30 min at room temperature. Another sample of beads (100l) was removed for evaluation of cross-linking. To quench residual crosslinking reagent, the beads were washed 2 times with 6 ml (2 volumes) of 200 mM ethanolamine, pH8 and then incubated in 30 ml (10 volumes) of 200 mM ethanolamine, pH8 by mixing end-over-end for 2 hours at room temperature. Finally the beads were washed 4 times with 6 ml (2 volumes) of PBS and stored in 6 ml of PBS with 0.01%NaN$_3$.

To determine the extent of crosslinking, the gel bead samples taken before and after DMP incubation were pelleted, supernates discarded, and the beads mixed with 2×SDS-PAGE sample buffer containing reducing agent. These samples were boiled and electrophoretically separated on a 10% polyacrylamide gel. After staining with Coomassie Blue, IgG heavy and light chains could be detected in the "before" samples, but not in the "after" samples, indicating good efficiency of crosslinking.

Based on protein concentration before and after incubation of the antibody with the beads, the resulting bed material was estimated to contain approximately 5 mg of monoclonal antibody per ml of protein A-agarose beads.

Purification of CMV gB by immunoaffinity column chromatography. Column buffers. PBS (137 mM NaCl, 2.7 mM KCl, 1.5 MM $KH_2PO_4$, 8.1 mM $Na_2HPO_4$), pH 7 (batch 1), pH 7.4 (batches 2–5), or pH 6.8 (batches 2–5); 0.1 M glycine, pH 2.5; 1 M tris, pH 8.5.

Columns. Column sizes varied from 0.3 to 4 ml volumes. When a new column was poured, it was stripped with 10 bed volumes (bv) of 0.1 M glycine, pH 2.5, followed by 10–20 bv of PBS, pH 7 or 7.4. At the end of each column run, the column was washed with at least 10 bv of PBS, pH 7. At the beginning of each run, it was washed again with at least 10 bv of PBS, pH 7. The columns were run at room temperature and, when not in use, stored at 4° C. in PBS+0.01% $NaN_3$.

Preparation of the crude gB sample. Roller bottles (850 $cm^2$) were seeded with Vero cells in MEM+10% FBS. Medium was changed to serum-free MEM 2–12 hours before infection. Cells were infected with vP1145 at an MOI of 5 pfu/cell in a volume of 10 ml/RB of serum-free MEM. Virus was absorbed at 37° C. for 60 min and then 30 ml of serum-free MEM was added to each RB and incubation continued at 37° C. Medium was harvested at 16–24 hours post infection. The medium was clarified by centrifugation at 3000 rpm (Beckman GPKR centrifuge GH 3.7 rotor) for 15 min. The supernatant was recovered and further clarified by centrifugation at 20,000 rpm in a Beckman SW28 rotor for 60 min. The clarified medium was then concentrated (10 to 40-fold) by ultrafiltration with buffer exchange to PBS, pH 7.4, using one or more of the following ultrafiltration devices having 30,000 MWCO: Centricell-60 (Polysciences #19182-6), Centriprep-30 (Amicon #4306), or polysulfone immersible filter units (Polysciences #2250). This material was applied to the column as described below.

Column procedure. The crude gB sample was applied to the column at a flow rate of 0.03–0.09 ml/min, controlled by stopcock or peristaltic pump. After application of the sample, the column was washed at a flow rate of 0.2–0.6 ml/min with 10 bv PBS, pH7 (batch 1), or 20 bv of PBS, pH7.4 followed by 20 bv of PBS, pH6.8 (batches 2–5). Bound material was eluted with 10 bv of 0.1 M glycine, pH 2.5, collecting 500 µl (Batch 1,3) or 1 ml (batch 2,4,5) fractions into tubes containing 50 µl (Batch 1,3) or 100 µl (batch 2,4,5) of 1.0 M Tris, pH 8.5. One column (#28) was eluted with 0.1N glycine+0.1M Tris, pH7. CMV gB fractions were identified by SDS-PAGE on a 10% gel, under reducing conditions, followed by silver stain (Bio-Rad kit #161-0443).

Treatment of eluted gB. After identification by SDS-PAGE and silver stain the CMV gB fractions were pooled and concentrated in one of 2 ways: 1) Dialysis against 0.1×PBS and 10-fold vacuum concentration (majority of batch 1), or 2) Precipitation with 70% ammonium sulfate and resuspension in PBS. Protein concentration of the gB samples was determined by bicinchoninic acid microplate assay (BCA reagents from Pierce, Rockford, Ill.). Five batches of gB were prepared and frozen in aliquots at −70° C.

Evaluation of purified gB. Slot blot. Slot blot analysis was utilized to measure relative quantities of CMV gB in crude preparations, flow-through fractions, and elution fractions from affinity column purification. Serial two-fold dilutions in PBS were made of each test sample, and these were applied to nitrocellulose paper with the Schleicher and Scheull Manifold II slot blot apparatus. Each test included serially diluted samples of purified gB with a known protein concentration (determined by BCA microplate assay) as a standard. CMV gB was detected with monoclonal CH380 diluted 1:100 followed by $^{125}I$ goat anti-mouse (NEN # NEX159, at 0.1 Ci/ml). Slot blot signals on the autoradiograph were scanned and analyzed by densitometry (PDI, Inc., Huntington Station, N.Y., Quantity One densitometer program). The amount of CMV gB in each test sample was determined by linear regression analysis as compared to a gB standard curve.

Western blot. Test samples were electrophoretically separated on a 10% gel under reducing conditions, and blotted onto nitrocellulose paper (Harlow and Lane, 1988). The blot was probed for the presence of CMVgB, mouse IgG, vaccinia, and Vero cell proteins with the following reagents:

| ANTIGEN | PRIMARY ANTIBODY | DETECTION |
|---|---|---|
| CMV gB | Monoclonal CH380 diluted 1:100 | $^{125}I$ goat anti-mouse (NEN # NEX159), 0.1 µ Ci/ml |
| Mouse IgG | $^{125}I$ goat anti-mouse (NEN # NEX159, at 0.1 µ Ci/ml | (See primary antibody) |
| Vaccinia proteins | Rabbit anti-vP410, rabbit #W29 week 39, 9/13/91, preabsorbed against Vero cells and diluted 1:100 | $^{125}I$ Protein A (NEN #NEX-146), 0.1 µ Ci/ml |
| Vero cell proteins | Rabbit anti-Vero cells, obtained from B. Meignier, PMsv, preabsorbed against ALVAC-infected CEF and diluted 1:100 | $^{25}I$ Protein A (NEN #NEX-146), 0.1 µ Ci/ml |

Immunoprecipitation/western blot assay. A combination IP/Western Blot was performed on Batch 1 gB utilizing the panel of monoclonal antibodies. Unlabeled crude and purified gB was subjected to immunoprecipitation followed by SDS-PAGE, the gel was blotted onto nitrocellulose, and gB-specific proteins detected with guinea pig anti-CMV gB (from Eva Gönczöl ), diluted 1:1000, and $^{125}I$ Protein A (NEN #NEX-146), 0.1 µCi/ml.

Analysis of the purity of the gB product. Samples from each batch of gB were analyzed by electrophoretic separation on a 10% gel under reducing conditions, followed by staining with Coomassie Blue. The dried gel was scanned and analyzed by densitometry (PDI, Inc., Huntington Station, N.Y., Quantity One densitometer program).

Immunoprecipitation assay comparing expression of CMV gB by three vaccinia COPAK recombinants. To choose a suitable recombinant, cell substrate and antibody for production and immunoaffinity purification of CMV gB, COPAK recombinants expressing 3 different forms of gB were compared by immunoprecipitation assay using guinea pig anti-gB and a panel of monoclonal antibodies. Recombinants vP1126, vP1128, and vP1145 elicit CMV neutralizing antibodies in mice and therefore express gB in an immunogenic form (Table 23). All of the CMV gB antibodies tested produced similar IP results. A representative assay, with guinea pig serum using both medium and cell fractions from HeLa and Vero cell infections, is shown in FIGS. 52A to D. As expected, CMV gB specific material was precipitated from both the cell and medium fractions of vP1128 and vP1145 infected cells, but in only the cell fraction with vP1126 infected cells. The apparent molecular weights of the gB specific bands correspond to previously published results (Britt and Auger, 1986; Britt and Vugler, 1989; Reis et.al., 1993). The cell fractions of all three CMV gB recombinants contained a major band of apparent molecular weight 130–140 kDa, consistent with the apparent molecular weight of the glycosylated uncleaved gB precursor. Less intense protein species with apparent MW of 110 kDa and 55 kDa were observed in the cell fractions and are consistent with the proteolytically processed mature protein species. The N-terminal product was previously reported to be 90–110 kDa and the C-terminal product 55–58 kDa (Britt and Auger, 1986). In HeLa cells a protein species with an apparent higher molecular mass (approximately 150 kDa) was also present (e.g., FIG. 52D, lane 4). This species probably also represents an uncleaved precursor form that is more highly glcosylated. In the medium fractions three gB bands were precipitated from vP1128 and vP1145 infected cells, representing the uncleaved precursor, and N-terminal and C-therminal processed polypeptides. By densitometric analysis, there was more gB-specific material precipitated from the medium fractions of Vero cells compared to HeLa, with recombinant vP1145 producing more gB-specific material than vP1128. This difference may be explained by the observation that more vaccinia E3L was precipitated from the cell fraction of vP1145 than the vP1128 cell fraction, indicating an overall higher level of vaccinia expression in this sample (FIGS. 53A and B). With vP1145, there was more gB specific material precipitated from the medium fraction than from the cell fraction in both HeLa and Vero cells (compare FIG. 52 A,B vs. C,D).

Figures 52A, 52B, 52C, 52D:
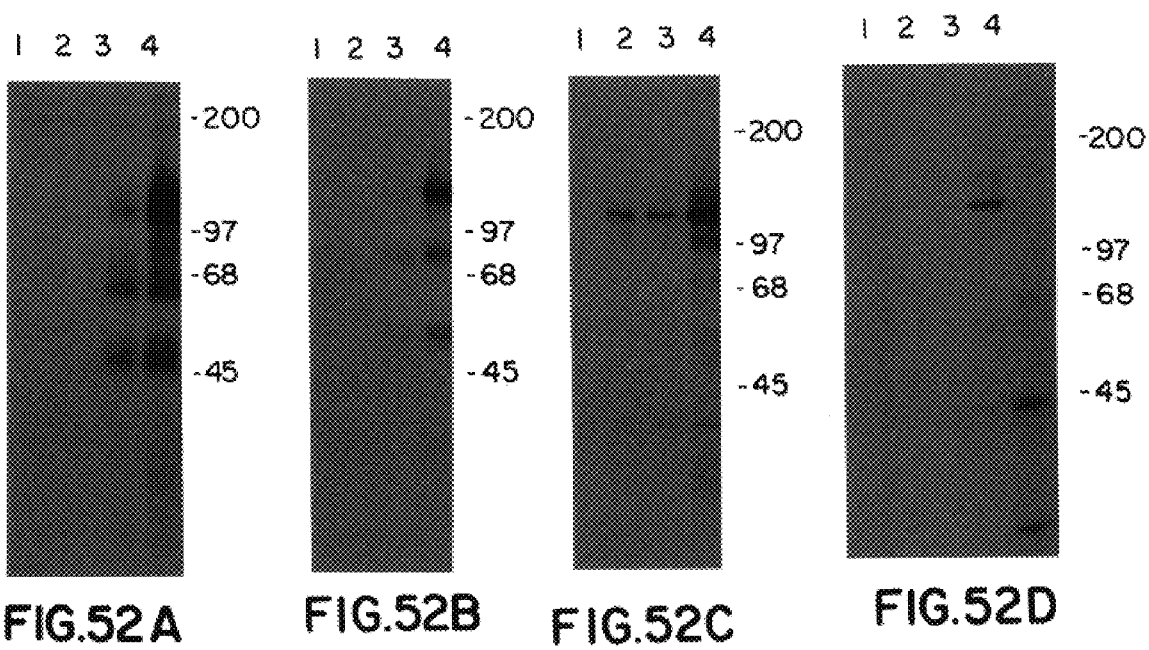
FIGS. 52A to D show expression of CMV gB by COPAK recombinants in Vero and HeLa cells (cell and medium fractions from infected cells radiolabeled with [S 35] methionine were immune precipitated with guinea pig anti-CMV gB; Vero medium (A), HeLa medium (B), Vero cell (C), and HeLa cell (D) fractions derived from infections by vP993 COPAK parent (lanes 1), vP1126 expressing the entire gB (lanes 2), vP1128 expressing gB without the transmembrane site (lanes 3), and vP1145 expressing the gB without transmembrane and with altered cleavage sites (lanes 4) are shown; far right lane contains molecular weight markers)
Figure 53A:
FIGS. 53A and B show vaccinia infection of Vero and HeLa cells detected by expression of vaccinia early protein E3L (cell fractions from infected cells radiolabeled with [35 S] methionine were immune precipitated with rabbit anti-p25 (E3L); Vero (A) and HeLa (B) cell fractions derived from infections by vP993 (lanes 1), vP1126 (lanes 2), vP1128 (lanes 3), and vP1145 (lanes 4) are shown; far right lane contains molecular weight markers)
Figure 53B:
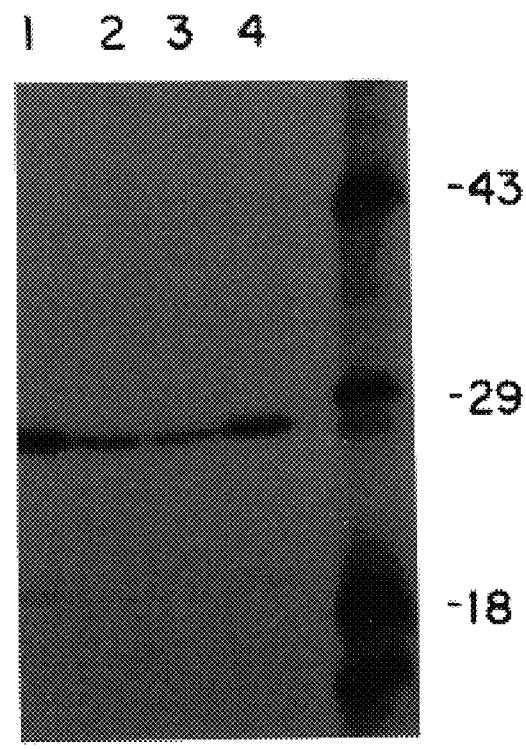
Figure 54:
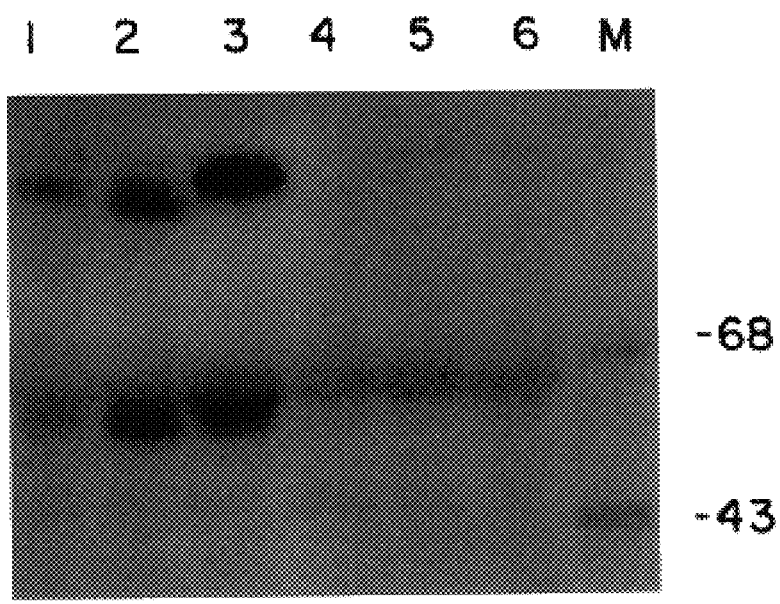
FIG. 54 shows comparison of CMV gB production by Vero, HeLa and MRC-5 cells (SDS-PAGE and western blot analysis were performed on the medium from MRC-5 cells (lanes 1, 4), Vero cells (lanes 2, 5), or HeLa cells (lanes 3, 6) after infection with vP1145 (lanes 1, 2, 3) or vP993 (lanes 4, 5, 6); CMV gB was detected with monoclonal CH380; molecular weight markers are present in lane M)

The three different sizes of gB precipitated from the medium of HeLa infected cells appear to have higher molecular weights than the three species produced in Vero cells (compare FIG. 52A vs. 52B). These differences may be due to different levels of glycosylation in HeLa cells compared to Vero, but this hypothesis was not examined further. To determine if the higher molecular weight gB-specific proteins would also be produced by another human cell line, MRC-5, a western blot assay was performed comparing the gB proteins in the medium of vP1145 infected HeLa, MRC-5, and Vero cells using monoclonal CH380 (FIG. 54). The result shows that the two gB bands detectable in this assay, gB precursor (approx. 140 kDa) and C terminal processing fragment (55–58 kDa), had apparently higher molecular weights in HeLa and MRC-5 than in VERO cells. The N-terminal processing fragment is not detectable by western blot using either monoclonal CH380 or the guinea pig anti-CMV gB serum.

Figure 55:
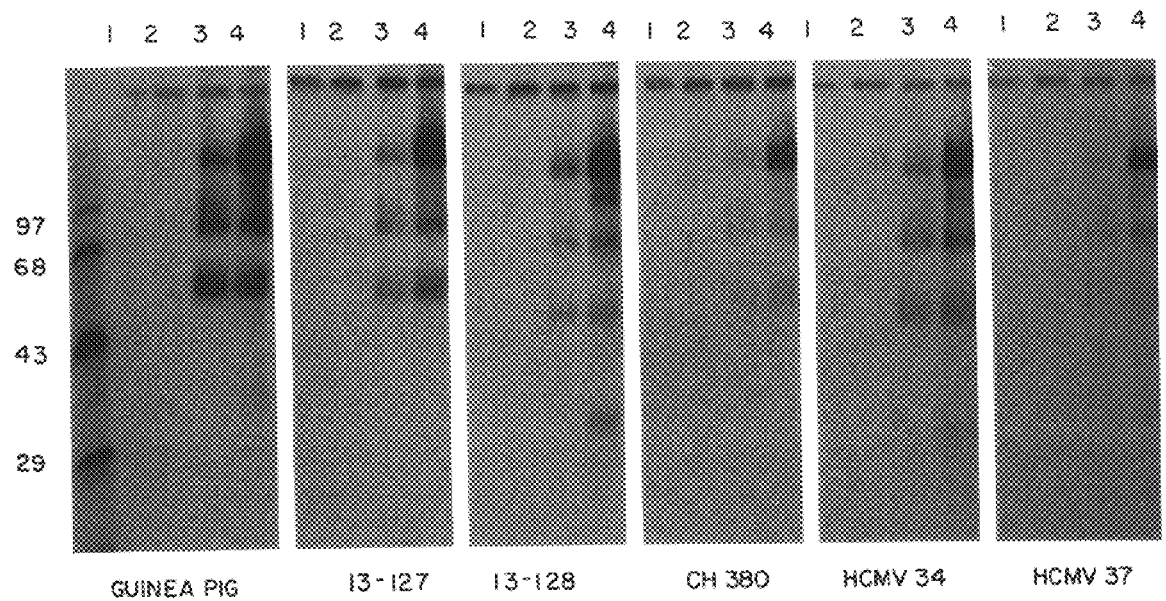
FIG. 55 shows immunoprecipitation of CMV gB by a panel of monoclonal antibodies and guinea pig anti-gB (radiolabeled medium fractions from Vero cells infected with vP993 (lanes 1), vP1126 (lanes 2), vP1128 (lanes 3), and vP1145 (lanes 4) were immune precipitated with guinea pig anti-CMV gB or with monoclonals 13–127, 13–128, CH380, HCMV 34, or HCMV 37; far left lane contains molecular weight markers)

MAb CH380 was chosen for use in immunoaffinity purification of gB, since a large quantity was readily available and no apparent differences were seen in the gB-specific proteins detected by the five different monoclonals in the IP assay (FIG. 55). Based on the IP analysis and the considerations that purification of secreted gB from the medium of infected cells eliminates the need to solubilize gB from cell membranes and purify it from cellular proteins, purification of CMV gB was initiated using the medium fraction of vP1145-infected Vero cells. Infection was done in serum-free medium, further reducing contaminating proteins in the crude material.

Purification of CMV qB. Fifteen separate immunoaffinity chromatography column runs, yielding a total of 3.1 mg of gB, are summarized in Table 24. Some of the material was used for further assays and the remainder was pooled in 5 separate batches of purified product, totaling 2.6 mg (Table 25,. Column runs 7, 8, 10, and 11 were sequential runs in the same column. The bed material from columns 19A, 19B, 19C, 21A, 21B, and 21C were pooled to make the column used for runs 28, 29, and 32, from which the largest amount of gB was obtained. Table 24 lists the Crude gB material applied to each column in terms of the number of vP1145-infected Vero roller bottles ($1\times10^8$ cells per RB) from which the crude material was derived, and amount of total protein and gB-specific protein in the crude. Based on analysis of 8 samples, the total protein content of the crude preparations ranged from 1.2 to 3.7 mg /RB with a mean value of 2.4 mg/RB (24 $\mu$g per $10^6$ cells). Utilizing a slot blot assay with purified gB as standard, the amount of gB present in the crude material was measured for 7 of the preparations: values ranged from 50 to 350 $\mu$g/RB with a mean of 153 $\mu$g/RB (1.5 $\mu$g/$10^6$ cells). Together these calculations indicate that the protein in the crude preparations consisted of approximately 6% gB. CMV gB yields ranged from 8 to 29 $\mu$g/RB with a mean of 20 $\mu$g/RB (0.2 $\mu$g/$10^6$ cells) (Table 24). Approximately fifty roller bottles ($1\times10^9$ cells) were required to produce 1 mg of CMV gB.

The capacity of the immunoabsorbent gel for gB was not fully evaluated. The 4 ml bed material used for column runs 28, 29, and 32, was initially divided into 0.6 ml mini-columns (column runs 19A, 19B, 19C, 21A, 21B, and 21C) and varying amounts of crude gB were applied to each column to determine where saturation of binding would occur. Unfortunately, the quantity of gB in the crude material applied to the columns was overestimated, and saturation was not demonstrated. The highest binding result (from column 19C) was used as an estimate of column capacity (300 $\mu$g/ml bed material). The amount of gB eluted from the mini-columns represented 8 to 25% of the gB protein applied to the columns (Table 24). Therefore, if the capacity of the 4 ml column is at least 1.2 mg and 25% of the gB applied is recovered, it was estimated that 4.9 mg of crude gB (from approximately 33 RB) must be applied to the column to obtain 1.2mg of purified gB. The result from column 28 is close to this estimate: material from 36 roller bottles was applied to the column #28, and 1 mg of gB was eluted.

Figure 56:
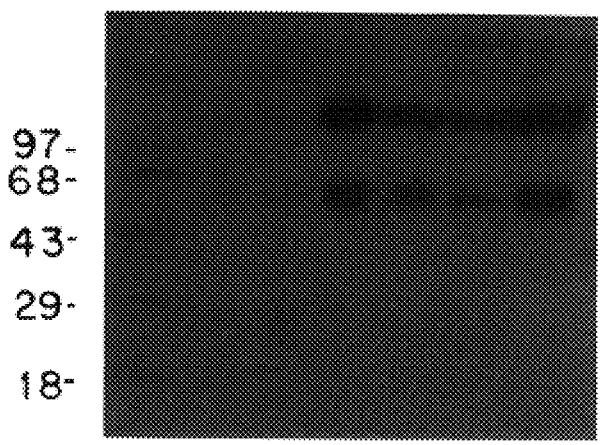
FIG. 56 shows western blot analysis of fractions and bed material from CMV gB immunoaffinity chromatography columns (column 19 fractions representing eluted gB (lane 5), flow through material (lane 6), and crude gB material applied to the column (lane 7) were analyzed by SDS-PAGE and western blot using monoclonal CH380; included in the assay was bed material from column 19 (lane 2) and column 11 (lane 3), as well as gB purified on column 7 (lane 4); molecular weight markers are present in lane 1)
Figure 57:
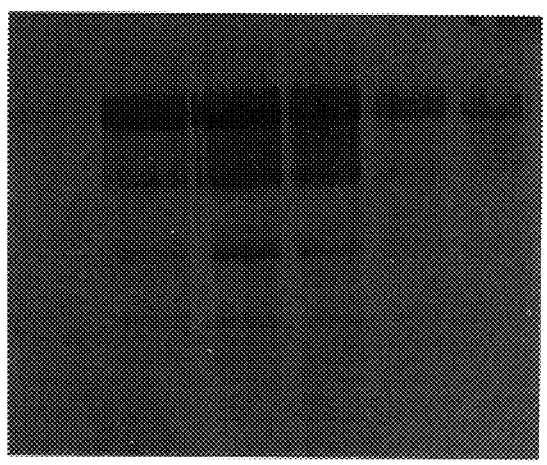
FIG. 57 shows SDS-PAGE analysis of CMV gB eluted from an immunoaffinity chromatography column (fractions 8.16 through 8.22, eluted from column 8, were electrophoretically separated on a 10% gel under reducing conditions, and stained with silver)

The gB applied to the columns but not eluted as purified material has not been quantitatively accounted for. Since only 8–25% of the gB applied to the column was recovered as purified gB, the remainder of the gB must be present in flow-through fractions, wash fractions, eluted fractions not pooled with the product, or bound to the column. CMV gB could be detected by western blot in the flow-through fractions (e.g., FIG. 56, lane 6). However, when the amount of gB in the flow-through fractions was estimated by slot blot analysis, it did not account for more than 20% of the applied gB. The wash fractions have not been evaluated. The pooled fractions chosen for the final gB product were peak fractions only and therefore trace amounts of gB in adjacent fractions could account for some of the missing gB. For example, FIG. 57 shows sequential fractions eluted from column 8. Fractions 8.17–8.21 were pooled for the gB product, but trace amounts remained in fractions 8.16 and 8.22. Evidence exists also for the retention of gB in the immunoabsorbent gel. Gel material, taken from columns 11 and 19C after elution and washes, contains gB specific material detectable by western blot (FIG. 56, lanes 2 and 3). The amount of gB remaining on the column has not been quantitatively evaluated.

Reapplication of flow-through material to the column was attempted when flow-through material from column run #7 was applied to column #10 (Table 24). The amount of gB eluted from column 10 (4.5 µg) was only 4% of that obtained from column 7 (110 µg). It was not possible to evaluate this result since the capacity of the bed material for gB, and the amounts of gB applied to the column and present in the flow-through fractions were not known. Because of the poor yield, this approach was not used again.

Evaluation of Purified gB. After pooling gB-containing eluted fractions, evaluation of purified gB consisted of 1) determination of total protein concentration, 2) SDS-PAGE analysis to identify gB specific and non-specific bands, and 3) confirmation of these bands with immunological reagents. Additionally, the purified gB was analyzed for degree of purity by densitometer scan, and for native conformation by ability to bind to a panel of CMV monoclonal antibodies.

Figure 58:
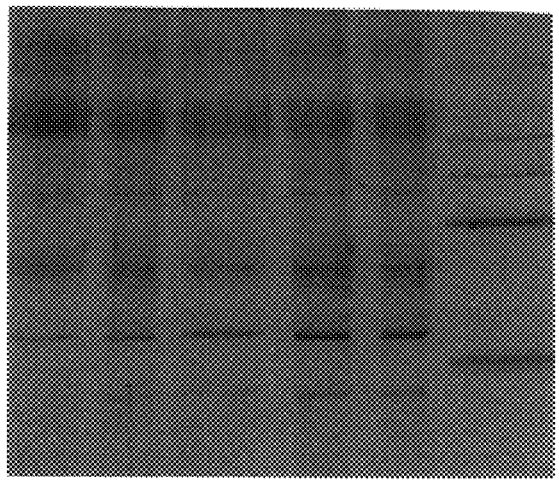
FIG. 58 shows SDS-PAGE analysis of five batches of immunoaffinity purified CMV gB (samples of batches 1 through 5 (lanes 1–5) were electrophoretically separated on a 10% gel under reducing conditions and stained with Coomassie Blue; Lane M contains molecular weight markers)
Figures 59, 59A:
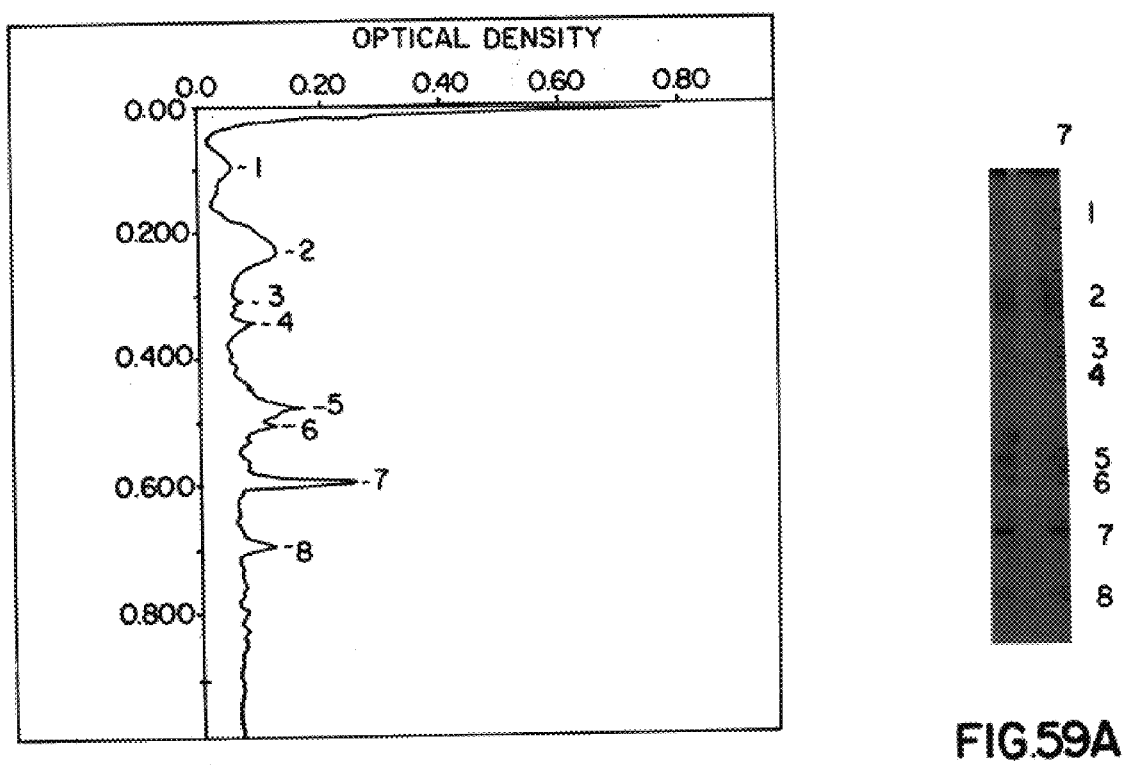
FIGS. 59, 59A shows characterization of immunoaffinity purified CMV gB (batch 5, analyzed by SDS-PAGE, as shown in FIGS. 58A and B, was scanned with a densitometer, and bands were defined (lane 7, labels 1 through 8) with FIG. 59A showing a densitometer tracing through lane 7)
Figure 60A:
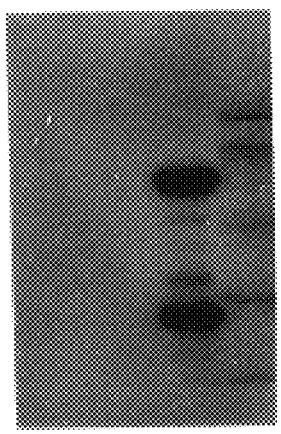
FIGS. 60A and B show immunoblot analysis of immunoaffinity purified CMV gB (purified HIV env (lanes 1), affinity purified CMV gB (lanes 2), crude CMV gB (lane B3), or monoclonal CH380 (lane A3) were electrophoretically separated on a 10% gel, blotted onto nitrocellulose paper and probed for the presence of mouse IgG H and L chains or CMVgB using goat anti-mouse IgG (A) or monoclonal CH380 (B), respectively; molecular weight markers are present in lanes 4)
Figure 60B:
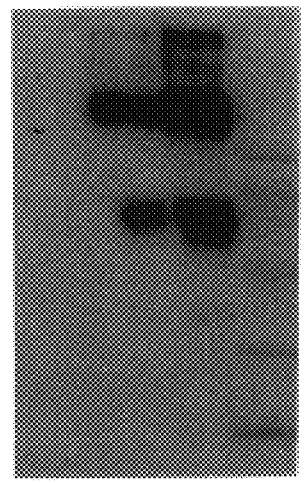
Figure 61A:
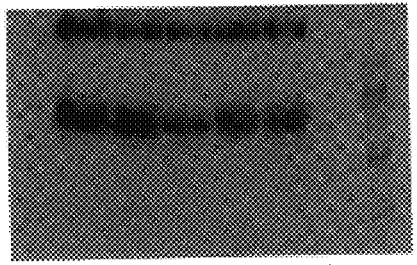
FIGS. 61A and B show immunoprecipitation/immunoblot analysis of affinity purified gB (Batch 1 immunoaffinity purified gB(l) or crude gB (B) was immunoprecipitated with monoclonals CH380 (lanes 1), 13–127 (lanes 2), 13–128 (lanes 3), HCMV 37 (lanes 4), or HCMV 34 (lanes 5); the immunoprecipitates were electrophoretically separated on a 10% gel under reducing conditions, blotted onto nitrocellulose and probed for the presence of gB, using guinea pig anti-CMB gB; far left lanes are molecular weight markers)

Fractions containing CMV gB eluted from each column were analyzed initially by SDS-PAGE and silver staining, and gB fractions were identified and pooled for each run. A typical elution profile is shown in FIG. 57. A portion of the eluted gB was used for analysis, and the remainder of the material was combined into 5 separate batches (Table 25). Each batch was analyzed by SDS-PAGE on a 10% gel under reducing conditions and stained with Coomassie Blue (FIG. 58). The stained gel was scanned on a densitometer and the molecular weight and relative quantity of each band was calculated: a typical scan is shown in FIGS. 59, 59A and analysis of the 5 batches is summarized in Table 26. By SDS-PAGE analysis batches 1–5 appear very similar (FIG. 58). The two major bands, having apparent molecular weights 120–130 and 51–59 kDa, represent the precursor gB protein and the C-terminal processing fragment. The wide diffuse appearance of these bands is probably due to variable glycosylation of this normally heavily glycosylated protein. The identity of these bands as gB-specific is supported by results from western blot analysis with monoclonal CH380 (FIG. 60B). The bands of apparent molecular weight 77–100 kDa, which appear as doublets in batches 2–5 (FIG. 58), are the correct size for the gB N-terminal processing fragment, identified in the medium of vP1145-infected cells by IP analysis (FIGS. 52A and B). These bands could not be verified as gB-specific by either western blot analysis (FIG. 60B), or a combination immunoprecipitation-western blot assay (FIGS. 61A and B), but the possibility should not be ruled out since neither the guinea pig anti-gB serum nor monoclonal CH380 are able to detect N-terminal processing fragments by western blot. A contaminating protein of approximately 39–45 kDa is present in each batch at a level of 6–15% of total protein (FIG. 58 and Table 26). Two more possible gB protein bands, one of greater than 200 kDa and the other 30–35 kDa are present in every batch (FIGS. 58, 59, and 59A; Table 26). Evidence that the large (~200 kDa) protein is gB is derived from western blot analysis with monoclonal CH380 which detects two proteins with molecular weights greater than 200 kDa (FIG. 60B, lanes 2&3). It is possible that the protein of approximately 30–35 kDa is also gB-specific (FIG. 58). In the IP analysis of medium of vP1145-infected cells, a protein of approximately 35 kDa was detected by 3 monoclonals (13–128, HCMV 34, and HCMV 37)(FIG. 55) and by the guinea pig serum (FIGS. 52A and B). A protein of this size was described by Reis et al. (1993) as a degradation product of gB.

Figure 62A:
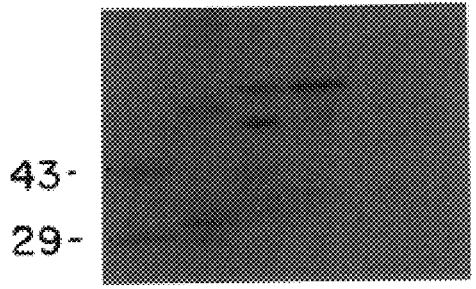
FIGS. 62A and B show immunoblot analysis of affinity purified CMV gB (Vero cells lysates (lanes A3, B2), CEF lysates (lane A2), vaccinia-infected Vero cells (lane B3), crude CMV gB (lanes 4), affinity purified CMV gB (lanes 5), or purified HIV env (lanes 6) were electrophoretically separated on a 10% gel under reducing conditions, blotted onto nitrocellulose, and probed for the presence of Vero cell proteins using rabbit anti-Vero cells (A), or vaccinia proteins using rabbit anti-vaccinia (B); molecular weight markers are present in lanes 1).
Figure 62B:
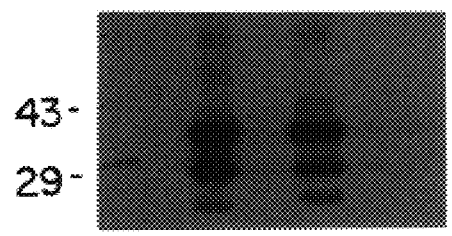

Assuming that contaminating proteins in the gB preparation would be derived from the cell substrate, the virus vector or the immunoabsorbent bed material, the preparation was probed for the presence of mouse IgG, Vero cell proteins, and vaccinia proteins. Proteins derived from Vero cells or mouse IgG could not be detected by western blot analysis (FIGS. 60A and 62A). However, contaminating vaccinia-specific proteins with molecular weights of approximately 35 and 20 kDa were detected in trace amounts (FIG. 62B, lane 5).

Figure 61B:
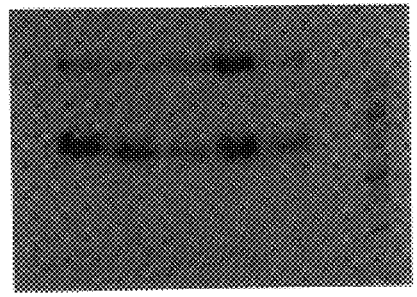

To determine if the eluted gB retained its native conformation, a combination immunoprecipitation/western blot assay was performed with a panel of monoclonals which included 3 neutralizing and one conformationally dependent antibody. Each monoclonal antibody precipitated the precursor and C-terminal fragment from purified gB (FIG. 61), suggesting that the gB eluted from the immunoaffinity column retained its native conformation In summary, the analysis of eluted gB in batches 1–5 demonstrates that the product contains at least two known gB-specific proteins, the precursor gB and C-terminal fragment, which together account for approximately 50% of the protein content (FIG. 58 and Table 26). Three other protein species, which account for 20–25% of total protein content (Table 26), could also be gB-specific although direct evidence has not been provided.

Immunogenicity of Purified gB. The five CMV gB batches were pooled and the final concentration determined. Several amounts of purified gB were adjuvanted with either alum or QS21 and used to inoculate mice. Serum from the mice was evaluated for the presence of HCMV neutralizing antibody. Table 27 demonstrates that all of the amounts of purified gB tested with both adjuvants were able to elicit HCMV neutralizing antibody.

Purified gB was used in a prime/boost protocol in combination with ALVAC-gB (vCP139) in mice. Table 28 demonstrates that mice receiving ALVAC gB (vCP139) on day 0 boosted on Day 29 with purified gB adjuvanted with QS21 or Alum developed higher levels of HCMV neutralizing anibody than mice receiving a second dose of ALVAC-gB vCP1319).

TABLE 23

Induction of HCMV Neutralizing Antibody in Mice

| | Days After Immunization | | |
|---|---|---|---|
| Immunogen[1] | 30 | 48 | 135 |
| vP1126 | 16[2] | 8 | 256 |
| vP1128 | 16 | 8 | 106 |
| vP1145 | 16 | 8 | 106 |

[1]Mice were immunized with 1 × 10[8] PFU of recombinant viruses (ip.) on day 0 and day 49.
[2]HCMV Neutralizing titer

TABLE 24

SUMMARY OF IMMUNOAFFINITY PURIFICATION COLUMNS

| COLUMN RUN | # VERO ROLLER BOTTLES[a] | COLUMN SIZE | CRUDE MATERIAL APPLIED TO COLUMN Total Protein[b] | gB-specific protein[c] | gB YIELD (% of applied) |
|---|---|---|---|---|---|
| 7 | 4 | 1 ml | 13.3 mg | nd[d] | 110 ug[b] |
| 8 | 6 | 1 ml | 14.4 mg | 22 mg | 84 μg[b] |
| 10 | Col 7 flow thru | 1 ml | nd | nd | 4.8 ug[b] |
| 11 | 4 | 1 ml | nd | nd | 100 ug[b] |
| 13 | 1 | 0.3 ml | nd | nd | 12 ug[b] |
| 19A | 1 | 0.6 ml | 2.9 mg | 240 μg | 41 μg[c] (17%) |
| 19B | 2 | 0.6 ml | 5.8 mg | 480 μg | 93 μg[c] (19%) |
| 19C | 3 | 0.6 ml | 8.7 mg | 720 μg | 185 μg[c] (25%) |
| 21A | 3 | 0.6 ml | 5.7 mg | 300 μg | 29 μg[c] (8%) |
| 21B | 5 | 0.6 ml | 9.5 mg | 500 μg | 120 μg[c] (13%) |
| 21C | 7 | 0.6 ml | 13.3 mg | 700 μg | 150 μg[c] (19%) |
| 23 | 3 | 6 ml | 5.7 mg | 300 μg | 25 μg[c] (8%) |
| 28 | 36 | 4 ml | 64.8 mg | nd | 100 μg[b] |
| 29 | 24 | 4 ml | 30 mg | nd | 480 μg[b] |
| 32 | 24 | 4 ml | nd | nd | 700 μg[b] |

[a]Cell density: $1 \times 10^8$ cells per roller bottle
[b]Protein concentration determined by Pierce BCA assay
[c]Estimated by slot blot analysis, using purified gB as standard
[d]Not determined

TABLE 25

CMV gB BATCHES

| BATCH # | TOTAL gB | VOLUME | CONCENTRATION | COLUMN RUN |
|---|---|---|---|---|
| 1 | 0.16 mg | 0.55 ml | 0.29 mg/ml | 7 |
|   |         |         |             | 8 |
|   |         |         |             | 10 |
|   |         |         |             | 11 |
|   |         |         |             | 13 |
| 2 | 1.0 mg | 1.0 ml | 1.0 mg/ml | 28 |
| 3 | 0.26 mg | 0.5 ml | 0.52 mg/ml | 21A |
|   |         |         |             | 21B |
|   |         |         |             | 21C |
|   |         |         |             | 23 |
| 4 | 0.48 mg | 0.5 ml | 0.96 mg/ml | 29 |
| 5 | 0.7 mg | 0.5 ml | 1.4 mg/ml | 32 |

TABLE 26

DENSITOMETRY ANALYSIS OF 5 BATCHES OF CMV gB

| PROTEIN BAND | APPARENT MOLECULAR WEIGHT (kDa)[a] | | | | | RELATIVE QUANTITY (%)[b] | | | | |
|---|---|---|---|---|---|---|---|---|---|---|
|  | B1 | B2 | B3 | B4 | B5 | B1 | B2 | B3 | B4 | B5 |
| >200 kDa | 222 | 208 | 221 | 225 | 217 | 10.6 | 6.7 | 7.5 | 8.3 | 7.4 |
| (gB?) | 192 |  |  |  |  | 8 |  |  |  |  |
| Precursor gB | 128 | 120 | 124 | 128 | 134 | 39 | 30 | 36.1 | 30 | 27.4 |
| N fragment | 83 | 94 | 99 | 101 | 100 | 9.6 | 3.6 | 3.2 | 4.5 | 3.5 |
| (?) |  | 77 | 84 | 88 | 89 |  | 9.7 | 6.3 | 6.6 | 6.3 |
| C fragment | 55 | 51 | 55.4 | 56.4 | 59 | 21 | 15.6 | 13.7 | 22.6 | 21 |
| Unknown | 42 | 39 | 42 | 44 | 45 | 6.1 | 12 | 15.4 | 14.3 | 15.8 |

TABLE 26-continued

DENSITOMETRY ANALYSIS OF 5 BATCHES OF CMV gB

| PROTEIN | APPARENT MOLECULAR WEIGHT (kDa)[a] | | | | | RELATIVE QUANTITY (%)[b] | | | | |
|---|---|---|---|---|---|---|---|---|---|---|
| BAND | B1 | B2 | B3 | B4 | B5 | B1 | B2 | B3 | B4 | B5 |
| contaminant gB degradation product (?) | 32 | 30 | 35 | 35 | 37 | 4.3 | 9.7 | 11.3 | 8.6 | 10 |

[a]Calculated from densitometer scan using molecular weight markers as standards (refer to FIG. 59, 59A)
[b]The density of each band is calculated from a 2 dimensional scan line through the band: the average pixel OD across the sample width is integrated under the curve to the baseline to obtain density (OD × cm). Relative quantity is the percentage of the total density of all bands in the lane. (refer to FIG. 59, 59A).

TABLE 27

HCMV Neutralizing Antibodies Elicited by purified gB protein in CBA Mice[1]

| Mouse | dose[3] | Adjuvant[3] | NT[2] 4w | NT[2] 6w | NT[2] 8w | NT[2] 9w |
|---|---|---|---|---|---|---|
| 201 | 2.5 | Alum | 32 | 256 | 256 | 256 |
| 203 | | | 8 | 64 | 128 | 128 |
| 204 | | | 8 | 12 | 16 | 16 |
| 206 | 5.0 | ALum | 48 | 512 | 192 | 192 |
| 207 | | | 12 | 192 | 512 | 512 |
| 208 | | | 16 | 192 | 192 | 192 |
| 209 | | | 16 | 128 | 256 | 256 |
| 210 | | | 8 | 128 | 256 | 256 |
| 211 | 10.0 | Alum | 32 | 256 | | |
| 213 | | | 32 | 96 | 256 | 256 |
| 214 | | | 32 | 256 | 256 | |
| 216 | 20.0 | Alum | 64 | 128 | 128 | 128 |
| 217 | | | 64 | 256 | 256 | 256 |
| 218 | | | 32 | 128 | 512 | 256 |
| 219 | | | 16 | 128 | 256 | 256 |
| 220 | | | 32 | 192 | 512 | 256 |
| 222 | 2.5 | QS21 | 8 | 192 | 512 | |
| 223 | | | 32 | >4096 | >4096 | 2048 |
| 224 | | | 16 | 1536 | | |
| 225 | | | 64 | 1024 | 1024 | 1024 |
| 226 | 5.0 | QS21 | 64 | >4096 | 1024 | 1024 |
| 227 | | | 96 | >4096 | | |
| 228 | | | 64 | >4096 | >4096 | >4096 |
| 229 | | | 64 | >256 | >4096 | |
| 230 | | | 32 | >4096 | 1536 | 2048 |
| 231 | 10.0 | QS21 | 64 | 2048 | 2048 | 2048 |
| 232 | | | 96 | 1536 | 2048 | |
| 233 | | | 96 | >4096 | | |
| 234 | | | 64 | 2048 | 2048 | 1024 |
| 236 | 20.0 | QS21 | 128 | 3072 | | |
| 239 | | | 96 | >4096 | >4096 | >4096 |

[1]Mice were inoculated S.C. at weeks 0 and 4.
[2]Sera were obtained ar 4, 6, 8 or 9 weeks after priming.
μg gB in either 15 μg QS21 or 25 μl Alum were used for each inoculation.

TABLE 28

Summary Of Prime-Boost Experiment

| Mice | NT Day 0 | antigen adj. | NT Day 29 | antigen adj. | NT Day 42 | NT Day 56 |
|---|---|---|---|---|---|---|
| 381 | 4 | ALV | 32 | gB + Alu | 384 | 768 |
| 382 | <4 | ALV | 8 | gB + Alu | 192 | 192 |
| 383 | 4 | ALV | 4 | gB + Alu | 192 | 256 |
| 384 | <4 | ALV | 48 | gB + Alu | 512 | 512 |
| 385 | 4 | ALV | 16 | gB + Alu | 256 | ND |
| 397 | 4 | ALV | 8 | gB + Alu | 128 | 192 |
| G.m. | 4 | | 13.5 | | 248 | 326 |
| 392 | <4 | ALV | <4 | gB + QS | 128 | 128 |
| 393 | <4 | ALV | 4 | gB + QS | >1024 | >1024 |
| 394 | <4 | ALV | 8 | gB + QS | >1024 | >1024 |
| 395 | <4 | ALV | 16 | gB + QS | 512 | 384 |
| 396 | <4 | ALV | 4 | gB + QS | 256 | 384 |
| 398 | 4 | ALV | 8 | gB + QS | >1024 | >1024 |
| G.m. | 4 | | 6.3 | | >512 | >522 |
| 373 | 4 | ALV | 16 | ALV | 128 | 96 |
| 376 | 4 | ALV | 4 | ALV | 8 | 12 |
| 378 | 8 | ALV | 4 | ALV | 8 | 4 |
| 379 | 4 | ALV | 8 | ALV | 128 | 128 |
| 380 | 4 | ALV | 16 | ALV | 64 | 64 |
| 399 | 4 | ALV | 4 | ALV | 96 | 192 |
| 400 | <4 | ALV | 4 | ALV | 64 | 128 |
| G.m. | 4 | | 6.5 | | 45.6 | 51.2 |

$5 \times 10^5$ TCD$_{50}$ of ALVAV-gB (vCP139), 5 μg gB + Alu, 1 ug gB + QS21 were given, s.c.
G.m. = geometric mean The results presented here demonstrate the ability of the NYVAC and ALVAC-HCMV recombinants and products therefrom to be employed in the compositions and utilities aforementioned, for instance, immunological, antigenic or vaccine compositions, or for use in preparing antigens or antibodies for assays, kits or tests, and, for example, as suitable for uses in vaccine or immunization strategies capable of preventing infection by HCMV; and, that the DNA of the recombinants is useful for probes or for preparing PCR primers.

Having thus described in detail preferred embodiments of the present invention, it is to be understood that the invention defined by the appended claims is not to be limited by particular details set forth in the above description as many apparent variations thereof are possible without departing from the spirit or scope thereof.

References

1. Akrigg, A., Wilkinson, G. W. G., and Oram, J. D., Virus Res. 2:107–121 (1985).
2. Albrecht, T. and Rapp, F., Virology 55:53–61 (1973).
3. Alp, N. J., Allport, T. D., Zanten, J. Van, Rodgers, B., Patrick Sissons, J. G. and Borysiewicz, L. K., J. Virol. 65:4812–4820 (1991).
4. Altenburger, W., C-P. Suter and J. Altenburger, Archives Virol. 105:15–27 (1989).

5. Aulitzky, W., Schulz, T., Tilg, H. et al., J. Infect. Dis. 163:1344–1347 (1991).
6. Baboonian, C., Blake, K., Booth, J. C., and Wiblin, C.N., J. Med. Virol. 29:139–145 (1989).
7. Behbehani, A. M., Microbiological Reviews 47:455–509 (1983).
8. Beninga, J., Kropff, B. and Mach, M., J. Gen. Virol. 76:153–160 (1995).
9. Bergoin, M., and Dales, S., In Comparative Virology, eds. K. Maramorosch and E. Kurstak, (Academic Press, NY) pp. 169–205 (1971).
10. Bertholet, C., Drillien, R., and Wittek, R., Proc. Natl. Acad. Sci. USA 82:2096–2100 (1985).
11. Biegalke, B. J. and Geballe, A. P., Virology 183:381–385 (1991).
12. Blanton, R., and Tevethia, M., Virology 112:262–273 (1981).
13. Borysiewicz, L. K., Hickling, J. K., Graham, S., Sinclair, J., Cranage, M. P., Smith, G. L., and Sissons, J. G. P., J. Exp. Med. 168:919–931 (1988).
14. Britt, W. J., Virology 135:369–378 (1984).
15. Britt, W. J. and Auger, D., J. Virol. 58:185–191 (1986).
16. Britt, W. J. and Vugler, L. G., J. Virol. 63:403–410 (1989).
17. Brockmeier, S., Lager, K., Tartaglia, J., Riviere, M., Paoletti, E. and Mengeling, W., Veterinary Microbiology 38:41–58 (1993).
18. Buller, R. M. L., G. L. Smith, Cremer, K., Notkins, A. L., and Moss, B., Nature 317:813–815 (1985).
19. Buller, R. M. L., Chakrabarti, S., Cooper, J. A., Twardzik, D. R., and Moss, B., J.Virol. 62:866–874 (1988).
20. Cadoz, M., A. Strady, B. Meignier, J. Taylor, J. Tartaglia, E. Paoletti and S. Plotkin, The Lancet, 339:1429–1432 (1992).
21. Cameron, J., and Preston, C., J. Gen. Virol. 54:421–424 (1981).
22. Charpentier, B., Michelson, S. and Martin, B., J. of Immunology 137:330–336 (1986).
23. Cherrington, J. M. and Mocarski, E. S., J. Virol. 63:1435–1440 (1989).
24. Child, S. J., Palumbo, G. J., Buller, R. M. L., and Hruby, D. E. Virology 174:625–629 (1990).
25. Clewell, D. B. and D. R. Helinski, Proc. Natl. Acad. Sci. USA 62:1159–1166 (1969).
26. Clewell, D. B., J. Bacteriol 110:667–676 (1972).
27. Colberg-Poley, A. M., Santomenna, L. D., Harlow, P. P., Benfield, P. A. and Tenney, D. J., J. Virol. 66:95–105 (1992).
28. Colinas, R. J., R. C. Condit and E. Paoletti, Virus Research 18:49–70 (1990).
29. Cooney, E. L., Corrier, A. C., Greenberg, P. D., et al., Lancet 337:567–572 (1991).
30. Cooney, E., McElrath, M., Corey, L., Hu, S., Collier, A., Arditti, D., Hoffman, M., Coorbs, R., Smith, G., and Greenberg, P., Proc. Natl. Acad. Sci. USA 90:1882–1886 (1993).
31. Cranage, M. P., Smith, G. L., Bell, S. E., Hart, H., Brown, C., Bankier, A. T., Tomlinson, P., Barrell, B. G. and Minson, T. C., J. Virol. 62:1416–1422 (1988).
32. Cranage, M. P., Kouzarides, T., Bankier, A., Satchwell, S., Weston, K., Tomlinson, P. and Barrell, B., EMBO J. 5:3057–3063 (1986).
33. DeMarchi, J. M., Schmidt, C. A., and Kaplan, A. S., J. Virol. 35:277–286 (1980).
34. Dreyfus, G., Adam, S. A. and Choi, Y. D.,Mol. Cell. Biol. 4:415–423 (1984).
35. Drilliem, R., Koehren, F. and Kirn, A., Virology 111:448–499 (1981).
36. Edbauer, C., R. Weinberg, J. Taylor, A. Rey-Senelonge, J. F. Bouquet, P. Desmettre, E. Paoletti, Virology 179:901–904 (1990).
37. Ehrlich, P. H., Moustafa, Z. A., Justice, J. C., Harfeldt, K. E., and Ostberg, L., Hybridoma 7:385–395 (1988).
38. Engelke, D. R., Hoener, P. A., and Collins, F. S., Proc. Natl. Acad. Sci. 85:544–548 (1988).
39. Etinger, H. M. and Altenburger, W., Vaccine 9:470–472 (1991).
40. Fenner, F., Virology 5:502–529 (1958).
41. Flexner, C., Hugen, A., and Moss, B., Nature 330:259–262 (1987).
42. Forman, S. J., Zaia, J. A., Clark, B. R., Wright, C. L., Mills, B. J., Pottathil, R., Racklin, B. C., Gallagher, M. T., Welte, K., and Blume, K. G., J. Immunol. 134:3391–3395 (1985).
43. Fries et al., 32nd Interscience Conference on Antimicrobial Agents and Chemotherapy, Anaheim, Calif. (October 1992).
44. Funahashi, S., T. Sato and H. Shida, J. Gen. Virol. 69:35–47 (1988).
45. Gallant, J. E., Moore, R. D., Richman, D. D. et al., J. Infect. Dis. 166:1223–1227 (1992).
46. Galloway, D. A., Buonaguro, F. M., Brandt, C. R., and McDougall, J. K., In Cancer Cells, DNA Tumor Viruses: Control of Gene Expression and Replication, eds. Botchan, M., Grodzicker, T., and Sharp, P. A. (Cold Spring Harbor Laboratory) 4:355–361 (1986).
47. Ghazal, P., Young, J., Giuletti, E., DeMattei, C., Garcia, J., Gaynor, J., Stenberg, R. M. and Nelson, J.A., J. Virol. 65:6735–6742 (1991).
48. Ghendon, Y.Z., and Chernos, V. I., Acta Virol. 8:359–368 (1964).
49. Gilbert, M. J., Riddell, S. R., Li, C. R. and Greenberg, P. D., J. Virol. 67:3461–3469 (1993).
50. Gillard, S., Spehner, D., Drillien, R., and Kirn, A., Proc. Natl. Acad. Sci. USA 83:5573–5577 (1986).
51. Glenn, J., Rev. Infect. Dis. 3:1151–1178 (1981).
52. Goebel, S. J., Johnson, G. P., Perkus, M. E., Davis, S.W., Winslow, J. P., Paoletti, E., Virology 179:247–266 (1990a).
53. Goebel, S. J., G. P. Johnson, M. E. Perkus, S. W. Davis, J. P. Winslow and E. Paoletti, Virology 179:517–563 (1990b).
54. Goldstein, D. J. and S. K. Weller, Virology 166:41–51 (1988).
55. Gönczöl, E., Ianacone, W. H. O., Starr, S., Meignier, B., and Plotkin, S. A., Vaccine 8:130–136 (1990).
56. Gönczöl, E., De Taisne, C., Hirka, G., Berencsi, K., Lin, W., Paoletti, E. and Plotkin, S., Vaccine 9:631–637 (1991).
57. Gönczöl E., Furlini, G., Ianacone, J., and Plotkin, S., J. Virol. Meth. 14:37–41 (1986).
58. Graham, B., Mathes, T., Belshe, R., Clements, M., Dolin, R., Wright, P., Gorse, G., Schwartz, D., Keefer, M., Bolognesi, D., Corey, L., Stablein, D., Esterlitz, J., Hu, S.-L., Smith, G., Fast, P., Koff, W. and the HIAID AIDS Vaccine Clinical Trials Network, J. Infect. Dis. 167:533–537 (1993).
59. Gretch, D. R., Kari, B., Gehrz, R. C., and Stinski, M. F., J. Virol. 62:1956–1962 (1988a).
60. Gretch, D. R., Kari, B., Rasmussen, L., Gehrz, R. C., and Stinski, M. F., J. Virol. 62:875–881 (1988b).
61. Gross, J. G., Bozzette, S. A., Mathews, W. C. et al., Ophthalmology 97:681–686 (1990).

62. Guo et al., J. Virol. 64:2399–2406 (1990).
63. Guo, P., Goebel, S., Davis, S., Perkus, M. E., Languet, B., Desmettre, P., Allen, G., and Paoletti, E., J. Virol. 63:4189–4198 (1989).
64. Hagemeier, C., Walker, S. M., Sissons, P. J. G. and Sinclair, J. H., J. Gen. Virol. 73:2385–2393 (1992).
65. Harlow, E. and Lane D., In Antibodies: A Laboratory Manual (Cold Spring Harbor University, Cold Spring Harbor, N.Y.) (1988).
66. Hruby, D. E. and L. A. Ball, J. Virol. 43:403–409 (1982).
67. Hruby, D. E., R. A. Maki, D. B. Miller and L. A. Ball, Proc. Natl. Acad. Sci. USA 80:3411–3415 (1983). 68. Hu, S. -L., Klaniecki, J., Dykers, T., Sridhar, P. and Travis, B., AIDS RES. Hum. Retroviruses 3:615–620 (1991).
69. Hu, S. -L., Abrams, K., Barber, G., Moran, P., Zarling, J., Langlois, A., Kuller, L., Morton, W. and Benveniste, R., Science 255:456–459 (1992).
70. Ichihashi, Y. and Dales, S., Virology 46:533–543 (1971).
71. Itamura, S., H. Iinuma, H. Shida, Y. Morikawa, K. Nerome and A. Oya, J. Gen. Virol. 71:2859–2865 (1990).
72. Jacobson, J. G., D. A. Leib, D. J. Goldstein, C. L. Bogard, P. A. Schaffer, S. K. Weller and D. M. Coen, Virology 173:276–283 (1989).
73. Jahn, G., Scholl, B. -C., Traupe, B. and Fleckenstein, B., J. Gen. Virol. 68:1327–1337 (1987).
74. Jamieson, A. T., G. A. Gentry and J. H. Subak-Sharpe, J. Gen. Virol. 24:465–480 (1974).
75. Jonjic, S., del Val, M., Keil, G. M., Reddehasse, M. J. and Koszinowski, U. H., J. Virol. 62:1653–1658 (1988).
76. Kari, B. and Gehrz, R., Arch. Virol. 114:213–228 (1990).
77. Kari, B., Lussenhop, N., Goertz, R., Wabuke-Bunoti, M., Radeke, R. and Gehrz, R. J. Virol. 60:345–352 (1986).
78. Kari, B., Liu, Y. -N. C., Goertz, R., Lussenshop, N. and Stinski, M. F., J. Gen. Virol. 71:2673–2680 (1990).
79. Kato, S., M. Takahashi, S. Kameyama and J. Kamahora, Biken's 2:353–363 (1959).
80. Kaye, J. F., Gompels, U. A. and Minson, A. C., J. Gen. Virol. 72:2693–2698 (1992).
81. Kieny, M. P., Lathe, R., Drillien, R., Spehner, D., Skory, S., Schmitt, D., Wiktor, T., Koprowski, H., and Lecocq, J. P., Nature (London) 312:163–166 (1984).
82. Kleitman, W., Schottle, A., Kleitmann, B., et al., In Cell Culture Rabies Vaccines and Their Protective Effect in Man., eds. Kuwert/Wiktor/Koprowski (International Green Cross-Geneva) pp. 330–337 (1981).
83. Knauf, V. C., and Nester, E. W., Plasmid 8:45–54 (1982).
84. Konishi, E., Pincus, S., Paoletti, E., Laegreid, W. W., Shope, R. E. and Mason, P. W., Virology 190:454–458 (1992).
85. Kotwal, G. J. and Moss, B., Nature (London) 335:176–178 (1988a).
86. Kotwal, G. J. and Moss, B., Virology 167:524–537 (1988b).
87. Kotwal, G. J., S. N. Isaacs, R. McKenzie, M. M. Frank and B. Moss, Science 250:827–830 (1990).
88. Kotwal, G. J., A. W. Hugin and B. Moss, Virology 171:579–587 (1989a).
89. Kotwal, G. J. and B. Moss, J. Virol. 63:600–606 (1989b).
90. Kunkel, T. A., Proc. Natl. Acad. Sci. USA 82:488–492 (1985).
91. Kuwert, E. K., Barsenbach, C., Werner, J., et al., In Cell Culture Rabies Vaccines and Their Protective Effect in Man., eds. Kuwert/Witkor/Koprowski (International Green Cross-Geneva) pp. 160–167 (1981).
92. Lafemina, R., Pizzorno, M. C., Mosca, J. D. and Hayward, G. S., Virology 172:584–600 (1989).
93. Lai, C. -K., and B. G-T., Pogo Virus Res. 12:239–250 (1989).
94. Liu, Y. -N. C., Klaus, A., Kari, B., Stinski, M. F., Eckhardt, J. and Gehrz, R. C., J. Virology 65:1644–1648 (1991).
95. Mandecki, W., Proc. Natl. Acad. Sci. USA 83:7177–7182 (1986).
96. Maniatis, T., Fritsch, E. F., and Sambrook, J., In Molecular cloning: a laboratory manual, (Cold Spring Harbor Laboratory, Cold Spring Harbor, N.Y.) (1982).
97. Marshall, G. S., Rabalais, G. P., Stout, G. G. and Waldeyer, S. L., J. Infect. Dis. 165:381–384 (1992).
98. Masuho, Y., Matsumoto, Y. -I., Sugano, T., Fujnaga, S. and Minamishima, Y., J. Gen. Virol. 68:1357–1461 (1987).
99. Matthews, R. E. F., Intervirology 17:42–44 (1982). 100. McDonough, S. and Spector, D., Virology 125:31–46 (1983).
101. Morgan, A. J., M. Mackett, S. Finerty, J. R. Arrand, F. T. Scullion and M. A. Epstein, J. Med. Virol. 25:189–195 (1988).
102. Moss, B., E. Winters and J. A. Cooper, J. Virol. 40:387–395 (1981).
103. Pachl, C., Probert, W. S., Hermsen, K. M., Masiarz, F. R., Rasmussen, L., Merigan, T. C. and Spaete, R. C., Virology 169:418–426 (1989).
104. Paez, E., Dallo, S. and Esteban, M., Proc. Natl. Acad. Sci. USA 82:3365–3369 (1985).
105. Palumbo, G. J., Pickup, D. J., Fredrickson, T. N., Mcintyre, L. J., and Buller, R. M. L., Virology 172:262–273 (1989).
106. Pande, H., Campo, K., Tanamachi, B. and Zaia, J. A., Virology 182:220–228 (1991).
107. Panicali, D. and E. Paoletti, Proc. Natl. Acad. Sci. USA 79:4927–4931 (1982).
108. Panicali, D., Davis, S. W., Mercer, S. R., and Paoletti, E., J. Virol. 37:1000–1010 (1981).
109. Patel, D. D., Ray, C. A., Drucker, R. P., and Pickup, D. J., Proc. Natl. Acad. Sci. USA 85:9431–9435 (1988).
110. Patel, D. D. and Pickup, D. J., EMBO 6:3787–3794 (1987).
111. Pereira, L., Hoffman, M., Tatsuno, M. and Dondero, D., Virology 139:73–86 (1984).
112. Pereira, L. and Hoffman, M., In Human Herpesvirus Infections: Pathogenesis, Diagnosis and Treatments, eds. Lopez, C. and Roizman, B. Second International Conference on Immunobiology and Prophyaxis of Human Herpesvirus Infections Oct. 13–16, 1985 (Raven Press, New York) pp. 69–92 (1986).
113. Perkus, M. E., D. Panicali, S. Mercer and E. Paoletti, Virology 152:285–297 (1986).
114. Perkus, M. E., Limbach, K., and Paoletti, E., J. Virol. 63:3829–3836 (1989).
115. Perkus, M. E., Taylor, J., Tartaglia, J., Pincus, S., Kauffman, E. B., Tine, J. A. and Paoletti, E., In Combined Vaccines and Simultaneous Administration: Current Issues and Perspective (Annals of the New York Academy of Sciences) in press (1994).
116. Perkus, M. E., Goebel, S. J., Davis, S. W., Johnson, G. P., Limbach, K., Norton, E. K., and Paoletti, E., Virology 179:276–286 (1990).
117. Perkus, M. E., Kauffman, E. B., Taylor, J., Mercer, S., Smith, D., VanderHoeven, J. and Paoletti, E., J. Tiss. Cult. Meth. 15:72–81 (1993).
118. Perkus, M. E., S. J. Goebel, S. W. Davis, G. P. Johnson, E. K. Norton and E. Paoletti, Virology 180:406–410 (1991).
119. Perkus, M. E., A. Piccini, B. R. Lipinskas and E. Paoletti, Science 229:981–984 (1985).

120. Pialoux, G., Excler, J. -L., Riviere, Y. et al., AIDS Research and Human Retroviruses 11:373–381 (1995).
121. Piccini, A., M. E. Perkus, and E. Paoletti, Methods in Enzymology 153:545–563 (1987).
122. Pickup, D. J., B. S. Ink, B. L. Parsons, W. Hu and W. K. Joklik, Proc. Natl. Acad. Sci. USA 81:6817–6821 (1984).
123. Pickup, D. J., B. S. Ink, W. Hu, C. A. Ray and W. K. Joklik, Proc. Natl. Acad. Sci. USA 83:7698–7702 (1986).
124. Plachter, B., Klages, S., Hagelmann, S., Britt, W., Landini, M. P. and Jahn, G., J. Clin. Microbiol. 28:1229–1235 (1990).
125. Plotkin, S. A., Smiley, M. L., Friedman, H. M., Starr, S. E., Fleisher, G. R. and Wrodaver, C., Lancet 1:528–530 (1984).
126. Plotkin, S. A., Starr, S. E., Friedman, H. M., Gönczöl, E. and Weibel, R. E., J. Infect. Dis. 159:860–865 (1989).
127. Plotkin, S. A., Farquhar, J. and Hornberger, E., J. Infect. Dis. 134:470–475 (1976).
128. Rasmussen, L., Nelson, M., Neff, M. and Merigan, Jr., T. C., Virology 163:308–318 (1988).
129. Rasmussen, L., Matkin, C., Spaete, R., Pachl, C. and Merigan, T. C., J. Infect. Dis. 164:835–842 (1991).
130. Rasmussen, L., Nelson, R. M., Kelsall, D. C. and Merigan, T. C., Proc. Natl. Acad. Sci. USA 81:876–880 (1984).
131. Reed, J. and Muench, H., Am. J. Hyg. 27:493–497 (1938).
132. Reis, B., Bogner, E., Reschke, M., Richter, A., Mockenhaupt, T. and Radsak, K., J. Gen. Virol. 74:1371–1379 (1993).
133. Riddell, S. R., Rabin, M., Geballe, A. P., Britt, W. J. and Greenberg, P. D., J. Immunol. 146:2795–2804 (1991).
134. Riddell, S. R., Watanabe, K. S., Goodrich, J. M., Li, C. R., Agha, M. E. and Greenberg, P. D., Science 257:238–241 (1992).
135. Roarty, J. D., Fisher, E. J., and Nussbaum, J. J., Ophthalmology 100:1685–1688 (1993).
136. Sanger, F., Nickel, S. Coulson, A. R., Proc. Natl. Acad. Sci. 74:5463–5467 (1977).
137. Santomenna, L. D. and Colberg-Poley, A. M., J. Virol. 64:2033–2040 (1990).
138. Schmidtt, J. F. C. and H. G. Stunnenberg, J. Virol. 62:1889–1897 (1988).
139. Seligmann, E. B., In Laboratory Techniques in Rabies, eds. M. M. Kaplan and H. Koprowski, (World Health Organization, Geneva) pp. 279–285 (1973).
140. Shapira, S. K., Chou, J., Richaud, F. V. and Casadaban, M. J., Gene 25:71–82 (1983).
141. Shida, H., Virology 150:451–462 (1986).
142. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62:4474–4480 (1988).
143. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6:3379–3384 (1987).
144. Slabaugh, M., N. Roseman, R. Davis and C. Mathews, J. Virol. 62:519–527 (1988).
145. Smith, J. S., P. A. Yager and G. M. Baer, In Laboratory Techniques in Rabies, eds. M. M. Kaplan and H. Koprowski (WHO Geneva) pp. 354–357 (1973).
146. Spaete, R. R., Gehrz, R. C. and Landini, M. P., J. Gen. Virol. 75:3287–3308 (1994).
147. Spaete, R. R., Thayer, R. M., Probert, W. S., Masiarz, F. R., Chamberlain, S. H., Rasmussen, L., Merigan, T. C. and Pachl, C., Virology 167:207–225 (1988).
148. Spaete, R. R., Perot, K., Scott, P. I., Nelson, J. A., Stinski, M. F. and Pachl, C., Virology 193:853–861 (1993).
149. Spaete, R. R., Perot, K., Scott, P. I., Bauer, D., Lee, A. S., Scott, M. H., Rasmussen, L., Britt, W. J. and Pachl, C., In Progress in cytomegalovirus research, ed. M. P. Landini, pp. 133–136 (1991).
150. Speir, E., Modali, R., Huang, E. -S et al., Science 265:391–394 (1994).
151. Stagno, S., Pass, R. F., Dworsky, M. E. and Alford, C. A., Semin. Perinatol 7:31–42 (1983).
152. Stanberry, L. R., Kit, S., Myers, M. G., J. Virol. 55:322–328 (1985).
153. Tabor, S. and C. C. Richardson, Proc. Natl. Acad. Sci. USA 84:4767–4771 (1987).
154. Tartaglia, J., Perkus, M. E., Taylor, J., Norton, E. K., Audonnet, J-C., Cox, W. I., Davis, S. W., Van der Hoeven, J., Meignier, B., Riviere, M., Languet, B., Paoletti, E., Virology 188:217–232 (1992).
155. Tartaglia, J., R. Gettig & E. Paoletti, Virology (In press).
156. Tartaglia, J. and Paoletti, E., In Immunochemistry of Viruses, II, eds. M. H. V. van Regenmortel & A. R. Neurath, (Elsevier Science Publishers, Amsterdam) pp. 125–151 (1990b).
157. Tartaglia, J., Perkus, M. E., Taylor, J., Norton, E. K., Audonnet, J. -C., Cox, W. I., Davis, S. W., Van Der Hoeven, J., Meignier, B., Riviere, M., Languet, B., Paoletti, E., Virology 188:217–232 (1992).
158. Tartaglia, J., J. Taylor, W. I. Cox, J. -C. Audonnet, M. E. Perkus, A. Radaelli, C. de Giuli Morghen, B. Meignier, M. Riviere, K. Weinhold & E. Paoletti, In AIDS Research Reviews, eds. W. Koff, F. Wong-Staal & R. C. Kenedy, Vol. 3, (Marcel Dekker, NY) pp. 361–378 (1993a).
159. Tartaglia, J., Jarrett, O., Neil, J. C., Desmettre, P., Paoletti, E., J. Virol. 67:2370–2375 (1993b).
160. Tartaglia, J., Pincus, S., Paoletti, E., Critical Reviews in Immunology 10:13–30 (1990a).
161. Taylor, J., R. Weinberg, J. Tartaglia, C. Richardson, G. Alkhatib, D. Briedis, M. Appel, E. Norton & E. Paoletti, Virology 187:321–328 (1992).
162. Taylor, J., Tartaglia, J., Moran, T., Webster, R. G., Boquet, J. -F., Quimby, F., Holmes, D., Laplace, E., Mickle, T. and Paoletti, E., In Proceedings of the Third International Symposium on Avian Influenza, Univ of Wisconsin[\M]Madison, Madison, Wis., pp. 311–335 (1993).
163. Taylor, J., Edbauer, C., Rey-Senelonge, A., Bouquet, J. -F., Norton, E., Goebel, S., Desmettre, P., Paoletti, E., J. Virol. 64:1441–1450 (1990). 164. Taylor, J., R. Weinberg, B. Lanquet, P. Desmettre, and E. Paoletti, Vaccine 6:497–503 (1988b).
165. Taylor, J., Weinberg, R., Kawaoka, Y., Webster, R. G., and Paoletti, E., Vaccine 6:504–508 (1988a). 166. Taylor, G., E. J. Stott, G. Wertz and A. Ball, J. Gen. Virol. 72:125–130 (1991a).
167. Taylor, J., C. Trimarchi, R. Weinberg, B. Languet, F. Guillemin, P. Desmettre and E. Paoletti, Vaccine 9:190–193 (1991b).
168. Wathen, M. W., Thomsen, D. R. and Stinski, M. F., J. Virol. 38:446–459 (1981).
169. Weir, J. P. and B. Moss, J. Virol. 46:530–537 (1983).
170. Weller, T. H., N. Engl. J. of Med. 285:203–214 (1971).
171. Yuen, L., and Moss, B., Proc. Natl. Acad. Sci. USA 84:6417–6421 (1987).
172. Zhou, J., L. Crawford, L. McLean, X. Sun, M. Stanley, N. Almond and G. L. Smith, J. Gen. Virol. 71:2185–2190 (1990).

What is claimed is:

1. A recombinant poxvirus containing therein exogenous DNA coding for an HCMV protein wherein the poxvirus is selected from the group consisting of:

(i) recombinant vaccinia virus wherein regions C7L-K1L, J2R, B13R+B14R, A26L, A56R and I4L have been deleted therefrom, or wherein the open reading frames for the thymidine kinase gene, the hemorrhagic regions, the A type inclusion body region, the hemegglutinin gene, the host range gene region, and the large subunit, ribonucleotide reductase have been deleted therefrom;

(ii) NYVAC vaccinia virus;

(iii) ALVAC canarypox virus; and (iv) attenuated canarypox virus wherein said canarypox virus is attenuated through more than 200 serial passages on chick embryo fibroblasts, a master seed therefrom was subjected to four successive plaque purifications under agar, from which a plaque clone was amplified through five additional passages, provided that the said HCMV protein is not solely gB, gH, or a combination thereof.

2. The recombinant poxvirus of claim 1 wherein the DNA coding for an HCMV protein is selected from the group consisting of gL, pp150, pp65, IE1, IE1with amino acids 2–32 deleted therefrom, IE1with amino acids 292–319 deleted therefrom, IE1exon 4 segment (SEQ ID NO:55), combinations thereof, and combinations of one or more thereof with gB, gB with transmembrane deleted therefrom (SEQ ID NO:42), gB with transmembrane deleted therefrom and with altered cleavage site (SEQ ID NO:44), and gH.

3. The recombinant poxvirus of claim 1 wherein the poxvirus is a vaccinia virus.

4. The recombinant poxvirus of claim 1 wherein J2R, B13R+B14R, A26L, A56R, C7L–K1L and I4L are deleted from the virus.

5. The recombinant poxvirus of claim 1 wherein a thymidine kinase gene, a hemorrhagic region, an A type inclusion body region, a hemagglutinin gene, a host range region, and a large subunit, ribonucleotide reductase are deleted from the virus.

6. The recombinant poxvirus of claim 1 which is a NYVAC recombinant virus.

7. The recombinant poxvirus of claim 1 wherein said virus is a canarypox virus.

8. The recombinant poxvirus of claim 7 wherein the canarypox virus is a Rentschler vaccine strain which was attenuated through more than 200 serial passages on chick embryo fibroblasts, a master seed therefrom was subjected to four successive plaque purifications under agar, from which a plaque clone was amplified through five additional passages.

9. The recombinant poxvirus of claims 1 which is an ALVAC recombinant.

10. The recombinant poxvirus of claim 1 wherein the DNA which codes for an HCMV protein is selected from the group consisting of: gL; pp150; pp65; IE1; IE1with amino acids 2–32 deleted therefrom; IE1with amino acids 292–319 deleted therefrom; IE1exon 4 segment (SEQ ID NO:55), gB and gH; gB and pp65; gB, gH and pp65; gB, gH, pp65 and IE1exon 4 segment (SEQ ID NO:55); gB, gH, pp65, pp150, and IE1with exon 4 segment deleted therefrom; gB, gH, pp65 and pp150; gB, gH, gL, pp65, pp150 and IE1 exon 4 segment (SEQ ID NO:55); and gB, gH, gL, pp65 and pp 150.

11. The recombinant poxvirus of claim 6 wherein the DNA which codes for an HCMV protein is selected from the group consisting of: gL; pp150; pp65; IE1; IE1with amino acids 2–32 deleted therefrom; IE1 with amino acids 292–319 deleted therefrom; IE1exon 4 segment (SEQ ID NO:55; gB and pp65; gB, gH, and pp65; gB, gH, pp65, and IE1exon 4 segment (SEQ ID NO:55); gB, gH, pp65, pp150, and IE1 exon 4 segment (SEQ ID NO:55); gB, gH, pp65 and pp150; gB, gH, gL, pp65, pp150 and IE1 exon 4 segment (SEQ ID NO:55); and gB, gH, gL, pp65 and pp150.

12. The recombinant poxvirus of claim which is claim 1 vCP260, vCP233, vCP244, vCP256, vCP284, vCP136, vCP139, orvCP280.

13. The recombinant poxvirus of claim 9 wherein the DNA which codes for an HCMV protein is selected from the group consisting of: gL; pp150; pp65; IE1; IE1with amino acids 2–32 deleted therefrom; IE1with amino acids 292–319 deleted therefrom; IE1exon 4 segment (SEQ ID NO:55); gB and pp65; gB, gH and pp65; gB, gH, pp65 and IE1exon 4 segment (SEQ ID NO:55); gB, gH, pp65, pp150 and IE1with exon 4 segment (SEQ ID NO:55); gB, gH, pp65 and pp150; gB, gH, gL, pp65, pp150 and IE1exon 4 segment (SEQ ID NO:55); and gB, gH, gL, pp65 and pp 150.

14. The recombinant poxvirus of claim 1 which is vP 1126, vP1128, vP1145, vP992, vP1184, vP1196, vP1210, vP1214, vP1216, vP1251, vP1262, vP1302, vP1173, vP1183, vP1205B, vP893, vP1161, vP1160, vP1186, vP1201, vP1238, vP1247 or NYVAC-gB, gH, gL, pp65, pp150, or vP1001.

15. An HCMV antigen prepared from in vitro expression of a virus as claimed in any one of claims 1, 2, 3, 4, 5, 6, 7, 8 or 9.

16. An antibody elicited by in vitro expression of an antigen from a virus as claimed in any one of claims 1, 2, 3, 4, 5, 6, 7, 8 or 9 or, by administration of an HCMV associated antigen from in vitro expression of the virus.

17. A method for expressing a gene product in a cell cultured in vitro, the method comprising introducing into the cell a virus as claimed in any one of claims 1, 2, 3, 4, 5, 6, 7, 8, or 9, and culturing the cell under conditions that permit expression of the HCMV gene product.

18. A method for treating a patient in need of immunological treatment or of inducing an immunological response in an individual or animal comprising administering to said patient or individual or animal a composition comprising a virus as claimed in any one of claims 1, 2, 3, 4, 5, 6, 7, 8 or 9 in admixture with a suitable carrier.

19. A composition for inducing an immunological response comprising a virus as claimed in any one of claims 1, 2, 3, 4, 5, 6, 7, 8 or 9 admixture with a suitable carrier.

20. The method of claim 18 further comprising administering an HCMV antigen either before or after administering the composition.

21. The method of claim 20 wherein the antigen is from the in vitro expression of a recombinant avipox virus or vaccinia virus.

* * * * *